US009249441B2

(12) United States Patent
Franklin et al.

(10) Patent No.: US 9,249,441 B2
(45) **Date of Patent: *Feb. 2, 2016**

(54) TAILORED OILS

(71) Applicant: Solazyme, Inc., South San Francisco, CA (US)

(72) Inventors: Scott Franklin, Woodside, CA (US); Aravind Somanchi, Redwood City, CA (US); George Rudenko, Mountain View, CA (US); Riyaz Bhat, South San Francisco, CA (US); Xinhua Zhao, Foster City, CA (US); Risha Bond, Mountain View, CA (US); Walter Rakitsky, San Diego, CA (US); Alejandro Marangoni, Guelph (CA); Diza Braksmayer, Chanhassen, MN (US)

(73) Assignee: Solazyme, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/474,244

(22) Filed: Sep. 1, 2014

(65) Prior Publication Data

US 2014/0377847 A1 Dec. 25, 2014

Related U.S. Application Data

(63) Continuation of application No. 13/941,353, filed on Jul. 12, 2013, now Pat. No. 8,846,375, which is a continuation of application No. 13/865,974, filed on Apr. 18, 2013, now Pat. No. 8,945,908.

(60) Provisional application No. 61/635,285, filed on Apr. 18, 2012, provisional application No. 61/639,838, filed on Apr. 27, 2012, provisional application No. 61/655,469, filed on Jun. 4, 2012, provisional application No. 61/672,196, filed on Jul. 16, 2012, provisional application No. 61/679,026, filed on Aug. 2, 2012, provisional application No. 61/715,998, filed on Oct. 19, 2012, provisional application No. 61/769,678, filed on Feb. 26, 2013, provisional application No. 61/788,963, filed on Mar. 13, 2013, provisional application No. 61/809,213, filed on Apr. 5, 2013.

(51) Int. Cl.

| | |
|---|---|
| ***C12N 1/20*** | (2006.01) |
| ***C12P 33/00*** | (2006.01) |
| ***C12P 7/64*** | (2006.01) |
| ***C12N 9/02*** | (2006.01) |
| ***C12N 9/10*** | (2006.01) |
| ***C12N 9/16*** | (2006.01) |
| ***A23D 9/00*** | (2006.01) |
| ***C07C 57/03*** | (2006.01) |
| ***C07J 9/00*** | (2006.01) |
| ***C12N 15/82*** | (2006.01) |
| ***A23D 9/013*** | (2006.01) |
| ***C11B 1/00*** | (2006.01) |
| *C12R 1/89* | (2006.01) |

(52) U.S. Cl.

CPC . *C12P 33/00* (2013.01); *A23D 9/00* (2013.01); *A23D 9/013* (2013.01); *C07C 57/03* (2013.01); *C07J 9/00* (2013.01); *C11B 1/00* (2013.01); *C12N 9/0071* (2013.01); *C12N 9/1029* (2013.01); *C12N 9/16* (2013.01); *C12N 15/8247* (2013.01); *C12P 7/64* (2013.01); *C12P 7/6409* (2013.01); *C12P 7/6445* (2013.01); *C12P 7/6463* (2013.01); *C12P 7/6472* (2013.01); *C12R 1/89* (2013.01); *Y02E 50/13* (2013.01)

(58) Field of Classification Search

CPC ................................ C12P 7/6463; C12P 7/64
USPC .................................. 435/195, 257.2, 320.1
See application file for complete search history.

(56) References Cited

U.S. PATENT DOCUMENTS

| | | | |
|---|---|---|---|
| 5,270,175 | A | 12/1993 | Moll et al. |
| 5,391,724 | A | 2/1995 | Kindl et al. |

(Continued)

FOREIGN PATENT DOCUMENTS

| | | | |
|---|---|---|---|
| WO | WO 95/31553 | A1 | 11/1995 |
| WO | WO 2007/121100 | | 10/2007 |

(Continued)

OTHER PUBLICATIONS

Aguirre et al., "Engineering challenges in biodiesel production from microalgae," Critical Reviews in Biotechnology, 33(3): 293-308, (2013).

Altschul et al., "Basic local alignment search tool," J Mol Biol, 215(3):403-410, (1990).

Amaro et al., "Advances and perspectives in using microalgae to produce biodiesel," Applied Energy, 88:3102-3410, (2011).

Appel et al., "A multicopy vector system for genetic studies in Mucor circinelloides and other zgomycetes," Molecular Genetics and Genomics, 271(5):595-602, (2004).

Apt et al., "Stable nuclear transformation of the diatom Phaeodactylum tricornutum," Mol Gen Genet, 252(5):572-579, (1996).

(Continued)

*Primary Examiner* — Tekchand Saidha
(74) *Attorney, Agent, or Firm* — Alston & Bird LLP

(57) ABSTRACT

Recombinant DNA techniques are used to produce oleaginous recombinant cells that produce triglyceride oils having desired fatty acid profiles and regiospecific or stereospecific profiles. Genes manipulated include those encoding stearoyl-ACP desturase, delta 12 fatty acid desaturase, acyl-ACP thioesterase, ketoacyl-ACP synthase, and lysophosphatidic acid acyltransferase. The oil produced can have enhanced oxidative or thermal stability, or can be useful as a frying oil, shortening, roll-in shortening, tempering fat, cocoa butter replacement, as a lubricant, or as a feedstock for various chemical processes. The fatty acid profile can be enriched in midchain profiles or the oil can be enriched in triglycerides of the saturated-unsaturated-saturated type.

3 Claims, 23 Drawing Sheets

(56) References Cited

U.S. PATENT DOCUMENTS

| | | | |
|---|---|---|---|
| 5,563,058 A | 10/1996 | Davies et al. | |
| 5,693,507 A | 12/1997 | Daniell et al. | |
| 5,910,630 A | 6/1999 | Davies et al. | |
| 5,968,791 A | 10/1999 | Davis et al. | |
| 6,680,426 B2 | 1/2004 | Daniell et al. | |
| 7,081,567 B2 | 7/2006 | Xue et al. | |
| 7,135,620 B2 | 11/2006 | Daniell et al. | |
| 7,468,267 B2 | 12/2008 | Monod et al. | |
| 7,588,931 B2 | 9/2009 | Damude et al. | |
| 7,879,591 B2 | 2/2011 | Damude et al. | |
| 7,883,882 B2 | 2/2011 | Franklin et al. | |
| 7,935,515 B2 | 5/2011 | Franklin et al. | |
| 7,939,710 B1 | 5/2011 | Apt et al. | |
| 8,119,583 B2 | 2/2012 | Day et al. | |
| 8,187,860 B2 | 5/2012 | Franklin et al. | |
| 8,222,010 B2 | 7/2012 | Franklin et al. | |
| 8,268,610 B2 | 9/2012 | Franklin et al. | |
| 8,278,261 B2 | 10/2012 | Day et al. | |
| 8,435,767 B2 | 5/2013 | Franklin et al. | |
| 8,450,083 B2 | 5/2013 | Day et al. | |
| 8,476,059 B2 | 7/2013 | Trimbur et al. | |
| 8,497,116 B2 | 7/2013 | Trimbur et al. | |
| 8,512,999 B2 | 8/2013 | Trimbur et al. | |
| 8,518,689 B2 | 8/2013 | Trimbur et al. | |
| 8,592,188 B2 | 11/2013 | Franklin et al. | |
| 8,633,012 B2 | 1/2014 | Franklin et al. | |
| 8,647,397 B2 | 2/2014 | Trimbur et al. | |
| 8,674,180 B2 | 3/2014 | Franklin et al. | |
| 8,697,427 B2 | 4/2014 | Franklin et al. | |
| 8,846,375 B2 * | 9/2014 | Franklin et al. | 435/257.2 |
| 2006/0048240 A1 | 3/2006 | Alexandrov et al. | |
| 2006/0075522 A1 | 4/2006 | Cleveland et al. | |
| 2006/0094088 A1 | 5/2006 | Picataggio et al. | |
| 2006/0153826 A1 | 7/2006 | Arnould et al. | |
| 2006/0162006 A9 | 7/2006 | Sherman et al. | |
| 2007/0009988 A1 | 1/2007 | Monod et al. | |
| 2007/0048848 A1 | 3/2007 | Sears | |
| 2007/0167396 A1 | 7/2007 | Dillon et al. | |
| 2007/0254354 A1 | 11/2007 | Millis et al. | |
| 2007/0261138 A1 | 11/2007 | Graham et al. | |
| 2008/0014620 A1 | 1/2008 | Op Den Camp et al. | |
| 2008/0229451 A1 | 9/2008 | Cao et al. | |
| 2008/0256666 A1 | 10/2008 | Zhu et al. | |
| 2009/0004715 A1 | 1/2009 | Trimbur et al. | |
| 2009/0011480 A1 | 1/2009 | Trimbur et al. | |
| 2009/0047721 A1 | 2/2009 | Trimbur et al. | |
| 2009/0061493 A1 | 3/2009 | Trimbur et al. | |
| 2009/0142322 A1 | 6/2009 | Ye | |
| 2009/0148918 A1 | 6/2009 | Trimbur et al. | |
| 2009/0271892 A1 | 10/2009 | Thomasset et al. | |
| 2009/0274736 A1 | 11/2009 | Dillon et al. | |
| 2010/0021912 A1 | 1/2010 | Farese et al. | |
| 2010/0035320 A1 | 2/2010 | Blanchard et al. | |
| 2010/0093031 A1 | 4/2010 | Kobayashi et al. | |
| 2010/0151112 A1 | 6/2010 | Franklin et al. | |
| 2010/0151538 A1 | 6/2010 | Franklin et al. | |
| 2010/0170144 A1 | 7/2010 | Day et al. | |
| 2010/0239712 A1 | 9/2010 | Brooks et al. | |
| 2010/0297292 A1 | 11/2010 | Brooks et al. | |
| 2010/0297295 A1 | 11/2010 | Brooks et al. | |
| 2010/0297296 A1 | 11/2010 | Brooks et al. | |
| 2010/0297323 A1 | 11/2010 | Brooks et al. | |
| 2010/0297325 A1 | 11/2010 | Brooks et al. | |
| 2010/0297331 A1 | 11/2010 | Brooks et al. | |
| 2010/0303957 A1 | 12/2010 | Brooks et al. | |
| 2010/0303961 A1 | 12/2010 | Brooks et al. | |
| 2010/0303989 A1 | 12/2010 | Brooks et al. | |
| 2010/0303990 A1 | 12/2010 | Brooks et al. | |
| 2010/0323414 A1 | 12/2010 | Trimbur et al. | |
| 2011/0014665 A1 | 1/2011 | Trimbur et al. | |
| 2011/0047863 A1 | 3/2011 | Trimbur et al. | |
| 2011/0190522 A1 | 8/2011 | Trimbur et al. | |
| 2011/0203168 A1 | 8/2011 | Franklin et al. | |
| 2011/0252696 A1 | 10/2011 | Franklin et al. | |
| 2011/0256268 A1 | 10/2011 | Franklin et al. | |
| 2011/0256282 A1 | 10/2011 | Piechocki et al. | |
| 2011/0293785 A1 | 12/2011 | Franklin et al. | |
| 2012/0028319 A1 | 2/2012 | Trimbur et al. | |
| 2012/0119862 A1 | 5/2012 | Franklin et al. | |
| 2012/0128851 A1 | 5/2012 | Brooks et al. | |
| 2012/0164701 A1 | 6/2012 | Trimbur et al. | |
| 2012/0203018 A1 | 8/2012 | Franklin et al. | |
| 2012/0277452 A1 | 11/2012 | Franklin et al. | |
| 2012/0324784 A1 | 12/2012 | Franklin et al. | |
| 2012/0329109 A1 | 12/2012 | Chua et al. | |
| 2013/0004646 A1 | 1/2013 | Franklin et al. | |
| 2013/0006006 A1 | 1/2013 | Day et al. | |
| 2013/0089916 A1 | 4/2013 | Franklin et al. | |
| 2013/0096211 A1 | 4/2013 | Franklin et al. | |
| 2013/0102039 A1 | 4/2013 | Franklin et al. | |
| 2013/0116462 A1 | 5/2013 | Durrett et al. | |
| 2013/0122180 A1 | 5/2013 | Brooks et al. | |
| 2013/0165677 A1 | 6/2013 | Franklin et al. | |
| 2013/0197247 A1 | 8/2013 | Franklin et al. | |
| 2013/0273621 A1 | 10/2013 | Franklin et al. | |
| 2013/0295268 A1 | 11/2013 | Day et al. | |
| 2013/0296591 A1 | 11/2013 | Day et al. | |
| 2013/0316410 A1 | 11/2013 | Franklin et al. | |
| 2013/0317240 A1 | 11/2013 | Franklin et al. | |
| 2013/0323382 A1 | 12/2013 | Franklin et al. | |
| 2013/0323823 A1 | 12/2013 | Franklin et al. | |
| 2013/0330790 A1 | 12/2013 | Trimbur et al. | |
| 2013/0331584 A1 | 12/2013 | Franklin et al. | |
| 2013/0338385 A1 | 12/2013 | Franklin et al. | |
| 2014/0170716 A1 | 6/2014 | Trimbur et al. | |
| 2014/0249342 A1 | 9/2014 | Franklin et al. | |
| 2014/0256024 A1 | 9/2014 | Franklin et al. | |
| 2014/0256600 A1 | 9/2014 | Dillon et al. | |
| 2014/0305031 A1 | 10/2014 | Day et al. | |
| 2014/0315267 A1 | 10/2014 | Franklin et al. | |
| 2014/0336100 A1 | 11/2014 | Day et al. | |
| 2015/0073163 A1 | 3/2015 | Chua et al. | |
| 2015/0125914 A1 | 5/2015 | Franklin et al. | |

FOREIGN PATENT DOCUMENTS

| | | |
|---|---|---|
| WO | WO 2007/141257 A1 | 12/2007 |
| WO | WO 2008/060571 A2 | 5/2008 |
| WO | WO 2008/130372 A2 | 10/2008 |
| WO | WO 2008/151149 A2 | 12/2008 |
| WO | WO 2009/126843 A2 | 10/2009 |
| WO | WO 2010/019813 A2 | 2/2010 |
| WO | WO 2010/045368 A2 | 4/2010 |
| WO | WO 2010/063031 A2 | 6/2010 |
| WO | WO 2010/063032 A2 | 6/2010 |
| WO | WO 2010/120923 A1 | 10/2010 |
| WO | WO 2010/120939 A2 | 10/2010 |
| WO | WO 2011/026008 A1 | 3/2011 |
| WO | WO 2011/130573 A1 | 10/2011 |
| WO | WO 2011/130576 A1 | 10/2011 |
| WO | WO 20011/130578 A2 | 10/2011 |
| WO | WO 2011/150410 A2 | 12/2011 |
| WO | WO 2011/150411 A1 | 12/2011 |
| WO | WO 2012/061647 A2 | 5/2012 |
| WO | WO 2012/106560 A1 | 8/2012 |
| WO | WO 2012/154626 A1 | 11/2012 |
| WO | WO 2013/082186 A2 | 6/2013 |
| WO | WO 2013/158938 | 10/2013 |
| WO | WO 2015/051319 A2 | 4/2015 |

OTHER PUBLICATIONS

Barnes et al., "Contribution of 5'- and 3'—untranslated regions of plastid mRNAs to the expression of Chlamydomonas reinhardtii chloroplast genes," Mol Genet Genomics, 274(6):625-636, (2005).

Bhunia et al., "Algal Biodiesel Production: Challenges and Opportunities," Bioenergy and Biofuel from Biowastes and Biomass, American Society of Civil Engineers, pp. 313-345, (2010).

Blowers et al., "Studies on Chlamydomonas chloroplast transformation: foreign DNA can be stably maintained in the chromosome," Plant Cell, 1(1):123-132, (1989).

Bordes et al., "An new recombinant protein expression system for high-throughput screening in the yeast Yarrowia lipolytica, " Journal of Microbiological Methods, 70(3):493-502, (2007).

(56) References Cited

OTHER PUBLICATIONS

Boutry et al., "Targeting of bacterial chloramphenicol acetyltransferase to mitochondria in transgenic plants," Nature, 328(6128):340-2, (1987).
Boynton et al., "Chloroplast Transformation in Chlamydomonas with High Velocity Microprojectiles," Science, 240(4858):1534-1538, (1988).
Broun et al., "Catalytic Plasticity of Fatty Acid Modification Enzymes Underlying Chemical Diversity of Plant Lipids," Science, 282:1315-1317, (1998). [Retrieved from the Internet Feb. 27, 2007: <URL: http://www.sciencemag.org>].
Chattopadhyay et al., "Effect of single amino acid mutations in the conserved GDNQ motif of L protein of Rinderpest virus on RNA synthesis in vitro and in vivo," Virus Research, 99:139-145, (2004).
Chen et al., "Recognition of prokaryotic transcription terminators by spinach chloroplast RNA polymerase," Nucleic Acids Research, 16(17):8411-8431, (1988).
Chen et al., "Highly Effective Expression of Rabbit Neutrophyl Peptide-1 Gene in Chlorella Ellipsoidea Cells," Current Genetics, 39:365-370, (2001).
Chica et al., "Semi-rational approaches to engineering enzyme activity: combining the benefits of directed evolution and rational design," Current Opinion in Biotechnology, 16:378-384, (2005).
Chow et al., "Electrotranformation of Chlorella Vulgaris," Plant Cell Reports, 18:778-780, (1999).
Cobley et al., "CpeR is an activator required for expression of the phycoerythrin operon (cpeBA) in the cyanobacterium Fremyella diplosiphon and is encoded in the phycoerythrin linker-polypeptide operon (cpeCDESTR)," Molecular Microbiology, 44(6):1517-1531, (2002).
Cobley et al., Construction of Shuttle Plasmids Which Can Be Efficiently Mobilized From *Escherichia coli* Into the Chromatically Adapting Cyanobacterium, Plasmid, 30:90-105, (1993).
Comai et al., "Chloroplast Transport of a Ribulose Biphosphate Carboxylase Small Subunit-5- Enolpyruvyl 3-Phosphoshikimate Synthase Chimeric Protein Requires Part of the Mature Small Subunit in Addition to the Transit Peptide," Journal of Biological Chemistry, 263(29):15104-15109 (1988).
Davies et al., "Expression of the Arylsulfatase Gene from the Beta 2-Tubulin Promoter in Chlamydomaonas reinhardtii," Nucleic Acids Research, 20(12):2959-2965, (1992).
Dawson et al., "Stable Transformation of Chlorella: Rescure of Nitrate Reductase-Deficient Mutants with the Nitrate Reductase Gene," Current Microbiology, 35:356-362, (1997).
Debuchy et al., "The argininosuccinate lyase gene of Chlamydomonas reinhardtii: an important tool for nuclear transformation and for correlating the genetic and molecular maps of the ARG7 locus," EMBO J., 8(10):2803-2809, (1989).
Deshnium et al., "Transformation of Synechococcus with a gene for choline oxidase enhances tolerance to salt stress," Plant Mol Biol, 29(5):897-907, (1995).
Devos et al., "Practical Limits of Function Prediction," Proteins: Structure, Function, and Genetics, 41:98-107, (2000).
Dunahay et al., "Genetic Engineering of Microalgae for Fuel Production," Applied Biochemistry and Biotechnology, 34/35:331-339 (1992).
El-Sheekh, MM., "Stable Transformation of the Intact Cells of Chlorella Kessleri with High Velocity Microprojectiles," Biologia Plantarium 42(2): 209-216, (1999).
EPO Supplementary European Search Report and European Search Opinion for application EP 12782478.7 mailed Oct. 22, 2014.
EPO Supplementary European Search Report and European Search Opinion for application EP 09829850.8 mailed May 16, 2014.
European Search Report and European Search Opinion for application EP08769988 mailed Jul. 1, 2011.
European Search Report and European Search Opinion for application EP11158642 mailed Jul. 1, 2011.
Falciatore et al., "Transformation of Nonselectable Reporter Genes in Marine Diatoms," Marine Biotechnology: 1:239-251, (1999).
Franklin et al., "Prospects for molecular farming in the green alga Chiamydomonas reinhardtii," Current Opinion in Plant Biology, 7:159-165, (2004).
Franzen et al., "Chloroplast transit peptides from the green alga Chlamydomonas reinhardtii share features with both mitochondrial and higher plant chloroplast presequences," FEBS Letters, 260(2):165-168, (1990).
Fromm et al., "Expression of Genes Transferred into Monocot and Dicot Plant Cells by Electroporation," Proc Natl Acad Sci, 82:5824-5828, (1985).
Gruber et al., "*Escherichia coli*-Anacystis nidulans plasmid shuttle vectors containing the PL promoter from bacteriophage lambda," Current Microbiology, 22(1):15-19, (1991).
Guo-Zhong et al., "The Actin Gene Promoter-driven Bar as a Dominant Selectable Marker for Nuclear Transformation of Dunaliella Salina," Acta Genetica Sinica, 32(4): 424-433, (2005).
Hall et al., "Expression of a foreign gene in Chlamydomonas reinhardtii," Gene, 124(1):75-81, (1993).
Hallmann et al., "Reporter Genes and Highly Regulated Promoters as Tools for Transformation Experiements in Volvox Carteri," Proc Natl Acad Sci U S A., 91(24)11562-11566, (1994).
Hanley-Bowdoin et al., "Chloroplast promoters," Trends in Biochemical Sciences, 12:67-70, (1987).
Hawkins et al., "Expression of Human Growth Hormone by the Eukaryotic Alga, Chlorella," Current Microbiology, 38:335-341, (1999).
Heifetz, "Genetic Engineering of the Chloroplast," Biochimie, 82:655-666, (2000).
Henikoff et al., "Amino Acid Substitution Matrices from Protein Blocks," Proc Natl Acad of Sci, 89(22):10915-10919, (1992).
Hiramatsu et al., "Expression of a chitinase gene and lysis of the host cell wall during Chlorella virus CVK2 infection," Virology, 260(2):308-315, (1999).
Hitz et al.,"Cloning of a Higher-Plant Plastid Omega-6 Fatty Acid Desaturase cDNA and its Expression in a Cyanobacterium," Plant Physiology, 105(2):635-641, (1994).
Huang et al., "Expression of Mercuric Reductase From Bacillus Megaterium MB1 in Eukaryotic *Microalga Chlorella* sp. DT: An Approach for Mercury Phytoremediation," Appl. Microbiol, Biotechnol., 72:197-205, (2006).
Iturriaga et al. "Heterologous transformation of Mucor circinelloides with the Phycomyces blakesleeanus leu1 gene," Current Genetics, 21(3):215-223, (1992).
Jakobiak et al., "The Bacterial Paromomycin Resistance Gene, aphH, as a Dominant Selectable Marker in Volvox carteri," Protist, 55: 381-393, (2004).
Jarvis et al. "Transient Expression of Firefly Luciferase in Protoplasts of the Green Alga Chlorella Ellipsoidea," Current Genet., 19: 317-322, (1991).
Jiang et al., "The actin gene promoter-driven bar as a dominant selectable marker for nuclear transformation of Dunaliefla salina," Yi Chuan Xue Bao, 32(4):424-433, (2005).
Kalscheuer et al., "Establishment of a Gene Transfer System for Rhodococcus Opacus PD630 Based on Electroporation and its Application for Recombinant Biosynthesis of Poly(3-hyroxyalkanoic acids)," Applied Microbiology and Biotechnology, 52(4):508-515, (1999).
Kang et al., "The regulation activity of Chlorella virus gene 5' upstream sequence in *Escherichia coli* and eucaryotic alage," Institute of Microbiology, Chinese Academy of Sciences, Beijing, 16(4):443-6, (2000). Abstract only.
Karlin et al., "Applications and statistics for multiple high-scoring segments in molecular sequences," Proc Natl Acad Sci, 90(12):5873-5877, (1993).
Kawasaki et al., "Characterization of Immediate Early Genes Expressed in Chlorovirus Infections," Nucleic Acids Symp Ser, 44:161-162, (2000).
Kawasaki et al., "Immediate Early Genes Expressed in Chlorovirus Infections," Virology, 318(1):214-223, (2004).
Kim et al. "Stable Integraion and Functional Expression of Flounder Growth Hormone Gene in Tranformed Microalga, Chlorella Ellipsoidea," Mar. Biotechnol. 4:63-73 (2002).

(56) References Cited

OTHER PUBLICATIONS

Kimchi-Sarfaty et al., "A 'Silent' Polymorphism in the MDR1 Gene Changes Substrate Specificity," Science, 315:525-528, (2007). [Retrieved from the Internet Nov. 1, 2007: <URL: http://www.sciencemag.org>].
Kindle, "High-Frequency Nuclear Transformation of Chlamydomonas reinhardtii," Proc Natl Acad Sci, 87(3):1228-1232, (1990).
Kisselev, "Polypeptide Release Factors in Prokaryotes and Eukaryotes: Same Function, Different Structure," Structure, 10:8-9, (2002).
Klein et al., "High-velocity microprojectiles for delivering nucleic acids into living cells," Nature, 327:70-73, (1987).
Knauf, "The application of genetic engineering to oilseed crops," Trends in Biotechnology, 5(2):40-47, (1987).
Kohler et al., "The green fluorescent protein as a marker to visualize plant mitochondria in vivo," Plant J, 11(3):613-621, (1997).
Koksharova, "Genetic Tools for Cyanobacteria," Appl Microbiol Biotechnol, 58(2):123-37, (2002).
Krebbers et al., "The maize chloroplast genes for the beta and epsilon subunits of the photosynthetic coupling factor CF1 are fused," Nucleic Acids Res, 10(16): 4985-5002, (1982).
Lapidot et al., "Stable Chloroplast Transformation of the Unicellular Red Alga Porphyridium Species," Plant Physiol, 129:7-12, (2002).
Lawford et al., "Performance Testing of Zymomonas Mobilis Metabolically Engeineered for Confermation of Glucose, Xylose, and Arabinose," Appl Biochem Biotechnol., 98-100:429-48, (2002).
Leon-Banares et al., "Transgenic microalgae as green cell-factories," Trends in Biotechnology, 22(1):45-52, (2004).
Levitan et al., "Dual targeting of the protein disulfide isomerase RB60 to the chloroplast and the endoplasmic reticulum," Proc Natl Acad Sci, 102(17):6225-6230, (2005).
Lu, "Biosynthesis and Gene Engineering of Plant Fatty Acids," Chinese Bulletin of Botany, 17(6):481-491, (2000). Abstract only.
Lumbreras et al., "Efficient Foreign Gene Expression in Chlamydomonas Reinhardtii Mediated by an Endogenous Intron," Plant Journal, 14(4):441-447, (1998).
Madzak et al., "Functional analysis of upstream regulating regions from Yarrowia lipolytica XPR2 promoter," Microbiology, 145:75-87, (1999).
Manuell et al., "Robust expression of a bioactive mammalian protein in Chlamydomonas chloroplast," Plant Biotech J, 5(3):402-412, (2007).
Maruyama et al., "Introduction of Foreign DNA Into Chlorella saccharophila by Electroporation," Biotechnology Techniques, 8:821-826, (1994).
Mayfield et al., "Expression and Assembly of a Fully Active Antibody in Algae," Proc Natl Acad Sci, 100(2):438-442, (2003).
Mayfield et al., "Stable nuclear transformation of Chlamydomonas reinhardtii by using a C. reinhardtii gene as the selectable marker," Proc. Natl. Acad. Sci. USA, Cell Biology, 87:2087-2091, (1990).
Meng et al., "Biodiesel production from oleaginous microorganisms," Renewable Energy, 34:1-5, (2009).
Mitra et al., "A Chlorella Virus Gene Promoter Functions as a Strong Promoter Both in Plants and Bacteria," Biochemical and Biophysical Research Communications, 204(1):189-194, (1994).
Mitra et al., "The Chlorella Virus Adenine Methyltransferase Gene Promoter is a Strong Promoter in Plants," Plant Molecular Biology, 26(1):85-93, (1994).
MULLET et al., "Multiple transcripts for higher plantrbcL andatpB genes and localization of the transcription initiation site of therbcL gene," Plant Molecular Biology, 4(1):39-54, (1985).
Nackley et al., "Human Catechol-O-Methyltransferase Haplotypes Modulate Protein Expression by Altering mRNA Secondary Structure," Science, 314:1930-1933, (2006).[Retrieved from the Internet Nov. 1, 2007: <URL: http://www.sciencemag.org>].
Napier et al., "Tailoring plant lipid composition: designer oilseeds come of age," Current Opinion in Plant Biology, 13:330-337, (2010).
Needleman et al., "A general method applicable to the search for similarities in the amino acid sequence of two proteins," Journal of Molecular Biology, 48(3):443-453, (1970).
Onai et al., "Natural Tranformation of the Termophillic Cyanbacterium Thermosynechococcus Elongatus BP-1: A Simple and Efficent Method for Gene Transfer," Mol Genet Genomics, 271(1):50-9, (2004).
Park et al., "Isolation and Characterization of Chlorella Virus From Fresh Water in Korea and Application in Chlorella Transformation System," Plant Pathol. J., 21(1):13-20, (2005).
PCT International Preliminary Report on Patentability (Chapter I) of May 31, 2011 for application PCT/US09/066142.
PCT International Preliminary Report on Patentability (Chapter I) of Aug. 13, 2012 for application PCT/US11/38463.
PCT International Preliminary Report on Patentability (Chapter I) of Dec. 7, 2009 for application PCT/US08/65563.
PCT International Preliminary Report on Patentability for application PCT/US2011/059224 mailed May 16, 2013.
PCT International Search Report and Written Opinion of the International Searching Authority for application PCT/US2013/037261 mailed Aug. 23, 2013.
PCT International Search Report for application PCT/US2011/038463 mailed Jan. 18, 2012.
PCT International Search Report for application PCT/US2011/059224 mailed Jun. 27, 2012.
PCT International Search Report for application PCT/US2012/023696 mailed May 23, 2012.
PCT international Search Report for application PCT/US2012/036690 mailed Aug. 30, 2012.
PCT International Search Report of Aug. 20, 2010 for application PCT/US2009/066142.
PCT International Search Report of Nov. 5, 2010 for application PCT/US2009/066141.
PCT International Search Report of Nov. 6, 2008 for application PCT/US2008/065563.
PCT Invitation to Pay Additional Fees from the International Searching Authority for application PCT/US2014/035476 mailed Dec. 1, 2014.
PCT Written Opinion of the International Search Authority of Aug. 20, 2010 for application PCT/US2009/066142.
PCT Written Opinion of the International Searching Authority for application PCT/US2011/038463 mailed Jan. 18, 2012.
PCT Written Opinion of the International Searching Authority for application PCT/US2012/023696 mailed May 23, 2012.
PCT Written Opinion of the International Searching Authority for application PCT/US2012/036690 mailed Aug. 30, 2012.
PCT Written Opinion of the International Searching Authority of Nov. 5, 2010 for application PCT/US2009/066141.
PCT Written Opinion of the International Searching Authority of Nov. 6, 2008 for application PCT/US2008/065563.
Pearson et al., "Improved tools for biological sequence comparison," Proc Natl Acad Sci, 85(8):2444-2448, (1988).
Radakovits et al., "Genetic Engineering of Algae for Enhanced Biofuel Production," Eukaryotic Cell, 9(04): 486-501, (2010).
Randolph-Anderson et al., "Further characterization of the respiratory deficient dum-1 mutation of Chiamydomonas reinhardtii and its use as a recipient for mitochondrial transformation," Mol Gen Genet, 236(2-3):235-244, (1993).
Roessler et al., "Genetic Engineering Approaches for Enhanced Production of Biodiesel Fuel from Microalgae," Enzymatic Conversion of Biomass for Fuels Production, Chapter 13, American Chemical Society, doi: 10.1021/bk-1994-0566.ch013, pp. 255-270, (1994).
Saha et al., "Transformation in Aspergillus ochraceus," Current Microbiology, 30(2):83-86, (1995).
Sakuradani, "Studies of Metabolic Engineering of Useful Lipid-producing Microorganisms," NISR Research Grant, (2004).
Sanford, "The biolistic process," Trends in Biotechnology, 6(12):299-302, (1988).
Sauna et al., "Silent Polymorphisms Speak: How They Affect Pharmacogenomics and the Treatment of Cancer," Cancer Res, 67(20):9609-9612 , (2007).

(56) References Cited

OTHER PUBLICATIONS

Schreier et al., "The use of nuclear-encoded sequences to direct the light-regulated synthesis and transport of a foreign protein into plant chloroplasts," EMBO J, 4(1):25-32, (1985).
Schultz et al., "A common core of secondary structure of the internal transcribed spacer 2 (ITS2) throughout the Eukaryota," RNA, 11(4):361-364, (2005).
Seffernick et al., "Melamine Deaminase and Atrazine Chlorohydrolase: 98 Percent Identical but Functionally Different," Journal of Bacteriology, 183(8):2405-2410, (2001).
Sen et al., "Developments in Directed Evolution for Improving Enzyme Functions," Appl Biochem Biotechnol, 143:212-223, (2007).
Shao et al., "Cloning and expression of metallothionein mutant α-KKs-α in Anabaena sp. PCC 7120," Marine Pollution Bulletin, 45(1012):163-167, (2002).
Skolnick et al., "From genes to protein structure and function: novel applications of computational approaches in the genomic era," Tibtech, 18: 34-39, (2000).
Smallwood et al., "Different Substitutions at Conserved Amino Acids in Domains II and III in the Sendai L RNA Polymerase Protein Inactivate Viral RNA Synthesis," Virology, 304:135-145, (2002).
Smith et al., "Comparison of Biosequences," Adv Appl Math, 2(4):482-489, (1981).
Stemmer et al., "Single-Step Assembly of a Gene and Entire Plasmid from Large Numbers of Oligodeoxyribonucleotides," Gene, 164:49-53, (1995).
Talebi et al., "Genetic manipulation, a feasible tool to enhance unique characteristic of Chlarella vulgaris as a feedstock for biodiesel production," Mol Biol Rep, 40:4421-4428, (2013).
Tan et al., "Establishment of a Micro-Particle Bombardment Transformation System for Dunaliella Salina," J Microbiol.;43(4):361-365, (2005).
Tang et al., "Insertion mutagenesis of Chlamydomonas reinhardtii by electroporation and heterologous DNA," Biochem Mol Biol Int, 36(5):1025-1035, (1995).
Tomasinsig et al., "The Cathelicidins—Structure, Function and Evolution," Current Protein and Peptide Science, 6: 23-34, (2005).
U.S. Appl. No. 12/131,766, Advisory Action mailed Oct. 13, 2011.
U.S. Appl. No. 12/131,766, Non-Final Office Action mailed Aug. 1, 2011.
U.S. Appl. No. 12/131,766, Non-Final Office Action mailed Nov. 23, 2010.
U.S. Appl. No. 12/131,766, Non-Final Office Action mailed Dec. 10, 2009.
U.S. Appl. No. 12/131,766, Requirement for Restriction/Election mailed Aug. 5, 2009.
U.S. Appl. No. 12/131,766, Requirement for Restriction/Election mailed Aug. 17, 2010.
U.S. Appl. No. 12/131,773, Advisory Action mailed Jan. 27, 2014.
U.S. Appl. No. 12/131,773, Final Office Action mailed Mar. 21, 2011.
U.S. Appl. No. 12/131,773, Final Office Action mailed Oct. 15, 2013.
U.S. Appl. No. 12/131,773, Non-Final Office Action mailed Jun. 5, 2013.
U.S. Appl. No. 12/131,773, Non-Final Office Action mailed Jun. 25, 2010.
U.S. Appl. No. 12/131,773, Non-Final Office Action mailed Dec. 15, 2009.
U.S. Appl. No. 12/131,773, Notice of Allowance and Examiner Initiated Interview Summary mailed Apr. 1, 2014.
U.S. Appl. No. 12/131,773, Requirement for Restriction/Election mailed Aug. 6, 2009.
U.S. Appl. No. 12/131,793, Final Office Action mailed Mar. 30, 2010.
U.S. Appl. No. 12/131,793, Notice of Allowance mailed Apr. 3, 2013.
U.S. Appl. No. 12/131,793, Non-Final Office Action mailed Jun. 21, 2012.
U.S. Appl. No. 12/131,793, Non-Final Office Action mailed Sep. 16, 2009.
U.S. Appl. No. 12/131,793, Non-Final Office Action mailed Nov. 13, 2012.
U.S. Appl. No. 12/131,793, Requirement for Restriction/Election mailed Aug. 6, 2009.
U.S. Appl. No. 12/131,804, Final Office Action mailed Feb. 2, 2011.
U.S. Appl. No. 12/131,804, Non-Final Office Action mailed Oct. 26, 2012.
U.S. Appl. No. 12/131,804, Non-Final Office Action mailed Mar. 3, 2010.
U.S. Appl. No. 12/131,804, Non-Final Office Action mailed Jun. 7, 2012.
U.S. Appl. No. 12/131,804, Requirement for Restriction/Election mailed Sep. 17, 2009.
U.S. Appl. No. 12/131,804, Requirement for Restriction/Election mailed Nov. 18, 2009.
U.S. Appl. No. 12/194,389, Final Office Action mailed Jan. 5, 2011.
U.S. Appl. No. 12/194,389, Non-Final Office Action mailed Feb. 4, 2010.
U.S. Appl. No. 12/194,389, Notice of Allowance mailed Jan. 15, 2014.
U.S. Appl. No. 12/194,389, Requirement for Restriction/Election mailed Oct. 5, 2010.
U.S. Appl. No. 12/194,389, Requirement for Restriction/Election mailed Nov. 2, 2009.
U.S. Appl. No. 12/628,140, Final Office Action mailed Mar. 15, 2013.
U.S. Appl. No. 12/628,140, Non-Final Office Action mailed Oct. 30, 2012.
U.S. Appl. No. 12/628,144, Final Office Action mailed Nov. 16, 2010.
U.S. Appl. No. 12/628,144, Final Office Action mailed Dec. 5, 2011.
U.S. Appl. No. 12/628,144, Final Office Action mailed Dec. 12, 2014.
U.S. Appl. No. 12/628,144, Non-Final Office Action mailed May 16, 2014.
U.S. Appl. No. 12/628,144, Non-Final Office Action mailed Jun. 7, 2011.
U.S. Appl. No. 12/628,144, Non-Final Office Action mailed Jul. 8, 2010.
U.S. Appl. No. 12/628,144, Requirement for Restriction/Election and Examiner Initiated Interview Summary mailed Oct. 07, 2014.
U.S. Application No. 12/628,147, Examiner Interview Summary Record mailed Mar. 3, 2011.
U.S. Appl. No. 12/628,147, Final Office Action mailed Jul. 12, 2012.
U.S. Appl. No. 12/628,147, Final Office Action mailed Oct. 1, 2010.
U.S. Appl. No. 12/628,147, Non-Final Office Action mailed May 25, 2010.
U.S. Appl. No. 12/628,147, Non-Final Office Action mailed Oct. 25, 2011.
U.S. Appl. No. 12/628,149, Non-Final Office Action mailed Jun. 25, 2010.
U.S. Appl. No. 12/628,149, Non-Final Office Action mailed Sep. 16, 2010.
U.S. Appl. No. 12/628,149, Notice of Allowance mailed Dec. 15, 2010.
U.S. Appl. No. 12/628,150, Non-Final Office Action mailed Apr. 29, 2010.
U.S. Appl. No. 12/628,150, Non-Final Office Action mailed Oct. 13, 2010.
U.S. Appl. No. 12/628,150, Notice of Allowance mailed Mar. 21, 2011.
U.S. Appl. No. 12/772,163, Non-Final Office Action mailed May 25, 2012.
U.S. Appl. No. 12/772,163, Non-Final Office Action mailed Dec. 12, 2012.
U.S. Appl. No. 12/772,163, Notice of Allowance mailed May 28, 2013.
U.S. Appl. No. 12/772,163, Requirement for Restriction/Election mailed Jun. 24, 2011.
U.S. Appl. No. 12/772,164, Final Office Action mailed May 24, 2012.
U.S. Appl. No. 12/772,164, Non-Final Office Action mailed Oct. 12, 2011.
U.S. Appl. No. 12/772,164, Requirement for Restriction/Election mailed Jul. 20, 2011.
U.S. Appl. No. 12/772,170, Final Office Action mailed Feb. 21, 2012.
U.S. Appl. No. 12/772,170, Non-Final Office Action mailed Sep. 13, 2011.

(56) References Cited

OTHER PUBLICATIONS

U.S. Appl. No. 12/772,170, Non-Final Office Action mailed Dec. 17, 2013.
U.S. Appl. No. 12/772,170, Notice of Allowance and Examiner-Initiated Interview Summary mailed Jul. 11, 2014.
U.S. Appl. No. 12/772,170, Requirement for Restriction/Election mailed Jul. 13, 2011.
U.S. Appl. No. 12/772,173, Final Office Action mailed May 7, 2012.
U.S. Appl. No. 12/772,173, Non-Final Office Action mailed Dec. 16, 2011.
U.S. Appl. No. 12/772,173, Notice of Allowance mailed Mar. 29, 2013.
U.S. Appl. No. 12/772,173, Requirement for Restriction/Election mailed Oct. 26, 2011.
U.S. Appl. No. 12/772,174, Non-Final Office Action mailed Nov. 29, 2011.
U.S. Appl. No. 12/772,174, Requirement for Restriction/Election mailed Aug. 10, 2011.
U.S. Appl. No. 12/960,388, Notice of Allowance mailed May 28, 2013.
U.S. Appl. No. 12/960,388, Requirement for Restriction/Election mailed Apr. 1, 2013.
U.S. Appl. No. 12/981,409, Non-Final Office Action mailed Jan. 6, 2012.
U.S. Appl. No. 12/981,409, Notice of Allowance mailed May 29, 2012.
U.S. Appl. No. 12/981,409, Requirement for Restriction/Election mailed Apr. 19, 2012.
U.S. Appl. No. 12/981,409, Requirement for Restriction/Election mailed Oct. 28, 2011.
U.S. Appl. No. 13/029,061, Requirement for Restriction/Election mailed Nov. 29, 2011.
U.S. Appl. No. 13/073,757, Non-Final Office Action mailed Aug. 15, 2011.
U.S. Appl. No. 13/073,757, Non-Final Office Action mailed Dec. 29, 2011.
U.S. Appl. No. 13/073,757, Notice of Allowance mailed Apr. 17, 2012.
U.S. Appl. No. 13/118,365, Final Office Action mailed Jul. 22, 2013.
U.S. Appl. No. 13/118,365, Non-Final Office Action mailed Feb. 11, 2013.
U.S. Appl. No. 13/118,365, Requirement for Restriction/Election mailed Oct. 11, 2012.
U.S. Appl. No. 13/273,179, Non-Final Office Action mailed Jan. 28, 2014.
U.S. Appl. No. 13/273,179, Notice of Allowance mailed Jul. 11, 2014.
U.S. Appl. No. 13/273,179, Requirement for Restriction/Election mailed Nov. 14, 2013.
U.S. Appl. No. 13/288,815, Final Office Action mailed Oct. 22, 2014.
U.S. Appl. No. 13/288,815, Non-Final Office Action mailed Jun. 18, 2014.
U.S. Appl. No. 13/288,815, Requirement for Restriction/Election mailed Jan. 30, 2014.
U.S. Appl. No. 13/365,253, Requirement for Restriction/Election mailed Dec. 16, 2014.
U.S. Appl. No. 13/406,417, Non-Final Office Action mailed Nov. 5, 2012.
U.S. Appl. No. 13/406,417, Requirement for Restriction/Election mailed Apr. 30, 2012.
U.S. Appl. No. 13/464,948, Final Office Action mailed Feb. 13, 2014.
U.S. App. No. 13/464,948, Non-Final Office Action mailed Oct. 9, 2013.
U.S. Appl. No. 13/464,948, Notice of Allowance mailed May 25, 2014.
U.S. Appl. No. 13/464,948, Requirement for Restriction/Election mailed Aug. 21, 2013.
U.S. Appl. No. 13/479,194, Non-Final Office Action mailed Mar. 26, 2014.
U.S. Appl. No. 13/479,200, Non-Final Office Action mailed Apr. 10, 2013.
U.S. Appl. No. 13/479,200, Non-Final Office Action mailed Sep. 9, 2013.
U.S. Appl. No. 13/479,200, Notice of Allowance mailed Nov. 25, 2013.
U.S. Appl. No. 13/479,200, Requirement for Restriction/Election mailed Jan. 15, 2013.
U.S. Appl. No. 13/527,480, Final Office Action mailed Jan. 16, 2014.
U.S. Appl. No. 13/527,480, Non-Final Office Action mailed Jun. 26, 2013.
U.S. Appl. No. 13/527,480, Requirement for Restriction/Election mailed May 3, 2013.
U.S. Appl. No. 13/543,666, Non-Final Office Action mailed Sep. 5, 2013.
U.S. Appl. No. 13/543,666, Notice of Allowance mailed Feb. 10, 2014.
U.S. Appl. No. 13/543,666, Requirement for Restriction/Election mailed Jan. 3, 2013.
U.S. Appl. No. 13/547,457, Final Office Action mailed Mar. 20, 2014.
U.S. Appl. No. 13/547,457, Non-Final Office Action mailed Jul. 8, 2013.
U.S. Appl. No. 13/547,457, Notice of Allowance and Examiner-Initiated Interview Summary mailed May 29, 2014.
U.S. Appl. No. 13/55,8252, Notice of Allowance mailed Oct. 23, 2013.
U.S. Appl. No. 13/550,412, Non-Final Office Action mailed Oct. 29, 2012.
U.S. Appl. No. 13/550,412, Notice of Allowance mailed Feb. 21, 2013.
U.S. Appl. No. 13/555,009, Requirement for Restriction/Election mailed Jun. 16, 2014.
U.S. Appl. No. 13/558,252, Final Office Action mailed Jul. 9, 2013.
U.S. Appl. No. 13/558,252, Non-Final Office Action mailed Jan. 18, 2013.
U.S. Appl. No. 13/621,722, Requirement for Restriction/Election mailed Jan. 31, 2013.
U.S. Appl. No. 13/621,722, Final Office Action mailed Oct. 25, 2013.
U.S. Appl. No. 13/621,722, Non-Final Office Action mailed May 9, 2013.
U.S. Appl. No. 13/621,722, Notice of Allowance and Examiner Initiated Interview Summary mailed Jan. 10, 2014.
U.S. Appl. No. 13/628,039, Non-Final Office Action mailed Jun. 4, 2013.
U.S. Appl. No. 13/628,039, Notice of Allowance and Examiner-Initiated Interview Summary mailed Feb. 20, 2014.
U.S. Appl. No. 13/628,039, Requirement for Restriction/Election mailed Mar. 7, 2013.
U.S. Appl. No. 13/630,757, Non-Final Office Action mailed Oct. 27, 2014.
U.S. Appl. No. 13/630,757, Requirement for Restriction/Election mailed Jun. 12, 2014.
U.S. Appl. No. 13/650,018, Non-Final Office Action mailed Dec. 23, 2013.
U.S. Appl. No. 13/650,018, Requirement for Restriction/Election mailed Aug. 22, 2013.
U.S. Appl. No. 13/650,024, Non-Final Office Action mailed Jul. 2, 2013.
U.S. Appl. No. 13/650,024, Notice of Allowance mailed Oct. 17, 2013.
U.S. Appl. No. 13/852,116, Final Office Action mailed Aug. 18, 2014.
U.S. Appl. No. 13/852,116, Non-Final Office Action mailed Mar. 26, 2014.
U.S. Appl. No. 13/852,116, Notice of Allowance mailed Nov. 7, 2014.
U.S. Application No. 13/865,974, Non-Final Office Action mailed May 2, 2014.
U.S. Appl. No. 13/865,974, Notice of Allowance mailed Oct. 22, 2014.
U.S. Appl. No. 13/865,974, Requirement for Restriction/Election mailed Jan. 29, 2014.
U.S. Appl. No. 13/941,346, Non-Final Action mailed Jan. 21, 2014.

(56) References Cited

OTHER PUBLICATIONS

U.S. Appl. No. 13/941,346, Final Office Action mailed Jun. 26, 2014.
U.S. Appl. No. 13/941,346, Non-Final Office Action mailed Nov. 3, 2014.
U.S. Appl. No. 13/941,353, Requirement for Restriction/Election mailed Jan. 16, 2014.
U.S. Appl. No. 13/941,357, Final Office Action mailed Nov. 6, 2014.
U.S. Appl. No. 13/941,357, Non-Final Office Action mailed Jun. 3, 2014.
U.S. Appl. No. 13/941,357, Requirement for Restriction/Election mailed Jan. 7, 2014.
U.S. Appl. No. 12/628,147, Notice of Allowance and Examiner Initiated Interview Summary mailed Aug. 7, 2012.
U.S. Appl. No. 12/772,173, Notice of Allowance mailed Jul. 10, 2013.
U.S. Appl. No. 13/650,018, Notice of Allowance mailed Aug. 14, 2014.
Van Etten et al., "Giant viruses infecting algae," Annu Rev Microbial, 53:447-494, (1999).
Vazquez-Bermudez et al., "Uptake of 2-Oxoglutarate in Synechococcus Strains Transformed with the *Escherichia coli* kgtP Gene," Journal of Bacteriology, 182(1)211-215, (2000).
Walker et al., "Characterization of the Dunaliella tertiolecta RbcS Genes and Their Promoter Activity in Chlamydomonas reinhardtii," Plant Cell Rep, 23(10-11):727-735, (2005).
Wang et al., "Rapid isolation and functional analysis of promoter sequences of the nitrate reductase gene from Chlorella ellipsoidea," J. Appl. Phycol., 16:11-16, (2004).
Whisstock et al., "Prediction of protein function from protein sequence and structure," Quarterly Reviews of Biophysics, 36(3):307-340, (2003).
Wirth et al., "Transforamtion of Various Species of Gram-Negitive Bacteria Belonging to 11 Difference Genera by Electroporation," Mol Gen Genet.; 216(1):175-177, (1989).
Wishart et al., "A Single Mutation Converts a Novel Phosphotyrosine Binding Domain into a Dual-specificity Phosphatase," The Journal of Biological Chemistry, 270(45)26782-26785, (1995).
Witkowski et al., "Conversion of β-Ketoacyl Synthase to a Malonyl Decarboxylase by Replacement of the Active-Site Cysteine with Glutamine," Biochemistry, 38:11643-11650, (1999).
Wolk et al., "Construction of Shuttle Vectors Capable of Conjugative Transfer From *Escherichia Coli*to Nitrogen-Fixing Filamentous Cyanobacteria," Proc Nati Acad Sci U S A., 81(5)1561-1565, (1984).
Wong et al., "Arabidopsis thaliana small subunit leader and transit peptide enhance the expression of Bacillus thuringiensis proteins in transgenic plants," Plant Mol Biol, 20(1):81-93, (1992).
Yamada et al., "Alternative expression of a chitosanase gene produces two different proteins in cells infected with Chlorella virus CVK2," Virology, 230(2):361-368, (1997).
Yu et al., "Modifications of the metabolic pathwasy of lipid and triacyglycerol production in microalgae," Microbial Cell Factories, 10:91, (2011). [Retrieved from the Internet Jul. 24, 2012: <URL: http://www.microbialcellfactories.com/content/10/1/91>].
PCT International Search Report and Written Opinion of the International Searching Authority for application PCT/US2014/035476 mailed Feb. 18, 2015.
PCT International Search Report and Written Opinion of the International Searching Authority for application PCT/US2014/059161 mailed Jun. 1, 2015.
PCT Invitation to Pay Additional Fees for application PCT/US2014/059161 mailed Mar. 9, 2015.
U.S. Appl. No. 13/288,815, Notice of Allowance mailed Feb. 26, 2015.
U.S. Appl. No. 13/555,009, Notice of Allowance mailed Jan. 9, 2015.
U.S. Appl. No. 13/630,757, Non-Final Office Action mailed Apr. 23, 2015.
U.S. Appl. No. 13/650,018, Notice of Allowance mailed Apr. 1, 2015.
U.S. Appl. No. 13/650,018, Notice of Allowance mailed Apr. 10, 2015.
U.S. Appl. No. 13/804,185, Non-Final Office Action mailed Jun. 1, 2015.
U.S. Appl. No. 13/804,185, Requirement for Restriction/Election mailed Mar. 16, 2015.
U.S. Appl. No. 13/849,330, Requirement for Restriction/Election mailed Jan. 21, 2015.
U.S. Appl. No. 13/941,342, Requirement for Restriction/Election mailed Apr. 13, 2015.
U.S. Appl. No. 13/941,346, Notice of Allowance mailed Feb. 23, 2015.
U.S. Appl. No. 13/941,357, Notice of Allowance mailed Mar. 30, 2015.
U.S. Appl. No. 14/184,288, Requirement for Restriction/Election mailed Jun. 9, 2015.
U.S. Appl. No. 14/276,943, Requirement for Restriction/Election mailed Jun. 4, 2015.
U.S. Appl. No. 14/285,354, Requirement for Restriction/Election mailed Jul. 20, 2015.

* cited by examiner

SAMPLE OIL PROFILES: LOW TO HIGH OLEIC CONTENT

| | capric-rich | lauric-rich | myristic-palmitic | high palmitic | balanced | stearic-palmitic-oleic | mixed palmitic-oleic | mixed palmitic-oleic-2 | high oleic | high-stability oleic |
|---|---|---|---|---|---|---|---|---|---|---|
| *Oil* | *RB Z* | *RBD-1* | *RBD-2* | *RBD-3* | *RBD Y* | *RBD X* | *RBD W* | *RBD-4* | *RDB-5* | *RBD-6* |
| C8:0 | 4.5 | 0.2 | 0.9 | 0.0 | 0.0 | 0.0 | 0.0 | 0.0 | 0.0 | 0.0 |
| C10:0 | 29.3 | 16.8 | 13.2 | 0.0 | 2.4 | 0.0 | 0.0 | 0.0 | 0.0 | 0.0 |
| C12:0 | 4.4 | 47.2 | 2.8 | 0.2 | 0.9 | 0.0 | 0.1 | 0.1 | 0.0 | 0.0 |
| C14:0 | 23.6 | 11.3 | 24.8 | 6.0 | 15.3 | 0.7 | 2.0 | 1.7 | 0.5 | 0.6 |
| C16:0 | 21.5 | 5.1 | 31.6 | 49.1 | 35.9 | 24.0 | 28.7 | 25.0 | 6.9 | 8.2 |
| C16:1 | 0.1 | 0.1 | 0.1 | 0.4 | 0.3 | 0.2 | 0.4 | 1.0 | 0.7 | 0.8 |
| C18:0 | 2.3 | 0.9 | 4.8 | 5.1 | 3.5 | 21.4 | 9.5 | 3.6 | 1.4 | 1.9 |
| **C18:1** | **8.5** | **12.8** | **13.9** | **28.7** | **29.6** | **43.5** | **48.9** | **59.4** | **79.5** | **85.9** |
| C18:2 | 4.6 | 4.2 | 4.8 | 8.3 | 10.3 | 7.8 | 8.0 | 7.4 | 8.9 | 0.05 |
| C18:3 | 0.3 | 0.3 | 0.2 | 0.3 | 0.2 | 0.1 | 0.2 | 0.2 | 0.2 | 0.0 |

Figure 1

| Lot | Name | Features | Benefits |
|---|---|---|---|
| RBD-6 | High Stability Oleic Rich | Very low levels of polyunsaturates < .1% combined with very high levels of mono unsaturates (oleic) >85% | Unprecedented low levels of polyunsaturates creates perhaps the most stable natural oleic-rich oil available anywhere in the world for use in industrial and food applications. Outstanding stability and low (oxidative) reactivity is ideal for use in snack foods or spray-coating applications in foods. Combination of low pour point and oxidative stability is attractive for industrial uses such as bio-based functional fluids and lubricants. Remarkable stability minimizes need for antioxidants to be added to the oil. |
| RBD-5 | High Oleic Sunflower Oil Mimetic | Low levels of polyunsaturates <10% combined with high levels of mono unsaturates (oleic) ~80% | Sugar-derived alternative to high oleic sunflower with better GHG profile (Brazilian production). Ideal oil for cooking and frying; balances stability with health benefits of polyunsaturates. The higher level of polyunsaturates (than high stability algal oil) lowers the pour point for food and industrial applications e.g. functional fluids. |
| RBD-1 | Lauric Rich Alternative to Palm Kernel Oil, Coconut oil | High levels of mid-chain length saturated fatty acids ($C_{10}$ -$C_{14}$) | Sugar-derived alternative to palm kernel oil and coconut oil with enhanced sustainability and fatty acid profiles for the oleochemical and food industries. Enhanced mid-chain fatty acid (C10 – C14) concentration will create sharper melting fat for confectionary coating application, and efficient foaming properties in soaps. Lauric-rich oil also interesting as food oil catching wave of coconut oil as lauric is neutral-to-heart-healthy; solid sat for baking and/or confectionery. |

Figure 13

| Lot | Name | Features | Benefits |
|---|---|---|---|
| RBD-3 | High Palmitic / Low Oleic | 50% palmitic and 30% oleic; similar profile to a specialty palm mid fraction used to create structure in food products | Very efficient structuring fat for food products maximizes structuring while minimizing saturated fat content. Sharp melting profile minimizes negative impact on sensory properties of food products. Replacement for specialty palm fractions in food products; enhanced sustainability profile compared to palm |
| RBD-2 | Myrisitc / Palmitic Rich | Highest level of myrisitc than any existing oil | Uniquely high concentration of myristic acid combined with capric and palmitic creates sharp melting profiles and higher solid fat content at low temperature than palm oil; enhanced sustainability profile compared to palm. Very unique solid fat content profile |
| RBD-4 | High Oleic Mid Palmitic | 60% oleic and 25% palmitic; higher oleic & lower palmitic than palm oil | High oleic content combined with mid palmitic levels produces very stable oil with solid fat content that makes it an excellent frying oil alternative: food product texture may be positively impacted by reduced liquid oil pick up. 30% saturated fats in range for shortening applications. Potentially good alternative to trans-fat-containing oils. |

Figure 14

| *test* | *RBD oil tested* | *result* | *test protocol* |
|---|---|---|---|
| OSI | RBD 502 | current max: 242 hours at 110 °C | AOCS Method Cd 12b-92 (modified) |
| pour point | RBD 437 | -19.5 °C | D97 |
| cloud point | RBD 437 | 7.5 °C | AOCS Cc 6-25 |
| flash point | RBD 437 | 245 °C | AOCS Cc 9b-55 |
| viscosity | average of RBD 437 and RBD 469 | 41.6 cSt | Viscosity (D445) at 40 °C |
| viscosity index | " | 195.5 | Viscosity Index (D445) |
| color | RBD 437 | 2.0 Red, 18.0 Yellow | Lovibond Color AOCS Cc 13j-97 (5 1/4 inch cell) |
| color (converted) | RBD 437 | 87.3, -8.7, 32.3 | Hunter Transmittance: L, a, b |
| bio-degradeability | | Ultimate Biodegradation* | OECD 301 B |

Figure 16

| ***TEST*** | ***TEST PROTOCOL*** | ***HIGH STABILITY ALGAL OIL*** | ***HIGH OLEIC ALGAL OIL*** | ***COMMENTS ON HIGH STABILITY ALGAL OIL*** |
|---|---|---|---|---|
| **OSI at 110 °C** | AOCS Method Cd 12b-92 | 41.0 – 56.6 hours (neat)<br>**242** hours (natural antioxidants) | 14.4 hours (neat)<br>-- | *HSAO outperforms natural plant-based oils with same additives* |
| **RPVOT** | ASTM D2272 | 33 min (neat)<br>**500 min** (prelim. formulation) | 30 minutes (neat)<br>-- | *Neat oil outperforms neat PAO; HSAO outperforms natural plant-based oils with same additives* |
| **4-Ball wear** | @40kg; unformulated | 0.64 mm | 0.60 mm | |
| **Copper Strip Corrosion** | ASTM D130, 24 hrs | 1A | 1A | |
| **Pour point** | ASTM D6749/D97; unformulated | -19.5 °C (neat)<br>**-29 °C** (w/ pp depressant) | -21 °C (neat)<br>-- | *Low pour point with high oxidative stability* |
| **Cloud point** | ASTM D7683/D2500 | -14 °C | -18 °C | |
| **Flash point** | D92 Cleveland Open Cup | **315 °C** | 330 °C | *Outperforms mineral oils* |
| **Viscosity** | Viscosity (D445) at 40 °C | 41.6 cSt | 38.6 cSt | |
| **Viscosity index** | Viscosity Index (D445) | 196 | 202 | |
| **VOCs** | ASTM E1868-10 | 0.37% (near-zero) | nm | *Outperforms mineral oils* |
| **Biodegradability** | OECD 301 B | **Ultimate Biodegradation:**<br>96% degradation by day 28 | Ultimate Biodegradation:<br>94% degradation by day 28 | *Outperforms mineral oils* |

Figure 19

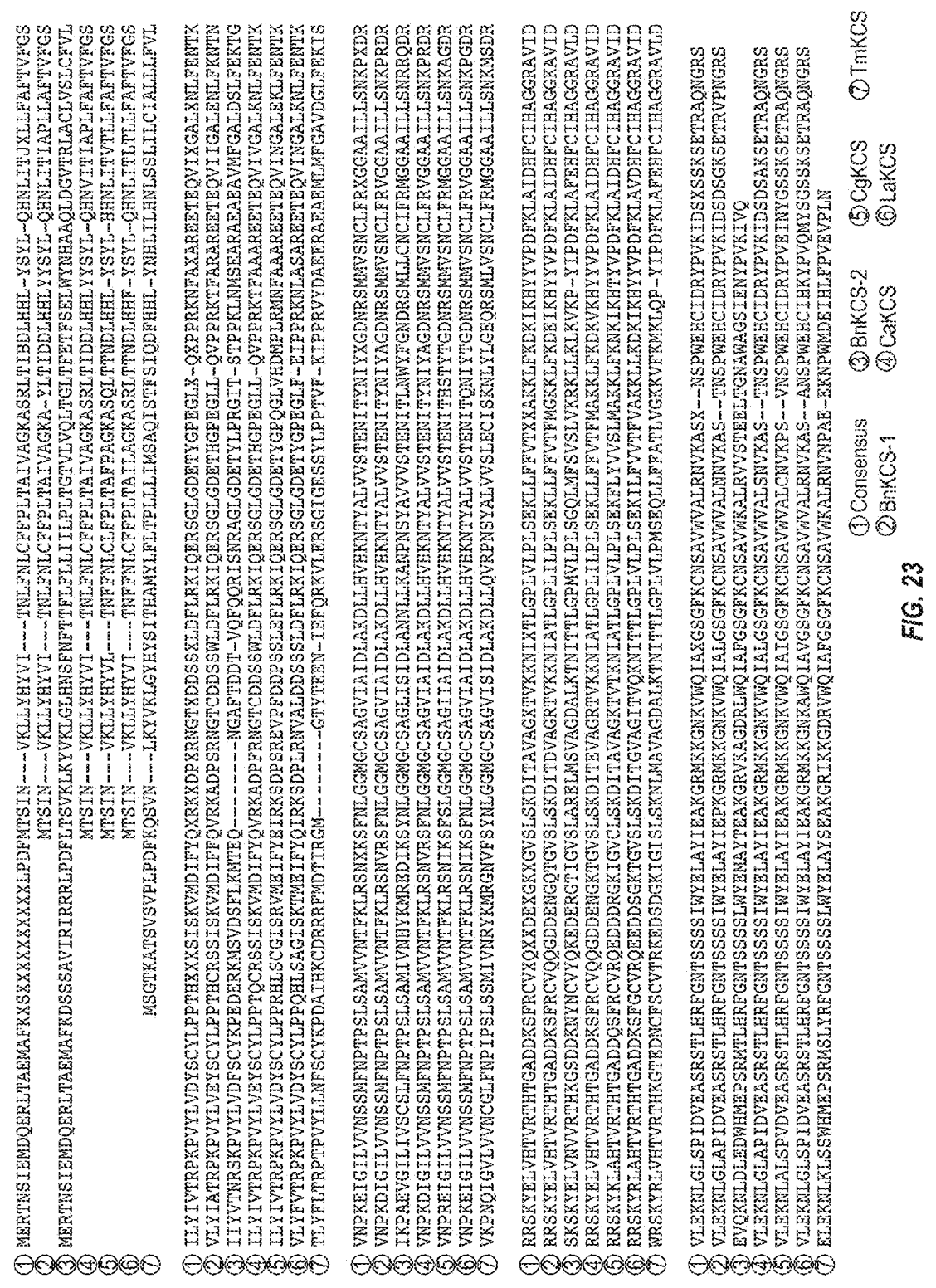

```
① MERTNSIEMDQERLTAEMAFKXSXXXXXXXXXXLPDFMTSIN---VKLLYHYVI---TNLFNLCFFPLTAIVAGKASRLTIBDLHHL-YSYL-QHNLITJXLLFAFTVFGS
②                                      MTSIN---VKLLYHYVI---TNLFNLCFFPLTAIVAGKA-YLTIDDLHHLYYSYL-QHNLITIAPLLAFTVFGS
③ MERTNSIEMDQERLTAEMAFKDSSSAVIRIRRRLPDFLTSVKLKYVKLGLHNSFNFTTFLFLLIILPLTGTVLVQLTGLTFETFSELWYNHAAQLDGVTRLACLVSLCFVL
④                                      MTSIN---VKLLYHYVI---TNLFNLCFFPLTAIVAGKASRLTIDDLHHLYYSYL-QHNVITIAPLFAFTVFGS
⑤                                      MTSIN---VKLLYHYVL---TNFFNLCLFPLTAFPAGKASQLTTNDLHHL-YSYL-HHNLITVTLLFAFTVFGS
⑥                                      MTSIN---VKLLYHYVI---TNFFNLCFFPLTAILAGKASRLTTNDLHHF-YSYL-QHNLITLTLLFAFTVFGS
⑦                    MSGTKATSVSVPLPDFKQSVN---LKYVKLGYHYSITHAMYLFLTPLLLIMSAQISTFSIQDFHHL-YNHLILHNLSSLILCIALLLFVL

① ILYIVTRPKPVYLVDYSCYLPPTHXXXSISKVMDIFYQXRKXDPXRNGTXDDSSXLDFLRKIQERSGLGDETYGPEGLX-QXPPRKNFAXAREETEQVIXGALXNLFENTK
② VLYIATRPKPVYLVEYSCYLPPTHCRSSISKVMDIFFQVRKADPSRNGTCDDSSWLDFLRKIQERSGLGDETHGPEGLL-QVPPRKTFARAREETEQVIIGALENLFKNTN
③ IIYVTNRSKPVYLVDFSCYKPEDERKMSVDSFLKMTEQ---------NGAFTDDT-VQFQQRISNRAGLGDETYLPRGIT-STPPKLNMSEARAEAEAVMFGALDSLFEKTG
④ ILYIVTRPKPVYLVEYSCYLPPTQCRSSISKVMDIFYQVRKADPFRNGTCDDSSWLDFLRKIQERSGLGDETHGPEGLL-QVPPRKTFAAAREETEQVIVGALKNLFENTK
⑤ ILYIVTRPKPVYLVDYSCYLPPRHLSCGISRVMEIFYEIRKSDPSREVPFDDPSSLEFLRKIQERSGLGDETYGPQGLVHDMPLRMNFAAAREETEQVINGALEKLFENTK
⑥ VLYFVTRPKPVYLVDYSCYLPPQHLSAGISKTMEIFYQIRKSDPLRNVALDDSSSLDFLRKIQERSGLGDETYGPEGLF-EIPPRKNLASAREETEQVINGALKNLFENTK
⑦ TLYFLTRPTPVYLLNFSCYKPDAIHKCDRRRFMDTIRGM---------GTYTEEN-IEFQRKVLERSGIGESSYLPPTVF-KIPPRVYDAEERAEAEMLMFGAVDGLFEKIS

① VNPKEIGILVVNSSMFNPTPSLSAMVVNTFKLRSNXKSFNLGGMGCSAGVIAIDLAKDLLHVHKNTYALVVSTENITYNIYXGDNRSMMVSNCLFRXGGAAILLSNKPXDR
② VNPKDIGILVVNSSMFNPTPSLSAMVVNTFKLRSNVRSFNLGGMGCSAGVIAIDLAKDLLHVHKNTYALVVSTENITYNIYAGDNRSMMVSNCLFRVGGAAILLSNKPRDR
③ IKPAEVGILIVSCSLFNPTPSLSAMIVNHYKMREDIKSYNLGGMGCSAGLISIDLANNLLKANPNSYAVVVSTENITLNWYFGNDRSMLLCNCIFRMGGAAILLSNRRQDR
④ VNPKDIGILVVNSSMFNPTPSLSAMVVNTFKLRSNVRSFNLGGMGCSAGVIAIDLAKDLLHVHKNTYALVVSTENITYNIYAGDNRSMMVSNCLFRVGGAAILLSNKPRDR
⑤ VNPREIGILVVNSSMFNPTPSLSAMVVNTFKLRSNIKSFSLGGMGCSAGIIAIDLAKDLLHVHKNTYALVVSTENITHSTYTGDNRSMMVSNCLFRMGGAAILLSNKAGDR
⑥ VNPKEIGILVVNSSMFNPTPSLSAMVVNTFKLRSNIKSFNLGGMGCSAGVIAIDLAKDLLHVHKNTYALVVSTENITQNIYTGDNRSMMVSNCLFRVGGAAILLSNKPGDR
⑦ VKPNQIGVLVVNCGLFNPIPSLSSMIVNRYKMRGNVFSYNLGGMGCSAGVISIDLAKDLLQVRPNSYALVVSLECISKNLYLGEQRSMLVSNCLFRMGGAAILLSNKMSDR

① RRSKYELVHTVRTHTGADDKSFRCVXQXXDEXGKXGVSLSKDITAVAGXTVKKNIXTLGPLVLPLSEKLLFFVTXXAKKLFKDKIKHYYVPDFKLAIDHFCIHAGGRAVID
② RRSKYELVHTVRTHTGADDKSFRCVQQGDDENGQTGVSLSKDITDVAGRTVKKNIATLGPLILPLSEKLLFFVTFMGKKLFKDEIKHYYVPDFKLAIDHFCIHAGGKAVID
③ SKSKYELVNVVRTHKGSDDKNYNCVYQKEDERGTIGVSLARELMSVAGDALKTNITTLGPMVLPLSGQLMFSVSLVKRKLLKLKVKP-YIPDFKLAFEHFCIHAGGRAVLD
④ RRSKYELVHTVRTHTGADDKSFRCVQQGDDENGKTGVSLSKDITEVAGRTVKKNIATLGPLILPLSEKLLFFVTFMAKKLFKDKVKHYYVPDFKLAIDHFCIHAGGRAVID
⑤ RRSKYKLAHTVRTHTGADDQSFRCVRQEDDDRGKIGVCLSKDITAVAGKTVTKNIATLGPLVLPLSEKFLYVVSLMAKKLFKNKIKHTYVPDFKLAIDHFCIHAGGRAVID
⑥ RRSKYRLAHTVRTHTGADDKSFGCVRQEEDDSGKTGVSLSKDITGVAGITVQKNITTLGPLVLPLSEKILFVVTFVAKKLLKDKIKHYYVPDFKLAVDHFCIHAGGRAVID
⑦ WRSKYRLVHTVRTHKGTEDNCFSCVTRKEDSDGKIGISLSKNLMAVAGDALKTNITTLGPLVLPMSEQLLFFATLVGKKVFKMKLQP-YIPDFKLAFEHFCIHAGGRAVLD

① VLEKNLGLSPIDVEASRSTLHRFGNTSSSSIWYELAYIEAKGRMKKGNKVWQIAXGSGFKCNSAVWVALRNVKASX--NSPWEHCIDRYPVKIDSXSSKSETRAQNGRS
② VLEKNLGLAPIDVEASRSTLHRFGNTSSSSIWYELAYIEPKGRMKKGNKVWQIALGSGFKCNSAVWVALNNVKAS--TNSPWEHCIDRYPVKIDSDSGKSETRVPNGRS
③ EVQKNLDLEDWHMEPSRMTLHRFGNTSSSSLWYEMAYTEAKGRVKAGDRLWQIAFGSGFKCNSAVWKALRVVSTEELTGNAWAGSIENYPVKIVQ
④ VLEKNLGLAPIDVEASRSTLHRFGNTSSSSIWYELAYIEAKGRMKKGNKVWQIALGSGFKCNSAVWVALSNVKAS--TNSPWEHCIDRYPVKIDSDSAKSETRAQNGRS
⑤ VLEKNLALSPVDVEASRSTLHRFGNTSSSSIWYELAYIEAKGRMKKGNKVWQIAIGSGFKCNSAVWVALCNVKPS--VNSPWEHCIDRYPVEINYGSSKSETRAQNGRS
⑥ VLEKNLGLSPIDVEASRSTLHRFGNTSSSSIWYELAYIEAKGRMKKGNKAWQIAVGSGFKCNSAVWVALRNVKAS--ANSPWEHCIHKYPVQMYSGSSKSETRAQNGRS
⑦ ELEKNLKLSSWHMEPSRMSLYRFGNTSSSSLWYELAYSEAKGRIKKGDRVWQIAFGSGFKCNSAVWKALRNVNPAE-EKNPWMDEIHLFPVEVPLN
```

① Consensus ② BnKCS-1 ③ BnKCS-2 ④ CaKCS ⑤ CgKCS ⑥ LaKCS ⑦ TmKCS

*FIG. 23*

TAILORED OILS

CROSS REFERENCE TO RELATED APPLICATIONS

This application is a continuation of U.S. application Ser. No. 13/941,353, filed Jul. 12, 2013, which is a continuation of U.S. application Ser. No. 13/865,974, filed Apr. 18, 2013, which claims the benefit under 35 USC 119(e) of U.S. Provisional Patent Application No. 61/635,285, filed Apr. 18, 2012, U.S. Provisional Patent Application No. 61/639,838, filed Apr. 27, 2012, U.S. Provisional Patent Application No. 61/655,469, filed Jun. 4, 2012, U.S. Provisional Patent Application No. 61/672,196, filed Jul. 16, 2012, U.S. Provisional Patent Application No. 61/679,026, filed Aug. 2, 2012, U.S. Provisional Patent Application No. 61/715,998, filed Oct. 19, 2012, U.S. Provisional Patent Application No. 61/769,678, filed Feb. 26, 2013, U.S. Provisional Patent Application No. 61/778,963, filed Mar. 13, 2013, and U.S. Provisional Patent Application No. 61/809,213, filed Apr. 5, 2013, all of which are incorporated by reference in relevant part, with the proviso that the definitions of terms herein shall be the complete and controlling definitions.

REFERENCE TO A SEQUENCE LISTING

This application includes an electronic sequence listing in a file named “451132-Sequence.txt”, created on Sep. 1, 2014 and containing 357,397 bytes, which is hereby incorporated by reference in its entirety for all purposes.

FIELD OF THE INVENTION

Embodiments of the present invention relate to oils/fats, fuels, foods, and oleochemicals and their production from cultures of genetically engineered cells. Specific embodiments relate to oils with a high content of triglycerides bearing fatty acyl groups upon the glycerol backbone in particular regiospecific patterns, highly stable oils, oils with high levels of oleic or mid-chain fatty acids, and products produced from such oils.

BACKGROUND OF THE INVENTION

PCT Publications WO2008/151149, WO2010/06032, WO2011/150410, WO2011/150411, WO2012/061647, and WO2012/106560 disclose oils and methods for producing those oils in microbes, including microalgae. These publications also describe the use of such oils to make oleochemicals and fuels.

Tempering is a process of converting a fat into a desired polymorphic form by manipulation of the temperature of the fat or fat-containing substance, commonly used in chocolate making.

Certain enzymes of the fatty acyl-CoA elongation pathway function to extend the length of fatty acyl-CoA molecules. Elongase-complex enzymes extend fatty acyl-CoA molecules in 2 carbon additions, for example myristoyl-CoA to palmitoyl-CoA, stearoyl-CoA to arachidyl-CoA, or oleyl-CoA to eicosanoyl-CoA, eicosanoyl-CoA to erucyl-CoA. In addition, elongase enzymes also extend acyl chain length in 2 carbon increments. KCS enzymes condense acyl-CoA molecules with two carbons from malonyl-CoA to form beta-ketoacyl-CoA. KCS and elongases may show specificity for condensing acyl substrates of particular carbon length, modification (such as hydroxylation), or degree of saturation. For example, the jojoba (*Simmondsia chinensis*) beta-ketoacyl- CoA synthase has been demonstrated to prefer monounsaturated and saturated C18- and C20-CoA substrates to elevate production of erucic acid in transgenic plants (Lassner et al., *Plant Cell,* 1996, Vol 8(2), pp 281-292), whereas specific elongase enzymes of *Trypanosoma brucei* show preference for elongating short and midchain saturated CoA substrates (Lee et al., *Cell,* 2006, Vol 126(4), pp 691-9).

The type II fatty acid biosynthetic pathway employs a series of reactions catalyzed by soluble proteins with intermediates shuttled between enzymes as thioesters of acyl carrier protein (ACP). By contrast, the type I fatty acid biosynthetic pathway uses a single, large multifunctional polypeptide.

The oleaginous, non-photosynthetic alga, *Protetheca moriformis*, stores copious amounts of triacylglyceride oil under conditions when the nutritional carbon supply is in excess, but cell division is inhibited due to limitation of other essential nutrients. Bulk biosynthesis of fatty acids with carbon chain lengths up to C18 occurs in the plastids; fatty acids are then exported to the endoplasmic reticulum where (if it occurs) elongation past C18 and incorporation into triacylglycerides (TAGs) is believed to occur. Lipids are stored in large cytoplasmic organelles called lipid bodies until environmental conditions change to favor growth, whereupon they are mobilized to provide energy and carbon molecules for anabolic metabolism.

SUMMARY OF THE INVENTION

In one aspect, the present invention provides an oleaginous microalgal cell, optionally comprising 23S rRNA having at least 65% nucleotide sequence identity to SEQ ID NO: 76, optionally obligately heterotrophic, and optionally comprising an exogenous sucrose invertase gene so that the cell can grow on sucrose as a sole carbon source, wherein the cell comprises an exogenous gene encoding an active LPAAT enzyme, and the cell produces an oil comprising triglycerides, wherein the oil is, by virtue of the LPAAT activity: (a) enriched in triglycerides with midchain fatty acids; or (b) enriched in triglycerides of the saturated-unsaturated-saturated type.

In some cases, the triglycerides of the oil comprise 40, 50, 60, 70, or 80% or more of C8:0, C10:0, C12:0, C14:0, or C16:0 fatty acids. In some cases, the cell further comprises an exogenous gene encoding an active FATB acyl-ACP thioesterase. In some cases, the triglycerides of the oil are enriched in midchain fatty acids by greater than 70% as a result of the expression of the exogenous LPAAT and acyl-ACP thioesterase. In some cases, the cell further comprises recombinant nucleic acids operable to encode an exogenous KAS I or KAS IV enzyme to reduce the activity of an endogenous KAS I enzyme. In some cases, the cell further comprises nucleic acids operable to reduce the expression of a delta 12 fatty acid desaturase, optionally via a regulatable promoter, so as to produce an oil with linoleic and linolenic acids totaling 5 area percent or less by FAME GC/FID. In some cases, the oil is enriched in triglycerides of the saturated-unsaturated-saturated type. In some cases, the oil is enriched in SOS, POS, and/or POP. In some cases, the oil comprises triglycerides comprising at least 50% SOS, and optionally less than 10% SSS.

In some cases, the cell further comprises a knockout or knockdown of a stearoyl-ACP desaturase gene, FatA gene, or both. In some cases, the cell further comprises recombinant nucleic acids operable to increase beta-ketoacyl CoA synthase activity. In some cases, the nucleic acids operable to increase beta-ketocyl synthase activity comprise an exogenous gene encoding a beta-ketoacyl CoA synthase.

In some cases, the ratio of stearate to oleate in oil is 3:1±20%. In some cases, POP, SOS, and POS in the oil comprise at least 30% in sum. In some cases, the oil comprises at least 30% POS. In some cases, the oil comprises POP at 16%±20%, POS at 38%±20%, and SOS at 23%±20%. In some cases, the fatty acid profile of the oil comprises 1 to 4% arachidic acid.

In some cases, the cell further comprises nucleic acids operable to reduce the expression of a delta 12 fatty acid desaturase, optionally via a regulatable promoter, so as to produce an oil with linoleic and linolenic acids totaling 5 area percent or less. In some cases, the oil has greater than 65% SOS, less than 45% unsaturated fatty acid, less than 5% polyunsaturated fatty acids, less than 1% lauric acid, and less than 2% trans fatty acids.

In some cases, the LPAAT has the amino acid sequence of SEQ ID NO: 78 or SEQ ID NO: 79 or a sequence having at least 95% identity to SEQ ID NO:78 or SEQ ID NO: 79.

In another aspect, the present invention provides a method for producing an oil comprising providing or cultivating a cell as discussed above, and extracting the oil, wherein the cell is optionally cultivated heterotrophically.

In another aspect, the present invention provides an oil comprising triglycerides produced by the method discussed above. In some cases, the oil comprises one or more of: at least 10% ergosterol; ergosterol and b-sitosterol, wherein the ratio of ergosterol to b-sitosterol is greater than 25:1; ergosterol and brassicasterol; ergosterol, brassicasterol, and poriferasterol, and the oil is optionally free from one or more of β-sitosterol, campesterol, and stigmasterol.

In some cases, the oil forms β polymorph crystals. In some cases, the crystals have a 2 L lamellae structure. In some cases, the crystals have a 3 L lamellae structure.

In some cases, the oil forms β' polymorph crystals. In some cases, the crystals have a 2 L lamellae structure. In some cases, the crystals have a 3 L lamellae structure.

In some cases, wherein the triglycerides of the oil have a fatty acid profile characterized in that the sum of the percentage of stearate and palmitate is equal to the percentage of oleate multiplied by 2.0+/−40%. In some cases, the oil has greater than 65% SOS triglycerides, less than 45% unsaturated fatty acid, less than 5% unsaturated fatty acids, less than 1% lauric acid, and less than 2% trans fatty acid. In some cases, the sum of the percent stearate and palmitate in the fatty acid profile of the oil is twice the percentage of oleate, ±20%. In some cases, the sn-2 profile of the oil has at least 40% oleate. In some cases, the oil is at least 40, 50, 60, 70, 80, or 90% SOS.

In some cases, the oil is a roll-in shortening having a melting temperature of between 30° C. and 40° C. In some cases, the oil comprises β' polymorphic crystals. In some cases, the oil has a solid fat content of less than 15% at 35° C. In some cases, the oil comprises 15 to 20% C8 to C14 fatty acids, 45-50% fatty acids of C16 and higher, and/or 30-25% unsaturated fatty acids.

In another aspect, the present invention provides a food, fuel or chemical product produced using the oil discussed above.

In another aspect, the present invention provides a natural oil or RBD oil produced from a natural oil, in which the oil comprises 3.5% or less saturated fatty acids, and optionally comprises greater than 50% oleic acid and/or greater than 1% palmitoleic acid. In some cases, the oil has between 0.1 and 3.5% saturated fatty acids. In some cases, the oil comprises at least 90% oleic acid. In some cases, the oil comprises at least 3% polyunsaturated fatty acids.

In another aspect, the present invention provides an oleaginous cell, optionally comprising 23S rRNA having at least 65% nucleotide sequence identity to SEQ ID NO: 76 and optionally obligately heterotrophic, wherein the cell produces an oil comprising 3.5% or less saturated fatty acids.

In some cases, the cell is a microalgal cell, optionally of the genus *Prototheca*. In some cases, the cell further comprises a FATA knockout or knockdown. In some cases, the cell comprises an exogenous gene encoding an enzyme active to desaturate palmitoyl-CoA to plamitoyl-CoA. In some cases, the exogenous gene is a PAD gene. In some cases, the exogenous gene is a SAD gene having desaturase activity toward palmitoyl-ACP. In some cases, the cell further comprises an overexpressed KAS II enzyme.

In some cases, the cell further comprises nucleic acids operable to reduce the expression of a delta 12 fatty acid desaturase, optionally via a regulatable promoter, so as to produce an oil with linoleic and linolenic acids totaling 5 area percent or less.

In another aspect, the present invention provides an oil produced by the cells discussed above, optionally refined, bleached and deodorized, wherein the oil comprises one or more of: at least 10% ergosterol; ergosterol and b-sitosterol, wherein the ratio of ergosterol to b-sitosterol is greater than 25:1; ergosterol and brassicasterol; and ergosterol, brassicasterol, and poriferasterol, and wherein the oil is optionally free from one or more of β-sitosterol, campesterol, and stigmasterol.

In another aspect, the present invention provides a method for producing an oil having 3.5% or less saturated fatty acids, wherein the method comprises providing or cultivating a cell as discussed above or herein, and extracting the oil from the cell.

In another aspect, the present invention provides a method for producing a food, wherein the method comprises incorporating an oil produced by the methods discussed above or herein into the food, wherein the finished food product has 3.5% or less saturated fat.

In another aspect, the present invention provides a recombinant oleaginous cell, optionally comprising 23S rRNA having at least 65% nucleotide sequence identity to SEQ ID NO: 76 and optionally obligately heterotrophic, wherein the cell comprises an exogenous gene encoding an active ketoacyl-CoA synthase enzyme.

In some cases, the cell produces an oil comprising greater than 20% erucic acid. In some cases, the cell produces an oil comprising greater than 60% erucic acid. In some cases, the cell comprises at least 40% oil. In some cases, the cell is of the genus *Prototheca*, and optionally of the species *Prototheca moriformis*. In some cases, the oil produced by the cell comprises one or more of: at least 10% ergosterol; ergosterol and b-sitosterol, wherein the ratio of ergosterol to b-sitosterol is greater than 25:1; ergosterol and brassicasterol; and ergosterol, brassicasterol, and poriferasterol, wherein the oil is optionally free from one or more of β-sitosterol, campesterol, and stigmasterol.

In another aspect, the present invention provides a chemical produced from the oil discussed above.

In another aspect, the present invention provides a method for producing an oil, wherein the method comprises providing or cultivating a cell as discussed above, and extracting an oil from the cell.

In another aspect, the present invention provides a recombinant oleaginous cell comprising recombinant nucleic acids operable to suppress the activity of a delta 12 fatty acid desaturase gene product so that the cell produces an oil with a triacylglycerol profile having less than 5% linoleic acid. In some cases, the cell produces an oil with a triacylglycerol profile having less than 3% linoleic acid. In some cases, the cell produces an oil with a triacylglycerol profile having less than 2% linoleic acid.

In some cases, the cell is a linoleic acid auxotroph or activity of the delta 12 fatty acid desaturase can be suppressed via environmental conditions so as to produce the oil. In some cases, the delta 12 fatty acid desaturase is regulatable via environmental conditions due to a regulatable promoter in operable linkage to the delta 12 fatty acid desaturase gene. In some cases, the regulatable promoter is regulatable by change in media pH or nitrogen levels.

In some cases, the cell further comprises recombinant nucleic acids operable to express an exogenous KAS II, LPAAT, or FATB enzyme. In some cases, the cell further comprises recombinant nucleic acids operable to knockout or knockdown the expression of a stearoyl ACP desaturase enzyme. In some cases, the cell further comprises recombinant nucleic acids operable to knockout or knockdown the expression of an endogenous FatA-encoded acyl-ACP thioesterase.

In some cases, the oil is stable at 110° C. so that the inflection point in conductance is not yet reached by 20 hours under conditions of the AOCS Cd 12b-92 Rancimat test. In some cases, the oil is stable at 110° C. so that the inflection point in conductance is not yet reached by 5 days under conditions of the AOCS Cd 12b-92 Rancimat test, when 1050 ppm of tocopherol and 500 pm of ascorbyl palmitate are added to the oil.

In another aspect, the present invention provides a method comprising: (a) providing a recombinant oleaginous cell, optionally comprising 23S rRNA having at least 65% nucleotide sequence identity to SEQ ID NO: 76, optionally obligately heterotrophic, wherein the cell comprises recombinant nucleic acids operable to modify the amount of a fatty acid made by the cell in response to a change in an environmental condition; (b) cultivating the cell under a first environmental condition that is permissive to synthesis of the fatty acid so as to allow for cell division and increase the number of cells; (c) cultivating the cell under a second environmental condition that, due to the recombinant nucleic acids, reduces the synthesis of the fatty acid and thus the amount of that fatty acid in an oil produced by the cell; and (d) extracting the oil from the cell.

In some cases, the cell comprises exogenous nucleic acids operable to reduce the activity of a delta 12 fatty acid desaturase so as to reduce the amount of linoleic acid in the oil. In some cases, the linoleic acid is depleted in the oil by at least than 50, 60, 70, 80, or 90%.

In some cases, the cell is cultivated heterotrophically. In some cases, the cell is a microalgal cell. In some cases, the cell produces at least 40, 50, 60, 70, 80, or 90% oil by dry cell weight.

In some cases, the first environmental condition is a first pH and the second environmental condition is a second pH of cultivation media.

In some cases, the oil, when extracted from the cell, is stable at 110° C. so that the inflection point in conductance is not yet reached by 20 hours under conditions of the AOCS Cd 12b-92 Rancimat test. In some cases, the oil, when extracted from the cell, is stable at 110° C. so that the inflection point in conductance is not yet reached by 5 days under conditions of the AOCS Cd 12b-92 Rancimat test, when 1050 ppm of tocopherol and 500 μm of ascorbyl palmitate are added to the oil.

In some cases, the cell comprises an exogenous gene encoding a KAS II enzyme and optionally a knockout or knockdown of a FatA gene. In some cases, the recombinant nucleic acids operable to modify the amount of a fatty acid made by the cell comprise an inhibitory RNA targeting a FAD gene, the production of the inhibitory RNA being under control of a regulatable promoter.

In some cases, the oil is characterized by a fatty acid profile with greater than 60% oleic acid and less than 3% polyunsaturates. In some cases, the oil is characterized by a fatty acid profile with greater than 70% oleic acid and less than 2% polyunsaturates. In some cases, the oil is characterized by a fatty acid profile with greater than 80% oleic acid and less than 1% polyunsaturates.

In another aspect, the present invention provides an oil produced by the method discussed above. In some cases, the oil comprises 0.01 to 2% linoleic acid and (i) 80 to 95% oleic acid or (ii) more than 40% of C8, C10, C12, C14 or C16 fatty acids. In some cases, the oil further comprises one or more of: at least 10% ergosterol; ergosterol and β-sitosterol, wherein the ratio of ergosterol to β-sitosterol is greater than 25:1; ergosterol and brassicasterol; and ergosterol, brassicasterol, and poriferasterol.

In another aspect, the present invention provies a product produced by the oil discussed above. In some cases, the product is a food, fuel or chemical. In some cases, the product is a frying oil, lubricating oil, cleaning solvent, surfactant, foam or lubricant. In some cases, the product is an oleic acid dimer.

In another aspect, the present invention provides a construct, vector, chromosome or host cell comprising nucleic acids encoding a protein having at least 90% identity to SEQ ID NOs: 77 to 79. In some cases, the nucleic acids encode a protein having at least 95% identity to SEQ ID NOs: 77 to 79. In some cases, the nucleic acids encode a protein having at least 98% identity to SEQ ID NOs: 77 to 79. In some cases, the nucleic acids have at least 80, 90, 95, 96, 97, 98, or 99% sequence identity to SEQ ID NOs:80-85 or equivalent sequences by virtue of the degeneracy of the genetic code.

These and other aspects and embodiments of the invention are described and/or exemplified in the accompanying drawings, a brief description of which immediately follows, the detailed description of the invention, and in the examples. Any or all of the features discussed above and throughout the application can be combined in various embodiments of the present invention.

BRIEF DESCRIPTION OF THE DRAWINGS

FIGS. 1-14 show fatty acid profiles and melting curves of refined, bleached and deodorized oils from genetically engineered *Prototheca moriformis* strains, as discussed in Example 4;

FIG. 16 shows various properties of natural oils with very low levels of polyunsaturated fatty acids in accordance with an embodiment of the invention.

FIG. 19 shows various properties of high-oleic and high-stability high-oleic algal oils.

FIG. 23 shows the pairwise alignment of heterologous FAE proteins expressed in STRAIN Z (SEQ ID NOs:111-117, respectively, in order of appearance).

DETAILED DESCRIPTION OF THE INVENTION

I. Definitions

Figure 2:
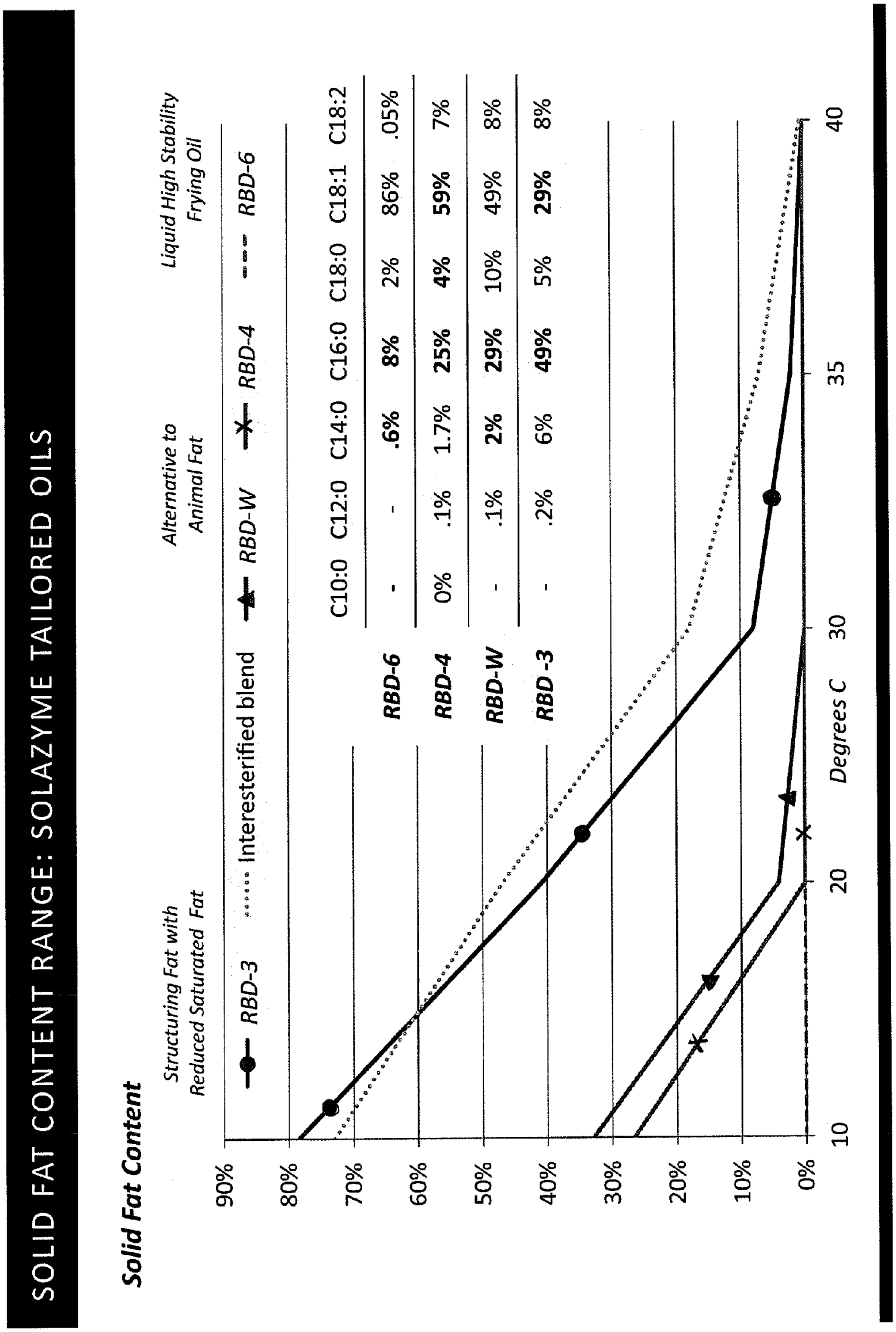
Figure 3:
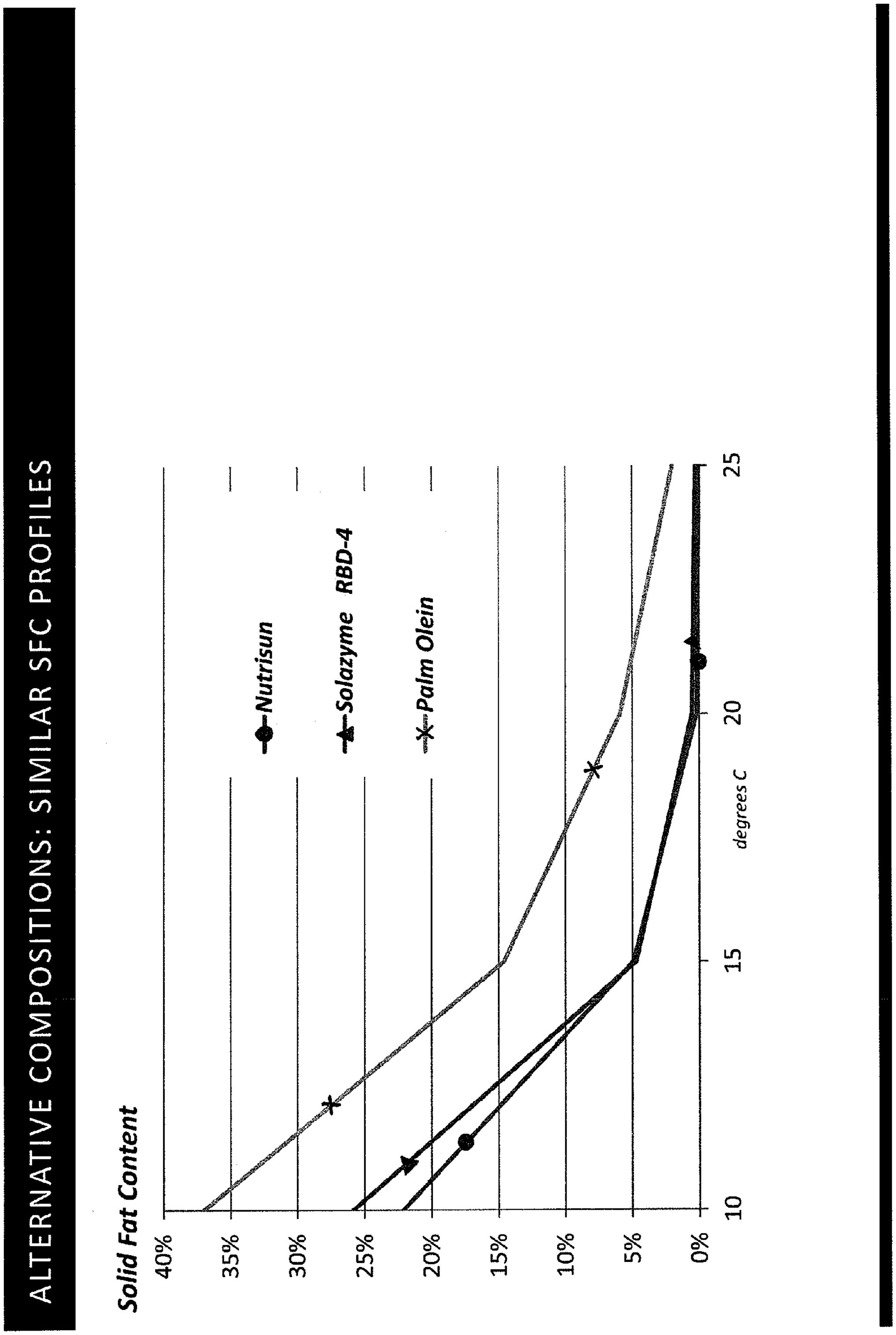

An "allele" is any of one or more alternative forms of a gene which relate to one trait or characteristic.

A "natural oil" or "natural fat" shall mean a predominantly triglyceride oil obtained from an organism, where the oil has not undergone blending with another natural or synthetic oil, or fractionation so as to substantially alter the fatty acid profile of the triglyceride. In connection with an oil comprising triglycerides of a particular regiospecificity, the natural oil or natural fat has not been subjected to interesterification or other synthetic process to obtain that regiospecific triglyceride profile, rather the regiospecificity is produced naturally, by a cell or population of cells. In connection with a natural oil or natural fat, and as used generally throughout the present disclosure, the terms oil and fat are used interchangeably, except where otherwise noted. Thus, an "oil" or a "fat" can be liquid, solid, or partially solid at room temperature, depending on the makeup of the substance and other conditions. Here, the term "fractionation" means removing material from the oil in a way that changes its fatty acid profile relative to the profile produced by the organism, however accomplished. The terms "natural oil" and "natural fat" encompass such oils obtained from an organism, where the oil has undergone minimal processing, including refining, bleaching and/or degumming, that does not substantially change its triglyceride profile. A natural oil can also be a "noninteresterified natural oil", which means that the natural oil has not undergone a process in which fatty acids have been redistributed in their acyl linkages to glycerol and remain essentially in the same configuration as when recovered from the organism.

"Exogenous gene" shall mean a nucleic acid that codes for the expression of an RNA and/or protein that has been introduced into a cell (e.g. by transformation/transfection), and is also referred to as a "transgene". A cell comprising an exogenous gene may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plastid) or as an episomal molecule.

"Fatty acids" shall mean free fatty acids, fatty acid salts, or fatty acyl moieties in a glycerolipid. It will be understood that fatty acyl groups of glycerolipids can be described in terms of the carboxylic acid or anion of a carboxylic acid that is produced when the triglyceride is hydrolyzed or saponified.

"Fixed carbon source" is a molecule(s) containing carbon, typically an organic molecule that is present at ambient temperature and pressure in solid or liquid form in a culture media that can be utilized by a microorganism cultured therein. Accordingly, carbon dioxide is not a fixed carbon source.

"In operable linkage" is a functional linkage between two nucleic acid sequences, such a control sequence (typically a promoter) and the linked sequence (typically a sequence that encodes a protein, also called a coding sequence). A promoter is in operable linkage with an exogenous gene if it can mediate transcription of the gene.

"Microalgae" are microbial organisms that contain a chloroplast or other plastid, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, *Volvox*, which is a simple multicellular photosynthetic microbe of two distinct cell types. Microalgae include cells such as *Chlorella, Dunaliella*, and *Prototheca*. Microalgae also include other microbial photosynthetic organisms that exhibit cell-cell adhesion, such as *Agmenellum, Anabaena*, and *Pyrobotrys*. Microalgae also include obligate heterotrophic microorganisms that have lost the ability to perform photosynthesis, such as certain dinoflagellate algae species and species of the genus *Prototheca.*

In connection with a recombinant cell, the term knockdown refers to a gene that has been partially suppressed (e.g., by about 1-95%) in terms of the production or activity of a protein encoded by the gene.

Also, in connection with a recombinant cell, the term knockout refers to a gene that has been completely or nearly completely (e.g., >95%) suppressed in terms of the production or activity of a protein encoded by the gene. Knockouts can be prepared by homologous recombination of a noncoding sequence into a coding sequence, gene deletion, mutation or other method.

An "oleaginous" cell is a cell capable of producing at least 20% lipid by dry cell weight, naturally or through recombinant or classical strain improvement. An "oleaginous microbe" or "oleaginous microorganism" is a microbe, including a microalga that is oleaginous. An oleaginous cell also encompasses a cell that has had some or all of its lipid or other content removed, and both live and dead cells.

An "ordered oil" or "ordered fat" is one that forms crystals that are primarily of a given polymorphic structure. For example, an ordered oil or ordered fat can have crystals that are greater than 50%, 60%, 70%, 80%, or 90% of the β or β' polymorphic form.

In connection with a natural oil, a "profile" is the distribution of particular species or triglycerides or fatty acyl groups within the oil. A "fatty acid profile" is the distribution of fatty acyl groups in the triglycerides of the oil without reference to attachment to a glycerol backbone. Fatty acid profiles are typically determined by conversion to a fatty acid methyl ester (FAME), followed by gas chromatography (GC) analysis with flame ionization detection (FID). The fatty acid profile can be expressed as one or more percent of a fatty acid in the total fatty acid signal determined from the area under the curve for that fatty acid. FAME-GC-FID measurement approximate weight percentages of the fatty acids. A "sn-2 profile" is the distribution of fatty acids found at the sn-2 position of the triacylglycerides in the oil. A "regiospecific profile" is the distribution of triglycerides with reference to the positioning of acyl group attachment to the glycerol backbone without reference to stereospecificity. In other words, a regiospecific profile describes acyl group attachment at sn-1/3 vs. sn-2. Thus, in a regiospecific profile, POS (palmitate-oleate-stearate) and SOP (stearate-oleate-palmitate) are treated identically. A "stereospecific profile" describes the attachment of acyl groups at sn-1, sn-2 and sn-3. Unless otherwise indicated, triglycerides such as SOP and POS are to be considered equivalent. A "TAG profile" is the distribution of fatty acids found in the triglycerides with reference to connection to the glycerol backbone, but without reference to the regiospecific nature of the connections. Thus, in a TAG profile, the percent of SSO in the oil is the sum of SSO and SOS, while in a regiospecific profile, the percent of SSO is calculated without inclusion of SOS species in the oil. In contrast to the weight percentages of the FAME-GC-FID analysis, triglyceride percentages are typically given as mole percentages; that is the percent of a given TAG molecule in a TAG mixture.

"Recombinant" is a cell, nucleic acid, protein or vector that has been modified due to the introduction of an exogenous nucleic acid or the alteration of a native nucleic acid. Thus, e.g., recombinant cells can express genes that are not found within the native (non-recombinant) form of the cell or express native genes differently than those genes are expressed by a non-recombinant cell. Recombinant cells can, without limitation, include recombinant nucleic acids that encode for a gene product or for suppression elements such as mutations, knockouts, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, using chemical synthesis, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

The terms "triglyceride", "triacylglyceride" and "TAG" are used interchangeably as is known in the art.

II. General

Illustrative embodiments of the present invention feature oleaginous cells that produce altered fatty acid profiles and/or altered regiospecific distribution of fatty acids in glycerolipids, and products produced from the cells. Examples of oleaginous cells include microbial cells having a type II fatty acid biosynthetic pathway, including plastidic oleaginous cells such as those of oleaginous algae. Specific examples of cells include heterotrophic or obligate heterotophic microalgae of the phylum Chlorophtya, the class Trebouxiophytae, the order Chlorellales, or the family Chlorellacae. Examples of oleaginous microalgae are also provided in Published PCT Patent Applications WO2008/151149, WO2010/06032, WO2011/150410, and WO2011/150411, including species of *Chlorella* and *Prototheca*, a genus comprising obligate heterotrophs. The oleaginous cells can be, for example, capable of producing 25, 30, 40, 50, 60, 70, 80, 85, or about 90% oil by cell weight, ±5%. Optionally, the oils produced can be low in highly unsaturated fatty acids such as DHA or EPA fatty acids. For example, the oils can comprise less than 5%, 2%, or 1% DHA and/or EPA. The above-mentioned publications also disclose methods for cultivating such cells and extracting oil, especially from microalgal cells; such methods are applicable to the cells disclosed herein and incorporated by reference for these teachings. When microalgal cells are used they can be cultivated autotrophically (unless an obligate heterotroph) or in the dark using a sugar (e.g., glucose, fructose and/or sucrose) In any of the embodiments described herein, the cells can be heterotrophic cells comprising an exogenous invertase gene so as to allow the cells to produce oil from a sucrose feedstock. Alternately, or in addition, the cells can metabolize xylose from cellulosic feedstocks. For example, the cells can be genetically engineered to express one or more xylose metabolism genes such as those encoding an active xylose transporter, a xylulose-5-phosphate transporter, a xylose isomerase, a xylulokinase, a xylitol dehydrogenase and a xylose reductase. See WO2012/154626, "GENETICALLY ENGINEERED MICROORGANISMS THAT METABOLIZE XYLOSE", published Nov. 15, 2012.

The oleaginous cells express one or more exogenous genes encoding fatty acid biosynthesis enzymes. As a result, some embodiments feature natural oils that were not obtainable from a non-plant or non-seed oil, or not obtainable at all.

The oleaginous cells produce a storage oil, which is primarily triacylglyceride and may be stored in storage bodies of the cell. A raw oil may be obtained from the cells by disrupting the cells and isolating the oil. WO2008/151149, WO2010/06032, WO2011/150410, and WO2011/1504 disclose heterotrophic cultivation and oil isolation techniques. For example, oil may be obtained by providing or cultivating, drying and pressing the cells. The oils produced may be refined, bleached and deodorized (RBD) as known in the art or as described in WO2010/120939. The raw or RBD oils may be used in a variety of food, chemical, and industrial products or processes. After recovery of the oil, a valuable residual biomass remains. Uses for the residual biomass include the production of paper, plastics, absorbents, adsorbents, drilling fluids, as animal feed, for human nutrition, or for fertilizer.

Where a fatty acid profile of a triglyceride (also referred to as a "triacylglyceride" or "TAG") cell oil is given here, it will be understood that this refers to a nonfractionated sample of the storage oil extracted from the cell analyzed under conditions in which phospholipids have been removed or with an analysis method that is substantially insensitive to the fatty acids of the phospholipids (e.g. using chromatography and mass spectrometry). The oil may be subjected to an RBD process to remove phospholipids, free fatty acids and odors yet have only minor or negligible changes to the fatty acid profile of the triglycerides in the oil. Because the cells are oleaginous, in some cases the storage oil will constitute the bulk of all the TAGs in the cell. Examples 1, 2, and 8 below give analytical methods for determining TAG fatty acid composition and regiospecific structure.

Broadly categorized, certain embodiments of the invention include (i) auxotrophs of particular fatty acids; (ii) cells that produce oils having low concentrations of polyunsaturated fatty acids, including cells that are auxotrophic for unsaturated fatty acids; (iii) cells producing oils having high concentrations of particular fatty acids due to expression of one or more exogenous genes encoding enzymes that transfer fatty acids to glycerol or a glycerol ester; (iv) cells producing regiospecific oils, and (v) genetic constructs or cells encoding a newly discovered gene encoding an LPAAT enzyme from *Cuphea* PSR23 (see Example 43). The embodiments also encompass the oils made by such cells, the residual biomass from such cells after oil extraction, olecochemicals, fuels and food products made from the oils and methods of cultivating the cells.

In any of the embodiments below, the cells used are optionally cells having a type II fatty acid biosynthetic pathway such as microalgal cells including heterotrophic or obligate heterotrophic microalgal cells, including cells classified as Chlorophyta, Trebouxiophyceae, Chlorellales, Chlorellaceae, or Chlorophyceae, or cells engineered to have a type II fatty acid biosynthetic pathway using the tools of synthetic biology (i.e., transplanting the genetic machinery for a type II fatty acid biosynthesis into an organism lacking such a pathway). In specific embodiments, the cell is of the species *Prototheca moriformis, Prototheca krugani, Prototheca stagnora* or *Prototheca zopfii* or has a 23S rRNA sequence with at least 65, 70, 75, 80, 85, 90 or 95% nucleotide identity SEQ ID NO: 76. By cultivating in the dark or using an obligate heterotroph, the natural oil produced can be low in chlorophyll or other colorants. For example, the natural oil can have less than 100, 50, 10, 5, 1, 0.0.5 ppm of chlorophyll without substantial purification.

The stable carbon isotope value δ13C is an expression of the ratio of $^{13}C/^{12}C$ relative to a standard (e.g. PDB, carbonite of fossil skeleton of *Belemnite americana* from Peedee formation of South Carolina). The stable carbon isotope value δ13C (‰) of the oils can be related to the δ13C value of the feedstock used. In some embodiments the oils are derived from oleaginous organisms heterotrophically grown on sugar derived from a C4 plant such as corn or sugarcane. In some embodiments the δ13C (‰) of the oil is from −10 to −17‰ or from −13 to −16‰.

In specific embodiments and examples discussed below, one or more fatty acid synthesis genes (e.g., encoding an acyl-ACP thioesterase, a keto-acyl ACP synthase, an LPAAT, a stearoyl ACP desaturase, or others described herein) is incorporated into a microalga. It has been found that for certain microalga, a plant fatty acid synthesis gene product is functional in the absence of the corresponding plant acyl carrier protein (ACP), even when the gene product is an enzyme, such as an acyl-ACP thioesterase, that requires binding of ACP to function. Thus, optionally, the microalgal cells can utilize such genes to make a desired oil without co-expression of the plant ACP gene.

III. Fatty Acid Auxotrophs/Reducing Fatty Acid Levels to Growth Inhibitory Conditions During an Oil Production Phase In an embodiment, the cell is genetically engineered so that all alleles of a lipid pathway gene are knocked out. Alternately, the amount or activity of the gene products of the alleles is knocked down so as to require supplementation with fatty acids. A first transformation construct can be generated bearing donor sequences homologous to one or more of the alleles of the gene. This first transformation construct may be introduced and selection methods followed to obtain an isolated strain characterized by one or more allelic disruptions. Alternatively, a first strain may be created that is engineered to express a selectable marker from an insertion into a first allele, thereby inactivating the first allele. This strain may be used as the host for still further genetic engineering to knockout or knockdown the remaining allele(s) of the lipid pathway gene. Complementation of the endogenous gene can be achieved through engineered expression of an additional transformation construct bearing the endogenous gene whose activity was originally ablated, or through the expression of a suitable heterologous gene. The expression of the complementing gene can either be regulated constitutively or through regulatable control, thereby allowing for tuning of expression to the desired level so as to permit growth or create an auxotrophic condition at will. In an embodiment, a population of the fatty acid auxotroph cells are used to screen or select for complementing genes; e.g., by transformation with particular gene candidates for exogenous fatty acid synthesis enzymes, or a nucleic acid library believed to contain such candidates.

Knockout of all alleles of the desired gene and complementation of the knocked-out gene need not be carried out sequentially. The disruption of an endogenous gene of interest and its complementation either by constitutive or inducible expression of a suitable complementing gene can be carried out in several ways. In one method, this can be achieved by co-transformation of suitable constructs, one disrupting the gene of interest and the second providing complementation at a suitable, alternative locus. In another method, ablation of the target gene can be effected through the direct replacement of the target gene by a suitable gene under control of an inducible promoter. In this way, expression of the targeted gene is now put under the control of a regulatable promoter. An additional approach is to replace the endogenous regulatory elements of a gene with an exogenous, inducible gene expression system. Under such a regime, the gene of interest can now be turned on or off depending upon the particular needs. A still further method is to create a first strain to express an exogenous gene capable of complementing the gene of interest, then to knockout out or knockdown all alleles of the gene of interest in this first strain. The approach of multiple allelic knockdown or knockout and complementation with exogenous genes may be used to alter the fatty acid profile, regiospecific profile, sn-2 profile, or the TAG profile of the engineered cell.

In a specific embodiment, the recombinant cell comprises nucleic acids operable to reduce the activity of an endogenous acyl-ACP thioesterase; for example a FatA or FatB acyl-ACP thioesterase having a preference for hydrolyzing fatty acyl-ACP chains of length C18 (e.g., stearate (C18:0) or oleate (C18:1), or C8:0-C16:0 fatty acids. The activity of an endogenous acyl-ACP thioesterase may be reduced by knockout or knockdown approaches. Knockdown may be achieved through the use of one or more RNA hairpin constructs, by promoter hijacking (substitution of a lower activity or inducible promoter for the native promoter of an endogenous gene), or by a gene knockout combined with introduction of a similar or identical gene under the control of an inducible promoter. Example 34 describes the engineering of a *Prototheca* strain in which two alleles of the endogenous fatty acyl-ACP thioesterase (FATA1) have been knocked out. The activity of the *Prototheca moriformis* FATA1 was complemented by the expression of an exogenous thioesterase. Example 36 details the use of RNA hairpin constructs to reduce the expression of FATA1 in *Prototheca.*

Accordingly, oleaginous cells, including those of organisms with a type II fatty acid biosynthetic pathway can have knockouts or knockdowns of acyl-ACP-thioesterase encoding alleles to such a degree as to eliminate or severely limit viability of the cells in the absence of fatty acid supplementation or genetic complementations. These strains can be used to select for transformants expressing acyl-ACP-thioesterase transgenes. Alternately, or in addition, the strains can be used to completely transplant exogenous acyl-ACP-thioesterases to give dramatically different fatty acid profiles of natural oils produced by such cells. For example, FATA expression can be completely or nearly completely eliminated and replaced with FATB genes that produce mid-chain fatty acids. In specific embodiments, these transformants produce natural oils with more than 50, 60, 70, 80, or 90% caprylic, capric, lauric, myristic, or palmitic acid, or total fatty acids of chain length less than 18 carbons. Such cells may require supplementation with longer chain fatty acids such as stearatic or oleic acid or switching of environmental conditions between growth permissive and restrictive states in the case of an inducible promoter regulating a FatA gene.

In an embodiment the oleaginous cells are cultured. The cells are fully auxotrophic or partially auxotrophic (i.e., lethality or synthetic sickness) with respect to one or more types of fatty acid. The cells are cultured with supplementation of the fatty acid(s) so as to increase the cell number, then allowing the cells to accumulate oil (e.g. to at least 40% by dry cell weight). Alternatively, the cells comprise a regulatable fatty acid synthesis gene that can be switched in activity based on environmental conditions and the environmental conditions during a first, cell division, phase favor production of the fatty acid and the environmental conditions during a second, oil accumulation, phase disfavor production of the fatty acid. In the case of an inducible gene, the regulation of the inducible gene can be mediated, without limitation, via environmental pH (for example, by using the AMT3 promoter as described in the Examples).

As a result of applying either of these supplementation or regulation methods, a cell oil may be obtained from the cell that has low amounts of one or more fatty acids essential for optimal cell propagation. Specific examples of oils that can be obtained include those low in stearic, linoleic and/or linolenic acids.

These cells and methods are illustrated in connection with low polyunsaturated oils in the section immediately below and in Example 6 (fatty acid desaturase auxotroph) in connection with oils low in polyunsaturated fatty acids and in Example 34 (acyl-ACP thioesterase auxotroph).

Likewise, fatty acid auxotrophs can be made in other fatty acid synthesis genes including those encoding a SAD, FAD, KASIII, KASI, KASII, KCS, elongase, GPAT, LPAAT, DGAT or AGPAT or PAP. These auxotrophs can also be used to select for complement genes or to eliminate native expression of these genes in favor of desired exogenous genes in order to alter the fatty acid profile, regiospecific profile, or TAG profile of natural oils produced by oleaginous cells.

Accordingly, in an embodiment of the invention, there is a method for producing an oil/fat. The method comprises cultivating a recombinant oleaginous cell in a growth phase under a first set of conditions that is permissive to cell division so as to increase the number of cells due to the presence of a fatty acid, cultivating the cell in an oil production phase under a second set of conditions that is restrictive to cell division but permissive to production of an oil that is depleted in the fatty acid, and extracting the oil from the cell, wherein the cell has a mutation or exogenous nucleic acids operable to suppress the activity of a fatty acid synthesis enzyme, the enzyme optionally being a stearoyl-ACP desaturase, delta 12 fatty acid desaturase, or a ketoacyl-ACP synthase. The oil produced by the cell can be depleted in the fatty acid by at least than 50, 60, 70, 80, or 90%. The cell can be cultivated heterotrophically. The cell can be a microalgal cell cultivated heterotrophically or autotrophically and may produce at least 40, 50, 60, 70, 80, or 90% oil by dry cell weight.

IV. Low Polyunsaturated Natural Oils

In an embodiment of the present invention, the natural oil produced by the cell has very low levels of polyunsaturated fatty acids. As a result, the natural oil can have improved stability, including oxidative stability. The natural oil can be a liquid or solid at room temperature, or a blend of liquid and solid oils, including the regiospecific or stererospecific oils, high stearate oils, or high mid-chain oils described infra. Oxidative stability can be measured by the Rancimat method using the AOCS Cd 12b-92 standard test at a defined temperature. For example, the OSI (oxidative stability index) test may be run at temperatures between 110° C. and 140° C. The oil is produced by cultivating cells (e.g., any of the plastidic microbial cells mentioned above or elsewhere herein) that are genetically engineered to reduce the activity of one or more fatty acid desaturase. For example, the cells may be genetically engineered to reduce the activity of one or more fatty acyl Δ12 desaturase(s) responsible for converting oleic acid (18:1) into linoleic acid (18:2) and/or one or more fatty acyl Δ15 desaturase(s) responsible for converting linoleic acid (18:2) into linolenic acid (18:3). Various methods may be used to inhibit the desaturase including knockout or mutation of one or more alleles of the gene encoding the desaturase in the coding or regulatory regions, inhibition of RNA transcription, or translation of the enzyme, including RNAi, siRNA, miRNA, dsRNA, antisense, and hairpin RNA techniques. Other techniques known in the art can also be used including introducing an exogenous gene that produces an inhibitory protein or other substance that is specific for the desaturase.

In a specific embodiment, fatty acid desaturase (e.g., Δ12 fatty acid desaturase) activity in the cell is reduced to such a degree that the cell is unable to be cultivated or is difficult to cultivate (e.g., the cell division rate is decreased more than 10, 20, 30, 40, 50, 60, 70, 80, 90, 95, 97 or 99%). Achieving such conditions may involve knockout, or effective suppression of the activity of multiple gene copies (e.g. 2, 3, 4 or more) of the desaturase or their gene products. A specific embodiment includes the cultivation in cell culture of a full or partial fatty acid auxotroph with supplementation of the fatty acid or a mixture of fatty acids so as to increase the cell number, then allowing the cells to accumulate oil (e.g. to at least 40% by cell weight). Alternatively, the cells comprise a regulatable fatty acid synthesis gene that can be switched in activity. For example, the regulation can be based on environmental conditions and the environmental conditions during a first, cell division, phase favor production of the fatty acid and the environmental conditions during a second, oil accumulation, phase disfavor production of the oil. For example, culture media pH can be used as an environmental control to switch expression of a lipid pathway gene to produce a state of high or low synthetic enzyme activity. Examples of such cells are described in Example 7.

In a specific embodiment, a cell is cultivated using a modulation of linoleic acid levels within the cell. In particular, the natural oil is produced by cultivating the cells under a first condition that is permissive to an increase in cell number due to the presence of linoleic acid and then cultivating the cells under a second condition that is characterized by linoleic acid starvation and thus is inhibitory to cell division, yet permissive of oil accumulation. For example, a seed culture of the cells may be produced in the presence of linoleic acid added to the culture medium. For example, the addition of linoleic acid to 0.25 g/L in the seed culture of a *Prototheca* strain deficient in linoleic acid production due to ablation of two alleles of a fatty acyl Δ12 desaturase (i.e., a linoleic auxotroph) was sufficient to support cell division to a level comparable to that of wild type cells. Optionally, the linoleic acid can then be consumed by the cells, or otherwise removed or diluted. The cells are then switched into an oil producing phase (e.g., supplying sugar under nitrogen limiting conditions as described in WO2010/063032). Surprisingly, oil production has been found to occur even in the absence of linoleic acid production or supplementation, as demonstrated in the obligate heterotroph oleaginous microalgae *Prototheca* but generally applicable to other oleaginous microalgae, microorganism, or even multicellular organisms (e.g., cultured plant cells). Under these conditions, the oil content of the cell can increase to about 10, 20, 30, 40, 50, 60, 70, 80, 90%, or more by dry cell weight, while the oil produced can have polyunsaturated fatty acid (e.g.; linoleic+linolenic) profile with 5%, 4%, 3%, 2%, 1%, 0.5%, 0.3%, 0.2%, 0.1%, 0.05% or less, as a percent of total triacylglycerol fatty acids in the oil. For example, the oil content of the cell can be 50% or more by dry cell weight and the triglyceride of the oil produced less than 3% polyunsaturated fatty acids.

These oils can also be produced without the need (or reduced need) to supplement the culture with linoleic acid by using cell machinery to produce the linoleic acid, but predominantly or only during the cell division phase. The linoleic-producing cell machinery may be regulatable so as to produce substantially less linoleic acid during the oil producing phase. The regulation may be via modulation of transcription of the desaturase gene(s). For example, the majority, and preferably all, of the fatty acid Δ12 desaturase activity can be placed under a regulatable promoter regulated to express the desaturase in the cell division phase, but to be reduced or turned off during the oil accumulation phase. The regulation can be linked to a cell culture condition such as pH, and/or nitrogen level, as described in the examples herein, or other environmental condition. In practice, the condition may be manipulated by adding or removing a substance (e.g., protons via addition of acid or base) or by allowing the cells to consume a substance (e.g, nitrogen-supplying nutrients) to effect the desired switch in regulation of the desaturase activity.

Other genetic or non-genetic methods for regulating the desaturase activity can also be used. For example, an inhibitor of the desaturase can be added to the culture medium in a manner that is effective to inhibit polyunsaturated fatty acids from being produced during the oil production phase.

Accordingly, in a specific embodiment of the invention, there is a method comprising providing a recombinant cell having a regulatable delta 12 fatty acid desaturase gene, under control of a recombinant regulatory element via an environmental condition. The cell is cultivated under conditions that favor cell multiplication. Upon reaching a given cell density, the cell media is altered to switch the cells to lipid production mode by nutrient limitation (e.g. reduction of available nitrogen). During the lipid production phase, the environmental condition is such that the activity of the delta 12 fatty acid desaturase is downregulated. The cells are then harvested and, optionally, the oil extracted. Due to the low level of delta 12 fatty acid desaturase during the lipid production phase, the oil has less polyunsaturated fatty acids and has improved oxidative stability. Optionally the cells are cultivated heterotrophically and optionally microalgal cells.

Using one or more of these desaturase regulation methods, it is possible to obtain a natural oil that it is believed has been previously unobtainable, especially in large scale cultivation in a bioreactor (e.g., more than 1000 L). The oil can have polyunsaturated fatty acid levels that are 5%, 4%, 3%, 2%, 1%, 0.5%, 0.3%, 0.2%, or less, as an area percent of total triacylglycerol fatty acids in the oil.

One consequence of having such low levels of polyunsaturates is that oils are exceptionally stable to oxidation. Indeed, in some cases the oils may be more stable than any previously known natural cell oil. In specific embodiments, the oil is stable, without added antioxidants, at 110° C. so that the inflection point in conductance is not yet reached by 10 hours, 15 hours, 20 hours, 30 hours, 40, hours, 50 hours, 60 hours, or 70 hours under conditions of the AOCS Cd 12b-92. Rancimat test, noting that for very stable oils, replenishment of water may be required in such a test due to evaporation that occurs with such long testing periods (see Example 5). For example the oil can have and OSI value of 40-50 hours or 41-46 hours at 110° C. without added antioxidants. When antioxidants (suitable for foods or otherwise) are added, the OSI value measured may be further increased. For example, with added tocopherol (100 ppm) and ascorbyl palmitate (500 ppm) or PANA and ascorbyl palmitate, such an oil can have an oxidative stability index (OSI value) at 110° C. in excess 100 or 200 hours, as measured by the Rancimat test. In another example, 1050 ppm of mixed tocopherols and 500 μm of ascorbyl palmitate are added to an oil comprising less than 1% linoleic acid or less than 1% linoleic+linolenic acids; as a result, the oil is stable at 110° C. for 1, 2, 3, 4, 5, 6, 7, 8, or 9, 10, 11, 12, 13, 14, 15, or 16, 20, 30, 40 or 50 days, 5 to 15 days, 6 to 14 days, 7 to 13 days, 8 to 12 days, 9 to 11 days, about 10 days, or about 20 days. The oil can also be stable at 130° C. for 1, 2, 3, 4, 5, 6, 7, 8, or 9, 10, 11, 12, 13, 14, 15, or 16, 20, 30, 40 or 50 days, 5 to 15 days, 6 to 14 days, 7 to 13 days, 8 to 12 days, 9 to 11 days, about 10 days, or about 20 days. In a specific example, such an oil was found to be stable for greater than 100 hours (about 128 hours as observed). In a further embodiment, the OSI value of the natural oil without added antioxidants at 120° C. is greater than 15 hours or 20 hours or is in the range of 10-15, 15-20, 20-25, or 25-50 hours, or 50-100 hours.

In an example, using these methods, the oil content of a microalgal cell is between 40 and about 85% by dry cell weight and the polyunsaturated fatty acids in the fatty acid profile of the oil is between 0.001% and 3% in the fatty acid profile of the oil and optionally yields a natural oil having an OSI induction time of at least 20 hours at 110° C. without the addition of antioxidants. In yet another example, there is a natural oil produced by RBD treatment of a natural oil from an oleaginous cell, the oil comprises between 0.001% and 2% polyunsaturated fatty acids and has an OSI induction time exceeding 30 hours at 110 C without the addition of antioxidants. In yet another example, there is a natural oil produced by RBD treatment of a natural oil from an oleaginous cell, the oil comprises between 0.001% and 1% polyunsaturated fatty acids and has an OSI induction time exceeding 30 hours at 110 C without the addition of antioxidants.

In another specific embodiment there is an oil with reduced polyusaturate levels produced by the above-described methods. The oil is combined with antioxidants such as PANA and ascorbyl palmitate. For example, it was found that when such an oil was combined with 0.5% PANA and 500 ppm of ascorbyl palmitate the oil had an OSI value of about 5 days at 130° C. or 21 days at 110° C. These remarkable results suggest that not only is the oil exceptionally stable, but these two antioxidants are exceptionally potent stabilizers of triglyceride oils and the combination of these antioxidants may have general applicability including in producing stable biodegradable lubricants (e.g., jet engine lubricants). In specific embodiments, the genetic manipulation of fatty acyl Δ12 desaturase results in a 2 to 30, or 5 to 25, or 10 to 20 fold increase in OSI (e.g., at 110° C.) relative to a strain without the manipulation. The oil can be produced by suppressing desaturase activity in a cell, including as described above.

Antioxidants suitable for use with the oils of the present invention include alpha, delta, and gamma tocopherol (vitamin E), tocotrienol, ascorbic acid (vitamin C), glutathione, lipoic acid, uric acid, β-carotene, lycopene, lutein, retinol (vitamin A), ubiquinol (coenzyme Q), melatonin, resveratrol, flavonoids, rosemary extract, propyl gallate (PG), tertiary butylhydroquinone (TBHQ), butylated hydroxyanisole (BHA), and butylated hydroxytoluene (BHT), N,N'-di-2-butyl-1,4-phenylenediamine, 2,6-di-tert-butyl-4-methylphenol, 2,4-dimethyl-6-tert-butylphenol, 2,4-dimethyl-6-tert-butylphenol, 2,4-dimethyl-6-tert-butylphenol, 2,6-di-tert-butyl-4-methylphenol, 2,6-di-tert-butylphenol, and phenyl-alpha-naphthylamine (PANA).

In addition to the desaturase modifications, in a related embodiment other genetic modifications may be made to further tailor the properties of the oil, as described throughout, including introduction or substitution of acyl-ACP thioesterases having altered chain length specificity and/or overexpression of an endogenous or exogenous gene encoding a KAS, SAD, LPAAT, or DGAT gene. For example, a strain that produces elevated oleic levels may also produce low levels of polyunsaturates. Such genetic modifications can include increasing the activity of stearoyl-ACP desaturase (SAD) by introducing an exogenous SAD gene, increasing elongase activity by introducing an exogenous KASII gene, and/or knocking down or knocking out a FATA gene.

In a specific embodiment, a high oleic natural oil with low polyunsaturates may be produced. For example, the oil may have a fatty acid profile with greater than 60, 70, 80, 90, or 95% oleic acid and less than 5, 4, 3, 2, or 1% polyunsaturates. In related embodiments, a natural oil is produced by a cell having recombinant nucleic acids operable to decrease fatty acid Δ12 desaturase activity and optionally fatty acid Δ15 desaturase so as to produce an oil having less than or equal to 3% polyunsaturated fatty acids with greater than 60% oleic acid, less than 2% polyunsaturated fatty acids and greater than 70% oleic acid, less than 1% polyunsaturated fatty acids and greater than 80% oleic acid, or less than 0.5% polyunsaturated fatty acids and greater than 90% oleic acid. It has been found that one way to increase oleic acid is to use recombinant nucleic acids operable to decrease expression of a FATA acyl-ACP thioesterase and optionally overexpress a KAS II gene; such a cell can produce an oil with greater than or equal to 75% oleic acid. Alternately, overexpression of KASII can be used without the FATA knockout or knockdown. Oleic acid levels can be further increased by reduction of delat 12 fatty acid desaturase activity using the methods above, thereby decreasing the amount of oleic acid the is converted into the unsaturates linoleic acid and linolenic acid. Thus, the oil produced can have a fatty acid profile with at least 75% oleic and at most 3%, 2%, 1%, or 0.5% linoleic acid. In a related example, the oil has between 80 to 95% oleic acid and about 0.001 to 2% linoleic acid, 0.01 to 2% linoleic acid, or 0.1 to 2% linoleic acid. Such oils will have a low freezing point, with excellent stability and are useful in foods, for frying, fuels, or in chemical applications. Further, these oils may exhibit a reduced propensity to change color over time. In an illustrative chemical application, the high oleic oil is used to produce a chemical. The oleic acid double bonds of the oleic acid groups of the triglycerides in the oil can be epoxidized or hydroxylated to make a polyol. The epoxidized or hydroxylated oil can be used in a variety of applications. One such application is the production of polyurethane (including polyurethane foam) via condensation of the hydroxylated triglyceride with an isocyante, as has been practiced with hydroxylated soybean oil or castor oil. See, e.g. US2005/0239915, US2009/0176904, US2005/0176839, US2009/0270520, and U.S. Pat. No. 4,264,743 and Zlatanic, et al, Biomacromolecules 2002, 3, 1048-1056 (2002) for examples of hydroxylation and polyurethane condensation chemistries. Suitable hydroxyl forming reactions include epoxidation of one or more double bonds of a fatty acid followed by acid catalyzed epoxide ring opening with water (to form a diol), alcohol (to form a hydroxyl ether), or an acid (to form a hydroxyl ester). There are multiple advantages of using the high-oleic/low polyunsaturated oil in producing a bio-based polyurethane: (1) the shelf-life, color or odor, of polyurethane foams may be improved; (2) the reproducibility of the product may be improved due to lack of unwanted side reactions resulting from polyunsaturates; (3) a greater degree of hydroxylation reaction may occur due to lack of polyunsaturates and the structural characteristics of the polyurethane product can be improved accordingly.

The low polyunsaturated or high oleic/low polyunsaturated oils described here may be advantageously used in chemical applications where yellowing is undesirable. For example, yellowing can be undesirable in paints or coatings made from the triglycerides fatty acids derived from the triglycerides. Yellowing may be caused by reactions involving polyunsaturated fatty acids and tocotrienols and/or tocopherols. Thus, producing the high stability oil in an oleaginous microbe with low levels of tocotrienols can be advantageous in elevating high color stability a chemical composition made using the oil. In contrast to commonly used plant oils, through appropriate choice of oleaginous microbe, the natural oils of these embodiments can have tocopherols and tocotrienols levels of 1 g/L or less. In a specific embodiment, a natural oil has a fatty acid profile with less than 2% with polyunsaturated fatty acids and less than 1 g/L for tocopherols, tocotrienols or the sum of tocopherols and tocotrienols. In another specific embodiment, the natural oil has a fatty acid profile with less than 1% with polyunsaturated fatty acids and less than 0.5 g/L for tocopherols, tocotrienols or the sum of tocopherols and tocotrienols Any of the high-stability (low-polyunsaturate) natural oils or derivatives thereof can be used to formulate foods, drugs, vitamins, nutraceuticals, personal care or other products, and are especially useful for oxidatively sensitive products. For example, the high-stability natural oil (e.g., less than or equal to 3%, 2% or 1% polyunsaturates) can be used to formulate a sunscreen (e.g. a composition having one or more of avobenzone, homosalate, octisalate, octocrylene or oxybenzone) or retinoid face cream with an increased shelf life due to the absence of free-radical reactions associated with polyunsaturated fatty acids. For example, the shelf-life can be increased in terms of color, odor, organoleptic properties or % active compound remaining after accelerated degradation for 4 weeks at 54° C. The high stability oil can also be used as a lubricant with excellent high-temperature stability. In addition to stability, the oils can be biodegradable, which is a rare combination of properties.

In another related embodiment, the fatty acid profile of a natural oil is elevated in C8 to C16 fatty acids through additional genetic modification, e.g. through overexpression of a short-chain to mid chain preferring acyl-ACP thioesterase or other modifications described here. A low polyunsaturated oil in accordance with these embodiments can be used for various industrial, food, or consumer products, including those requiring improved oxidative stability. In food applications, the oils may be used for frying with extended life at high temperature, or extended shelf life.

Where the oil is used for frying, the high stability of the oil may allow for frying without the addition of antioxidant and/or defoamers (e.g. silicone). As a result of omitting defoamers, fried foods may absorb less oil. Where used in fuel applications, either as a triglyceride or processed into biodiesel or renewable diesel (see, e.g., WO2008/151149 WO2010/063032, and WO2011/150410), the high stability can promote storage for long periods, or allow use at elevated temperatures. For example, the fuel made from the high stability oil can be stored for use in a backup generator for more than a year or more than 5 years. The frying oil can have a smoke point of greater than 200° C., and free fatty acids of less than 0.1%.

The low polyunsaturated oils may be blended with food oils, including structuring fats such as those that form beta or beta prime crystals, including those produced as described below. These oils can also be blended with liquid oils. If mixed with an oil having linoleic acid, such as corn oil, the linoleic acid level of the blend may approximate that of high oleic plant oils such as high oleic sunflower oils (e.g., about 80% oleic and 8% linoleic).

Blends of the low polyunsaturated natural oil can be interesterified with other oils. For example, the oil can be chemically or enzymatically interesterified. In a specific embodiment, a low polyunsaturated oil according to an embodiment of the invention has at least 10% oleic acid in its fatty acid profile and less than 5% polyunsaturates and is enzymatically interesterified with a high saturate oil (e.g. hydrogenated soybean oil or other oil with high stearate levels) using an enzyme that is specific for sn-1 and sn-2 triacylglycerol positions. The result is an oil that includes a stearate-oleate-stearate (SOS). Methods for interesterification are known in the art; see for example, "Enzymes in Lipid Modification," Uwe T. Bornschuer, ed., Wiley_VCH, 2000, ISBN 3-527-30176-3.

High stability oils can be used as spray oils. For example, dried fruits such as raisins can be sprayed with a high stability oil having less than 5, 4, 3, 2, or 1% polyunsaturates. As a result, the spray nozzle used will become clogged less frequently due to polymerization or oxidation product buildup in the nozzle that might otherwise result from the presence of polyunsaturates.

In a further embodiment, an oil that is high is SOS, such as those described below can be improved in stability by knockdown or regulation of delta 12 fatty acid desaturase.

V. Cells with Exogenous Acyltransferases

In various embodiments of the present invention, one or more genes encoding an acyltransferase (an enzyme responsible for the condensation of a fatty acid with glycerol or a glycerol derivative to form an acylglyceride) can be introduced into an oleaginous cell (e.g., a plastidic microalgal cell) so as to alter the fatty acid composition of a natural oil produced by the cell. The genes may encode one or more of a glycerol-3-phosphate acyltransferase (GPAT), lysophosphatidic acid acyltransferase (LPAAT), also known as 1-acylglycerol-3-phosphate acyltransferase (AGPAT), phosphatidic acid phosphatase (PAP), or diacylglycerol acyltransferase (DGAT) that transfers an acyl group to the sn-3 position of DAG, thereby producing a TAG.

Recombinant nucleic acids may be integrated into a plasmid or chromosome of the cell. Alternately, the gene encodes an enzyme of a lipid pathway that generates TAG precursor molecules through fatty acyl-CoA-independent routes separate from that above. Acyl-ACPs may be substrates for plastidial GPAT and LPAAT enzymes and/or mitochondrial GPAT and LPAAT enzymes. Among further enzymes capable of incorporating acyl groups (e.g., from membrane phospholipids) to produce TAGs is phospholipid diacylglycerol acyltransferase (PDAT). Still further acyltransferases, including lysophosphosphatidylcholine acyltransferase (LPCAT), lysophosphosphatidylserine acyltransferase (LPSAT), lysophosphosphatidylethanolamine acyltransferase (LPEAT), and lysophosphosphatidylinositol acyltransferase (LPIAT), are involved in phospholipid synthesis and remodeling that may impact triglyceride composition.

The exogenous gene can encode an acyltransferase enzyme having preferential specificity for transferring an acyl substrate comprising a specific number of carbon atoms and/or a specific degree of saturation is introduced into a oleaginous cell so as to produce an oil enriched in a given regiospecific triglyceride. For example, the coconut (*Cocos nucifera*) lysophosphatidic acid acyltransferase has been demonstrated to prefer C12:0-CoA substrates over other acyl-CoA substrates (Knutzon et al., *Plant Physiology*, Vol. 120, 1999, pp 739-746), whereas the 1-acyl-sn-3-glycerol-3-phosphate acyltransferase of maturing safflower seeds shows preference for linoleoyl-CoA and oleyl-CoA substrates over other acyl-CoA substrates, including stearoyl-CoA (Ichihara et al., *European Journal of Biochemistry*, Vol. 167, 1989, pp 339-347). Furthermore, acyltransferase proteins may demonstrate preferential specificity for one or more short-chain, medium-chain, or long-chain acyl-CoA or acyl-ACP substrates, but the preference may only be encountered where a particular, e.g. medium-chain, acyl group is present in the sn-1 or sn-3 position of the lysophosphatidic acid donor substrate. As a result of the exogenous gene, a TAG oil can be produced by the cell in which a particular fatty acid is found at the sn-2 position in greater than 20, 30, 40, 50, 60, 70, 90, or 90% of the TAG molecules.

In some embodiments of the invention, the cell makes an oil rich in saturated-unsaturated-saturated (sat-unsat-sat) TAGs. Sat-unsat-sat TAGS include 1,3-dihexadecanoyl-2-

(9Z-octadecenoyl)-glycerol (referred to as 1-palmitoyl-2-oleyl-glycero-3-palmitoyl), 1,3-dioctadecanoyl-2-(9Z-octadecenoyl)-glycerol (referred to as 1-stearoyl-2-oleyl-glycero-3-stearoyl), and 1-hexadecanoyl-2-(9Z-octadecenoyl)-3-octadecanoy-glycerol (referred to as 1-palmitoyl-2-oleyl-glycero-3-stearoyl). These molecules are more commonly referred to as POP, SOS, and POS, respectively, where 'P' represents palmitic acid, 'S' represents stearic acid, and 'O' represents oleic acid. Further examples of saturated-unsaturated-saturated TAGs include MOM, LOL, MOL, COC and COL, where 'M' represents myristic acid, 'L' represents lauric acid, and 'C' represents capric acid (C8:0). Trisaturates, triglycerides with three saturated fatty acyl groups, are commonly sought for use in food applications for their greater rate of crystallization than other types of triglycerides. Examples of trisaturates include PPM, PPP, LLL, SSS, CCC, PPS, PPL, PPM, LLP, and LLS. In addition, the regiospecific distribution of fatty acids in a TAG is an important determinant of the metabolic fate of dietary fat during digestion and absorption.

According to certain embodiments of the present invention, oleaginous cells are transformed with recombinant nucleic acids so as to produce natural oils that comprise an elevated amount of a specified regiospecific triglyceride, for example 1-acyl-2-oleyl-glycero-3-acyl, or 1-acyl-2-lauric-glycero-3-acyl where oleic or lauric acid respectively is at the sn-2 position, as a result of introduced recombinant nucleic acids. Alternately, caprylic, capric, myristic, or palmitic acid may be at the sn-2 position. The amount of the specified regiospecific triglyceride present in the natural oil may be increased by greater than 5%, greater than 10%, greater than 15%, greater than 20%, greater than 25%, greater than 30%, greater than 35%, greater than 40%, greater than 50%, greater than 60%, greater than 70%, greater than 80%, greater than 90%, greater than 100-500%, or greater than 500% than in the natural oil produced by the microorganism without the recombinant nucleic acids. As a result, the sn-2 profile of the cell triglyceride may have greater than 10, 20, 30, 40, 50, 60, 70, 80, or 90% of the particular fatty acid.

The identity of the acyl chains located at the distinct stereospecific or regiospecific positions in a glycerolipid can be evaluated through one or more analytical methods known in the art (see Luddy et al., *J. Am. Oil Chem. Soc.*, 41, 693-696 (1964), Brockerhoff, *J. Lipid Res.*, 6, 10-15 (1965), Angers and Aryl, *J. Am. Oil Chem. Soc.*, Vol. 76:4, (1999), Buchgraber et al., *Eur. J. Lipid Sci. Technol.*, 106, 621-648 (2004)), or in accordance with Examples 1, 2, and 8 given below.

The positional distribution of fatty acids in a triglyceride molecule can be influenced by the substrate specificity of acyltransferases and by the concentration and type of available acyl moieties. Nonlimiting examples of enzymes suitable for altering the regiospecificity of a triglyceride produced in a recombinant microorganism are listed in Tables 1-4. One of skill in the art may identify additional suitable proteins.

TABLE 1

Glycerol-3-phosphate acyltransferases and GenBank accession numbers.

| | | |
|---|---|---|
| glycerol-3-phosphate acyltransferase | *Arabidopsis thaliana* | BAA00575 |
| glycerol-3-phosphate acyltransferase | *Chlamydomonas reinhardtii* | EDP02129 |
| glycerol-3-phosphate acyltransferase | *Chlamydomonas reinhardtii* | Q886Q7 |
| acyl-(acyl-carrier-protein): glycerol-3-phosphate acyltransferase | *Cucurbita moschata* | BAB39688 |

TABLE 1-continued

Glycerol-3-phosphate acyltransferases and GenBank accession numbers.

| | | |
|---|---|---|
| glycerol-3-phosphate acyltransferase | *Elaeis guineensis* | AAF64066 |
| glycerol-3-phosphate acyltransferase | *Garcina mangostana* | ABS86942 |
| glycerol-3-phosphate acyltransferase | *Gossypium hirsutum* | ADK23938 |
| glycerol-3-phosphate acyltransferase | *Jatropha curcas* | ADV77219 |
| plastid glycerol-3-phosphate acyltransferase | *Jatropha curcas* | ACR61638 |
| plastidial glycerol-phosphate acyltransferase | *Ricinus communis* | EEF43526 |
| glycerol-3-phosphate acyltransferase | *Vica faba* | AAD05164 |
| glycerol-3-phosphate acyltransferase | *Zea mays* | ACG45812 |

Lysophosphatidic acid acyltransferases suitable for use with the microbes and methods of the invention include, without limitation, those listed in Table 2.

TABLE 2

Lysophosphatidic acid acyltransferases and GenBank accession numbers.

| | | |
|---|---|---|
| 1-acyl-sn-glycerol-3-phosphate acyltransferase | *Arabidopsis thaliana* | AEE85783 |
| 1-acyl-sn-glycerol-3-phosphate acyltransferase | *Brassica juncea* | ABQ42862 |
| 1-acyl-sn-glycerol-3-phosphate acyltransferase | *Brassica juncea* | ABM92334 |
| 1-acyl-sn-glycerol-3-phosphate acyltransferase | *Brassica napus* | CAB09138 |
| lysophosphatidic acid acyltransferase | *Chlamydomonas reinhardtii* | EDP02300 |
| lysophosphatidic acid acyltransferase | *Limnanthes alba* | AAC49185 |
| 1-acyl-sn-glycerol-3-phosphate acyltransferase (putative) | *Limnanthes douglasii* | CAA88620 |
| acyl-CoA:sn-1-acylglycerol-3-phosphate acyltransferase | *Limnanthes douglasii* | ABD62751 |
| 1-acylglycerol-3-phosphate O-acyltransferase | *Limnanthes douglasii* | CAA58239 |
| 1-acyl-sn-glycerol-3-phosphate acyltransferase | *Ricinus communis* | EEF39377 |

Diacylglycerol acyltransferases suitable for use with the microbes and methods of the invention include, without limitation, those listed in Table 3.

TABLE 3

Diacylglycerol acyltransferases and GenBank accession numbers.

| | | |
|---|---|---|
| diacylglycerol acyltransferase | *Arabidopsis thaliana* | CAB45373 |
| diacylglycerol acyltransferase | *Brassica juncea* | AAY40784 |
| putative diacylglycerol acyltransferase | *Elaeis guineensis* | AEQ94187 |
| putative diacylglycerol acyltransferase | *Elaeis guineensis* | AEQ94186 |
| acyl CoA:diacylglycerol acyltransferase | *Glycine max* | AAT73629 |
| diacylglycerol acyltransferase | *Helianthus annus* | ABX61081 |
| acyl-CoA:diacylglycerol acyltransferase 1 | *Olea europaea* | AAS01606 |
| diacylglycerol acyltransferase | *Ricinus communis* | AAR11479 |

Phospholipid diacylglycerol acyltransferases suitable for use with the microbes and methods of the invention include, without limitation, those listed in Table 4.

TABLE 4

Phospholipid diacylglycerol acyltransferases and GenBank accession numbers.

| | | |
|---|---|---|
| phospholipid: diacylglycerol acyltransferase | *Arabidopsis thaliana* | AED91921 |

TABLE 4-continued

| Phospholipid diacylglycerol acyltransferases and GenBank accession numbers. | | |
|---|---|---|
| putativephospholipid: diacylglycerol acyltransferase | *Elaeis guineensis* | AEQ94116 |
| phospholipid: diacylglycerol acyltransferase 1-like | *Glycine max* | XP_003541296 |
| phospholipid: diacylglycerol acyltransferase | *Jatropha curcas* | AEZ56255 |
| phospholipid: diacylglycerol acyltransferase | *Ricinus communis* | ADK92410 |
| phospholipid: diacylglycerol acyltransferase | *Ricinus communis* | AEW99982 |

In embodiment of the invention, known or novel LPAAT genes are transformed into the oleaginous cells so as to alter the fatty acid profile of triglycerides produced by those cells, most notably by altering the sn-2 profile of the triglycerides. For example, by virtue of expressing an exogenous active LPAAT in an oleaginous cell, the percent of unsaturated fatty acid at the sn-2 position is increased by 10, 20, 30, 40, 50, 60, 70, 80, 90% or more. For example, a cell may produce triglycerides with 30% unsaturates (which may be primarily 18:1 and 18:2 and 18:3 fatty acids) at the sn-2 position. In this example, introduction of the LPAAT activity increases the unsaturates at the sn-2 position by 20% so that 36% of the triglycerides comprise unsaturates at the sn-2 position. Alternately, an exogenous LPAAT can be used to increase mid-chain fatty acids including saturated mid-chains such as C8:0, C10:0, C12:0, C14:0 or C16:0 moieties at the sn-2 position. As a result, mid-chain levels in the overall fatty acid profile may be increased. Examples 43 and 44 describe altering the sn-2 and fatty acid profiles in an oleaginous microbe. As can be seen from those examples, the choice of LPAAT gene is important in that different LPAATs can cause a shift in the sn-2 and fatty acid profiles toward different acyl group chain-lengths or saturation levels. For example, the LPAAT of Example 43 increases C10-C14 fatty acids and the LPAAT of Example 44 causes an increase in C16 and C18 fatty acids. As in these examples, introduction of an exogenous LPAAT can be combined with introduction of exogenous acyl-ACP thioesterase. Combining a mid-chain preferring LPAAT and a mid-chain preferring FatB was found to give an additive effect; the fatty acid profile was shifted more toward the mid-chain fatty acids more when both an exogenous LPAAT and FatB gene was present than when only an exogenous FatB gene was present. In a specific embodiment, the oil produced by a cell comprising an exogenous mid-chain specific LPAAT and (optionally) an exogenous FatB acyl-ACP thioesterase gene can have a fatty acid profile with 40, 50, 60, 70, 80% or more of C8:0, C10:0, C12:0, C14:0, or C16:0 fatty acids (separately or in sum).

Specific embodiments of the invention are a nucleic acid construct, a cell comprising the nucleic acid construct, a method of cultivating the cell to produce a triglyceride, and the triglyceride oil produced where the nucleic acid construct has a promoter operably linked to a novel LPAAT coding sequence. The coding sequence can have an initiation codon upstream and a termination codon downstream followed by a 3 UTR sequence. In a particular, specific embodiment, the LPAAT gene has a coding sequence have at least 80, 85, 90, 95, or 98% sequence identity to any of the cDNAs of SEQ ID NOs: 80 to 85 or, a functional fragment thereof including equivalent sequences by virtue of degeneracy of the genetic code. Introns can be inserted into the sequence as well. Alternately, the LPAAT gene codes for the amino acid sequence of SEQ ID NOs 77-79 or functional fragments thereof. Plants expressing the novel LPAAT are expressly included in the embodiments and can be produced using known genetic engineering techniques.

VI. Cells with Exogenous Elongases or Elongase Complex Enzymes

In various embodiments of the present invention, one or more genes encoding elongases or components of the fatty acyl-CoA elongation complex can be introduced into an oleaginous cell (e.g., a plastidic microalgal cell) so as to alter the fatty acid composition of the cell or of a natural oil produced by the cell. The genes may encode a beta-ketoacyl-CoA synthase (also referred to as 3-ketoacyl synthase, beta-ketoacyl synthase or KCS), a ketoacyl-CoA reductase, a hydroxyacyl-CoA dehydratase, enoyl-CoA reductase, or elongase. The enzymes encoded by these genes are active in the elongation of acyl-coA molecules liberated by acyl-ACP thioesterases. Recombinant nucleic acids may be integrated into a plasmid or chromosome of the cell. In a specific embodiment, the cell is of Chlorophyta, including heterotrophic cells such as those of the genus *Prototheca*.

Beta-Ketoacyl-CoA synthase and elongase enzymes suitable for use with the microbes and methods of the invention include, without limitation, those listed in Table 5.

TABLE 5

| Beta-Ketoacyl-CoA synthases and elongases listed with GenBank accession numbers. |
|---|
| *Trypanosoma brucei* elongase 3 (GenBank Accession No. AAX70673), *Marchanita polymorpha* (GenBank Accession No. AAP74370), *Trypanosoma cruzi* fatty acid elongase, putative (GenBank Accession No. EFZ33366), *Nannochloropsis oculata* fatty acid elongase (GenBank Accession No. ACV21066.1), *Leishmania donovani* fatty acid elongase, putative (GenBank Accession No. CBZ32733.1), *Glycine max* 3-ketoacyl-CoA synthase 11-like (GenBank Accession No. XP_003524525.1), *Medicago truncatula* beta-ketoacyl-CoA synthase (GenBank Accession No. XP_003609222), *Zea mays* fatty acid elongase (GenBank Accession No. ACG36525), *Gossypium hirsutum* beta-ketoacyl-CoA synthase (GenBank Accession No. ABV60087), *Helianthus annuus* beta-ketoacyl-CoA synthase (GenBank Accession No. ACC60973.1), *Saccharomyces cerevisiae* ELO1 (GenBank Accession No. P39540), *Simmondsia chinensis* beta-ketoacyl-CoA synthase (GenBank Accession No. AAC49186), *Tropaeolum majus* putative fatty acid elongase (GenBank Accession No. AAL99199, *Brassica napus* fatty acid elongase (GenBank Accession No. AAA96054) |

In an embodiment of the invention, an exogenous gene encoding a beta-ketoacyl-CoA synthase or elongase enzyme having preferential specificity for elongating an acyl substrate comprising a specific number of carbon atoms and/or a specific degree of acyl chain saturation is introduced into a oleaginous cell so as to produce a cell or an oil enriched in fatty acids of specified chain length and/or saturation. Example 40 describes engineering of *Prototheca* strains in which exogenous elongases with preferences for extending midchain fatty acyl-CoAs have been overexpressed to increase the concentration of stearate. Examples 42 and 54 describe engineering of *Prototheca* in which exogenous elongases or beta-ketoacyl-CoA synthases with preferences for extending monounsaturated and saturated C18- and C20-CoA substrates are overexpressed to increase the concentration of erucic acid.

In specific embodiments, the oleaginous cell produces an oil comprising greater than 0.5, 1, 2, 5, 10, 20, 30, 40, 50, 60 70, or 80% erucic and/or eicosenoic acid. Alternately, the cell produces an oil comprising 0.5-5, 5-10, 10-15, 15-20, 20-30, 30-40, 40-50, 50-60, 60-70, 70-80, 80-90, or 90-99% erucic or eicosenoic acid. The cell may comprise recombinant acids described above in connection with high-oleic oils with a further introduction of an exogenous beta-ketoacyl-CoA synthase that is active in elongating oleoyl-CoA. As a result of the expression of the exogenous beta-ketoacyl-CoA synthase, the natural production of erucic or eicosenoic acid by the cell can be increased by more than 2, 3, 4, 5, 10, 20, 30, 40, 50, 70, 100, 130, 170 or 200 fold. The high erucic and/or eicosenoic oil can also be a high stability oil; e.g., one comprising less than 5, 4, 3, 2, or 1% polyunsaturates. In a specific embodiment, the cell is a microalgal cell, optionally cultivated heterotrophically. As in the other embodiments, the fat can be produced by genetic engineering of a plastidic cell, including heterotrophic microalgae of the phylum Chlorophyta, the class Trebouxiophytae, the order Chlorellales, or the family Chlorellacae. Preferably, the cell is oleaginous and capable of accumulating at least 40% oil by dry cell weight. The cell can be an obligate heterotroph, such as a species of *Prototheca*, including *Prototheca moriformis* or *Prototheca* zopfii.

VII. Regiospecific and Stereospecific Oils/Fats

In an embodiment, a recombinant cell produces a natural fat or oil having a given regiospecific makeup. As a result, the cell can produce triglyceride fats having a tendency to form crystals of a given polymorphic form; e.g., when heated to above melting temperature and then cooled to below melting temperature of the fat. For example, the fat may tend to form crystal polymorphs of the β or β' form (e.g., as determined by X-ray diffraction analysis), either with or without tempering. The fats may be ordered fats. In specific embodiments, the fat may directly form either β or β' crystals upon cooling; alternatively, the fat can proceed through a β form to a β' form. Such fats can be used as structuring laminating or coating fats for food applications. The natural fats can be incorporated into candy, dark or white chocolate, chocolate flavored confections, ice cream, margarines or other spreads, cream fillings, pastries, or other food products. Optionally, the fats can be semisolid yet free of artificially produced trans-fatty acids. Such fats can also be useful in skin care and other consumer or industrial products.

As in the other embodiments, the fat can be produced by genetic engineering of a plastidic cell, including heterotrophic microalgae of the phylum Chlorophyta, the class Trebouxiophytae, the order Chlorellales, or the family Chlorellacae. Preferably, the cell is oleaginous and capable of accumulating at least 40% oil by dry cell weight. The cell can be an obligate heterotroph, such as a species of *Prototheca*, including *Prototheca moriformis* or *Prototheca zopfii*. The fats can also be produced in autotrophic algae or plants. Optionally, the cell is capable of using sucrose to produce oil and a recombinant invertase gene may be introduced to allow metabolism of sucrose, as described in PCT Publications WO2008/151149, WO2010/06032, WO2011/150410, WO2011/150411, and international patent application PCT/US12/23696. The invertase may be codon optimized and integrated into a chromosome of the cell, as may all of the genes mentioned here.

In an embodiment, the natural fat has at least 30, 40, 50, 60, 70, 80, or 90% fat of the general structure [saturated fatty acid (sn-1)-unsaturated fatty acid (sn-2)-saturated fatty acid (sn-3)]. This is denoted below as Sat-Unsat-Sat fat. In a specific embodiment, the saturated fatty acid in this structure is preferably stearate or palmitate and the unsaturated fatty acid is preferably oleate. As a result, the fat can form primarily β or β' polymorphic crystals, or a mixture of these, and have corresponding physical properties, including those desirable for use in foods or personal care products. For example, the fat can melt at mouth temperature for a food product or skin temperature for a cream, lotion or other personal care product (e.g., a melting temperature of 30 to 40, or 32 to 35° C.). Optionally, the fats can have a 2 L or 3 L lamellar structure (e.g., as determined by X-ray diffraction analysis). Optionally, the fat can form this polymorphic form without tempering.

In a specific related embodiment, a natural fat triglyceride has a high concentration of SOS (i.e. triglyceride with stearate at the terminal sn-1 and sn-3 positions, with oleate at the sn-2 position of the glycerol backbone). For example, the fat can have triglycerides comprising at least 50, 60, 70, 80 or 90% SOS. In an embodiment, the fat has triglyceride of at least 80% SOS. Optionally, at least 50, 60, 70, 80 or 90% of the sn-2 linked fatty acids are unsaturated fatty acids. In a specific embodiment, at least 95% of the sn-2 linked fatty acids are unsaturated fatty acids. In addition, the SSS (tri-stearate) level can be less than 20, 10 or 5% and/or the C20:0 fatty acid (arachidic acid) level may be less than 6%, and optionally greater than 1% (e.g., from 1 to 5%). For example, in a specific embodiment, a natural fat produced by a recombinant cell has at least 70% SOS triglyceride with at least 80% sn-2 unsaturated fatty acyl moieties. In another specific embodiment, a natural fat produced by a recombinant cell has TAGs with at least 80% SOS triglyceride and with at least 95% sn-2 unsaturated fatty acyl moieties. In yet another specific embodiment, a natural fat produced by a recombinant cell has TAGs with at least 80% SOS, with at least 95% sn-2 unsaturated fatty acyl moieties, and between 1 to 6% C20 fatty acids.

In yet another specific embodiment, the sum of the percent stearate and palmitate in the fatty acid profile of the natural fat is twice the percentage of oleate, ±10, 20, 30 or 40% [e.g., (% P+% S) % O=2.0±20%]. Optionally, the sn-2 profile of this fat is at least 40%, and preferably at least 50, 60, 70, or 80% oleate. Also optionally, this fat may be at least 40, 50, 60, 70, 80, or 90% SOS. Optionally, the fat comprises between 1 to 6% C20 fatty acids.

In any of these embodiments, the high SatUnsatSat fat may tend to form β' polymorphic crystals. Unlike previously available plant fats like cocoa butter, the SatUnsatSat fat produced by the cell may form β' polymorphic crystals without tempering. In an embodiment, the polymorph forms upon heating to above melting temperature and cooling to less that the melting temperature for 3, 2, 1, or 0.5 hours. In a related embodiment, the polymorph forms upon heating to above 60° C. and cooling to 10° C. for 3, 2, 1, or 0.5 hours.

In various embodiments the fat forms polymorphs of the β form, β' form, or both, when heated above melting temperature and the cooled to below melting temperature, and optionally proceeding to at least 50% of polymorphic equilibrium within 5, 4, 3, 2, 1, 0.5 hours or less when heated to above melting temperature and then cooled at 10° C. The fat may form β' crystals at a rate faster than that of cocoa butter.

Optionally, any of these fats can have less than 2 mole % diacylglycerol, or less than 2 mole % mono and diacylglycerols, in sum.

In an embodiment, the fat may have a melting temperature of between 30-60° C., 30-40° C., 32 to 37° C., 40 to 60° C. or 45 to 55° C. In another embodiment, the fat can have a solid fat content (SFC) of 40 to 50%, 15 to 25%, or less than 15% at 20° C. and/or have an SFC of less than 15% at 35° C.

The cell used to make the fat may include recombinant nucleic acids operable to modify the saturate to unsaturate ratio of the fatty acids in the cell triglyceride in order to favor the formation of SatUnsatSat fat. For example, a knock-out or knock-down of stearoyl-ACP desaturase (SAD) gene can be used to favor the formation of stearate over oleate or expression of an exogenous mid-chain-preferring acyl-ACP thioesterase can increase the levels mid-chain saturates. Alternately a gene encoding a SAD enzyme can be overexpressed to increase unsaturates.

In a specific embodiment, the cell has recombinant nucleic acids operable to elevate the level of stearate in the cell. As a result, the concentration of SOS may be increased. Example 9 demonstrates that the regiospecific profile of the recombinant microbe is enriched for the SatUnsatSat triglycerides POP, POS, and SOS as a result of overexpressing a *Brassica napus* C18:0-preferring thioesterase. An additional way to increase the stearate of a cell is to decrease oleate levels. For cells having high oleate levels (e.g., in excess of one half the stearate levels) one can also employ recombinant nucleic acids or classical genetic mutations operable to decrease oleate levels. For example, the cell can have a knockout, knockdown, or mutation in one or more FATA alleles, which encode an oleate liberating acyl-ACP thioesterase, and/or one or more alleles encoding a stearoyl ACP desaturase (SAD). Example 35 describes the inhibition of SAD2 gene product expression using hairpin RNA to produce a fatty acid profile of 37% stearate in *Prototheca moriformis* (UTEX 1435), whereas the wildtype strain produced less than 4% stearate, a more than 9-fold improvement. Moreover, while the strains of Example 35 are engineered to reduce SAD activity, sufficient SAD activity remains to produce enough oleate to make SOS, POP, and POS. See the TAG profiles of Example 47. In specific examples, one of multiple SAD encoding alleles may be knocked out and/or one or more alleles are downregulated using inhibition techniques such as antisense, RNAi, or siRNA, hairpin RNA or a combination thereof. In various embodiments, the cell can produce TAGs that have 20-30, 30-40, 40-50, 50-60, 60-70, 70-80, 80-90, or 90 to about 100% stearate. In other embodiments, the cells can produce TAGs that are 20-30, 30-40, 40-50, 50-60, 60-70, 70-80, 80-90, or 90 to about 100% SOS. Optionally, or in addition to genetic modification, stearoyl ACP desaturase can be inhibited chemically; e.g., by addition of sterculic acid to the cell culture during oil production.

Surprisingly, knockout of a single FATA allele has been found to increase the presence of C18 fatty acids produced in microalgae. By knocking out one allele, or otherwise suppressing the activity of the FATA gene produce (e.g., using hairpin) RNA, while also suppressing the activity of stearoyl-ACP desaturase (using techniques disclosed herein), stearate levels in the cell can be increased.

Another genetic modification to increase stearate levels includes increasing a ketoacyl ACP synthase (KAS) activity in the cell so as to increase the rate of stearate production. It has been found that in microalgae, increasing KASII activity is effective in increasing C18 synthesis and particularly effective in elevating stearate levels in cell triglyceride in combination with recombinant DNA effective in decreasing SAD activity. Recombinant nucleic acids operable to increase KASII (e.g, an exogenous KasII gene) can be also be combined with a knockout or knockdown of a FatA gene, or with knockouts or knockdowns of both a FatA gene and a SAD gene).

Optionally, the cell can include an exogenous stearate liberating acyl-ACP thioesterase, either as a sole modification or in combination with one or more other stearate-increasing genetic modifications. For example the cell be may engineered to overexpress an acyl-ACP thioesterase with preference for cleaving C18:0-ACPs. Example 9 describes the expression of exogenous C18:0-preferring acyl-ACP thioesterases to increase stearate in the fatty acid profile of *Prototheca moriformis* (UTEX 1435) from about 3.7% to about 30.4%. Example 41 provides additional examples of C18:0-preferring acyl-ACP thioesterases function to elevate C18:0 levels in *Prototheca*. Introduction of the thioesterase can be combined with a knockout or knockdown of one or more endogenous acyl-ACP thioesterase alleles. Introduction of the thioesterase can also be combined with overexpression of an elonagase or beta-ketoacyl-CoA synthase. In addition, one or more exogenous genes (e.g., encoding SAD or KASII) can be regulated via an environmental condition (e.g., by placement in operable linkage with a regulatable promoter). In a specific example, pH and/or nitrogen level is used to regulate an amt03 promoter. The environmental condition may then be modulated to tune the cell to produce the desired amount of stearate appearing in cell triglycerides (e.g., to twice the oleate concentration). As a result of these manipulations, the cell may exhibit an increase in stearate of at least 5, 10, 15, or 20 fold.

As a further modification alone or in combination with the other stearate increasing modifications, the cell can comprise recombinant nucleic acids operable to express an elongase or a beta-ketoacyl-CoA synthase. For example, overexpression of a C18:0-preferring acyl-ACP thioesterases may be combined with overexpression of a midchain-extending elongase or KCS to increase the production of stearate in the recombinant cell. One or more of the exogenous genes (e.g., enoding a thioesterase, elongase, or KCS) can be regulated via an environmental condition (e.g., by placement in operable likage with a regulatable promoter). In a specific example, pH and/or nitrogen level is used to regulate an amt03 promoter. The environmental condition may then be modulated to tune the cell to produce the desired amount of stearate appearing in cell triglycerides (e.g., to twice the oleate concentration). As a result of these manipulations, the cell may exhibit an increase in stearate of at least 5, 10, 15, or 20 fold. In addition to stearate, arachidic, behenic, lignoceric, and cerotic acids may also be produced.

In specific embodiments, due to the genetic manipulations of the cell to increase stearate levels, the ratio of stearate to oleate in the oil produced by the cell is 3:1±30% (i.e, in the range of 2.7:1 to 3.3:1), 3:1±20% or 3:1±10%.

Alternately, the cell can be engineered to favor formation of SatUnsatSat where Sat is palmitate or a mixture of palmitate and stearate. In this case introduction of an exogenous palmitate liberating acyl-ACP thioesterase can promote palmitate formation. In this embodiment, the cell can produce triglycerides, that are at least 30, 40, 50, 60, 70, or 80% POP, or triglycerides in which the sum of POP, SOS, and POS is at least 30, 40, 50, 60, 70, 80, or 90% of cell triglycerides. In other related embodiments, the POS level is at least 30, 40, 50, 60, 70, 80, or 90% of the triglycerides produced by the cell.

In a specific embodiment, the melting temperature of the oil is similar to that of cocoa butter (about 30-32° C.). The POP, POS and SOS levels can approximate cocoa butter at about 16, 38, and 23% respectively. For example, POP can be 16%±20%, POS can be 38%±20%, and SOS can be 23%±20%. Or, POP can be 16%±15%, POS can be 38%±15%, an SOS can be 23%±15%. Or, POP can be 16%±10%, POS can be 38%±10%, an SOS can be 23%±10%.

As a result of the recombinant nucleic acids that increase stearate, a proportion of the fatty acid profile may be arachidic acid. For example, the fatty acid profile can be 0.01% to 5%, 0.1 to 4%, or 1 to 3% arachidic acid. Furthermore, the regiospecific profile may have 0.01% to 4%, 0.05% to 3%, or 0.07% to 2% AOS, or may have 0.01% to 4%, 0.05% to 3%, or 0.07% to 2% AOA. It is believed that AOS and AOA may reduce blooming and fat migration in confection comprising the fats of the present invention, among other potential benefits.

In addition to the manipulations designed to increase stearate and/or palmitate, and to modify the SatUnsatSat levels, the levels of polyunsaturates may be suppressed, including as described above by reducing delta 12 fatty acid desaturase activity (e.g., as encoded by a Fad gene) and optionally supplementing the growth medium or regulating FAD expression. It has been discovered that, in microalgae (as evidenced by work in *Prototheca* strains), polyunsaturates are preferentially added to the sn-2 position. Thus, to elevate the percent of triglycerides with oleate at the sn-2 position, production of linoleic acid by the cell may be suppressed. The techniques described herein, in connection with highly oxidatively stable oils, for inhibiting or ablating fatty acid desaturase (FAD) genes or gene products may be applied with good effect toward producing SatUnsatSat oils by reducing polyunsaturates at the sn-2 position. As an added benefit, such oils can have improved oxidatively stability. As also described herein, the fats may be produced in two stages with polyunsaturates supplied or produced by the cell in the first stage with a deficit of polyunsaturates during the fat producing stage. The fat produced may have a fatty acid profile having less than or equal to 15, 10, 7, 5, 4, 3, 2, 1, or 0.5% polyunsaturates. In a specific embodiment, the oil/fat produced by the cell has greater than 50% SatUnsatSat, and optionally greater than 50% SOS, yet has less than 3% polyunsaturates. Optionally, polyunsaturates can be approximated by the sum of linoleic and linolenic acid area % in the fatty acid profile.

In an embodiment, the natural fat is a shea stearin substitute having 65% to 95% SOS and optionally 0.001 to 5% SSS. In a related embodiment, the fat has 65% to 95% SOS, 0.001 to 5% SSS, and optionally 0.1 to 8% arachidic acid containing triglcyerides. In another related embodiment, the fat has 65% to 95% SOS and the sum of SSS and SSO is less than 10% or less than 5%.

The cell's regiospecific preference can be learned using the analytical method described below (Examples 1-2, 8). Despite balancing the saturates and unsaturates as describe above, it is possible that the cell enzymes do not place the unsaturated fatty acid at the sn-2 position. In this case, genetic manipulations can confer the desired regiospecificity by (i) reducing the activity of endogenous sn-2 specific acyl transferases (e.g., LPAAT) and/or (ii) introducing an exogenous LPAAT with the desired specificity (i.e., introduction of oleate at sn-2). Where an exogenous LPAAT is introduced, preferably the gene encoding the LPAAT is integrated into a host chromosome and is targeted to the endoplasmic reticulum. In some cases, the host cell may have both specific and non-specific LPAAT alleles and suppressing the activity of one of these alleles (e.g., with a gene knockout) will confer the desired specificity. For example, genes encoding the LPAATs of SEQ ID NO: 78 and SEQ ID NO: 79 or an LPAAT comprising at least 90, 95, 98, or 99% amino acid identity to either of these sequences can be used to add oleate to the sn-2 position in order to boost the levels of SatUnsatSat TAGs. The genes can have at least 80, 85, 90, 95, 96, 97, 98, or 99% nucleotide identity to any of SEQ ID NOs: 80 to 85 or equivalent sequences by virtue of the degeneracy of the genetic code. These genes can be manifest as recombinant nucleic acid constructs, vectors, chromosomes or host cells comprising these sequences or functional fragments thereof, which can be found by systematic deletion of nucleic acid from the sequences using known techniques. As a result of expression of the genes, the amount of sat-unsat-sat TAGs such as SOS, POS, POP, or triglycerides with C8 to C16 fatty acids at the sn-2 position can be increased in a host cell.

In an embodiment, fats produced by cells according to the invention are used to produce a confection, candy coating, or other food product. As a result, a food product like a chocolate or candy bar may have the "snap" (e.g., when broken) of a similar product produced using cocoa butter. The fat used may be in a beta polymorphic form or tend to a beta polymorphic form. In an embodiment, a method includes adding such a fat to a confection. Optionally, the fat can be a cocoa butter equivalent per EEC regulations, having greater than 65% SOS, less than 45% unsaturated fatty acid, less than 5% polyunsaturated fatty acids, less than 1% lauric acid, and less than 2% trans fatty acid. The fats can also be used as cocoa butter extenders, improvers, replacers, or anti-blooming agents, or as shea butter replacers, including in food and personal care products. High SOS fats produced using the cells and methods disclosed here can be used in any application or formulation that calls for shea butter or shea fraction. However, unlike shea butter, fats produced by the embodiments of the invention can have low amounts of unsaponifiables; e.g. less than 7, 5, 3, or 2% unsaponifiables. In addition, shea butter tends to degrade quickly due to the presence of diacylglycerides whereas fats produced by the embodiments of the invention can have low amounts of diacylglycerides; e.g., less than 5, 4, 3, 2, 1, or 0.5% diacylglycerides.

In an embodiment of the invention there is a natural fat suitable as a shortening, and in particular, as a roll-in shortening. Thus, the shortening may be used to make pastries or other multi-laminate foods. The shortening can be produced using methods disclosed herein for producing engineered organisms and especially heterotrophic microalgae. In an embodiment, the shortening has a melting temperature of between 40 to 60° C. and preferably between 45-55° C. and can have a triglyceride profile with 15 to 20% medium chain fatty acids (C8 to C14), 45-50% long chain saturated fatty acids (C16 and higher), and 30-35% unsaturated fatty acids (preferably with more oleic than linoleic). The shortening may form β' polymorphic crystals, optionally without passing through the β polymorphic form. The shortening may be thixotrophic. The shortening may have a solid fat content of less than 15% at 35° C. In a specific embodiment, there is a natural oil suitable as a roll-in shortening produced by a recombinant microalga, where the oil has a yield stress between 400 and 700 or 500 and 600 Pa and a storage modulus of greater than $1\times10^5$ Pa or $1\times10^6$ Pa. (see Example 46)

A structured solid-liquid fat system can be produced using the structuring oils by blending them with an oil that is a liquid at room temperature (e.g., an oil high in tristearin or triolein). The blended system may be suitable for use in a food spread, mayonnaise, dressing, shortening; i.e. by forming an oil-water-oil emulsion. The structuring fats according to the embodiments described here, and especially those high in SOS, can be blended with other oils/fats to make a cocoa butter equivalent, replacer, or extender. For example, a natural fat having greater than 65% SOS can be blended with palm mid-fraction to make a cocoa butter equivalent.

In general, such high Sat-Unsat-Sat fats or fat systems can be used in a variety of other products including whipped toppings, margarines, spreads, salad dressings, baked goods (e.g. breads, cookies, crackers muffins, and pastries), cheeses, cream cheese, mayonnaise, etc.

In a specific embodiment, a Sat-Unsat-Sat fat described above is used to produce a margarine, spread, or the like. For example, a margarine can be made from the fat using any of the recipes or methods found in U.S. Pat. Nos. 7,118,773, 6,171,636, 4,447,462, 5,690,985, 5,888,575, 5,972,412, 6,171,636, or international patent publications WO9108677A1.

In an embodiment, a fat comprises a natural (e.g., from microalgal cells) fat optionally blended with another fat and is useful for producing a spread or margarine or other food product is produced by the genetically engineered cell and has glycerides derived from fatty acids which comprises:

(a) at least 10 weight % of C18 to C24 saturated fatty acids,
(b) which comprise stearic and/or arachidic and/or behenic and/or lignoceric acid and
(c) oleic and/or linoleic acid, while
(d) the ratio of saturated C18 acid/saturated (C20+C22+C24)-acids≥1, preferably ≥5, more preferably ≥10, which glycerides contain:
(e) ≤5 weight % of linolenic acid calculated on total fatty acid weight
(f) ≤5 weight % of trans fatty acids calculated on total fatty acid weight
(g) ≤75 weight %, preferably ≤60 weight % of oleic acid at the sn-2 position: which glycerides contain calculated on total glycerides weight
(h) ≥8 weight % HOH+HHO triglycerides
(i) ≤5 weight % of trisaturated triglycerides, and optionally one or more of the following properties:
(j) a solid fat content of >10% at 10° C.
(k) a solid fat content ≤15% at 35° C.,
(l) a solid fat content of >15% at 10° C. and a solid fat content ≤25% at 35° C.,
(m) the ratio of (HOH+HHO) and (HLH+HHL) triglycerides is >1, and preferably >2,
where H stands for C18-C24 saturated fatty acid, O for oleic acid, and L for linoleic acid.

Optionally, the solid content of the fat (% SFC) is 11 to 30 at 10° C., 4 to 15 at 20° C., 0.5 to 8 at 30° C., and 0 to 4 at 35° C. Alternately, the % SFC of the fat is 20 to 45 at 10° C., 14 to 25 at 20° C., 2 to 12 at 30° C., and 0 to 5 at 35° C. In related embodiment, the % SFC of the fat is 30 to 60 at 10° C., 20 to 55 at 20° C., 5 to 35 at 30° C., and 0 to 15 at 35° C. The C12-C16 fatty acid content can be ≤15 weight %. The fat can have ≤5 weight % disaturated diglycerides.

In related embodiments there is a spread, margarine or other food product made with the natural oil or natural oil blend. For example, the natural fat can be used to make an edible W/O emulsion spread comprising 70-20 wt. % of an aqueous phase dispersed in 30-80 wt. % of a fat phase which fat phase is a mixture of 50-99 wt. % of a vegetable triglyceride oil A and 1-50 wt. % of a structuring triglyceride fat B, which fat consists of 5-100 wt. % of a hardstock fat C and up to 95 wt. % of a fat D, where at least 45 wt. % of the hardstock fat C triglycerides consist of SatOSat triglycerides and where Sat denotes a fatty acid residue with a saturated C18-C24 carbon chain and O denotes an oleic acid residue and with the proviso that any hardstock fat C which has been obtained by fractionation, hydrogenation, esterification or interesterification of the fat is excluded. The hardstock fat can be a natural fat produced by a cell according to the methods disclosed herein. Accordingly, the hardstock fat can be a fat having a regiospecific profile having at least 50, 60, 70, 80, or 90% SOS. The W/O emulsion can be prepared to methods known in the art including in U.S. Pat. No. 7,118,773.

In related embodiment, the cell also expresses an endogenous hydrolyase enzyme that produces ricinoleic acid. As a result, the oil (e.g., a liquid oil or structured fat) produced may be more easily emulsified into a margarine, spread, or other food product or non-food product. For example, the oil produced may be emulsified using no added emulsifiers or using lower amounts of such emulsifiers. The U.S. patent application Ser. No. 13/365,253 discloses methods for expressing such hydroxylases in microalgae and other cells. In specific embodiments, a natural oil comprises at least 1, 2, or 5% SRS, where S is stearate and R is ricinoleic acid.

In an alternate embodiment, a natural oil that is a cocoa butter mimetic as described above can be fractionated to remove trisaturates (e.g., tristearin and tripalmitin, SSP, and PPS). For example, it has been found that microalgae engineered to decrease SAD activity to increase SOS concentration make an oil that can be fractionated to remove trisaturated. See Example 47. In specific embodiments, the melting temperature of the fractionated natural oil is similar to that of cocoa butter (about 30-32° C.). The POP, POS and SOS levels can approximate cocoa butter at about 16, 38, and 23% respectively. For example, POP can be 16%±20%, POS can be 38%±20%, an SOS can be 23%±20%. Or, POP can be 16%±15%, POS can be 38%±15%, an SOS can be 23%±15%. Or, POP can be 16%±10%, POS can be 38%±10%, an SOS can be 23%±10%. In addition, the tristearin levels can be less than 5% of the triacylglycerides.

VIII. High Mid-Chain Oils

In an embodiment of the present invention, the cell has recombinant nucleic acids operable to elevate the level of midchain fatty acids (e.g., C8:0, C10:0, C12:0, C14:0, or C16:0 fatty acids) in the cell or in the oil of the cell. One way to increase the levels of midchain fatty acids in the cell or in the oil of the cell is to engineer a cell to express an exogenous acyl-ACP thioesterase that has activity towards midchain fatty acyl-ACP substrates (e.g., one encoded by a FatB gene), either as a sole modification or in combination with one or more other genetic modifications. An additional genetic modification to increase the level of midchain fatty acids in the cell or oil of the cell is the expression of an exogenous lysophosphatidic acid acyltransferase gene encoding an active lysophosphatidic acid acyltransferase (LPAAT) that catalyzes the transfer of a mid-chain fatty-acyl group to the sn-2 position of a substituted acylglyceroester. In a specific related embodiment, both an exogenous acyl-ACP thioesterase and LPAAT are stably expressed in the cell. In an embodiment, recombinant nucleic acids are introduced into an oleaginous cell (and especially into a plastidic microbial cell) that cause expression of an exogenous mid-chain-specific thioesterase and an exogenous LPAAT that catalyzes the transfer of a mid-chain fatty-acyl group to the sn-2 position of a substituted acylglyceroester. As a result, the cell can be made to increase the percent of a midchain fatty acid in the TAGs that it produces by 10, 20 30, 40, 50, 60, 70, 80, 90-fold, or more. Introduction of the exogenous LPAAT can increase midchain fatty acids at the sn-2 position by 1.2, 1.5, 1.7, 2, 3, 4 fold or more compared to introducing an exogenous mid-chain preferring acyl-ACP thioesterase alone. In an embodiment, the mid-chain fatty acid is greater than 30, 40, 50 60, 70, 80, or 90% of the TAG fatty acids produced by the cell. In various embodiments, the mid-chain fatty acid is lauric, myristic, or palmitic. Examples 3, 43, and 44 describe expression of plant LPAATs in microalgal cells with resulting alterations in fatty acid profiles. As in the examples, the cells can also express an exogenous acyl-ACP thioesterase (which can also be from a plant) with a preference for a given fatty acyl-ACP chain length. For example, a microalgal cell can comprise exogenous genes encoding a LPAAT and an acyl-ACP thioesterase that preferentially cleave C8, C10, C12, C14, C8-C12, or C8-C10 fatty acids. In a specific embodiment, such a cell is capable of producing a natural oil with a fatty acid profile comprising 10-20, 20-30, 30-40, 40-50, 50-60, 60-70, 70-80, 80-90, or 90-99%, >20%, >30%, >40%, ≥50%, >60%, >70%, >80% or >90% C8, C10, C12, C14, C8-C12, or C8-C10 fatty acids. Other LPAATs can preferentially cleave C16 or C18 fatty acids (see Example 44). Further genetic manipulation of the fatty acid desaturase pathway (e.g., as described infra) can increase the stability of the oils.

Any of these natural oils can be interesterified. Interesterification can, for example, be used to lower the melting temperature or pour-point of the oil. In a specific embodiment, the natural oil comprises at least 50% of the sum of caprylic anc capric acids and may be interesterified to reduce the pour point and/or kinematic viscosity. Such an oil (natural or interesterified) can optionally be a high stability oil comprising, for example, less than 2% polyunsaturated fatty acids.

Alternately, or in addition to expression of an exogenous LPAAT, the cell may comprise recombinant nucleic acids that are operable to express an exogenous KASI or KASIV enzyme and optionally to decrease or eliminate the activity of a KASII, which is particularly advantageous when a mid-chain-preferring acyl-ACP thioesterase is expressed. Example 37 describes the engineering of *Prototheca* cells to overexpress KASI or KASIV enzymes in conjunction with a mid-chain preferring acyl-ACP thioesterase to generate strains in which production of C10-C12 fatty acids is about 59% of total fatty acids. Mid-chain production can also be increased by suppressing the activity of KASI and/or KASII (e.g., using a knockout or knockdown). Example 38 details the chromosomal knockout of different alleles of *Prototheca moriformis* (UTEX 1435) KASI in conjunction with overexpression of a mid-chain preferring acyl-ACP thioesterase to achieve fatty acid profiles that are about 76% or 84% C10-C14 fatty acids. Example 39 provides recombinant cells and oils characterized by elevated midchain fatty acids as a result of expression of KASI RNA hairpin polynucleotides. In addition to any of these modifications, unsaturated or polyunsaturated fatty acid production can be suppressed (e.g., by knockout or knockdown) of a SAD or FAD enzyme.

In a particular embodiment, a recombinant cell produces TAG having 40% lauric acid or more. In another related embodiment, a recombinant cell produces TAG having a fatty acid profile of 40% or more of myristic, caprylic, capric, or palmitic acid. For example, an oleaginous recombinant clorophyte cell can produce 40% lauric or myristic acid in an oil that makes up 40, 50, or 60% or more of the cell's dry weight.

In a specific embodiment, a recombinant cell comprises nucleic acids operable to express a product of an exogenous gene encoding a lysophosphatidic acid acyltransferase that catalyzes the transfer of a mid-chain fatty-acyl group to the sn-2 position of a substituted acylglyceroester and nucleic acids operable to express a product of an acyl-ACP thioesterase exogenous gene encoding an active acyl-ACP thioesterase that catalyzes the cleavage of mid-chain fatty acids from ACP. As a result, in one embodiment, the oil produced can be characterized by a fatty acid profile elevated in C10 and C12 fatty acids and reduced in C16, C18, and C18:1 fatty acids as a result of the recombinant nucleic acids. See Example 3, in which overexpression of a *Cuphea wrightii* acyl-ACP thioesterase and a *Cocos nucifera* LPAAT gene increased the percentage of C12 fatty acids from about 0.04% in the untransformed cells to about 46% and increased the percentage of C10 fatty acids from about 0.01% in the untransformed cells to about 11%. In related embodiments, the increase in midchain fatty acid production is greater than 70%, from 75-85%, from 70-90%, from 90-200%, from 200-300%, from 300-400%, from 400-500%, or greater than 500%.

Average chain length can also be reduced by overexpression of a C18-specific acyl-ACP thioesterase. Recombinant nucleic acids operable to overexpress a C18 or other acyl-ACP thioesterase may be used alone or in combination with the other constructs described here to further reduce average chain length. Among other uses, the oils produced can be used as cooa-butter/milkfat substitute. See Example 45 and the discussion of FIG. 17. In an embodiment, one of the above described high mid-chain producing cells is further engineered to produce a low polyunsaturated oil by knocking out or knocking down one or more fatty acyl desturases, as described above in section IV. Accordingly, the oil produced can have the high stability characteristic mentioned in that section or in corresponding Examples. In a specific embodiment, the cell produces an oil comprising greater than 30% midchain fatty acids and 5% or less polyunsaturates. In a related embodiment, the cell produces an oil comprising greater than 40% midchain fatty acids and 4% or less polyunsaturates. In a further related embodiment, the cell produces an oil comprising greater than 50% midchain fatty acids and 3% or less polyunsaturates.

The high mid-chain oils or fatty acids derived from hydrolysis of these oils may be particularly useful in food, fule and oleochemical applications including the production of lubricants and surfactants. For example, fatty acids derived from the cells can be esterified, cracked, reduced to an aldehyde or alcohol, aminated, sulfated, sulfonated, or subjected to other chemical process known in the art.

In some embodiments, the natural oil is interesterified and the kinematic viscosity of the interesterified natural oil is less than 30, 20, 15, 10, 9, 8, 7, 6, 5, 4, 3, 2, or 1 centiStokes at 40° C. In some embodiments, the kinematic viscosity is less than 3 centiStokes at 40° C. In some embodiments, the pour point of an interesterified natural oil is less than, 5° C., 0° C., −10° C., −12° C., −15° C., −20° C., −25° C., −30° C., −35° C., −40° C., −45° C., or −50° C. In some embodiments, the pour point is less than −10° C. In some embodiments, the pour point is less than −20° C.

Example 53 describes the use of a plant FatB gene in algae to produce oils in microalgae with greater than 60% myristate. In an embodiment, a gene encoding a protein having at least 90, 95, 96, 97, 98, or 99% amino acid identity to SEQ ID NO:87 or SEQ ID NO:89 is used, optionally in combination with a mid-chain preferred LPAAT as described above.

IX. High Oleic/Palmitic Oil

In another embodiment, there is a high oleic oil with about 60% oleic acid, 25% palmitic acid and optionally 5% polyunsaturates or less. The high oleic oil can be produced using the methods disclosed in U.S. patent application Ser. No.

13/365,253, which is incorporated by reference in relevant part. For example, the cell can have nucleic acids operable to suppress an acyl-ACP thioesterase (e.g., knockout or knockdown of a gene encoding FATA) while also expressing an gene that increases KASII activity. The cell can have further modifications to inhibit expression of delta 12 fatty acid desaturase, including regulation of gene expression as described above. As a result, the polyunsaturates can be less than or equal to 5, 4, 3, 2, or 1 area %.

X. Low Saturate Oil

In an embodiment, a natural oil is produced from a recombinant cell. The oil produced has a fatty acid profile that has less that 4%, 3%, 2%, 1% (area %), saturated fatty acids. In a specific embodiment, the oil has 0.1 to 3.5% saturated fatty acids. Certain of such oils can be used to produce a food with negligible amounts of saturated fatty acids. Optionally, these oils can have fatty acid profiles comprising at least 90% oleic acid or at least 90% oleic acid with at least 3% polyunsaturated fatty acids. In an embodiment, a natural oil produced by a recombinant cell comprises at least 90% oleic acid, at least 3% of the sum of linoleic and linolenic acid and has less than 3.5% saturated fatty acids. In a related embodiment, a natural oil produced by a recombinant cell comprises at least 90% oleic acid, at least 3% of the sum of linoleic and linolenic acid and has less than 3.5% saturated fatty acids, the majority of the saturated fatty acids being comprised of chain length 10 to 16. These oils may be produced by recombinant oleaginous cells including but not limited to those described here and in U.S. patent application Ser. No. 13/365,253. For example, overexpression of a KASII enzyme in a cell with a highly active SAD can produce a high oleic oil with less than or equal to 3.5% saturates. Optionally, an oleate-specific acyl-ACP thioesterase is also overexpressed and/or an endogenous thioesterase having a propensity to hydrolyze acyl chains of less than C18 knocked out or suppressed. The oleate-specific acyl-ACP thioesterase may be a transgene with low activity toward ACP-palmitate and ACP-stearate so that the ratio of oleic acid relative to the sum of palmitic acid and stearic acid in the fatty acid profile of the oil produced is greater than 3, 5, 7, or 10. Alternately, or in addition, a FATA gene may be knocked out or knocked down, as in Example 36 below. A FATA gene may be knocked out or knocked down and an exogenous KASII overexpressed. Another optional modification is to increase KASI and/or KASIII activity, which can further suppress the formation of shorter chain saturates. Optionally, one or more acyltransferases (e.g., an LPAAT) having specificity for transferring unsaturated fatty acyl moieties to a substituted glycerol is also overexpressed and/or an endogenous acyltransferase is knocked out or attenuated. An additional optional modification is to increase the activity of KCS enzymes having specificity for elongating unsaturated fatty acids and/or an endogenous KCS having specificity for elongating saturated fatty acids is knocked out or attenuated. Optionally, oleate is increased at the expense of linoleate production by knockout or knockdown of a delta 12 fatty acid desaturase; e.g., using the techniques of Section IV of this patent application.

As described in Example 51, levels of saturated fats may also be reduced by introduction of an exogenous gene that desaturates palmitic acid to palmitoleic acid. Examples of suitable genes for use in the oleaginous cells are found in the plants, including Macfadyena unguis (Cat's claw), *Macadamia integrifolia* (Macadamia nut) and *Hippophae rhamnoides* (sea buckthorn). Variant exogenous or endogenous SADs that desaturate palmitoyl-ACP can also be used and are further discussed in Example 51. Optionally, the PAD or SAD gene has at least 95% amino acid sequence identity to the gene product described in Example 51. This modification can be used alone, or in combination with oleate-increasing modifications such as those described immediately above, in section IX and in the Examples, including knockout or knockdown of one or more endogenous FATA alleles and/or overexpression of KASII. In one embodiment, an oleaginous cell such as an oleaginous microalgae has a combination of (i) a FATA knockout or knockdown with (ii) expression of an exogenous PAD gene (this could also be a variant SAD with PAD activity, see Example 55) and/or a mutation in an endogenous SAD gene to give PAD activity. Such as cell may further comprise an overexpressed endogenous or exogenous KASII gene. In accordance with any of these embodiments of the invention, the oleaginous cell produces an oil having a fatty acid profile with 1-2, 2-3, 3-4, 5-6, 7-8, 9-10, 10-15, 15-20, 20-30, 30-40, 40-60, 60-70, 70-80, 80-90, or 90-100 area percent palmitoleic acid. In a specific embodiment, the cell produces greater than 50% oleic acid, greater than 1% palmitoleic acid, and 3.5 area % or less of saturated fatty acids.

In addition to the above genetic modifications, the low saturate oil can be a high-stability oil by virtue of low amounts of polyunsaturated fatty acids. Methods and characterizations of high-stability, low-polyunsaturated oils are described in the section above entitled Low Polyunsaturated Oils, including method to reduce the activity of endogenous Δ12 fatty acid desaturase. In a specific embodiment, an oil is produced by a oleaginous microbial cell having a type II fatty acid synthetic pathway and has no more than 3.5% saturated fatty acids and also has no more than 3% polyunsaturated fatty acids. In another specific embodiment, the oil has no more than 3% saturated fatty acids and also has no more than 2% polyunsaturated fatty acids. In another specific embodiment, the oil has no more than 3% saturated fatty acids and also has no more than 1% polyunsaturated fatty acids.

The low saturate and low saturate/high stability oil can be blended with less expensive oils to reach a targeted saturated fatty acid level at less expense. For example, an oil with 1% saturated fat can be blended with an oil having 7% saturated fat (e.g. high-oleic sunflower oil) to give an oil having 3% saturated fat.

Oils produced according to embodiments of the present invention can be used in the transportation fuel, oleochemical, and/or food and cosmetic industries, among other applications. For example, transesterification of lipids can yield long-chain fatty acid esters useful as biodiesel. Other enzymatic and chemical processes can be tailored to yield fatty acids, aldehydes, alcohols, alkanes, and alkenes. In some applications, renewable diesel, jet fuel, or other hydrocarbon compounds are produced. The present disclosure also provides methods of cultivating microalgae for increased productivity and increased lipid yield, and/or for more cost-effective production of the compositions described herein. The methods described here allow for the production of oils from plastidic cell cultures at large scale; e.g., 1000, 10,000, 100,000 liters or more.

In an embodiment, an oil extracted from the cell has 3.5%, 3%, 2.5%, or 2% saturated fat or less and is incorporated into a food product. The finished food product has 3.5, 3, 2.5, or 2% saturated fat or less.

XI. Cocoa Butter/Milk-Fat Blend Mimetics

Figure 17:
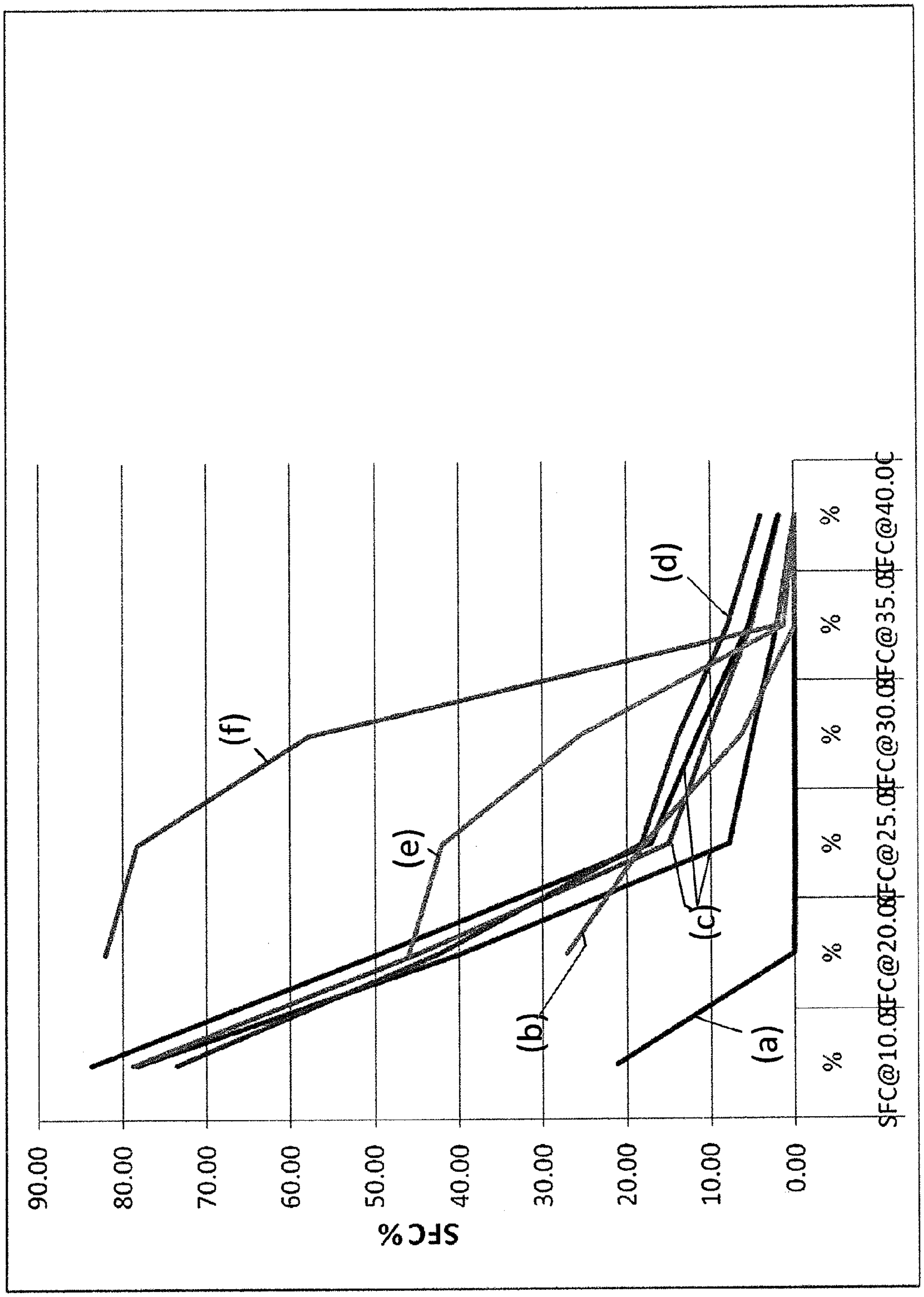
FIG. 17 shows a plot of percent solid fat content for various oils as follows: (a) *P. moriformis* RBD oil without lipid pathway engineering; (b) Brazilian cocoa butter +25% milkfat; (c) three replicates of *P. moriformis* RBD oil from a strain expressing hairpin nucleic acids that reduce levels of a SAD allele thus reducing oleic acid and increasing stearic acid in the TAG profile; (d) *P. moriformis* RBD oil from a strain overexpressing an endogenous OTE (oleoyl acyl-ACP thioesterase, see Example 45); (e) Malaysian cocoa butter +25% milkfat; and (f) Malaysian cocoa butter. The cocoa butter and cocoa butter milkfat values are literature values (Bailey's Industrial Oils and Fat Products, $6^{th}$ ed.).

In certain embodiments, the cell produces a natural oil that has a temperature-dependent solid fat content ("SFC-curve")

that approximates a blend of cocoa butter and milkfat. Such oils may be used where the cocoa butter/milkfat blend could be used; for example, in chocolates other confections, ice cream or other frozen desserts, pastries, or dough, including for quickbreads, or other baked goods. The oils may inhibit blooming, enhance flavor, enhance texture, or reduce costs. In a specific example, the natural oil approximates. Accordingly, an embodiment of the invention is using a natural oil from a recombinant microalgal cell to replace a cocoa butter/milkfat blend in a recipe. In a related embodiment, FIG. 17 shows a plot of % solid fat content for various oils as follows (a) *P. moriformis* RBD oil without lipid pathway engineering, (b) Brazilian cocoa butter +25% milkfat, (c) three replicates of *P. moriformis* RBD oil from a strain expressing hairpin nucleic acids that reduce levels of a SAD allele thus reducing oleic acid and increasing stearic acid in the TAG profile, (d) *P. moriformis* RBD oil from a strain overexpressing an endogenous OTE (oleoyl acyl-ACP thioesterase, see Example 45), (e) Malaysian cocoa butter +25% milkfat, and (f) Malaysian cocoa butter. The cocoa butter and cocoa butter milkfat values are literature values (Bailey's Industrial Oils and Fat Products, $6^{th}$ ed.)

In an embodiment of the present invention, a natural oil that is similar in thermal properties to a 75% cocoa butter/25% milkfat blend is produced by a microalgal or other cell described above. The cell comprises recombinant nucleic acids operable to alter the fatty acid profile of triglycerides produced by the cell so as that the oil has a solid fat content (e.g., as determined by NMR) of 38%±30% at 20° C., 32%±30% at 25° C., 17%±30% at 30° C., and less than 5%±30% at 35° C. For the sake of clarity, ±10% refers to percent of the percent SFC (e.g., 30% of 5% SFC is 1.5% SFC so the range is 3.5 to 6.5% SFC at 35° C.). In related embodiments, the oil has a solid fat content (e.g., as determined by NMR) of 38%±20% at 20° C., 32%±20% at 25° C., 17%±20% at 30° C., and less than 5%±20% at 35° C. or the oil has a solid fat content (e.g., as determined by NMR) of 38%±10% at 20° C., 32%±10% at 25° C., 17%±10% at 30° C., and less than 5%±10% at 35° C.

XII. Minor Oil Components

The oils produced according to the above methods in some cases are made using a microalgal host cell. As described above, the microalga can be, without limitation, fall in the classification of Chlorophyta, Trebouxiophyceae, Chlorellales, Chlorellaceae, or Chlorophyceae. It has been found that microalgae of Trebouxiophyceae can be distinguished from vegetable oils based on their sterol profiles. Oil produced by *Chlorella protothecoides* was found to produce sterols that appeared to be brassicasterol, ergosterol, campesterol, stigmasterol, and β-sitosterol, when detected by GC-MS. However, it is believed that all sterols produced by *Chlorella* have C24β stereochemistry. Thus, it is believed that the molecules detected as campesterol, stigmasterol, and β-sitosterol, are actually 22,23-dihydrobrassicasterol, proferasterol and clionasterol, respectively. Thus, the oils produced by the microalgae described above can be distinguished from plant oils by the presence of sterols with C24β stereochemistry and the absence of C24α stereochemistry in the sterols present. For example, the oils produced may contain 22,23-dihydrobrassicasterol while lacking campesterol; contain clionasterol, while lacking in β-sitosterol, and/or contain poriferasterol while lacking stigmasterol. Alternately, or in addition, the oils may contain significant amounts of $\Delta^7$-poriferasterol.

In one embodiment, the oils provided herein are not vegetable oils. Vegetable oils are oils extracted from plants and plant seeds. Vegetable oils can be distinguished from the non-plant oils provided herein on the basis of their oil content. A variety of methods for analyzing the oil content can be employed to determine the source of the oil or whether adulteration of an oil provided herein with an oil of a different (e.g. plant) origin has occurred. The determination can be made on the basis of one or a combination of the analytical methods. These tests include but are not limited to analysis of one or more of free fatty acids, fatty acid profile, total triacylglycerol content, diacylglycerol content, peroxide values, spectroscopic properties (e.g. UV absorption), sterol profile, sterol degradation products, antioxidants (e.g. tocopherols), pigments (e.g. chlorophyll), d13C values and sensory analysis (e.g. taste, odor, and mouth feel). Many such tests have been standardized for commercial oils such as the Codex Alimentarius standards for edible fats and oils.

Sterol profile analysis is a particularly well-known method for determining the biological source of organic matter. Campesterol, b-sitosterol, and stigamsterol are common plant sterols, with b-sitosterol being a principle plant sterol. For example, b-sitosterol was found to be in greatest abundance in an analysis of certain seed oils, approximately 64% in corn, 29% in rapeseed, 64% in sunflower, 74% in cottonseed, 26% in soybean, and 79% in olive oil (Gul et al. J. Cell and Molecular Biology 5:71-79, 2006).

Oil isolated from *Prototheca moriformis* strain UTEX1435 were separately clarified (CL), refined and bleached (RB), or refined, bleached and deodorized (RBD) and were tested for sterol content according to the procedure described in JAOCS vol. 60, no. 8, August 1983. Results of the analysis are shown below (units in mg/100 g):

| | Sterol | Crude | Clarified | Refined & bleached | Refined, bleached, & deodorized |
|---|---|---|---|---|---|
| 1 | Ergosterol | 384 (56%) | 398 (55%) | 293 (50%) | 302 (50%) |
| 2 | 5,22-cholestadien-24-methyl-3-ol (Brassicasterol) | 14.6 (2.1%) | 18.8 (2.6%) | 14 (2.4%) | 15.2 (2.5%) |
| 3 | 24-methylcholest-5-en-3-ol (Campersterol or 22,23-dihydrobrassicasterol) | 10.7 (1.6%) | 11.9 (1.6%) | 10.9 (1.8%) | 10.8 (1.8%) |
| 4 | 5,22-cholestadien-24-ethyl-3-ol (Stigmaserol or poriferasterol) | 57.7 (8.4%) | 59.2 (8.2%) | 46.8 (7.9%) | 49.9 (8.3%) |
| 5 | 24-ethylcholest-5-en-3-ol (β-Sitosterol or clionasterol) | 9.64 (1.4%) | 9.92 (1.4%) | 9.26 (1.6%) | 10.2 (1.7%) |
| 6 | Other sterols | 209 | 221 | 216 | 213 |
| | Total sterols | 685.64 | 718.82 | 589.96 | 601.1 |

These results show three striking features. First, ergosterol was found to be the most abundant of all the sterols, accounting for about 50% or more of the total sterols. The amount of ergosterol is greater than that of campesterol, β-sitosterol, and stigamsterol combined. Ergosterol is steroid commonly found in fungus and not commonly found in plants, and its presence particularly in significant amounts serves as a useful marker for non-plant oils. Secondly, the oil was found to contain brassicasterol. With the exception of rapeseed oil, brassicasterol is not commonly found in plant based oils. Thirdly, less than 2% β-sitosterol was found to be present. β-sitosterol is a prominent plant sterol not commonly found in microalgae, and its presence particularly in significant amounts serves as a useful marker for oils of plant origin. In summary, *Prototheca moriformis* strain UTEX1435 has been found to contain both significant amounts of ergosterol and only trace amounts of β-sitosterol as a percentage of total sterol content. Accordingly, the ratio of ergosterol:β-sitosterol or in combination with the presence of brassicasterol can be used to distinguish this oil from plant oils.

In some embodiments, the oil content of an oil provided herein contains, as a percentage of total sterols, less than 20%, 15%, 10%, 5%, 4%, 3%, 2%, or 1% β-sitosterol. In other embodiments the oil is free from β-sitosterol.

In some embodiments, the oil is free from one or more of β-sitosterol, campesterol, or stigmasterol. In some embodiments the oil is free from β-sitosterol, campesterol, and stigmasterol. In some embodiments the oil is free from campesterol. In some embodiments the oil is free from stigmasterol.

In some embodiments, the oil content of an oil provided herein comprises, as a percentage of total sterols, less than 20%, 15%, 10%, 5%, 4%, 3%, 2%, or 1% 24-ethylcholest-5-en-3-ol. In some embodiments, the 24-ethylcholest-5-en-3-ol is clionasterol. In some embodiments, the oil content of an oil provided herein comprises, as a percentage of total sterols, at least 1%, 2%, 3%, 4%, 5%, 6%, 7%, 8%, 9%, or 10% clionasterol.

In some embodiments, the oil content of an oil provided herein contains, as a percentage of total sterols, less than 20%, 15%, 10%, 5%, 4%, 3%, 2%, or 1% 24-methylcholest-5-en-3-ol. In some embodiments, the 24-methylcholest-5-en-3-ol is 22,23-dihydrobrassicasterol. In some embodiments, the oil content of an oil provided herein comprises, as a percentage of total sterols, at least 1%, 2%, 3%, 4%, 5%, 6%, 7%, 8%, 9%, or 10% 22,23-dihydrobrassicasterol.

In some embodiments, the oil content of an oil provided herein contains, as a percentage of total sterols, less than 20%, 15%, 10%, 5%, 4%, 3%, 2%, or 1% 5,22-cholestadien-24-ethyl-3-ol. In some embodiments, the 5,22-cholestadien-24-ethyl-3-ol is poriferasterol. In some embodiments, the oil content of an oil provided herein comprises, as a percentage of total sterols, at least 1%, 2%, 3%, 4%, 5%, 6%, 7%, 8%, 9%, or 10% poriferasterol.

In some embodiments, the oil content of an oil provided herein contains ergosterol or brassicasterol or a combination of the two. In some embodiments, the oil content contains, as a percentage of total sterols, at least 5%, 10%, 20%, 25%, 35%, 40%, 45%, 50%, 55%, 60%, or 65% ergosterol. In some embodiments, the oil content contains, as a percentage of total sterols, at least 25% ergosterol. In some embodiments, the oil content contains, as a percentage of total sterols, at least 40% ergosterol. In some embodiments, the oil content contains, as a percentage of total sterols, at least 5%, 10%, 20%, 25%, 35%, 40%, 45%, 50%, 55%, 60%, or 65% of a combination of ergosterol and brassicasterol.

In some embodiments, the oil content contains, as a percentage of total sterols, at least 1%, 2%, 3%, 4% or 5% brassicasterol. In some embodiments, the oil content contains, as a percentage of total sterols less than 10%, 9%, 8%, 7%, 6%, or 5% brassicasterol.

In some embodiments the ratio of ergosterol to brassicasterol is at least 5:1, 10:1, 15:1, or 20:1.

In some embodiments, the oil content contains, as a percentage of total sterols, at least 5%, 10%, 20%, 25%, 35%, 40%, 45%, 50%, 55%, 60%, or 65% ergosterol and less than 20%, 15%, 10%, 5%, 4%, 3%, 2%, or 1% β-sitosterol. In some embodiments, the oil content contains, as a percentage of total sterols, at least 25% ergosterol and less than 5% β-sitosterol. In some embodiments, the oil content further comprises brassicasterol.

XIII. Fuels and Chemicals

The oils discussed above alone or in combination are useful in the production of foods, fuels and chemicals (including plastics, foams, films, etc). The oils, triglycerides, fatty acids from the oils may be subjected to C—H activation, hydroamino methylation, methoxy-carbonation, ozonolysis, enzymatic transformations, epoxidation, methylation, dimerization, thiolation, metathesis, hydro-alkylation, lactonization, or other chemical processes.

The oils can be converted to alkanes (e.g., renewable diesel) or esters (e.g., methyl or ethyl esters for biodisesel produced by transesterification). The alkanes or esters may be used as fuel, as solvents or lubricants, or as a chemical feedstock. Methods for production of renewable diesel and biodiesel are well established in the art. See, for example, WO2011/150411.

In a specific embodiment of the present invention, a high-oleic or high-oleic-high stability oil described above is esterified. For example, the oils can be transesterified with methanol to an oil that is rich in methyl oleate. As described in Example 49, such formulations have been found to compare favorably with methyl oleate from soybean oil.

In another specific example, the oil is converted to C36 diacids or products of C36 diacids. Fatty acids produced from the oil can be polymerized to give a composition rich in C36 dimer acids. In a specific example, high-oleic oil is split to give a high-oleic fatty acid material which is polymerized to give a composition rich in C36-dimer acids. Optionally, the oil is high oleic high stability oil (e.g., greater than 60% oleic acid with less than 3% polyunsaturates, greater than 70% oleic acid with less than 2% polyunsaturates, or greater than 80% oleic acid with less than 1% polyunsaturates). It is believed that using a high oleic, high stability, starting material will give lower amounts of cyclic products, which may be desirable in some cases. After hydrolyzing the oil, one obtains a high concentration of oleic acid. In the process of making dimer acids, a high oleic acid stream will convert to a "cleaner" C36 dimer acid and not produce trimers acids (C54) and other more complex cyclic by-products which are obtained due to presence of C18:2 and C18:3 acids. For example, the oil can be hydrolyzed to fatty acids and the fatty acids purified and dimerized at 250° C. in the presence of montmorillonite clay. See SRI Natural Fatty Acid, March 2009. A product rich in C36 dimers of oleic acid is recovered.

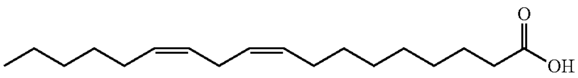

Linoleic Acid

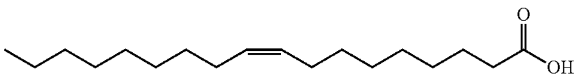

Oleic Acid

250 C, montmorillonite clay

-continued

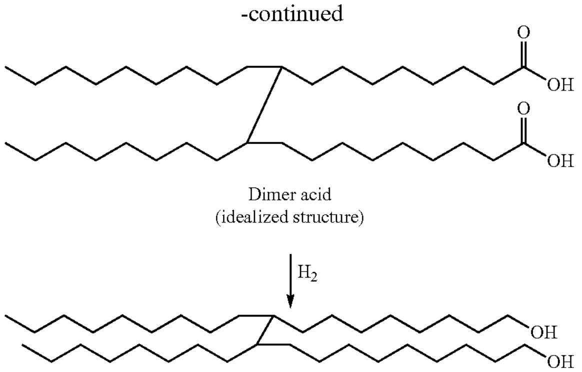

Dimer acid
(idealized structure)

Dimer alcohol
(idealized structure)

Further, the C36 dimer acids can be esterified and hydrogenated to give diols. The diols can be polymerized by catalytic dehydration. Polymers can also produced by transesterification of dimerdiols with dimethyl carbonate.

For the production of fuel in accordance with the methods of the invention lipids produced by cells of the invention are harvested, or otherwise collected, by any convenient means. Lipids can be isolated by whole cell extraction. The cells are first disrupted, and then intracellular and cell membrane/cell wall-associated lipids as well as extracellular hydrocarbons can be separated from the cell mass, such as by use of centrifugation. Intracellular lipids produced in oleaginous cells are, in some embodiments, extracted after lysing the cells. Once extracted, the lipids are further refined to produce oils, fuels, or oleochemicals.

Various methods are available for separating lipids from cellular lysates. For example, lipids and lipid derivatives such as fatty aldehydes, fatty alcohols, and hydrocarbons such as alkanes can be extracted with a hydrophobic solvent such as hexane (see Frenz et al. 1989, Enzyme Microb. Technol., 11:717). Lipids and lipid derivatives can also be extracted using liquefaction (see for example Sawayama et al. 1999, Biomass and Bioenergy 17:33-39 and Inoue et al. 1993, Biomass Bioenergy 6(4):269-274); oil liquefaction (see for example Minowa et al. 1995, Fuel 74(12):1735-1738); and supercritical $CO_2$ extraction (see for example Mendes et al. 2003, Inorganica Chimica Acta 356:328-334). Miao and Wu describe a protocol of the recovery of microalgal lipid from a culture of *Chlorella protothecoides* in which the cells were harvested by centrifugation, washed with distilled water and dried by freeze drying. The resulting cell powder was pulverized in a mortar and then extracted with n-hexane. Miao and Wu, Biosource Technology (2006) 97:841-846.

Lipids and lipid derivatives can be recovered by extraction with an organic solvent. In some cases, the preferred organic solvent is hexane. Typically, the organic solvent is added directly to the lysate without prior separation of the lysate components. In one embodiment, the lysate generated by one or more of the methods described above is contacted with an organic solvent for a period of time sufficient to allow the lipid and/or hydrocarbon components to form a solution with the organic solvent. In some cases, the solution can then be further refined to recover specific desired lipid or hydrocarbon components. Hexane extraction methods are well known in the art.

Lipids produced by cells in vivo, or enzymatically modified in vitro, as described herein can be optionally further processed by conventional means. The processing can include "cracking" to reduce the size, and thus increase the hydrogen:carbon ratio, of hydrocarbon molecules. Catalytic and thermal cracking methods are routinely used in hydrocarbon and triglyceride oil processing. Catalytic methods involve the use of a catalyst, such as a solid acid catalyst. The catalyst can be silica-alumina or a zeolite, which result in the heterolytic, or asymmetric, breakage of a carbon-carbon bond to result in a carbocation and a hydride anion. These reactive intermediates then undergo either rearrangement or hydride transfer with another hydrocarbon. The reactions can thus regenerate the intermediates to result in a self-propagating chain mechanism. Hydrocarbons can also be processed to reduce, optionally to zero, the number of carbon-carbon double, or triple, bonds therein. Hydrocarbons can also be processed to remove or eliminate a ring or cyclic structure therein. Hydrocarbons can also be processed to increase the hydrogen:carbon ratio. This can include the addition of hydrogen ("hydrogenation") and/or the "cracking" of hydrocarbons into smaller hydrocarbons.

Thermal methods involve the use of elevated temperature and pressure to reduce hydrocarbon size. An elevated temperature of about 800° C. and pressure of about 700 kPa can be used. These conditions generate "light," a term that is sometimes used to refer to hydrogen-rich hydrocarbon molecules (as distinguished from photon flux), while also generating, by condensation, heavier hydrocarbon molecules which are relatively depleted of hydrogen. The methodology provides homolytic, or symmetrical, breakage and produces alkenes, which may be optionally enzymatically saturated as described above.

Catalytic and thermal methods are standard in plants for hydrocarbon processing and oil refining. Thus hydrocarbons produced by cells as described herein can be collected and processed or refined via conventional means. See Hillen et al. (Biotechnology and Bioengineering, Vol. XXIV:193-205 (1982)) for a report on hydrocracking of microalgae-produced hydrocarbons. In alternative embodiments, the fraction is treated with another catalyst, such as an organic compound, heat, and/or an inorganic compound. For processing of lipids into biodiesel, a transesterification process is used as described below in this Section.

Hydrocarbons produced via methods of the present invention are useful in a variety of industrial applications. For example, the production of linear alkylbenzene sulfonate (LAS), an anionic surfactant used in nearly all types of detergents and cleaning preparations, utilizes hydrocarbons generally comprising a chain of 10-14 carbon atoms. See, for example, U.S. Pat. Nos. 6,946,430; 5,506,201; 6,692,730; 6,268,517; 6,020,509; 6,140,302; 5,080,848; and 5,567,359. Surfactants, such as LAS, can be used in the manufacture of personal care compositions and detergents, such as those described in U.S. Pat. Nos. 5,942,479; 6,086,903; 5,833,999; 6,468,955; and 6,407,044.

Increasing interest is directed to the use of hydrocarbon components of biological origin in fuels, such as biodiesel, renewable diesel, and jet fuel, since renewable biological starting materials that may replace starting materials derived from fossil fuels are available, and the use thereof is desirable. There is an urgent need for methods for producing hydrocarbon components from biological materials. The present invention fulfills this need by providing methods for production of biodiesel, renewable diesel, and jet fuel using the lipids generated by the methods described herein as a biological material to produce biodiesel, renewable diesel, and jet fuel.

Traditional diesel fuels are petroleum distillates rich in paraffinic hydrocarbons. They have boiling ranges as broad as 370° to 780° F., which are suitable for combustion in a compression ignition engine, such as a diesel engine vehicle. The American Society of Testing and Materials (ASTM) establishes the grade of diesel according to the boiling range, along with allowable ranges of other fuel properties, such as cetane number, cloud point, flash point, viscosity, aniline point, sulfur content, water content, ash content, copper strip corrosion, and carbon residue. Technically, any hydrocarbon distillate material derived from biomass or otherwise that meets the appropriate ASTM specification can be defined as diesel fuel (ASTM D975), jet fuel (ASTM D1655), or as biodiesel if it is a fatty acid methyl ester (ASTM D6751).

After extraction, lipid and/or hydrocarbon components recovered from the microbial biomass described herein can be subjected to chemical treatment to manufacture a fuel for use in diesel vehicles and jet engines.

Biodiesel is a liquid which varies in color—between golden and dark brown—depending on the production feedstock. It is practically immiscible with water, has a high boiling point and low vapor pressure. Biodiesel refers to a diesel-equivalent processed fuel for use in diesel-engine vehicles. Biodiesel is biodegradable and non-toxic. An additional benefit of biodiesel over conventional diesel fuel is lower engine wear. Typically, biodiesel comprises C14-C18 alkyl esters. Various processes convert biomass or a lipid produced and isolated as described herein to diesel fuels. A preferred method to produce biodiesel is by transesterification of a lipid as described herein. A preferred alkyl ester for use as biodiesel is a methyl ester or ethyl ester.

Biodiesel produced by a method described herein can be used alone or blended with conventional diesel fuel at any concentration in most modern diesel-engine vehicles. When blended with conventional diesel fuel (petroleum diesel), biodiesel may be present from about 0.1% to about 99.9%. Much of the world uses a system known as the "B" factor to state the amount of biodiesel in any fuel mix. For example, fuel containing 20% biodiesel is labeled B20. Pure biodiesel is referred to as B100.

Biodiesel can be produced by transesterification of triglycerides contained in oil-rich biomass. Thus, in another aspect of the present invention a method for producing biodiesel is provided. In a preferred embodiment, the method for producing biodiesel comprises the steps of (a) cultivating a lipid-containing microorganism using methods disclosed herein (b) lysing a lipid-containing microorganism to produce a lysate, (c) isolating lipid from the lysed microorganism, and (d) transesterifying the lipid composition, whereby biodiesel is produced. Methods for growth of a microorganism, lysing a microorganism to produce a lysate, treating the lysate in a medium comprising an organic solvent to form a heterogeneous mixture and separating the treated lysate into a lipid composition have been described above and can also be used in the method of producing biodiesel. The lipid profile of the biodiesel is usually highly similar to the lipid profile of the feedstock oil.

Lipid compositions can be subjected to transesterification to yield long-chain fatty acid esters useful as biodiesel. Preferred transesterification reactions are outlined below and include base catalyzed transesterification and transesterification using recombinant lipases. In a base-catalyzed transesterification process, the triacylglycerides are reacted with an alcohol, such as methanol or ethanol, in the presence of an alkaline catalyst, typically potassium hydroxide. This reaction forms methyl or ethyl esters and glycerin (glycerol) as a byproduct.

Transesterification has also been carried out, as discussed above, using an enzyme, such as a lipase instead of a base. Lipase-catalyzed transesterification can be carried out, for example, at a temperature between the room temperature and 80° C., and a mole ratio of the TAG to the lower alcohol of greater than 1:1, preferably about 3:1. Lipases suitable for use in transesterification include, but are not limited to, those listed in Table 9. Other examples of lipases useful for transesterification are found in, e.g., U.S. Pat. Nos. 4,798,793; 4,940,845 5,156,963; 5,342,768; 5,776,741 and WO89/01032. Such lipases include, but are not limited to, lipases produced by microorganisms of *Rhizopus, Aspergillus, Candida, Mucor, Pseudomonas, Rhizomucor, Candida*, and *Humicola* and pancreas lipase.

Subsequent processes may also be used if the biodiesel will be used in particularly cold temperatures. Such processes include winterization and fractionation. Both processes are designed to improve the cold flow and winter performance of the fuel by lowering the cloud point (the temperature at which the biodiesel starts to crystallize). There are several approaches to winterizing biodiesel. One approach is to blend the biodiesel with petroleum diesel. Another approach is to use additives that can lower the cloud point of biodiesel. Another approach is to remove saturated methyl esters indiscriminately by mixing in additives and allowing for the crystallization of saturates and then filtering out the crystals. Fractionation selectively separates methyl esters into individual components or fractions, allowing for the removal or inclusion of specific methyl esters. Fractionation methods include urea fractionation, solvent fractionation and thermal distillation.

Another valuable fuel provided by the methods of the present invention is renewable diesel, which comprises alkanes, such as C10:0, C12:0, C14:0, C16:0 and C18:0 and thus, are distinguishable from biodiesel. High quality renewable diesel conforms to the ASTM D975 standard. The lipids produced by the methods of the present invention can serve as feedstock to produce renewable diesel. Thus, in another aspect of the present invention, a method for producing renewable diesel is provided. Renewable diesel can be produced by at least three processes: hydrothermal processing (hydrotreating); hydroprocessing; and indirect liquefaction. These processes yield non-ester distillates. During these processes, triacylglycerides produced and isolated as described herein, are converted to alkanes.

In one embodiment, the method for producing renewable diesel comprises (a) cultivating a lipid-containing microorganism using methods disclosed herein (b) lysing the microorganism to produce a lysate, (c) isolating lipid from the lysed microorganism, and (d) deoxygenating and hydrotreating the lipid to produce an alkane, whereby renewable diesel is produced. Lipids suitable for manufacturing renewable diesel can be obtained via extraction from microbial biomass using an organic solvent such as hexane, or via other methods, such as those described in U.S. Pat. No. 5,928,696. Some suitable methods may include mechanical pressing and centrifuging.

In some methods, the microbial lipid is first cracked in conjunction with hydrotreating to reduce carbon chain length and saturate double bonds, respectively. The material is then isomerized, also in conjunction with hydrotreating. The naptha fraction can then be removed through distillation, followed by additional distillation to vaporize and distill components desired in the diesel fuel to meet an ASTM D975 standard while leaving components that are heavier than desired for meeting the D975 standard. Hydrotreating, hydrocracking, deoxygenation and isomerization methods of chemically modifying oils, including triglyceride oils, are well known in the art. See for example European patent applications EP1741768 (A1); EP1741767 (A1); EP1682466 (A1); EP1640437 (A1); EP1681337 (A1); EP1795576 (A1); and U.S. Pat. Nos. 7,238,277; 6,630,066; 6,596,155; 6,977, 322; 7,041,866; 6,217,746; 5,885,440; 6,881,873.

In one embodiment of the method for producing renewable diesel, treating the lipid to produce an alkane is performed by hydrotreating of the lipid composition. In hydrothermal processing, typically, biomass is reacted in water at an elevated temperature and pressure to form oils and residual solids. Conversion temperatures are typically 300° to 660° F., with pressure sufficient to keep the water primarily as a liquid, 100 to 170 standard atmosphere (atm). Reaction times are on the order of 15 to 30 minutes. After the reaction is completed, the organics are separated from the water. Thereby a distillate suitable for diesel is produced.

In some methods of making renewable diesel, the first step of treating a triglyceride is hydroprocessing to saturate double bonds, followed by deoxygenation at elevated temperature in the presence of hydrogen and a catalyst. In some methods, hydrogenation and deoxygenation occur in the same reaction. In other methods deoxygenation occurs before hydrogenation. Isomerization is then optionally performed, also in the presence of hydrogen and a catalyst. Naphtha components are preferably removed through distillation. For examples, see U.S. Pat. No. 5,475,160 (hydrogenation of triglycerides); U.S. Pat. No. 5,091,116 (deoxygenation, hydrogenation and gas removal); U.S. Pat. No. 6,391,815 (hydrogenation); and U.S. Pat. No. 5,888,947 (isomerization).

One suitable method for the hydrogenation of triglycerides includes preparing an aqueous solution of copper, zinc, magnesium and lanthanum salts and another solution of alkali metal or preferably, ammonium carbonate. The two solutions may be heated to a temperature of about 20° C. to about 85° C. and metered together into a precipitation container at rates such that the pH in the precipitation container is maintained between 5.5 and 7.5 in order to form a catalyst. Additional water may be used either initially in the precipitation container or added concurrently with the salt solution and precipitation solution. The resulting precipitate may then be thoroughly washed, dried, calcined at about 300° C. and activated in hydrogen at temperatures ranging from about 100° C. to about 400° C. One or more triglycerides may then be contacted and reacted with hydrogen in the presence of the above-described catalyst in a reactor. The reactor may be a trickle bed reactor, fixed bed gas-solid reactor, packed bubble column reactor, continuously stirred tank reactor, a slurry phase reactor, or any other suitable reactor type known in the art. The process may be carried out either batchwise or in continuous fashion. Reaction temperatures are typically in the range of from about 170° C. to about 250° C. while reaction pressures are typically in the range of from about 300 psig to about 2000 psig. Moreover, the molar ratio of hydrogen to triglyceride in the process of the present invention is typically in the range of from about 20:1 to about 700:1. The process is typically carried out at a weight hourly space velocity (WHSV) in the range of from about 0.1 $hr^{-1}$ to about 5 $hr^{-1}$. One skilled in the art will recognize that the time period required for reaction will vary according to the temperature used, the molar ratio of hydrogen to triglyceride, and the partial pressure of hydrogen. The products produced by the such hydrogenation processes include fatty alcohols, glycerol, traces of paraffins and unreacted triglycerides. These products are typically separated by conventional means such as, for example, distillation, extraction, filtration, crystallization, and the like.

Petroleum refiners use hydroprocessing to remove impurities by treating feeds with hydrogen. Hydroprocessing conversion temperatures are typically 300° to 700° F. Pressures are typically 40 to 100 atm. The reaction times are typically on the order of 10 to 60 minutes. Solid catalysts are employed to increase certain reaction rates, improve selectivity for certain products, and optimize hydrogen consumption.

Suitable methods for the deoxygenation of an oil includes heating an oil to a temperature in the range of from about 350° F. to about 550° F. and continuously contacting the heated oil with nitrogen under at least pressure ranging from about atmospheric to above for at least about 5 minutes.

Suitable methods for isomerization include using alkali isomerization and other oil isomerization known in the art.

Hydrotreating and hydroprocessing ultimately lead to a reduction in the molecular weight of the triglyceride feed. The triglyceride molecule is reduced to four hydrocarbon molecules under hydroprocessing conditions: a propane molecule and three heavier hydrocarbon molecules, typically in the C8 to C18 range.

Thus, in one embodiment, the product of one or more chemical reaction(s) performed on lipid compositions of the invention is an alkane mixture that comprises ASTM D975 renewable diesel. Production of hydrocarbons by microorganisms is reviewed by Metzger et al. Appl Microbiol Biotechnol (2005) 66: 486-496 and A Look Back at the U.S. Department of Energy's Aquatic Species Program: Biodiesel from Algae, NREL/TP-580-24190, John Sheehan, Terri Dunahay, John Benemann and Paul Roessler (1998).

The distillation properties of a diesel fuel is described in terms of T10-T90 (temperature at 10% and 90%, respectively, volume distilled). The T10-T90 of the material produced in Example 13 was 57.9° C. Methods of hydrotreating, isomerization, and other covalent modification of oils disclosed herein, as well as methods of distillation and fractionation (such as cold filtration) disclosed herein, can be employed to generate renewable diesel compositions with other T10-T90 ranges, such as 20, 25, 30, 35, 40, 45, 50, 60 and 65° C. using triglyceride oils produced according to the methods disclosed herein.

Methods of hydrotreating, isomerization, and other covalent modification of oils disclosed herein, as well as methods of distillation and fractionation (such as cold filtration) disclosed herein, can be employed to generate renewable diesel compositions with other T10 values, such as T10 between 180 and 295, between 190 and 270, between 210 and 250, between 225 and 245, and at least 290.

Methods of hydrotreating, isomerization, and other covalent modification of oils disclosed herein, as well as methods of distillation and fractionation (such as cold filtration) disclosed herein can be employed to generate renewable diesel compositions with certain T90 values, such as T90 between 280 and 380, between 290 and 360, between 300 and 350, between 310 and 340, and at least 290.

The FBP of the material produced in Example 13 was 300° C. Methods of hydrotreating, isomerization, and other covalent modification of oils disclosed herein, as well as methods of distillation and fractionation (such as cold filtration) disclosed herein, can be employed to generate renewable diesel compositions with other FBP values, such as FBP between 290 and 400, between 300 and 385, between 310 and 370, between 315 and 360, and at least 300.

Other oils provided by the methods and compositions of the invention can be subjected to combinations of hydrotreating, isomerization, and other covalent modification including oils with lipid profiles including (a) at least 1%-5%, preferably at least 4%, C8-C14; (b) at least 0.25%-1%, preferably at least 0.3%, C8; (c) at least 1%-5%, preferably at least 2%, C10; (d) at least 1%-5%, preferably at least 2%, C12; and (3) at least 20%-40%, preferably at least 30% C8-C14.

A traditional ultra-low sulfur diesel can be produced from any form of biomass by a two-step process. First, the biomass is converted to a syngas, a gaseous mixture rich in hydrogen and carbon monoxide. Then, the syngas is catalytically converted to liquids. Typically, the production of liquids is accomplished using Fischer-Tropsch (FT) synthesis. This technology applies to coal, natural gas, and heavy oils. Thus, in yet another preferred embodiment of the method for producing renewable diesel, treating the lipid composition to produce an alkane is performed by indirect liquefaction of the lipid composition.

The present invention also provides methods to produce jet fuel. Jet fuel is clear to straw colored. The most common fuel is an unleaded/paraffin oil-based fuel classified as Aeroplane A-1, which is produced to an internationally standardized set of specifications. Jet fuel is a mixture of a large number of different hydrocarbons, possibly as many as a thousand or more. The range of their sizes (molecular weights or carbon numbers) is restricted by the requirements for the product, for example, freezing point or smoke point. Kerosone-type Aeroplane fuel (including Jet A and Jet A-1) has a carbon number distribution between about 8 and 16 carbon numbers. Wide-cut or naphtha-type Aeroplane fuel (including Jet B) typically has a carbon number distribution between about 5 and 15 carbons.

In one embodiment of the invention, a jet fuel is produced by blending algal fuels with existing jet fuel. The lipids produced by the methods of the present invention can serve as feedstock to produce jet fuel. Thus, in another aspect of the present invention, a method for producing jet fuel is provided. Herewith two methods for producing jet fuel from the lipids produced by the methods of the present invention are provided: fluid catalytic cracking (FCC); and hydrodeoxygenation (HDO).

Fluid Catalytic Cracking (FCC) is one method which is used to produce olefins, especially propylene from heavy crude fractions. The lipids produced by the method of the present invention can be converted to olefins. The process involves flowing the lipids produced through an FCC zone and collecting a product stream comprised of olefins, which is useful as a jet fuel. The lipids produced are contacted with a cracking catalyst at cracking conditions to provide a product stream comprising olefins and hydrocarbons useful as jet fuel.

In one embodiment, the method for producing jet fuel comprises (a) cultivating a lipid-containing microorganism using methods disclosed herein, (b) lysing the lipid-containing microorganism to produce a lysate, (c) isolating lipid from the lysate, and (d) treating the lipid composition, whereby jet fuel is produced. In one embodiment of the method for producing a jet fuel, the lipid composition can be flowed through a fluid catalytic cracking zone, which, in one embodiment, may comprise contacting the lipid composition with a cracking catalyst at cracking conditions to provide a product stream comprising $C_2$-$C_5$ olefins.

In certain embodiments of this method, it may be desirable to remove any contaminants that may be present in the lipid composition. Thus, prior to flowing the lipid composition through a fluid catalytic cracking zone, the lipid composition is pretreated. Pretreatment may involve contacting the lipid composition with an ion-exchange resin. The ion exchange resin is an acidic ion exchange resin, such as Amberlyst™-15 and can be used as a bed in a reactor through which the lipid composition is flowed, either upflow or downflow. Other pretreatments may include mild acid washes by contacting the lipid composition with an acid, such as sulfuric, acetic, nitric, or hydrochloric acid. Contacting is done with a dilute acid solution usually at ambient temperature and atmospheric pressure.

The lipid composition, optionally pretreated, is flowed to an FCC zone where the hydrocarbonaceous components are cracked to olefins. Catalytic cracking is accomplished by contacting the lipid composition in a reaction zone with a catalyst composed of finely divided particulate material. The reaction is catalytic cracking, as opposed to hydrocracking, and is carried out in the absence of added hydrogen or the consumption of hydrogen. As the cracking reaction proceeds, substantial amounts of coke are deposited on the catalyst. The catalyst is regenerated at high temperatures by burning coke from the catalyst in a regeneration zone. Coke-containing catalyst, referred to herein as "coked catalyst", is continually transported from the reaction zone to the regeneration zone to be regenerated and replaced by essentially coke-free regenerated catalyst from the regeneration zone. Fluidization of the catalyst particles by various gaseous streams allows the transport of catalyst between the reaction zone and regeneration zone. Methods for cracking hydrocarbons, such as those of the lipid composition described herein, in a fluidized stream of catalyst, transporting catalyst between reaction and regeneration zones, and combusting coke in the regenerator are well known by those skilled in the art of FCC processes. Exemplary FCC applications and catalysts useful for cracking the lipid composition to produce $C_2$-$C_5$ olefins are described in U.S. Pat. Nos. 6,538,169, 7,288,685, which are incorporated in their entirety by reference.

Suitable FCC catalysts generally comprise at least two components that may or may not be on the same matrix. In some embodiments, both two components may be circulated throughout the entire reaction vessel. The first component generally includes any of the well-known catalysts that are used in the art of fluidized catalytic cracking, such as an active amorphous clay-type catalyst and/or a high activity, crystalline molecular sieve. Molecular sieve catalysts may be preferred over amorphous catalysts because of their much-improved selectivity to desired products. In some preferred embodiments, zeolites may be used as the molecular sieve in the FCC processes. Preferably, the first catalyst component comprises a large pore zeolite, such as a Y-type zeolite, an active alumina material, a binder material, comprising either silica or alumina and an inert filler such as kaolin.

In one embodiment, cracking the lipid composition of the present invention, takes place in the riser section or, alternatively, the lift section, of the FCC zone. The lipid composition is introduced into the riser by a nozzle resulting in the rapid vaporization of the lipid composition. Before contacting the catalyst, the lipid composition will ordinarily have a temperature of about 149° C. to about 316° C. (300° F. to 600° F.). The catalyst is flowed from a blending vessel to the riser where it contacts the lipid composition for a time of abort 2 seconds or less.

The blended catalyst and reacted lipid composition vapors are then discharged from the top of the riser through an outlet and separated into a cracked product vapor stream including olefins and a collection of catalyst particles covered with substantial quantities of coke and generally referred to as "coked catalyst." In an effort to minimize the contact time of the lipid composition and the catalyst which may promote further conversion of desired products to undesirable other products, any arrangement of separators such as a swirl arm arrangement can be used to remove coked catalyst from the product stream quickly. The separator, e.g. swirl arm separator, is located in an upper portion of a chamber with a stripping zone situated in the lower portion of the chamber. Catalyst separated by the swirl arm arrangement drops down into the stripping zone. The cracked product vapor stream comprising cracked hydrocarbons including light olefins and some catalyst exit the chamber via a conduit which is in communication with cyclones. The cyclones remove remaining catalyst particles from the product vapor stream to reduce particle concentrations to very low levels. The product vapor stream then exits the top of the separating vessel. Catalyst separated by the cyclones is returned to the separating vessel and then to the stripping zone. The stripping zone removes adsorbed hydrocarbons from the surface of the catalyst by counter-current contact with steam.

Low hydrocarbon partial pressure operates to favor the production of light olefins. Accordingly, the riser pressure is set at about 172 to 241 kPa (25 to 35 psia) with a hydrocarbon partial pressure of about 35 to 172 kPa (5 to 25 psia), with a preferred hydrocarbon partial pressure of about 69 to 138 kPa (10 to 20 psia). This relatively low partial pressure for hydrocarbon is achieved by using steam as a diluent to the extent that the diluent is 10 to 55 wt-% of lipid composition and preferably about 15 wt-% of lipid composition. Other diluents such as dry gas can be used to reach equivalent hydrocarbon partial pressures.

The temperature of the cracked stream at the riser outlet will be about 510° C. to 621° C. (950° F. to 1150° F.). However, riser outlet temperatures above 566° C. (1050° F.) make more dry gas and more olefins. Whereas, riser outlet temperatures below 566° C. (1050° F.) make less ethylene and propylene. Accordingly, it is preferred to run the FCC process at a preferred temperature of about 566° C. to about 630° C., preferred pressure of about 138 kPa to about 240 kPa (20 to 35 psia). Another condition for the process is the catalyst to lipid composition ratio which can vary from about 5 to about 20 and preferably from about 10 to about 15.

In one embodiment of the method for producing a jet fuel, the lipid composition is introduced into the lift section of an FCC reactor. The temperature in the lift section will be very hot and range from about 700° C. (1292° F.) to about 760° C. (1400° F.) with a catalyst to lipid composition ratio of about 100 to about 150. It is anticipated that introducing the lipid composition into the lift section will produce considerable amounts of propylene and ethylene.

In another embodiment of the method for producing a jet fuel using the lipid composition or the lipids produced as described herein, the structure of the lipid composition or the lipids is broken by a process referred to as hydrodeoxygenation (HDO). HDO means removal of oxygen by means of hydrogen, that is, oxygen is removed while breaking the structure of the material. Olefinic double bonds are hydrogenated and any sulphur and nitrogen compounds are removed. Sulphur removal is called hydrodesulphurization (HDS). Pretreatment and purity of the raw materials (lipid composition or the lipids) contribute to the service life of the catalyst.

Generally in the HDO/HDS step, hydrogen is mixed with the feed stock (lipid composition or the lipids) and then the mixture is passed through a catalyst bed as a co-current flow, either as a single phase or a two phase feed stock. After the HDO/MDS step, the product fraction is separated and passed to a separate isomerzation reactor. An isomerization reactor for biological starting material is described in the literature (FI 100 248) as a co-current reactor.

The process for producing a fuel by hydrogenating a hydrocarbon feed, e.g., the lipid composition or the lipids herein, can also be performed by passing the lipid composition or the lipids as a co-current flow with hydrogen gas through a first hydrogenation zone, and thereafter the hydrocarbon effluent is further hydrogenated in a second hydrogenation zone by passing hydrogen gas to the second hydrogenation zone as a counter-current flow relative to the hydrocarbon effluent. Exemplary HDO applications and catalysts useful for cracking the lipid composition to produce $C_2$-$C_5$ olefins are described in U.S. Pat. No. 7,232,935, which is incorporated in its entirety by reference.

Typically, in the hydrodeoxygenation step, the structure of the biological component, such as the lipid composition or lipids herein, is decomposed, oxygen, nitrogen, phosphorus and sulphur compounds, and light hydrocarbons as gas are removed, and the olefinic bonds are hydrogenated. In the second step of the process, i.e. in the so-called isomerization step, isomerzation is carried out for branching the hydrocarbon chain and improving the performance of the paraffin at low temperatures.

In the first step, i.e. HDO step, of the cracking process, hydrogen gas and the lipid composition or lipids herein which are to be hydrogenated are passed to a HDO catalyst bed system either as co-current or counter-current flows, said catalyst bed system comprising one or more catalyst bed(s), preferably 1-3 catalyst beds. The HDO step is typically operated in a co-current manner. In case of a HDO catalyst bed system comprising two or more catalyst beds, one or more of the beds may be operated using the counter-current flow principle. In the HDO step, the pressure varies between 20 and 150 bar, preferably between 50 and 100 bar, and the temperature varies between 200 and 500° C., preferably in the range of 300-400° C. In the HDO step, known hydrogenation catalysts containing metals from Group VII and/or VIB of the Periodic System may be used. Preferably, the hydrogenation catalysts are supported Pd, Pt, Ni, NiMo or a CoMo catalysts, the support being alumina and/or silica. Typically, NiMo/$Al_2O_3$ and CoMo/$Al_2O_3$ catalysts are used.

Prior to the HDO step, the lipid composition or lipids herein may optionally be treated by prehydrogenation under milder conditions thus avoiding side reactions of the double bonds. Such prehydrogenation is carried out in the presence of a prehydrogenation catalyst at temperatures of 50-400° C. and at hydrogen pressures of 1-200 bar, preferably at a temperature between 150 and 250° C. and at a hydrogen pressure between 10 and 100 bar. The catalyst may contain metals from Group VIII and/or VIB of the Periodic System. Preferably, the prehydrogenation catalyst is a supported Pd, Pt, Ni, NiMo or a CoMo catalyst, the support being alumina and/or silica.

A gaseous stream from the HDO step containing hydrogen is cooled and then carbon monoxide, carbon dioxide, nitrogen, phosphorus and sulphur compounds, gaseous light hydrocarbons and other impurities are removed therefrom. After compressing, the purified hydrogen or recycled hydrogen is returned back to the first catalyst bed and/or between the catalyst beds to make up for the withdrawn gas stream. Water is removed from the condensed liquid. The liquid is passed to the first catalyst bed or between the catalyst beds.

After the HDO step, the product is subjected to an isomerization step. It is substantial for the process that the impurities are removed as completely as possible before the hydrocarbons are contacted with the isomerization catalyst. The isomerization step comprises an optional stripping step, wherein the reaction product from the HDO step may be purified by stripping with water vapour or a suitable gas such as light hydrocarbon, nitrogen or hydrogen. The optional stripping step is carried out in counter-current manner in a unit upstream of the isomerization catalyst, wherein the gas and liquid are contacted with each other, or before the actual isomerization reactor in a separate stripping unit utilizing counter-current principle.

After the stripping step the hydrogen gas and the hydrogenated lipid composition or lipids herein, and optionally an n-paraffin mixture, are passed to a reactive isomerization unit comprising one or several catalyst bed(s). The catalyst beds of the isomerization step may operate either in co-current or counter-current manner.

It is important for the process that the counter-current flow principle is applied in the isomerization step. In the isomerization step this is done by carrying out either the optional stripping step or the isomerization reaction step or both in counter-current manner. In the isomerzation step, the pressure varies in the range of 20-150 bar, preferably in the range of 20-100 bar, the temperature being between 200 and 500° C., preferably between 300 and 400° C. In the isomerization step, isomerization catalysts known in the art may be used. Suitable isomerization catalysts contain molecular sieve and/or a metal from Group VII and/or a carrier. Preferably, the isomerization catalyst contains SAPO-11 or SAPO41 or ZSM-22 or ZSM-23 or ferrierite and Pt, Pd or Ni and $Al_2O_3$ or $SiO_2$. Typical isomerization catalysts are, for example, Pt/SAPO-11/$Al_2O_3$, Pt/ZSM-22/$Al_2O_3$, Pt/ZSM-23/$Al_2O_3$ and Pt/SAPO-11/$SiO_2$. The isomerization step and the HDO step may be carried out in the same pressure vessel or in separate pressure vessels. Optional prehydrogenation may be carried out in a separate pressure vessel or in the same pressure vessel as the HDO and isomerization steps.

Thus, in one embodiment, the product of one or more chemical reactions is an alkane mixture that comprises HRJ-5. In another embodiment, the product of the one or more chemical reactions is an alkane mixture that comprises ASTM D1655 jet fuel. In some embodiments, the composition conforming to the specification of ASTM 1655 jet fuel has a sulfur content that is less than 10 ppm. In other embodiments, the composition conforming to the specification of ASTM 1655 jet fuel has a T10 value of the distillation curve of less than 205° C. In another embodiment, the composition conforming to the specification of ASTM 1655 jet fuel has a final boiling point (FBP) of less than 300° C. In another embodiment, the composition conforming to the specification of ASTM 1655 jet fuel has a flash point of at least 38° C. In another embodiment, the composition conforming to the specification of ASTM 1655 jet fuel has a density between 775K/$M^3$ and 840K/$M^3$. In yet another embodiment, the composition conforming to the specification of ASTM 1655 jet fuel has a freezing point that is below −47° C. In another embodiment, the composition conforming to the specification of ASTM 1655 jet fuel has a net Heat of Combustion that is at least 42.8 MJ/K. In another embodiment, the composition conforming to the specification of ASTM 1655 jet fuel has a hydrogen content that is at least 13.4 mass %. In another embodiment, the composition conforming to the specification of ASTM 1655 jet fuel has a thermal stability, as tested by quantitative gravimetric JFTOT at 260° C., which is below 3 mm of Hg. In another embodiment, the composition conforming to the specification of ASTM 1655 jet fuel has an existent gum that is below 7 mg/dl.

Thus, the present invention discloses a variety of methods in which chemical modification of microalgal lipid is undertaken to yield products useful in a variety of industrial and other applications. Examples of processes for modifying oil produced by the methods disclosed herein include, but are not limited to, hydrolysis of the oil, hydroprocessing of the oil, and esterification of the oil. Other chemical modification of microalgal lipid include, without limitation, epoxidation, oxidation, hydrolysis, sulfations, sulfonation, ethoxylation, propoxylation, amidation, and saponification. The modification of the microalgal oil produces basic oleochemicals that can be further modified into selected derivative oleochemicals for a desired function. In a manner similar to that described above with reference to fuel producing processes, these chemical modifications can also be performed on oils generated from the microbial cultures described herein. Examples of basic oleochemicals include, but are not limited to, soaps, fatty acids, fatty esters, fatty alcohols, fatty nitrogen compounds including fatty amides, fatty acid methyl esters, and glycerol. Examples of derivative oleochemicals include, but are not limited to, fatty nitriles, esters, dimer acids, quats, surfactants, fatty alkanolamides, fatty alcohol sulfates, resins, emulsifiers, fatty alcohols, olefins, drilling muds, polyols, polyurethanes, polyacrylates, rubber, candles, cosmetics, metallic soaps, soaps, alpha-sulphonated methyl esters, fatty alcohol sulfates, fatty alcohol ethoxylates, fatty alcohol ether sulfates, imidazolines, surfactants, detergents, esters, quats, ozonolysis products, fatty amines, fatty alkanolamides, ethoxysulfates, monoglycerides, diglycerides, triglycerides (including medium chain triglycerides), lubricants, hydraulic fluids, greases, dielectric fluids, mold release agents, metal working fluids, heat transfer fluids, other functional fluids, industrial chemicals (e.g., cleaners, textile processing aids, plasticizers, stabilizers, additives), surface coatings, paints and lacquers, electrical wiring insulation, and higher alkanes.

Hydrolysis of the fatty acid constituents from the glycerolipids produced by the methods of the invention yields free fatty acids that can be derivatized to produce other useful chemicals. Hydrolysis occurs in the presence of water and a catalyst which may be either an acid or a base. The liberated free fatty acids can be derivatized to yield a variety of products, as reported in the following: U.S. Pat. No. 5,304,664 (Highly sulfated fatty acids); U.S. Pat. No. 7,262,158 (Cleansing compositions); U.S. Pat. No. 7,115,173 (Fabric softener compositions); U.S. Pat. No. 6,342,208 (Emulsions for treating skin); U.S. Pat. No. 7,264,886 (Water repellant compositions); U.S. Pat. No. 6,924,333 (Paint additives); U.S. Pat. No. 6,596,768 (Lipid-enriched ruminant feedstock); and U.S. Pat. No. 6,380,410 (Surfactants for detergents and cleaners).

In some methods, the first step of chemical modification may be hydroprocessing to saturate double bonds, followed by deoxygenation at elevated temperature in the presence of hydrogen and a catalyst. In other methods, hydrogenation and deoxygenation may occur in the same reaction. In still other methods deoxygenation occurs before hydrogenation. Isomerization may then be optionally performed, also in the presence of hydrogen and a catalyst. Finally, gases and naphtha components can be removed if desired. For example, see U.S. Pat. No. 5,475,160 (hydrogenation of triglycerides); U.S. Pat. No. 5,091,116 (deoxygenation, hydrogenation and gas removal); U.S. Pat. No. 6,391,815 (hydrogenation); and U.S. Pat. No. 5,888,947 (isomerization).

In some embodiments of the invention, the triglyceride oils are partially or completely deoxygenated. The deoxygenation reactions form desired products, including, but not limited to, fatty acids, fatty alcohols, polyols, ketones, and aldehydes. In general, without being limited by any particular theory, the deoxygenation reactions involve a combination of various different reaction pathways, including without limitation: hydrogenolysis, hydrogenation, consecutive hydrogenation-hydrogenolysis, consecutive hydrogenolysis-hydrogenation, and combined hydrogenation-hydrogenolysis reactions, resulting in at least the partial removal of oxygen from the fatty acid or fatty acid ester to produce reaction products, such as fatty alcohols, that can be easily converted to the desired chemicals by further processing. For example, in one embodiment, a fatty alcohol may be converted to olefins through FCC reaction or to higher alkanes through a condensation reaction.

One such chemical modification is hydrogenation, which is the addition of hydrogen to double bonds in the fatty acid constituents of glycerolipids or of free fatty acids. The hydrogenation process permits the transformation of liquid oils into semi-solid or solid fats, which may be more suitable for specific applications.

Hydrogenation of oil produced by the methods described herein can be performed in conjunction with one or more of the methods and/or materials provided herein, as reported in the following: U.S. Pat. No. 7,288,278 (Food additives or medicaments); U.S. Pat. No. 5,346,724 (Lubrication products); U.S. Pat. No. 5,475,160 (Fatty alcohols); U.S. Pat. No. 5,091,116 (Edible oils); U.S. Pat. No. 6,808,737 (Structural fats for margarine and spreads); U.S. Pat. No. 5,298,637 (Reduced-calorie fat substitutes); U.S. Pat. No. 6,391,815 (Hydrogenation catalyst and sulfur adsorbent); U.S. Pat. Nos. 5,233,099 and 5,233,100 (Fatty alcohols); U.S. Pat. No. 4,584,139 (Hydrogenation catalysts); U.S. Pat. No. 6,057,375 (Foam suppressing agents); and U.S. Pat. No. 7,118,773 (Edible emulsion spreads).

One skilled in the art will recognize that various processes may be used to hydrogenate carbohydrates. One suitable method includes contacting the carbohydrate with hydrogen or hydrogen mixed with a suitable gas and a catalyst under conditions sufficient in a hydrogenation reactor to form a hydrogenated product. The hydrogenation catalyst generally can include Cu, Re, Ni, Fe, Co, Ru, Pd, Rh, Pt, Os, Ir, and alloys or any combination thereof, either alone or with promoters such as W, Mo, Au, Ag, Cr, Zn, Mn, Sn, B, P, Bi, and alloys or any combination thereof. Other effective hydrogenation catalyst materials include either supported nickel or ruthenium modified with rhenium. In an embodiment, the hydrogenation catalyst also includes any one of the supports, depending on the desired functionality of the catalyst. The hydrogenation catalysts may be prepared by methods known to those of ordinary skill in the art.

In some embodiments the hydrogenation catalyst includes a supported Group VIII metal catalyst and a metal sponge material (e.g., a sponge nickel catalyst). Raney nickel provides an example of an activated sponge nickel catalyst suitable for use in this invention. In other embodiment, the hydrogenation reaction in the invention is performed using a catalyst comprising a nickel-rhenium catalyst or a tungsten-modified nickel catalyst. One example of a suitable catalyst for the hydrogenation reaction of the invention is a carbon-supported nickel-rhenium catalyst.

In an embodiment, a suitable Raney nickel catalyst may be prepared by treating an alloy of approximately equal amounts by weight of nickel and aluminum with an aqueous alkali solution, e.g., containing about 25 weight % of sodium hydroxide. The aluminum is selectively dissolved by the aqueous alkali solution resulting in a sponge shaped material comprising mostly nickel with minor amounts of aluminum. The initial alloy includes promoter metals (i.e., molybdenum or chromium) in the amount such that about 1 to 2 weight % remains in the formed sponge nickel catalyst. In another embodiment, the hydrogenation catalyst is prepared using a solution of ruthenium (III) nitrosylnitrate, ruthenium (III) chloride in water to impregnate a suitable support material. The solution is then dried to form a solid having a water content of less than about 1% by weight. The solid may then be reduced at atmospheric pressure in a hydrogen stream at 300° C. (uncalcined) or 400° C. (calcined) in a rotary ball furnace for 4 hours. After cooling and rendering the catalyst inert with nitrogen, 5% by volume of oxygen in nitrogen is passed over the catalyst for 2 hours.

In certain embodiments, the catalyst described includes a catalyst support. The catalyst support stabilizes and supports the catalyst. The type of catalyst support used depends on the chosen catalyst and the reaction conditions. Suitable supports for the invention include, but are not limited to, carbon, silica, silica-alumina, zirconia, titania, ceria, vanadia, nitride, boron nitride, heteropolyacids, hydroxyapatite, zinc oxide, chromia, zeolites, carbon nanotubes, carbon fullerene and any combination thereof.

The catalysts used in this invention can be prepared using conventional methods known to those in the art. Suitable methods may include, but are not limited to, incipient wetting, evaporative impregnation, chemical vapor deposition, wash-coating, magnetron sputtering techniques, and the like.

The conditions for which to carry out the hydrogenation reaction will vary based on the type of starting material and the desired products. One of ordinary skill in the art, with the benefit of this disclosure, will recognize the appropriate reaction conditions. In general, the hydrogenation reaction is conducted at temperatures of 80° C. to 250° C., and preferably at 90° C. to 200° C., and most preferably at 100° C. to 150° C. In some embodiments, the hydrogenation reaction is conducted at pressures from 500 KPa to 14000 KPa.

The hydrogen used in the hydrogenolysis reaction of the current invention may include external hydrogen, recycled hydrogen, in situ generated hydrogen, and any combination thereof. As used herein, the term “external hydrogen” refers to hydrogen that does not originate from the biomass reaction itself, but rather is added to the system from another source.

In some embodiments of the invention, it is desirable to convert the starting carbohydrate to a smaller molecule that will be more readily converted to desired higher hydrocarbons. One suitable method for this conversion is through a hydrogenolysis reaction. Various processes are known for performing hydrogenolysis of carbohydrates. One suitable method includes contacting a carbohydrate with hydrogen or hydrogen mixed with a suitable gas and a hydrogenolysis catalyst in a hydrogenolysis reactor under conditions sufficient to form a reaction product comprising smaller molecules or polyols. As used herein, the term “smaller molecules or polyols” includes any molecule that has a smaller molecular weight, which can include a smaller number of carbon atoms or oxygen atoms than the starting carbohydrate. In an embodiment, the reaction products include smaller molecules that include polyols and alcohols. Someone of ordinary skill in the art would be able to choose the appropriate method by which to carry out the hydrogenolysis reaction.

In some embodiments, a 5 and/or 6 carbon sugar or sugar alcohol may be converted to propylene glycol, ethylene glycol, and glycerol using a hydrogenolysis catalyst. The hydrogenolysis catalyst may include Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. The hydrogenolysis catalyst may also include a carbonaceous pyropolymer catalyst containing transition metals (e.g., chromium, molybdenum, tungsten, rhenium, manganese, copper, cadmium) or Group VIII metals (e.g., iron, cobalt, nickel, platinum, palladium, rhodium, ruthenium, iridium, and osmium). In certain embodiments, the hydrogenolysis catalyst may include any of the above metals combined with an alkaline earth metal oxide or adhered to a catalytically active support. In certain embodiments, the catalyst described in the hydrogenolysis reaction may include a catalyst support as described above for the hydrogenation reaction.

The conditions for which to carry out the hydrogenolysis reaction will vary based on the type of starting material and the desired products. One of ordinary skill in the art, with the benefit of this disclosure, will recognize the appropriate conditions to use to carry out the reaction. In general, they hydrogenolysis reaction is conducted at temperatures of 110° C. to 300° C., and preferably at 170° C. to 220° C., and most preferably at 200° C. to 225° C. In some embodiments, the hydrogenolysis reaction is conducted under basic conditions, preferably at a pH of 8 to 13, and even more preferably at a pH of 10 to 12. In some embodiments, the hydrogenolysis reaction is conducted at pressures in a range between 60 KPa and 16500 KPa, and preferably in a range between 1700 KPa and 14000 KPa, and even more preferably between 4800 KPa and 11000 KPa.

The hydrogen used in the hydrogenolysis reaction of the current invention can include external hydrogen, recycled hydrogen, in situ generated hydrogen, and any combination thereof.

In some embodiments, the reaction products discussed above may be converted into higher hydrocarbons through a condensation reaction in a condensation reactor. In such embodiments, condensation of the reaction products occurs in the presence of a catalyst capable of forming higher hydrocarbons. While not intending to be limited by theory, it is believed that the production of higher hydrocarbons proceeds through a stepwise addition reaction including the formation of carbon-carbon, or carbon-oxygen bond. The resulting reaction products include any number of compounds containing these moieties, as described in more detail below.

In certain embodiments, suitable condensation catalysts include an acid catalyst, a base catalyst, or an acid/base catalyst. As used herein, the term "acid/base catalyst" refers to a catalyst that has both an acid and a base functionality. In some embodiments the condensation catalyst can include, without limitation, zeolites, carbides, nitrides, zirconia, alumina, silica, aluminosilicates, phosphates, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and any combination thereof. In some embodiments, the condensation catalyst can also include a modifier. Suitable modifiers include La, Y, Sc, P, B, Bi, Li, Na, K, Rb, Cs, Mg, Ca, Sr, Ba, and any combination thereof. In some embodiments, the condensation catalyst can also include a metal. Suitable metals include Cu, Ag, Au, Pt, Ni, Fe, Co, Ru, Zn, Cd, Ga, In, Rh, Pd, Ir, Re, Mn, Cr, Mo, W, Sn, Os, alloys, and any combination thereof.

In certain embodiments, the catalyst described in the condensation reaction may include a catalyst support as described above for the hydrogenation reaction. In certain embodiments, the condensation catalyst is self-supporting. As used herein, the term "self-supporting" means that the catalyst does not need another material to serve as support. In other embodiments, the condensation catalyst in used in conjunction with a separate support suitable for suspending the catalyst. In an embodiment, the condensation catalyst support is silica.

The conditions under which the condensation reaction occurs will vary based on the type of starting material and the desired products. One of ordinary skill in the art, with the benefit of this disclosure, will recognize the appropriate conditions to use to carry out the reaction. In some embodiments, the condensation reaction is carried out at a temperature at which the thermodynamics for the proposed reaction are favorable. The temperature for the condensation reaction will vary depending on the specific starting polyol or alcohol. In some embodiments, the temperature for the condensation reaction is in a range from 80° C. to 500° C., and preferably from 125° C. to 450° C., and most preferably from 125° C. to 250° C. In some embodiments, the condensation reaction is conducted at pressures in a range between 0 Kpa to 9000 KPa, and preferably in a range between 0 KPa and 7000 KPa, and even more preferably between 0 KPa and 5000 KPa.

The higher alkanes formed by the invention include, but are not limited to, branched or straight chain alkanes that have from 4 to 30 carbon atoms, branched or straight chain alkenes that have from 4 to 30 carbon atoms, cycloalkanes that have from 5 to 30 carbon atoms, cycloalkenes that have from 5 to 30 carbon atoms, aryls, fused aryls, alcohols, and ketones. Suitable alkanes include, but are not limited to, butane, pentane, pentene, 2-methylbutane, hexane, hexene, 2-methylpentane, 3-methylpentane, 2,2,-dimethylbutane, 2,3-dimethylbutane, heptane, heptene, octane, octene, 2,2,4-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, nonyldecane, nonyldecene, eicosane, eicosene, uneicosane, uneicosene, doeicosane, doeicosene, trieicosane, trieicosene, tetraeicosane, tetraeicosene, and isomers thereof. Some of these products may be suitable for use as fuels.

In some embodiments, the cycloalkanes and the cycloalkenes are unsubstituted. In other embodiments, the cycloalkanes and cycloalkenes are mono-substituted. In still other embodiments, the cycloalkanes and cycloalkenes are multi-substituted. In the embodiments comprising the substituted cycloalkanes and cycloalkenes, the substituted group includes, without limitation, a branched or straight chain alkyl having 1 to 12 carbon atoms, a branched or straight chain alkylene having 1 to 12 carbon atoms, a phenyl, and any combination thereof. Suitable cycloalkanes and cycloalkenes include, but are not limited to, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, isomers and any combination thereof.

In some embodiments, the aryls formed are unsubstituted. In another embodiment, the aryls formed are mono-substituted. In the embodiments comprising the substituted aryls, the substituted group includes, without limitation, a branched or straight chain alkyl having 1 to 12 carbon atoms, a branched or straight chain alkylene having 1 to 12 carbon atoms, a phenyl, and any combination thereof. Suitable aryls for the invention include, but are not limited to, benzene, toluene, xylene, ethyl benzene, para xylene, meta xylene, and any combination thereof.

The alcohols produced in the invention have from 4 to 30 carbon atoms. In some embodiments, the alcohols are cyclic. In other embodiments, the alcohols are branched. In another embodiment, the alcohols are straight chained. Suitable alcohols for the invention include, but are not limited to, butanol, pentanol, hexanol, heptanol, octanol, nonanol, decanol, undecanol, dodecanol, tridecanol, tetradecanol, pentadecanol, hexadecanol, heptyldecanol, octyldecanol, nonyldecanol, eicosanol, uneicosanol, doeicosanol, trieicosanol, tetraeicosanol, and isomers thereof.

The ketones produced in the invention have from 4 to 30 carbon atoms. In an embodiment, the ketones are cyclic. In another embodiment, the ketones are branched. In another embodiment, the ketones are straight chained. Suitable ketones for the invention include, but are not limited to, butanone, pentanone, hexanone, heptanone, octanone, nonanone, decanone, undecanone, dodecanone, tridecanone, tetradecanone, pentadecanone, hexadecanone, heptyldecanone, octyldecanone, nonyldecanone, eicosanone, uneicosanone, doeicosanone, trieicosanone, tetraeicosanone, and isomers thereof.

Another such chemical modification is interesterification. Naturally produced glycerolipids do not have a uniform distribution of fatty acid constituents. In the context of oils, interesterification refers to the exchange of acyl radicals between two esters of different glycerolipids. The interesterification process provides a mechanism by which the fatty acid constituents of a mixture of glycerolipids can be rearranged to modify the distribution pattern. Interesterification is a well-known chemical process, and generally comprises heating (to about 200° C.) a mixture of oils for a period (e.g, 30 minutes) in the presence of a catalyst, such as an alkali metal or alkali metal alkylate (e.g., sodium methoxide). This process can be used to randomize the distribution pattern of the fatty acid constituents of an oil mixture, or can be directed to produce a desired distribution pattern. This method of chemical modification of lipids can be performed on materials provided herein, such as microbial biomass with a percentage of dry cell weight as lipid at least 20%.

Directed interesterification, in which a specific distribution pattern of fatty acids is sought, can be performed by maintaining the oil mixture at a temperature below the melting point of some TAGs which might occur. This results in selective crystallization of these TAGs, which effectively removes them from the reaction mixture as they crystallize. The process can be continued until most of the fatty acids in the oil have precipitated, for example. A directed interesterification process can be used, for example, to produce a product with a lower calorie content via the substitution of longer-chain fatty acids with shorter-chain counterparts. Directed interesterification can also be used to produce a product with a mixture of fats that can provide desired melting characteristics and structural features sought in food additives or products (e.g., margarine) without resorting to hydrogenation, which can produce unwanted trans isomers.

Interesterification of oils produced by the methods described herein can be performed in conjunction with one or more of the methods and/or materials, or to produce products, as reported in the following: U.S. Pat. No. 6,080,853 (Nondigestible fat substitutes); U.S. Pat. No. 4,288,378 (Peanut butter stabilizer); U.S. Pat. No. 5,391,383 (Edible spray oil); U.S. Pat. No. 6,022,577 (Edible fats for food products); U.S. Pat. No. 5,434,278 (Edible fats for food products); U.S. Pat. No. 5,268,192 (Low calorie nut products); U.S. Pat. No. 5,258,197 (Reduce calorie edible compositions); U.S. Pat. No. 4,335,156 (Edible fat product); U.S. Pat. No. 7,288,278 (Food additives or medicaments); U.S. Pat. No. 7,115,760 (Fractionation process); U.S. Pat. No. 6,808,737 (Structural fats); U.S. Pat. No. 5,888,947 (Engine lubricants); U.S. Pat. No. 5,686,131 (Edible oil mixtures); and U.S. Pat. No. 4,603,188 (Curable urethane compositions).

In one embodiment in accordance with the invention, transesterification of the oil, as described above, is followed by reaction of the transesterified product with polyol, as reported in U.S. Pat. No. 6,465,642, to produce polyol fatty acid polyesters. Such an esterification and separation process may comprise the steps as follows: reacting a lower alkyl ester with polyol in the presence of soap; removing residual soap from the product mixture; water-washing and drying the product mixture to remove impurities; bleaching the product mixture for refinement; separating at least a portion of the unreacted lower alkyl ester from the polyol fatty acid polyester in the product mixture; and recycling the separated unreacted lower alkyl ester.

Transesterification can also be performed on microbial biomass with short chain fatty acid esters, as reported in U.S. Pat. No. 6,278,006. In general, transesterification may be performed by adding a short chain fatty acid ester to an oil in the presence of a suitable catalyst and heating the mixture. In some embodiments, the oil comprises about 5% to about 90% of the reaction mixture by weight. In some embodiments, the short chain fatty acid esters can be about 10% to about 50% of the reaction mixture by weight. Non-limiting examples of catalysts include base catalysts, sodium methoxide, acid catalysts including inorganic acids such as sulfuric acid and acidified clays, organic acids such as methane sulfonic acid, benzenesulfonic acid, and toluenesulfonic acid, and acidic resins such as Amberlyst 15. Metals such as sodium and magnesium, and metal hydrides also are useful catalysts.

Another such chemical modification is hydroxylation, which involves the addition of water to a double bond resulting in saturation and the incorporation of a hydroxyl moiety. The hydroxylation process provides a mechanism for converting one or more fatty acid constituents of a glycerolipid to a hydroxy fatty acid. Hydroxylation can be performed, for example, via the method reported in U.S. Pat. No. 5,576,027. Hydroxylated fatty acids, including castor oil and its derivatives, are useful as components in several industrial applications, including food additives, surfactants, pigment wetting agents, defoaming agents, water proofing additives, plasticizing agents, cosmetic emulsifying and/or deodorant agents, as well as in electronics, pharmaceuticals, paints, inks, adhesives, and lubricants. One example of how the hydroxylation of a glyceride may be performed is as follows: fat may be heated, preferably to about 30-50° C. combined with heptane and maintained at temperature for thirty minutes or more; acetic acid may then be added to the mixture followed by an aqueous solution of sulfuric acid followed by an aqueous hydrogen peroxide solution which is added in small increments to the mixture over one hour; after the aqueous hydrogen peroxide, the temperature may then be increased to at least about 60° C. and stirred for at least six hours; after the stirring, the mixture is allowed to settle and a lower aqueous layer formed by the reaction may be removed while the upper heptane layer formed by the reaction may be washed with hot water having a temperature of about 60° C.; the washed heptane layer may then be neutralized with an aqueous potassium hydroxide solution to a pH of about 5 to 7 and then removed by distillation under vacuum; the reaction product may then be dried under vacuum at 100° C. and the dried product steam-deodorized under vacuum conditions and filtered at about 50° to 60° C. using diatomaceous earth.

Hydroxylation of microbial oils produced by the methods described herein can be performed in conjunction with one or more of the methods and/or materials, or to produce products, as reported in the following: U.S. Pat. No. 6,590,113 (Oil-based coatings and ink); U.S. Pat. No. 4,049,724 (Hydroxylation process); U.S. Pat. No. 6,113,971 (Olive oil butter); U.S. Pat. No. 4,992,189 (Lubricants and lube additives); U.S. Pat. No. 5,576,027 (Hydroxylated milk); and U.S. Pat. No. 6,869,597 (Cosmetics).

Hydroxylated glycerolipids can be converted to estolides. Estolides consist of a glycerolipid in which a hydroxylated fatty acid constituent has been esterified to another fatty acid molecule. Conversion of hydroxylated glycerolipids to estolides can be carried out by warming a mixture of glycerolipids and fatty acids and contacting the mixture with a mineral acid, as described by Isbell et al., *JAOCS* 71(2):169-174 (1994). Estolides are useful in a variety of applications, including without limitation those reported in the following: U.S. Pat. No. 7,196,124 (Elastomeric materials and floor coverings); U.S. Pat. No. 5,458,795 (Thickened oils for high-temperature applications); U.S. Pat. No. 5,451,332 (Fluids for industrial applications); U.S. Pat. No. 5,427,704 (Fuel additives); and U.S. Pat. No. 5,380,894 (Lubricants, greases, plasticizers, and printing inks).

Another such chemical modification is olefin metathesis. In olefin metathesis, a catalyst severs the alkylidene carbons in an alkene (olefin) and forms new alkenes by pairing each of them with different alkylidine carbons. The olefin metathesis reaction provides a mechanism for processes such as truncating unsaturated fatty acid alkyl chains at alkenes by ethenolysis, cross-linking fatty acids through alkene linkages by self-metathesis, and incorporating new functional groups on fatty acids by cross-metathesis with derivatized alkenes.

In conjunction with other reactions, such as transesterification and hydrogenation, olefin metathesis can transform unsaturated glycerolipids into diverse end products. These products include glycerolipid oligomers for waxes; short-chain glycerolipids for lubricants; homo- and hetero-bifunctional alkyl chains for chemicals and polymers; short-chain esters for biofuel; and short-chain hydrocarbons for jet fuel. Olefin metathesis can be performed on triacylglycerols and fatty acid derivatives, for example, using the catalysts and methods reported in U.S. Pat. No. 7,119,216, US Patent Pub. No. 2010/0160506, and U.S. Patent Pub. No. 2010/0145086.

Olefin metathesis of bio-oils generally comprises adding a solution of Ru catalyst at a loading of about 10 to 250 ppm under inert conditions to unsaturated fatty acid esters in the presence (cross-metathesis) or absence (self-metathesis) of other alkenes. The reactions are typically allowed to proceed from hours to days and ultimately yield a distribution of alkene products. One example of how olefin metathesis may be performed on a fatty acid derivative is as follows: A solution of the first generation Grubbs Catalyst (dichloro[2(1-methylethoxy-α-O)phenyl]methylene-α-C] (tricyclohexyl-phosphine) in toluene at a catalyst loading of 222 ppm may be added to a vessel containing degassed and dried methyl oleate. Then the vessel may be pressurized with about 60 psig of ethylene gas and maintained at or below about 30° C. for 3 hours, whereby approximately a 50% yield of methyl 9-decenoate may be produced.

Olefin metathesis of oils produced by the methods described herein can be performed in conjunction with one or more of the methods and/or materials, or to produce products, as reported in the following: PCT/US07/081,427 (α-olefin fatty acids) and U.S. patent application Ser. No. 12/281,938 (petroleum creams), Ser. No. 12/281,931 (paintball gun capsules), Ser. No. 12/653,742 (plasticizers and lubricants), Ser. No. 12/422,096 (bifunctional organic compounds), and Ser. No. 11/795,052 (candle wax).

Other chemical reactions that can be performed on microbial oils include reacting triacylglycerols with a cyclopropanating agent to enhance fluidity and/or oxidative stability, as reported in U.S. Pat. No. 6,051,539; manufacturing of waxes from triacylglycerols, as reported in U.S. Pat. No. 6,770,104; and epoxidation of triacylglycerols, as reported in "The effect of fatty acid composition on the acrylation kinetics of epoxidized triacylglycerols", Journal of the American Oil Chemists' Society, 79:1, 59-63, (2001) and Free Radical Biology and Medicine, 37:1, 104-114 (2004).

The generation of oil-bearing microbial biomass for fuel and chemical products as described above results in the production of delipidated biomass meal. Delipidated meal is a byproduct of preparing algal oil and is useful as animal feed for farm animals, e.g., ruminants, poultry, swine and aquaculture. The resulting meal, although of reduced oil content, still contains high quality proteins, carbohydrates, fiber, ash, residual oil and other nutrients appropriate for an animal feed. Because the cells are predominantly lysed by the oil separation process, the delipidated meal is easily digestible by such animals. Delipidated meal can optionally be combined with other ingredients, such as grain, in an animal feed. Because delipidated meal has a powdery consistency, it can be pressed into pellets using an extruder or expander or another type of machine, which are commercially available.

The invention, having been described in detail above, is exemplified in the following examples, which are offered to illustrate, but not to limit, the claimed invention.

XIV. Examples

Example 1

Fatty Acid Analysis by Fatty Acid Methyl Ester Detection

Lipid samples were prepared from dried biomass. 20-40 mg of dried biomass was resuspended in 2 mL of 5% $H_2SO_4$ in MeOH, and 200 ul of toluene containing an appropriate amount of a suitable internal standard (C19:0) was added. The mixture was sonicated briefly to disperse the biomass, then heated at 70-75° C. for 3.5 hours. 2 mL of heptane was added to extract the fatty acid methyl esters, followed by addition of 2 mL of 6% $K_2CO_3$ (aq) to neutralize the acid. The mixture was agitated vigorously, and a portion of the upper layer was transferred to a vial containing $Na_2SO_4$ (anhydrous) for gas chromatography analysis using standard FAME GC/FID (fatty acid methyl ester gas chromatography flame ionization detection) methods.

Example 2

Triacylglyceride Purification from Oil and Methods for Triacylglyceride Lipase Digestion The triacylglyceride (TAG) fraction of each oil sample was isolated by dissolving ~10 mg of oil in dichloromethane and loading it onto a Bond-Elut aminopropyl solid-phase extraction cartridge (500 mg) preconditioned with heptane. TAGs were eluted with dicholoromethane-MeOH (1:1) into a collection tube, while polar lipids were retained on the column. The solvent was removed with a stream of nitrogen gas. Tris buffer and 2 mg porcine pancreatic lipase (Type II, Sigma, 100-400 units/mg) were added to the TAG fraction, followed by addition of bile salt and calcium chloride solutions. The porcine pancreatic lipase cleaves sn-1 and sn-3 fatty acids, thereby generating 2-monoacylglycerides and free fatty acids. This mixture was heated with agitation at 40° C. for three minutes, cooled briefly, then quenched with 6 N HCl. The mixture was then extracted with diethyl ether and the ether layer was washed with water then dried over sodium sulfate. The solvent was removed with a stream of nitrogen. To isolate the monoacylglyceride (MAG) fraction, the residue was dissolved in heptane and loaded onto a second aminopropyl solid phase extraction cartridge pretreated with heptane. Residual TAGs were eluted with diethyl ether-dichloromethane-heptane (1:9:40), diacylglycerides (DAGs) were eluted with ethyl acetate-heptane (1:4), and MAGs were eluted from the cartridge with dichloromethane-methanol (2:1). The resulting MAG, DAG, and TAG fractions were then concentrated to dryness with a stream of nitrogen and subjected to routine direct transesterificiation method of GC/FID analysis as described in Example 1.

Example 3

Engineering Microorganisms for Fatty Acid and Sn-2 Profiles Increased in Lauric Acid Through Exogenous LPAAT Expression This example describes the use of recombinant polynucleotides that encode a *C. nucifera* 1-acyl-sn-glycerol-3-phosphate acyltransferase (Cn LPAAT) enzyme to engineer a microorganism in which the fatty acid profile and the sn-2 profile of the transformed microorganism has been enriched in lauric acid.

A classically mutagenized strain of *Prototheca moriformis* (UTEX 1435), Strain A, was initially transformed with the plasmid construct pSZ1283 according to biolistic transformation methods as described in PCT/US2009/066141, PCT/US2009/066142, PCT/US2011/038463, PCT/US2011/038464, and PCT/US2012/023696. pSZ1283, described in PCT/US2011/038463, PCT/US2011/038464, and PCT/US2012/023696 hereby incorporated by reference, comprised the coding sequence of the *Cuphea wrightii* FATB2 (CwTE2) thioesterase (SEQ ID NO: 10), 5' (SEQ ID NO: 1) and 3' (SEQ ID NO: 2) homologous recombination targeting sequences (flanking the construct) to the 6S genomic region for integration into the nuclear genome, and a *S. cerevisiae* suc2 sucrose invertase coding region (SEQ ID NO: 4), to express the protein sequence given in SEQ ID NO: 3, under the control of *C. reinhardtii* β-tubulin promoter/5'UTR (SEQ ID NO: 5) and *Chlorella vulgaris* nitrate reductase 3' UTR (SEQ ID NO: 6). This *S. cerevisiae* suc2 expression cassette is listed as SEQ ID NO: 7 and served as a selectable marker. The CwTE2 protein coding sequence to express the protein sequence given in SEQ ID NO: 11, was under the control of the *P. moriformis* Amt03 promoter/5'UTR (SEQ ID NO: 8) and *C. vulgaris* nitrate reductase 3'UTR. The protein coding regions of CwTE2 and suc2 were codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

Upon transformation of pSZ1283 into Strain A, positive clones were selected on agar plates with sucrose as the sole carbon source. Primary transformants were then clonally purified and a single transformant, Strain B, was selected for further genetic modification. This genetically engineered strain was transformed with plasmid construct pSZ2046 to interrupt the pLoop genomic locus of Strain B. Construct pSZ2046 comprised the coding sequence of the *C. nucifera* 1-acyl-sn-glycerol-3-phosphate acyltransferase (Cn LPAAT) enzyme (SEQ ID NO: 12), 5' (SEQ ID NO: 13) and 3' (SEQ ID NO: 14) homologous recombination targeting sequences (flanking the construct) to the pLoop genomic region for integration into the nuclear genome, and a neomycin resistance protein-coding sequence under the control of *C. reinhardtii* β-tubulin promoter/5'UTR (SEQ ID NO: 5), and *Chlorella vulgaris* nitrate reductase 3' UTR (SEQ ID NO: 6). This NeoR expression cassette is listed as SEQ ID NO: 15 and served as a selectable marker. The Cn LPAAT protein coding sequence was under the control of the *P. moriformis* Amt03 promoter/5'UTR (SEQ ID NO: 8) and *C. vulgaris* nitrate reductase 3'UTR. The protein coding regions of Cn LPAAT and NeoR were codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696. The amino acid sequence of Cn LPAAT is provided as SEQ ID NO: 16.

Upon transformation of pSZ2046 into Strain B, thereby generating Strain C, positive clones were selected on agar plates comprising G418 (Geneticin). Individual transformants were clonally purified and grown at pH 7.0 under conditions suitable for lipid production as detailed in PCT/US2009/066141, PCT/US2009/066142, PCT/US2011/038463, PCT/US2011/038464, and PCT/US2012/023696. Lipid samples were prepared from dried biomass from each transformant and fatty acid profiles from these samples were analyzed using standard fatty acid methyl ester gas chromatography flame ionization (FAME GC/FID) detection methods as described in Example 1. The fatty acid profiles (expressed as Area % of total fatty acids) of *P. moriformis* UTEX 1435 (U1) grown on glucose as a sole carbon source, untransformed Strain B and five pSZ2046 positive transformants (Strain C, 1-5) are presented in Table 6.

TABLE 6

Effect of LPAAT expression on fatty acid profiles of transformed *Prototheca moriformis* (UTEX 1435) comprising a mid-chain preferring thioesterase.

| Area % Fatty acid | U1 | Strain B | Strain C-1 | Strain C-2 | Strain C-3 | Strain C-4 | Strain C-5 |
|---|---|---|---|---|---|---|---|
| C10:0 | 0.01 | 5.53 | 11.37 | 11.47 | 10.84 | 11.13 | 11.12 |
| C12:0 | 0.04 | 31.04 | 46.63 | 46.47 | 45.84 | 45.80 | 45.67 |
| C14:0 | 1.27 | 15.99 | 15.14 | 15.12 | 15.20 | 15.19 | 15.07 |
| C16:0 | 27.20 | 12.49 | 7.05 | 7.03 | 7.30 | 7.20 | 7.19 |
| C18:0 | 3.85 | 1.30 | 0.71 | 0.72 | 0.74 | 0.74 | 0.74 |
| C18:1 | 58.70 | 24.39 | 10.26 | 10.41 | 10.95 | 11.31 | 11.45 |
| C18:2 | 7.18 | 7.79 | 7.05 | 6.93 | 7.30 | 6.88 | 7.01 |
| C10-C12 | 0.50 | 36.57 | 58.00 | 57.94 | 56.68 | 56.93 | 56.79 |

As shown in Table 6, the fatty acid profile of Strain B expressing CwTE2 showed increased composition of C10:0, C12:0, and C14:0 fatty acids and a decrease in C16:0, C18:0, and C18:1 fatty acids relative to the fatty acid profile of the untransformed UTEX 1435 strain. The impact of additional genetic modification on the fatty acid profile of the transformed strains, namely the expression of CnLPAAT in Strain B, is a still further increase in the composition of C10:0 and C12:0 fatty acids, a still further decrease in C16:0, C18:0, and C18:1 fatty acids, but no significant effect on the C14:0 fatty acid composition. These data indicate that the CnLPAAT shows substrate preference in the context of a microbial host organism.

The untransformed *P. moriformis* Strain A is characterized by a fatty acid profile comprising less than 0.5% C12 fatty acids and less than 1% C10-C12 fatty acids. In contrast, the fatty acid profile of Strain B expressing a *C. wrightii* thioesterase comprised 31% C12:0 fatty acids, with C10-C12 fatty acids comprising greater than 36% of the total fatty acids. Further, fatty acid profiles of Strain C, expressing a higher plant thioesterase and a CnLPAAT enzyme, comprised between 45.67% and 46.63% C12:0 fatty acids, with C10-C12% fatty acids comprising between 71 and 73% of total fatty acids. The result of expressing an exogenous thioesterase was a 62-fold increase in the percentage of C12 fatty acid present in the engineered microbe. The result of expressing an exogenous thioesterase and exogenous LPAAT was a 92-fold increase in the percentage of C12 fatty acids present in the engineered microbe.

The TAG fraction of oil samples extracted from Strains A, B, and C were analyzed for the sn-2 profile of their triacylglycerides. The TAGs were extracted and processed as described in Example 2 and analysed as in Examples 1 and 2. The fatty acid composition and the sn-2 profiles of the TAG fraction of oil extracted from Strains A, B, and C (expressed as Area % of total fatty acids) are presented in Table 7. Values not reported are indicated as "n.r."

TABLE 7

Effect of LPAAT expression on the fatty acid composition and the sn-2 profile of TAGs produced from transformed *Prototheca moriformis* (UTEX 1435) comprising a mid-chain preferring thioesterase.

| Area % fatty acid | Strain A (untransformed) FA | Strain A (untransformed) sn-2 profile | Strain B (pSZ1500) FA | Strain B (pSZ1500) sn-2 profile | Strain C (pSZ1500 + pSZ2046) FA | Strain C (pSZ1500 + pSZ2046) sn-2 profile |
|---|---|---|---|---|---|---|
| C10:0 | n.r. | n.r. | 11.9 | 14.2 | 12.4 | 7.1 |
| C12:0 | n.r. | n.r. | 42.4 | 25 | 47.9 | 52.8 |
| C14:0 | 1.0 | 0.6 | 12 | 10.4 | 13.9 | 9.1 |
| C16:0 | 23.9 | 1.6 | 7.2 | 1.3 | 6.1 | 0.9 |
| C18:0 | 3.7 | 0.3 | n.r | n.r. | 0.8 | 0.3 |
| C18:1 | 64.3 | 90.5 | 18.3 | 36.6 | 9.9 | 17.5 |
| C18:2 | 4.5 | 5.8 | 5.8 | 10.8 | 6.5 | 10 |
| C18:3 | n.r. | n.r. | n.r. | n.r. | 1.1 | 1.6 |

As shown in Table 7, the fatty acid composition of triglycerides (TAGs) isolated from Strain B expressing CwTE2 was increased for C10:0, C12:0, and C14:0 fatty acids and decrease in C16:0 and C18:1 fatty acids relative to the fatty acid profile of TAGs isolated from untransformed Strain A. The impact of additional genetic modification on the fatty acid profile of the transformed strains, namely the expression of CnLPAAT, was a still further increase in the composition of C10:0 and C12:0 fatty acids, a still further decrease in C16:0, C18:0, and C18:1 fatty acids, but no significant effect on the C14:0 fatty acid composition. These data indicate that expression of the exogenous CnLPAAT improves the midchain fatty acid profile of transformed microbes.

The untransformed *P. moriformis* Strain A is characterized by an sn-2 profile of about 0.6% C14, about 1.6% C16:0, about 0.3% C18:0, about 90% C18:1, and about 5.8% C18:2. In contrast to Strain A, Strain B, expressing a *C. wrightii* thioesterase is characterized by an sn-2 profile that is higher in midchain fatty acids and lower in long chain fatty acids. C12 fatty acids comprised 25% of the sn-2 profile of Strain B. The impact of additional genetic modification on the sn-2 profile of the transformed strains, namely the expression of CnLPAAT, was still a further increase in C12 fatty acids (from 25% to 52.8%), a decrease in C18:1 fatty acids (from 36.6% to 17.5%), and a decrease in C10:0 fatty acids. (The sn-2 profile composition of C14:0 and C16:0 fatty acids was relatively similar for Strains B and C.)

These data demonstrate the utility and effectiveness of polynucleotides permitting exogenous LPAAT expression to alter the fatty acid profile of engineered microorganisms, and in particular in increasing the concentration of C10:0 and C12:0 fatty acids in microbial cells. These data further demonstrate the utility and effectiveness of polynucleotides permitting exogenous thioesterase and exogenous LPAAT expression to alter the sn-2 profile of TAGs produced by microbial cells, in particular in increasing the C12 composition of sn-2 profiles and decreasing the C18:1 composition of sn-2 profiles.

Example 4

Thermal Behavior of Oils Produced from Recombinant Microalgae

FIGS. 1-14 include fatty acid profiles and melting curves of refined, bleached and deodorized oils from genetically engineered *Prototheca moriformis* strains. In some cases, modifications of the melting curves are obtained via genetic engineering. For example, some of the oils produced have shallower or sharper melting transitions relative to control microalgal oils (i.e., those produced from strains lacking a given genetic modification) or relative to widely available plant oils. In addition, FIG. 12 shows scanning calorimetry for a high palmitic oil when tempered by holding at room temperature for several days (lower trace) and for the same oil after performing the first scan (upper trace). The scans ranged from −60° C. to +50° C. with a heating rate of 10° C./minute. The differences between the two traces suggests that tempering of the oil caused a change in crystal structure within the oil.

Figure 10:
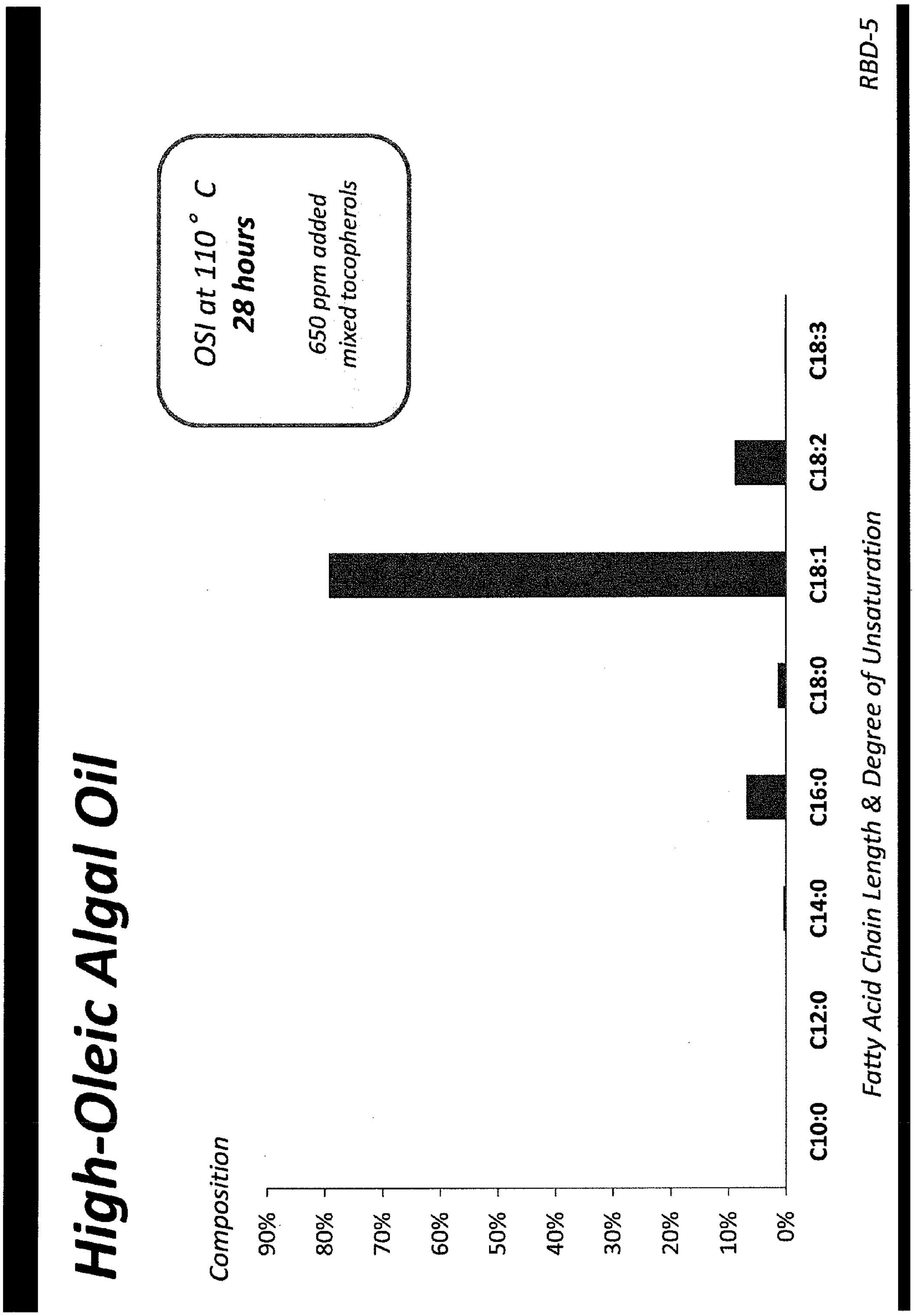
Figure 11:
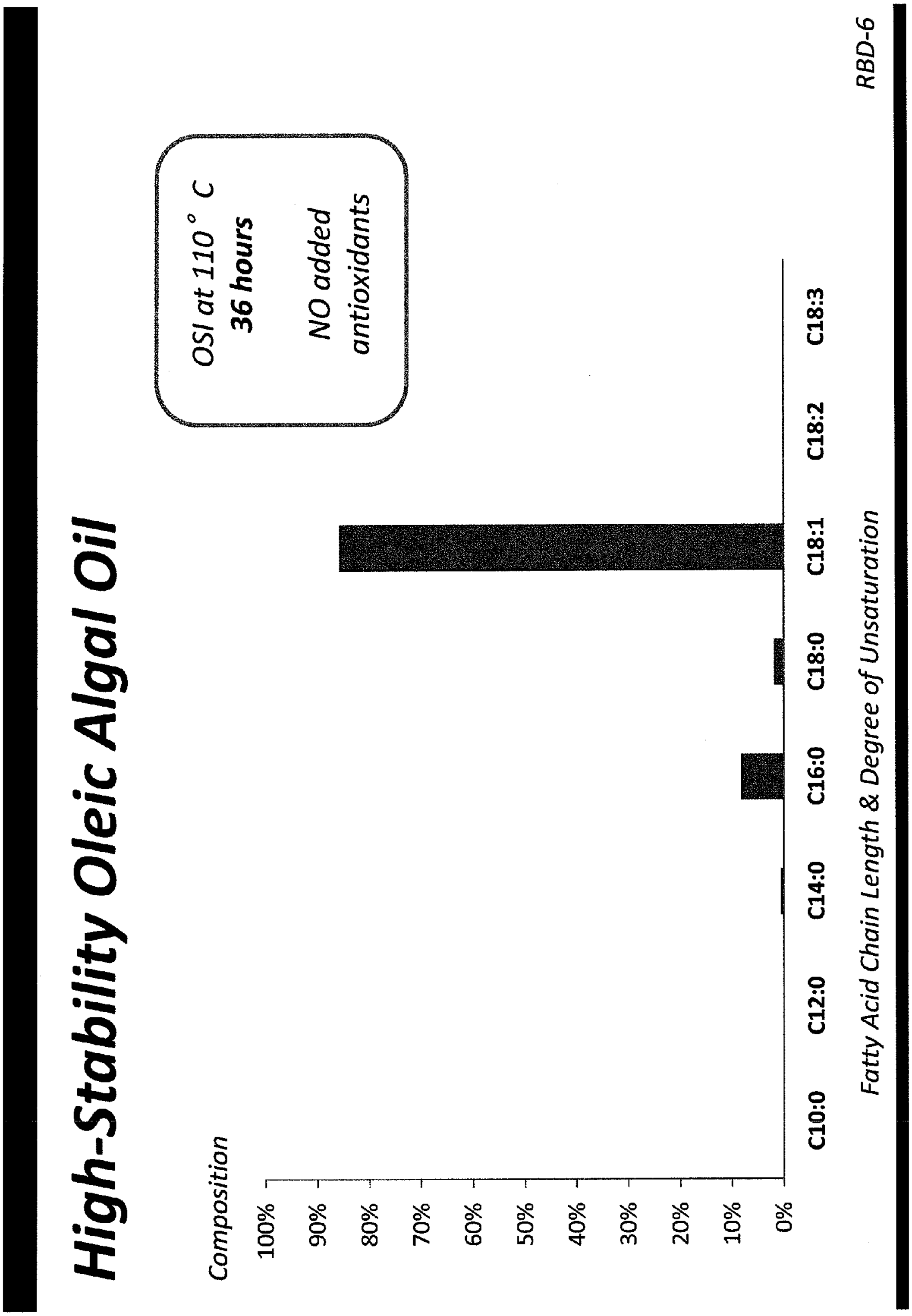
Figure 12:
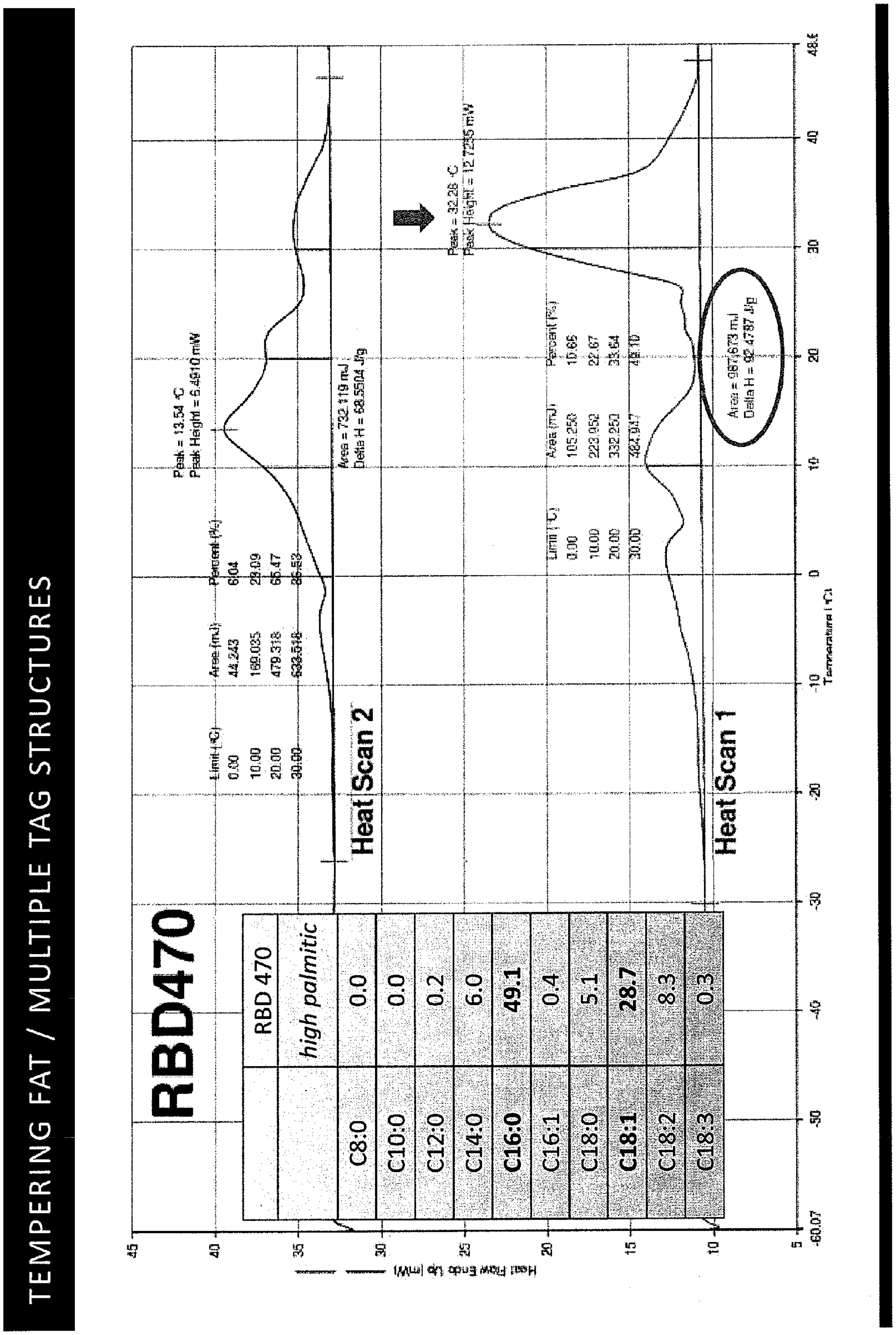
Figure 15:
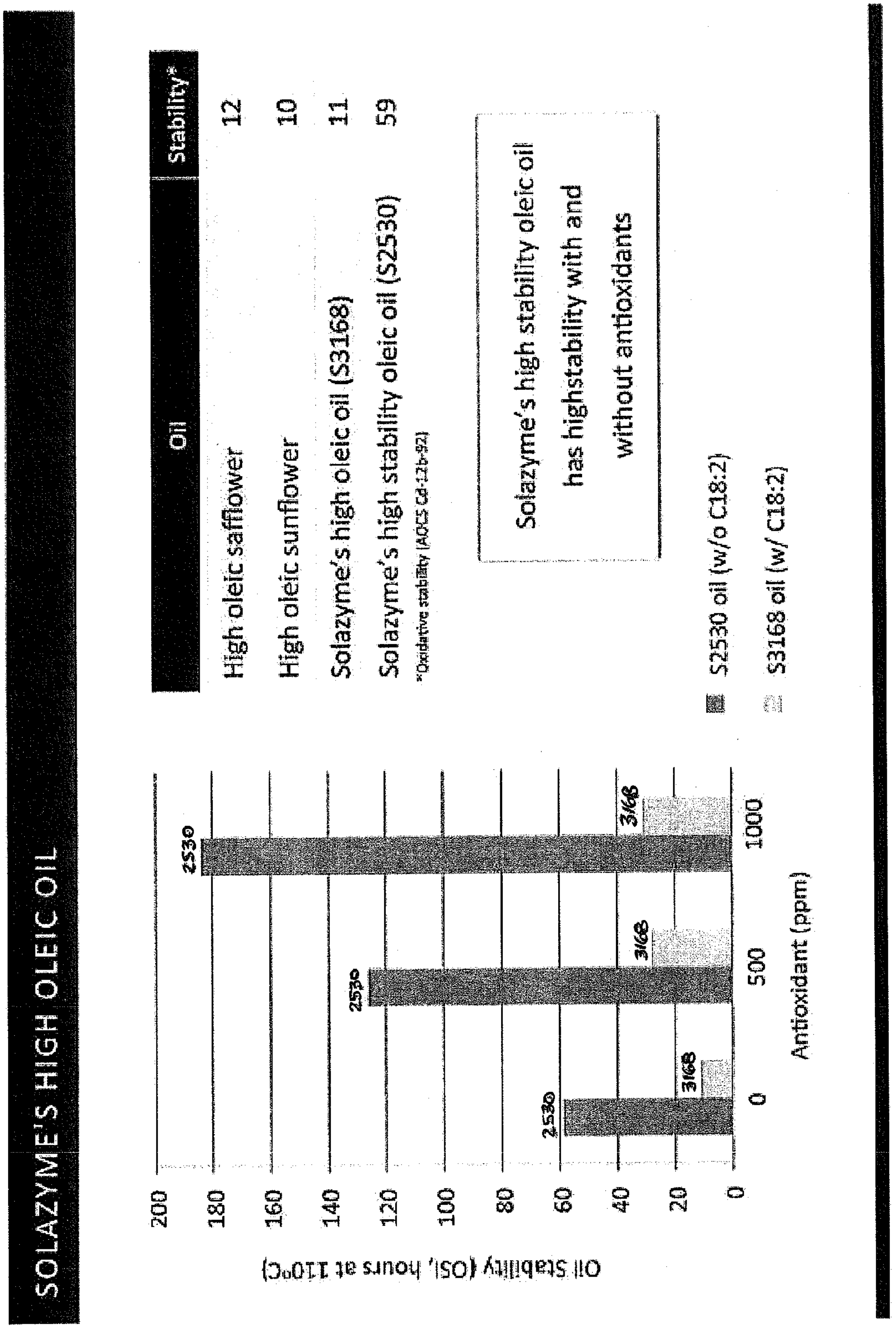
FIG. 15 shows the stability of different oils as a function of antioxidant concentration, as discussed in Example 5.

Also of note, FIGS. 10 and 11 show stability testing of RBD-5 and RBD 6. Remarkably, RBD-6, an oil with less than 0.1% 18:2 and 18:3 fatty acids was substantially stable as measured by the oxidative stability index (AOCS Method Cd 12b-92) even after 36 hours of heating at 110° C.

Table 8, below, gives details of the genetic engineering of the strains identified in FIGS. 1-13.

TABLE 8

Genetically engineered strains.

| | |
|---|---|
| RB Z | *Ulmus Americana* thioesterase |
| RBD-1 | *Cuphea wrightii* FATB2 thioesterase driven by amt03 |
| RBD-2 | *Ulmus americana* thioesterase |
| RBD-3 | Native *C. hookeriana* C16:0-specific thioesterase with amt03 promoter |
| RBD Y | *Ulmus Americana* thioesterase with Btub promoter |
| RBD X | SAD2B knockout with native *C wrightii* FAT2B thioesterase, amt03 promoter |
| RBD W | SAD2B KO with Native *C. wrightii* FATB2 driven by amt03 at insertion site |
| RBD-4 | control strain |
| RBD-5 | FATA-1 knockout with *Carthamus oleate* sp. TE driven by amt03 promoter at insertion site |
| RBD-6 | FADc knockout with *Carthamus tinctorius* oleoyl thioesterase |

Example 5

Characteristics of Processed Oil Produced from Engineered Microorganisms

Methods and effects of transforming *Prototheca moriformis* (UTEX 1435) with transformation vector pSZ1500 (SEQ ID NO: 17) have been previously described in PCT Application Nos. PCT/US2011/038463, PCT/US2011/038464, and PCT/US2012/023696.

A classically mutagenized (for higher oil production) derivative of *Protheca moriformis* (UTEX 1435), Strain A, was transformed with pSZ1500 according to biolistic transformation methods as described in PCT/US2009/066141, PCT/US2009/066142, PCT/US2011/038463, PCT/US2011/038464, and PCT/US2012/023696. pSZ1500 comprised nucleotide sequence of the *Carthamus tinctorius* oleyl-thioesterase (CtOTE) gene, codon-optimized for expression in *P. moriformis* UTEX 1435. The pSZ1500 expression construct included 5' (SEQ ID NO: 18) and 3' (SEQ ID NO: 19) homologous recombination targeting sequences (flanking the construct) to the FADc genomic region for integration into the nuclear genome and a *S. cerevisiae* suc2 sucrose invertase coding region under the control of *C. reinhardtii* β-tubulin promoter/5'UTR (SEQ ID NO: 5) and *Chlorella vulgaris* nitrate reductase 3' UTR (SEQ ID NO: 6). This *S. cerevisiae* suc2 expression cassette is listed as SEQ ID NO: 7 and served as a selection marker. The CtOTE coding region was under the control of the *P. moriformis* Amt03 promoter/5'UTR (SEQ ID NO: 8) and *C. vulgaris* nitrate reductase 3'UTR, and the native transit peptide was replaced with the *C. protothecoides* stearoyl-ACP desaturase transit peptide (SEQ ID NO: 9). The protein coding regions of CtOTE and suc2 were codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

Primary pSZ1500 transformants of Strain A were selected on agar plates containing sucrose as a sole carbon source, clonally purified, and a single engineered line, Strain D was selected for analysis. Strain D was grown as described in PCT/US2009/066141, PCT/US2009/066142, PCT/US2011/038463, PCT/US2011/038464, and PCT/US2012/023696. Hexane extraction of the oil from the generated biomass was then performed using standard methods, and the resulting triglyceride oil was determined to be free of residual hexane. Other methods of extraction of oil from microalgae using an expeller press are described in PCT Application No. PCT/US2010/031108 and are hereby incorporated by reference.

Different lots of oil extracted from biomass of Strain D were refined, bleached, and deodorized using standard vegetable oil processing methods. These procedures generated oil samples RBD437, RBD469, RBD501, RBD 502, RBD503, and RBD529, which were subjected to analytical testing protocols according to methods defined through the American Oil Chemists' Society, the American Society for Testing and Materials, and the International Organization for Standardization. The results of these analyses are summarized below in Tables 9-14.

TABLE 9

Analytical results for oil sample RBD469.

| Method Number | Test Description | Results | Units |
|---|---|---|---|
| AOCS Ca 3a-46 | Insoluble impurities | <0.01 | % |
| AOCS Ca 5a-40 | Free Fatty Acids (Oleic) | 0.02 | % |
| AOCS Ca 5a-40 | Acid Value | 0.04 | mg KOH/g |
| AOCS CA 9f-57 | Neutral oil | 98.9 | % |
| D97 | Cloud Point | −15 | deg C. |
| D97 | Pour Point | −18 | deg C. |
| | Karl Fischer Moisture | 0.01 | % |
| AOCS Cc 13d-55 (modified) | Chlorophyll | <0.01 | ppm |
| | Iodine Value | 78.3 | g $I_2$/100 g |
| AOCS Cd 8b-90 | Peroxide Value | 0.31 | meq/kg |
| ISO 6885 | p-Anisidine Value | 0.65 | |
| AOCS Cc 18-80 | Dropping Melting point (Mettler) | 6.2 | deg C. |
| AOCS Cd 11d-96 | Tricylglicerides | 98.6 | % |
| AOCS Cd 11d-96 | Monoglyceride | <0.01 | % |
| AOCS Cd 11d-96 | Diglicerides | 0.68 | % |
| AOCS Cd 20-91 | Total Polar Compounds | 2.62 | % |
| IUPAC, 2.507 and 2.508 | Oxidized & Polymerized Tricylglicerides | 17.62 | % |

TABLE 9-continued

Analytical results for oil sample RBD469.

| Method Number | Test Description | Results | Units |
|---|---|---|---|
| AOCS Cc 9b-55 | Flash Point | 244 | deg C. |
| AOCS Cc 9a-48 | Smoke Point | 232 | deg C. |
| AOCS Cd 12b-92 | Oxidataive Stability Index Rancimat (110° C.) | 31.6 | hours |
| AOCS Ca 6a-40 | Unsaponified Matter | 2.28 | % |

RBD469 oil was analyzed for trace element content, solid fat content, and Lovibond color according to AOCS methods. Results of these analyses are presented below in Table 10, Table 10, and Table 11.

TABLE 10

ICP Elemental Analysis of RBD469 oil.

| Method Number | Test Description | Results in ppm |
|---|---|---|
| AOCS Ca 20-99 and | Phosphorus | 1.09 |
| AOCS Ca 17-01 | Calcium | 0.1 |
| (modified) | Magnesium | 0.04 |
| | Iron | <0.02 |
| | Sulfur | 28.8 |
| | Copper | <0.05 |
| | Potassium | <0.50 |
| | Sodium | <0.50 |
| | Silicon | 0.51 |
| | Boron | 0.06 |
| | Aluminum | <0.20 |
| | Lead | <0.20 |
| | Lithium | <0.02 |
| | Nickel | <0.20 |
| | Vanadium | <0.05 |
| | Zinc | <0.02 |
| | Arsenic | <0.20 |
| | Mercury | <0.20 |
| | Cadmium | <0.03 |
| | Chromium | <0.02 |
| | Manganese | <0.05 |
| | Silver | <0.05 |
| | Titanium | <0.05 |
| | Selenium | <0.50 |
| UOP779 | Chloride organic | <1 |
| UOP779 | Chloride inorganic | 7.24 |
| AOCS Ba 4e-93 | Nitrogen | 6.7 |

TABLE 11

Solid Fat Content of RBD469 Oil

| Method Number | Solid Fat Content | Result |
|---|---|---|
| AOCS Cd 12b-93 | Solid Fat Content 10° C. | 0.13% |
| AOCS Cd 12b-93 | Solid Fat Content 15° C. | 0.13% |
| AOCS Cd 12b-93 | Solid Fat Content 20° C. | 0.28% |
| AOCS Cd 12b-93 | Solid Fat Content 25° C. | 0.14% |
| AOCS Cd 12b-93 | Solid Fat Content 30° C. | 0.08% |
| AOCS Cd 12b-93 | Solid Fat Content 35° C. | 0.25% |

TABLE 12

Lovibond Color of RBD469 Oil

| Method Number | Color | Result | Unit |
|---|---|---|---|
| AOCS Cc 13j-97 | red | 2 | Unit |
| AOCS Cc 13j-97 | yellow | 27 | Unit |

RBD469 oil was subjected to transesterification to produce fatty acid methyl esters (FAMEs). The resulting FAME profile of RBD469 is shown in Table 12.

TABLE 13

| FAME Profile of RBD469 Oil | |
|---|---|
| Fatty Acid | Area % |
| C10 | 0.01 |
| C12:0 | 0.04 |
| C14:0 | 0.64 |
| C15:0 | 0.08 |
| C16:0 | 8.17 |
| C16:1 iso | 0.39 |
| C16:1 | 0.77 |
| C17:0 | 0.08 |
| C18:0 | 1.93 |
| C18:1 | 85.88 |
| C18:1 iso | 0.05 |
| C18:2 | 0.05 |
| C20:0 | 0.3 |
| C20:1 | 0.06 |
| C20:1 | 0.44 |
| C22:0 | 0.11 |
| C23:0 | 0.03 |
| C24:0 | 0.1 |
| Total FAMEs Identified | 99.13 |

The oil stability indexes (OSI) of 6 RBD oil samples without supplemented antioxidants and 3 RBD oil samples supplemented with antioxidants were analyzed according to the Oil Stability Index AOCS Method Cd 12b-92. Shown in Table 14 are the results of OSI AOCS Cd 12b-92 tests, conducted at 110° C., performed using a Metrohm 873 Biodiesel Rancimat. Results, except where indicated with an astericks (*), are the average of multiple OSI runs. Those samples not analyzed are indicated (NA).

TABLE 14

Oil Stability Index at 110° C. of RBD oil samples with and without antioxidants.

| Antioxidant added | Antioxidant Concentration | OSI (hours) for each RBD Sample RBD437 | RBD469 | RBD502 | RBD501 | RBD503 | RBD529 |
|---|---|---|---|---|---|---|---|
| None | 0 | 65.41 | 38.33 | 72.10 | 50.32 | 63.04 | 26.68 |
| Tocopherol & Ascorbyl Palmitate | 35 ppm/16.7 ppm | 77.72 | 48.60 | 82.67 | NA | NA | NA |
| Tocopherol & Ascorbyl Palmitate | 140 ppm/66.7 ppm | 130.27 | 81.54* | 211.49* | NA | NA | NA |
| Tocopherol & Ascorbyl Palmitate | 1050 ppm/500 ppm | >157* | >144 | 242.5* | NA | NA | NA |
| Tocopherol | 50 ppm | NA | 46.97 | NA | NA | NA | NA |
| TBHQ | 20 ppm | 63.37 | 37.4 | NA | NA | NA | NA |

The untransformed *P. moriformis* (UTEX 1435) acid profile comprises less than 60% C18:1 fatty acids and greater than 7% C18:2 fatty acids. In contrast, Strain D (comprising pSZ1500) exhibited fatty acid profiles with an increased composition of C18:1 fatty acids (to above 85%) and a decrease in C18:2 fatty acids (to less than 0.06%). Upon refining, bleaching, and degumming, RBD oils samples prepared from the oil made from strain E exhibited OSI values >26 hrs. With addition of antioxidants, the OSI of RBD oils prepared from oils of Strain D increased from 48.60 hours to greater than 242 hours. In other experiments, OSI values of over 400 hours were achieved. Additional properties of a low polyunsaturated oil according to embodiments of the invention are given in FIG. 16.

Example 6

Improving the Levels of Oleic Acid of Engineered Microbes Through Allelic Disruption of a Fatty Acid Desaturase and an Acyl-ACP Thioesterase This example describes the use of a transformation vector to disrupt a FATA locus of a *Prototheca moriformis* strain previously engineered for high oleic acid and low linoleic acid production. The transformation cassette used in this example comprised a selectable marker and nucleotide sequences encoding a *P. moriformis* KASII enzyme to engineer microorganisms in which the fatty acid profile of the transformed microorganism has been altered for further increased oleic acid and lowered palmitic acid levels.

Strain D, described in Example 5 and in PCT/US2012/023696, is a classically mutagenized (for higher oil production) derivative of *P. moriformis* (UTEX 1435) subsequently transformed with the transformation construct pSZ1500 (SEQ ID NO: 17) according to biolistic transformation methods as described in PCT/US2009/066141, PCT/US2009/066142, PCT/US2011/038463, PCT/US2011/038464, and PCT/US2012/023696. This strain was used as the host for transformation with construct pSZ2276 to increase expression of a KASII enzyme while concomitantly ablating an endogenous acyl-ACP thioesterase genetic locus to generate Strain E. The pSZ2276 transformation construct included 5' (SEQ ID NO: 20) and 3' (SEQ ID NO: 21) homologous recombination targeting sequences (flanking the construct) to the FATA1 genomic region for integration into the *P. moriformis* nuclear genome, an *A. thaliana* THIC protein coding region under the control of the *C. protothecoides* actin promoter/5'UTR (SEQ ID NO: 22) and *C. vulgaris* nitrate reductase 3' UTR (SEQ ID NO: 6). This AtTHIC expression cassette is listed as SEQ ID NO: 23 and served as a selection marker. The *P. moriformis* KASII protein coding region was under the control of the *P. moriformis* Amt03 promoter/5'UTR (SEQ ID NO: 8) and *C. vulgaris* nitrate reductase 3'UTR, and the native transit peptide of the KASII enzyme was replaced with the *C. protothecoides* stearoyl-ACP desaturase transit peptide (SEQ ID NO: 9). The codon-optimized sequence of PmKASII comprising a *C. protothecoides* S106 stearoyl-ACP desaturase transit peptide is provided the sequence listings as SEQ ID NO: 24. SEQ ID NO: 25 provides the protein translation of SEQ ID NO: 24. The protein coding regions of PmKASII and suc2 were codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

Primary pSZ2276 transformants of Strain D were selected on agar plates lacking thiamine, clonally purified, and a single engineered line, strain E was selected for analysis. Strain E was cultivated under heterotrophic lipid production conditions at pH5.0 and pH7.0 as described in PCT/US2009/066141, PCT/US2009/066142, PCT/US2011/038463, PCT/US2011/038464, and PCT/US2012/023696. Lipid samples were prepared from dried biomass from each transformant and fatty acid profiles from these samples were analyzed using standard fatty acid methyl ester gas chromatography flame ionization (FAME GC/FID) detection methods as described in Example 1. The fatty acid profiles (expressed as Area % of total fatty acids) from the transgenic line arising from transformation with pSZ2276 into Strain D are shown in Table 15.

TABLE 15

Fatty acid profiles of *Prototheca moriformis* (UTEX 1435) Strains A, D, and E engineered for increased oleic acid and lowered linoleic acid levels.

| Strain | Transformation Construct(s) | pH | Area % Fatty Acid C16:0 | C18:0 | C18:1 | C18:2 | C20:1 |
|---|---|---|---|---|---|---|---|
| Strain A | None | pH 5 | 26.6 | 3.3 | 60.5 | 6.7 | 0.07 |
| Strain A | None | pH 7 | 28.3 | 4.1 | 58 | 6.5 | 0.06 |
| Strain D | pSZ1500 | pH 5 | 17 | 3.6 | 77.1 | 0.01 | 0.14 |
| Strain D | pSZ1500 | pH 7 | 19.5 | 5.3 | 72.6 | 0.01 | 0.09 |
| Strain E | pSZ1500 + pSZ2276 | pH 5 | 4.1 | 2.36 | 88.5 | 0.04 | 3.1 |
| Strain E | pSZ1500 + pSZ2276 | pH 7 | 2.1 | 7.8 | 87.9 | 0.01 | 0.5 |

As shown in Table 15, targeted interruption of FADc alleles with a CtOTE expression cassette impacted the fatty acid profiles of transformed microorganisms. Fatty acid profiles of Strain D (comprising the pSZ1500 transformation vector) showed increased composition of C18:1 fatty acids with a concomitant decrease in C16:0 and C18:2 fatty acids relative to Strain A. Subsequent transformation of Strain D with pSZ2276 to overexpress a *P. moriformis* (UTEX 1435) KASII protein while concomitantly ablating a FATA genetic locus (thereby generating Strain E) resulted in still further impact on the fatty acid profiles of the transformed microorganisms. Fatty acid profiles of Strain E showed increased composition of C18:1 fatty acids, with a further decrease in C16:0 fatty acids relative to Strains A and D. Propagation of Strain E in culture conditions at pH 7, to induce expression from the Amt03 promoter, resulted in a fatty acid profile that was higher in C18:0 and C18:1 fatty acids and lower in C16:0 fatty acids, relative to the same strain cultured at pH 5.

These data demonstrate the utility of multiple genetic modifications to impact the fatty acid profile of a host organism for increased levels of oleic acid with concomitant decreased levels of linoleic acid and palmitic acid. Further, this example illustrates the use of recombinant polynucleotides to target gene interruption of an endogenous FATA allele with a cassette comprising a pH-regulatable promoter to control expression of an exogenous KASII protein-coding region in order to alter the fatty acid profile of a host microbe.

Example 7

Conditional Expression of a Fatty Acid Desaturase

This example describes the use of a transformation vector to conditionally express a delta 12 fatty acid desaturase (FADs) in a *Prototheca moriformis* strain previously engineered for high oleic acid and very low linoleic acid production in both seed and lipid productivity stages of propagation. Very low linoleic acid levels in natural oils are sought for use in certain applications. However, absence of linoleic acid during cell division phase ("seed stage") of a host microbe is disadvantageous. Linoleic acid may be supplemented to the seed medium to hasten cell division and not added during lipid production, but this addition imposes unwanted costs. To overcome this challenge, a transformation cassette was constructed for regulated expression of a FAD2 enzyme such that levels of linoleic acids sufficient for cell division could be achieved and oil with very low levels of linoleic acids could be produced during the oil production phase of culture of a microorgansim. The transformation cassette used in this example comprised a selectable marker, a pH-regulatable promoter, and nucleotide sequences encoding a *P. moriformis* FAD2 enzyme to engineer microorganisms in which the fatty acid profile of the transformed microorganism has been altered for increased oleic acid production and regulatable linoleic acid production.

Strain D, described in Examples 5, 6, and in PCT/US2012/023696, is a classically mutagenized (for higher oil production) derivative of *P. moriformis* (UTEX 1435) subsequently transformed with the transformation construct pSZ1500 (SEQ ID NO: 17) according to biolistic transformation methods as described in PCT/US2009/066141, PCT/US2009/066142, PCT/US2011/038463, PCT/US2011/038464, and PCT/US2012/023696. This strain was used as the host for transformation with construct pSZ2413 to introduce a pH-driven promoter for regulation of a *P. moriformis* FAD2 enzyme. The pSZ2413 transformation construct included 5' (SEQ ID NO: 1) and 3' (SEQ ID NO: 2) homologous recombination targeting sequences (flanking the construct) to the 6S genomic region for integration into the *P. moriformis* nuclear genome, an *A. thaliana* THIC protein coding region under the control of the *C. protothecoides* actin promoter/5'UTR (SEQ ID NO: 22) and *C. vulgaris* nitrate reductase 3' UTR (SEQ ID NO: 6). This AtTHIC expression cassette is listed as SEQ ID NO: 23 and served as a selection marker. The *P. moriformis* FAD2 protein coding region was under the control of the *P. moriformis* Amt03 promoter/5'UTR (SEQ ID NO: 8) and *C. vulgaris* nitrate reductase 3'UTR. The codon-optimized sequence of PmFAD2 is provided the sequence listings as SEQ ID NO: 26. SEQ ID NO: 27 provides the protein translation of SEQ ID NO: 26. The protein coding regions of PmFAD2 and suc2 were codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

Primary pSZ2413 transformants of Strain D were selected on agar plates lacking thiamine, clonally purified, and isolates of the engineered line, Strain F were selected for analysis. These isolates were cultivated under heterotrophic lipid production conditions at pH7.0 (to activate expression of FAD2 from the PmAmt03 promoter) and at pH5.0, as described in PCT/US2009/066141, PCT/US2009/066142, PCT/US2011/038463, PCT/US2011/038464, and PCT/US2012/023696. Lipid samples were prepared from dried biomass from each transformant and fatty acid profiles from these samples were analyzed using standard fatty acid methyl ester gas chromatography flame ionization (FAME GC/FID) detection methods as described in Example 1. The resulting profile of C18:2 fatty acids (expressed in Area %) from nine representative isolates of transgenic Strain F (F-1 through F-9) arising from transformation with pSZ2413 into Strain D are shown in Table 16.

TABLE 16

C18:2 fatty acid profiles of *Prototheca moriformis* (UTEX 1435) Strains A, D, and F.

| Strain | Transformation Construct (s) | Area % C18:2 pH 5.0 | Area % C18:2 pH 7.0 |
|---|---|---|---|
| A | None | 07 | 26 |
| D | pSZ1500 | 01 | 01 |
| F-1 | pSZ1500 + pSZ2413 | 37 | 29 |
| F-2 | pSZ1500 + pSZ2413 | 45 | 87 |
| F-3 | pSZ1500 + pSZ2413 | 50 | 79 |
| F-4 | pSZ1500 + pSZ2413 | 57 | 06 |
| F-5 | pSZ1500 + pSZ2413 | 57 | 58 |
| F-6 | pSZ1500 + pSZ2413 | 60 | 88 |
| F-7 | pSZ1500 + pSZ2413 | 62 | 52 |
| F-8 | pSZ1500 + pSZ2413 | 63 | 79 |
| F-9 | pSZ1500 + pSZ2413 | 77 | 53 |

As shown in Table 16 the impact of regulated expression of the PmFAD2 enzyme, effected though strain culture at different pH levels, is a clear increase in the composition of C18:2 fatty acids in the transformed microorganism. Linoleic acid comprises about 6% to about 7.3% of fatty acids of Strain A. In contrast, Strain D (comprising the pSZ1500 transformation vector to ablate both FAD2 alleles) is characterized by a fatty acid profile of 0.01% linoleic acid. Transformation of Strain D with pSZ2413 to generate Strain F results in a recombinant microbe in which the production of linoleic acid is regulated by the Amt03 promoter. Propagation of Strain F isolates in culture conditions at pH 7, to induce FAD2 expression from the Amt03 promoter, resulted in a fatty acid profile characterized by about 4.5% to about 7.5% linoleic acid. In contrast, propagation of Strain F isolates in culture conditions at pH 5 resulted in a fatty acid profile characterized by about 0.33 to about 0.77% linoleic acid.

These data demonstrate the utility of and effectiveness of recombinant polynucleotides permitting conditional expression of a FAD2 enzyme to alter the fatty acid profile of engineered microorganisms, and in particular in regulating the production of C18:2 fatty acids in microbial cells.

Example 8

Analysis of Regiospecific Profile

LC/MS TAG distribution analyses were carried out using a Shimadzu Nexera ultra high performance liquid chromatography system that included a SIL-30AC autosampler, two LC-30AD pumps, a DGU-20A5 in-line degasser, and a CTO-20A column oven, coupled to a Shimadzu LCMS 8030 triple quadrupole mass spectrometer equipped with an APCI source. Data was acquired using a Q3 scan of m/z 350-1050 at a scan speed of 1428 u/sec in positive ion mode with the CID gas (argon) pressure set to 230 kPa. The APCI, desolvation line, and heat block temperatures were set to 300, 250, and 200° C., respectively, the flow rates of the nebulizing and drying gases were 3.0 L/min and 5.0 L/min, respectively, and the interface voltage was 4500 V. Oil samples were dissolved in dichloromethane-methanol (1:1) to a concentration of 5 mg/mL, and 0.8 μL of sample was injected onto Shimadzu Shim-pack XR-ODS III (2.2 μm, 2.0×200 mm) maintained at 30° C. A linear gradient from 30% dichloromethane-2-propanol (1:1)/acetonitrile to 51% dichloromethane-2-propanol (1:1)/acetonitrile over 27 minutes at 0.48 mL/min was used for chromatographic separations.

Example 9

Engineering Microbes for Increased Production of SOS, POP, and POS Triacylglycerides This example describes the use of recombinant polynucleotides that encode a C18:0-preferring *Brassica napus* thioesterase (BnOTE) enzyme to engineer a microorganism in which the triacylglyceride distribution of the transformed microorganism has been enriched in SOS, POS, and POP triacylglycerides.

A classically mutagenized strain of *Prototheca moriformis* (UTEX 1435), Strain A, was initially transformed with the plasmid construct pSZ1358 according to biolistic transformation methods as described in PCT/US2009/066141, PCT/US2009/066142, PCT/US2011/038463, PCT/US2011/038464, and PCT/US2012/023696. pSZ1358, described in PCT/US2012/023696, hereby incorporated by reference, comprised the coding sequence of the *Brassica napus* thioesterase (BnOTE) thioesterase (SEQ ID NO: 28), 5' (SEQ ID NO: 1) and 3' (SEQ ID NO: 2) homologous recombination targeting sequences (flanking the construct) to the 6S genomic region for integration into the nuclear genome, and a *S. cerevisiae* suc2 sucrose invertase coding region (SEQ ID NO: 4), to express the protein sequence given in SEQ ID NO: 3, under the control of *C. reinhardtii* β-tubulin promoter/5'UTR (SEQ ID NO: 5) and *Chlorella vulgaris* nitrate reductase 3' UTR (SEQ ID NO: 6). This *S. cerevisiae* suc2 expression cassette is listed as SEQ ID NO: 7 and served as a selectable marker. The BnOTE protein coding sequence to express the protein sequence given in SEQ ID NO: 29, was under the control of the *P. moriformis* Amt03 promoter/5'UTR (SEQ ID NO: 8) and *C. vulgaris* nitrate reductase 3'UTR. The protein coding regions of BnOTE and suc2 were codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

Primary pSZ1358 transformants of Strain A were selected on agar plates containing sucrose as a sole carbon source, clonally purified, and single engineered line, Strain G was selected for analysis. Strain G was cultivated under heterotrophic lipid production conditions at pH7.0 (to activate expression of BnOTE from the PmAmt03 promoter) as described in PCT/US2009/066141, PCT/US2009/066142, PCT/US2011/038463, PCT/US2011/038464, and PCT/US2012/023696. Oil samples obtained from Strain A and Strain G were analyzed for fatty acid composition using methods described in Examples 1 and 2, and, using the methods described in Example 8, for the regiospecificity of triacylglcyerides in the oil. Fatty acid profiles of TAGs isolated from Strain A and G are shown in Table 17. Table 18 presents the regiospecificity profile of POP, POS, and SOS TAGs present in oil samples from Strain A and G.

TABLE 17

Effect of BnOTE expression on the fatty acid composition and the sn-2 profile of TAGs produced from transformed *Prototheca moriformis*.

| Area % Fatty acid | Strain A FA profile | Strain G (pSZ1358) FA profile |
|---|---|---|
| C10:0 | n.r. | 0.5 |
| C12:0 | n.r. | 0.5 |
| C14:0 | 1.0 | 1.3 |
| C16:0 | 23.9 | 25.8 |
| C18:0 | 3.7 | 30.4 |
| C18:1 | 64.3 | 30.2 |
| C18:2 | 4.5 | 8.8 |
| C18:3 α | n.r. | 0.4 |

TABLE 18

Effect of BnOTE expression on the regiospecific profile of POP, POS, and SOS TAGs produced from transformed *Prototheca moriformis*.

| | Strain A (untransformed) | | Strain G (pSZ1358) | | Cocoa Butter | |
|---|---|---|---|---|---|---|
| TAG | Area % | Normalized Area % | Area % | Normalized Area % | Area % | Normalized Area % |
| POP | 13.09 | 76.8 | 10.6 | 23.5 | 17.9 | 22.1 |
| POS | 3.51 | 20.5 | 21.0 | 46.6 | 39.2 | 48.4 |
| SOS | 0.45 | 2.6 | 13.5 | 29.9 | 23.9 | 29.5 |
| total | 17.05 | 100 | 45.0 | 100 | 81.1 | 100 |

As shown in Table 17, the fatty acid composition of TAGs isolated from Strain G expressing BnOTE was markedly increased for C18:0 fatty acids (from 3.7% to 30.4%) and decreased in C18:1 fatty acids (from 64.3% to 30.2%) relative to the fatty acid profile of TAGs isolated from untransformed Strain A. The fatty acid composition of TAGs isolated from Strain A was characterized by about 23.9% palmitic acid, 3.7% stearic acid, and 64.3% oleic acid, a ratio for P:S:O of about 6.5:1:17.4. In contrast, the fatty acid composition of TAGs isolated from Strain G was characterized by about 25.8% palmitic acid, 30.4% stearic acid, and 30.2% oleic acid, a ratio for P:O:S of about 1:1.18:1.17.

The impact of expression of a C18:0 preferring thioesterease on the regiospecific profile of POP, POS, and SOS TAGs of oils produced from the transformed microorganism was an increase in all three TAGs as a proportion of the total TAGs present in the oil. As shown in Table 18, the sum of POP+POS+SOS TAGs accounted for 45% of the TAGs produced by Strain G, whereas POP, POS, and SOS TAGs summed to only about 17% of TAGs produced in Strain A. The percentages of POP, POS and SOS of strain G are compared to Cocoa butter in Table 18. As can be seen, ratios of POP, POS and SOS of Strain G are very similar to the ratios observed in cocoa butter.

These data demonstrate the utility and effectiveness of polynucleotides permitting exogenous thioesterase expression to alter the fatty acid and regiospecific profiles of TAGs of engineered microorganisms, in particular to increase the distribution of POP, POS, and SOS TAGs.

Examples 10-33

Engineering of Microorganisms

Examples 10-33 below describe the engineering of various microorganisms in accordance with the present invention. To alter the fatty acid profile of a microorganism, microorganisms can be genetically modified wherein endogenous or exogenous lipid biosynthesis pathway enzymes are expressed, overexpressed, or attenuated. Steps to genetically engineer a microbe to alter its fatty acid profile as to the degree of fatty acid unsaturation and to decrease or increase fatty acid chain length comprise the design and construction of a transformation vector (e.g., a plasmid), transformation of the microbe with one or more vectors, selection of transformed microbes (transformants), growth of the transformed microbe, and analysis of the fatty acid profile of the lipids produced by the engineered microbe.

Transgenes that alter the fatty acid profiles of host organisms can be expressed in numerous eukaryotic microbes. Examples of expression of transgenes in eukaryotic microbes including *Chlamydomonas reinhardtii, Chlorella ellipsoidea, Chlorella saccarophila, Chlorella vulgaris, Chlorella kessleri, Chlorella sorokiniana, Haematococcus pluvialis, Gonium pectorale, Volvox carteri, Dunaliella tertiolecta, Dunaliella viridis, Dunaliella salina, Closterium peracerosum-strigosum-littorale* complex, *Nannochloropsis* sp., *Thalassiosira pseudonana, Phaeodactylum tricornutum, Navicula saprophila, Cylindrotheca fusiformis, Cyclotella cryptica, Symbiodinium microadriacticum, Amphidinium* sp., *Chaetoceros* sp., *Mortierella alpina*, and *Yarrowia lipolytica* can be found in the scientific literature. These expression techniques can be combined with the teachings of the present invention to produce engineered microorganisms with altered fatty acid profiles.

Transgenes that alter the fatty acid profiles of host organisms or alter the regiospecific distribution of glycerolipids produced by host organisms can also be expressed in numerous prokaryotic microbes. Examples of expression of transgenes in oleaginous microbes including *Rhodococcus opacus* can be found in the literature. These expression techniques can be combined with the teachings of the present invention to produce engineered microorganisms with altered fatty acid profiles.

Tables 19A-D. Codon preference listing.

| Amino Acid | Codon | Chlorella sorokiniana | Chlorella vulgaris | Chlorella ellipsoidea | Chlorella kessleri | Dunaliella tertiolecta | Volvox carteri | Haematococcus pluvialis |
|---|---|---|---|---|---|---|---|---|
| Ala | GCG | 0.20 | 0.25 | 0.15 | 0.14 | 0.09 | 0.25 | 0.21 |
| Ala | GCA | 0.05 | 0.24 | 0.32 | 0.10 | 0.17 | 0.13 | 0.27 |
| Ala | GCT | 0.12 | 0.16 | 0.26 | 0.18 | 0.31 | 0.26 | 0.17 |

-continued

| Amino Acid | Codon | *Chlorella sorokiniana* | *Chlorella vulgaris* | *Chlorella ellipsoidea* | *Chlorella kessleri* | *Dunaliella tertiolecta* | *Volvox carteri* | *Haematococcus pluvialis* |
|---|---|---|---|---|---|---|---|---|
| Ala | GCC | 0.63 | 0.35 | 0.27 | 0.58 | 0.43 | 0.36 | 0.35 |
| Arg | AGG | 0.03 | 0.09 | 0.10 | 0.09 | 0.26 | 0.08 | 0.14 |
| Arg | AGA | 0.04 | 0.05 | 0.14 | 0.01 | 0.09 | 0.03 | 0.05 |
| Arg | CGG | 0.06 | 0.19 | 0.09 | 0.06 | 0.06 | 0.17 | 0.15 |
| Arg | CGA | 0.00 | 0.10 | 0.08 | 0.00 | 0.08 | 0.08 | 0.10 |
| Arg | CGT | 0.06 | 0.09 | 0.37 | 0.14 | 0.12 | 0.22 | 0.13 |
| Arg | CGC | 0.81 | 0.48 | 0.22 | 0.71 | 0.40 | 0.43 | 0.42 |
| Asn | AAT | 0.04 | 0.16 | 0.43 | 0.06 | 0.27 | 0.23 | 0.21 |
| Asn | AAC | 0.96 | 0.84 | 0.57 | 0.94 | 0.73 | 0.77 | 0.79 |
| Asp | GAT | 0.13 | 0.25 | 0.47 | 0.12 | 0.40 | 0.35 | 0.27 |
| Asp | GAC | 0.87 | 0.75 | 0.53 | 0.88 | 0.60 | 0.65 | 0.73 |
| Cys | TGT | 0.06 | 0.13 | 0.43 | 0.09 | 0.20 | 0.17 | 0.27 |
| Cys | TGC | 0.94 | 0.87 | 0.57 | 0.91 | 0.80 | 0.83 | 0.64 |
| End | TGA | 0.00 | 0.72 | 0.14 | 0.14 | 0.36 | 0.24 | 0.70 |
| End | TAG | 0.33 | 0.11 | 0.29 | 0.00 | 0.00 | 0.18 | 0.22 |
| End | TAA | 0.67 | 0.17 | 4.00 | 0.86 | 0.64 | 0.59 | 0.09 |
| Gln | CAG | 0.42 | 0.40 | 0.15 | 0.40 | 0.27 | 0.29 | 0.33 |
| Gln | CAA | 0.04 | 0.04 | 0.21 | 0.40 | 0.27 | 0.07 | 0.10 |
| Glu | GAG | 0.53 | 0.50 | 0.33 | 0.40 | 0.27 | 0.53 | 0.49 |
| Glu | GAA | 0.02 | 0.06 | 0.31 | 0.40 | 0.27 | 0.11 | 0.07 |
| Gly | GGG | 0.04 | 0.16 | 0.19 | 0.08 | 0.10 | 0.12 | 0.22 |
| Gly | GGA | 0.02 | 0.11 | 0.13 | 0.07 | 0.13 | 0.12 | 0.11 |
| Gly | GGT | 0.03 | 0.12 | 0.39 | 0.24 | 0.25 | 0.23 | 0.15 |
| Gly | GGC | 0.91 | 0.61 | 0.29 | 0.96 | 0.51 | 0.53 | 0.52 |
| His | CAT | 0.14 | 0.16 | 0.30 | 0.08 | 0.25 | 0.35 | 0.27 |
| His | CAC | 0.86 | 0.84 | 0.70 | 0.93 | 0.75 | 0.65 | 0.73 |
| Ile | ATA | 0.00 | 0.04 | 0.07 | 0.01 | 0.04 | 0.08 | 0.09 |
| Ile | ATT | 0.15 | 0.30 | 0.63 | 0.29 | 0.31 | 0.35 | 0.29 |
| Ile | ATC | 0.85 | 0.66 | 0.65 | 0.69 | 0.65 | 0.57 | 0.62 |
| Leu | TTG | 0.03 | 0.07 | 0.03 | 0.05 | 0.14 | 0.14 | 0.16 |
| Leu | TTA | 0.00 | 0.01 | 0.32 | 0.00 | 0.02 | 0.03 | 0.02 |
| Leu | CTG | 0.72 | 0.61 | 0.34 | 0.61 | 0.60 | 0.45 | 0.53 |
| Leu | CTA | 0.01 | 0.03 | 0.03 | 0.04 | 0.04 | 0.07 | 0.07 |
| Leu | CTT | 0.04 | 0.08 | 0.16 | 0.06 | 0.06 | 0.14 | 0.09 |
| Leu | CTC | 0.20 | 0.20 | 0.12 | 0.24 | 0.14 | 0.17 | 0.13 |
| Lys | AAG | 0.98 | 0.94 | 0.54 | 0.98 | 0.90 | 0.90 | 0.84 |
| Lys | AAA | 0.02 | 0.06 | 0.46 | 0.02 | 0.10 | 0.10 | 0.16 |
| Met | ATG | 1.00 | 1.00 | 1.00 | 1.00 | 1.00 | 1.00 | 1.00 |
| Phe | TTT | 0.28 | 0.32 | 0.42 | 0.31 | 0.24 | 0.27 | 0.35 |
| Phe | TTC | 0.72 | 0.68 | 0.58 | 0.69 | 0.76 | 0.73 | 0.65 |
| Pro | CCG | 0.18 | 0.31 | 0.09 | 0.07 | 0.04 | 0.34 | 0.15 |
| Pro | CCA | 0.06 | 0.17 | 0.36 | 0.07 | 0.04 | 0.20 | 0.24 |
| Pro | CCT | 0.10 | 0.14 | 0.25 | 0.17 | 0.04 | 0.19 | 0.29 |
| Pro | CCC | 0.66 | 0.38 | 0.29 | 0.69 | 0.04 | 0.27 | 0.32 |
| Ser | AGT | 0.03 | 0.04 | 0.14 | 0.02 | 0.08 | 0.08 | 0.07 |
| Ser | AGC | 0.27 | 0.38 | 0.18 | 0.18 | 0.31 | 0.27 | 0.31 |
| Ser | TCG | 0.12 | 0.14 | 0.08 | 0.10 | 0.02 | 0.19 | 0.10 |
| Ser | TCA | 0.03 | 0.08 | 0.14 | 0.08 | 0.09 | 0.09 | 0.14 |
| Ser | TCT | 0.09 | 0.11 | 0.26 | 0.18 | 0.19 | 0.14 | 0.13 |
| Ser | TCC | 0.47 | 0.24 | 0.20 | 0.44 | 0.30 | 0.24 | 0.24 |
| Thr | ACG | 0.11 | 0.20 | 0.13 | 0.05 | 0.12 | 0.27 | 0.19 |
| Thr | ACA | 0.01 | 0.20 | 0.32 | 0.07 | 0.20 | 0.12 | 0.23 |
| Thr | ACT | 0.12 | 0.13 | 0.29 | 0.12 | 0.24 | 0.20 | 0.18 |
| Thr | ACC | 0.76 | 0.47 | 0.26 | 0.76 | 0.44 | 0.41 | 0.40 |
| Trp | TGG | 1.00 | 1.00 | 1.00 | 1.00 | 1.00 | 1.00 | 1.00 |
| Tyr | TAT | 0.07 | 0.15 | 0.43 | 0.27 | 0.28 | 0.24 | 0.19 |
| Tyr | TAC | 0.93 | 0.85 | 0.57 | 0.73 | 0.72 | 0.76 | 0.81 |
| Val | GTG | 0.71 | 0.54 | 0.37 | 0.60 | 0.54 | 0.46 | 0.62 |
| Val | GTA | 0.00 | 0.05 | 0.25 | 0.03 | 0.09 | 0.07 | 0.09 |
| Val | GTT | 0.11 | 0.14 | 0.24 | 0.09 | 0.14 | 0.17 | 0.09 |
| Val | GTC | 0.18 | 0.27 | 0.14 | 0.28 | 0.23 | 0.30 | 0.21 |

| Amino Acid | Codon | *Closterium peracerosum-strigosum-littorale* complex | *Dunaliella viridis* | *Dunaliella salina* | *Gonium pectorale* | *Phaeodactylum tricornutum* | *Chaetoceros compressum* |
|---|---|---|---|---|---|---|---|
| Ala | GCG | 0.48 | 0.13 | 0.15 | 0.43 | 0.15 | 0.08 |
| Ala | GCA | 0.10 | 0.27 | 0.20 | 0.09 | 0.10 | 0.37 |
| Ala | GCT | 0.15 | 0.25 | 0.27 | 0.08 | 0.23 | 0.36 |
| Ala | GCC | 0.26 | 0.35 | 0.39 | 0.41 | 0.52 | 0.18 |
| Arg | AGG | 0.04 | 0.25 | 0.22 | 0.13 | 0.02 | 0.14 |

-continued

| Amino Acid | Codon | *Closterium peracerosum-strigosum-littorale* complex | *Dunaliella viridis* | *Dunaliella salina* | *Gonium pectorale* | *Phaeodactylum tricornutum* | *Chaetoceros compressum* |
|---|---|---|---|---|---|---|---|
| Arg | AGA | 0.00 | 0.06 | 0.05 | 0.00 | 0.04 | 0.29 |
| Arg | CGG | 0.18 | 0.08 | 0.12 | 0.40 | 0.10 | 0.00 |
| Arg | CGA | 0.00 | 0.06 | 0.06 | 0.05 | 0.12 | 0.19 |
| Arg | CGT | 0.13 | 0.15 | 0.13 | 0.08 | 0.41 | 0.38 |
| Arg | CGC | 0.64 | 0.39 | 0.43 | 0.35 | 0.31 | 0.00 |
| Asn | AAT | 0.04 | 0.17 | 0.23 | 0.07 | 0.30 | 0.58 |
| Asn | AAC | 0.96 | 0.83 | 0.77 | 0.93 | 0.65 | 0.42 |
| Asp | GAT | 0.30 | 0.38 | 0.40 | 0.11 | 0.41 | 0.53 |
| Asp | GAC | 0.70 | 0.62 | 0.60 | 0.89 | 0.59 | 0.47 |
| Cys | TGT | 0.06 | 0.24 | 0.17 | 0.20 | 0.39 | 0.44 |
| Cys | TGC | 0.94 | 0.76 | 0.83 | 0.90 | 0.61 | 0.56 |
| End | TGA | 0.75 | 0.31 | 0.37 | 0.50 | 0.06 | 0.50 |
| End | TAG | 0.00 | 0.15 | 0.14 | 0.00 | 0.13 | 0.00 |
| End | TAA | 0.25 | 0.54 | 0.49 | 0.50 | 0.81 | 0.50 |
| Gln | CAG | 0.53 | 0.36 | 0.32 | 0.31 | 0.23 | 0.16 |
| Gln | CAA | 0.09 | 0.12 | 0.08 | 0.07 | 0.14 | 0.19 |
| Glu | GAG | 0.31 | 0.44 | 0.51 | 0.56 | 0.21 | 0.28 |
| Glu | GAA | 0.06 | 0.09 | 0.09 | 0.07 | 0.42 | 0.37 |
| Gly | GGG | 0.31 | 0.14 | 0.10 | 0.18 | 0.08 | 0.12 |
| Gly | GGA | 0.06 | 0.11 | 0.12 | 0.09 | 0.34 | 0.33 |
| Gly | GGT | 0.09 | 0.22 | 0.22 | 0.07 | 0.30 | 0.39 |
| Gly | GGC | 0.53 | 0.54 | 0.56 | 0.65 | 0.28 | 0.16 |
| His | CAT | 0.33 | 0.25 | 0.25 | 0.43 | 0.28 | 0.84 |
| His | CAC | 0.67 | 0.75 | 0.75 | 0.57 | 0.72 | 0.16 |
| Ile | ATA | 0.03 | 0.03 | 0.03 | 0.07 | 0.03 | 0.12 |
| Ile | ATT | 0.23 | 0.25 | 0.31 | 0.33 | 0.51 | 0.65 |
| Ile | ATC | 0.74 | 0.72 | 0.66 | 0.59 | 0.46 | 0.23 |
| Leu | TTG | 0.04 | 0.11 | 0.12 | 0.04 | 0.26 | 0.11 |
| Leu | TTA | 0.00 | 0.01 | 0.01 | 0.00 | 0.02 | 0.14 |
| Leu | CTG | 0.31 | 0.60 | 0.61 | 0.64 | 0.15 | 0.05 |
| Leu | CTA | 0.01 | 0.05 | 0.04 | 0.01 | 0.05 | 0.08 |
| Leu | CTT | 0.04 | 0.07 | 0.08 | 0.05 | 0.18 | 0.51 |
| Leu | CTC | 0.60 | 0.16 | 0.14 | 0.26 | 0.34 | 0.11 |
| Lys | AAG | 0.86 | 0.87 | 0.89 | 0.93 | 0.75 | 0.52 |
| Lys | AAA | 0.14 | 0.13 | 0.11 | 0.07 | 0.25 | 0.48 |
| Met | ATG | 1.00 | 1.00 | 1.00 | 1.00 | 1.00 | 1.00 |
| Phe | TTT | 0.09 | 0.25 | 0.29 | 0.10 | 0.44 | 0.65 |
| Phe | TTC | 0.91 | 0.75 | 0.71 | 0.90 | 0.56 | 0.35 |
| Pro | CCG | 0.28 | 0.10 | 0.08 | 0.53 | 0.29 | 0.05 |
| Pro | CCA | 0.15 | 0.10 | 0.17 | 0.09 | 0.12 | 0.45 |
| Pro | CCT | 0.12 | 0.10 | 0.30 | 0.04 | 0.20 | 0.33 |
| Pro | CCC | 0.44 | 0.10 | 0.45 | 0.34 | 0.40 | 0.17 |
| Ser | AGT | 0.04 | 0.09 | 0.06 | 0.02 | 0.12 | 0.14 |
| Ser | AGC | 0.05 | 0.31 | 0.32 | 0.20 | 0.12 | 0.07 |
| Ser | TCG | 0.22 | 0.04 | 0.06 | 0.42 | 0.19 | 0.08 |
| Ser | TCA | 0.16 | 0.08 | 0.10 | 0.09 | 0.06 | 0.31 |
| Ser | TCT | 0.05 | 0.17 | 0.15 | 0.07 | 0.15 | 0.23 |
| Ser | TCC | 0.47 | 0.31 | 0.30 | 0.20 | 0.35 | 0.18 |
| Thr | ACG | 0.30 | 0.16 | 0.13 | 0.42 | 0.23 | 0.10 |
| Thr | ACA | 0.06 | 0.21 | 0.18 | 0.03 | 0.13 | 0.38 |
| Thr | ACT | 0.22 | 0.18 | 0.23 | 0.08 | 0.19 | 0.27 |
| Thr | ACC | 0.42 | 0.46 | 0.46 | 0.47 | 0.45 | 0.25 |
| Trp | TGG | 1.00 | 1.00 | 1.00 | 1.00 | 1.00 | 1.00 |
| Tyr | TAT | 0.07 | 0.16 | 0.21 | 0.12 | 0.18 | 0.67 |
| Tyr | TAC | 0.93 | 0.84 | 0.79 | 0.88 | 0.82 | 0.33 |
| Val | GTG | 0.50 | 0.64 | 0.62 | 0.57 | 0.22 | 0.30 |
| Val | GTA | 0.02 | 0.03 | 0.05 | 0.04 | 0.09 | 0.27 |
| Val | GTT | 0.06 | 0.11 | 0.11 | 0.04 | 0.22 | 0.10 |
| Val | GTC | 0.42 | 0.22 | 0.23 | 0.35 | 0.47 | 0.33 |

| Amino Acid | Codon | *Cylindrotheca fusiformis* | *Amphidinium carterae* | *Symbiodinium micro-adriacticum* | *Nanno-chloropsis* sp | *Cyclotella cryptica* | *Navicula pelliculosa* | *Thalassiosira pseudonana* | *C. reinhar dtii* |
|---|---|---|---|---|---|---|---|---|---|
| Ala | GCG | 0.07 | 0.17 | 0.22 | 0.24 | 0.11 | 0.00 | 0.11 | 0.35 |
| Ala | GCA | 0.14 | 0.33 | 0.26 | 0.10 | 0.16 | 0.13 | 0.25 | 0.08 |
| Ala | GCT | 0.35 | 0.29 | 0.20 | 0.17 | 0.45 | 0.44 | 0.33 | 0.13 |
| Ala | GCC | 0.43 | 0.20 | 0.32 | 0.48 | 0.27 | 0.44 | 0.30 | 0.43 |
| Arg | AGG | 0.09 | 0.15 | 0.27 | 0.00 | 0.09 | 0.05 | 0.18 | 0.05 |
| Arg | AGA | 0.14 | 0.03 | 0.27 | 0.00 | 0.05 | 0.10 | 0.17 | 0.01 |

-continued

| Amino Acid | Codon | *Cylindrotheca fusiformis* | *Amphidinium carterae* | *Symbiodinium micro-adriacticum* | *Nanno-chloropsis* sp | *Cyclotella cryptica* | *Navicula pelliculosa* | *Thalassiosira pseudonana* | *C. reinhar dtii* |
|---|---|---|---|---|---|---|---|---|---|
| Arg | CGG | 0.06 | 0.08 | 0.09 | 0.00 | 0.04 | 0.05 | 0.06 | 0.20 |
| Arg | CGA | 0.16 | 0.18 | 0.09 | 0.29 | 0.08 | 0.35 | 0.11 | 0.04 |
| Arg | CGT | 0.34 | 0.18 | 0.09 | 0.14 | 0.47 | 0.20 | 0.34 | 0.09 |
| Arg | CGC | 0.22 | 0.40 | 0.18 | 0.57 | 0.28 | 0.25 | 0.15 | 0.62 |
| Asn | AAT | 0.42 | 0.37 | 0.21 | 0.00 | 0.25 | 0.47 | 0.43 | 0.09 |
| Asn | AAC | 0.58 | 0.63 | 0.79 | 1.00 | 0.75 | 0.53 | 0.57 | 0.91 |
| Asp | GAT | 0.54 | 0.54 | 0.50 | 0.20 | 0.52 | 0.20 | 0.56 | 0.14 |
| Asp | GAC | 0.46 | 0.46 | 0.50 | 0.80 | 0.48 | 0.80 | 0.44 | 0.86 |
| Cys | TGT | 0.44 | 0.75 | 0.50 | 0.00 | 0.29 | 0.10 | 0.54 | 0.10 |
| Cys | TGC | 0.56 | 0.25 | 0.50 | 1.00 | 0.71 | 0.90 | 0.46 | 0.90 |
| End | TGA | 0.13 | 0.50 | 1.00 | 0.00 | 0.10 | 0.00 | 0.31 | 0.27 |
| End | TAG | 0.10 | 0.00 | 0.00 | 0.00 | 0.00 | 0.00 | 0.38 | 0.22 |
| End | TAA | 0.77 | 0.50 | 0.00 | 1.00 | 0.90 | 1.00 | 0.31 | 0.52 |
| Gln | CAG | 0.12 | 0.33 | 0.28 | 0.41 | 0.19 | 0.21 | 0.16 | 0.38 |
| Gln | CAA | 0.25 | 0.15 | 0.17 | 0.00 | 0.17 | 0.28 | 0.19 | 0.04 |
| Glu | GAG | 0.23 | 0.41 | 0.50 | 0.59 | 0.38 | 0.17 | 0.40 | 0.55 |
| Glu | GAA | 0.39 | 0.10 | 0.06 | 0.00 | 0.26 | 0.34 | 0.26 | 0.03 |
| Gly | GGG | 0.06 | 0.19 | 0.32 | 0.10 | 0.10 | 0.03 | 0.12 | 0.11 |
| Gly | GGA | 0.47 | 0.10 | 0.12 | 0.05 | 0.45 | 0.28 | 0.51 | 0.06 |
| Gly | GGT | 0.35 | 0.34 | 0.16 | 0.25 | 0.22 | 0.13 | 0.23 | 0.11 |
| Gly | GGC | 0.12 | 0.37 | 0.40 | 0.60 | 0.24 | 0.56 | 0.14 | 0.72 |
| His | CAT | 0.39 | 0.12 | 0.40 | 0.00 | 0.42 | 1.00 | 0.50 | 0.11 |
| His | CAC | 0.61 | 0.88 | 0.60 | 1.00 | 0.58 | 0.00 | 0.50 | 0.89 |
| Ile | ATA | 0.06 | 0.05 | 0.00 | 0.00 | 0.04 | 0.00 | 0.08 | 0.03 |
| Ile | ATT | 0.42 | 0.53 | 0.38 | 0.14 | 0.53 | 0.73 | 0.38 | 0.22 |
| Ile | ATC | 0.52 | 0.42 | 0.63 | 0.86 | 0.42 | 0.27 | 0.54 | 0.75 |
| Leu | TTG | 0.26 | 0.35 | 0.39 | 0.22 | 0.20 | 0.16 | 0.29 | 0.04 |
| Leu | TTA | 0.09 | 0.01 | 0.00 | 0.00 | 0.03 | 0.00 | 0.05 | 0.01 |
| Leu | CTG | 0.09 | 0.22 | 0.39 | 0.09 | 0.06 | 0.12 | 0.08 | 0.73 |
| Leu | CTA | 0.05 | 0.00 | 0.04 | 0.00 | 0.03 | 0.04 | 0.06 | 0.03 |
| Leu | CTT | 0.37 | 0.31 | 0.13 | 0.04 | 0.39 | 0.36 | 0.20 | 0.05 |
| Leu | CTC | 0.13 | 0.12 | 0.04 | 0.65 | 0.29 | 0.32 | 0.32 | 0.15 |
| Lys | AAG | 0.60 | 0.93 | 0.85 | 1.00 | 0.70 | 0.83 | 0.76 | 0.95 |
| Lys | AAA | 0.40 | 0.07 | 0.15 | 0.00 | 0.30 | 0.17 | 0.24 | 0.05 |
| Met | ATG | 1.00 | 1.00 | 1.00 | 1.00 | 1.00 | 1.00 | 1.00 | 1.00 |
| Phe | TTT | 0.37 | 0.21 | 0.25 | 0.20 | 0.31 | 0.78 | 0.38 | 0.16 |
| Phe | TTC | 0.63 | 0.79 | 0.75 | 0.80 | 0.69 | 0.22 | 0.62 | 0.84 |
| Pro | CCG | 0.11 | 0.14 | 0.18 | 0.08 | 0.10 | 0.21 | 0.16 | 0.33 |
| Pro | CCA | 0.33 | 0.42 | 0.09 | 0.08 | 0.16 | 0.29 | 0.31 | 0.08 |
| Pro | CCT | 0.32 | 0.22 | 0.41 | 0.25 | 0.35 | 0.21 | 0.31 | 0.13 |
| Pro | CCC | 0.24 | 0.22 | 0.32 | 0.58 | 0.39 | 0.29 | 0.23 | 0.47 |
| Ser | AGT | 0.12 | 0.13 | 0.09 | 0.00 | 0.09 | 0.13 | 0.18 | 0.04 |
| Ser | AGC | 0.09 | 0.24 | 0.14 | 0.13 | 0.08 | 0.28 | 0.11 | 0.35 |
| Ser | TCG | 0.13 | 0.03 | 0.05 | 0.00 | 0.15 | 0.25 | 0.17 | 0.25 |
| Ser | TCA | 0.12 | 0.25 | 0.05 | 0.00 | 0.12 | 0.08 | 0.12 | 0.05 |
| Ser | TCT | 0.30 | 0.16 | 0.23 | 0.13 | 0.39 | 0.25 | 0.23 | 0.07 |
| Ser | TCC | 0.24 | 0.19 | 0.45 | 0.75 | 0.18 | 0.03 | 0.19 | 0.25 |
| Thr | ACG | 0.09 | 0.14 | 0.10 | 0.28 | 0.10 | 0.18 | 0.21 | 0.30 |
| Thr | ACA | 0.15 | 0.28 | 0.10 | 0.00 | 0.15 | 0.09 | 0.19 | 0.08 |
| Thr | ACT | 0.39 | 0.12 | 0.10 | 0.17 | 0.33 | 0.41 | 0.28 | 0.10 |
| Thr | ACC | 0.37 | 0.47 | 0.70 | 0.56 | 0.43 | 0.32 | 0.32 | 0.52 |
| Trp | TGG | 1.00 | 1.00 | 1.00 | 1.00 | 1.00 | 1.00 | 1.00 | 1.00 |
| Tyr | TAT | 0.38 | 0.32 | 0.20 | 0.00 | 0.38 | 0.20 | 0.39 | 0.10 |
| Tyr | TAC | 0.62 | 0.68 | 0.80 | 1.00 | 0.62 | 0.80 | 0.61 | 0.90 |
| Val | GTG | 0.11 | 0.65 | 0.67 | 0.31 | 0.16 | 0.18 | 0.29 | 0.67 |
| Val | GTA | 0.06 | 0.05 | 0.00 | 0.00 | 0.09 | 0.09 | 0.16 | 0.03 |
| Val | GTT | 0.38 | 0.08 | 0.11 | 0.15 | 0.42 | 0.09 | 0.28 | 0.07 |
| Val | GTC | 0.46 | 0.21 | 0.22 | 0.54 | 0.33 | 0.64 | 0.27 | 0.22 |

| Amino Acid | Codon | *Yarrowia lipolytica* | *Mortierella alpina* | *Rhodococcus opacus* |
|---|---|---|---|---|
| Ala | GCG | 0.08 | 0.14 | 0.35 |
| Ala | GCA | 0.11 | 0.12 | 0.14 |
| Ala | GCT | 0.35 | 0.29 | 0.09 |
| Ala | GCC | 0.46 | 0.45 | 0.43 |
| Arg | AGG | 0.05 | 0.05 | 0.05 |
| Arg | AGA | 0.13 | 0.06 | 0.02 |
| Arg | CGG | 0.12 | 0.06 | 0.26 |
| Arg | CGA | 0.52 | 0.09 | 0.12 |
| Arg | CGT | 0.11 | 0.32 | 0.11 |
| Arg | CGC | 0.07 | 0.42 | 0.44 |

-continued

| Amino Acid | Codon | *Yarrowia lipolytica* | *Mortierella alpina* | *Rhodococcus opacus* |
|---|---|---|---|---|
| Asn | AAT | 0.17 | 0.15 | 0.21 |
| Asn | AAC | 0.83 | 0.85 | 0.79 |
| Asp | GAT | 0.35 | 0.42 | 0.24 |
| Asp | GAC | 0.65 | 0.58 | 0.76 |
| Cys | TGT | 0.46 | 0.13 | 0.26 |
| Cys | TGC | 0.54 | 0.87 | 0.74 |
| End | TGA | 0.16 | 0.05 | 0.72 |
| End | TAG | 0.38 | 0.25 | 0.17 |
| End | TAA | 0.46 | 0.70 | 0.11 |

-continued

| Amino Acid | Codon | *Yarrowia lipolytica* | *Mortierella alpina* | *Rhodococcus opacus* |
|---|---|---|---|---|
| Gln | CAG | 0.33 | 0.36 | 0.28 |
| Gln | CAA | 0.08 | 0.06 | 0.06 |
| Glu | GAG | 0.44 | 0.49 | 0.45 |
| Glu | GAA | 0.14 | 0.09 | 0.22 |
| Gly | GGG | 0.05 | 0.03 | 0.18 |
| Gly | GGA | 0.28 | 0.29 | 0.15 |
| Gly | GGT | 0.32 | 0.32 | 0.20 |
| Gly | GGC | 0.34 | 0.36 | 0.48 |
| His | CAT | 0.34 | 0.27 | 0.20 |
| His | CAC | 0.66 | 0.73 | 0.80 |
| Ile | ATA | 0.03 | 0.01 | 0.05 |
| Ile | ATT | 0.44 | 0.33 | 0.14 |
| Ile | ATC | 0.53 | 0.66 | 0.81 |
| Leu | TTG | 0.09 | 0.27 | 0.09 |
| Leu | TTA | 0.02 | 0.00 | 0.01 |
| Leu | CTG | 0.37 | 0.26 | 0.41 |
| Leu | CTA | 0.05 | 0.02 | 0.03 |
| Leu | CTT | 0.18 | 0.12 | 0.06 |
| Leu | CTC | 0.29 | 0.32 | 0.40 |
| Lys | AAG | 0.84 | 0.91 | 0.80 |
| Lys | AAA | 0.16 | 0.09 | 0.20 |
| Met | ATG | 1.00 | 1.00 | 1.00 |
| Phe | TTT | 0.38 | 0.39 | 0.09 |

-continued

| Amino Acid | Codon | *Yarrowia lipolytica* | *Mortierella alpina* | *Rhodococcus opacus* |
|---|---|---|---|---|
| Phe | TTC | 0.62 | 0.61 | 0.91 |
| Pro | CCG | 0.10 | 0.07 | 0.52 |
| Pro | CCA | 0.10 | 0.08 | 0.09 |
| Pro | CCT | 0.32 | 0.36 | 0.07 |
| Pro | CCC | 0.47 | 0.49 | 0.32 |
| Ser | AGT | 0.07 | 0.05 | 0.08 |
| Ser | AGC | 0.11 | 0.14 | 0.23 |
| Ser | TCG | 0.16 | 0.32 | 0.33 |
| Ser | TCA | 0.08 | 0.08 | 0.07 |
| Ser | TCT | 0.28 | 0.12 | 0.05 |
| Ser | TCC | 0.30 | 0.29 | 0.24 |
| Thr | ACG | 0.11 | 0.17 | 0.28 |
| Thr | ACA | 0.14 | 0.10 | 0.11 |
| Thr | ACT | 0.26 | 0.23 | 0.07 |
| Thr | ACC | 0.49 | 0.49 | 0.53 |
| Trp | TGG | 1.00 | 1.00 | 1.00 |
| Tyr | TAT | 0.18 | 0.20 | 0.18 |
| Tyr | TAC | 0.82 | 0.80 | 0.82 |
| Val | GTG | 0.33 | 0.22 | 0.37 |
| Val | GTA | 0.05 | 0.02 | 0.05 |
| Val | GTT | 0.26 | 0.27 | 0.10 |
| Val | GTC | 0.36 | 0.49 | 0.49 |

TABLE 20

| Lipid biosynthesis pathway proteins. |
|---|
| 3-Ketoacyl ACP synthase |
| *Cuphea hookeriana* 3-ketoacyl-ACP synthase (GenBank Acc. No. AAC68861.1), *Cuphea wrightii* beta-ketoacyl-ACP synthase II (GenBank Acc. No. AAB37271.1), *Cuphea lanceolata* beta-ketoacyl-ACP synthase IV (GenBank Acc. No. CAC59946.1), *Cuphea wrightii* beta-ketoacyl-ACP synthase II (GenBank Acc. No. AAB37270.1), *Ricinus communis* ketoacyl-ACP synthase (GenBank Acc. No. XP_002516228), *Gossypium hirsutum* ketoacyl-ACP synthase (GenBank Acc. No. ADK23940.1), *Glycine max* plastid 3-keto-acyl-ACP synthase II-A (GenBank Acc No. AAW88763.1), *Elaeis guineensis* beta-ketoacyl-ACP synthase II (GenBank Acc. No. AAF26738.2), *Helianthus annuus* plastid 3-keto-acyl-ACP synthase I (GenkBank Acc. No. ABM53471.1), *Glycine max*3-keto-acyl-ACP synthase I (GenkBank Acc. No. NP_001238610.1), *Helianthus annuus* plastid 3-keto-acyl-ACP synthase II (GenBank Acc ABI18155.1), *Brassica napus* beta-ketoacyl-ACP synthetase 2 (GenBank Acc. No. AAF61739.1), *Perilla frutescens* beta-ketoacyl-ACP synthase II (GenBank Acc. No. AAC04692.1), *Helianthus annus* beta-ketoacyl-ACP synthase II (GenBank Accession No. ABI18155), *Ricinus communis* beta-ketoacyl-ACP synthase II (GenBank Accession No. AAA33872), *Haematococcus pluvialis* beta-ketoacyl acyl carrier protein synthase (GenBank Accession No. HM560033.1), *Jatropha curcasbeta* ketoacyl-ACP synthase I (GenBank Accession No. ABJ90468.1), *Populus trichocarpa* beta-ketoacyl-ACP synthase I (GenBank Accession No. XP_002303661.1), *Coriandrum sativum* beta-ketoacyl-ACP synthetase I (GenBank Accession No. AAK58535.1), *Arabidopsis thaliana* 3-oxoacyl-[acyl-carrier-protein] synthase I (GenBank Accession No. NP_001190479.1), *Vitis vinifera* 3-oxoacyl-[acyl-carrier-protein] synthase I (GenBank Accession No. XP_002272874.2) |
| Fatty acyl-ACP Thioesterases |
| *Umbellularia californica* fatty acyl-ACP thioesterase (GenBank Acc. No. AAC49001), *Cinnamomum camphora* fatty acyl-ACP thioesterase (GenBank Acc. No. Q39473), *Umbellularia californica* fatty acyl-ACP thioesterase (GenBank Acc. No. Q41635), *Myristica fragrans* fatty acyl-ACP thioesterase (GenBank Acc. No. AAB71729), *Myristica fragrans* fatty acyl-ACP thioesterase (GenBank Acc. No. AAB71730), *Elaeis guineensis* fatty acyl-ACP thioesterase (GenBank Acc. No. ABD83939), *Elaeis guineensis* fatty acyl-ACP thioesterase (GenBank Acc. No. AAD42220), *Populus tomentosa* fatty acyl-ACP thioesterase (GenBank Acc. No. ABC47311), *Arabidopsis thaliana* fatty acyl-ACP thioesterase (GenBank Acc. No. NP_172327), *Arabidopsis thaliana* fatty acyl-ACP thioesterase (GenBank Acc. No. CAA85387), *Arabidopsis thaliana* fatty acyl-ACP thioesterase (GenBank Acc. No. CAA85388), *Gossypium hirsutum* fatty acyl-ACP thioesterase (GenBank Acc. No. Q9SQI3), *Cuphea lanceolata* fatty acyl-ACP thioesterase (GenBank Acc. No. CAA54060), *Cuphea hookeriana* fatty acyl-ACP thioesterase (GenBank Acc. No. AAC72882), *Cuphea calophylla* subsp. *mesostemon* fatty acyl-ACP thioesterase (GenBank Acc. No. ABB71581), *Cuphea lanceolata* fatty acyl-ACP thioesterase (GenBank Acc. No. CAC19933), *Elaeis guineensis* fatty acyl-ACP thioesterase (GenBank Acc. No. AAL15645), *Cuphea hookeriana* fatty acyl-ACP thioesterase (GenBank Acc. No. Q39513), *Gossypium hirsutum* fatty acyl-ACP thioesterase (GenBank Acc. No. AAD01982), *Vitis vinifera* fatty acyl-ACP thioesterase (GenBank Acc. No. CAN81819), *Garcinia mangostana* fatty acyl-ACP thioesterase (GenBank Acc. No. AAB51525), *Brassica juncea* fatty acyl-ACP thioesterase (GenBank Acc. No. ABI18986), *Madhuca longifolia* fatty acyl-ACP thioesterase (GenBank Acc. No. AAX51637), *Brassica napus* fatty acyl-ACP thioesterase (GenBank Acc. No. ABH11710), |

TABLE 20-continued

| Lipid biosynthesis pathway proteins. |
|---|
| *Brassica napus* fatty acyl-ACP thioesterase (GenBank Acc. No. CAA52070.1), *Oryza sativa* (indica cultivar-group) fatty acyl-ACP thioesterase (GenBank Acc. No. EAY86877), *Oryza sativa* (japonica cultivar-group) fatty acyl-ACP thioesterase (GenBank Acc. No. NP_001068400), *Oryza sativa* (indica cultivar-group) fatty acyl-ACP thioesterase (GenBank Acc. No. EAY99617), *Cuphea hookeriana* fatty acyl-ACP thioesterase (GenBank Acc. No. AAC49269), *Ulmus Americana* fatty acyl-ACP thioesterase (GenBank Acc. No. AAB71731), *Cuphea lanceolata* fatty acyl-ACP thioesterase (GenBank Acc. No. CAB60830), *Cuphea palustris* fatty acyl-ACP thioesterase (GenBank Acc. No. AAC49180), *Iris germanica* fatty acyl-ACP thioesterase (GenBank Acc. No. AAG43858, *Iris germanica* fatty acyl-ACP thioesterase (GenBank Acc. No. AAG43858.1), *Cuphea palustris* fatty acyl-ACP thioesterase (GenBank Acc. No. AAC49179), *Myristica fragrans* fatty acyl-ACP thioesterase (GenBank Acc. No. AAB71729), *Myristica fragrans* fatty acyl-ACP thioesterase (GenBank Acc. No. AAB717291.1), *Cuphea hookeriana* fatty acyl-ACP thioesterase GenBank Acc. No. U39834), *Umbelluaria californica* fatty acyl-ACP thioesterase (GenBank Acc. No. M94159), *Cinnamomum camphora* fatty acyl-ACP thioesterase (GenBank Acc. No. U31813), *Ricinus communis* fatty acyl-ACP thioesterase (GenBank Acc. No. ABS30422.1), *Helianthus annuus* acyl-ACP thioesterase (GenBank Accession No. AAL79361.1), *Jatropha curcas* acyl-ACP thioesterase (GenBank Accession No. ABX82799.3), *Zea mays* oleoyl-acyl carrier protein thioesterase, (GenBank Accession No. ACG40089.1), *Haematococcus pluvialis* fatty acyl-ACP thioesterase (GenBank Accession No. HM560034.1)<br>Desaturase Enzymes |
| *Linum usitatissimum* fatty acid desaturase 3C, (GenBank Acc. No. ADV92272.1), *Ricinus communis* omega-3 fatty acid desaturase, endoplasmic reticulum, putative, (GenBank Acc. No. EEF36775.1), *Vernicia fordii* omega-3 fatty acid desaturase, (GenBank Acc. No. AAF12821), *Glycine max* chloroplast omega 3 fatty acid desaturase isoform 2, (GenBank Acc. No. ACF19424.1), *Prototheca moriformis* FAD-D omega 3 desaturase (SEQ ID NO: 221), *Prototheca moriformis* linoleate desaturase (SEQ ID NO: 220), *Carthamus tinctorius* delta 12 desaturase, (GenBank Accession No. ADM48790.1), *Gossypium hirsutum* omega-6 desaturase, (GenBank Accession No. CAA71199.1), *Glycine max* microsomal desaturase (GenBank Accession No. BAD89862.1), *Zea mays* fatty acid desaturase (GenBank Accession No. ABF50053.1), *Brassica napa* linoleic acid desaturase (GenBank Accession No. AAA32994.1), *Camelina sativa* omega-3 desaturase (SEQ ID NO: 214), *Prototheca moriformis* delta 12 desaturase allele 2 (SEQ ID NO: 212), *Camelina sativa* omega-3 FAD7-1 (SEQ ID NO: 215), *Helianthus annuus* stearoyl-ACP desaturase, (GenBank Accession No. AAB65145.1), *Ricinus communis* stearoyl-ACP desaturase, (GenBank Accession No. AACG59946.1), *Brassica juncea* plastidic delta-9-stearoyl-ACP desaturase (GenBank Accession No. AAD40245.1), *Glycine max* stearoyl-ACP desaturase (GenBank Accession No. ACJ39209.1), *Olea europaea* stearoyl-ACP desaturase (GenBank Accession No. AAB67840.1), *Vernicia fordii* stearoyl-acyl-carrier protein desaturase, (GenBank Accession No. ADC32803.1), *Descurainia sophia* delta-12 fatty acid desaturase (GenBank Accession No. ABS86964.2), *Euphorbia lagascae* delta12-oleic acid desaturase (GenBank Acc. No. AAS57577.1), *Chlorella vulgaris* delta 12 fatty acid desaturease (GenBank Accession No. ACF98528), *Chlorella vulgaris* omega-3 fatty acid desaturease (GenBank Accession No. BAB78717), *Haematococcus pluvialis* omega-3 fatty acid desaturase (GenBank Accession No. HM560035.1), *Haematococcus pluvialis* stearoyl-ACP-desaturase GenBank Accession No. EF586860.1, *Haematococcus pluvialis* stearoyl-ACP-desaturase GenBank Accession No. EF523479.1<br>Oleate 12-hydroxylase Enzymes |
| *Ricinus communis* oleate 12-hydroxylase (GenBank Acc. No. AAC49010.1), *Physaria lindheimeri* oleate 12-hydroxylase (GenBank Acc. No. ABQ01458.1), *Physaria lindheimeri* mutant bifunctional oleate 12-hydroxylase: desaturase (GenBank Acc. No. ACF17571.1), *Physaria lindheimeri* bifunctional oleate 12-hydroxylase: desaturase (GenBank Accession No. ACQ42234.1), *Physaria lindheimeri* bifunctional oleate 12-hydroxylase: desaturase (GenBank Acc. No. AAC32755.1), *Arabidopsis lyrata* subsp. *Lyrata* (GenBank Acc. No. XP_002884883.1)<br>Glycerol-3-phosphate Enzymes |
| *Arabidopsis thaliana* glycerol-3-phosphate acyltransferase BAA00575, *Chlamydomonas reinhardtii* glycerol-3-phosphate acyltransferase (GenBank Acc. No. EDP02129), *Chlamydomonas reinhardtii* glycerol-3-phosphate acyltransferase (GenBank Acc. No. Q886Q7), *Cucurbita moschata* acyl-(acyl-carrier-protein): glycerol-3-phosphate acyltransferase (GenBank Acc. No. BAB39688), *Elaeis guineensis* glycerol-3-phosphate acyltransferase, ((GenBank Acc. No. AAF64066), *Garcina mangostana* glycerol-3-phosphate acyltransferase (GenBank Acc. No. ABS86942), *Gossypium hirsutum* glycerol-3-phosphate acyltransferase (GenBank Acc. No. ADK23938), *Jatropha curcas* glycerol-3-phosphate acyltransferase (GenBank Acc. No. ADV77219), *Jatropha curcas* plastid glycerol-3-phosphate acyltransferase (GenBank Acc. No. ACR61638), *Ricinus communis* plastidial glycerol-phosphate acyltransferase (GenBank Acc. No. EEF43526), *Vica faba* glycerol-3-phosphate acyltransferase (GenBank Accession No. AAD05164), *Zea mays* glycerol-3-phosphate acyltransferase (GenBank Acc. No. ACG45812)<br>Lysophosphatidic acid acyltransferase Enzymes |
| *Arabidopsis thaliana* 1-acyl-sn-glycerol-3-phosphate acyltransferase (GenBank Accession No. AEE85783), *Brassica juncea* 1-acyl-sn-glycerol-3-phosphate acyltransferase (GenBank Accession No. ABQ42862), *Brassica juncea* 1-acyl-sn-glycerol-3-phosphate acyltransferase |

TABLE 20-continued

| Lipid biosynthesis pathway proteins. |
| --- |
| (GenBank Accession No. ABM92334), *Brassica napus* 1-acyl-sn-glycerol-3-phosphate acyltransferase (GenBank Accession No. CAB09138), *Chlamydomonas reinhardtii* lysophosphatidic acid acyltransferase (GenBank Accession No. EDP02300), *Cocos nucifera* lysophosphatidic acid acyltransferase (GenBank Acc. No. AAC49119), *Limnanthes alba* lysophosphatidic acid acyltransferase (GenBank Accession No. EDP02300), *Limnanthes douglasii* 1-acyl-sn-glycerol-3-phosphate acyltransferase (putative) (GenBank Accession No. CAA88620), *Limnanthes douglasii* acyl-CoA: sn-1-acylglycerol-3-phosphate acyltransferase (GenBank Accession No. ABD62751), *Limnanthes douglasii* 1-acylglycerol-3-phosphate O-acyltransferase (GenBank Accession No. CAA58239), *Ricinus communis* 1-acyl-sn-glycerol-3-phosphate acyltransferase (GenBank Accession No. EEF39377) |
| Diacylglycerol acyltransferase Enzymes |
| *Arabidopsis thaliana* diacylglycerol acyltransferase (GenBank Acc. No. CAB45373), *Brassica juncea* diacylglycerol acyltransferase (GenBank Acc. No. AAY40784), *Elaeis guineensis* putative diacylglycerol acyltransferase (GenBank Acc. No. AEQ94187), *Elaeis guineensis* putative diacylglycerol acyltransferase (GenBank Acc. No. AEQ94186), *Glycine max* acyl CoA: diacylglycerol acyltransferase (GenBank Acc. No. AAT73629), *Helianthus annus* diacylglycerol acyltransferase (GenBank Acc. No. ABX61081), *Olea europaea* acyl-CoA: diacylglycerol acyltransferase 1 (GenBank Acc. No. AAS01606), *Ricinus communis* diacylglycerol acyltransferase (GenBank Acc. No. AAR11479) |
| Phospholipid diacylglycerol acyltransferase Enzymes |
| *Arabidopsis thaliana* phospholipid: diacylglycerol acyltransferase (GenBank Acc. No. AED91921), *Elaeis guineensis* putative phospholipid: diacylglycerol acyltransferase (GenBank Acc. No. AEQ94116), *Glycine max* phospholipid: diacylglycerol acyltransferase 1-like (GenBank Acc. No. XP_003541296), *Jatropha curcas* phospholipid: diacylglycerol acyltransferase (GenBank Acc. No. AEZ56255), *Ricinus communis* phospholipid: diacylglycerol acyltransferase (GenBank Acc. No. ADK92410), *Ricinus communis* phospholipid: diacylglycerol acyltransferase (GenBank Acc. No. AEW99982) |

Example 10

Engineering *Chlorella sorokiniana*

Expression of recombinant genes in accordance with the present invention in *Chlorella sorokiniana* can be accomplished by modifying the methods and vectors taught by Dawson et al. as discussed herein. Briefly, Dawson et al., *Current Microbiology* Vol. 35 (1997) pp. 356-362, reported the stable nuclear transformation of *Chlorella sorokiniana* with plasmid DNA. Using the transformation method of microprojectile bombardment, Dawson introduced the plasmid pSV72-NR9, encoding the full *Chlorella vulgaris* nitrate reductase gene (NR, GenBank Accession No. U39931), into mutant *Chlorella sorokiniana* (NR-mutants). The NR-mutants are incapable of growth without the use of nitrate as a source of nitrogen. Nitrate reductase catalyzes the conversion of nitrate to nitrite. Prior to transformation, *Chlorella sorokiniana* NR-mutants were unable to grow beyond the microcolony stage on culture medium comprising nitrate ($NO_3^-$) as the sole nitrogen source. The expression of the *Chlorella vulgaris* NR gene product in NR-mutant *Chlorella sorokiniana* was used as a selectable marker to rescue the nitrate metabolism deficiency. Upon transformation with the pSV72-NR9 plasmid, NR-mutant *Chlorella sorokiniana* stably expressing the *Chlorella vulgaris* NR gene product were obtained that were able to grow beyond the microcolony stage on agar plates comprising nitrate as the sole carbon source. Evaluation of the DNA of the stable transformants was performed by Southern analysis and evaluation of the RNA of the stable transformants was performed by RNase protection. Selection and maintenance of the transformed *Chlorella sorokiniana* (NR mutant) was performed on agar plates (pH 7.4) comprising 0.2 g/L $MgSO_4$, 0.67 g/L $KH_2PO_4$, 3.5 g/L $K_2HPO_4$, 1.0 g/L $Na_3C_6H_8O_7.H_2O$ and 16.0 g/L agar, an appropriate nitrogen source (e.g., $NO_3$), micronutrients, and a carbon source. Dawson also reported the propagation of *Chlorella sorokiniana* and *Chlorella sorokiniana* NR mutants in liquid culture medium. Dawson reported that the plasmid pSV72-NR9 and the promoter and 3' UTR/terminator of the *Chlorella vulgaris* nitrate reductase gene were suitable to enable heterologous gene expression in *Chlorella sorokiniana* NR-mutants. Dawson also reported that expression of the *Chlorella vulgaris* nitrate reductase gene product was suitable for use as a selectable marker in *Chlorella sorokiniana* NR-mutants.

In an embodiment of the present invention, vector pSV72-NR9, comprising nucleotide sequence encoding the *Chlorella vulgaris* nitrate reductase (CvNR) gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Chlorella sorokiniana* to reflect the codon bias inherent in nuclear genes of *Chlorella sorokiniana* in accordance with Tables 19A-D. For each lipid biosynthesis pathway protein of Table 20, the codon-optimized gene sequence can individually be operably linked to the CvNR promoter upstream of the protein-coding sequence and operably linked to the CvNR 3'UTR/terminator at the 3' region, or downstream, of the protein-coding sequence. The transformation construct may additionally comprise homology regions to the *Chlorella sorokiniana* genome for targeted genomic integration of the transformation vector. Homology regions may be selected to disrupt one or more genomic sites of endogenous lipid biosynthesis pathway genes. Stable transformation of *Chlorella sorokiniana* with the transformation vector is achieved through well-known transformation techniques including microprojectile bombardment or other known methods. Activity of the CvNR gene product can be used as a selectable marker to rescue the nitrogen assimiliation deficiency of *Chlorella* sorokiniana NR mutant strains and to select for *Chlorella sorokiniana* NR-mutants stably expressing the transformation vector. Growth media suitable for *Chlorella sorokiniana* lipid production include, but are not limited to 0.5 g/L $KH_2PO_4$, 0.5 g/L $K_2HPO_4$, 0.25 g/L $MgSO_4$-$7H_2O$, with supplemental micronutrients and the appropriate nitrogen and carbon sources (Patterson, *Lipids* Vol. 5:7 (1970), pp. 597-600). Evaluation of fatty acid profiles of *Chlorella sorokiniana* lipids can be assessed through standard lipid extraction and analytical methods described herein.

Example 11

Engineering *Chlorella vulgaris*

Expression of recombinant genes in accordance with the present invention in *Chlorella vulgaris* can be accomplished by modifying the methods and vectors taught by Chow and Tung et al. as discussed herein. Briefly, Chow and Tung et al., *Plant Cell Reports*, Volume 18 (1999), pp. 778-780, reported the stable nuclear transformation of *Chlorella vulgaris* with plasmid DNA. Using the transformation method of electroporation, Chow and Tung introduced the plasmid pIG121-Hm (GenBank Accession No. AB489142) into *Chlorella vulgaris*. The nucleotide sequence of pIG121-Hm comprised sequence encoding a beta-glucuronidase (GUS) reporter gene product operably-linked to a CaMV 35S promoter upstream of the GUS protein-coding sequence and further operably linked to the 3' UTR/terminator of the nopaline synthase (nos) gene downstream of the GUS protein-coding sequence. The sequence of plasmid pIG121-Hm further comprised a hygromycin B antibiotic resistance cassette. This hygromycin B antibiotic resistance cassette comprised a CaMV 35S promoter operably linked to sequence encoding the hygromycin phosphotransferase (hpt, GenBank Accession No. BAH24259) gene product. Prior to transformation, *Chlorella vulgaris* was unable to be propagated in culture medium comprising 50 ug/ml hygromycin B. Upon transformation with the pIG121-Hm plasmid, transformants of *Chlorella vulgaris* were obtained that were propagated in culture medium comprising 50 ug/ml hyrgromycin B. The expression of the hpt gene product in *Chlorella vulgaris* enabled propagation of transformed *Chlorella vulgaris* in the presence of 50 ug/mL hyrgromycin B, thereby establishing the utility of the a hygromycin B resistance cassette as a selectable marker for use in *Chlorella vulgaris*. Detectable activity of the GUS reporter gene indicated that CaMV 35S promoter and nos 3'UTR are suitable for enabling heterologous gene expression in *Chlorella vulgaris*. Evaluation of the genomic DNA of the stable transformants was performed by Southern analysis. Selection and maintenance of transformed *Chlorella vulgaris* was performed on agar plates comprising YA medium (agar and 4 g/L yeast extract). The propagation of *Chlorella vulgaris* in liquid culture medium was conducted as discussed by Chow and Tung. Propagation of *Chlorella vulgaris* in media other than YA medium has been described (for examples, see Chader et al., *Revue des Energies Renouvelabes*, Volume 14 (2011), pp. 21-26 and Illman et al., *Enzyme and Microbial Technology*, Vol. 27 (2000), pp. 631-635). Chow and Tung reported that the plasmid pIG121-Hm, the CaMV 35S promoter, and the *Agrobacterium tumefaciens* nopaline synthase gene 3'UTR/terminator are suitable to enable heterologous gene expression in *Chlorella vulgaris*. In addition, Chow and Tung reported the hyromycin B resistance cassette was suitable for use as a selectable marker in *Chlorella vulgaris*. Additional plasmids, promoters, 3'UTR/terminators, and selectable markers suitable for enabling heterologous gene expression in *Chlorella vulgaris* have been discussed in Chader et al., *Revue des Energies Renouvelabes*, Volume 14 (2011), pp. 21-26.

In an embodiment of the present invention, pIG121-Hm, comprising the nucleotide sequence encoding the hygromycin B gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Chlorella vulgaris* to reflect the codon bias inherent in nuclear genes of *Chlorella vulgaris* in accordance with Tables 19A-D. For each lipid biosynthesis pathway protein of Table 20, the codon-optimized gene sequence can individually be operably linked to the CaMV 35S promoter upstream of the protein-coding sequence and operably linked to the *Agrobacterium tumefaciens* nopaline synthase gene 3'UTR/terminator at the 3' region, or downstream, of the protein-coding sequence. The transformation construct may additionally comprise homology regions to the *Chlorella vulgaris* genome for targeted genomic integration of the transformation vector. Homology regions may be selected to disrupt one or more genomic sites of endogenous lipid biosynthesis pathway genes. Stable transformation of *Chlorella vulgaris* with the transformation vector is achieved through well-known transformation techniques including electroporation or other known methods. Activity of the hygromycin B resistance gene product can be used as a marker to select for *Chlorella vulgaris* transformed with the transformation vector on, but not limited to, agar medium comprising hygromycin. Growth media suitable for *Chlorella vulgaris* lipid production include, but are not limited to BG11 medium (0.04 g/L $KH_2PO_4$, 0.075 g/L $CaCl_2$, 0.036 g/L citric acid, 0.006 g/L Ammonium Ferric Citrate, 1 mg/L EDTA, and 0.02 g/L $Na_2CO_3$) supplemented with trace metals, and optionally 1.5 g/L NaNO3. Additional media suitable for culturing *Chlorella vulgaris* for lipid production include, for example, Watanabe medium (comprising 1.5 g/L $KNO_3$, 1.25 g/L $KH_2PO_4$, 1.25 g $l^{-1}$ $MgSO_4.7H_2O$, 20 mg $l^{-1}$ $FeSO_4.7H_2O$ with micronutrients and low-nitrogen medium (comprising 203 mg/l $(NH_4)_2HPO_4$, 2.236 g/l KCl, 2.465 g/l $MgSO_4$, 1.361 g/l $KH_2PO_4$ and 10 mg/l $FeSO_4$) as reported by Illman et al., *Enzyme and Microbial Technology*, Vol. 27 (2000), pp. 631-635. Evaluation of fatty acid profiles of *Chlorella vulgaris* lipids can be assessed through standard lipid extraction and analytical methods described herein.

Example 12

Engineering *Chlorella ellipsoidea*

Expression of recombinant genes in accordance with the present invention in *Chlorella ellipsoidea* can be accomplished by modifying the methods and vectors taught by Chen et al. as discussed herein. Briefly, Chen et al., *Current Genetics*, Vol. 39:5 (2001), pp. 365-370, reported the stable transformation of *Chlorella ellipsoidea* with plasmid DNA. Using the transformation method of electroporation, Chen introduced the plasmid pBinUΩNP-1 into *Chlorella ellipsoidea*. The nucleotide sequence of pBinUΩNP-1 comprised sequence encoding the neutrophil peptide-1 (NP-1) rabbit gene product operably linked to a *Zea mays* Ubiquitin (ubi1) gene promoter upstream of the NP-1 protein-coding region and operably linked to the 3' UTR/terminator of the nopaline synthase (nos) gene downstream of the NP-1 protein-coding region. The sequence of plasmid pBinUΩNP-1 further comprised a G418 antibiotic resistance cassette. This G418 antibiotic resistance cassette comprised sequence encoding the aminoglycoside 3'-phosphotransferase (aph 3') gene product. The aph 3' gene product confers resistance to the antibiotic G418. Prior to transformation, *Chlorella ellipsoidea* was unable to be propagated in culture medium comprising 30 ug/mL G418. Upon transformation with the pBinUΩNP-1 plasmid, transformants of *Chlorella ellipsoidea* were obtained that were propagated in selective culture medium comprising 30 ug/mL G418. The expression of the aph 3' gene product in *Chlorella ellipsoidea* enabled propagation of transformed *Chlorella ellipsoidea* in the presence of 30 ug/mL G418, thereby establishing the utility of the G418 antibiotic resistance cassette as selectable marker for use in *Chlorella ellipsoidea*. Detectable activity of the NP-1 gene product indicated that the ubi1 promoter and nos 3' UTR are suitable for enabling heterologous gene expression in *Chlorella ellipsoidea*. Evaluation of the genomic DNA of the stable transformants was performed by Southern analysis. Selection and maintenance of the transformed *Chlorella ellipsoidea* was performed on Knop medium (comprising 0.2 g/L $K_2HPO_4$, 0.2 g/L $MgSO_4.7H_2O$, 0.12 g/L KCl, and 10 mg/L FeCl3, pH 6.0-8.0 supplemented with 0.1% yeast extract and 0.2% glucose) with 15 ug/mL G418 (for liquid cultures) or with 30 ug/mL G418 (for solid cultures comprising 1.8% agar). Propagation of *Chlorella ellipsoidea* in media other than Knop medium has been reported (see Cho et al., Fisheries Science, Vol. 73:5 (2007), pp. 1050-1056, Jarvis and Brown, *Current Genetics*, Vol. 19 (1991), pp. 317-321 and Kim et al., *Marine Biotechnology*, Vol. 4 (2002), pp. 63-73). Additional plasmids, promoters, 3'UTR/terminators, and selectable markers suitable for enabling heterologous gene expression in *Chlorella ellipsoidea* have been reported (see Jarvis and Brown and Kim et al., *Marine Biotechnology*, Vol. 4 (2002), pp. 63-73). Chen reported that the plasmid pBinUΩNP-1, the ubi1 promoter, and the *Agrobacterium tumefaciens* nopaline synthase gene 3'UTR/terminator are suitable to enable exogenous gene expression in *Chlorella ellipsoidea*. In addition, Chen reported that the G418 resistance cassette encoded on pBinUΩNP-1 was suitable for use as a selectable marker in *Chlorella ellipsoidea.*

In an embodiment of the present invention, vector pBinUΩNP-1, comprising the nucleotide sequence encoding the aph 3' gene product, conferring resistance to G418, for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Chlorella ellipsoidea* to reflect the codon bias inherent in nuclear genes of *Chlorella ellipsoidea* in accordance with Tables 19A-D. For each lipid biosynthesis pathway protein of Table 20, the codon-optimized gene sequence can individually be operably linked to the *Zea mays* ubi1 promoter upstream of the protein-coding sequence and operably linked to the *Agrobacterium tumefaciens* nopaline synthase gene 3'UTR/terminator at the 3' region, or downstream, of the protein-coding sequence. The transformation construct may additionally comprise homology regions to the *Chlorella ellipsoidea* genome for targeted genomic integration of the transformation vector. Homology regions may be selected to disrupt one or more genomic sites of endogenous lipid biosynthesis pathway genes. Stable transformation of *Chlorella ellipsoidea* with the transformation vector is achieved through well-known transformation techniques including electroporation or other known methods. Activity of the aph 3' gene product can be used as a marker to select for *Chlorella ellipsoidea* transformed with the transformation vector on, but not limited to, Knop agar medium comprising G418. Growth media suitable for *Chlorella ellipsoidea* lipid production include, but are not limited to, Knop medium and those culture medium reported by Jarvis and Brown and Kim et al. Evaluation of fatty acid profiles of *Chlorella ellipsoidea* lipids can be assessed through standard lipid extraction and analytical methods described herein.

Example 13

Engineering *Chlorella kessleri*

Expression of recombinant genes in accordance with the present invention in *Chlorella kessleri* can be accomplished by modifying the methods and vectors taught by El-Sheekh et al. as discussed herein. Briefly, El-Sheekh et al., *Biologia Plantarium*, Vol. 42:2 (1999), pp. 209-216, reported the stable transformation of *Chlorella kessleri* with plasmid DNA. Using the transformation method of microprojectile bombardment, El-Sheekh introduced the plasmid pBI121 (GenBank Accession No. AF485783) into *Chlorella kessleri*. Plasmid pBI121 comprised a kanamycin/neomycin antibiotic resistance cassette. This kanamycin/neomycin antibiotic resistance cassette comprised the *Agrobacterium tumefaciens* nopaline synthase (nos) gene promoter, sequence encoding the neomycin phosphotransferase II (nptII) gene product (GenBank Accession No. AAL92039) for resistance to kanamycin and G418, and the 3' UTR/terminator of the *Agrobacterium tumefaciens* nopaline synthase (nos) gene. pBI121 further comprised sequence encoding a beta-glucuronidase (GUS) reporter gene product operably linked to a CaMV 35S promoter and operably linked to a 3' UTR/terminator of the nos gene. Prior to transformation, *Chlorella kessleri* was unable to be propagated in culture medium comprising 15 ug/L kanamycin. Upon transformation with the pBI121plasmid, transformants of *Chlorella kessleri* were obtained that were propagated in selective culture medium comprising 15 mg/L kanamycin. The express ion of the nptII gene product in *Chlorella kessleri* enabled propagation in the presence of 15 mg/L kanamycin, thereby establishing the utility of the kanamycin/neomycin antibiotic resistance cassette as selectable marker for use in *Chlorella kessleri*. Detectable activity of the GUS gene product indicated that the CaMV 35S promoter and nos 3' UTR are suitable for enabling heterologous gene expression in *Chlorella kessleri*. Evaluation of the genomic DNA of the stable transformants was performed by Southern analysis. As reported by El-Sheekh, selection and maintenance of transformed *Chlorella kessleri* was conducted on semisolid agar plates comprising YEG medium (1% yeast extract, 1% glucose) and 15 mg/L kanamycin. El-Sheekh also reported the propagation of *Chlorella kessleri* in YEG liquid culture media. Additional media suitable for culturing *Chlorella kessleri* for lipid production are disclosed in Sato et al., *BBA Molecular and Cell Biology of Lipids*, Vol. 1633 (2003), pp. 27-34). El-Sheekh reported that the plasmid pBI121, the CaMV promoter, and the nopaline synthase gene 3'UTR/terminator are suitable to enable heterologous gene expression in *Chlorella* kessleri. In addition, El-Sheekh reported that the kanamycin/neomycin resistance cassette encoded on pBI121 was suitable for use as a selectable marker in *Chlorella kessleri.*

In an embodiment of the present invention, vector pBI121, comprising the nucleotide sequence encoding the kanamycin/neomycin resistance gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Chlorella kessleri* to reflect the codon bias inherent in nuclear genes of *Chlorella kessleri* in accordance with Tables 19A-D. For each lipid biosynthesis pathway protein of Table 20, the codon-optimized gene sequence can individually be operably linked to the CaMV 35S promoter upstream of the protein-coding sequence and operably linked to the *Agrobacterium tumefaciens* nopaline synthase gene 3'UTR/terminator at the 3' region, or downstream, of the protein-coding sequence. The transformation construct may additionally comprise homology regions to the *Chlorella kessleri* genome for targeted genomic integration of the transformation vector. Homology regions may be selected to disrupt one or more genomic sites of endogenous lipid biosynthesis pathway genes. Stable transformation of *Chlorella kessleri* with the transformation vector is achieved through well-known transformation techniques including microprojectile bombardment or other known methods. Activity of the nptII gene product can be used as a marker to select for *Chlorella kessleri* transformed with the transformation vector on, but not limited to, YEG agar medium comprising kanamycin or neomycin. Growth media suitable for *Chlorella kessleri* lipid production include, but are not limited to, YEG medium, and those culture media reported by Sato et al. Evaluation of fatty acid profiles of *Chlorella kessleri* lipids can be assessed through standard lipid extraction and analytical methods described herein.

Example 14

Engineering *Dunaliella tertiolecta*

Expression of recombinant genes in accordance with the present invention in *Dunaliella tertiolecta* can be accomplished by modifying the methods and vectors taught by Walker et al. as discussed herein. Briefly, Walker et al., *Journal of Applied Phycology*, Vol. 17 (2005), pp. 363-368, reported stable nuclear transformation of *Dunaliella tertiolecta* with plasmid DNA. Using the transformation method of electroporation, Walker introduced the plasmid pDbleFLAG1.2 into *Dunaliella tertiolecta*. pDbleFLAG1.2 comprised sequence encoding a bleomycin antibiotic resistance cassette, comprising sequence encoding the *Streptoalloteichus hindustanus* Bleomycin binding protein (ble), for resistance to the antibiotic phleomycin, operably linked to the promoter and 3' UTR of the *Dunaliella tertiolecta ribulose*-1,5-bisphosphate carboxylase/oxygenase small subunit gene (rbcS1, GenBank Accession No. AY530155). Prior to transformation, *Dunaliella tertiolecta* was unable to be propagated in culture medium comprising 1 mg/L phleomycin. Upon transformation with the pDbleFLAG1.2 plasmid, transformants of *Dunaliella tertiolecta* were obtained that were propagated in selective culture medium comprising 1 mg/L phleomycin. The expression of the ble gene product in *Dunaliella tertiolecta* enabled propagation in the presence of 1 mg/L phleomycin, thereby establishing the utility of the bleomycin antibiotic resistance cassette as selectable marker for use in *Dunaliella tertiolecta*. Evaluation of the genomic DNA of the stable transformants was performed by Southern analysis. As reported by Walker, selection and maintenance of transformed *Dunaliella tertiolecta* was conducted in *Dunaliella* medium (DM, as described by Provasoli et al., *Archiv fur Mikrobiologie*, Vol. 25 (1957), pp. 392-428) further comprising 4.5 g/L NaCl and 1 mg/L pheomycin. Additional media suitable for culturing *Dunaliella tertiolecta* for lipid production are discussed in Takagi et al., *Journal of Bioscience and Bioengineering*, Vol. 101:3 (2006), pp. 223-226 and in Massart and Hanston, Proceedings Venice 2010, Third International Symposium on Energy from Biomass and Waste. Walker reported that the plasmid pDbleFLAG1.2 and the promoter and 3' UTR of the *Dunaliella tertiolecta* ribulose-1,5-bisphosphate carboxylase/oxygenase small subunit gene are suitable to enable heterologous expression in *Dunaliella tertiolecta*. In addition, Walker reported that the bleomycin resistance cassette encoded on pDbleFLAG1.2 was suitable for use as a selectable marker in *Dunaliella tertiolecta*.

In an embodiment of the present invention, vector pDbleFLAG1.2, comprising the nucleotide sequence encoding the ble gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Dunaliella tertiolecta* to reflect the codon bias inherent in nuclear genes of *Dunaliella tertiolecta* in accordance with Tables 19A-D. For each lipid biosynthesis pathway protein of Table 20, the codon-optimized gene sequence can individually be operably linked to the rbcS1 promoter upstream of the protein-coding sequence and operably linked to the rbcS1 3'UTR/terminator at the 3' region, or downstream, of the protein-coding sequence. The transformation construct may additionally comprise homology regions to the *Dunaliella tertiolecta* genome for targeted genomic integration of the transformation vector. Homology regions may be selected to disrupt one or more genomic sites of endogenous lipid biosynthesis pathway genes. Stable transformation of *Dunaliella tertiolecta* with the transformation vector is achieved through well-known transformation techniques including electroporation or other known methods. Activity of the ble gene product can be used as a marker to select for *Dunaliella tertiolecta* transformed with the transformation vector on, but not limited to, DM medium comprising pheomycin. Growth medium suitable for *Dunaliella tertiolecta* lipid production include, but are not limited to DM medium and those culture media described by Takagi et al. and Massart and Hanston. Evaluation of fatty acid profiles of *Dunaliella tertiolecta* lipids can be assessed through standard lipid extraction and analytical methods described herein.

Example 15

Engineering *Volvox carteri*

Expression of recombinant genes in accordance with the present invention in *Volvox carteri* can be accomplished by modifying the methods and vectors taught by Hallman and Rappel et al. as discussed herein. Briefly, Hallman and Rappel et al., *The Plant Journal*, Volume 17 (1999), pp. 99-109, reported the stable nuclear transformation of *Volvox carteri* with plasmid DNA. Using the transformation method of microprojectile bombardment, Hallman and Rappel introduced the pzeoE plasmid into *Volvox carteri*. The pzeoE plasmid comprised sequence encoding a bleomycin antibiotic resistance cassette, comprising sequence encoding the *Streptoalloteichus hindustanus* Bleomycin binding protein (ble), for resistance to the antibiotic zeocin, operably linked to and the promoter and 3' UTR of the *Volvox carteri* beta-tubulin gene (GenBank Accession No. L24547). Prior to transformation, *Volvox carteri* was unable to be propagated in culture medium comprising 1.5 ug/ml zeocin. Upon transformation with the pzeoE plasmid, transformants of *Volvox carteri* were obtained that were propagated in selective culture medium comprising greater than 20 ug/ml zeocin. The expression of the ble gene product in *Volvox carteri* enabled propagation in the presence of 20 ug/ml zeocin, thereby establishing the utility of the bleomycin antibiotic resistance cassette as selectable marker for use in *Volvox carteri*. Evaluation of the genomic DNA of the stable transformants was performed by Southern analysis. As reported by Hallman and Rappel, selection and maintenance of transformed *Volvox carteri* was conducted in *Volvox* medium (VM, as described by Provasoli and Pintner, The Ecology of Algae, Special Publication No. 2 (1959), Tyron, C. A. and Hartman, R. T., eds., Pittsburgh: University of Pittsburgh, pp. 88-96) with 1 mg/L pheomycin. Media suitable for culturing *Volvox carteri* for lipid production are also discussed by Starr in Starr R, C, *Dev Biol* Suppl., Vol. 4 (1970), pp. 59-100). Hallman and Rappel reported that the plasmid pzeoE and the promoter and 3' UTR of the *Volvox carteri* beta-tubulin gene are suitable to enable heterologous expression in *Volvox carteri*. In addition, Hallman and Rappel reported that the bleomycin resistance cassette encoded on pzeoE was suitable for use as a selectable marker in *Volvox carteri*. Additional plasmids, promoters, 3'UTR/terminators, and selectable markers suitable for enabling heterologous gene expression in *Volvox carteri* and suitable for use as selective markers *Volvox carteri* in have been reported (for instance see Hallamann and Sumper, *Proceedings of the National Academy of Sciences*, Vol. 91 (1994), pp 11562-11566 and Hallman and Wodniok, *Plant Cell Reports*, Volume 25 (2006), pp. 582-581).

In an embodiment of the present invention, vector pzeoE, comprising the nucleotide sequence encoding the ble gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 19, each protein-coding sequence codon-optimized for expression in *Volvox carteri* to reflect the codon bias inherent in nuclear genes of *Volvox carteri* in accordance with Tables 19A-D. For each lipid biosynthesis pathway protein of Table 20, the codon-optimized gene sequence can individually be operably linked to the *Volvox carteri* beta-tubulin promoter upstream of the protein-coding sequence and operably linked to the *Volvox carteri* beta-tubulin 3'UTR/terminator at the 3' region, or downstream, of the protein-coding sequence. The transformation construct may additionally comprise homology regions to the *Volvox carteri* genome for targeted genomic integration of the transformation vector. Homology regions may be selected to disrupt one or more genomic sites of endogenous lipid biosynthesis pathway genes. One skilled in the art can identify such homology regions within the sequence of the *Volvox carteri* genome (referenced in the publication by Prochnik et al., *Science*, Vol. 329:5988 (2010), pp 223-226). Stable transformation of *Volvox carteri* with the transformation vector is achieved through well-known transformation techniques including microprojectile bombardment or other known methods. Activity of the ble gene product can be used as a marker to select for *Volvox carteri* transformed with the transformation vector on, but not limited to, VM medium comprising zeocin. Growth medium suitable for *Volvox* carteri lipid production include, but are not limited to VM medium and those culture media discussed by Starr. Evaluation of fatty acid profiles of *Volvox carteri* lipids can be assessed through standard lipid extraction and analytical methods described herein.

Example 16

Engineering *Haematococcus pluvialis*

Expression of recombinant genes in accordance with the present invention in *Haematococcus pluvialis* can be accomplished by modifying the methods and vectors taught by Steinbrenner and Sandmann et al. as discussed herein. Briefly, Steinbrenner and Sandmann et al., *Applied and Environmental Microbiology*, Vol. 72:12 (2006), pp. 7477-7484, reported the stable nuclear transformation of *Haematococcus pluvialis* with plasmid DNA. Using the transformation method of microprojectile bombardment, Steinbrenner introduced the plasmid pPlat-pds-L504R into *Haematococcus pluvialis*. The plasmid pPlat-pds-L504R comprised a norflurazon resistance cassette, which comprised the promoter, protein-coding sequence, and 3'UTR of the *Haematococcus pluvialis* phytoene desaturase gene (Pds, GenBank Accession No. AY781170), wherein the protein-coding sequence of Pds was modified at position 504 (thereby changing a leucine to an arginine) to encode a gene product (Pds-L504R) that confers resistance to the herbicide norflurazon. Prior to transformation with pPlat-pds-L504R, *Haematococcus pluvialis* was unable to propagate on medium comprising 5 uM norflurazon. Upon transformation with the pPlat-pds-L504R plasmid, transformants of *Haematococcus pluvialis* were obtained that were propagated in selective culture medium comprising 5 uM norflurazon. The expression of the Pds-L504R gene product in *Haematococcus pluvialis* enabled propagation in the presence of 5 uM norflurazon, thereby establishing the utility of the norflurazon herbicide resistance cassette as selectable marker for use in *Haematococcus pluvialis*. Evaluation of the genomic DNA of the stable transformants was performed by Southern analysis. As reported by Steinbrenner, selection and maintenance of transformed *Haematococcus pluvialis* was conducted on agar plates comprising OHA medium (OHM (0.41 g/L $KNO_3$, 0.03 g/L $Na_2HPO_4$, 0.246 g/L $MgSO_4.7H_2O$, 0.11 g/L $CaCl_2.2H_2O$, 2.62 mg/L $Fe_{(III)}$citrate×$H_2O$, 0.011 mg/L $CoCl_2.6H_2O$, 0.012 mg/L $CuSO_4.5H_2O$, 0.075 mg/L $Cr_2O_3$, 0.98 mg/L $MnCl_2.4H_2O$, 0.12 mg/L $Na_2MoO_4{\times}2H_2O$, 0.005 mg/L $SeO_2$ and 25 mg/L biotin, 17.5 mg/L thiamine, and 15 mg/L vitamin B12), supplemented with 2.42 g/L Tris-acetate, and 5 mM norflurazon. Propagation of *Haematococcus pluvialis* in liquid culture was performed by Steinbrenner and Sandmann using basal medium (basal medium as described by Kobayashi et al., *Applied and Environmental Microbiology*, Vol. 59 (1993), pp. 867-8'73). Steinbrenner and Sandmann reported that the pPlat-pds-L504R plasmid and promoter and 3' UTR of the *Haematococcus pluvialis* phytoene desaturase gene are suitable to enable heterologous expression in *Haematococcus pluvialis*. In addition, Steinbrenner and Sandmann reported that the norflurazon resistance cassette encoded on pPlat-pds-L504R was suitable for use as a selectable marker in *Haematococcus pluvialis*. Additional plasmids, promoters, 3'UTR/terminators, and selectable markers suitable for enabling heterologous gene expression in *Haematococcus pluvialis* have been reported (see Kathiresan et al., *Journal of Phycology*, Vol. 45 (2009), pp 642-649).

In an embodiment of the present invention, vector pPlat-pds-L504R, comprising the nucleotide sequence encoding the Pds-L504R gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Haematococcus pluvialis* to reflect the codon bias inherent in nuclear genes of *Haematococcus pluvialis* in accordance with Tables 19 A-D. For each lipid biosynthesis pathway protein of Table 20, the codon-optimized gene sequence can individually be operably linked to the *Haematococcus pluvialis* pds gene promoter upstream of the protein-coding sequence and operably linked to the *Haematococcus pluvialis* pds gene 3'UTR/terminator at the 3' region, or downstream, of the protein-coding sequence. The transformation construct may additionally comprise homology regions to the *Haematococcus pluvialis* genome for targeted genomic integration of the transformation vector. Homology regions may be selected to disrupt one or more genomic sites of endogenous lipid biosynthesis pathway genes. Stable transformation of *Haematococcus pluvialis* with the transformation vector is achieved through well-known transformation techniques including microprojectile bombardment or other known methods. Activity of the Pds-L504R gene product can be used as a marker to select for *Haematococcus pluvialis* transformed with the transformation vector on, but not limited to, OHA medium comprising norflurazon. Growth media suitable for *Haematococcus pluvialis* lipid production include, but are not limited to basal medium and those culture media described by Kobayashi et al., Kathiresan et al, and Gong and Chen, *Journal of Applied Phycology*, Vol. 9:5 (1997), pp. 437-444). Evaluation of fatty acid profiles of *Haematococcus pluvialis* lipids can be assessed through standard lipid extraction and analytical methods described herein.

Example 17

Engineering *Closterium peracerosum-strigosum-littorale* Complex

Expression of recombinant genes in accordance with the present invention in *Closterium peracerosum-strigosum-littorale* complex can be accomplished by modifying the methods and vectors taught by Abe et al. as discussed herein. Briefly, Abe et al., *Plant Cell Physiology*, Vol. 52:9 (2011), pp. 1676-1685, reported the stable nuclear transformation of *Closterium peracerosum-strigosum-littorale* complex with plasmid DNA. Using the transformation methods of microprojectile bombardment, Abe introduced the plasmid pSA106 into *Closterium peracerosum-strigosum-littorale* complex. Plasmid pSA106 comprised a bleomycin resistance cassette, comprising sequence encoding the *Streptoalloteichus hindustanus* Bleomycin binding protein gene (ble, GenBank Accession No. CAA37050) operably linked to the promoter and 3' UTR of the *Closterium peracerosum-strigosum-littorale* complex Chlorophyll a/b-binding protein gene (CAB, GenBank Accession No. AB363403). Prior to transformation with pSA106, *Closterium peracerosum-strigosum-littorale* complex was unable to propagate on medium comprising 3 ug/ml phleomycin. Upon transformation with pSA106, transformants of *Closterium peracerosum-strigosum-littorale* complex were obtained that were propagated in selective culture medium comprising 3 ug/ml phleomycin. The expression of the ble gene product in *Closterium peracerosum-strigosum-littorale* complex enabled propagation in the presence of 3 ug/ml phleomycin, thereby establishing the utility of the bleomycin antibiotic resistance cassette as selectable marker for use in *Closterium peracerosum-strigosum-littorale* complex. Evaluation of the genomic DNA of the stable transformants was performed by Southern analysis. As reported by Abe, selection and maintenance of transformed *Closterium peracerosum-strigosum-littorale* complex was conducted first in top agar with C medium (0.1 g/L $KNO_3$, 0.015 g/L $Ca(NO_3)_2.4H_2O$, 0.05 g/L glycerophosphate-Na2, 0.04 g/L $MgSO_4.7H_2O$, 0.5 g/L Tris(hydroxylmethyl)aminomethane, trace minerals, biotin, vitamins $B_1$ and $B_{12}$) and then subsequently isolated to agar plates comprising C medium supplemented with phleomycin. As reported by Abe, propagation of *Closterium peracerosum-strigosum-littorale* complex in liquid culture was performed in C medium. Additional liquid culture medium suitable for propagation of *Closterium peracerosum-strigosum-littorale* complex are discussed by Sekimoto et al., *DNA Research,* 10:4 (2003), pp. 147-153. Abe reported that the pSA106 plasmid and promoter and 3' UTR of the *Closterium peracerosum-strigosum-littorale* complex CAB gene are suitable to enable heterologous gene expression in *Closterium peracerosum-strigosum-littorale* complex. In addition, Abe reported that the bleomycin resistance cassette encoded on pSA106 was suitable for use as a selectable marker in *Closterium peracerosum-strigosum-littorale* complex. Additional plasmids, promoters, 3'UTR/terminators, and selectable markers suitable for enabling heterologous gene expression in *Closterium peracerosum-strigosum*-littorale complex have been reported (see Abe et al., *Plant Cell Physiology*, Vol. 49 (2008), pp. 625-632).

In an embodiment of the present invention, vector pSA106, comprising the nucleotide sequence encoding the ble gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Closterium peracerosum-strigosum-littorale* complex to reflect the codon bias inherent in nuclear genes of *Closterium peracerosum-strigosum-littorale* complex in accordance with Tables 19A-D. For each lipid biosynthesis pathway protein of Table 20, the codon-optimized gene sequence can individually be operably linked to the *Closterium peracerosum-strigosum-littorale* complex CAB gene promoter upstream of the protein-coding sequence and operably linked to the *Closterium peracerosum-strigosum-littorale* complex CAB gene 3'UTR/terminator at the 3' region, or downstream, of the protein-coding sequence. The transformation construct may additionally comprise homology regions to the *Closterium peracerosum-strigosum-littorale* complex genome for targeted genomic integration of the transformation vector. Homology regions may be selected to disrupt one or more genomic sites of endogenous lipid biosynthesis pathway genes. Stable transformation of *Closterium peracerosum-strigosum-littorale* complex with the transformation vector is achieved through well-known transformation techniques including microprojectile bombardment or other known methods. Activity of the ble gene product can be used as a marker to select for *Closterium peracerosum-strigosum-littorale* complex transformed with the transformation vector on, but not limited to, C medium comprising phleomycin. Growth media suitable for *Closterium peracerosum-strigosum-littorale* complex lipid production include, but are not limited to C medium and those culture media reported by Abe et al. and Sekimoto et al. Evaluation of fatty acid profiles of *Closterium peracerosum-strigosum-littorale* complex lipids can be assessed through standard lipid extraction and analytical methods described herein.

Example 18

Engineering *Dunaliella viridis*

Expression of recombinant genes in accordance with the present invention in *Dunaliella viridis* can be accomplished by modifying the methods and vectors taught by Sun et al. as discussed herein. Briefly, Sun et al., *Gene*, Vol. 377 (2006), pp. 140-149, reported the stable transformation of *Dunaliella viridis* with plasmid DNA. Using the transformation method of electoporation, Sun introduced the plasmid pDVNR, encoding the full *Dunaliella viridis* nitrate reductase gene into mutant *Dunaliella viridis* (*Dunaliella viridis* NR-mutants). The NR-mutants are incapable of growth without the use of nitrate as a source of nitrogen. Nitrate reductase catalyzes the conversion of nitrate to nitrite. Prior to transformation, *Dunaliella viridis* NR-mutants were unable to propagate in culture medium comprising nitrate ($NO_3^-$) as the sole nitrogen source. The expression of the *Dunaliella viridis* NR gene product in NR-mutant *Dunaliella viridis* was used as a selectable marker to rescue the nitrate metabolism deficiency. Upon transformation with the pDVNR plasmid, NR-mutant *Dunaliella viridis* stably expressing the *Dunaliella viridis* NR gene product were obtained that were able to grow on agar plates comprising nitrate as the sole carbon source. Evaluation of the DNA of the stable transformants was performed by Southern analysis. Selection and maintenance of the transformed *Dunaliella viridis* (NR mutant) was performed on agar plates comprising 5 mM $KNO_3$. Sun also reported the propagation of *Dunaliella viridis* and *Dunaliella viridis* NR mutants in liquid culture medium. Additional media suitable for propagation of *Dunaliella viridis* are reported by Gordillo et al., *Journal of Applied Phycology*, Vol. 10:2 (1998), pp. 135-144 and by Moulton and Burford, *Hydrobiologia*, Vols. 204-205:1 (1990), pp. 401-408. Sun reported that the plasmid pDVNR and the promoter and 3' UTR/terminator of the *Dunaliella viridis* nitrate reductase gene were suitable to enable heterologous expression in *Dunaliella viridis* NR-mutants. Sun also reported that expression of the *Dunaliella viridis* nitrate reductase gene product was suitable for use as a selectable marker in *Dunaliella viridis* NR-mutants.

In an embodiment of the present invention, vector pDVNR, comprising the nucleotide sequence encoding the *Dunaliella viridis* nitrate reductase (DvNR) gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected Table 20, each protein-coding sequence codon-optimized for expression in *Dunaliella viridis* to reflect the codon bias inherent in nuclear genes of *Dunaliella viridis* in accordance with Tables 19A-D. For each lipid biosynthesis pathway protein of Table 20, the codon-optimized gene sequence can individually be operably linked to the DvNR promoter upstream of the protein-coding sequence and operably linked to the DvNR 3' UTR/terminator at the 3' region, or downstream, of the protein-coding sequence. The transformation construct may additionally comprise homology regions to the *Dunaliella viridis* genome for targeted genomic integration of the transformation vector. Homology regions may be selected to disrupt one or more genomic sites of endogenous lipid biosynthesis pathway genes. Stable transformation of *Dunaliella viridis* NR mutants with the transformation vector is achieved through well-known transformation techniques including electorporation or other known methods. Activity of the DvNR gene product can be used as a selectable marker to rescue the nitrogen assimiliation deficiency of *Dunaliella viridis* NR mutant strains and to select for *Dunaliella viridis* NR-mutants stably expressing the transformation vector. Growth media suitable for *Dunaliella viridis* lipid production include, but are not limited to those discussed by Sun et al., Moulton and Burford, and Gordillo et al. Evaluation of fatty acid profiles of *Dunaliella viridis* lipids can be assessed through standard lipid extraction and analytical methods described herein.

Example 19

Engineering *Dunaliella salina*

Expression of recombinant genes in accordance with the present invention in *Dunaliella salina* can be accomplished by modifying the methods and vectors taught by Geng et al. as discussed herein. Briefly, Geng et al., *Journal of Applied Phycology*, Vol. 15 (2003), pp. 451-456, reported the stable transformation of *Dunaliella salina* with plasmid DNA. Using the transformation method of electroporation, Geng introduced the pUΩHBsAg-CAT plasmid into *Dunaliella salina*. pUΩHBsAg-CAT comprises a hepatitis B surface antigen (HBsAG) expression cassette comprising sequence encoding the hepatitis B surface antigen operably linked to a *Zea mays* ubi1 promoter upstream of the HBsAG protein-coding region and operably linked to the 3'UTR/terminator of the *Agrobacterium tumefaciens* nopaline synthase gene (nos) downstream of the HBsAG protein-coding region. pUΩHBsAg-CAT further comprised a chloramphenicol resistance cassette, comprising sequence encoding the chloramphenicol acetyltransferase (CAT) gene product, conferring resistance to the antibiotic chloramphenicol, operably linked to the simian virus 40 promoter and enhancer. Prior to transformation with pUΩHBsAg-CAT, *Dunaliella salina* was unable to propagate on medium comprising 60 mg/L chloramphenicol. Upon transformation with the pUΩHBsAg-CAT plasmid, transformants of *Dunaliella salina* were obtained that were propagated in selective culture medium comprising 60 mg/L chloramphenicol. The expression of the CAT gene product in *Dunaliella salina* enabled propagation in the presence of 60 mg/L chloramphenicol, thereby establishing the utility of the chloramphenicol resistance cassette as selectable marker for use in *Dunaliella salina*. Detectable activity of the HBsAg gene product indicated that ubi1 promoter and nos 3'UTR/terminator are suitable for enabling gene expression in *Dunaliella salina*. Evaluation of the genomic DNA of the stable transformants was performed by Southern analysis. Geng reported that selection and maintenance of the transformed *Dunaliella salina* was performed on agar plates comprising Johnson's medium (J1, described by Borowitzka and Borowitzka (eds), Micro-algal Biotechnology. Cambridge University Press, Cambridge, pp. 460-461) with 60 mg/L chloramphenicol. Liquid propagation of *Dunaliella salina* was performed by Geng in J1 medium with 60 mg/L chloramphenicol. Propagation of *Dunaliella salina* in media other than J1 medium has been discussed (see Feng et al., *Mol. Bio. Reports*, Vol. 36 (2009), pp. 1433-1439 and Borowitzka et al., *Hydrobiologia*, Vols. 116-117:1 (1984), pp. 115-121). Additional plasmids, promoters, 3'UTR/terminators, and selectable markers suitable for enabling heterologous gene expression in *Dunaliella salina* have been reported by Feng et al. Geng reported that the plasmid pUΩHBsAg-CAT, the ubi1 promoter, and the *Agrobacterium tumefaciens* nopaline synthase gene 3'UTR/terminator are suitable to enable exogenous gene expression in *Dunaliella salina*. In addition, Geng reporteds that the CAT resistance cassette encoded on pUΩ-HBsAg-CAT was suitable for use as a selectable marker in *Dunaliella salina.*

In an embodiment of the present invention, vector pUΩH-BsAg-CAT, comprising the nucleotide sequence encoding the CAT gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected Table 20, each protein-coding sequence codon-optimized for expression in *Dunaliella salina* to reflect the codon bias inherent in nuclear genes of *Dunaliella salina* in accordance with Tables 19A-D. For each lipid biosynthesis pathway protein of Table 20, the codon-optimized gene sequence can individually be operably linked to the ubi1 promoter upstream of the protein-coding sequence and operably linked to the *Agrobacterium tumefaciens* nopaline synthase gene 3'UTR/terminator at the 3' region, or downstream, of the protein-coding sequence. The transformation construct may additionally comprise homology regions to the *Dunaliella salina* genome for targeted genomic integration of the transformation vector. Homology regions may be selected to disrupt one or more genomic sites of endogenous lipid biosynthesis pathway genes. Stable transformation of *Dunaliella salina* with the transformation vector is achieved through well-known transformation techniques including electroporation or other known methods. Activity of the CAT gene product can be used as a selectable marker to select for *Dunaliella salina* transformed with the transformation vector in, but not limited to, J1 medium comprising chloramphenicol. Growth medium suitable for *Dunaliella salina* lipid production include, but are not limited to J1 medium and those culture media described by Feng et al. and Borowitzka et al. Evaluation of fatty acid profiles of *Dunaliella salina* lipids can be assessed through standard lipid extraction and analytical methods described herein.

Example 20

Engineering *Gonium pectoral*

Expression of recombinant genes in accordance with the present invention in *Gonium pectoral* can be accomplished by modifying the methods and vectors taught by Lerche and Hallman et al. as discussed herein. Briefly, Lerche and Hallman et al., *BMC Biotechnology*, Volume 9:64, 2009, reported the stable nuclear transformation of *Gonium pectorale* with plasmid DNA. Using the transformation method of microprojectile bombardment, Lerche introduced the plasmid pPmr3 into *Gonium pectorale*. Plasmid pPmr3 comprised a paromomycin resistance cassette, comprising a sequence encoding the aminoglycoside 3'-phosphotransferase (aphVIII) gene product (GenBank Accession No. AAB03856) of *Streptomyces rimosus* for resistance to the antibiotic paromomycin, operably linked to the *Volvox carteri* hsp70A-rbcS3 hybrid promoter upstream of the aphVIII protein-coding region and operably linked to the 3' UTR/terminator of the *Volvox carteri* rbcS3 gene downstream of the aphVIII protein-coding region. Prior to transformation with pPmr3, *Gonium pectorale* was unable to propagate on medium comprising 0.06 ug/ml paromomycin. Upon transformation with pPmr3, transformants of *Gonium pectorale* were obtained that were propagated in selective culture medium comprising 0.75 and greater ug/ml paromomycin. The expression of the aphVIII gene product in *Gonium pectorale* enabled propagation in the presence of 0.75 and greater ug/ml paromomycin, thereby establishing the utility of the paromomycin antibiotic resistance cassette as selectable marker for use in *Gonium pectorale*. Evaluation of the genomic DNA of the stable transformants was performed by Southern analysis. Lerche and Hallman reported that selection and maintenance of the transformed *Gonium pectorale* was performed in liquid Jaworski's medium (20 mg/L $Ca(NO_3)_2.4H_2O$, 12.4 mg/L $KH_2PO_4$, 50 mg/L $MgSO_4.7H_2O$, 15.9 mg/L $NaHCO_3$, 2.25 mg/L EDTA-FeNa, 2.25 mg/L EDTA $Na_2$, 2.48 g/L $H_3BO_3$, 1.39 g/L $MnCl_2.4H_2O$, 1 mg/L $(NH_4)_6MO_7O_24.4H_2O$, 0.04 mg/L vitamin B12, 0.04 mg/L Thiamine-HCl, 0.04 mg/L biotin, 80 mg/L $NaNO_3$, 36 mg/L $Na_4HPO_4.12H_2O$) with 1.0 ug/ml paromomycin. Additional plasmids, promoters, 3'UTR/terminators, and selectable markers suitable for enabling heterologous gene expression in *Gonium pectorale* are further discussed by Lerche and Hallman. Lerche and Hallman reported that the plasmid pPmr3, *Volvox carteri* hsp70A-rbcS3 hybrid promoter, and the 3' UTR/terminator of the *Volvox carteri* rbcS3 gene are suitable to enable exogenous gene expression in *Gonium pectorale*. In addition, Lerche and Hallman reported that the paromomycin resistance cassette encoded pPmr3 was suitable for use as a selectable marker in *Gonium pectorale.*

In an embodiment of the present invention, vector pPmr3, comprising the nucleotide sequence encoding the aphVIII gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected Table 20, each protein-coding sequence codon-optimized for expression in *Gonium pectorale* to reflect the codon bias inherent in nuclear genes of *Gonium pectorale* in accordance with Tables 19A-D. For each lipid biosynthesis pathway protein of Table 20, the codon-optimized gene sequence can individually be operably linked to the *Volvox carteri* hsp70A-rbcS3 hybrid promoter upstream of the protein-coding sequence and operably linked to the *Volvox carteri* rbcS3 gene 3'UTR/terminator at the 3' region, or downstream, of the protein-coding sequence. The transformation construct may additionally comprise homology regions to the *Gonium pectorale* genome for targeted genomic integration of the transformation vector. Homology regions may be selected to disrupt one or more genomic sites of endogenous lipid biosynthesis pathway genes. Stable transformation of *Gonium pectorale* with the transformation vector can be achieved through well-known transformation techniques including microprojectile bombardment or other known methods. Activity of the aphVIII gene product can be used as a selectable marker to select for *Gonium pectorale* transformed with the transformation vector in, but not limited to, Jaworski's medium comprising paromomycin. Growth media suitable for *Gonium pectorale* lipid production include Jawaorski's medium and media reported by Stein, American Journal of Botany, Vol. 45:9 (1958), pp. 664-672. Evaluation of fatty acid profiles of *Gonium pectorale* lipids can be assessed through standard lipid extraction and analytical methods described herein.

Example 21

Engineering *Phaeodactylum tricornutum*

Expression of recombinant genes in accordance with the present invention in *Phaeodactylum tricornutum* can be accomplished by modifying the methods and vectors taught by Apt et al. as discussed herein. Briefly, Apt et al., *Molecular*

*and General Genetics*, Vol. 252 (1996), pp. 572-579, reported the stable nuclear transformation of *Phaeodactylum tricornutum* with vector DNA. Using the transformation technique of microprojectile bombardment, Apt introduced the plasmid pfcpA into *Phaeodactylum tricornutum*. Plasmid pfcpA comprised a bleomycin resistance cassette, comprising sequence encoding the *Streptoalloteichus hindustanus* Bleomycin binding protein (ble), for resistance to the antibiotics phleomycin and zeocin, operably linked to the promoter of the *Phaeodactylum tricornutum* fucoxanthin chlorophyll a binding protein gene (fcpA) upstream of the ble protein-coding region and operably linked to the 3' UTR/terminator of the *Phaeodactylum tricornutum* fcpA gene at the 3' region, or downstream of the ble protein-coding region. Prior to transformation with pfcpA, *Phaeodactylum tricornutum* was unable to propagate on medium comprising 50 ug/ml zeocin. Upon transformation with pfcpA, transformants of *Phaeodactylum tricornutum* were obtained that were propagated in selective culture medium comprising 50 ug/ml zeocin. The expression of the ble gene product in *Phaeodactylum tricornutum* enabled propagation in the presence of 50 ug/ml zeocin, thereby establishing the utility of the bleomycin antibiotic resistance cassette as selectable marker for use in *Phaeodactylum tricornutum*. Evaluation of the genomic DNA of the stable transformants was performed by Southern analysis. Apt reported that selection and maintenance of the transformed *Phaeodactylum tricornutum* was performed on agar plates comprising LDM medium (as reported by Starr and Zeikus, *Journal of Phycology*, Vol. 29, Supplement, (1993)) with 50 mg/L zeocin. Apt reported liquid propagation of *Phaeodactylum tricornutum* transformants in LDM medium with 50 mg/L zeocin. Propagation of *Phaeodactylum tricornutum* in medium other than LDM medium has been discussed (by Zaslayskaia et al., *Science*, Vol. 292 (2001), pp. 2073-2075, and by Radokovits et al., *Metabolic Engineering*, Vol. 13 (2011), pp. 89-95). Additional plasmids, promoters, 3'UTR/terminators, and selectable markers suitable for enabling heterologous gene expression in *Phaeodactylum tricornutum* have been reported in the same report by Apt et al., by Zaslayskaia et al., and by Radokovits et al.). Apt reported that the plasmid pfcpA, and the *Phaeodactylum tricornutum* fcpA promoter and 3' UTR/terminator are suitable to enable exogenous gene expression in *Phaeodactylum tricornutum*. In addition, Apt reported that the bleomycin resistance cassette encoded on pfcpA was suitable for use as a selectable marker in *Phaeodactylum tricornutum*.

In an embodiment of the present invention, vector pfcpA, comprising the nucleotide sequence encoding the ble gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected Table 20, each protein-coding sequence codon-optimized for expression in *Phaeodactylum tricornutum* to reflect the codon bias inherent in nuclear genes of *Phaeodactylum tricornutum* in accordance with Tables 19A-D. For each lipid biosynthesis pathway protein of Table 20, the codon-optimized gene sequence can individually be operably linked to the *Phaeodactylum tricornutum* fcpA gene promoter upstream of the protein-coding sequence and operably linked to the *Phaeodactylum tricornutum* fcpA gene 3'UTR/terminator at the 3' region, or downstream, of the protein-coding sequence. The transformation construct may additionally comprise homology regions to the *Phaeodactylum tricornutum* genome for targeted genomic integration of the transformation vector. Homology regions may be selected to disrupt one or more genomic sites of endogenous lipid biosynthesis pathway genes. One skilled in the art can identify such homology regions within the sequence of the *Phaeodactylum tricornutum* genome (referenced in the publication by Bowler et al., *Nature*, Vol. 456 (2008), pp. 239-244). Stable transformation of *Phaeodactylum tricornutum* with the transformation vector is achieved through well-known transformation techniques including microprojectile bombardment or other known methods. Activity of the ble gene product can be used as a marker to select for *Phaeodactylum tricornutum* transformed with the transformation vector in, but not limited to, LDM medium comprising paromomycin. Growth medium suitable for *Phaeodactylum tricornutum* lipid production include, but are not limited to f/2 medium as reported by Radokovits et al. Evaluation of fatty acid profiles of *Phaeodactylum tricornutum* lipids can be assessed through standard lipid extraction and analytical methods described herein.

Example 22

Engineering *Chaetoceros* sp.

Expression of recombinant genes in accordance with the present invention in *Chaetoceros* sp. can be accomplished by modifying the methods and vectors taught by Yamaguchi et al. as discussed herein. Briefly, Yamaguchi et al., Phycological Research, Vol. 59:2 (2011), pp. 113-119, reported the stable nuclear transformation of *Chaetoceros* sp. with plasmid DNA. Using the transformation method of microprojectile bombardment, Yamaguchi introduced the plasmid pTpfcp/nat into *Chaetoceros* sp. pTpfcp/nat comprised a nourseothricin resistance cassette, comprising sequence encoding the nourseothricin acetyltransferase (nat) gene product (GenBank Accession No. AAC60439) operably linked to the *Thalassiosira pseudonana* fucoxanthin chlorophyll a/c binding protein gene (fcp) promoter upstream of the nat protein-coding region and operably linked to the *Thalassiosira pseudonana* fcp gene 3' UTR/terminator at the 3' region (downstream of the nat protein coding-sequence). The nat gene product confers resistance to the antibiotic nourseothricin. Prior to transformation with pTpfcp/nat, *Chaetoceros* sp. was unable to propagate on medium comprising 500 ug/ml nourseothricin. Upon transformation with pTpfcp/nat, transformants of *Chaetoceros* sp. were obtained that were propagated in selective culture medium comprising 500 ug/ml nourseothricin. The expression of the nat gene product in *Chaetoceros* sp. enabled propagation in the presence of 500 ug/ml nourseothricin, thereby establishing the utility of the nourseothricin antibiotic resistance cassette as selectable marker for use in *Chaetoceros* sp. Evaluation of the genomic DNA of the stable transformants was performed by Southern analysis. Yamaguchi reported that selection and maintenance of the transformed *Chaetoceros* sp. was performed on agar plates comprising f/2 medium (as reported by Guilard, R. R., Culture of Phytoplankton for feeding marine invertebrates, In Culture of Marine Invertebrate Animals, Smith and Chanley (eds) 1975, Plenum Press, New York, pp. 26-60) with 500 ug/ml nourseothricin. Liquid propagation of *Chaetoceros* sp. transformants, as performed by Yamaguchi, was carried out in f/2 medium with 500 mg/L nourseothricin. Propagation of *Chaetoceros* sp. in additional culture medium has been reported (for example in Napolitano et al., *Journal of the World Aquaculture Society*, Vol. 21:2 (1990), pp. 122-130, and by Volkman et al., *Journal of Experimental Marine Biology and Ecology*, Vol. 128:3 (1989), pp. 219-240). Additional plasmids, promoters, 3'UTR/terminators, and selectable markers suitable for enabling heterologous gene expression in *Chaetoceros* sp. have been reported in the same report by Yamaguchi et al. Yamaguchi reported that the plasmid pTpfcp/nat, and the *Thalassiosira pseudonana* fcp promoter and 3' UTR/terminator are suitable to enable exogenous gene expression in *Chaetoceros* sp. In addition, Yamaguchi reported that the nourseothricin resistance cassette encoded on pTpfcp/nat was suitable for use as a selectable marker in *Chaetoceros* sp.

In an embodiment of the present invention, vector pTpfcp/nat, comprising the nucleotide sequence encoding the nat gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in the closely-related *Chaetoceros compressum* to reflect the codon bias inherent in nuclear genes of *Chaetoceros compressum* in accordance with Tables 19A-D. For each lipid biosynthesis pathway protein of Table 20, the codon-optimized gene sequence can individually be operably linked to the *Thalassiosira pseudonana* fcp gene promoter upstream of the protein-coding sequence and operably linked to the *Thalassiosira pseudonana* fcp gene 3'UTR/terminator at the 3' region, or downstream, of the protein-coding sequence. The transformation construct may additionally comprise homology regions to the *Chaetoceros* sp. genome for targeted genomic integration of the transformation vector. Homology regions may be selected to disrupt one or more genomic sites of endogenous lipid biosynthesis pathway genes. Stable transformation of *Chaetoceros* sp. with the transformation vector is achieved through well-known transformation including microprojectile bombardment or other known methods. Activity of the nat gene product can be used as a selectable marker to select for *Chaetoceros* sp. transformed with the transformation vector in, but not limited to, f/2 agar medium comprising nourseothricin. Growth medium suitable for *Chaetoceros* sp. lipid production include, but are not limited to, f/2 medium, and those culture media discussed by Napolitano et al. and Volkman et al. Evaluation of fatty acid profiles of *Chaetoceros* sp lipids can be assessed through standard lipid extraction and analytical methods described herein.

Example 23

Engineering *Cylindrotheca fusiformis*

Expression of recombinant genes in accordance with the present invention in *Cylindrotheca fusiformis* can be accomplished by modifying the methods and vectors taught by Poulsen and Kroger et al. as discussed herein. Briefly, Poulsen and Kroger et al., *FEBS Journal*, Vol. 272 (2005), pp. 3413-3423, reported the transformation of *Cylindrotheca fusiformis* with plasmid DNA. Using the transformation method of microprojectile bombardment, Poulsen and Kroger introduced the pCF-ble plasmid into *Cylindrotheca fusiformis*. Plasmid pCF-ble comprised a bleomycin resistance cassette, comprising sequence encoding the *Streptoalloteichus hindustanus* Bleomycin binding protein (ble), for resistance to the antibiotics zeocin and phleomycin, operably linked to the *Cylindrotheca fusiformis* fucozanthin chlorophyll a/c binding protein gene (fcpA, GenBank Accesssion No. AY125580) promoter upstream of the ble protein-coding region and operably linked to the *Cylindrotheca fusiformis* fcpA gene 3'UTR/terminator at the 3' region (down-stream of the ble protein-coding region). Prior to transformation with pCF-ble, *Cylindrotheca fusiformis* was unable to propagate on medium comprising 1 mg/ml zeocin. Upon transformation with pCF-ble, transformants of *Cylindrotheca fusiformis* were obtained that were propagated in selective culture medium comprising 1 mg/ml zeocin. The expression of the ble gene product in *Cylindrotheca fusiformis* enabled propagation in the presence of 1 mg/ml zeocin, thereby establishing the utility of the bleomycin antibiotic resistance cassette as selectable marker for use in *Cylindrotheca fusiformis*. Poulsen and Kroger reported that selection and maintenance of the transformed *Cylindrotheca fusiformis* was performed on agar plates comprising artificial seawater medium with 1 mg/ml zeocin. Poulsen and Kroger reported liquid propagation of *Cylindrotheca fusiformis* transformants in artificial seawater medium with 1 mg/ml zeocin. Propagation of *Cylindrotheca fusiformis* in additional culture medium has been discussed (for example in Liang et al., *Journal of Applied Phycology*, Vol. 17:1 (2005), pp. 61-65, and by Orcutt and Patterson, *Lipids*, Vol. 9:12 (1974), pp. 1000-1003). Additional plasmids, promoters, and 3'UTR/terminators for enabling heterologous gene expression in *Chaetoceros* sp. have been reported in the same report by Poulsen and Kroger. Poulsen and Kroger reported that the plasmid pCF-ble and the *Cylindrotheca fusiformis* fcp promoter and 3' UTR/terminator are suitable to enable exogenous gene expression in *Cylindrotheca fusiformis*. In addition, Poulsen and Kroger reported that the bleomycin resistance cassette encoded on pCF-ble was suitable for use as a selectable marker in *Cylindrotheca fusiformis*.

In an embodiment of the present invention, vector pCF-ble, comprising the nucleotide sequence encoding the ble gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected Table 20, each protein-coding sequence codon-optimized for expression in *Cylindrotheca fusiformis* to reflect the codon bias inherent in nuclear genes of *Cylindrotheca fusiformis* in accordance with Tables 19A-D. For each lipid biosynthesis pathway protein of Table 20, the codon-optimized gene sequence can individually be operably linked to the *Cylindrotheca fusiformis* fcp gene promoter upstream of the protein-coding sequence and operably linked to the *Cylindrotheca fusiformis* fcp gene 3'UTR/terminator at the 3' region, or downstream, of the protein-coding sequence. The transformation construct may additionally comprise homology regions to the *Cylindrotheca fusiformis* genome for targeted genomic integration of the transformation vector. Homology regions may be selected to disrupt one or more genomic sites of endogenous lipid biosynthesis pathway genes. Stable transformation of *Cylindrotheca fusiformis* with the transformation vector is achieved through well-known transformation techniques including microprojectile bombardment or other known methods. Activity of the ble gene product can be used as a selectable marker to select for *Cylindrotheca fusiformis* transformed with the transformation vector in, but not limited to, artificial seawater agar medium comprising zeocin. Growth media suitable for *Cylindrotheca fusiformis* lipid production include, but are not limited to, artificial seawater and those media reported by Liang et al. and Orcutt and Patterson. Evaluation of fatty acid profiles of *Cylindrotheca fusiformis* lipids can be assessed through standard lipid extraction and analytical methods described herein.

Example 24

Engineering *Amphidinium* sp.

Expression of recombinant genes in accordance with the present invention in *Amphidinium* sp. can be accomplished by modifying the methods and vectors taught by ten Lohuis and Miller et al. as discussed herein. Briefly, ten Lohuis and Miller et al., *The Plant Journal, Vol.* 13:3 (1998), pp. 427-435, reported the stable transformation of *Amphidinium* sp. with plasmid DNA. Using the transformation technique of agitation in the presence of silicon carbide whiskers, ten Lohuis introduced the plasmid pMT NPT/GUS into *Amphidinium* sp. pMT NPT/GUS comprised a neomycin resistance cassette, comprising sequence encoding the neomycin phosphotransferase II (nptII) gene product (GenBank Accession No. AAL92039) operably linked to the *Agrobacterium tumefaciens* nopaline synthase (nos) gene promoter upstream, or 5' of the nptII protein-coding region and operably linked to the 3' UTR/terminator of the nos gene at the 3' region (downstream of the nptII protein-coding region). The nptII gene product confers resistance to the antibiotic G418. The pMT NPT/GUS plasmid further comprised sequence encoding a beta-glucuronidase (GUS) reporter gene product operably-linked to a CaMV 35S promoter and further operably linked to the CaMV 35S 3' UTR/terminator. Prior to transformation with pMT NPT/GUS, *Amphidinium* sp. was unable to be propagated on medium comprising 3 mg/ml G418. Upon transformation with pMT NPT/GUS, transformants of *Amphidinium* sp. were obtained that were propagated in selective culture medium comprising 3 mg/ml G418. The expression of the nptII gene product in *Amphidinium* sp. enabled propagation in the presence of 3 mg/ml G418, thereby establishing the utility of the neomycin antibiotic resistance cassette as selectable marker for use in *Amphidinium* sp. Detectable activity of the GUS reporter gene indicated that CaMV 35S promoter and 3'UTR are suitable for enabling gene expression in *Amphidinium* sp. Evaluation of the genomic DNA of the stable transformants was performed by Southern analysis. ten Lohuis and Miller reported liquid propagation of *Amphidinium* sp transformants in medium comprising seawater supplemented with F/2 enrichment solution (provided by the supplier Sigma) and 3 mg/ml G418 as well as selection and maintenance of *Amphidinium* sp. transformants on agar medium comprising seawater supplemented with F/2 enrichment solution and 3 mg/ml G418. Propagation of *Amphidinium* sp. in additional culture medium has been reported (for example in Mansour et al., *Journal of Applied Phycology*, Vol. 17:4 (2005) pp. 287-v300). An additional plasmid, comprising additional promoters, 3'UTR/terminators, and a selectable marker for enabling heterologous gene expression in *Amphidinium* sp. have been reported in the same report by ten Lohuis and Miller. ten Lohuis and Miller reported that the plasmid pMT NPT/GUS and the promoter and 3' UTR/terminator of the nos and CaMV 35S genes are suitable to enable exogenous gene expression in *Amphidinium* sp. In addition, ten Lohuis and Miller reported that the neomycin resistance cassette encoded on pMT NPT/GUS was suitable for use as a selectable marker in *Amphidinium* sp.

In an embodiment of the present invention, vector pMT NPT/GUS, comprising the nucleotide sequence encoding the nptII gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Amphidinium* sp. to reflect the codon bias inherent in nuclear genes of the closely-related species, *Amphidinium carterae* in accordance with Tables 19A-D. For each lipid biosynthesis pathway protein of Table 20, the codon-optimized gene sequence can individually be operably linked to the *Agrobacterium tumefaciens* nopaline synthase (nos) gene promoter upstream of the protein-coding sequence and operably linked to the nos 3'UTR/terminator at the 3' region, or downstream, of the protein-coding sequence. The transformation construct may additionally comprise homology regions to the *Amphidinium* sp. genome for targeted genomic integration of the transformation vector. Homology regions may be selected to disrupt one or more genomic sites of endogenous lipid biosynthesis pathway genes. Stable transformation of *Amphidinium* sp. with the transformation vector is achieved through well-known transformation techniques including silicon fibre-mediated microinjection or other known methods. Activity of the nptII gene product can be used as a selectable marker to select for *Amphidinium* sp. transformed with the transformation vector in, but not limited to, seawater agar medium comprising G418. Growth media suitable for *Amphidinium* sp. lipid production include, but are not limited to, artificial seawater and those media reported by Mansour et al. and ten Lohuis and Miller. Evaluation of fatty acid profiles of *Amphidinium* sp. lipids can be assessed through standard lipid extraction and analytical methods described herein.

Example 25

Engineering *Symbiodinium microadriacticum*

Expression of recombinant genes in accordance with the present invention in *Symbiodinium microadriacticum* can be accomplished by modifying the methods and vectors taught by ten Lohuis and Miller et al. as discussed herein. Briefly, ten Lohuis and Miller et al., *The Plant Journal*, Vol. 13:3 (1998), pp. 427-435, reported the stable transformation of *Symbiodinium microadriacticum* with plasmid DNA. Using the transformation technique of silicon fibre-mediated microinjection, ten Lohuis introduced the plasmid pMT NPT/GUS into *Symbiodinium microadriacticum*. pMT NPT/GUS comprised a neomycin resistance cassette, comprising sequence encoding the neomycin phosphotransferase II (nptII) gene product (GenBank Accession No. AAL92039) operably linked to the *Agrobacterium tumefaciens* nopaline synthase (nos) gene promoter upstream, or 5' of the nptII protein-coding region and operably linked to the 3' UTR/terminator of the nos gene at the 3' region (down-stream of the nptII protein-coding region). The nptII gene product confers resistance to the antibiotic G418. The pMT NPT/GUS plasmid further comprised sequence encoding a beta-glucuronidase (GUS) reporter gene product operably-linked to a CaMV 35S promoter and further operably linked to the CaMV 35S 3' UTR/terminator. Prior to transformation with pMT NPT/GUS, *Symbiodinium microadriacticum* was unable to be propagated on medium comprising 3 mg/ml G418. Upon transformation with pMT NPT/GUS, transformants of *Symbiodinium microadriacticum* were obtained that were propagated in selective culture medium comprising 3 mg/ml G418. The expression of the nptII gene product in *Symbiodinium microadriacticum* enabled propagation in the presence of 3 mg/ml G418, thereby establishing the utility of the neomycin antibiotic resistance cassette as selectable marker for use in *Symbiodinium microadriacticum*. Detectable activity of the GUS reporter gene indicated that CaMV 35S promoter and 3'UTR are suitable for enabling gene expression in *Symbiodinium microadriacticum*. Evaluation of the genomic DNA of the stable transformants was performed by Southern analysis. ten Lohuis and Miller reported liquid propagation of *Symbiodinium microadriacticum* transformants in medium comprising seawater supplemented with F/2 enrichment solution (provided by the supplier Sigma) and 3 mg/ml G418 as well as selection and maintenance of *Symbiodinium microadriacticum* transformants on agar medium comprising seawater supplemented with F/2 enrichment solution and 3 mg/ml G418. Propagation of *Symbiodinium microadriacticum* in additional culture medium has been discussed (for example in Iglesias-Prieto et al., *Proceedings of the National Academy of Sciences*, Vol. 89:21 (1992) pp. 10302-10305). An additional plasmid, comprising additional promoters, 3'UTR/terminators, and a selectable marker for enabling heterologous gene expression in *Symbiodinium microadriacticum* have been discussed in the same report by ten Lohuis and Miller. ten Lohuis and Miller reported that the plasmid pMT NPT/GUS and the promoter and 3' UTR/terminator of the nos and CaMV 35S genes are suitable to enable exogenous gene expression in *Symbiodinium microadriacticum*. In addition, ten Lohuis and Miller reported that the neomycin resistance cassette encoded on pMT NPT/GUS was suitable for use as a selectable marker in *Symbiodinium microadriacticum*.

In an embodiment of the present invention, vector pMT NPT/GUS, comprising the nucleotide sequence encoding the nptII gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected Table 20, each protein-coding sequence codon-optimized for expression in *Symbiodinium microadriacticum* to reflect the codon bias inherent in nuclear genes of *Symbiodinium microadriacticum* in accordance with Tables 19A-D. For each lipid biosynthesis pathway protein of Table 20, the codon-optimized gene sequence can individually be operably linked to the *Agrobacterium tumefaciens* nopaline synthase (nos) gene promoter upstream of the protein-coding sequence and operably linked to the nos 3'UTR/terminator at the 3' region, or downstream, of the protein-coding sequence. The transformation construct may additionally comprise homology regions to the *Symbiodinium microadriacticum* genome for targeted genomic integration of the transformation vector. Homology regions may be selected to disrupt one or more genomic sites of endogenous lipid biosynthesis pathway genes. Stable transformation of *Symbiodinium microadriacticum* with the transformation vector is achieved through well-known transformation techniques including silicon fibre-mediated microinjection or other known methods. Activity of the nptII gene product can be used as a selectable marker to select for *Symbiodinium microadriacticum* transformed with the transformation vector in, but not limited to, seawater agar medium comprising G418. Growth media suitable for *Symbiodinium microadriacticum* lipid production include, but are not limited to, artificial seawater and those media reported by Iglesias-Prieto et al. and ten Lohuis and Miller. Evaluation of fatty acid profiles of *Symbiodinium microadriacticum* lipids can be assessed through standard lipid extraction and analytical methods described herein.

Example 26

Engineering *Nannochloropsis* sp.

Expression of recombinant genes in accordance with the present invention in *Nannochloropsis* sp. W2J3B can be accomplished by modifying the methods and vectors taught by Kilian et al. as discussed herein. Briefly, Kilian et al., *Proceedings of the National Academy of Sciences*, Vol. 108: 52 (2011) pp. 21265-21269, reported the stable nuclear transformation of *Nannochloropsis* with a transformation construct. Using the transformation method of electroporation, Kilian introduced the transformation construct C2 into *Nannochloropsis* sp. W2J3B. The C2 transformation construct comprised a bleomycin resistance cassette, comprising the coding sequence for the *Streptoalloteichus hindustanus* Bleomycin binding protein (ble), for resistance to the antibiotics phleomycin and zeocin, operably linked to and the promoter of the *Nannochloropsis* sp. W2J3B violaxanthin/chlorophyll a-binding protein gene VCP2 upstream of the ble protein-coding region and operably linked to the 3'UTR/terminator of the *Nannochloropsis* sp. W2J3B violaxanthin/chlorophyll a-binding gene VCP1 downstream of the ble protein-coding region. Prior to transformation with C2, *Nannochloropsis* sp. W2J3B was unable to propagate on medium comprising 2 ug/ml zeocin. Upon transformation with C2, transformants of *Nannochloropsis* sp. W2J3B were obtained that were propagated in selective culture medium comprising 2 ug/ml zeocin. The expression of the ble gene product in *Nannochloropsis* sp. W2J3B enabled propagation in the presence of 2 ug/ml zeocin, thereby establishing the utility of the bleomycin antibiotic resistance cassette as selectable marker for use in *Nannochloropsis*. Evaluation of the genomic DNA of the stable transformants was performed by PCR. Kilian reported liquid propagation of *Nannochloropsis* sp. W2J3B transformants in F/2 medium (reported by Guilard and Ryther, *Canadian Journal of Microbiology*, Vol. 8 (1962), pp. 229-239) comprising fivefold levels of trace metals, vitamins, and phosphate solution, and further comprising 2 ug/ml zeocin. Kilian also reported selection and maintenance of *Nannochloropsis* sp. W2J3B transformants on agar F/2 medium comprising artificial seawater 2 mg/ml zeocin. Propagation of *Nannochloropsis* in additional culture medium has been discussed (for example in Chiu et al., *Bioresour Technol., Vol.* 100:2 (2009), pp. 833-838 and Pal et al., *Applied Microbiology and Biotechnology*, Vol. 90:4 (2011), pp. 1429-1441.). Additional transformation constructs, comprising additional promoters and 3'UTR/terminators for enabling heterologous gene expression in *Nannochloropsis* sp. W2J3B and selectable markers for selection of transformants have been described in the same report by Kilian. Kilian reported that the transformation construct C2 and the promoter of the *Nannochloropsis* sp. W2J3B violaxanthin/chlorophyll a-binding protein gene VCP2 and 3' UTR/terminator of the *Nannochloropsis* sp. W2J3B violaxanthin/chlorophyll a-binding protein gene VCP1 are suitable to enable exogenous gene expression in *Nannochloropsis* sp. W2J3B. In addition, Kilian reported that the bleomycin resistance cassette encoded on C2 was suitable for use as a selectable marker in *Nannochloropsis* sp. W2J3B.

In an embodiment of the present invention, transformation construct C2, comprising the nucleotide sequence encoding the ble gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Nannochloropsis* sp. W2J3B to reflect the codon bias inherent in nuclear genes of *Nannochloropsis* sp. in accordance with Tables 19A-D. For each lipid biosynthesis pathway protein of Table 20, the codon-optimized gene sequence can individually be operably linked to the *Nannochloropsis* sp. W2J3B VCP2 gene promoter upstream of the protein-coding sequence and operably linked to the *Nannochloropsis* sp. W2J3B VCP1 gene 3'UTR/terminator at the 3' region, or downstream, of the protein-coding sequence. The transformation construct may additionally comprise homology regions to the *Nannochloropsis* sp. W2J3B genome for targeted genomic integration of the transformation vector. Homology regions may be selected to disrupt one or more genomic sites of endogenous lipid biosynthesis pathway genes. Stable transformation of *Nannochloropsis* sp. W2J3B with the transformation vector is achieved through well-known transformation techniques including electroporation or other known methods. Activity of the ble gene product can be used as a selectable marker to select for *Nannochloropsis* sp. W2J3B transformed with the transformation vector in, but not limited to, F/2 medium comprising zeocin. Growth media suitable for *Nannochloropsis* sp. W2J3B lipid production include, but are not limited to, F/2 medium and those media reported by Chiu et al. and Pal et al. Evaluation of fatty acid profiles of *Nannochloropsis* sp. W2J3B lipids can be assessed through standard lipid extraction and analytical methods described herein.

Example 27

Engineering *Cyclotella cryptica*

Expression of recombinant genes in accordance with the present invention in *Cyclotella cryptica* can be accomplished by modifying the methods and vectors taught by Dunahay et al. as discussed herein. Briefly, Dunahay et al., *Journal of Phycology*, Vol. 31 (1995), pp. 1004-1012, reported the stable transformation of *Cyclotella cryptica* with plasmid DNA. Using the transformation method of microprojectile bombardment, Dunahay introduced the plasmid pACCNPT5.1 into *Cyclotella cryptica*. Plasmid pACCNPT5.1 comprised a neomycin resistance cassette, comprising the coding sequence of the neomycin phosphotransferase II (nptII) gene product operably linked to the promoter of the *Cyclotella cryptica* acetyl-CoA carboxylase (ACCase) gene (GenBank Accession No. L20784) upstream of the nptII coding-region and operably linked to the 3'UTR/terminator of the *Cyclotella cryptica* ACCase gene at the 3' region (downstream of the nptII coding-region). The nptII gene product confers resistance to the antibiotic G418. Prior to transformation with pACCNPT5.1, *Cyclotella cryptica* was unable to propagate on 50% artificial seawater medium comprising 100 ug/ml G418. Upon transformation with pACCNPT5.1, transformants of *Cyclotella cryptica* were obtained that were propagated in selective 50% artificial seawater medium comprising 100 ug/ml G418. The expression of the nptII gene product in *Cyclotella cryptica* enabled propagation in the presence of 100 ug/ml G418, thereby establishing the utility of the neomycin antibiotic resistance cassette as selectable marker for use in *Cyclotella cryptica*. Evaluation of the genomic DNA of the stable transformants was performed by Southern analysis. Dunahay reported liquid propagation of *Cyclotella cryptica* in artificial seawater medium (ASW, as discussed by Brown, L., *Phycologia*, Vol. 21 (1982), pp. 408-410) supplemented with 1.07 mM sodium silicate and with 100 ug/ml G418. Dunahay also reported selection and maintenance of *Cyclotella cryptica* transformants on agar plates comprising ASW medium with 100 ug/ml G418. Propagation of *Cyclotella cryptica* in additional culture medium has been discussed (for example in Sriharan et al., *Applied Biochemistry and Biotechnology*, Vol. 28-29:1 (1991), pp. 317-326 and Pahl et al., *Journal of Bioscience and Bioengineering*, Vol. 109:3 (2010), pp. 235-239). Dunahay reported that the plasmid pACCNPT5.1 and the promoter of the *Cyclotella cryptica* acetyl-CoA carboxylase (ACCase) gene are suitable to enable exogenous gene expression in *Cyclotella cryptica*. In addition, Dunahay reported that the neomycin resistance cassette encoded on pACCNPT5.1 was suitable for use as a selectable marker in *Cyclotella cryptica*.

In an embodiment of the present invention, vector pACCNPT5.1, comprising the nucleotide sequence encoding the nptII gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Cyclotella cryptica* to reflect the codon bias inherent in nuclear genes of *Cyclotella cryptica* in accordance with Tables 19A-D. For each lipid biosynthesis pathway protein of Table 20, the codon-optimized gene sequence can individually be operably linked to the *Cyclotella cryptica* ACCase promoter upstream of the protein-coding sequence and operably linked to the *Cyclotella cryptica* ACCase 3'UTR/terminator at the 3' region, or downstream, of the protein-coding sequence. The transformation construct may additionally comprise homology regions to the *Cyclotella cryptica* genome for targeted genomic integration of the transformation vector. Homology regions may be selected to disrupt one or more genomic sites of endogenous lipid biosynthesis pathway genes. Stable transformation of *Cyclotella cryptica* with the transformation vector is achieved through well-known transformation techniques including microprojectile bombardment or other known methods. Activity of the nptII gene product can be used as a marker to select for *Cyclotella cryptica* transformed with the transformation vector in, but not limited to, agar ASW medium comprising G418. Growth media suitable for *Cyclotella cryptica* lipid production include, but are not limited to, ASW medium and those media reported by Sriharan et al., 1991 and Pahl et al. Evaluation of fatty acid profiles of *Cyclotella cryptica* lipids can be assessed through standard lipid extraction and analytical methods described herein.

Example 28

Engineering *Navicula saprophila*

Expression of recombinant genes in accordance with the present invention in *Navicula saprophila* can be accomplished by modifying the methods and vectors taught by Dunahay et al. as discussed herein. Briefly, Dunahay et al., *Journal of Phycology*, Vol. 31 (1995), pp. 1004-1012, reported the stable transformation of *Navicula saprophila* with plasmid DNA. Using the transformation method of microprojectile bombardment, Dunahay introduced the plasmid pACCNPT5.1 into *Navicula saprophila*. Plasmid pACCNPT5.1 comprised a neomycin resistance cassette, comprising the coding sequence of the neomycin phosphotransferase II (nptII) gene product operably linked to the promoter of the *Cyclotella cryptica* acetyl-CoA carboxylase (ACCase) gene (GenBank Accession No. L20784) upstream of the nptII coding-region and operably linked to the 3'UTR/terminator of the *Cyclotella cryptica* ACCase gene at the 3' region (downstream of the nptII coding-region). The nptII gene product confers resistance to the antibiotic G418. Prior to transformation with pACCNPT5.1, *Navicula saprophila* was unable to propagate on artificial seawater medium comprising 100 ug/ml G418. Upon transformation with pACCNPT5.1, transformants of *Navicula saprophila* were obtained that were propagated in selective artificial seawater medium comprising 100 ug/ml G418. The expression of the nptII gene product in *Navicula saprophila* enabled propagation in the presence of G418, thereby establishing the utility of the neomycin antibiotic resistance cassette as selectable marker for use in *Navicula saprophila*. Evaluation of the genomic DNA of the stable transformants was performed by Southern analysis. Dunahay reported liquid propagation of *Navicula saprophila* in artificial seawater medium (ASW, as discussed by Brown, L., *Phycologia*, Vol. 21 (1982), pp. 408-410) supplemented with 1.07 mM sodium silicate and with 100 ug/ml G418. Dunahay also reported selection and maintenance of *Navicula saprophila* transformants on agar plates comprising ASW medium with 100 ug/ml G418. Propagation of *Navicula saprophila* in additional culture medium has been discussed (for example in Tadros and Johansen, *Journal of Phycology*, Vol. 24:4 (1988), pp. 445-452 and Sriharan et al., *Applied Biochemistry and Biotechnology*, Vol. 20-21:1 (1989), pp. 281-291). Dunahay reported that the plasmid pACCNPT5.1 and the promoter of the *Cyclotella cryptica* acetyl-CoA carboxylase (ACCase) gene are suitable to enable exogenous gene expression in *Navicula saprophila*. In addition, Dunahay reported that the neomycin resistance cassette encoded on pACCNPT5.1 was suitable for use as a selectable marker in *Navicula saprophila*.

In an embodiment of the present invention, vector pACCNPT5.1, comprising the nucleotide sequence encoding the nptII gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Navicula saprophila* to reflect the codon bias inherent in nuclear genes of the closely-related *Navicula pelliculosa* in accordance with Tables 19A-D. For each lipid biosynthesis pathway protein of Table 20, the codon-optimized gene sequence can individually be operably linked to the *Cyclotella cryptica* ACCase gene promoter upstream of the protein-coding sequence and operably linked to the *Cyclotella cryptica* ACCase gene 3'UTR/terminator at the 3' region, or downstream, of the protein-coding sequence. The transformation construct may additionally comprise homology regions to the *Navicula saprophila* genome for targeted genomic integration of the transformation vector. Homology regions may be selected to disrupt one or more genomic sites of endogenous lipid biosynthesis pathway genes. Stable transformation of *Navicula saprophila* with the transformation vector is achieved through well-known transformation techniques including microprojectile bombardment or other known methods. Activity of the nptII gene product can be used as a selectable marker to select for *Navicula saprophila* transformed with the transformation vector in, but not limited to, agar ASW medium comprising G418. Growth media suitable for *Navicula saprophila* lipid production include, but are not limited to, ASW medium and those media reported by Sriharan et al. 1989 and Tadros and Johansen. Evaluation of fatty acid profiles of *Navicula saprophila* lipids can be assessed through standard lipid extraction and analytical methods described herein.

Example 29

Engineering *Thalassiosira pseudonana*

Expression of recombinant genes in accordance with the present invention in *Thalassiosira pseudonana* can be accomplished by modifying the methods and vectors taught by Poulsen et al. as discussed herein. Briefly, Poulsen et al., *Journal of Phycology*, Vol. 42 (2006), pp. 1059-1065, reported the stable transformation of *Thalassiosira pseudonana* with plasmid DNA. Using the transformation method of microprojectile bombardment, Poulsen introduced the plasmid pTpfcp/nat in to *Thalassiosira pseudonana*. pTpfcp/nat comprised a nourseothricin resistance cassette, comprising sequence encoding the nourseothricin acetyltransferase (nat) gene product (GenBank Accession No. AAC60439) operably linked to the *Thalassiosira pseudonana* fucoxanthin chlorophyll a/c binding protein gene (fcp) promoter upstream of the nat protein-coding region and operably linked to the *Thalassiosira pseudonana fcp gene* 3' UTR/terminator at the 3' region (downstream of the nat protein coding-sequence). The nat gene product confers resistance to the antibiotic nourseothricin. Prior to transformation with pTpfcp/nat, *Thalassiosira pseudonana* was unable to propagate on medium comprising 10 ug/ml nourseothricin. Upon transformation with pTpfcp/nat, transformants of *Thalassiosira pseudonana* were obtained that were propagated in selective culture medium comprising 100 ug/ml nourseothricin. The expression of the nat gene product in *Thalassiosira pseudonana* enabled propagation in the presence of 100 ug/ml nourseothricin, thereby establishing the utility of the nourseothricin antibiotic resistance cassette as selectable marker for use in *Thalassiosira pseudonana*. Evaluation of the genomic DNA of the stable transformants was performed by Southern analysis. Poulsen reported that selection and maintenance of the transformed *Thalassiosira pseudonana* was performed in liquid culture comprising modified ESAW medium (as discussed by Harrison et al., *Journal of Phycology*, Vol. 16 (1980), pp. 28-35) with 100 ug/ml nourseothricin. Propagation of *Thalassiosira pseudonana* in additional culture medium has been discussed (for example in Volkman et al., *Journal of Experimental Marine Biology and Ecology*, Vol. 128:3 (1989), pp. 219-240). An additional plasmid, comprising additional selectable markers suitable for use in *Thalassiosira pseudonana* has been discussed in the same report by Poulsen. Poulsen reported that the plasmid pTpfcp/nat, and the *Thalassiosira pseudonana* fcp promoter and 3' UTR/terminator are suitable to enable exogenous gene expression in *Thalassiosira pseudonana*. In addition, Poulsen reported that the nourseothricin resistance cassette encoded on pTpfcp/nat was suitable for use as a selectable marker in *Thalassiosira pseudonana*.

In an embodiment of the present invention, vector pTpfcp/nat, comprising the nucleotide sequence encoding the nat gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Thalassiosira pseudonana* to reflect the codon bias inherent in nuclear genes of *Thalassiosira pseudonana* in accordance with Tables 19A-D. For each lipid biosynthesis pathway protein of Table 20, the codon-optimized gene sequence can individually be operably linked to the *Thalassiosira pseudonana* fcp gene promoter upstream of the protein-coding sequence and operably linked to the *Thalassiosira pseudonana* fcp gene 3'UTR/terminator at the 3' region, or downstream, of the protein-coding sequence. The transformation construct may additionally comprise homology regions to the *Thalassiosira pseudonana* genome for targeted genomic integration of the transformation vector.

Homology regions may be selected to disrupt one or more genomic sites of endogenous lipid biosynthesis pathway genes. One skilled in the art can identify such homology regions within the sequence of the *Thalassiosira pseudonana* genome (referenced in the publication by Armbrust et al., *Science*, Vol. 306: 5693 (2004): pp. 79-86). Stable transformation of *Thalassiosira pseudonana* with the transformation vector is achieved through well-known transformation techniques including microprojectile bombardment or other known methods. Activity of the nat gene product can be used as a marker to select for *Thalassiosira pseudonana* transformed with the transformation vector in but not limited to, ESAW agar medium comprising nourseothricin. Growth media suitable for *Thalassiosira pseudonana* lipid production include, but are not limited to, ESAW medium, and those culture media discussed by Volkman et al. and Harrison et al. Evaluation of fatty acid profiles of *Thalassiosira pseudonana* lipids can be assessed through standard lipid extraction and analytical methods described herein.

Example 30

Engineering *Chlamydomonas reinhardtii*

Expression of recombinant genes in accordance with the present invention in *Chlamydomonas reinhardtii* can be accomplished by modifying the methods and vectors taught by Cerutti et al. as discussed herein. Briefly, Cerutti et al., *Genetics*, Vol. 145:1 (1997), pp. 97-110, reported the stable nuclear transformation of *Chlamydomonas reinhardtii* with a transformation vector. Using the transformation method of microprojectile bombardment, Cerutti introduced transformation construct P[1030] into *Chlamydomonas reinhardtii*. Construct P[1030] comprised a spectinomycin resistance cassette, comprising sequence encoding the aminoglucoside 3"-adenyltransferase (aadA) gene product operably linked to the *Chlamydomonas reinhardtii* ribulose-1,5-bisphosphate carboxylase/oxygenase small subunit gene (RbcS2, GenBank Accession No. X04472) promoter upstream of the aadA protein-coding region and operably linked to the *Chlamydomonas reinhardtii* RbcS2 gene 3' UTR/terminator at the 3' region (downstream of the aadA protein coding-sequence). The aadA gene product confers resistance to the antibiotic spectinomycin. Prior to transformation with P[1030], *Chlamydomonas reinhardtii* was unable to propagate on medium comprising 90 ug/ml spectinomycin. Upon transformation with P[1030], transformants of *Chlamydomonas reinhardtii* were obtained that were propagated in selective culture medium comprising 90 ug/ml spectinomycin, thereby establishing the utility of the spectinomycin antibiotic resistance cassette as a selectable marker for use in *Chlamydomonas reinhardtii*. Evaluation of the genomic DNA of the stable transformants was performed by Southern analysis. Cerutti reported that selection and maintenance of the transformed *Chlamydomonas reinhardtii* was performed on agar plates comprising Tris-acetate-phosphate medium (TAP, as described by Harris, The *Chlamydomonas Sourcebook*, Academic Press, San Diego, 1989) with 90 ug/ml spectinomycin. Cerutti additionally reported propagation of *Chlamydomonas reinhardtii* in TAP liquid culture with 90 ug/ml spectinomycin. Propagation of *Chlamydomonas reinhardtii* in alternative culture medium has been discussed (for example in Dent et al., *African Journal of Microbiology Research*, Vol. 5:3 (2011), pp. 260-270 and Yantao et al., *Biotechnology and Bioengineering*, Vol. 107:2 (2010), pp. 258-268). Additional constructs, comprising additional selectable markers suitable for use in *Chlamydomonas reinhardtii* as well as numerous regulatory sequences, including protomers and 3' UTRs suitable for promoting heterologous gene expression in *Chlamydomonas reinhardtii* are known in the art and have been discussed (for a review, see Radakovits et al., *Eurkaryotic Cell*, Vol. 9:4 (2010), pp. 486-501). Cerutti reported that the transformation vector P[1030] and the *Chlamydomonas reinhardtii* promoter and 3' UTR/terminator are suitable to enable exogenous gene expression in *Chlamydomonas reinhardtii*. In addition, Cerutti reported that the spectinomycin resistance cassette encoded on P[1030] was suitable for use as a selectable marker in *Chlamydomonas reinhardtii*.

In an embodiment of the present invention, vector P[1030], comprising the nucleotide sequence encoding the aadA gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Chlamydomonas reinhardtii* to reflect the codon bias inherent in nuclear genes of *Chlamydomonas reinhardtii* in accordance with Tables 19A-D. For each lipid biosynthesis pathway protein of Table 20, the codon-optimized gene sequence can individually be operably linked to the *Chlamydomonas reinhardtii* RbcS2 promoter upstream of the protein-coding sequence and operably linked to the *Chlamydomonas reinhardtii* RbcS2 3'UTR/terminator at the 3' region, or downstream, of the protein-coding sequence. The transformation construct may additionally comprise homology regions to the *Chlamydomonas reinhardtii* genome for targeted genomic integration of the transformation vector. Homology regions may be selected to disrupt one or more genomic site of an endogenous lipid biosynthesis pathway gene. One skilled in the art can identify such homology regions within the sequence of the *Chlamydomonas reinhardtii* genome (referenced in the publication by Merchant et al., *Science*, Vol. 318:5848 (2007), pp. 245-250). Stable transformation of *Chlamydomonas reinhardtii* with the transformation vector is achieved through well-known transformation techniques including microprojectile bombardment or other known methods. Activity of the aadA gene product can be used as a marker to select for *Chlamydomonas reinhardtii* transformed with the transformation vector on, but not limited to, TAP agar medium comprising spectinomycin. Growth media suitable for *Chlamydomonas reinhardtii* lipid production include, but are not limited to, ESAW medium, and those culture media discussed by Yantao et al. and Dent et al. Evaluation of fatty acid profiles of *Chlamydomonas reinhardtii* lipids can be assessed through standard lipid extraction and analytical methods described herein.

Example 31

Engineering *Yarrowia lipolytica*

Expression of recombinant genes in accordance with the present invention in *Yarrowia lipolytica* can be accomplished by modifying the methods and vectors taught by Fickers et al. as discussed herein. Briefly, Fickers et al., *Journal of Microbiological Methods*, Vol. 55 (2003), pp. 727-737, reported the stable nuclear transformation of *Yarrowia lipolytica* with plasmid DNA. Using a lithium acetate transformation method, Fickers introduced the plasmid JMP123 into *Yarrowia lipolytica*. Plasmid JMP123 comprised a hygromycin B resistance cassette, comprising sequence encoding the hygromycin B phosphotransferase gene product (hph), operably-linked to the *Yarrowia lipolytica* LIP2 gene promoter (GenBank Accession No. AJ012632) upstream of the hph protein-coding region and operably linked to the *Yarrowia lipolytica* LIP2 gene 3'UTR/terminator downstream of the hph protein-coding region. Prior to transformation with JMP123, *Yarrowia lipolytica* were unable to propagate on medium comprising 100 ug/ml hygromycin. Upon transformation with JMP123, transformed *Yarrowia lipolytica* were obtained that were able to propagate on medium comprising 100 ug/ml hygromycin, thereby establishing the hygromycin B antibiotic resistance cassette as a selectable marker for use in *Yarrowia lipolytica*. The nucleotide sequence provided on JMP123 of the promoter and 3'UTR/terminator of the *Yarrowia lipolytica* LIP2 gene served as donor sequences for homologous recombination of the hph coding sequence into the LIP2 locus. Evaluation of the genomic DNA of the stable transformants was performed by Southern. Fickers reported that selection and maintenance of the transformed *Yarrowia lipolytica* was performed on agar plates comprising standard YPD medium (Yeast Extract Peptone Dextrose) with 100 ug/ml hygromycin. Liquid culturing of transformed *Yarrowia lipolytica* was performed in YPD medium with hygromycin. Other media and techniques used for culturing *Yarrowia lipolytica* have been reported and numerous other plasmids, promoters, 3' UTRs, and selectable markers for use in *Yarrowia lipolytica* have been reported (for example see Pignede et al., *Applied and Environmental Biology*, Vol. 66:8 (2000), pp. 3283-3289, Chuang et al., *New Biotechnology*, Vol. 27:4 (2010), pp. 277-282, and Barth and Gaillardin, (1996), In: K,W. (Ed.), Nonconventional Yeasts in Biotechnology. Sprinter-Verlag, Berlin-Heidelber, pp. 313-388). Fickers reported that the transformation vector JMP123 and the *Yarrowia lipolytica* LIP2 gene promoter and 3' UTR/terminator are suitable to enable heterologous gene expression in *Yarrowia lipolytica*. In addition, Fickers reported that the hygromycin resistance cassette encoded on JMP123 was suitable for use as a selectable marker in *Yarrowia lipolytica.*

In an embodiment of the present invention, vector JMP123, comprising the nucleotide sequence encoding the hph gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Yarrowia lipolytica* to reflect the codon bias inherent in nuclear genes of *Yarrowia lipolytica* in accordance with Tables 19A-D. For each lipid biosynthesis pathway protein of Table 20, the codon-optimized gene sequence can individually be operably linked to the *Yarrowia lipolytica* LIP2 gene promoter upstream of the protein-coding sequence and operably linked to the *Yarrowia lipolytica* LIP2 gene 3'UTR/terminator at the 3' region, or downstream, of the protein-coding sequence. The transformation construct may additionally comprise homology regions to the *Yarrowia lipolytica* genome for targeted genomic integration of the transformation vector. Homology regions may be selected to disrupt one or more genomic sites of endogenous lipid biosynthesis pathway genes. One skilled in the art can identify such homology regions within the sequence of the *Yarrowia lipolytica* genome (referenced in the publication by Dujun et al., *Nature*, Vol. 430 (2004), pp. 35-44). Stable transformation of *Yarrowia lipolytica* with the transformation vector is achieved through well-known transformation techniques including lithium acetate transformation or other known methods. Activity of the hph gene product can be used as a marker to select for *Yarrowia lipolytica* transformed with the transformation vector on, but not limited to, YPD medium comprising hygromycin. Growth media suitable for *Yarrowia lipolytica* lipid production include, but are not limited to, YPD medium, and those culture media described by Chuang et al. Evaluation of fatty acid profiles of *Yarrowia lipolytica* lipids can be assessed through standard lipid extraction and analytical methods described herein.

Example 32

Engineering *Mortierella alpine*

Expression of recombinant genes in accordance with the present invention in *Mortierella alpine* can be accomplished by modifying the methods and vectors taught by Mackenzie et al. as discussed herein. Briefly, Mackenzie et al., *Applied and Environmental Microbiology*, Vol. 66 (2000), pp. 4655-4661, reported the stable nuclear transformation of *Mortierella alpina* with plasmid DNA. Using a protoplast transformation method, MacKenzie introduced the plasmid pD4 into *Mortierella alpina*. Plasmid pD4 comprised a hygromycin B resistance cassette, comprising sequence encoding the hygromycin B phosphotransferase gene product (hpt), operably-linked to the *Mortierella alpina* histone H4.1 gene promoter (GenBank Accession No. AJ249812) upstream of the hpt protein-coding region and operably linked to the *Aspergillus nidulans* N-(5'-phosphoribosyl)anthranilate isomerase (trpC) gene 3'UTR/terminator downstream of the hpt protein-coding region. Prior to transformation with pD4, *Mortierella alpina* were unable to propagate on medium comprising 300 ug/ml hygromycin. Upon transformation with pD4, transformed *Mortierella* alpina were obtained that were propagated on medium comprising 300 ug/ml hygromycin, thereby establishing the hygromycin B antibiotic resistance cassette as a selectable marker for use in *Mortierella alpina*. Evaluation of the genomic DNA of the stable transformants was performed by Southern. Mackenzie reported that selection and maintenance of the transformed *Mortierella alpina* was performed on PDA (potato dextrose agar) medium comprising hygromycin. Liquid culturing of transformed *Mortierella alpina* by Mackenzie was performed in PDA medium or in S2GYE medium (comprising 5% glucose, 0.5% yeast extract, 0.18% $NH_4SO_4$, 0.02% $MgSO_4$-$7H_2O$, 0.0001% $FeCl_3$-$6H_2O$, 0.1%, trace elements, 10 mM $K_2HPO_4$—$NaH_2PO_4$), with hygromycin. Other media and techniques used for culturing *Mortierella alpina* have been reported and other plasmids, promoters, 3' UTRs, and selectable markers for use in *Mortierella alpina* have been reported (for example see Ando et al., *Applied and Environmental Biology*, Vol. 75:17 (2009) pp. 5529-35 and Lu et al., *Applied Biochemistry and Biotechnology*, Vol. 164:7 (2001), pp. 979-90). Mackenzie reported that the transformation vector pD4 and the *Mortierella alpina* histone H4.1 promoter and *A. nidulans* trpC gene 3' UTR/terminator are suitable to enable heterologous gene expression in *Mortierella alpina*. In addition, Mackenzie reported that the hygromycin resistance cassette encoded on pD4 was suitable for use as a selectable marker in *Mortierella* alpina.

In an embodiment of the present invention, vector pD4, comprising the nucleotide sequence encoding the hpt gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Mortierella alpina* to reflect the codon bias inherent in nuclear genes of *Mortierella alpina* in accordance with Tables 19A-D. For each lipid biosynthesis pathway protein of Table 20, the codon-optimized gene sequence can individually be operably linked to the *Mortierella alpina* histone H4.1 gene promoter upstream of the protein-coding sequence and operably linked to the *A. nidulans* trpC 3'UTR/terminator at the 3' region, or downstream, of the protein-coding sequence. The transformation construct may additionally comprise homology regions to the *Mortierella* alpina genome for targeted genomic integration of the transformation vector. Homology regions may be selected to disrupt one or more genomic sites of endogenous lipid biosynthesis pathway genes. One skilled in the art can identify such homology regions within the sequence of the *Mortierella alpina* genome (referenced in the publication by Wang et al., *PLOS One*, Vol. 6:12 (2011)). Stable transformation of *Mortierella alpina* with the transformation vector is achieved through well-known transformation techniques including protoplast transformation or other known methods. Activity of the hpt gene product can be used as a marker to select for *Mortierella alpina* transformed with the transformation vector on, but not limited to, PDA medium comprising hygromycin. Growth media suitable for *Mortierella alpina* lipid production include, but are not limited to, S2GYE medium, and those culture media described by Lu et al. and Ando et al. Evaluation of fatty acid profiles of *Mortierella alpina* lipids can be assessed through standard lipid extraction and analytical methods described herein.

Example 33

Engineering *Rhodococcus opacus* PD630

Expression of recombinant genes in accordance with the present invention in *Rhodococcus opacus* PD630 can be accomplished by modifying the methods and vectors taught by Kalscheuer et al. as discussed herein. Briefly, Kalscheuer et al., *Applied and Environmental Microbiology*, Vol. 52 (1999), pp. 508-515, reported the stable transformation of *Rhodococcus opacus* with plasmid DNA. Using the transformation method of electroporation, Kalscheuer introduced the plasmid pNC9501 into *Rhodococcus opacus* PD630. Plasmid pNC9501 comprised a thiostrepton resistance (thio$^r$) cassette, comprising the full nucleotide sequence of the *Streptomyces azureus* 23S rRNA A1067 methyltransferase gene, including the gene's promoter and 3' terminator sequence. Prior to transformation with pNC9501, *Rhodococcus opacus* was unable to propagate on medium comprising 1 mg/ml thiostrepton. Upon transformation of *Rhodococcus opacus* PD630 with pNC9501, transformants were obtained that propagated on culture medium comprising 1 mg/ml thiostrepton, thereby establishing the use of the thiostrepton resistance cassette as a selectable marker in *Rhodococcus opacus* PD630. A second plasmid described by Kalscheuer, pAK68, comprised the resistance thio$^r$ cassette as well as the gene sequences of the *Ralstonia eutropha* beta-ketothiolase (phaB), acetoacetyl-CoA reductase (phaA), and poly3-hydroxyalkanoic acid synthase (phaC) genes for polyhydroxyalkanoate biosynthesis, driven by the lacZ promoter. Upon pAK68 transformation of a *Rhodococcus opacus* PD630 strain deficient in polyhydroxyalkanoate biosynthesis, transformed *Rhodococcus opacus* PD630 were obtained that produced higher amounts of polyhydroxyalkanoates than the untransformed strain. Detectable activity of the introduced *Ralstonia eutropha* phaB, phaA, and phaC enzymes indicted that the regulatory elements encoded on the pAK68 plasmid were suitable for heterologous gene expression in *Rhodococcus opacus* PD630. Kalscheuer reported that selection and maintenance of the transformed *Rhodococcus opacus* PD630 was performed on standard Luria Broth (LB) medium, nutrient broth (NB), or mineral salts medium (MSM) comprising thiostrepton. Other media and techniques used for culturing *Rhodococcus opacus* PD630 have been described (for example see Kurosawa et al., *Journal of Biotechnology*, Vol. 147:3-4 (2010), pp. 212-218 and Alverez et al., *Applied Microbial and Biotechnology*, Vol. 54:2 (2000), pp. 218-223). Kalscheuer reported that the transformation vectors pNC9501 and pAK68, the promoters of the *Streptomyces azureus* 23S rRNA A1067 methyltransferase gene and lacZ gene are suitable to enable heterologous gene expression in *Rhodococcus opacus* PD630. In addition, Kalscheuer reported that the thio$^r$ cassette encoded on pNC9501 and pAK68 was suitable for use as a selectable marker in *Rhodococcus opacus* PD630.

In an embodiment of the present invention, vector pNC9501, comprising the nucleotide sequence encoding the thio$^r$ gene product for use as a selectable marker, is constructed and modified to further comprise a lipid biosynthesis pathway expression cassette sequence, thereby creating a transformation vector. The lipid biosynthesis pathway expression cassette encodes one or more lipid biosynthesis pathway proteins selected from Table 20, each protein-coding sequence codon-optimized for expression in *Rhodococcus opacus* PD630 to reflect the codon bias inherent in nuclear genes of *Rhodococcus opacus* in accordance with Tables 19A-D. For each lipid biosynthesis pathway protein of Table 20, the codon-optimized gene sequence can individually be operably linked to the lacZ gene promoter upstream of the protein-coding sequence. The transformation construct may additionally comprise homology regions to the *Rhodococcus opacus* PD630 genome for targeted genomic integration of the transformation vector. Homology regions may be selected to disrupt one or more genomic sites of endogenous lipid biosynthesis pathway genes. One skilled in the art can identify such homology regions within the sequence of the *Rhodococcus opacus* PD630 genome (referenced in the publication by Holder et al., *PLOS Genetics*, Vol. 7:9 (2011). Transformation of *Rhodococcus opacus* PD630 with the transformation vector is achieved through well-known transformation techniques including electoporation or other known methods. Activity of the *Streptomyces azureus* 23S rRNA A1067 methyltransferase gene product can be used as a marker to select for *Rhodococcus* opacus PD630 transformed with the transformation vector on, but not limited to, LB medium comprising thiostrepton. Growth media suitable *Rhodococcus opacus* PD630 lipid production include, but are not limited to those culture media discussed by Kurosawa et al. and Alvarez et al. Evaluation of fatty acid profiles of *Rhodococcus opacus* PD630 lipids can be assessed through standard lipid extraction and analytical methods described herein.

Example 34

Engineering Microalgae for Fatty Acid Auxotrophy

Strain B of Example 3, *Prototheca moriformis* (UTEX 1435) engineered to express a *Cuphea wrightii* thioesterase (CwTE2), was used as the host organism for further genetic modification to knockout both endogenous thioesterase alleles, FATA1-1 and FATA1-2. Here, a first transformation construct was generated to integrate a neomycin expression cassette into Strain B at the FATA1-1 locus. This construct, pSZ2226, included 5' (SEQ ID NO: 30) and 3' (SEQ ID NO: 31) homologous recombination targeting sequences (flanking the construct) to the FATA1-1 locus of the nuclear genome and a neomycin resistance protein-coding sequence under the control of the *C. reinhardtii* β-tubulin promoter/5'UTR (SEQ ID NO: 5) and the *Chlorella vulgaris* nitrate reductase 3' UTR (SEQ ID NO: 6). This NeoR expression cassette is listed as SEQ ID NO: 15 and served as a selectable marker.

Upon transformation of pSZ2226 into Strain B, individual transformants were selected on agar plates comprising sucrose and G418. A single isolate, Strain H, was selected for further genetic modification. A second transformation construct, pSZ2236, was generated to integrate polynucleotides enabling expression of a thiamine selectable marker into Strain H at the FATA1-2 locus. pSZ2236 included 5' (SEQ ID NO: 32) and 3' (SEQ ID NO: 33) homologous recombination targeting sequences (flanking the construct) to the FATA1-2 genomic region for integration into the *P. moriformis* (UTEX 1435) nuclear genome and an *A. thaliana* THIC protein coding region under the control of the *C. protothecoides* actin promoter/5'UTR (SEQ ID NO: 22) and *C. vulgaris* nitrate reductase 3' UTR (SEQ ID NO: 6). This AtTHIC expression cassette is listed as SEQ ID NO: 23 and served as a selectable marker. Upon transformation of Strain H with pSZ2236 to generate Strain I, individual transformants, were selected on agar plates comprising free fatty acids. Strain I was able to propagate on agar plates and in medium lacking thiamine and supplemented with free fatty acids.

Example 35

Engineering Microorganisms for Increased Production of Stearic Acid

A classically mutagenized strain of *Prototheca moriformis* (UTEX 1435), Strain J, was transformed with the plasmid construct pSZ2281 according to biolistic transformation methods as described in PCT/US2009/066141, PCT/US2009/066142, PCT/US2011/038463, PCT/US2011/038464, and PCT/US2012/023696. pSZ2281 included polynucleotides encoding RNA hairpins (SAD2hpC, SEQ ID NO: 34) to down-regulate the expression of stearoyl-ACP desaturase, 5' (SEQ ID NO: 1) and 3' (SEQ ID NO: 2) homologous recombination targeting sequences (flanking the construct) to the 6S genomic region for integration into the nuclear genome, and a *S. cerevisiae* suc2 sucrose invertase coding region (SEQ ID NO: 4), to express the protein sequence given in SEQ ID NO: 3, under the control of *C. reinhardtii* β-tubulin promoter/5'UTR (SEQ ID NO: 5) and *Chlorella vulgaris* nitrate reductase 3' UTR (SEQ ID NO: 6). This *S. cerevisiae* suc2 expression cassette is listed as SEQ ID NO: 7 and served as a selectable marker. The polynucleotide sequence encoding the SAD2hpC RNA hairpin was under the control of the *C. protothecoides* actin promoter/5'UTR (SEQ ID NO: 22) and *C. vulgaris* nitrate reductase 3' UTR (SEQ ID NO: 6).

Upon transformation of Strain J with construct pSZ2281, thereby generating Strain K, positive clones were selected on agar plates containing sucrose as a sole carbon source. Individual transformants were clonally purified and propagated under heterotrophic conditions suitable for lipid production as those detailed in PCT/US2009/066141, PCT/US2009/066142, PCT/US2011/038463, PCT/US2011/038464, and PCT/US2012/023696. Lipid samples were prepared from dried biomass and analyzed using standard fatty acid methyl ester gas chromatography flame ionization detection methods as described in Example 1 (also see PCT/US2012/023696). The fatty acid profiles (expressed as Area % of total fatty acids) of *P. moriformis* UTEX Strain J propagated on glucose as a sole carbon source and three representative isolates of Strain K, propagated on sucrose as a sole carbon source, are presented in Table 21.

TABLE 21

Fatty acid profiles of *Prototheca moriformis* (UTEX 1435) cells engineered to express a hairpin RNA construct targeting stearoyl ACP desaturase gene/gene products.

| Area % Fatty acid | Strain J | Strain K-1 | Strain K-2 | Strain K-3 | Strain K-4 |
|---|---|---|---|---|---|
| C8:0 | | | | | 0.02 |
| C10:0 | 0.01 | 0.00 | 0.02 | 0.02 | 0.04 |
| C12:0 | 0.03 | 0.05 | 0.05 | 0.05 | 0.08 |
| C14:0 | 1.22 | 0.89 | 0.87 | 0.77 | 1.2 |
| C16:0 | 26.75 | 29.23 | 28.96 | 27.55 | 28.06 |
| C18:0 | 3.06 | 37.39 | 36.76 | 36.41 | 40.82 |
| C18:1 | 59.62 | 23.90 | 24.76 | 26.92 | 22.02 |
| C18:2 | 7.33 | 5.44 | 5.54 | 5.54 | 4.53 |
| C18:3 | | | | | 0.14 |
| C20:0 | | | | | 1.43 |

The data presented in Table 21 show a clear impact of the expression of SAD2 hairpin RNA construct on the C18:0 and C18:1 fatty acid profiles of the transformed organism. The fatty acid profiles of Strain K transformants comprising a SAD2 hairpin RNA construct demonstrated an increase in the percentage of saturated C18:0 fatty acids with a concomitant diminution of unsaturated C18:1 fatty acids. Fatty acid profiles of the untransformed strain comprise about 3% C18:0. Fatty acid profiles of the transformed strains comprise about 37% C18:0. These data illustrate the successful expression and use of polynucleotides enabling expression of a SAD RNA hairpin construct in *Prototheca moriformis* to alter the percentage of saturated fatty acids in the engineered host microbes, and in particular in increasing the concentration of C18:0 fatty acids and decreasing C18:1 fatty acids in microbial cells.

Also shown in Table 21, strain K-4 had a yet further elevated level of stearate. Strain K4 was created by inserting the construct of strains K1-K3 into the SAD2B locus. Thus, by knocking out one copy of the SAD gene and inhibiting the remaining copies at the RNA level, a further reduction in oleic acid and corresponding increase in stearate was obtained. Triglyceride analysis of RBD oil obtained from strain K4 showed about 12% POP, 27% POS and 18% SOS.

Example 36

Engineering Microorganisms for Increased Production of Oleic Acid Through Knockdown of an Endogenous Acyl-ACP Thioesterase A classically mutagenized strain of *Prototheca moriformis* (UTEX 1435), Strain J, was transformed independently with each of the constructs pSZ2402-pSZ2407 according to biolistic transformation methods as described in PCT/US2009/066141, PCT/US2009/066142, PCT/US2011/038463, PCT/US2011/038464, and PCT/US2012/023696. Each of the constructs pSZ2402-pSZ2407 included different polynucleotides encoding a hairpin RNA targeted against *Prototheca moriformis* FATA1 mRNA transcripts to down-regulate the expression of fatty acyl-ACP thioesterase, 5' (SEQ ID NO: 1) and 3' (SEQ ID NO: 2) homologous recombination targeting sequences (flanking the construct) to the 6S genomic region for integration into the nuclear genome, and a *S. cerevisiae* suc2 sucrose invertase coding region (SEQ ID NO: 4) to express the protein sequence given in SEQ ID NO: 3 under the control of *C. reinhardtii* β-tubulin promoter/5'UTR (SEQ ID NO: 5) and *Chlorella vulgaris* nitrate reductase 3' UTR (SEQ ID NO: 6). This *S. cerevisiae* suc2 expression cassette is listed as SEQ ID NO: 7 and served as a selectable marker. Sequence listing identities for the polynucleotides corresponding to each hairpin are listed in Table 22. The polynucleotide sequence encoding each RNA hairpin was under the control of the *C. reinhardtii* β-tubulin promoter/5'UTR (SEQ ID NO: 5) and *C. vulgaris* nitrate reductase 3' UTR (SEQ ID NO: 6).

TABLE 22

Plasmid constructs used to transform *Prototheca moriformis* (UTEX 1435) Strain J.

| Plasmid construct | Hairpin designation | SEQ ID NO: |
|---|---|---|
| pSZ2402 | PmFATA-hpB | SEQ ID NO: 40 |
| pSZ2403 | PmFATA-hpC | SEQ ID NO: 41 |
| pSZ2404 | PmFATA-hpD | SEQ ID NO: 42 |
| pSZ2405 | PmFATA-hpE | SEQ ID NO: 43 |
| pSZ2406 | PmFATA-hpF | SEQ ID NO: 44 |
| pSZ2407 | PmFATA-hpG | SEQ ID NO: 45 |

Upon independent transformation of Strain J with each of the constructs listed in Table 22, positive clones were selected on agar plates containing sucrose as a sole carbon source. Individual transformants were clonally purified and propagated under heterotrophic conditions suitable for lipid production as those detailed in PCT/US2009/066141, PCT/US2009/066142, PCT/US2011/038463, PCT/US2011/038464, and PCT/US2012/023696. Lipid samples were prepared from dried biomass and analyzed using standard fatty acid methyl ester gas chromatography flame ionization detection methods as described in Example 1 (also see PCT/US2012/023696). The fatty acid profiles (expressed as Area % of total fatty acids) of *P. moriformis* (UTEX 1435) Strain J propagated on glucose as a sole carbon source and representative isolates of each transformation of Strain J, propagated on sucrose as a sole carbon source, are presented in Table 23.

TABLE 23

Fatty acid profiles of *Prototheca moriformis* (UTEX 1435) cells engineered to express hairpin RNA constructs targeting fatty acyl-ACP thioesterase gene/gene products.

| | Area % Fatty Acid | | | | | | |
|---|---|---|---|---|---|---|---|
| Construct | C10:0 | C12:0 | C14:0 | C16:0 | C18:0 | C18:1 | C18:2 |
| Strain J untransformed | 0 | 0.05 | 1.32 | 26.66 | 3.1 | 59.07 | 7.39 |
| PmFATA-hpB | 0.04 | 0.07 | 1.36 | 24.88 | 2.24 | 61.92 | 6.84 |
| | 0 | 0.08 | 1.33 | 25.34 | 2.39 | 61.72 | 6.5 |
| | 0 | 0.07 | 1.29 | 25.44 | 2.26 | 61.7 | 6.69 |
| | 0 | 0.06 | 1.33 | 25.1 | 2.37 | 61.56 | 6.87 |
| PmFATA-hpC | 0 | 0.08 | 1.18 | 22.03 | 1.71 | 63.8 | 8.63 |
| | 0 | 0.07 | 1.21 | 24.5 | 2.23 | 62.32 | 7.19 |
| | 0 | 0.08 | 1.29 | 24.93 | 2.24 | 62.02 | 7.01 |
| | 0.05 | 0.06 | 1.29 | 25.45 | 2.26 | 61.81 | 6.76 |
| PmFATA-hpD | 0 | 0.02 | 0.68 | 15.8 | 1.88 | 72.64 | 6.96 |
| | 0 | 0.03 | 0.78 | 17.56 | 1.7 | 71.8 | 6.03 |
| | 0 | 0.03 | 0.92 | 19.04 | 2.03 | 68.82 | 7.05 |
| | 0 | 0.04 | 1.27 | 23.14 | 2.25 | 65.27 | 6.07 |
| PmFATA-hpE | 0 | 0.03 | 0.79 | 18.55 | 2.13 | 69.66 | 6.77 |
| | 0 | 0.04 | 1.11 | 21.01 | 1.74 | 65.18 | 8.55 |
| | 0 | 0.03 | 1.08 | 21.11 | 1.54 | 64.76 | 8.87 |
| | 0 | 0.03 | 1.17 | 21.93 | 1.71 | 63.89 | 8.77 |
| PmFATA-hpF | 0.03 | 0.04 | 0.34 | 8.6 | 1.69 | 78.08 | 8.87 |
| | 0 | 0.03 | 0.49 | 10.2 | 1.52 | 76.97 | 8.78 |
| | 0 | 0.03 | 1 | 20.47 | 2.22 | 66.34 | 7.45 |
| | 0 | 0.03 | 1.03 | 21.61 | 1.88 | 65.39 | 7.76 |
| PmFATA-hpG | 0 | 0.03 | 1.03 | 20.57 | 2.36 | 64.73 | 8.75 |
| | 0 | 0.03 | 1.2 | 24.39 | 2.47 | 61.9 | 7.49 |
| | 0 | 0.04 | 1.29 | 24.14 | 2.29 | 61.41 | 8.22 |

The data presented in Table 23 show a clear impact of the expression of FATA hairpin RNA constructs on the C18:0 and C18:1 fatty acid profiles of the transformed organism. The fatty acid profiles of Strain J transformants comprising a FATA hairpin RNA construct demonstrated an increase in the percentage of C18:1 fatty acids with a concomitant diminution of C16:0 and C18:0 fatty acids. Fatty acid profiles of the untransformed Strain J are about 26.66% C16:0, 3% C18:0, and about 59% C18:1 fatty acids. In contrast, the fatty acid profiles of the transformed strains comprise as low as 8.6% C16:0 and 1.54% C18:0 and greater than 78% C18:1 fatty acids.

These data illustrate the utility and successful use of polynucleotide FATA RNA hairpin constructs in *Prototheca moriformis* to alter the fatty acids profile of engineered microbes, and in particular in increasing the concentration of C18:1 fatty acids and decreasing C18:0 and C16:0 fatty acids in microbial cells.

Example 37

Engineering Microorganisms for Increased Production of Mid-Chain Fatty Acids Through KASI or KASIV Overexpression This example describes the use of recombinant polynucleotides that encode KASI or KASIV enzymes to engineer microorganisms in which the fatty acid profiles of the transformed microorganisms have been enriched in lauric acid, C10:0, and total saturated fatty acids.

Each of the constructs pSZD1132, pSZD1133, pSZD1134, or pSZD1201 was used independently to transform Strain B of Example 3, *Prototheca moriformis* (UTEX 1435) engineered to express a *Cuphea wrightii* thioesterase (CwTE2), according to biolistic transformation methods as described in PCT/US2009/066141, PCT/US2009/066142, PCT/US2011/038463, PCT/US2011/038464, and PCT/US2012/023696. Each of the above constructs included different polynucleotides encoding a KASI or KASIV enzyme, 5' (SEQ ID NO: 13) and 3' (SEQ ID NO: 14) homologous recombination targeting sequences (flanking the construct) to the pLoop genomic region for integration into the nuclear genome, and a neomycin resistance protein-coding sequence under the control of the *C. reinhardtii* (3-tubulin promoter/5'UTR (SEQ ID NO: 5) and the *Chlorella vulgaris* nitrate reductase 3' UTR (SEQ ID NO: 6). This NeoR expression cassette is listed as SEQ ID NO: 15 and served as a selectable marker. Sequence listing identities for the polynucleotides corresponding to each construct are listed in Table 20. The polynucleotide sequence encoding each KAS enzyme was under the control of the *P. moriformis* UTEX 1435 Amt03 promoter/5'UTR (SEQ ID NO: 8) and *C. vulgaris* nitrate reductase 3' UTR (SEQ ID NO: 6). The protein coding regions of the KAS enzymes and neomycin resistance gene were codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

Upon transformation of individual plasmids into Strain B, positive clones were selected on agar plates comprising G418. Individual transformants were clonally purified and grown on sucrose as a sole carbon source at pH 7.0 under conditions suitable for lipid production as detailed in PCT/US2009/066141, PCT/US2009/066142, PCT/US2011/038463, PCT/US2011/038464, and PCT/US2012/023696. Lipid samples were prepared from dried biomass from each transformant and fatty acid profiles from these samples were analyzed using standard fatty acid methyl ester gas chromatography flame ionization (FAME GC/FID) detection methods as described in Example 1. The fatty acid profiles (expressed as Area % of total fatty acids) of Strain B and four positive transformants of each of pSZ2046 (Strains M-P, 1-4) are presented in Table 24.

TABLE 24

Plasmid constructs used to transform *Prototheca moriformis* (UTEX 1435) Strain B.

| Plasmid construct | KASI/KASIV source | Transit peptide | SEQ ID NO: |
|---|---|---|---|
| pSZD1134 | *Cuphea wrightii* GenBank Accession No. U67317 | Native | SEQ ID NO: 46 |
| pSZD1201 | *Cuphea wrightii* | PmSAD | SEQ ID NO: 47 |
| pSZD1132 | *Cuphea pulcherrima* GenBank Accession No. AAC68860 | Native | SEQ ID NO: 48 |
| pSZD1133 | *Cuphea hookeriana* | Native | SEQ ID NO: 49 |

TABLE 25

Fatty acid profiles of *Prototheca moriformis* (UTEX 1435) Strain Bengineered for increased C10, lauric acid, and total saturated fatty acids.

| Plasmid construct(s) | No. | Fatty Acid (Area %) C10 | C12 | C14 | C16 | C18:0 | C18:1 | C18:2 | C10-C12 | % Saturates/ Total |
|---|---|---|---|---|---|---|---|---|---|---|
| pSZ1283 | | 7.89 | 35.49 | 16.58 | 11.5 | 1.09 | 19.64 | 6.49 | 43.38 | 72.55 |
| pSZ1283, pSZD1134 | 1 | 14.94 | 43.97 | 12.19 | 7.56 | 0.72 | 14.11 | 5.31 | 58.91 | 79.38 |
| pSZ1283, pSZD1134 | 2 | 10.27 | 39.61 | 15.35 | 9.61 | 0.94 | 17.1 | 5.88 | 49.88 | 75.78 |
| pSZ1283, pSZD1134 | 3 | 11.69 | 41.83 | 15.21 | 8.77 | 0.83 | 15.04 | 5.40 | 53.52 | 78.33 |
| D1134-20 | 4 | 10.76 | 40.77 | 15.32 | 9.19 | 0.88 | 16.06 | 5.76 | 51.53 | 76.92 |
| pSZ1283, pSZD1132 | 1 | 10.77 | 40.31 | 15.21 | 9.43 | 0.88 | 16.18 | 5.97 | 51.08 | 76.6 |
| pSZ1283, pSZD1132 | 2 | 9.19 | 37.03 | 15.02 | 10.52 | 1.00 | 19.63 | 6.29 | 46.22 | 72.76 |
| pSZ1283, pSZD1132 | 3 | 8.97 | 36.09 | 15.01 | 10.77 | 1.05 | 20.38 | 6.39 | 45.06 | 71.89 |

TABLE 25-continued

Fatty acid profiles of *Prototheca moriformis* (UTEX 1435) Strain Bengineered for increased C10, lauric acid, and total saturated fatty acids.

| | | Fatty Acid (Area %) | | | | | | | | |
|---|---|---|---|---|---|---|---|---|---|---|
| Plasmid construct(s) | No. | C10 | C12 | C14 | C16 | C18:0 | C18:1 | C18:2 | C10-C12 | % Saturates/ Total |
| pSZ1283, pSZD1132 | 4 | 9.51 | 38.12 | 14.96 | 9.96 | 0.94 | 18.93 | 6.32 | 47.63 | 73.49 |
| pSZ1283, pSZD1201 | 1 | 13.06 | 46.21 | 9.84 | 7.12 | 0.75 | 16.7 | 5.22 | 59.27 | 76.98 |
| pSZ1283, pSZD1201 | 2 | 11.02 | 43.91 | 13.01 | 7.78 | 0.86 | 16.53 | 5.77 | 54.93 | 76.58 |
| pSZ1283, pSZD1201 | 3 | 11.59 | 45.14 | 12.41 | 7.61 | 0.82 | 15.72 | 5.65 | 56.73 | 77.57 |
| pSZ1283, pSZD1201 | 4 | 10.66 | 41.32 | 13.74 | 8.75 | 0.68 | 18.64 | 5.21 | 51.98 | 75.15 |
| pSZ1283, pSZD1133 | 1 | 6.90 | 36.08 | 15.15 | 11.02 | 1.00 | 21.74 | 6.77 | 42.98 | 70.15 |
| pSZ1283, pSZD1133 | 2 | 7.01 | 35.88 | 15.01 | 10.75 | 1.07 | 22.02 | 6.93 | 42.89 | 69.72 |
| pSZ1283, pSZD1133 | 3 | 10.65 | 41.94 | 12.38 | 8.48 | 0.85 | 18.28 | 6.15 | 52.59 | 74.3 |
| pSZ1283, pSZD1133 | 4 | 10.23 | 41.88 | 12.58 | 8.52 | 0.82 | 18.48 | 6.22 | 52.11 | 74.03 |

The data presented in Table 25 show a clear impact of the exogenous expression of KASI and KASIV enzymes on the C10:0 and C12 fatty acid profiles of the transformed organism. The fatty acid profiles of Strain B, expressing the *Cuphea wrightii* thioesterase alone, comprised about 8% C10:0 and about 35.5% C12:0, with saturated fatty acids accounting for 72.55% of total fatty acids. In contrast, transformants of Strain B engineered to additionally express a *Cuphea wrightii* KASI with a *P. moriformis* stearoyl ACP desaturase transit peptide were characterized by a fatty acid profile of about 13% C10:0 and about 46% C12:0. Saturated fatty acids accounted for as high as 77% in transformants of Strain B co-expressing the *C. wrightii* KASI fusion protein. Similarly, transformants of Strain B engineered to express the *C. wrightii* KASI with the enzyme's native transit peptide were characterized by a fatty acid profile of about 15% C10, about 44% C12, and about 79% saturated fatty acids. The fatty acid profiles or many transformants of Strain B expressing either *Cuphea pulcherrima* KASIV or *Cuphea hookeriana* KASIV also displayed elevated C10% and C12% levels, compared to the fatty acid profile of Strain B itself.

These data demonstrate the utility and effectiveness of polynucleotides enabling expression of KASI and KASIV constructs in *Prototheca moriformis* (UTEX 1435) to alter the percentage of saturated fatty acids in the engineered host microbes, and in particular in increasing the concentration of C10:0 and C12:0 fatty acids in microbial cells.

Example 38

Engineering Microorganisms for Increased Production of Mid-Chain Fatty Acids Through KASI Knockout This example describes the use of recombinant polynucleotides that disrupt different KASI alleles to engineer microorganisms in which the fatty acid profiles of the transformed microorganisms have been enriched in C10:0 and midchain fatty acids.

Constructs pSZ2302 and pSZ2304 were used to independently transform Strain B of Example 3, *Prototheca moriformis* (UTEX 1435) engineered to express a *Cuphea wrightii* thioesterase (CwTE2), according to biolistic transformation methods as described in PCT/US2009/066141, PCT/US2009/066142, PCT/US2011/038463, PCT/US2011/038464, and PCT/US2012/023696. pSZ2302 included 5' (SEQ ID NO: 50) and 3' (SEQ ID NO: 51) homologous recombination targeting sequences (flanking the construct) to the KAS1 allele 1 genomic region for integration into the *P. moriformis* nuclear genome, an *A. thaliana* THIC protein coding region under the control of the *C. protothecoides* actin promoter/5'UTR (SEQ ID NO: 22) and *C. vulgaris* nitrate reductase 3' UTR (SEQ ID NO: 6). pSZ2304 included 5'(SEQ ID NO: 52) and 3' (SEQ ID NO: 53) homologous recombination targeting sequences (flanking the construct) to the KAS1 allele 2 genomic region for integration into the *P. moriformis* nuclear genome, an *A. thaliana* THIC protein coding region under the control of the *C. protothecoides* actin promoter/5'UTR (SEQ ID NO: 22) and *C. vulgaris* nitrate reductase 3' UTR (SEQ ID NO: 6). This AtTHIC expression cassette is listed as SEQ ID NO: 23 and served as a selection marker. The protein coding region of AtTHIC was codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

Upon independent transformation pSZ2302 and pSZ2304 into Strain B, thereby generating Strain Q and R, positive clones were selected on agar plates comprising thiamine. Individual transformants were clonally purified and cultivated on sucrose as a sole carbon source at pH 5.0 or pH 7.0 under heterotrophic conditions suitable for lipid production as detailed in PCT/US2009/066141, PCT/US2009/066142, PCT/US2011/038463, PCT/US2011/038464, and PCT/US2012/023696. Lipid samples were prepared from dried biomass from each transformant and fatty acid profiles from these samples were analyzed using fatty acid methyl ester gas chromatography flame ionization (FAME GC/FID) detection methods as described in Example 1. The fatty acid profiles (expressed as Area % of total fatty acids) of Strain B and positive pSZ2302 (Strain Q, 1-5) and pSZ2304 (Strain R, 1-5) transformants are presented in Tables 26 and 27.

TABLE 26

Fatty acid profiles of *Prototheca moriformis* (UTEX 1435) Strains B, Q, and R engineered for increased midchain fatty acids, cultured at pH 5.0.

| Strain | Transformation plasmid(s) | Fatty Acid (Area %) C10:0 | C12:0 | C14:0 | C16:0 | C18:0 | C18:1 | C18:2 | C10-C14 |
|---|---|---|---|---|---|---|---|---|---|
| UTEX 1435 | None | 0.00 | 0.04 | 1.28 | 26.67 | 3.05 | 59.96 | 7.19 | 1.32 |
| Strain B | pSZ1283 | 0.01 | 0.09 | 1.09 | 21.60 | 2.21 | 65.15 | 7.94 | 1.19 |
| Strain Q-1 | pSZ1283, pSZ2302 | 0.08 | 1.21 | 7.52 | 38.71 | 1.38 | 38.32 | 8.75 | 8.81 |
| Strain Q-2 | pSZ1283, pSZ2302 | 0.15 | 1.36 | 7.51 | 38.23 | 1.33 | 38.27 | 8.94 | 9.02 |
| Strain Q-3 | pSZ1283, pSZ2302 | 0.16 | 1.43 | 7.49 | 38.88 | 1.30 | 37.58 | 8.73 | 9.08 |
| Strain Q-4 | pSZ1283, pSZ2302 | 0.00 | 1.71 | 7.42 | 37.67 | 1.43 | 37.26 | 10.38 | 9.13 |
| Strain Q-5 | pSZ1283, pSZ2302 | 0.13 | 1.21 | 7.36 | 38.81 | 1.31 | 38.07 | 8.71 | 8.7 |
| Strain R-1 | pSZ1283, pSZ2304 | 0.19 | 1.78 | 8.47 | 40.11 | 1.34 | 33.46 | 9.98 | 10.44 |
| Strain R-2 | pSZ1283, pSZ2304 | 0.90 | 8.00 | 7.78 | 28.96 | 1.15 | 30.26 | 17.14 | 16.68 |
| Strain R-3 | pSZ1283, pSZ2304 | 0.26 | 3.58 | 7.77 | 34.98 | 1.56 | 32.86 | 14.60 | 11.61 |
| Strain R-4 | pSZ1283, pSZ2304 | 1.64 | 13.50 | 7.61 | 21.38 | 0.90 | 36.13 | 14.73 | 22.75 |
| Strain R-5 | pSZ1283, pSZ2304 | 1.03 | 9.63 | 7.56 | 25.61 | 1.00 | 31.70 | 18.23 | 18.22 |

TABLE 27

Fatty acid profiles of *Prototheca moriformis* (UTEX 1435), Strains B, Q, and R engineered for increased midchain fatty acids, cultured at pH 7.0.

| Strain | Transformation plasmid(s) | Fatty Acid (Area %) C10:0 | C12:0 | C14:0 | C16:0 | C18:0 | C18:1 | C18:2 | C10-C14 |
|---|---|---|---|---|---|---|---|---|---|
| UTEX 1435 | None | 0.01 | 0.04 | 1.34 | 27.94 | 3.24 | 57.46 | 7.88 | 1.39 |
| Strain B | pSZ1283 | 4.72 | 29.57 | 15.56 | 12.63 | 1.20 | 27.65 | 7.39 | 49.85 |
| Strain Q-1 | pSZ1283, pSZ2302 | 16.00 | 50.61 | 9.52 | 5.33 | 0.54 | 11.79 | 5.28 | 76.13 |
| Strain Q-2 | pSZ1283, pSZ2302 | 16.32 | 49.79 | 9.82 | 5.52 | 0.54 | 12.28 | 4.87 | 75.93 |
| Strain Q-3 | pSZ1283, pSZ2302 | 15.08 | 47.58 | 10.23 | 5.93 | 0.56 | 15.12 | 4.50 | 72.89 |
| Strain Q-4 | pSZ1283, pSZ2302 | 14.27 | 47.30 | 10.44 | 6.17 | 0.56 | 15.50 | 4.59 | 72.01 |
| Strain Q-5 | pSZ1283, pSZ2302 | 14.75 | 47.28 | 10.32 | 6.04 | 0.59 | 15.50 | 4.65 | 72.35 |
| Strain R-1 | pSZ1283, pSZ2304 | 21.25 | 55.42 | 7.97 | 3.65 | 0.00 | 5.46 | 5.66 | 84.64 |
| Strain R-2 | pSZ1283, pSZ2304 | 13.00 | 55.05 | 10.88 | 5.78 | 0.28 | 7.90 | 6.29 | 78.93 |
| Strain R-3 | pSZ1283, pSZ2304 | 12.89 | 53.15 | 11.11 | 6.13 | 0.00 | 9.87 | 6.13 | 77.15 |
| Strain R-4 | pSZ1283, pSZ2304 | 12.80 | 51.64 | 13.86 | 6.69 | 0.00 | 7.51 | 6.70 | 78.3 |
| Strain R-5 | pSZ1283, pSZ2304 | 16.61 | 51.42 | 9.84 | 5.27 | 0.33 | 11.15 | 4.79 | 77.87 |

The data presented in Tables 26 and 27 show a clear impact of disruption of different KASI alleles on the fatty acid profiles of the transformed organisms. When cultivated at pH 5.0, the fatty acid profiles of *Prototheca moriformis* (UTEX 1435) and *Prototheca moriformis* (UTEX 1435) Strain B, expressing a *Cuphea wrightii* FATB2 thioesterase under control of a pH regulatable promoter were very similar. These profiles were characterized by about 1% C14:0, about 21-26% C16:0, about 2-3% C18:0, about 60-65% C18:1, about 7% C18:2, with C10-C14 fatty acids comprising about 1.19-1.3% of total fatty acids. In contrast, when cultivated at pH 5.0, Strain B further engineered to disrupt KASI allele 1 (Strain Q) or KASI allele 2 (Strain R) demonstrated altered fatty acid profiles that were characterized by increased levels of C12, increased levels of C14, decreased levels of C18, and decreased levels of C18:1 fatty acids compared to Strain B or UTEX 1435. The fatty acid profiles of isolates of Strains Q and R differed in that Strain R (allele 2 knockout) isolates had generally greater C12s and lower C16s and C18:1s than Strain Q (allele 1 knockout).

When cultivated at pH 7.0, the fatty acid profile of *Prototheca moriformis* (UTEX 1435) is distinct from that *Prototheca moriformis* (UTEX 1435) Strain B expressing a *Cuphea wrightii* FATB2 thioesterase under control of a pH regulatable promoter. When cultured at pH 7.0, Strain B was characterized by a fatty acid profile elevated in C10, C12, and C14 fatty acids (these comprised about 50% of the total fatty acids). When cultured at pH 7.0, Strain Q and Strain R demonstrated fatty acid profiles with still further increases in C10, C12, and C14 fatty acids and still further decreases in C18:0 and C18:1 fatty acids relative to that of Strain B. Again, differences in fatty acid profiles between Strain Q and R were observed with the profile of Strain R comprising greater percentage levels of C12 and lower levels of C18:1 than that of Strain Q.

These data illustrate the successful expression and use of polynucleotides enabling expression of KASI and KASIV constructs in *Prototheca moriformis* to alter the percentage of saturated fatty acids in the engineered host microbes, and in particular in increasing the concentration of C10:0 and C12:0 fatty acids and decreasing the concentration of C18:0 and C18:1 fatty acids in microbial cells. In addition, the data here indicate the different KASI alleles can be disrupted to result in altered fatty acid profiles of the transformed organisms.

Example 39

Engineering Microorganisms for Increased Production of Mid-Chain Fatty Acids Through KASI Knockdown This example describes the use of recombinant polynucleotides that encode RNA hairpins to attenuate a KASI enzyme to engineer a microorganism in which the fatty acid profile of the transformed microorganism has been enriched in mid-chain fatty acids.

A classically mutagenized strain of *Prototheca moriformis* (UTEX 1435), Strain S, was transformed independently with each of the constructs pSZ2482-pSZ2485 according to biolistic transformation methods as described in PCT/US2009/066141, PCT/US2009/066142, PCT/US2011/038463, PCT/US2011/038464, and PCT/US2012/023696. Each of the constructs pSZ2482-pSZ2485 included different polynucleotides encoding hairpin RNAs targeted against *Prototheca moriformis* (UTEX 1435) KASI mRNA transcripts to down-regulate the expression of fatty acyl-ACP thioesterase, 5' (SEQ ID NO: 1) and 3' (SEQ ID NO: 2) homologous recombination targeting sequences (flanking the construct) to the 6S genomic region for integration into the nuclear genome, and a *S. cerevisiae* suc2 sucrose invertase coding region (SEQ ID NO: 4) to express the protein sequence given in SEQ ID NO: 3 under the control of *C. reinhardtii* β-tubulin promoter/5'UTR (SEQ ID NO: 5) and *Chlorella vulgaris* nitrate reductase 3' UTR (SEQ ID NO: 6). This *S. cerevisiae* suc2 expression cassette is listed as SEQ ID NO: 7 and served as a selectable marker. Sequence listing identities for the polynucleotides corresponding to each KASI hairpin are listed in Table 28. The polynucleotide sequence encoding each RNA hairpin was under the control of the *P. moriformis* Amt03 promoter/5'UTR (SEQ ID NO: 8) and *C. vulgaris* nitrate reductase 3' UTR (SEQ ID NO: 6). The protein coding region of the suc2 expression cassette was codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

TABLE 28

Plasmid constructs used to transform *Prototheca moriformis* (UTEX 1435) Strain S.

| Transformation construct | Hairpin | SEQ ID NO: |
|---|---|---|
| pSZ2482 | KASI hairpin B | SEQ ID NO: 54 |
| pSZ2483 | KASI hairpin C | SEQ ID NO: 55 |
| pSZ2484 | KASI hairpin D | SEQ ID NO: 56 |
| pSZ2485 | KASI hairpin E | SEQ ID NO: 57 |

Upon independent transformation of Strain S with each of the constructs listed in Table 28, positive clones were selected on agar plates containing sucrose as a sole carbon source. Individual transformants were clonally purified and propagated under heterotrophic conditions suitable for lipid production as those detailed in PCT/US2009/066141, PCT/US2009/066142, PCT/US2011/038463, PCT/US2011/038464, and PCT/US2012/023696. Lipid samples were prepared from dried biomass and analyzed using fatty acid methyl ester gas chromatography flame ionization detection methods as described in Example 1 (also see PCT/US2012/023696). The fatty acid profiles (expressed as Area % of total fatty acids) of *P. moriformis* UTEX 1435 propagated on glucose as a sole carbon source and four representative isolates of each transformation of Strain S, propagated on sucrose as a sole carbon source, are presented in Table 29.

TABLE 29

Fatty acid profiles of *Prototheca moriformis* (UTEX 1435) cells engineered to express hairpin RNA constructs targeting KASI gene/gene products.

| | | | Fatty Acid (Area %) | | | | | | | |
|---|---|---|---|---|---|---|---|---|---|---|
| Strain | Plasmid | Number | C10:0 | C12:0 | C14:0 | C16:0 | C18:0 | C18:1 | C18:2 | C18:3 |
| UTEX 1435 | none | 1 | 0.00 | 0.04 | 1.45 | 27.97 | 3.18 | 58.35 | 6.78 | 0.60 |
| Strain S | pSZ2482 | 1 | 0.19 | 0.74 | 8.47 | 38.30 | 2.15 | 36.24 | 9.45 | 1.42 |
| | | 2 | 0.07 | 0.25 | 4.16 | 32.46 | 2.62 | 49.57 | 7.73 | 0.82 |
| | | 3 | 0.03 | 0.10 | 2.68 | 27.48 | 2.65 | 56.40 | 8.14 | 0.55 |
| | | 4 | 0.03 | 0.10 | 2.60 | 27.44 | 2.01 | 55.54 | 9.15 | 0.78 |
| | pSZ2483 | 1 | 0.00 | 0.06 | 1.94 | 30.58 | 1.55 | 53.26 | 9.31 | 0.76 |
| | | 2 | 0.20 | 0.05 | 1.76 | 28.01 | 2.31 | 56.61 | 8.70 | 0.60 |
| | | 3 | 0.00 | 0.06 | 1.60 | 24.38 | 2.65 | 58.25 | 9.93 | 1.15 |
| | | 4 | 0.00 | 0.04 | 1.56 | 26.65 | 2.96 | 60.06 | 6.92 | 0.52 |
| | pSZ2484 | 1 | 0.72 | 3.71 | 19.15 | 38.03 | 1.68 | 14.22 | 15.00 | 4.21 |
| | | 2 | 0.66 | 2.76 | 16.34 | 38.19 | 1.78 | 18.52 | 14.91 | 3.38 |
| | | 3 | 0.69 | 2.96 | 16.20 | 37.28 | 1.77 | 19.05 | 15.26 | 3.48 |
| | | 4 | 0.18 | 0.70 | 8.61 | 36.80 | 2.35 | 36.22 | 10.89 | 1.10 |
| | pSZ2485 | 1 | 0.00 | 0.04 | 1.41 | 25.34 | 3.16 | 60.12 | 7.78 | 0.48 |
| | | 2 | 0.03 | 0.04 | 1.41 | 23.85 | 2.19 | 61.23 | 8.75 | 0.67 |
| | | 3 | 0.00 | 0.04 | 1.41 | 24.41 | 2.23 | 60.64 | 8.69 | 0.67 |
| | | 4 | 0.00 | 0.04 | 1.41 | 24.51 | 2.16 | 60.85 | 8.91 | 0.66 |

The data presented in Table 29 show a clear impact of the expression of KAS hairpin RNA constructs on the fatty acid profiles of the transformed organisms. The fatty acid profiles of Strain S transformants comprising either pSZ2482 or pSZ2484 KASI hairpin RNA construct demonstrated an increase in the percentage of C10, C12, C14, and C16 fatty acids with a concomitant diminution of C18:0 and C18:1 fatty acids relative to the fatty acid profile of UTEX 1435.

These data illustrate the utility and successful use of polynucleotide KASI RNA hairpin constructs in *Prototheca moriformis* (UTEX 1435) to alter the fatty acids profile of engineered microbes, and in particular in increasing the concentration of midchain fatty acids and decreasing C18:0 and C18:1 fatty acids in microbial cells.

Example 40

Engineering Microorganisms for Increased Production of Stearic Acid Through Elongase Overexpression This example describes the use of recombinant polynucleotides that encode elongases to engineer a microorganism in which the fatty acid profile of the transformed microorganism has been enriched in stearic acid, arachidic acid, and docosadienoic acid.

A classically mutagenized strain of *Prototheca moriformis* (UTEX 1435), Strain J, was transformed independently with each of the constructs pSZ2323, pSZ2324, or pSZ2328 according to biolistic transformation methods as described in PCT/US2009/066141, PCT/US2009/066142, PCT/US2011/038463, PCT/US2011/038464, and PCT/US2012/023696. Each of the constructs included a protein coding region to overexpress an elongase, 5' (SEQ ID NO: 1) and 3' (SEQ ID NO: 2) homologous recombination targeting sequences (flanking the construct) to the 6S genomic region for integration into the nuclear genome, and a *S. cerevisiae* suc2 sucrose invertase coding region (SEQ ID NO: 4) to express the protein sequence given in SEQ ID NO: 3 under the control of *C. reinhardtii* β-tubulin promoter/5'UTR (SEQ ID NO: 5) and *Chlorella vulgaris* nitrate reductase 3' UTR (SEQ ID NO: 6). This *S. cerevisiae* suc2 expression cassette is listed as SEQ ID NO: 7 and served as a selectable marker. Sequence listing identities for the polynucleotides corresponding to each elongase are listed in Table 30. The polynucleotide sequence encoding each elongase was under control of the *P. moriformis* Amt03 promoter/5'UTR (SEQ ID NO: 8) and *C. vulgaris* nitrate reductase 3' UTR (SEQ ID NO: 6). The protein coding regions of the exogenous elongases and the suc2 expression cassette were codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

TABLE 30

Plasmid constructs used to transform *Prototheca moriformis* (UTEX 1435) Strain J.

| Plasmid construct | Elongase source | GenBank Accession No. | SEQ ID NO: |
|---|---|---|---|
| pSZ2328 | *Marchantia polymorpha* | AAP74370 | 58, 59 |
| pSZ2324 | *Trypanosoma brucei* | AAX70673 | 60, 61 |
| pSZ2323 | *Saccharomyces cerevisiae* | P39540 | 62, 63 |

Upon independent transformation of Strain J with the constructs listed in Table 30, positive clones were selected on agar plates containing sucrose as a sole carbon source. Individual transformants were clonally purified and propagated under heterotrophic conditions suitable for lipid production as those detailed in PCT/US2009/066141, PCT/US2009/066142, PCT/US2011/038463, PCT/US2011/038464, and PCT/US2012/023696. Lipid samples were prepared from dried biomass and analyzed using fatty acid methyl ester gas chromatography flame ionization detection methods as described in Example 1 (also see PCT/US2012/023696). The fatty acid profiles (expressed as Area % of total fatty acids) of *P. moriformis* UTEX 1435 Strain J propagated on glucose as a sole carbon source and three representative isolates of each transformation of Strain J, propagated on sucrose as a sole carbon source are presented in Table 31.

TABLE 31

Fatty acid profiles of *Prototheca moriformis* (UTEX 1435) Strain J cells engineered to overexpress elongases.

| Plasmid | | Fatty Acid Area % | | | | | | | | |
|---|---|---|---|---|---|---|---|---|---|---|
| construct | No. | C14:0 | C16:0 | C16:1 | C18:0 | C18:1 | C18:2 | C18:3α | C20:0 | C22:2n6 |
| None | 1 | 1.39 | 27.42 | 0.77 | 3.33 | 57.46 | 8.05 | 0.61 | 0.30 | 0.03 |
| pSZ2328 | 1 | 1.25 | 19.23 | 0.85 | 8.26 | 57.54 | 9.34 | 0.79 | 0.73 | 0.94 |
| pSZ2328 | 2 | 1.22 | 17.76 | 0.69 | 7.86 | 60.56 | 9.38 | 0.59 | 0.6 | 0.47 |
| pSZ2328 | 3 | 1.26 | 18.37 | 0.92 | 7.83 | 58.77 | 10.01 | 0.72 | 0.64 | 0.52 |
| pSZ2324 | 1 | 1.51 | 22.97 | 1.09 | 8.71 | 53.01 | 9.63 | 0.65 | 0.68 | 0.55 |
| pSZ2324 | 2 | 1.29 | 20.6 | 0.92 | 7.53 | 56.97 | 9.92 | 0.73 | 0.64 | 0.43 |
| pSZ2324 | 3 | 1.28 | 20.59 | 0.93 | 7.33 | 57.52 | 9.68 | 0.65 | 0.58 | 0.42 |
| pSZ2323 | 1 | 1.65 | 27.27 | 0.67 | 3.56 | 56.68 | 8.72 | 0.33 | 0.36 | 0.00 |
| pSZ2323 | 2 | 1.56 | 28.44 | 0.74 | 3.36 | 55.22 | 9.07 | 0.46 | 0.39 | 0.03 |
| pSZ2323 | 3 | 1.64 | 28.7 | 0.75 | 3.34 | 55.29 | 8.59 | 0.49 | 0.36 | 0.02 |

The data presented in Table 31 show a clear impact of the expression of *Marchantia polymorpha* and *Trypanosoma brucei* enzymes on the C14, C16, C18:0, C20:0, and C22:2n6 fatty acid profiles of the transformed organisms. The fatty acid profile of untransformed Strain J was about 27.42% C16:0, about 3% C18:0, about 57.5% C18:1, about 0.3% C20:0 and about 0.03% C22:2n6 fatty acids. In contrast to that of Strain J, the fatty acid profiles of Strain J transformed with different plasmid constructs to express elongases comprised lower percentage levels of C16 and higher percentage levels of C18:0, C20:0, and C22:2n6 fatty acids. The result of overexpression of *Marchantia polymorpha* elongase was about a 2.5 fold increase in percentage levels of C18:0 fatty acids, a 2 fold increase in percentage levels of C20:0 fatty acids, and about a 15 to 30 fold increase in percentage levels of C22:2n6 fatty acids relative to the fatty acid profile of Strain J.

These data illustrate the successful use of polynucleotides encoding elongases for expression in *Prototheca moriformis* (UTEX 1435) to alter the fatty acid profile of engineered microbes, and in particular in increasing the concentration of C18:0, C20:0, and C22:2n6 fatty acids and decreasing C16:0 fatty acids in recombinant microbial cells.

Example 41

Engineering Microorganisms for Increased Production of Stearic Acid Through Acyl-ACP Thioesterase Overexpression This example describes the use of recombinant polynucleotides that encode different C18:0-preferring acyl-ACP thioesterases to engineer microorganisms in which the fatty acid profiles of the transformed microorganisms have been enriched in stearic acid.

Classically mutagenized strains of *Prototheca moriformis* (UTEX 1435), Strain J or Strain A, were transformed independently with the constructs listed in Table 32 according to biolistic transformation methods as described in PCT/US2009/066141, PCT/US2009/066142, PCT/US2011/038463, PCT/US2011/038464, and PCT/US2012/023696. Each of the constructs included a protein coding region to overexpress a fatty acyl-ACP thioesterase with a C-terminal 3×FLAG® epitope tag, 5' (SEQ ID NO: 1) and 3' (SEQ ID NO: 2) homologous recombination targeting sequences (flanking the construct) to the 6S genomic region for integration into the nuclear genome, and a *S. cerevisiae* suc2 sucrose invertase coding region (SEQ ID NO: 4) to express the protein sequence given in SEQ ID NO: 3 under the control of *C. reinhardtii* β-tubulin promoter/5'UTR (SEQ ID NO: 5) and *Chlorella vulgaris* nitrate reductase 3' UTR (SEQ ID NO: 6). This *S. cerevisiae* suc2 expression cassette is listed as SEQ ID NO: 7 and served as a selectable marker. Sequence listing identities for the polynucleotides corresponding to each thioesterase are listed in Table 32. The polynucleotide sequence encoding each thioesterase was under control of the *P. moriformis* Amt03 promoter/5'UTR (SEQ ID NO: 8) and *C. vulgaris* nitrate reductase 3' UTR (SEQ ID NO: 6). The protein coding regions of the exogenous thioesterases and the suc2 expression cassette were codon optimized to reflect the codon bias inherent in *P. moriformis* UTEX 1435 nuclear genes as described in PCT/US2009/066141, PCT/US2009/066142, PCT/US2011/038463, PCT/US2011/038464, and PCT/US2012/023696.

TABLE 32

Plasmid constructs used to transform *Prototheca moriformis* (UTEX 1435) Strain A or Strain J.

| Plasmid construct | Acyl-ACP Thioesterase, GenBank Accession No. | Acyl-ACP Thioesterase source | Transit Peptide source | SEQ ID NO: |
|---|---|---|---|---|
| pSZD581 | FATA, CAA52070 | *Brassica napus* | native | 64, 65 |
| pSZD643 | FATA, CAA52070 | *Brassica napus* | UTEX 250 SAD | 66, 67 |
| pSZD645 | FATA, AAA33019 | *C. tinctorius* | UTEX 250 SAD | 68, 69 |
| pSZD644 | FATA, ABS30422 | *Ricinis communis* | native | 70, 71 |
| pSZD1323 | FATA, AAB51523 | *G. mangostana* | native | 72, 73 |
| pSZD1320 | FATA | *Theobroma cacao* | native | 74, 75 |

Upon independent transformation of Strain A or J with the constructs listed in Table 32, positive clones were selected on agar plates containing sucrose as a sole carbon source. Individual transformants were clonally purified and propagated under heterotrophic conditions suitable for lipid production as those detailed in PCT/US2009/066141, PCT/US2009/066142, PCT/US2011/038463, PCT/US2011/038464, and PCT/US2012/023696. Lipid samples were prepared from dried biomass and analyzed using fatty acid methyl ester gas chromatography flame ionization detection methods as described in Example 1 (also see PCT/US2012/023696). The fatty acid profiles (expressed as Area % of total fatty acids) of *P. moriformis* UTEX 1435 Strain J propagated on glucose as a sole carbon source and representative isolates of each transformation of Strain J, propagated on sucrose as a sole carbon source are presented in Table 33.

TABLE 33

Fatty acid profiles of *Prototheca moriformis* (UTEX 1435) Strain J cells engineered to overexpress exogenous acyl-ACP thioesterase enzymes.

| Strain | Plasmid construct | No. | Fatty Acid Area % C14:0 | C16:0 | C18:0 | C18:1 | C18:2 | C18:3α |
|---|---|---|---|---|---|---|---|---|
| A | None | 1 | 1.08 | 25.48 | 3.23 | 59.70 | 8.25 | 0.70 |
| J | None | 1 | 1.41 | 27.33 | 3.38 | 57.07 | 8.15 | 0.64 |
| A | pSZD581 | 1 | 1.02 | 26.60 | 14.47 | 44.80 | 10.05 | 0.65 |
| | | 2 | 1.08 | 28.24 | 13.57 | 43.89 | 10.07 | 0.68 |
| | | 3 | 0.97 | 24.70 | 9.13 | 50.85 | 11.27 | 0.82 |
| A | pSZD643 | 1 | 1.39 | 26.97 | 16.21 | 44.10 | 8.43 | 0.83 |
| | | 2 | 1.37 | 27.91 | 11.15 | 48.31 | 8.40 | 0.78 |
| A | pSZD645 | 1 | 0.90 | 23.39 | 8.35 | 50.69 | 13.34 | 0.96 |
| A | pSZD644 | 1 | 1.67 | 19.70 | 4.40 | 59.15 | 12.32 | 1.01 |
| J | pSZD1323 | 1 | 1.33 | 23.26 | 9.28 | 53.42 | 10.35 | 0.69 |
| | | 2 | 1.47 | 26.84 | 7.36 | 52.78 | 9.29 | 0.64 |
| | | 3 | 1.43 | 26.31 | 6.05 | 54.45 | 9.37 | 0.66 |
| J | pSZD1320 | 1 | 1.30 | 24.76 | 3.84 | 60.90 | 6.96 | 0.55 |
| | | 2 | 1.36 | 26.30 | 3.27 | 58.19 | 8.66 | 0.48 |
| | | 3 | 1.39 | 25.51 | 3.18 | 58.78 | 8.85 | 0.45 |

The data presented in Table 33 show a clear impact of the expression of exogenous acyl-ACP enzymes on the fatty acid profiles of the transformed microorganisms. The fatty acid profiles of untransformed Strain A and J were about 25% C16:0, about 3.3% C18:0, about 57 to 60% C18:1. In contrast, the fatty acid profiles of Strain A transformed with different plasmid constructs to express acyl-ACP enzymes comprised greater percentage levels of C18:0 and lower percentage levels of C18:1 fatty acids than that of Strain A. Expression of FATA enzymes from *B. napus, C. tinctorius, R. communis* and *G. mangostana* in Strain A or J enabled the accumulation of stearate levels in the transformed organisms. The result of overexpression of a *Brassica napus* acyl-ACP thioestearse was about a 2 to 5 fold increase in the percentage levels of C18:0 fatty acids of the fatty acid profile of the transformed organisms relative to the fatty acid profile of Strain A. Fatty acid profiles of cells engineered to overexpress a *G. mangostana* acyl-ACP FATA thioesterase with a *C. protothecoides* SAD1 transit peptide were characterized by about a 2 to 3 fold increase in the percentage levels of C18:0 fatty acids of the fatty acid profile of the transformed organism relative to the fatty acid profile of Strain J.

These data illustrate the utility and effective use of polynucleotides encoding fatty acyl-ACP thioesterases for expression in *Prototheca moriformis* (UTEX 1435) to alter the fatty acid profile of engineered microbes, and in particular in increasing the concentration of C18:0 and decreasing C18:1 fatty acids in recombinant microbial cells.

Example 42

Engineering Microorganisms for Increased Production of Erucic Acid Through Elongase or Beta-Ketoacyl-CoA Synthase Overexpression In an embodiment of the present invention, a recombinant polynucleotide transformation vector operable to express an exogenous elongase or beta-ketoacyl-CoA synthase in an optionally plastidic oleaginous microbe is constructed and employed to transform *Prototheca moriformis* (UTEX 1435) according to the biolistic transformation methods as described in PCT/US2009/066141, PCT/US2009/066142, PCT/US2011/038463, PCT/US2011/038464, and PCT/US2012/023696 to obtain a cell increased for production of erucic acid. The transformation vector includes a protein coding region to overexpress an elongase or beta-ketoacyl-CoA synthase such as those listed in Table 5, promoter and 3'UTR control sequences to regulate expression of the exogenous gene, 5' and 3' homologous recombination targeting sequences targeting the recombinant polynucleotides for integration into the *P. moriformis* (UTEX 1435) nuclear genome, and nucleotides operable to express a selectable marker. The protein-coding sequences of the transformation vector are codon-optimized for expression in *P. moriformis* (UTEX 1435) as described in PCT/US2009/066141, PCT/US2009/066142, PCT/US2011/038463, PCT/US2011/038464, and PCT/US2012/023696. Recombinant polynucleotides encoding promoters, 3' UTRs, and selectable markers operable for expression in *P. moriformis* (UTEX 1435) are disclosed herein and in PCT/US2009/066141, PCT/US2009/066142, PCT/US2011/038463, PCT/US2011/038464, and PCT/US2012/023696.

Upon transformation of the transformation vector into *P. moriformis* (UTEX 1435) or a classically-mutagenized strain of *P. moriformis* (UTEX 1435), positive clones are selected on agar plates. Individual transformants are clonally purified and cultivated under heterotrophic conditions suitable for lipid production as detailed in PCT/US2009/066141, PCT/US2009/066142, PCT/US2011/038463, PCT/US2011/038464, and PCT/US2012/023696. Lipid samples are prepared from dried biomass from each transformant and fatty acid profiles from these samples are analyzed using fatty acid methyl ester gas chromatography flame ionization (FAME GC/FID) detection methods as described in Example 1. As a result of these manipulations, the cell may exhibit an increase in erucic acid of at least 5, 10, 15, or 20 fold.

Example 43

Generation of Capric, Lauric, and Myristic Acid Rich Oils in Strain UTEX1435 by the Expression of *Cuphea* PSR23LPAATs We tested the effect of expression of two 1-acyl-sn-glycerol-3-phosphate acyltransferases (LPAATs) in a previously described *P. moriformis* (UTEX 1435) transgenic strain, expressing the acyl ACP thioesterase (FATB2) from *Cuphea wrightii*. The LPAAT2 and LPAAT3 genes from *Cuphea* PSR23 (CuPSR23) were identified by analysis of a combination of CuPSR23 genomic sequences and transcriptomic sequences derived from seed RNAs. The two LPAATs have not been previously described. The genes were codon optimized to reflect UTEX 1435 codon usage. Transformations, cell culture, lipid production and fatty acid analysis were all carried out as previously described.

Increased Capric, Lauric, and Myristic Accumulation in Strain B by the Expression of the *Cuphea* PSR23 1-Acyl-Sn-Glycerol-3-Phosphate Acyltransferases (LPAAT2 and LPAAT3) [pSZ2299 and pSZ2300, Respectively]:

In this example, transgenic strains were generated via transformation of strain B with the constructs pSZ2299 or pSZ2300, encoding CuPSR23LPAAT2 and LPAAT3, respectively. The transgenic strains were selected for resistance to the antibiotic G418. Construct pSZ2299 can be written as pLOOP5'::CrTUB2:NeoR:CvNR::PmAMT3:CuPSR23LPAAT2-1:CvNR::pLOOP3'. Construct pSZ2300 can be written as pLOOP5'::CrTUB2:NeoR:CvNR::PmAMT3:CuPSR23LPAAT3-1:CvNR::pLOOP3'. The sequence of the transforming DNA (pSZ2299 and pSZ2300) is provided below. The relevant restriction sites in the construct from 5'-3', BspQI, KpnI, XbaI, Mfe I, BamHI, EcoRI, SpeI, XhoI, SacI, BspQI, respectively, are indicated in lowercase, bold, and underlined. BspQI sites delimit the 5' and 3' ends of the transforming DNA. Bold, lowercase sequences at the 5' and 3' end of the construct represent genomic DNA from UTEX 1435 that target integration to the pLoop locus via homologous recombination. Proceeding in the 5' to 3' direction, the selection cassette has the *C. reinhardtii* β-tubulin promoter driving expression of the NeoR gene (conferring resistance to G418) and the *Chlorella vulgaris* Nitrate Reductase (NR) gene 3' UTR. The promoter is indicated by lowercase, boxed text. The initiator ATG and terminator TGA for NeoR are indicated by uppercase italics, while the coding region is indicated with lowercase italics. The 3' UTR is indicated by lowercase underlined text. The spacer region between the two cassettes is indicated by upper case text. The second cassette containing the codon optimized LPAAT2 gene (pSZ2299) or LPAAT3 gene (pSZ2300) from *Cuphea* PSR23 is driven by the *Prototheca moriformis* endogenous AMT3 promoter, and has the same *Chlorella vulgaris* Nitrate Reductase (NR) gene 3' UTR. In this cassette, the AMT3 promoter in indicated by lowercase, boxed text. The initiator ATG and terminator TGA for the CuPSR23LPAAT2 and LPAAT3 genes are indicated in uppercase italics, while the coding regions are indicated by lowercase italics. The 3' UTR is indicated by lowercase underlined text. The final constructs were sequenced to ensure correct reading frames and targeting sequences.

pSZ2299 Transforming Construct (SEQ ID NO: 90)

gctcttccgctaacggaggtctgtcaccaaatggaccccgtctattgcgggaaaccacggcgatggcacgtttcaaaacttgat gaaatacaatattcagtatgtcgcgggcggcgacggcggggagctgatgtcgcgctgggtattgcttaatcgccagcttcgcc cccgtcttggcgcgaggcgtgaacaagccgaccgatgtgcacgagcaaatcctgacactagaagggctgactcgcccggca cggctgaattacacaggcttgcaaaaataccagaatttgcacgcaccgtattcgcggtattttgttggacagtgaatagcgatg cggcaatggcttgtggcgttagaaggtgcgacgaaggtggtgccaccactgtgccagccagtcctggcggctcccagggccc cgatcaagagccaggacatccaaactacccacagcatcaacgccccggcctatactcgaaccccacttgcactctgcaatggt atgggaaccacggggcagtcttgtgtgggtcgcgcctatcgcggtcggcgaagaccgggaaggtaccctttcttgcgctatgac acttccagcaaaaggtagggcgggctgcgagacggcttcccggcgctgcatgcaacaccgatgatgcttcgacccccgaagctcc ttcggggctgcatgggcgctccgatgccgctccagggcgagcgctgtttaaatagccaggcccccgattgcaaagacattatagcga gctaccaaagccatattcaaacacctagatcactaccacttctacacaggccactcgagcttgtgatcgcactccgctaagggggcgc ctcttcctcttcgtttcagtcacaacccgcaaactctagaatatca*ATGatcgagcaggacggcctccacgccggctcccccgccg*

*cctgggtggagcgcctgttcggctacgactgggcccagcagaccatcggctgctccgacgccgccgtgttccgcctgtccgccca*

*gggccgccccgtgctgttcgtgaagaccgacctgtccggcgccctgaacgagctgcaggacgaggccgcccgcctgtcctggct*

*ggccaccaccggcgtgccctgcgccgccgtgctggacgtggtgaccgaggccggccgcgactggctgctgctgggcgaggtgc*

*ccggccaggacctgctgtcctcccacctggcccccgccgagaaggtgtccatcatggccgacgccatgcgccgcctgcacaccc*

*tggaccccgccacctgccccttcgaccaccaggccaagcaccgcatcgagcgcgcccgcacccgcatggaggccggcctggtg*

*gaccaggacgacctggacgaggagcaccagggcctggcccccgccgagctgttcgcccgcctgaaggcccgcatgcccgacg*

*gcgaggacctggtggtgacccacggcgacgcctgcctgcccaacatcatggtggagaacggccgcttctccggcttcatcgactg*

*cggccgcctgggcgtggccgaccgctaccaggacatcgccctggccacccgcgacatcgccgaggagctgggcggcgagtgg*

*gccgaccgcttcctggtgctgtacggcatcgccgcccccgactcccagcgcatcgccttctaccgcctgctggacgagttcttcTG*

*A*caattggcagcagcagctcggatagtatcgacacactctggacgctggtcgtgtgatggactgttgccgccacacttgctgccttga cctgtgaatatccctgccgcttttatcaaacagcctcagtgtgtttgatcttgtgtgtacgcgcttttgcgagttgctagctgcttgtgctattt gcgaataccacccccagcatccccttccctcgtttcatatcgcttgcatcccaaccgcaacttatctacgctgtcctgctatccctcagcg ctgctcctgctcctgctcactgcccctcgcacagccttggtttgggctccgcctgtattctcctggtactgcaacctgtaaaccagcactg caatgctgatgcacgggaagtagtgggatgggaacacaaatggaggatccCGCGTCTCGAACAGAGCGCGCA

GAGGAACGCTGAAGGTCTCGCCTCTGTCGCACCTCAGCGCGGCATACACCACAA

TAACCACCTGACGAATGCGCTTGGTTCTTCGTCCATTAGCGAAGCGTCCGGTTCA

CACACGTGCCACGTTGGCGAGGTGGCAGGTGACAATGATCGGTGGAGCTGATGG

TCGAAACGTTCACAGCCTAGGGATATCgaattc*ggccgacaggacgcgcgtcaaaggtgctggtcgtgt*

*atgccctggccggcaggtcgttgctgctgctggttagtgattccgcaaccctgattttggcgtcttattttggcgtggcaaacgctggc*

*gcccgcgagccgggccggcggcgatgcggtgccccacggctgccggaatccaagggaggcaagagcgcccgggtcagttga*

*agggctttacgcgcaaggtacagccgctcctgcaaggctgcgtggtggaattggacgtgcaggtcctgctgaagttcctccaccg*

-continued cctcaccagcggacaaagcaccggtgtatcaggtccgtgtcatccactctaaagagctcgactacgacctactgatggccctaga ttcttcatcaaaaacgcctgagacacttgcccaggattgaaactccctgaagggaccaccaggggccctgagttgttccttcccc cgtggcgagctgccagccaggctgtacctgtgatcgaggctggcgggaaaataggcttcgtgtgctcaggtcatgggaggtgca ggacagctcatgaaacgccaacaatcgcacaattcatgtcaagctaatcagctatttcctcttcacgagctgtaattgtcccaaaat tctggtctaccggggtgatccttcgtgtacgggcccttccctcaaccctaggtatgcgcgcatgcggtcgccgcgcaactcgcgc gagggccgagggtttgggacgggccgtcccgaaatgcagttgcacccggatgcgtggcacctttttttgcgataatttatgcaatgg actgctctgcaaaattctggctctgtcgccaaccctaggatcagcggcgtaggatttcgtaatcattcgtcctgatggggagctacc gactaccctaatatcagcccgactgcctgacgccagcgtccacttttgtgcacacattccattcgtgcccaagacatttcattgtggt gcgaagcgtccccagttacgctcacctgtttcccgacctccttactgttctgtcgacagagcgggcccacaggccggtcgcagcc actagtATGgcgatcgcggccgcggcggtgatcttcctgttcggcctgatcttcttcgcctccggcctgatcatcaacctgttccagg cgctgtgcttcgtcctgatccgcccctgtccaagaacgcctaccgccgcatcaaccgcgtgttcgcggagctgctgctgtccgagc tgctgtgcctgttcgactggtgggcgggcgcgaagctgaagctgttcaccgaccccgagacgttccgcctgatgggcaaggagca cgccctggtcatcatcaaccacatgaccgagctggactggatggtgggctgggtgatgggccagcacttcggctgcctgggctcc atcatctccgtcgccaagaagtccacgaagttcctgcccgtgctgggctggtccatgtggttctccgagtacctgtacctggagcgct cctgggccaaggacaagtccaccctgaagtcccacatcgagcgcctgatcgactacccccctgcccttctggctggtcatcttcgtcg agggcacccgcttcacgcgcacgaagctgctggcggcccagcagtacgcggtctcctccggcctgcccgtcccccgcaacgtcc tgatcccccgcacgaagggcttcgtctcctgcgtgtcccacatgcgctccttcgtccccgcggtgtacgacgtcacggtggcgttccc caagacgtcccccccccccacgctgctgaacctgttcgagggccagtccatcatgctgcacgtgcacatcaagcgccacgccatg aaggacctgcccgagtccgacgacgccgtcgcggagtggtgccgcgacaagttcgtcgagaaggacgccctgctggacaagc acaacgcggaggacacgttctccggccaggaggtgtgccactccggctcccgccagctgaagtccctgctggtcgtgatctcctg ggtcgtggtgacgacgttcggcgccctgaagttcctgcagtggtcctcctggaagggcaaggcgttctccgccatcggcctgggca tcgtcaccctgctgatgcacgtgctgatcctgtcctcccaggccgagcgctccaaccccgccgaggtggcccaggccaagctgaa gaccggcctgtccatctccaagaaggtgacggacaaggagaacTGAttaattaactcgaggcagcagcagctcggatagtatc gacacactctggacgctggtcgtgtgatggactgttgccgccacacttgctgccttgacctgtgaatatccctgccgcttttatcaaacag cctcagtgtgtttgatcttgtgtgtacgcgcttttgcgagttgctagctgcttgtgctatttgcgaataccacccccagcatccccttccctcg tttcatatcgcttgcatcccaaccgcaacttatctacgctgtcctgctatccctcagcgctgctcctgctcctgctcactgcccctcgcaca gccttggtttgggctccgcctgtattctcctggtactgcaacctgtaaaccagcactgcaatgctgatgcacgggaagtagtgggatgg gaacacaaatggaaagcttgagctcagaggcgacggtcctgctaccgtacgacgttgggcacgcccatgaaagtttgtataccg agcttgttgagcgaactgcaagcgcggctcaaggatacttgaactcctggattgatatcggtccaataatggatggaaaatcc gaacctcgtgcaagaactgagcaaacctcgttacatggatgcacagtcgccagtccaatgaacattgaagtgagcgaactgtt cgcttcggtggcagtactactcaaagaatgagctgctgttaaaaatgcactctcgttctctcaagtgagtggcagatgagtgctc

-continued acgccttgcacttcgctgcccgtgtcatgccctgcgccccaaaatttgaaaaaagggatgagattattgggcaatggacgacgt cgtcgctccgggagtcaggaccggcggaaaataagaggcaacacactccgcttcttagctcttcg pSZ2300 Transforming Construct (SEQ ID NO: 91)

gctcttccgctaacggaggtctgtcaccaaatggaccccgtctattgcgggaaaccacggcgatggcacgtttcaaaacttgat gaaatacaatattcagtatgtcgcgggcggcgacggcggggagctgatgtcgcgctgggtattgcttaatcgccagcttcgcc cccgtcttggcgcgaggcgtgaacaagccgaccgatgtgcacgagcaaatcctgacactagaagggctgactcgcccggca cggctgaattacacaggcttgcaaaaataccagaatttgcacgcaccgtattcgcggtattttgttggacagtgaatagcgatg cggcaatggcttgtggcgttagaaggtgcgacgaaggtggtgccaccactgtgccagccagtcctggcggctcccagggccc cgatcaagagccaggacatccaaactacccacagcatcaacgccccggcctatactcgaaccccacttgcactctgcaatggt atgggaaccacggggcagtcttgtgtgggtcgcgcctatcgcggtcggcgaagaccgggaaggtaccctttcttgcgctatgac acttccagcaaaaggtagggcgggctgcgagacggcttcccggcgctgcatgcaacaccgatgatgcttcgacccccccgaagctcc ttcggggctgcatgggcgctccgatgccgctccagggcgagcgctgtttaaatagccaggcccccgattgcaaagacattatagcga gctaccaaagccatattcaaacacctagatcactaccacttctacacaggccactcgagcttgtgatcgcactccgctaagggggcgc ctcttcctcttcgtttcagtcacaacccgcaaactctagaatatca*ATGatcgagcaggacggcctccacgccggctcccccgccg*

*cctgggtggagcgcctgttcggctacgactgggcccagcagaccatcggctgctccgacgccgccgtgttccgcctgtccgccca*

*gggccgccccgtgctgttcgtgaagaccgacctgtccggcgccctgaacgagctgcaggacgaggccgcccgcctgtcctggct*

*ggccaccaccggcgtgccctgcgccgccgtgctggacgtggtgaccgaggccggccgcgactggctgctgctgggcgaggtgc*

*ccggccaggacctgctgtcctcccacctggcccccgccgagaaggtgtccatcatggccgacgccatgcgccgcctgcacaccc*

*tggaccccgccacctgccccacgaccaccaggccaagcaccgcatcgagcgcgcccgcacccgcatggaggccggcctggtg*

*gaccaggacgacctggacgaggagcaccagggcctggcccccgccgagctgttcgcccgcctgaaggcccgcatgcccgacg*

*gcgaggacctggtggtgacccacggcgacgcctgcctgcccaacatcatggtggagaacggccgcttctccggcttcatcgactg*

*cggccgcctgggcgtggccgaccgctaccaggacatcgccctggccacccgcgacatcgccgaggagctgggcggcgagtgg*

*gccgaccgcttcctggtgctgtacggcatcgccgcccccgactcccagcgcatcgccttctaccgcctgctggacgagttcttcTG*

*A*caattggcagcagcagctcggatagtatcgacacactctggacgctggtcgtgtgatggactgttgccgccacacttgctgccttga cctgtgaatatccctgccgcttttatcaaacagcctcagtgtgtttgatcttgtgtgtacgcgcttttgcgagttgctagctgcttgtgctattt gcgaataccacccccagcatccccttccctcgtttcatatcgcttgcatcccaaccgcaacttatctacgctgtcctgctatccctcagcg ctgctcctgctcctgctcactgcccctcgcacagccttggtttgggctccgcctgtattctcctggtactgcaacctgtaaaccagcactg caatgctgatgcacgggaagtagtgggatgggaacacaaatggaggatccCGCGTCTCGAACAGAGCGCGCA

GAGGAACGCTGAAGGTCTCGCCTCTGTCGCACCTCAGCGCGGCATACACCACAA

TAACCACCTGACGAATGCGCTTGGTTCTTCGTCCATTAGCGAAGCGTCCGGTTCA

CACACGTGCCACGTTGGCGAGGTGGCAGGTGACAATGATCGGTGGAGCTGATGG

TCGAAACGTTCACAGCCTAGGGATATCgaattc*ggccgacaggacgcgcgtcaaaggtgctggtcgtgt*

*atgccctggccggcaggtcgttgctgctgctggttagtgattccgcaaccctgattttggcgtcttattttggcgtggcaaacgctggc*

-continued gcccgcgagccgggccggcggcgatgcggtgccccacggctgccggaatccaagggaggcaagagcgcccgggtcagttga agggctttacgcgcaaggtacagccgctcctgcaaggctgcgtggtggaattggacgtgcaggtcctgctgaagttcctccaccg cctcaccagcggacaaagcaccggtgtatcaggtccgtgtcatccactctaaagagctcgactacgacctactgatggccctaga ttcttcatcaaaaacgcctgagacacttgcccaggattgaaactccctgaagggaccaccaggggccctgagttgttccttccccc cgtggcgagctgccagccaggctgtacctgtgatcgaggctggcgggaaaataggcttcgtgtgctcaggtcatgggaggtgca ggacagctcatgaaacgccaacaatcgcacaattcatgtcaagctaatcagctatttcctcttcacgagctgtaattgtcccaaaat tctggtctaccgggggtgatccttcgtgtacgggcccttccctcaaccctaggtatgcgcgcatgcggtcgccgcgcaactcgcgc gagggccgagggtttgggacgggccgtcccgaaatgcagttgcacccggatgcgtggcacctttttttgcgataatttatgcaatgg actgctctgcaaaattctggctctgtcgccaaccctaggatcagcggcgtaggatttcgtaatcattcgtcctgatggggagctacc gactaccctaatatcagcccgactgcctgacgccagcgtccacttttgtgcacacattccattcgtgcccaagacatttcattgtggt gcgaagcgtccccagttacgctcacctgtttcccgacctccttactgttctgtcgacagagcgggcccacaggccggtcgcagcc actagtATGgccatcgcggcggccgcggtgatcgtgcccctgtccctgctgttcttcgtgtccggcctgatcgtcaacctggtgcag gccgtctgcttcgtcctgatccgccccctgtccaagaacacgtaccgccgcatcaaccgcgtggtcgcggagctgctgtggctgga gctggtgtggctgatcgactggtgggcgggcgtgaagatcaaggtcttcacggaccacgagacgttccacctgatgggcaagga gcacgccctggtcatctgcaaccacaagtccgacatcgactggctggtcggctgggtcctgggccagcgctccggctgcctgggc tccaccctggcggtcatgaagaagtcctccaagttcctgcccgtcctgggctggtccatgtggttctccgagtacctgttcctggagc gctcctgggccaaggacgagatcacgctgaagtccggcctgaaccgcctgaaggactaccccctgcccttctggctggcgctgtt cgtggagggcacgcgcttcacccgcgcgaagctgctggcggcgcagcagtacgccgcgtcctccggcctgcccgtgccccgca acgtgctgatcccccgcacgaagggcttcgtgtcctccgtgtcccacatgcgctccttcgtgcccgcgatctacgacgtcaccgtgg ccatccccaagacgtcccccccccccacgctgatccgcatgttcaagggccagtcctccgtgctgcacgtgcacctgaagcgcca cctgatgaaggacctgcccgagtccgacgacgccgtcgcgcagtggtgccgcgacatcttcgtggagaaggacgcgctgctgg acaagcacaacgccgaggacaccttctccggccaggagctgcaggagaccggccgccccatcaagtccctgctggtcgtcatct cctgggccgtcctggaggtgttcggcgccgtcaagttcctgcagtggtcctccctgctgtcctcctggaagggcctggcgttctccgg catcggcctgggcgtgatcaccctgctgatgcacatcctgatcctgttctcccagtccgagcgctccacccccgccaaggtggccc ccgcgaagcccaagaacgagggcgagtcctccaagaccgagatggagaaggagaagTGAttaattaactcgaggcagcag cagctcggatagtatcgacacactctggacgctggtcgtgtgatggactgttgccgccacacttgctgccttgacctgtgaatatccctg ccgcttttatcaaacagcctcagtgtgtttgatcttgtgtgtacgcgcttttgcgagttgctagctgcttgtgctatttgcgaataccaccccc agcatccccttccctcgtttcatatcgcttgcatcccaaccgcaacttatctacgctgtcctgctatccctcagcgctgctcctgctcctgct cactgcccctcgcacagccttggtttgggctccgcctgtattctcctggtactgcaacctgtaaaccagcactgcaatgctgatgcacgg gaagtagtgggatgggaacacaaatggaaagcttgagctcagcggcgacggtcctgctaccgtacgacgttgggcacgcccatg aaagtttgtataccgagcttgttgagcgaactgcaagcgcggctcaaggatacttgaactcctggattgatatcggtccaataa tggatggaaaatccgaacctcgtgcaagaactgagcaaacctcgttacatggatgcacagtcgccagtccaatgaacattga agtgagcgaactgttcgcttcggtggcagtactactcaaagaatgagctgctgttaaaaatgcactctcgttctctcaagtgagt

-continued

```
ggcagatgagtgctcacgccttgcacttcgctgcccgtgtcatgccctgcgccccaaaatttgaaaaaagggatgagattattg

ggcaatggacgacgtcgtcgctccgggagtcaggaccggcggaaaataagaggcaacacactccgcttcttagctcttcg
```

To determine the impact of the CuPSR23LPAAT2 and LPAAT3 genes on mid-chain fatty acid accumulation, the above constructs containing the codon optimized CuPSR23 LPAAT2 or LPAAT3 genes driven by the UTEX 1453 AMT3 promoter were transformed into strain B.

Primary transformants were clonally purified and grown under standard lipid production conditions at pH7.0 (all the strains require growth at pH 7.0 to allow for maximal expression of the CuPSR23LPAAT2 or LPAAT3 gene driven by the pH-regulated AMT3 promoter). The resulting profiles from a set of representative clones arising from these transformations are shown in Table 34, below. D1520 represents clones of Strain B with CuPSR23LPAAT2 and D1521 represents clones of Strain B with CuPSR23LPAAT3.

TABLE 34

Fatty acid profiles of Strain B and representative transgenic lines transformed with pSZ2299 and pSZ2300 DNA.

| Sample ID | C10:0 | C12:0 | C14:0 | C16:0 | C18:0 | C18:1 | C18:2 |
|---|---|---|---|---|---|---|---|
| Strain B | 4.83 | 28.54 | 15.64 | 12.64 | 1.3 | 27.99 | 7.75 |
| D1520-A | 8.59 | 35.09 | 16.55 | 11.96 | 1.69 | 19.49 | 5.59 |
| D1520-B | 8.13 | 33.93 | 16.46 | 12.44 | 1.57 | 20.66 | 5.96 |
| D1520-C | 7.6 | 33.1 | 16.21 | 12.65 | 1.5 | 21.41 | 6.48 |
| D1520-D | 7.35 | 32.54 | 16.03 | 12.79 | 1.67 | 22.16 | 6.41 |
| D1520-E | 7.28 | 32.21 | 16.2 | 12.99 | 1.73 | 22.39 | 6.28 |
| D1521-A | 6.14 | 31.5 | 15.98 | 12.96 | 1.96 | 22.52 | 8 |
| D1521-B | 6.17 | 31.38 | 15.98 | 12.87 | 2.08 | 22.54 | 7.92 |
| D1521-C | 5.99 | 31.31 | 15.75 | 12.79 | 2.23 | 22.45 | 8.36 |
| D1521-D | 5.95 | 31.05 | 15.71 | 12.84 | 2.48 | 22.69 | 8.32 |
| D1521-E | 5.91 | 30.58 | 15.85 | 13.22 | 1.97 | 23.55 | 7.84 |

The transgenic CuPSR23LPAAT2 strains (D1520A-E) show a significant increase in the accumulation of C10:0, C12:0, and C14:0 fatty acids with a concomitant decrease in C18:1 and C18:2. The transgenic CuPSR23LPAAT3 strains (D1521A-E) show a significant increase in the accumulation of C10:0, C12:0, and C14:0 fatty acids with a concomitant decrease in C18:1. The expression of the CuPSR23LPAAT in these transgenic lines appears to be directly responsible for the increased accumulation of mid-chain fatty acids in general, and especially laurates. While the transgenic lines show a shift from longer chain fatty acids (C16:0 and above) to mid-chain fatty acids, the shift is targeted predominantly to C10:0 and C12:0 fatty acids with a slight effect on C14:0 fatty acids. The data presented also show that co-expression of the LPAAT2 and LPAAT3 genes from *Cuphea* PSR23 and the FATB2 from *C. wrightii* (expressed in the strain Strain B) have an additive effect on the accumulation of C12:0 fatty acids.

Our results suggest that the LPAAT enzymes from *Cuphea* PSR23 are active in the algal strains derived from UTEX 1435. These results also demonstrate that the enzyme functions in conjunction with the heterologous FatB2 acyl-ACP thioesterase enzyme expressed in Strain B, which is derived from *Cuphea wrightii.*

Example 44

Alteration of Fatty Acid Levels in Strain UTEX1435 by the Expression of *Cuphea* Psr23LPAATX in Combination with *Cuphea wrightii* FATB2

Here we demonstrate the effect of expression of a 1-acyl-sn-glycerol-3-phosphate acyltransferase (LPAAT) in a previously described *P. moriformis* (UTEX 1435) transgenic strain, Strain B. As described above, Strain B is a transgenic strain expressing the acyl ACP thioesterase (FATB2) from *Cuphea wrightii*, which accumulates C12:0 fatty acids between 40 to 49%. Further to Example 43, a third CuPSR23LPAAT, LPAATx, was identified by analysis of a combination of CuPSR23 genomic sequences and transcriptomic sequences derived from seed RNAs. Expression of a mid-chain specific LPAAT should thus increase the percentage of TAGs that have a capric acid (C10:0 fatty acid), lauric acid (C12:0 fatty acid), or myrisitc acid (C14:0 fatty acid) at the sn-2 position, and should consequently elevate the overall levels of these fatty acids. In Example 43, LPAAT2 and LPAAT3 were shown to increase caprate, laurate, and myristate accumulation in strain B. LPAATx was introduced into strain B to determine its effect on fatty acid levels in this strain. The LPAATx gene was codon optimized to reflect UTEX 1435 codon usage. Transformations, cell culture, lipid production and fatty acid analysis were all carried out as previously described.

Decreased Caprate, Laurate, and Myristate Accumulation and Increased Palmitate and Stearate Accumulation in Strain Strain B by the Expression of the *Cuphea* PSR23 1-Acyl-Sn-Glycerol-3-Phosphate Acyltransferase (LPAATx) [pSZ2575]:

In this example, transgenic strains were generated via transformation of strain B with the construct pSZ2575 encoding CuPSR23LPAATx. The transgenic strains were selected for resistance to the antibiotic G418. Construct pSZ2575 can be written as pLOOP5'::CrTUB2:NeoR:CvNR::PmAMT3:CuPSR23LPAATx:CvNR::pLOOP3'. The sequence of the transforming DNA is provided below (pSZ2575). The relevant restriction sites in the construct from 5'-3', BspQ1, KpnI, XbaI, MfeI, BamHI, EcoRI, SpeI, XhoI, SacI, BspQ1, respectively, are indicated in lowercase, bold, and underlined. BspQ1 sites delimit the 5' and 3' ends of the transforming DNA. Bold, lowercase sequences at the 5' and 3' end of the construct represent genomic DNA from UTEX 1435 that target integration to the pLoop locus via homologous recombination. Proceeding in the 5' to 3' direction, the selection cassette has the *C. reinhardtii* β-tubulin promoter driving expression of the NeoR gene (conferring resistance to G418) and the *Chlorella vulgaris* Nitrate Reductase (NR) gene 3' UTR. The promoter is indicated by lowercase, boxed text. The initiator ATG and terminator TGA for NeoR are indicated by uppercase italics, while the coding region is indicated with lowercase italics. The 3' UTR is indicated by lowercase underlined text. The spacer region between the two cassettes is indicated by upper case text. The second cassette containing the codon optimized LPAATx gene (pSZ2575) from *Cuphea* PSR23 is driven by the *Prototheca moriformis* endogenous AMT3 promoter, and has the same *Chlorella vulgaris* Nitrate Reductase (NR) gene 3' UTR. In this cassette, the AMT3 promoter is indicated by lowercase, boxed text. The initiator ATG and terminator TGA for the CuPSR23LPAATx genes are indicated in uppercase italics, while the coding region is indicated by lowercase italics. The 3' UTR is indicated by lowercase underlined text. The final construct was sequenced to ensure correct reading frame and targeting sequences.

pSZ2575 Transforming Construct (SEQ ID NO: 92)

gctcttccgctaacggaggtctgtcaccaaatggaccccgtctattgcgggaaaccacggcgatggcacgtttcaaaacttgat gaaatacaatattcagtatgtcgcgggcggcgacggcggggagctgatgtcgcgctgggtattgcttaatcgccagcttcgcc cccgtcttggcgcgaggcgtgaacaagccgaccgatgtgcacgagcaaatcctgacactagaagggctgactcgcccggca cggctgaattacacaggcttgcaaaaataccagaatttgcacgcaccgtattcgcggtattttgttggacagtgaatagcgatg cggcaatggcttgtggcgttagaaggtgcgacgaaggtggtgccaccactgtgccagccagtcctggcggctcccagggccc cgatcaagagccaggacatccaaactacccacagcatcaacgccccggcctatactcgaaccccacttgcactctgcaatggt atgggaaccacggggcagtcttgtgtgggtcgcgcctatcgcggtcggcgaagaccgggaaggtaccctttcttgcgctatgac acttccagcaaaaggtagggcgggctgcgagacggcttcccggcgctgcatgcaacaccgatgatgcttcgacccccccgaagctcc ttcggggctgcatgggcgctccgatgccgctccagggcgagcgctgtttaaatagccaggcccccgattgcaaagacattatagcga gctaccaaagccatattcaaacacctagatcactaccacttctacacaggccactcgagcttgtgatcgcactccgctaagggggcgc ctcttcctcttcgtttcagtcacaacccgcaaactctagaatatcaATGatcgagcaggacggcctccacgccggctcccccgccg cctgggtggagcgcctgttcggctacgactgggcccagcagaccatcggctgctccgacgccgccgtgttccgcctgtccgccca gggccgccccgtgctgttcgtgaagaccgacctgtccggcgccctgaacgagctgcaggacgaggccgcccgcctgtcctggct ggccaccaccggcgtgccctgcgccgccgtgctggacgtggtgaccgaggccggccgcgactggctgctgctgggcgaggtgc ccggccaggacctgctgtcctcccacctggcccccgccgagaaggtgtccatcatggccgacgccatgcgccgcctgcacaccc tggaccccgccacctgccccttcgaccaccaggccaagcaccgcatcgagcgcgcccgcacccgcatggaggccggcctggtg gaccaggacgacctggacgaggagcaccagggcctggcccccgccgagctgttcgcccgcctgaaggcccgcatgcccgacg gcgaggacctggtggtgacccacggcgacgcctgcctgcccaacatcatggtggagaacggccgcttctccggcttcatcgactg cggccgcctgggcgtggccgaccgctaccaggacatcgccctggccacccgcgacatcgccgaggagctgggcggcgagtgg gccgaccgcttcctggtgctgtacggcatcgccgcccccgactcccagcgcatcgccttctaccgcctgctggacgagttcttcTG Acaattggcagcagcagctcggatagtatcgacacactctggacgctggtcgtgtgatggactgttgccgccacacttgctgccttga cctgtgaatatccctgccgcttttatcaaacagcctcagtgtgtttgatcttgtgtgtacgcgctttgcgagttgctagctgcttgtgctattt gcgaataccacccccagcatccccttccctcgtttcatatcgcttgcatcccaaccgcaacttatctacgctgtcctgctatccctcagcg ctgctcctgctcctgctcactgcccctcgcacagcctggtttgggctccgcctgtattctcctggtactgcaacctgtaaaccagcactg caatgctgatgcacgggaagtagtgggatgggaacacaaatggaggatccCGCGTCTCGAACAGAGCGCGCA

GAGGAACGCTGAAGGTCTCGCCTCTGTCGCACCTCAGCGCGGCATACACCACAA

TAACCACCTGACGAATGCGCTTGGTTCTTCGTCCATTAGCGAAGCGTCCGGTTCA

CACACGTGCCACGTTGGCGAGGTGGCAGGTGACAATGATCGGTGGAGCTGATGG

-continued

TCGAAACGTTCACAGCCTAGGGATATCgaattcggccgacaggacgcgcgtcaaaggtgctggtcgtgt atgccctggccggcaggtcgttgctgctgctggttagtgattccgcaaccctgattttggcgtcttattttggcgtggcaaacgctggc gcccgcgagccgggccggcggcgatgcggtgccccacggctgccggaatccaagggaggcaagagcgcccgggtcagttga agggctttacgcgcaaggtacagccgctcctgcaaggctgcgtggtggaattggacgtgcaggtcctgctgaagttcctccaccg cctcaccagcggacaaagcaccggtgtatcaggtccgtgtcatccactctaaagagctcgactacgacctactgatggccctaga ttcttcatcaaaaacgcctgagacacttgcccaggattgaaactccctgaagggaccaccaggggccctgagttgttccttccccc cgtggcgagctgccagccaggctgtacctgtgatcgaggctggcgggaaaataggcttcgtgtgctcaggtcatgggaggtgca ggacagctcatgaaacgccaacaatcgcacaattcatgtcaagctaatcagctatttcctcttcacgagctgtaattgtcccaaaat tctggtctaccgggggtgatccttcgtgtacgggcccttccctcaaccctaggtatgcgcgcatgcggtcgccgcgcaactcgcgc gagggccgagggtttgggacgggccgtcccgaaatgcagttgcacccggatgcgtggcacctttttttgcgataatttatgcaatgg actgctctgcaaaattctggctctgtcgccaaccctaggatcagcggcgtaggatttcgtaatcattcgtcctgatggggagctacc gactaccctaatatcagcccgactgcctgacgccagcgtccacttttgtgcacacattccattcgtgcccaagacatttcattgtggt gcgaagcgtggggagttacgctcacctgtttcccgacctccttactgttctgtcgacagagcgggcccacaggccggtcgcagcca ctagtATGgagatcccccccccactgcctgtgctccccctcccccgcccccctcccagctgtactacaagaagaagaagcacgcc atcctgcagacccagacccccctaccgctaccgcgtgtcccccacctgcttcgccccccccccgcctgcgcaagcagcacccctacc ccctgcccgtgctgtgctaccccaagctgctgcacttctcccagccccgctacccctggtgcgctcccacctggccgaggccggc gtggcctaccgccccggctacgagctgctgggcaagatccgcggcgtgtgcttctacgccgtgaccgccgccgtggccctgctgct gttccagtgcatgctgctgctgcaccccttcgtgctgctgttcgaccccttcccccgcaaggcccaccacacccatcgccaagctgtg gtccatctgctccgtgtccctgttctacaagatccacatcaagggcctggagaacctgcccccccccccactcccccgccgtgtacgt gtccaaccaccagtccttcctggacatctacaccctgctgaccctgggccgcacctcaagttcatctccaagaccgagatcttcctg taccccatcatcggctgggccatgtacatgctgggcaccatcccccctgaagcgcctggactcccgctcccagctggacaccctga agcgctgcatggacctgatcaagaagggcgcctccgtgttcttcttccccgagggcacccgctccaaggacggcaagctgggcg ccttcaagaagggcgccttctccatcgccgccaagtccaaggtgcccgtggtgcccatcaccctgatcggcaccggcaagatcat gcccccccggctccgagctgaccgtgaaccccggcaccgtgcaggtgatcatccacaagcccatcgagggctccgacgccgagg ccatgtgcaacgaggcccgcgccaccatctcccactccctggacgacTGAttaattaactcgaggcagcagcagctcggatagt atcgacacactctggacgctggtcgtgtgatggactgttgccgccacacttgctgccttgacctgtgaatatccctgccgcttttatcaaa cagcctcagtgtgtttgatcttgtgtgtacgcgcttttgcgagttgctagctgcttgtgctatttgcgaataccacccccagcatccccttcc ctcgtttcatatcgcttgcatcccaaccgcaacttatctacgctgtcctgctatccctcagcgctgctcctgctcctgctcactgcccctcgc cacgccttggtttgggctccgcctgtattctcctggtactgcaacctgtaaaccagcactgcaatgctgatgcacgggaagtagtgggat gggaacacaaatggaaagcttgagctcagcggcgacggtcctgctaccgtacgacgttgggcacgcccatgaaagtttgtatac cgagcttgttgagcgaactgcaagcgcggctcaaggatacttgaactcctggattgatatcggtccaataaggatggaaaat ccgaacctcgtgcaagaactgagcaaacctcgttacatggatgcacagtcgccagtccaatgaacattgaagtgagcgaact gttcgcttcggtggcagtactactcaaagaatgagctgctgttaaaaatgcactctcgttctctcagtgagtggcagatgagtg ctcacgcctgcacttcgctgcccgtgtcatgccctgcgccccaaaatttgaaaaaagggatgagattattgggcaatggacga cgtcgtcgctccgggagtcaggaccggcggaaaataagaggcaacacactccgcttcttagctcttcg

To determine the impact of the CuPSR23LPAATx gene on fatty acid accumulation, the above construct containing the codon optimized CuPSR23LPAATx gene driven by the UTEX 1453 AMT3 promoter was transformed into strain B.

Primary transformants were clonally purified and grown under low nitrogen conditions at pH7.0; the strains require growth at pH 7.0 to allow for maximal expression of the CuPSR23LPAATx and CwFATB2 genes driven by the pH-regulated AMT3 promoter. The resulting profiles from a set of representative clones arising from these transformations are shown in Table 35, below. D1542 represents clones of Strain B with CuPSR23LPAATx.

TABLE 35

Fatty acid profiles of Strain B and representative transgenic lines transformed with pSZ2575.

| Sample ID | C10:0 | C12:0 | C14:0 | C16:0 | C18:0 | C18:1 | C18:2 |
|---|---|---|---|---|---|---|---|
| Strain B | 4.77 | 28.63 | 15.48 | 12.65 | 1.28 | 28.20 | 7.57 |
| D1542-A | 1.19 | 13.25 | 10.48 | 21.34 | 4.49 | 32.07 | 14.78 |
| D1542-B | 1.15 | 14.01 | 10.62 | 20.61 | 3.99 | 32.12 | 15.24 |
| D1542-C | 1.21 | 13.69 | 10.83 | 20.40 | 3.59 | 33.54 | 15.05 |
| D1542-D | 1.56 | 16.83 | 11.51 | 18.44 | 2.94 | 33.97 | 12.74 |
| D1542-E | 2.15 | 18.58 | 11.94 | 18.22 | 3.17 | 32.63 | 11.62 |

The transgenic CuPSR23LPAATx strains (D1542A-E) show a significant decrease in the accumulation of C10:0, C12:0, and C14:0 fatty acids relative to the parent, Strain B, with a concomitant increase in C16:0, C18:0, C18:1 and C18:2. The expression of the CuPSR23LPAATx gene in these transgenic lines appears to be directly responsible for the decreased accumulation of mid-chain fatty acids (C10-C14) and the increased accumulation of C16:0 and C18 fatty acids, with the most pronounced increase observed in palmitates (C16:0). The data presented also show that despite the expression of the midchain specific FATB2 from *C. wrightii* (present in Strain B), the expression of CuPSR23LPAATx appears to favor incorporation of longer chain fatty acids into TAGs.

Our results suggest that the LPAATx enzyme from *Cuphea* PSR23 is active in the algal strains derived from UTEX 1435. Contrary to *Cuphea* PSR23LPAAT2 and LPAAT3, which increase mid-chain fatty acid levels, CuPSR23LPAATx leads to increased C16:0 and C18:0 levels. These results demonstrate that the different LPAATs derived from CuPSR23 (LPAAT2, LPAAT3, and LPAATx) exhibit different fatty acid specificities in Strain B as judged by their effects on overall fatty acid levels.

Example 45

Reduction in Chain Length of Fatty Acid Profile as a Result of Overexpressing an Endogenous Microalgal FATA Acyl-ACP Thioesterase Here, we demonstrate that over expression of the *Prototheca moriformis* endogenous thioesterases FATA1 in UTEX1435 results in a clear diminution of cell triglyceride C18:0 and C18:1 acyl chains with an increase in C16:0, C14:0.

Constructs Used for the Over Expression of the *P. moriformis* FATA1 Gene (pSZ2422, pSZ2421):

To over express the PmFATA1 in *P. moriformis* STRAIN J, a codon optimized PmFATA1 gene was been transformed into STRAIN J. The *Saccharomyces cerevisiae* invertase gene was utilized as the selectable marker to confer the ability of growing on sucrose media. The construct pSZ2422 that have been expressed in STRAIN J can be written as: 6SA::CrTUB2-ScSUC2-CvNR3':PmAMT3-Pm FATA1 (opt)-CvNR3'::6SB, and the construct pSZ2421 can be written as 6SA::CrTUB2-ScSUC2-CvNR3':PmAMT3-S106SAD TP-Pm FATA1 (opt)-CvNR3'::6SB.

The sequence of the transforming DNA is provided below. Relevant restriction sites in the construct pSZ2422 are indicated in lowercase, bold and underlining and are 5'-3' BspQ 1, Kpn I, Xba I, Mfe I, BamH I, EcoR I, Spe I, Asc I, Cla I, Sac I, BspQ I, respectively. BspQI sites delimit the 5' and 3' ends of the transforming DNA. Bold, lowercase sequences represent genomic DNA from STRAIN J that permit targeted integration at 6s locus via homologous recombination. Proceeding in the 5' to 3' direction, the *C. reinhardtii* β-tubulin promoter driving the expression of the yeast sucrose invertase gene (conferring the ability of STRAIN J to metabolize sucrose) is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by an endogenous amt03 promoter of *P. moriformis*, indicated by boxed italics text. The Initiator ATG and terminator TGA codons of the PmFATA1 are indicated by uppercase, bold italics, while the remainder of the gene is indicated by bold italics. The *C. vulgaris* nitrate reductase 3' UTR is again indicated by lowercase underlined text followed by the STRAIN J 6S genomic region indicated by bold, lowercase text.

Relevant restriction sites in the construct pSZ2421 are the same as pSZ2422. In pSZ2421, the PmFATA1 is fused to the *Chlorella protothecoides* S106 stearoyl-ACP desaturase transit peptide and the transit peptide is located between initiator ATG of PmFATA1 and the Asc I site.

Nucleotide sequence of transforming DNA contained in pSZ2422

(SEQ ID NO: 93)

gctcctcgccgccgccactcctgctcgagcgcgcccgcgcgtgcgccgccagcgccttggccttttcgccgcgctcgtgcgcgtc gctgatgtccatcaccaggtccatgaggtctgccttgcgccggctgagccactgcttcgtccgggcggccaagaggagcatga gggaggactcctggtccagggtcctgacgtggtcgcggctctgggagcgggccagcatcatctggctctgccgcaccgaggc cgcctccaactggtcctccagcagccgcagtcgccgccgaccctggcagaggaagacaggtgaggggggtatgaattgtaca gaacaaccacgagccttgtctaggcagaatccctaccagtcatggctttacctggatgacggcctgcgaacagctgtccagcg accctcgctgccgccgcttctcccgcacgcttctttccagcaccgtgatggcgcgagccagcgccgcacgctggcgctgcgctt cgccgatctgaggacagtcggggaactctgatcagtctaaacccccttgcgcgttagtgttgccatcctttgcagaccggtgag agccgacttgttgtgcgccacccccacaccacctcctcccagaccaattctgtcaccttttggcgaaggcatcggcctcggcc tgcagagaggacagcagtgcccagccgctgggggttggcggatgcacgctcaggtaccctttcttgcgctatgacacttccagca aaaggtagggcgggctgcgagacggcttcccggcgctgcatgcaacaccgatgatgcttcgacccccgaagctccttcggggctg catgggcgctccgatgccgctccagggcgagcgctgtttaaatagccaggcccccgattgcaaagacattatagcgagctaccaaag ccatattcaaacacctagatcactaccacttctacacaggccactcgagcttgtgatcgcactccgctaagggggcgcctcttcctcttc gtttcagtcacaacccgcaaactctagaatatca*ATG**ctgctgcaggccttcctgttcctgctggccggcttcgccgccagatcag*

*cgcctccatgacgaacgagacgtccgaccgccccctggtgcacttcacccccaacaagggctggatgaacgaccccaacggcc*

*tgtggtacgacgagaaggacgccaagtggcacctgtacaccagtacaacccgaacgacaccgtctgggggacgcccagactg*

*gggccacgccacgtccgacgacctgaccaactgggaggaccagcccatcgccatcgccccgaagcgcaacgactccggcgc*

*cactccggctccatggtggtggactacaacaacacctccggcacttcaacgacaccatcgacccgcgccagcgctgcgtggcca*

*tctggacctacaacaccccggagtccgaggagcagtacatctcctacagcctggacggcggctacaccacaccgagtaccaga*

*agaaccccgtgctggccgccaactccacccagaccgcgacccgaaggtcactggtacgagccctcccagaagtggatcatgac*

*cgcggccaagtcccaggactacaagatcgagatctactcctccgacgacctgaagtcctggaagctggagtccgcgacgccaa*

*cgagggcacctcggctaccagtacgagtgccccggcctgatcgaggtccccaccgagcaggaccccagcaagtcctactgggt*

*gatgacatctccatcaaccccggcgccccggccggcggctccacaaccagtacttcgtcggcagcttcaacggcacccacttcg*

*aggccttcgacaaccagtcccgcgtggtggacttcggcaaggactactacgccctgcagaccacttcaacaccgacccgaccta*

*cgggagcgccctgggcatcgcgtgggcctccaactgggagtactccgccacgtgcccaccaacccctggcgctcctccatgtccc*

*tcgtgcgcaagactccctcaacaccgagtaccaggccaacccggagacggagctgatcaacctgaaggccgagccgatcctg*

*aacatcagcaacgccggcccctggagccggttcgccaccaacaccacgttgacgaaggccaacagctacaacgtcgacctgtc*

*caacagcaccggcaccctggagacgagctggtgtacgccgtcaacaccacccagacgatctccaagtccgtgacgcggacctc*

*tccctctggacaagggcctggaggaccccgaggagtacctccgcatgggcttcgaggtgtccgcgtcctccacttcctggaccgc*

*gggaacagcaaggtgaagacgtgaaggagaacccctacttcaccaaccgcatgagcgtgaacaaccagcccacaagagcg*

*agaacgacctgtcctactacaaggtgtacggcttgctggaccagaacatcctggagctgtacttcaacgacggcgacgtcgtgtcc*

*accaacacctacttcatgaccaccgggaacgccctgggctccgtgaacatgacgacgggggtggacaacctgactacatcgac*

*aagttccaggtgcgcgaggtcaag**TGAc*aattggcagcagcagctcggatagtatcgacacactctggacgctggtcgtgtgat ggactgttgccgccacacttgctgccttgacctgtgaatatccctgccgcttttatcaaacagcctcagtggtgtttgatcttgtgtacgcg cttttgcgagttgctagctgcttgtgctatttgcgaataccacccccagcatccccttccctcgtttcatatcgcttgcatcccaaccgcaac ttatctacgctgtcctgctatccctcagcgctgctcctgctcctgctcactgcccctcgcacagccttggtttgggctccgcctgtattctcc tggtactgcaacctgtaaaccagcactgcaatgctgatgcacgggaagtagtgggatgggaacacaaatggaggatcccgcgtctcg aacagagcgcgcagaggaacgctgaaggtctcgcctctgtcgcacctcagcgcggcatacaccacaataaccacctgacgaatgcg -continued cttggttcttcgtccattagcgaagcgtccggttcacacacgtgccacgttggcgaggtggcaggtgacaatgatcggtggagctgatg gtcgaaacgttcacagcctagggatatcgaattc***ggccgacaggacgcgcgtcaaaggtgctggtcgtgtatgccctggccggca*

*ggtcgttgctgctgctggttagtgattccgcaaccctgattttggcgtcttattttggcgtggcaaacgctggcgcccgcgagccggg*

*ccggcggcgatgcggtgccccacggctgccggaatccaagggaggcaagagcgccgggtcagttgaagggctttacgcgca*

*aggtacagccgctcctgcaaggctgcgtggtggaattggacgtgcaggtcctgctgaagttcctccaccgcctcaccagcggaca*

*aagcaccggtgtatcaggtccgtgtcatccactgtaaagaactcgactacgacctactgatggccctagattcttcatcaaaaacg*

*cctgagacacttgcccaggattgaaactccctgaagggaccaccaggggccctgagttgttcctcccccgtggcgagctgcca*

*gccaggctgtacctgtgatcgaggctggcgggaaaataggcttcgtgtgctcaggtcatgggaggtgcaggacagctcatgaaa*

*cgccaacaatcgcacaattcatgtcaagctaatcagctatttcctcttcacgagctgtaattgtcccaaaattctggtctaccgggg*

*tgatccttcgtgtacgggcccttccctcaaccctaggtatgcgcgcatgcggtcgccgcgcaactcgcgcgagggccgagggtttg*

*ggacgggccgtcccgaaatgcagttgcacccggatgcgtggcacctttttgcgataatttatgcaatggactgctctgcaaaattct*

*ggctctgtcgccaaccctaggatcagcggcgtaggatttcgtaatcattcgtcctgatggggagctaccgactaccctaatatcagc*

*ccgactgcctgacgccagcgtccacttttgtgcacacattccattcgtgcccaagacatttcattgtggtgcgaagcgtcccagtta*

*cgctcacctgtttcccgacctccttactgttctgtcgacagagcgggcccacaggccggtcgcagcc*actagtATGgcccccac

*ctccctgctggcctccaccggcgtgtcctccgcctccctgtggtcctccgcccgctcctccgcctgcgccttccccgtggaccacgcc*

*gtgcgcggcgcccccagcgcccccctgcccatgcagcgccgctgcttccgcaccgtggccgtgcgcgggcgcgccgccgcccc*

*cgccgtggccgtgcgccccgagcccgcccaggagttctgggagcagctggagccctgcaagatggccgaggacaagcgcatc*

*ttcctgaggagcaccgcatccgcggcaacgaggtgggcccctcccagcgcctgaccatcaccgccgtggccaacatcctgca*

*ggaggccgccggcaaccacgccgtggccatgtggggccgctcctccgagggcttcgccaccgaccccgagctgcaggaggcc*

*ggcctgatcttgtgatgacccgcatgcagatccagatgtaccgctacccccgctggggcgacctgatgcaggtggagacctggtt*

*ccagaccgccggcaagctgggcgcccagcgcgagtgggtgctgcgcgacaagctgaccggcgaggccctgggcgccgccac*

*ctcctcctgggtgatgatcaacatccgcacccgccgcccctgccgcatgcccgagctggtgcgcgtgaagtccgccttcttcgccc*

*gcgagcccccccgcctggccctgccccccgccgtgacccgcgccaagctgcccaacatcgccaccccgccccccctgcgcggc*

*caccgccaggtggcccgccgcaccgacatggacatgaacggccacgtgaacaacgtggcctacctggcctggtgcctggaggc*

*cgtgcccgagcacgtgttctccgactaccacctgtaccagatggagatcgacttcaaggccgagtgccacgccggcgacgtgatc*

*tcctcccaggccgagcagatcccccccaggaggccctgacccacaacggcgccggccgcaacccctggtgcttcgtgcactcc*

*atcctgcgcgccgagaccgagctggtgcgcgcccgcaccacctggtccgcccccatcgacgcccccgccgccaagcccccaa*

*ggcctcccacatggactacaaggaccacgacggcgactacaaggaccacgacatcgactacaaggacgacgacgacaagT*

*GA*atcgatagatctcttaaggcagcagcagctcggatagtatcgacacactctggacgctggtcgtgtgatggactgttgccgccac -continued acttgctgccttgacctgtgaatatccctgccgcttttatcaaacagcctcagtgtgtttgatcttgtgtgtacgcgcttttgcgagttgctag ctgcttgtgctatttgcgaataccacccccagcatccccaccctcgatcatatcgcttgcatcccaaccgcaacttatctacgctgtcctg ctatccctcagcgctgctcctgctcctgctcactgcccctcgcacagccttggtttgggctccgcctgtattctcctggtactgcaacctgt aaaccagcactgcaatgctgatgcacgggaagtagtgggatgggaacacaaatggaaagcttaattaagagctcttgttttccagaa ggagttgctccttgagcctttcattctcagcctcgataacctccaaagccgctctaattgtggaggggggttcgaatttaaaagctt ggaatgttggttcgtgcgtctggaacaagcccagacttgttgctcactgggaaaaggaccatcagctccaaaaaacttgccgc tcaaaccgcgtacctctgctttcgcgcaatctgccctgttgaaatcgccaccacattcatattgtgacgcttgagcagtctgtaat tgcctcagaatgtggaatcatctgcccccctgtgcgagcccatgccaggcatgtcgcgggcgaggacacccgccactcgtacag cagaccattatgctacctcacaatagttcataacagtgaccatatttctcgaagctccccaacgagcacctccatgctctgagtg gccacccccccggccctggtgcttgcggagggcaggtcaaccggcatggggctaccgaaatccccgaccggatcccaccaccc ccgcgatgggaagaatctctccccgggatgtgggcccaccaccagcacaacctgctggcccaggcgagcgtcaaaccatacc acacaaatatccttggcatcggccctgaattccttctgccgctctgctacccggtgcttctgtccgaagcaggggttgctaggga tcgctccgagtccgcaaacccttgtcgcgtggcggggcttgttcgagcttgaagagc

To determine the impact on fatty acid profiles when the endogenous FATA1 gene have been over expressed in STRAIN J, both the *P. moriformis* FATA1 with native transit peptide and PmFATA1 fused to a *Chlorella protothecoides* SAD transit peptide were driven by the amt03 promoter and the resulting plasmids were transformed independently into STRAIN J.

Primary transformants were clonally purified and grown under low-nitrogen lipid production conditions at pH7.0 (all the plasmids require growth at pH 7.0 to allow for maximal PmFATA1 gene expression when driven by the pH regulated amt03 promoter). The resulting profiles from representative clones arising from transformations with pSZ2422 and pSZ2421 into STRAIN J are shown in the tables below.

In Table 36, below, the impact of over expressing native PmFATA1 is a clear diminution of C18:1 chain lengths with an increase in C16:0, C14:0, and possibly in C18:0. Considering the protein localization of processing, we also tried the PmFATA1 fused to a *Chlorella protothecoides* stearoyl-ACP desaturase transit peptide. Similar to the results we observed in the amt03-native PmFATA1 construct, the C16:0 and C14:0 levels are significantly higher than the parental strain STRAIN J.

TABLE 36

Fatty acid profiles in Strain J and derivative transgenic lines transformed with pSZ2422 DNA.

| Sample ID | C14:0 | C16:0 | C18:0 | C18:1 | C18:2 |
|---|---|---|---|---|---|
| pH 7; Strain J; T374; D1377-7 96well | 7.69 | 55.00 | 4.92 | 24.94 | 5.19 |
| pH 7; Strain J; T374; D1377-13 96well | 6.39 | 54.11 | 5.85 | 25.91 | 5.76 |
| pH 7; Strain J; T374; D1377-14 96well | 6.57 | 53.55 | 4.68 | 27.18 | 5.74 |
| pH 7; Strain J; T374; D1377-16 96well | 5.29 | 49.93 | 4.24 | 30.76 | 7.27 |
| pH 7; Strain J; T374; D1377-9 96well | 4.76 | 49.10 | 4.75 | 32.36 | 6.77 |
| pH 7; Strain J; T374; D1377-19 96well | 4.28 | 46.06 | 5.14 | 35.87 | 6.69 |
| Ctrl-pH 7; Strain J | 1.42 | 27.63 | 3.31 | 57.20 | 8.00 |

TABLE 37

Fatty acid profiles in STRAIN J and derivative transgenic lines transformed with pSZ2421 DNA.

| Sample ID | C14:0 | C16:0 | C18:0 | C18:1 | C18:2 |
|---|---|---|---|---|---|
| pH 7; STRAIN J; T374; D1376-21 96well | 6.76 | 57.06 | 4.12 | 23.66 | 6.07 |
| pH 7; STRAIN J; T374; D1376-22 96well | 6.56 | 54.62 | 5.44 | 25.69 | 5.64 |
| pH 7; STRAIN J; T374; D1376-23 96well | 4.54 | 48.38 | 4.27 | 33.23 | 7.24 |
| pH 7; STRAIN J; T374; D1376-19 96well | 4.48 | 47.66 | 4.60 | 34.28 | 6.91 |
| pH 7; STRAIN J; T374; D1376-20 96well | 4.53 | 47.30 | 4.67 | 34.51 | 6.80 |
| pH 7; STRAIN J; T374; D1376-17 96well | 3.56 | 42.70 | 4.03 | 39.85 | 7.52 |
| Ctrl-pH 7; STRAIN J | 1.42 | 27.63 | 3.31 | 57.20 | 8.00 |

Thus, we conclude that percent myristic and lauric acid levels in the fatty acid profile of a microalgal cell can be increased by overexpression of a C18-preferring acyl-ACP thioesterase.

Example 46

Natural Oils Suitable for Use as Roll-In Shortenings

The nutritional and functional properties of edible fats have been traditionally associated with specific chemical compositions and crystallization conditions. Switching from one oil source to another is usually a difficult task since both the melting behavior and structure of the fat changes dramatically, leading to adverse changes in functionality. In recent history, we can recall the painful period when partially hydrogenated fats were replaced with palm oil and palm oil fractions. We examined how the yield stress, elastic modulus, polymorphism, microstructure and melting profile of two fats with vastly different chemical compositions can be matched. Oil A was produced from *Prototheca moriformis* cells expressing an exogenous invertase and an *Ulmus americana* acyl-ACP thioesterase with a *Chlorella protothecoides* plastid targeting sequence. Oil B was produced from *Prototheca moriformis* cells expressing an exogenous invertase and a *Cuphea hookeriana* acyl-ACP thioesterase. Oil A contained greater than 62% (w/w) medium chain fatty acids, or MCT (C8:0-C14:0), 23% (C16:0+C18:0) and 9% C18:1, while Oil B contained less than 2% C8:0-C14:0, 54% (C16:0+C18:0) and 29% C18:1. Oil A was thus a medium chain triglyceride rich fat, while Oil B resembled palm oil. Both oils had a solid fat content of ~45% at 20° C., and very similar SFC versus temperature profiles. DSC (dynamic scanning calorimetry) melting profiles showed two major peaks centered around ~12-13° C. and ~28-35° C. Both fats were in the beta-prime polymorphic form (as determined by X-ray diffraction) and displayed asymmetric, elongated crystallite morphology with characteristic features. The yield stresses and storage moduli (G') of Oil A and Oil B were 520-550 Pa, and $7\times10^6$ Pa-$1.8\times10^7$ Pa, respectively. A yield stress in this region suggests a satisfactory plasticity, which combined with a high storage modulus makes for an ideal roll-in shortening. Thus, it is possible to alter the chemical composition of a food oil while retaining its lamination functionality.

Other suitable enzymes for use with the cells and methods of any of the above embodiments of the invention include those that have at least 70% amino acid identity with one of the proteins listed in the description above and that exhibit the corresponding desired enzymatic activity. In additional embodiments, the enzymatic activity is present in a sequence that has at least about 75%, at least about 80%, at least about 85%, at least about 90%, at least about 95%, or at least about 99% identity with one of the above described nucleic acid sequences, all of which are hereby incorporated by reference as if fully set forth.

Example 47

Fractionation to Remove Trisaturates from a Tailored Microbial Oil that is a Cocoa Butter Mimetic A refined bleached and deodorized oil was obtained from Strain K4 (see Example 35). The oil was heated to 70° C. and cooled at 0.5° C. per min to 36° C. and held at 36° C. for 1 hour. An approximately 2.5 ml sample was then centrifuged at 36° C. for 1 hour at 4300. A liquid supernatant was recovered and analysed using lipase and mass spectrometry. The sample was found to be depleted in tristearin (SSS), SSP, and PPS. The triacylglycerols of the sample were found to be very similar to that of cocoa butter and the liquid supernatant was even closer to that of cocoa butter in terms of low amounts of trisaturates.

TABLE 38

TAG profile of oil from the K4 strain before and after fractionation as compared to cocoa butter.

| TAG | K4 oil | fractionation upper layer (liquid) | cocoa butter |
|---|---|---|---|
| OOL (+?) | 0.12 | 0.12 | 0.00 |
| POL | 0.23 | 0.31 | 0.33 |
| PLP | 2.41 | 3.38 | 1.58 |
| MOP | 0.93 | 1.25 | 0.00 |
| PPM (+MMS) | 0.42 | 0.29 | 0.00 |
| OOO | 0.23 | 0.34 | 0.00 |
| SOL | 0.36 | 0.47 | 0.32 |
| OOP | 0.95 | 1.42 | 2.44 |
| PLS | 5.66 | 7.90 | 2.90 |
| POP (+MSO) | 11.80 | 15.20 | 17.93 |
| PPP + MPS | 2.22 | 1.07 | 0.36 |
| OOS | 1.19 | 1.68 | 3.02 |
| SLS (+PLA) | 3.96 | 5.11 | 1.77 |
| POS | 27.22 | 32.80 | 40.25 |

TABLE 38-continued

TAG profile of oil from the K4 strain before and after fractionation as compared to cocoa butter.

| TAG | K4 oil | fractionation upper layer (liquid) | cocoa butter |
|---|---|---|---|
| PPS (+SSM) | 6.47 | 1.52 | 0.49 |
| MaOO | 0.00 | 0.00 | 0.36 |
| SLA | 0.31 | 0.34 | 0.00 |
| SOS (+POA) | 17.84 | 22.50 | 24.93 |
| SSP (+PPA) | 9.24 | 0.96 | 0.63 |
| SOA (+POB) | 1.39 | 1.68 | 1.51 |
| SSS (+PSA) | 5.25 | 0.23 | 0.33 |
| SOB + LgOP | 0.38 | 0.44 | 0.27 |
| SSA | 0.41 | 0.00 | 0.00 |
| SOLg | 0.41 | 0.00 | 0.00 |
| PSLg + ASB | 0.26 | 0.00 | 0.00 |
| SOHx | 0.12 | 0.51 | 0.00 |
| SSLg | 0.21 | 0.14 | 0.15 |
| SUM area % | 100.00 | 99.67 | 99.57 |

Example 48

Production of High-Stearate Triglyceride Oil in an Oleaginous Cell by Overexpression of KASII, Knockout of One Sad Allele and Repression of a Second Sad Allele The oleaginous, non-photosynthetic alga, *Protetheca moriformis*, stores copious amounts of triacylglyceride oil under conditions where the nutritional carbon supply is in excess, but cell division is inhibited due to limitation of other essential nutrients. Bulk biosynthesis of fatty acids with carbon chain lengths up to C18 occurs in the plastids; fatty acids are then exported to the endoplasmic reticulum where elongation past C18 and incorporation into triacylglycerides (TAGs) is believed to occur. Lipids are stored in large cytoplasmic organelles called lipid bodies until environmental conditions change to favor growth, whereupon they are rapidly mobilized to provide energy and carbon molecules for anabolic metabolism. Wild-type *P. moriformis* storage lipid is mainly comprised of ~60% oleic (C18:1), ~25-30% palmitic (C16:0), and ~5-8% linoleic (C18:2) acids, with minor amounts of stearic (C18:0), myristic (C14:0), α-linolenic (C18:3 α), and palmitoleic (C16:1) acids. This fatty acid profile results from the relative activities and substrate affinities of the enzymes of the endogeneous fatty acid biosynthetic pathway. *P. moriformis* is amenable to manipulation of fatty acid and lipid biosynthesis using molecular genetic tools, enabling the production of oils with fatty acid profiles that are very different to the wild-type composition. Herein we describe strains where we have modified the expression of stearoyl-ACP desaturase (SAD) and β-ketoacyl-ACP synthase II (KASII) genes in order to generate strains with up to 57% stearate and as little as 7% palmitate. We identify additional strains with up to 55% stearate and as low as 2.4% linoleate when we perform similar modifications in conjunction with down-regulating the expression of the FATA thioesterase and the FAD2 fatty acid desaturase genes.

Soluble SADs are plastid-localized, di-iron enzymes which catalyze the desaturation of acyl carrier protein (ACP)-bound stearate to oleate (C18:1 cis-$\Delta^9$). Previously, we have established that hairpin constructs targeting the SAD1 or SAD2 transcripts activate the cellular RNA interference (RNAi) machinery, down-regulating SAD activity and resulting in elevated levels of C18:0 in the storage lipid. SAD activity is also reduced in strains where we disrupt one of the two alleles of SAD2, encoding the major SADs that are expressed during storage lipid biosynthesis. The Fatty Acid Desaturase 2 (FAD2) gene encodes an endoplasmic reticulum membrane-associated desaturase that converts oleate to linoleate (C18:2 cis-$\Delta^9$, cis-$\Delta^{12}$). Hairpin RNAi constructs targeting FAD2 reduce linoleate levels to 1-2%. KASII is a fatty acid synthase which specifically catalyzes the condensation of malonyl-ACP with palmitoyl (C16:0)-ACP to form β-keto-stearoyl-ACP. We have shown that overexpression of KASII in *P. moriformis* causes C16:0 levels to decrease with a concommitent increase in C18:1 abundance. In the examples below we demonstrate that by down-regulating SAD gene expression using RNAi, disrupting an allele of the SAD2 gene, and overexpressing the KASII fatty acid synthase, we generate strains capable of accumulating stearate in excess of 50% of the total fatty acids, and with SOS as the major TAG species. SOS levels increase up to 47% in strains which combine SAD2 and FAD2 down-regulation with KASII overexpression.

Constructs Used for SAD2 Knockout/RNAi in S1920:

A DNA construct, pSZ2282, was made to simultaneously disrupt the SAD2-1 allele and express a SAD2 hairpin construct in S1920. A version of the *Saccharomyces cerevisiae* SUC2 gene, encoding sucrose invertase, which was codon-optimized for expression in *P. moriformis*, was utilized as a selectable marker for transformation. The sequence of the transforming DNA is provided immediately below. Relevant restriction sites are indicated in lowercase, bold, and are from 5'-3' BspQI, KpnI, AscI, MfeI, BamHI, AvrII, EcoRV, EcoRI, SpeI, BamHI, HinDIII, and SacI, respectively. BspQI sites delimit the 5' and 3' ends of the transforming DNA. Underlined sequences at the 5' and 3' flanks of the construct represent genomic DNA from *P. moriformis* that enable targeted integration of the transforming DNA via homologous recombination at the SAD2-1 locus. Proceeding in the 5' to 3' direction, the *Chlamydomonas* reinhardtii TUB2 promoter driving the expression of the *Saccharomyces cerevisiae* SUC2 gene (encoding sucrose hydrolyzing activity, thereby permitting the strain to grow on sucrose) is indicated by lowercase, boxed text. The initiator ATG and terminator TGA for SUC2 are indicated by uppercase italics, while the coding region is indicated with lowercase italics. The 3' UTR of the *Chlorella vulgaris* nitrate reductase (NR) gene is indicated by small capitals, followed by a spacer region indicated by lowercase text. A second *C. reinhardtii* TUB2 promoter sequence, indicated by lowercase boxed text, drives expression of the SAD2 hairpin C sequence. The sense and antisense strands are indicated with uppercase, bold italics, and are separated by the *P. moriformis* $\Delta^{12}$-fatty acid desaturase (FAD2) intron and the first 10 bases of the FAD2 second exon (uppercase italics). A second *C. vulgaris* NR 3' UTR is indicated by small capitals.

Nucleotide sequence of the the transforming DNA from pSZ2282:

(SEQ ID NO: 94)

gctcttcgggtcgccgcgctgcctcgcgtcccctggtggtgcgcgcggtcgccagcgaggccccgctgggcgttccgccctcggtgca gcgcccctcccccgtggtctactccaagctggacaagcagcaccgcctgacgcccgagcgcctggagctggtgcagagcatggggc agtttgcggaggagagggtgctgcccgtgctgcaccccgtggacaagctgtggcagccgcaggactttttgcccgaccccgagtcgc ccgacttcgaggatcaggtggcggagctgcgcgcgcgcgccaaggacctgcccgacgagtactttgtggtgctggtggggacatg atcacggaggaggcgctgccgacctacatggccatgctcaacacgctggacggcgtgcgcgacgacacgggcgcggccgaccacc cgtgggcgcgctggacgcggcagtgggtggccgaggagaaccggcacggcgacctgctgaacaagtactgctggctgacggggc gcgtcaacatgcgggccgtggaggtgaccatcaacaacctgatcaagagcggcatgaacccgcagacggacaacaacccttattt ggggttcgtctacacctccttccaggagcgcgccaccaagtaggtaccctttcttgcgctatgacacttccagcaaaaggtagggcg ggctgcgagacggcttcccggcgctgcatgcaacaccgatgatgcttcgacccccgaagctccttcggggctgcatgggcgctccg atgccgctccagggcgagcgctgtttaaatagccaggcccccgattgcaaagacattatagcgagctaccaaagccatattcaaac acctagatcactaccacttctacacaggccactcgagcttgtgatcgcactccgctaagggggcgcctcttcctcttcgtttcagtcac aacccgcaaacggcgcgcc*ATGctgctgcaggccttcctgttcctgctggccggcttcgccgccaagatcagcgcctccatgac*

*gaacgagacgtccgaccgccccctggtgcacttcacccccaacaagggctggatgaacgaccccaacggcctgtggtacgac*

*gagaaggacgccaagtggcacctgtacttccagtacaacccgaacgacaccgtctgggggacgcccttgttctggggccacg*

*ccacgtccgacgacctgaccaactgggaggaccagcccatcgccatcgccccgaagcgcaacgactccggcgccttctccggc*

*tccatggtggtggactacaacaacacctccggcttcttcaacgacaccatcgacccgcgccagcgctgcgtggccatctggacc*

*tacaacaccccggagtccgaggagcagtacatctcctacagcctggacggcggctacaccttcaccgagtaccagaagaacc*

*ccgtgctggccgccaactccacccagttccgcgacccgaaggtcttctggtacgagccctcccagaagtggatcatgaccgcgg*

*ccaagtcccaggactacaagatcgagatctactcctccgacgacctgaagtcctggaagctggagtccgcgttcgccaacgag*

*ggcttcctcggctaccagtacgagtgccccggcctgatcgaggtccccaccgagcaggaccccagcaagtcctactgggtgat*

*gttcatctccatcaaccccggcgccccggccggcggctccttcaaccagtacttcgtcggcagcttcaacggcacccacttcgag*

-continued

*gccttcgacaaccagtcccgcgtggtggacttcggcaaggactactacgccctgcagaccttcttcaacaccgacccgacctac*

*gggagcgccctgggcatcgcgtgggcctccaactgggagtactccgccttcgtgcccaccaacccctggcgctcctccatgtccc*

*tcgtgcgcaagttctccctcaacaccgagtaccaggccaacccggagacggagctgatcaacctgaaggccgagccgatcct*

*gaacatcagcaacgccggcccctggagccggttcgccaccaacaccacgttgacgaaggccaacagctacaacgtcgacctg*

*tccaacagcaccggcaccctggagttcgagctggtgtacgccgtcaacaccacccagacgatctccaagtccgtgttcgcgga*

*cctctccctctggttcaagggcctggaggaccccgaggagtacctccgcatgggcttcgaggtgtccgcgtcctccttcttcctgg*

*accgcgggaacagcaaggtgaagttcgtgaaggagaacccctacttcaccaaccgcatgagcgtgaacaaccagcccttca*

*agagcgagaacgacctgtcctactacaaggtgtacggcttgctggaccagaacatcctggagctgtacttcaacgacggcga*

*cgtcgtgtccaccaacacctacttcatgaccaccgggaacgccctgggctccgtgaacatgacgacgggggtggacaacctgt*

*tctacatcgacaagttccaggtgcgcgaggtcaagTGA*caattgGCAGCAGCAGCTCGGATAGTATCGACACACTCTGGAC GCTGGTCGTGTGATGGACTGTTGCCGCCACACTTGCTGCCTTGACCTGTGAATATCCCTGCCGCTTTTATCAAACAGCCTCA GTGTGTTTGATCTTGTGTGTACGCGCTTTTGCGAGTTGCTAGCTGCTTGTGCTATTTGCGAATACCACCCCCAGCATCCCCT TCCCTCGTTTCATATCGCTTGCATCCCAACCGCAACTTATCTACGCTGTCCTGCTATCCCTCAGCGCTGCTCCTGCTCCTGCT CACTGCCCCTCGCACAGCCTTGGTTTGGGCTCCGCCTGTATTCTCCTGGTACTGCAACCTGTAAACCAGCACTGCAATGCT GATGCACGGGAAGTAGTGGGATGGGAACACAAATGGAggatcccgcgtctcgaacagagcgcgcagaggaacgctgaaggt ctcgcctctgtcgcacctcagcgcggcatacaccacaataaccacctgacgaatgcgcttggttcttcgtccattagcgaagcgtccg gttcacacacgtgccacgttggcgaggtggcaggtgacaatgatcggtggagctgatggtcgaaacgttcacagcctagggatatc gaattcctttcttgcgctatgacacttccagcaaaaggtagggcgggctgcgagacggcttcccggcgctgcatgcaacaccgatga tgcttcgacccccccgaagctccttcggggctgcatgggcgctccgatgccgctccagggcgagcgctgtttaaatagccaggccccc gattgcaaagacattatagcgagctaccaaagccatattcaaacacctagatcactaccacttctacacaggccactcgagcttgtg atcgcactccgctaagggggcgcctcttcctcttcgtttcagtcacaacccgcaaacactagt*GCGCTGGACGCGGCAGTG*

*GGTGGCCGAGGAGAACCGGCACGGCGACCTGCTGAACAAGTACTGTTGGCTGACGGGGCGCGTC*

*AACATGCGGGCCGTGGAGGTGACCATGAACAACCTGATCAAGAGCGGCATGAACCCGCAGACGG*

*ACAACAACCCTTACTTGGGCTTCGTCTACACCTCCTTCCAGGAGCGCGCGACCAGTACAGCCACGG*

*CAACACCGCGCGCCTTGCGGCCGAGCA**GTGTGTTTGAGGGTTTTGGTTGCCCGTATCGAGGTCCTGG*

*TGGCGCGCATGGGGGAGAAGGCGCCTGTCCCGCTGACCCCCCCGGCTACCCTCCCGGCACCTTCCAG*

*GGCGCGTACG*ggatcc*TGCTCGGCCGCAAGGCGCGCGGTGTTGCCGTGGCTGTACTTGGTCGCGCGC*

*TCCTGGAAGGAGGTGTAGACGAAGCCCAAGTAAGGGTTGTTGTCCGTCTGCGGGTTCATGCCGCT*

*CTTGATCAGGTTGTTGATGGTCACCTCCACGGCCCGCATGTTGACGCGCCCCGTCAGCCAACAGTAC*

*TTGTTCAGCAGGTCGCCGTGCCGGTTCTCCTCGGCCACCCACTGCCGCGTCCAGCGC*aagcttGCAGCAG CAGCTCGGATAGTATCGACACACTCTGGACGCTGGTCGTGTGATGGACTGTTGCCGCCACACTTGCTGCCTTGACCTGTGA ATATCCCTGCCGCTTTTATCAAACAGCCTCAGTGTGTTTGATCTTGTGTGTACGCGCTTTTGCGAGTTGCTAGCTGCTTGTG CTATTTGCGAATACCACCCCCAGCATCCCCTTCCCTCGTTTCATATCGCTTGCATCCCAACCGCAACTTATCTACGCTGTCCT GCTATCCCTCAGCGCTGCTCCTGCTCCTGCTCACTGCCCCTCGCACAGCCTTGGTTTGGGCTCCGCCTGTATTCTCCTGGTA CTGCAACCTGTAAACCAGCACTGCAATGCTGATGCACGGGAAGTAGTGGGATGGGAACACAAATGGAAAGcTGgagctc cagccacggcaacaccgcgcgccttgcggccgagcacggcgacaagaacctgagcaagatctgcgggctgatcgccagcgacga gggccggcacgagatcgcctacacgcgcatcgtggacgagttcttccgcctcgaccccgagggcgccgtcgccgcctacgccaaca tgatgcgcaagcagatcaccatgcccgcgcacctcatggacgacatgggccacggcgaggccaacccgggccgcaacctcttcgc cgacttctccgcggtcgccgagaagatcgacgtctacgacgccgaggactactgccgcatcctggagcacctcaacgcgcgctgga aggtggacgagcgccaggtcagcggccaggccgccgcggaccaggagtacgtcctgggcctgccccagcgcttccggaaactcgc cgagaagaccgccgccaagcgcaagcgcgtcgcgcgcaggcccgtcgccttctcctggatctccgggcgcgagatcatggtctagg gagcgacgagtgtgcgtgcggggctggcgggagtgggacgccctcctcgctcctctctgttctgaacggaacaatcggccaccccg cgctacgcgccacgcatcgagcaacgaagaaaaccccccgatgataggttgcggtggctgccgggatatagatccggccgcacat caaagggcccctccgccagagaagaagctcctttcccagcagactcctgaagagc

Identification and Analysis of SAD2 Knockout/Knockdown Strains:

Construct D1283, derived from pSZ2282, was transformed into S1920 as described previously. Primary transformants were clonally purified and grown under standard lipid production conditions at pH 5. The resulting fatty acid profiles from representative clones arising from transformation with pSZ2282 into S1920 are summarized in Table 39, below. D1283 transformants accumulated up to ~42% C18:0 at the expense of C18:1, indicating that SAD activity was significantly reduced in these strains.

TABLE 39

Fatty acid profiles of D1283 [pSZ2282] primary transformants, compared to the wild-type parental strain, S1920.

| | | Strain | | | | | | |
|---|---|---|---|---|---|---|---|---|
| | | S1920 | D1283-4 | D1283-7 | D1283-19 | D1283-27 | D1283-40 | D1283-24 |
| Fatty Acid | C12:0 | 0.04 | 0.05 | 0.06 | 0.07 | 0.06 | 0.04 | 0.05 |
| Area % | C14:0 | 1.31 | 0.92 | 1.07 | 1.01 | 1.08 | 1.03 | 0.96 |
| | C16:0 | 26.68 | 28.23 | 29.21 | 27.24 | 27.67 | 27.02 | 27.07 |
| | C16:1 | 0.78 | 0.05 | 0.06 | 0.08 | 0.33 | 0.14 | 0.12 |
| | C17:0 | 0.11 | 0.12 | 0.15 | 0.10 | 0.10 | 0.12 | 0.13 |
| | C18:0 | 3.15 | **41.98** | **40.94** | **34.20** | **26.26** | **23.18** | **22.82** |
| | C18:1 | 59.30 | 19.37 | 18.17 | 26.87 | 34.77 | 38.74 | 39.38 |
| | C18:2 | 7.47 | 6.22 | 7.43 | 7.42 | 7.31 | 7.25 | 7.38 |
| | C18:3α | 0.57 | 0.93 | 1.03 | 0.75 | 0.71 | 0.72 | 0.51 |
| | C20:0 | 0.32 | 1.81 | 1.67 | 1.75 | 1.35 | 1.36 | 1.23 |
| | C20:1 | 0.00 | 0.10 | 0.00 | 0.12 | 0.00 | 0.12 | 0.11 |
| | C22:0 | 0.05 | 0.17 | 0.13 | 0.20 | 0.16 | 0.16 | 0.15 |
| | C24:0 | 0.00 | 0.00 | 0.00 | 0.10 | 0.00 | 0.00 | 0.00 |
| sum C18 | | 70.40 | 68.5 | 67.57 | 69.24 | 69.05 | 69.89 | 70.09 |
| saturates | | 31.66 | 73.28 | 73.23 | 64.67 | 56.68 | 52.91 | 52.41 |
| unsaturates | | 68.12 | 26.67 | 26.69 | 35.24 | 43.12 | 46.97 | 47.50 |

In Table 39, Stearate (C18:0) levels greater than the wild-type level are highlighted with bold text.

The fatty acid profiles of transformants D1283-4 and −7 were determined to be stable after more than 30 generations of growth in the absence of selection (growth on sucrose). The performance of selected strains in shake flask assays was then evaluated, and the fatty acid profiles and lipid titers are presented in Table 40, below. S4495 had the highest level of C18:0 (~44%) and the best lipid titer (~26%) relative to the S1920 parent, and so was selected for further fermentation development.

TABLE 40

Fatty acid profiles and lipid titers of SAD2 knockout/knock-down strains derived from D1283 primary transformants, compared to the wild-type parental strain, S1920.

| | | | Primary | | | | | |
|---|---|---|---|---|---|---|---|---|
| | | | T342; D1283-4 | | | T342; D1283-7 | | |
| | | | Strain | | | | | |
| | | S1920 | S4490 | S4491 | S4492 | S4493 | S4494 | S4495 |
| Fatty Acid | C14:0 | 1.59 | 1.61 | 1.58 | 1.55 | 1.81 | 1.84 | 1.34 |
| Area % | C16:0 | 30.47 | 29.41 | 28.58 | 29.24 | 28.77 | 29.09 | 28.47 |
| | C16:1 | 0.82 | 0.05 | 0.07 | 0.05 | 0.07 | 0.05 | 0.06 |
| | C17:0 | 0.10 | 0.30 | 0.29 | 0.28 | 0.46 | 0.37 | 0.19 |
| | C18:0 | 3.58 | **42.85** | **41.86** | **48.38** | **39.99** | **41.41** | **44.42** |
| | C18:1 | 56.96 | 13.52 | 15.55 | 13.49 | 13.57 | 12.98 | 15.64 |
| | C18:2 | 5.50 | 8.01 | 7.85 | 7.65 | 10.37 | 9.47 | 5.72 |
| | C18:3α | 0.37 | 0.78 | 0.73 | 0.82 | 0.95 | 0.91 | 0.64 |
| | C20:0 | 0.22 | 2.06 | 2.11 | 2.11 | 1.98 | 1.98 | 2.32 |
| | C22:0 | 0.05 | 0.32 | 0.34 | 0.33 | 0.33 | 0.32 | 0.35 |
| | C24:0 | 0.03 | 0.43 | 0.42 | 0.44 | 0.49 | 0.49 | 0.37 |
| lipid titer (% parent) | | 100 | 12.3 | 12.6 | 13.6 | 6.2 | 8.2 | 25.9 |

In Table 40, Stearate (C18:0) levels greater than the wild-type level are highlighted with bold text.

We optimized the performance of S4495 in 7-L fermentations, and found that we could match the ~44% C18:0 level obtained in shake flasks, with lipid productivities that were ~45% of the wild-type parent. The fatty acid profiles and lipid titers of representative S4495 fermentations are summarized in Table 41, below. Fermentation of S4495 under optimal conditions yielded nearly 44% C18:0, which was similar to the stearate level that accumulated in shake flask assays. S4495 produced high C18:0 levels at both flask and 7-L scale and had acceptable lipid productivity in 7-L fermentations; consequently this strain was selected as a base strain for additional modifications aimed at increasing C18:0 accumulation.

TABLE 41

Fatty acid profiles and lipid titers of S4495, compared to a control transgenic strain S2074.

| Strain | | S2074 | S4495 | S4495 | S4495 |
|---|---|---|---|---|---|
| Fermentation | | 110088F14 | 120489F5 | 120531F8 | 120580F1 |
| Fatty | C4:0 | 1.47 | 1.18 | 1.15 | 1.27 |
| Acid | C16:0 | 25.66 | 28.68 | 28.38 | 28.35 |
| Area % | C16:1 | 0.71 | 0.11 | 0.09 | 0.06 |
| | C18:0 | 3.16 | **41.63** | **42.40** | **43.67** |
| | C18:1 | 62.24 | 20.78 | 19.38 | 17.63 |
| | C18:2 | 5.90 | 5.06 | 5.38 | 5.58 |
| | C18:3α | 0.16 | 0.24 | 0.25 | 0.25 |
| | C20:0 | 0.24 | 1.36 | 1.99 | 2.11 |
| | C22:0 | 0.05 | 0.19 | 0.28 | 0.31 |
| | C24:0 | 0.05 | 0.34 | 0.29 | 0.31 |
| sum C18 | | 71.46 | 67.71 | 67.41 | 67.13 |
| saturates | | 30.63 | 73.38 | 74.49 | 76.02 |
| unsaturates | | 69.01 | 26.19 | 25.10 | 23.52 |
| total lipid (g/L) | | 930 | 383 | 539 | 475 |

In Table 41, Stearate (C18:0) levels greater than the control are highlighted with bold text. S2074 contains *S. cerevisiae* SUC2, encoding sucrose invertase, integrated at the 6S locus, and has a fatty acid profile that is indistinguishable from the S1920 wild-type parent.

Constructs Used for KASII Overexpression in S4495:

DNA construct pSZ2734 was made to overexpress a codon-optimized *P. moriformis* KASII gene in S4495. The neoR gene from transposon Tn5, conferring resistance to aminoglycoside antibiotics, was used as a selectable marker for transformation. The sequence of the transforming DNA is provided immediately below. Relevant restriction sites are indicated in lowercase, bold, and are from 5'-3' BspQI, KpnI, XbaI, MfeI, BamHI, AvrII, EcoRV, SpeI, AscI, ClaI, BglII, AflII, HinDIII and SacI, respectively. BspQI sites delimit the 5' and 3' ends of the transforming DNA. Underlined sequences at the 5' and 3' flanks of the construct represent genomic DNA from *P. moriformis* that enable targeted integration of the transforming DNA via homologous recombination at the 6S locus. Proceeding in the 5' to 3' direction, the *C. reinhardtii* TUB2 promoter driving the expression of neoR (encoding aminoglycoside phosphotransferase activity, thereby permitting the strain to grow on G418) is indicated by lowercase, boxed text. The initiator ATG and terminator TGA for neoR are indicated by uppercase italics, while the coding region is indicated with lowercase italics. The 3' UTR of the *C. vulgaris* NR gene is indicated by small capitals, followed by a spacer region indicated by lowercase text. The *P. moriformis* SAD2-2 promoter sequence, indicated by boxed text, drives expression of the codon-optimized *P. moriformis* KASII gene. The region encoding the KASII plastid targeting sequence is indicated by uppercase italics. The sequence that encodes the mature *P. moriformis* KASII polypeptide is indicated with bold, underlined, uppercase italics, while a 3×FLAG epitope encoding sequence is in bold italics. A second *C. vulgaris* NR 3' UTR is indicated by small capitals.

Nucleotide sequence of the the transforming DNA from pSZ2734:

(SEQ ID NO: 95)

gctcttcgccgccgccactcctgctcgagcgcgcccgcgcgtgcgccgccagcgccttggccttttcgccgcgctcgtgcgcgtcgct gatgtccatcaccaggtccatgaggtctgccttgcgccggctgagccactgcttcgtccgggcggccaagaggagcatgagggagg actcctggtccagggtcctga cgtggtcgcggctctgggagcgggccagcatcatctggctctgccgcaccgaggccgcctccaact ggtcctccagcagccgcagtcgccgccgaccctggcagaggaagacaggtgaggggtgttatgaattgtacagaacaaccacgagc cttgtctaggcagaatccctaccagtcatggctttacctggatgacggcctgcgaacagctgtccagcgaccctcgctgccgccgctt ctcccgcacgcttctttccagcaccgtgatggcgcgagccagcgccgcacgctggcgctgcgcttcgccgatctgaggacagtcggg gaactctgatcagtctaaacccccttgcgcgttagtgttgccatcctttgcagaccggtgagagccgacttgttgtgcgccaccccca caccacctcctcccagaccaattctgtcacctttttggcgaaggcatcggcctcggcctgcagagaggacagcagtgcccagccgct gggggttggcggatgcacgctcaggtaccctttcttgcgctatgacacttccagcaaaaggtagggcgggctgcgagacggcttccc ggcgctgcatgcaacaccgatgatgcttcgacccccgaagctccttcggggctgcatgggcgctccgatgccgctccagggcgag cgctgtttaaatagccaggcccccgattgcaaagacattatagcgagctaccaaagccatattcaaacacctagatcactaccactt ctacacaggccactcgagcttgtgatcgcactccgctaagggggcgcctcttcctcttcgtttcagtcacaacccgcaaactctagaa tatca*ATGatcgagcaggacggcctccacgccggctcccccgccgcctgggtggagcgcctgttcggctacgactgggcccag*

*cagaccatcggctgctccgacgccgccgtgttccgcctgtccgcccagggccgccccgtgctgttcgtgaagaccgacctgtccg*

*gcgccctgaacgagctgcaggacgaggccgcccgcctgtcctggctggccaccaccggcgtgccctgcgccgccgtgctggac*

*gtggtgaccgaggccggccgcgactggctgctgctgggcgaggtgcccggccaggacctgctgtcctcccacctggcccccgc*

*cgagaaggtgtccatcatggccgacgccatgcgccgcctgcacaccctggaccccgccacctgccccttcgaccaccaggcca*

*agcaccgcatcgagcgcgcccgcacccgcatggaggccggcctggtggaccaggacgacctggacgaggagcaccagggc*

*ctggcccccgccgagctgttcgcccgcctgaaggcccgcatgcccgacggcgaggacctggtggtgacccacggcgacgcctg*

*cctgcccaacatcatggtggagaacggccgcttctccggcttcatcgactgcggccgcctgggcgtggccgaccgctaccagg*

*acatcgccctggccacccgcgacatcgccgaggagctgggcggcgagtgggccgaccgcttcctggtgctgtacggcatcgcc*

*gcccccgactcccagcgcatcgccttctaccgcctgctggacgagttcttcTGA*caattgGCAGCAGCAGCTCGGATAG

TATCGACACACTCTGGACGCTGGTCGTGTGATGGACTGTTGCCGCCACACTTGCTGCCTTGACCTGT

GAATATCCCTGCCGCTTTTATCAAACAGCCTCAGTGTGTTTGATCTTGTGTGTACGCGCTTTTGCGAG

TTGCTAGCTGCTTGTGCTATTTGCGAATACCACCCCCAGCATCCCCTTCCCTCGTTTCATATCGCTTGC

ATCCCAACCGCAACTTATCTACGCTGTCCTGCTATCCCTCAGCGCTGCTCCTGCTCCTGCTCACTGCCC

CTCGCACAGCCTTGGTTTGGGCTCCGCCTGTATTCTCCTGGTACTGCAACCTGTAAACCAGCACTGCA

ATGCTGATGCACGGGAAGTAGTGGGATGGGAACACAAATGGAggatcccgcgtctcgaacagagcgcgcaga ggaacgctgaaggtctcgcctctgtcgcacctcagcgcggcatacaccacaataaccacctgacgaatgcgcttggttcttcgtccat tagcgaagcgtccggttcacacacgtgccacgttggcgaggtggcaggtgacaatgatcggtggagctgatggtcgaaacgttcac agcctagggatatcCTGAAGAATGGGAGGCAGGTGTTGTTGATTATGAGTGTGTAAAAGAAAGGGGTA

GAGAGCCGTCCTGACATCCGACTACTATGCAGGTAGCCGCTCGCCCATGCCCGCCTGGCTGAATATT

-continued

GATGCATGCCCATCAAGGCAGGCAGGCATTTCTGTGCACGCACCAAGCCCACAATCTTCCACAACAC

ACAGCATGTACCAACGCACGCGTAAAAGTTGGGGTGCTGCCAGTGCGTCATGCCAGGCATGATGTG

CTCCTGCACATCCGCCATGATCTCCTCCATCGTCTCGGGTGTTTCCGGCGCCTGGTCCGGGAGCCGTT

CCGCCAGATACCAGACGCCACCTCCGACCTCACGGGGTACTTTTCGAGCGTCTGCCGGTAGTCGAC

GATCGCGTCCACCATGGAGTAGCCGAGGCGCCGGAACTGGCGTGACGGAGGGAGGAGAGGGAGG

AGAGAGAGGGGGGGGGGGGGGGGGATGATTACACGCCAGTCTCACAACGCATGCAAGACCCGT

TTGATTATGAGTACAATCATGCACTACTAGATGGATGAGCGCCAGGCATAAGGCACACCGACGTTG

ATGGCATGAGCAACTCCGCATCATATTTCCTATTGTCCTCACGCCAAGCCGGTCACCATCCGCATGC

TCATATTACAGCGCACGCACCGCTTCGTGATCCACCGGGTGAACGTAGTCCTCGACGGAAACATCTG

GCTCGGGCCTCGTGCTGGCACTCCCTCCCATGCCGACAACCTTTCTGCTGTCACCACGACCCACGATG

CAACGCGACACGACCCGGTGGGACTGATCGGTTCACTGCACCTGCATGCAATTGTCACAAGCGCAT

ACTCCAATCGTATCCGTTTGATTTCTGTGAAAACTCGCTCGACCGCCCGCGTCCCGCAGGCAGCGAT

GACGTGTGCGTGACCTGGGTGTTTCGTCGAAAGGCCAGCAACCCCAAATCGCAGGCGATCCGGAGA

TTGGGATCTGATCCGAGCTTGGACCAGATCCCCCACGATGCGGCACGGGAACTGCATCGACTCGGC

GCGGAACCCAGCTTTCGTAAATGCCAGATTGGTGTCCGATACCTTGATTTGCCATCAGCGAAACAAG

ACTTCAGCAGCGAGCGTATTTGGCGGGCGTGCTACCAGGGTTGCATACATTGCCCATTTCTGTCTGG

ACCGCTTTACCGGCGCAGAGGGTGAGTTGATGGGGTTGGCAGGCATCGAAACGCGCGTGCATGGT

GTGTGTGTCTGTTTTCGGCTGCACAATTTCAATAGTCGGATGGGCGACGGTAGAATTGGGTGTTGC

GCTCGCGTGCATGCCTCGCCCCGTCGGGTGTCATGACCGGGACTGGAATCCCCCCTCGCGACCCTCC

TGCTAACGCTCCCGACTCTCCCGCCCGCGCGCAGGATAGACTCTAGTTCAACCAATCGACAactagt*AT*

*GCAGACCGCCCACCAGCGCCCCCCCACCGAGGGCCACTGCTTCGGCGCCCGCCTGCCCACCGCCTCCC*

*GCCGCGCCGTGCGCCGCGCCTGGTCCCGCATCGCCCGCG*ggcgcgcc*GCCGCCGCCGCCGACGCCAAC*

*CCCGCCCGCCCCGAGCGCCGCGTGGTGATCACCGGCCAGGGCGTGGTGACCTCCCTGGGCCAGACC*

*ATCGAGCAGTTCTACTCCTCCCTGCTGGAGGGCGTGTCCGGCATCTCCCAGATCCAGAAGTTCGACA*

*CCACCGGCTACACCACCACCATCGCCGGCGAGATCAAGTCCCTGCAGCTGGACCCCTACGTGCCCAA*

*GCGCTGGGCCAAGCGCGTGGACGACGTGATCAAGTACGTGTACATCGCCGGCAAGCAGGCCCTGG*

*AGTCCGCCGGCCTGCCCATCGAGGCCGCCGGCCTGGCCGGCGCCGGCCTGGACCCCGCCCTGTGCG*

*GCGTGCTGATCGGCACCGCCATGGCCGGCATGACCTCCTTCGCCGCCGGCGTGGAGGCCCTGACCC*

*GCGGCGGCGTGCGCAAGATGAACCCCTTCTGCATCCCCTTCTCCATCTCCAACATGGGCGGCGCCAT*

-continued

*GCTGGCCATGGACATCGGCTTCATGGGCCCCAACTACTCCATCTCCACCGCCTGCGCCACCGGCAAC*

*TACTGCATCCTGGGCGCCGCCGACCACATCCGCCGCGGCGACGCCAACGTGATGCTGGCCGGCGGC*

*GCCGACGCCGCCATCATCCCCTCCGGCATCGGCGGCTTCATCGCCTGCAAGGCCCTGTCCAAGCGCA*

*ACGACGAGCCCGAGCGCGCCTCCCGCCCCTGGGACGCCGACCGCGACGGCTTCGTGATGGGCGAG*

*GGCGCCGGCGTGCTGGTGCTGGAGGAGCTGGAGCACGCCAAGCGCCGCGGCGCCACCATCCTGGC*

*CGAGCTGGTGGGCGGCGCCGCCACCTCCGACGCCCACCACATGACCGAGCCGACCCCCAGGGCCG*

*CGGCGTGCGCCTGTGCCTGGAGCGCGCCCTGGAGCGCGCCCGCCTGGCCCCCGAGCGCGTGGGCTA*

*CGTGAACGCCCACGGCACCTCCACCCCCGCCGGCGACGTGGCCGAGTACCGCGCCATCCGCGCCGT*

*GATCCCCCAGGACTCCCTGCGCATCAACTCCACCAAGTCCATGATCGGCCACCTGCTGGGCGGCGCC*

*GGCGCCGTGGAGGCCGTGGCCGCCATCCAGGCCCTGCGCACCGGCTGGCTGCACCCCAACCTGAAC*

*CTGGAGAACCCCGCCCCCGGCGTGGACCCCGTGGTGCTGGTGGGCCCCCGCAAGGAGCGCGCCGA*

*GGACCTGGACGTGGTGCTGTCCAACTCCTTCGGCTTGGCGGCCACAACTCCTGCGTGATCTTCCGC*

*AAGTACGACGAGATGGACTACAAGGACCACGACGGCGACTACAAGGACCACGACATCGACTACA*

*AGGACGACGACGACAAGTGA*atcgatagatctcttaagGCAGCAGCAGCTCGGATAGTATCGACACACTC

TGGACGCTGGTCGTGTGATGGACTGTTGCCGCCACACTTGCTGCCTTGACCTGTGAATATCCCTGCC

GCTTTTATCAAACAGCCTCAGTGTGTTTGATCTTGTGTGTACGCGCTTTTGCGAGTTGCTAGCTGCTT

GTGCTATTTGCGAATACCACCCCCAGCATCCCCTTCCCTCGTTTCATATCGCTTGCATCCCAACCGCAA

CTTATCTACGCTGTCCTGCTATCCCTCAGCGCTGCTCCTGCTCCTGCTCACTGCCCCTCGCACAGCCTT

GGTTTGGGCTCCGCCTGTATTCTCCTGGTACTGCAACCTGTAAACCAGCACTGCAATGCTGATGCAC

GGGAAGTAGTGGGATGGGAACACAAATGGAaagctttaattaagagctcttgttttccagaaggagttgctccttgag cctttcattctcagcctcgataacctccaaagccgctctaattgtggagggggttcgaatttaaaagcttggaatgttggttcgtgcgt ctggaacaagcccagacttgttgctcactgggaaaaggaccatcagctccaaaaaacttgccgctcaaaccgcgtacctctgctttc gcgcaatctgccctgttgaaatcgccaccacattcatattgtgacgcttgagcagtctgtaattgcctcagaatgtggaatcatctgcc ccctgtgcgagcccatgccaggcatgtcgcgggcgaggacacccgccactcgtacagcagaccattatgctacctcacaatagttca taacagtgaccatatttctcgaagctccccaacgagcacctccatgctctgagtggccaccccccggccctggtgcttgcggagggc aggtcaaccggcatggggctaccgaaatccccgaccggatcccaccacccccgcgatgggaagaatctctccccgggatgtgggcc caccaccagcacaacctgctggcccaggcgagcgtcaaaccataccacacaaatatccttggcatcggccctgaattccttctgccg ctctgctacccggtgcttctgtccgaaagcaggggttgctagggatcgctccgagtccgcaaacccttgtcgcgtggcggggcttgttc gagcttgaagagc

Overexpression of KASII in Strain X:

Construct D1643 derived from pSZ2734 was transformed into S4495 as described previously. Primary transformants were clonally purified and grown under standard lipid production conditions at pH 5. The resulting fatty acid profiles from representative clones arising from transformation of S4495 with D1643 are summarized in Table 42, below. Overexpression of KASII in the SAD2 knockout/knock-down S4495 background resulted in multiple strains accumulating over 50% C18:0 and with substantially reduced levels of C16:0. We also observed that KASII over-expressing lines had lower overall ratios of saturated to unsaturated fatty acids compared to S4495.

TABLE 42

Fatty acid profiles of D1653 [pSZ2734] primary transformants, compared to the S4495 base strain and the wild-type parental strain, S1920.

| | | Strain | | | | | | | | | | | | | |
|---|---|---|---|---|---|---|---|---|---|---|---|---|---|---|---|
| | | S1920 | S4495 | D1653-89 | D1653-10A | D1653-2B | D1653-5B | D1653-7A | D1653-75 | D1653-90 | D1653-98 | D1653-72 | D1653-68 | D1653-82 | D1653-66 |
| Fatty Acid Area % | C12:0 | 0.04 | 0.06 | 0.27 | 0.23 | 0.20 | 0.19 | 0.24 | 0.13 | 0.12 | 0.27 | 0.16 | 0.18 | 0.25 | 0.22 |
| | C14:0 | 1.44 | 1.06 | 1.65 | 1.65 | 1.79 | 1.67 | 1.70 | 1.53 | 1.50 | 1.74 | 1.57 | 1.64 | 1.48 | 1.56 |
| | C16:0 | 29.23 | 29.83 | **8.16** | **11.45** | **10.68** | **10.11** | **9.27** | **11.14** | **11.08** | **9.40** | **9.78** | **9.95** | **8.12** | **8.63** |
| | C16:1 | 0.88 | 8.10 | 0.04 | 0.00 | 0.00 | 0.00 | 0.00 | 0.04 | 0.04 | 0.00 | 0.04 | 0.00 | 0.05 | 0.00 |
| | C18:0 | 2.97 | 40.17 | 54.25 | 58.87 | 53.61 | 53.46 | 53.32 | 53.32 | 53.15 | 52.43 | 52.20 | 51.23 | 30.52 | 50.02 |
| | C18:1 | 98.07 | 20.15 | 23.92 | 22.12 | 22.26 | 23.48 | 24.02 | 22.73 | 23.45 | 23.94 | 25.21 | 26.07 | 28.00 | 28.29 |
| | C18:2 | 6.25 | 6.25 | 6.75 | 6.05 | 6.42 | 6.25 | 6.56 | 6.19 | 5.96 | 6.88 | 6.28 | 6.31 | 6.59 | 6.31 |
| | C18:3α | 0.50 | 0.68 | 0.79 | 0.88 | 0.78 | 0.79 | 0.79 | 0.85 | 0.82 | 0.86 | 0.78 | 0.78 | 0.78 | 0.83 |
| | C20:0 | 0.22 | 1.88 | 3.21 | 2.81 | 3.01 | 2.91 | 3.02 | 2.86 | 2.77 | 3.21 | 2.74 | 2.80 | 2.87 | 2.80 |
| | C20:1 | 0.02 | 0.07 | 0.19 | 0.21 | 0.34 | 0.27 | 0.28 | 0.12 | 0.11 | 0.41 | 0.14 | 0.30 | 0.28 | 0.26 |
| | C22:0 | 0.05 | 0.26 | 0.41 | 0.34 | 0.40 | 0.37 | 0.37 | 0.36 | 0.35 | 0.42 | 0.36 | 0.37 | 0.36 | 0.32 |
| | C24:0 | 0.04 | 0.27 | 0.49 | 0.38 | 0.42 | 0.41 | 0.45 | 0.38 | 0.36 | 0.46 | 0.39 | 0.37 | 0.41 | 0.41 |
| sum C18 | | 67.78 | 66.24 | 85.51 | 82.92 | 83.01 | 83.98 | 84.60 | 83.09 | 83.38 | 84.11 | 84.47 | 84.30 | 85.89 | 85.45 |
| saturates | | 33.97 | 73.52 | 68.94 | 70.63 | 70.11 | 69.12 | 68.37 | 69.72 | 69.33 | 67.98 | 67.20 | ***66.54*** | ***64.01*** | ***64.03*** |
| unsaturates | | 65.71 | 26.28 | 31.29 | 29.26 | 29.74 | 30.79 | 31.65 | 29.93 | 30.38 | 32.09 | 32.45 | ***33.46*** | ***35.70*** | ***35.75*** |

In Table 42, Stearate (C18:0) levels greater than the wild-type level are highlighted with bold text. Palmitate (C16:0) levels lower than S4495 or S1920 are highlighted with bold. For three strains the ratio of saturated to unsaturated fatty acids is ≤2:1; these are highlighted with bold, italicized text.

Stable lines were isolated from the primary transformants shown in Table 42. The fatty acid profiles and lipid titers of shake flask cultures are presented in Table 43, below. The strains accumulated up to 55% C18:0, with as low as 7% C16:0, with comparable lipid titers to the S4495 parent. The saturates:unsaturates ratios were substantially reduced compared to S4495. Strains S5665 and S5675 were selected for evaluation in 3-L high-density fermentations.

TABLE 43

Shake flask assays of strains derived from D1653, expressing KASII, driven by the PmSAD2-2 promoter, targeted to the 6S locus.

| | | | | Primary | | | | | | | | | |
|---|---|---|---|---|---|---|---|---|---|---|---|---|---|
| | | | | D1653-6B | | D1653-9B | D1653-10A | | D1653-72 | | D1653-89 | | |
| | | Strain | | | | | | | | | | | |
| | | S1920 | S4495 | S5664 | S5665 | S5669 | S5670 | S5671 | S5672 | S5673 | S5674 | S5675 | S5677 |
| Fatty Acid Area % | C10:0 | 0.02 | 0.04 | 0.08 | 0.09 | 0.12 | 0.06 | 0.06 | 0.08 | 0.09 | 0.12 | 0.12 | 0.12 |
| | C12:0 | 0.04 | 0.09 | 0.28 | 0.29 | 0.35 | 0.20 | 0.20 | 0.23 | 0.20 | 0.32 | 0.32 | 0.33 |
| | C14:0 | 1.42 | 1.12 | 1.81 | 1.66 | 1.73 | 1.75 | 1.72 | 1.50 | 1.61 | 1.38 | 1.43 | 1.88 |
| | C16:0 | 25.59 | 28.56 | **9.39** | **8.61** | **8.44** | **9.98** | **10.11** | **8.26** | **8.95** | **6.81** | **7.21** | **6.63** |
| | C16:1 | 1.06 | 0.10 | 0.06 | 0.05 | 0.00 | 0.06 | 0.06 | 0.04 | 0.04 | 0.03 | 0.03 | 0.03 |
| | C18:0 | 2.60 | 40.13 | 47.60 | 52.47 | 55.12 | 50.25 | 49.73 | 54.56 | 54.01 | 52.96 | 53.68 | 52.12 |
| | C18:1 | 62.08 | 20.74 | 27.78 | 23.93 | 21.31 | 25.37 | 25.70 | 22.86 | 22.87 | 24.37 | 23.99 | 25.17 |
| | C18:2 | 6.16 | 6.83 | 7.98 | 7.62 | 7.72 | 7.55 | 7.64 | 7.20 | 7.24 | 8.11 | 7.83 | 8.04 |
| | C18:3α | 0.40 | 0.89 | 1.21 | 1.22 | 1.49 | 1.17 | 1.07 | 1.20 | 1.29 | 1.28 | 1.24 | 1.31 |
| | C20:0 | 0.18 | 1.82 | 2.62 | 2.93 | 2.75 | 2.65 | 2.66 | 2.07 | 2.72 | 3.43 | 3.10 | 3.59 |
| | C20:1 | 0.04 | 0.18 | 0.32 | 0.36 | 0.39 | 0.34 | 0.34 | 0.35 | 0.34 | 0.48 | 0.41 | 0.47 |
| | C20:1 | 0.07 | 0.00 | 0.00 | 0.00 | 0.00 | 0.00 | 0.00 | 0.00 | 0.00 | 0.00 | 0.00 | 0.00 |
| | C20:1 | 0.15 | 0.08 | 0.11 | 0.09 | 0.11 | 0.10 | 0.10 | 0.09 | 0.10 | 0.12 | 0.10 | 0.12 |
| | C22:0 | 0.02 | 0.20 | 0.28 | 0.30 | 0.24 | 0.29 | 0.28 | 0.30 | 0.27 | 0.32 | 0.29 | 0.35 |
| | C24:0 | 0.00 | 0.08 | 0.16 | 0.29 | 0.00 | 0.03 | 0.15 | 0.16 | 0.02 | 0.05 | 0.04 | 0.07 |

TABLE 43-continued

Shake flask assays of strains derived from D1653, expressing KASII, driven by the PmSAD2-2 promoter, targeted to the 6S locus.

| | | | Primary | | | | | | | | | |
|---|---|---|---|---|---|---|---|---|---|---|---|---|
| | | | D1653-6B | | D1653-9B | D1653-10A | | D1653-72 | | D1653-89 | | |
| | Strain | | | | | | | | | | | |
| | S1920 | S4495 | S5664 | S5665 | S5669 | S5670 | S5671 | S5672 | S5673 | S5674 | S5675 | S5677 |
| sum C18 | 71.23 | 67.58 | 84.57 | 83.13 | 85.63 | 84.34 | 84.13 | 85.81 | 85.40 | 86.71 | 86.73 | 86.63 |
| saturates | 29.86 | 71.97 | ***62.22*** | ***66.63*** | 68.74 | ***65.20*** | ***64.90*** | 68.05 | 67.90 | ***65.37*** | ***66.17*** | ***64.57*** |
| unsaturates | 69.91 | 27.76 | ***37.50*** | ***33.15*** | 31.07 | ***34.57*** | ***34.89*** | 31.78 | 31.87 | ***34.37*** | ***33.59*** | ***35.13*** |
| % parent lipid titer | 100.0 | 58.2 | 43.4 | 48.8 | 27.5 | 44.1 | 47.4 | 59.0 | 47.6 | 43.2 | 48.4 | 44.4 |

In Table 43, S4495 is the parent strain; S1920 is the wild-type base strain. Stearate (C18:0) levels at least two-fold higher than in the wild-type strain are highlighted in bold. Palmitate levels that are less than in S1920 and S4495 are highlighted bold. Bold italics indicate that the saturates:unsaturates ratio is ≤2:1.

The fatty acid profiles and performance metrics of strains S5665 and S5675 are detailed in Table 44, below. The fatty acid profile of the parent strain S4495, grown under the same fermentation conditions, is presented for comparison. The strains that over-express KASII accumulate about 11% more C18:0 than the S4495 parent. C16:0 is reduced to 7-9%, and levels of unsaturated fatty acids increase by 4-5%. The lipid titers of S5665 and S5675 were comparable to S4495, indicating that KASII over-expression did not have deleterious effects on lipid production.

TABLE 44

End point fatty acid profiles of biomass from S4495, S5665 and S5775 fermentations.

| Strain | S4495 | S5665 | S5675 |
|---|---|---|---|
| Fermentation | 120580F1 | 130097F3 | 130098F4 |
| pH | 5 | 5 | 5 |
| temp (° C.) | 32 | 32 | 32 |
| [N] (mM) | 300 | 300 | 300 |
| N/P | 1.4 | 1.4 | 1.4 |
| DO % | 30 | 30 | 30 |
| sugar | 570 | 570 | 570 |
| Fe (µM) | 557.5 | 557.5 | 557.5 |
| C14:0 | 1.27 | 1.50 | 1.35 |
| C16:0 | 28.35 | **8.88** | **7.33** |
| C16:1 | 0.06 | 0.02 | 0.03 |
| C18:0 | **43.67** | **56.88** | **57.24** |
| C18:1 | 17.63 | 21.57 | 21.66 |
| C18:2 | 5.58 | 6.06 | 6.94 |
| C18:3α | 0.25 | 0.29 | 0.22 |
| C20:0 | 2.11 | 3.28 | 3.46 |
| C22:0 | 0.31 | 0.40 | 0.40 |
| C24:0 | 0.31 | 0.37 | 0.40 |
| sum C18 | 67.13 | 84.80 | 86.06 |
| saturates | 76.02 | 71.31 | 70.18 |
| unsaturates | 23.52 | 27.94 | 28.85 |
| total lipid (g/L) | 475 | 529 | 418 |

The fermentations were cultured for 6 days using a fed-batch process. The S4495 fatty acid profile from fermentation 120580F1 was presented in Table 41, and is shown again in Table 44 for comparison with S5665 and S5675. All fermentations were carried out at 32° C., pH 5, with a nitrogen/phosphorus (N/P) ratio of 1.4, 30% dissolved oxygen (DO), 300 mM nitrogen [N], and 557.5 µM iron. The sugar source was 70% sucrose (S70). Stearate (C18:0) levels higher than in the wild-type strain are indicated with bold. Palmitate (C16:0) levels that are less than in the wild-type are highlighted bold.

Lab scale oils were prepared from biomass derived from the shake flasks and fermentations described above. The TAG compositions of these oils were determined by LC/MS. SOS is the major TAG species in both S5665 and S5675, ranging from 33-35% in the biomass from shake flasks, and reaching 37% in the high-density fermentation biomass. The major palmitate-containing TAGs are substantially reduced, and trisaturate levels are less than half of those observed in S4495 oils. These results demonstrate that KASII over-expression in a high-stearate background significantly improves SOS accumulation, and reduces the accumulation of trisaturated TAGs.

Constructs Used for FATA-1 Disruption, KASII Over-Expression and FAD2 RNAi in S1920

A DNA construct, pSZ2419, was made to simultaneously disrupt the FATA-1 allele, over-express *P. moriformis* KASII and express a FAD2 hairpin construct in S1920. A version of the *S. cerevisiae* SUC2 gene, encoding sucrose invertase, which was codon-optimized for expression in *P. moriformis*, was utilized as a selectable marker for transformation. The sequence of the transforming DNA is provided immediately below. Relevant restriction sites are indicated in lowercase, bold, and are from 5'-3' BspQI, KpnI, AscI, MfeI, BamHI, AvrII, EcoRV, EcoRI, SpeI, AscI, ClaI, BglII, AflII, HinDIII, SacI, SpeI, and XhoI, respectively. BspQI sites delimit the 5' and 3' ends of the transforming DNA. Underlined sequences at the 5' and 3' flanks of the construct represent genomic DNA from *P. moriformis* that enable targeted integration of the transforming DNA via homologous recombination at the FATA-1 locus. Proceeding in the 5' to 3' direction, the *C. reinhardtii* TUB2 promoter driving the expression of the *S. cerevisiae* SUC2 gene (encoding sucrose hydrolyzing activity, thereby permitting the strain to grow on sucrose) is indicated by lowercase, boxed text. The initiator ATG and terminator TGA for SUC2 are indicated by uppercase italics, while the coding region is indicated with lowercase italics. The 3' UTR of the *C. vulgaris* nitrate reductase (NR) gene is indicated by small capitals, followed by a spacer region indicated by lowercase text. The *P. moriformis* AMT3 promoter, indicated by lowercase boxed text, drives expression of the *P. moriformis* KASII gene. The region encoding the plastid targeting peptide from *Chlorella protothecoides* SAD1 is indicated by uppercase italics. The sequence that encodes the mature *P. moriformis* KASII polypeptide is indicated with bold, underlined, uppercase italics, while a 3×FLAG epitope encoding sequence is in bold italics. A second *C. vulgaris* NR 3' UTR is indicated by small capitals. A second *C. reinhardtii* TUB2 promoter sequence, indicated by lowercase boxed text, drives expression of the *P. moriformis* FAD2 hairpin A sequence. The sense and antisense strands are indicated with uppercase, bold italics, and are separated by the FAD2 intron and the first 10 bases of the FAD2 second exon (uppercase italics). A third *C. vulgaris* NR 3' UTR is indicated by small capitals, followed by a second spacer region that is indicated by lowercase text.

Nucleotide sequence of the the transforming DNA from pSZ2419:

(SEQ ID NO: 96)

gctcttcggagtcactgtgccactgagttcgactggtagctgaatggagtcgctgctccactaaacgaattgtcagcaccgccagcc ggccgaggacccgagtcatagcgagggtagtagcgcgccatggcaccgaccagcctgcttgccagtactggcgtctcttccgcttct ctgtggtcctctgcgcgctccagcgcgtgcgcttttccggtggatcatgcggtccgtggcgcaccgcagcggccgctgcccatgcagc gccgctgcttccgaacagtggcggtcagggccgcacccgcggtagccgtccgtccggaacccgcccaagagttttgggagcagctt gagccctgcaagatggcggaggacaagcgcatcttcctggaggagcaccggtgcgtggaggtccggggctgaccggccgtcgcat tcaacgtaatcaatcgcatgatgatcagaggacacgaagtcttggtggcggtggccagaaacactgtccattgcaagggcataggg atgcgttccttcacctctcatttctcatttctgaatccctccctgctcactctttctcctcctccttcccgttcacgcagcattcggggtacc ctttcttgcgctatgacacttccagcaaaaggtagggcgggctgcgagacggcttcccggcgctgcatgcaacaccgatgatgcttc gacccccgaagctccttcggggctgcatgggcgctccgatgccgctccagggcgagcgctgtttaaatagccaggcccccgattgc aaagacattatagcgagctaccaaagccatattcaaacacctagatcactaccacttctacacaggccactcgagcttgtgatcgca ctccgctaagggggcgcctcttcctcttcgtttcagtcacaacccgcaaacggcgcgcc*ATGctgctgcaggccttcctgttcctgct*

*ggccggcttcgccgccaagatcagcgcctccatgacgaacgagacgtccgaccgccccctggtgcacttcacccccaacaagg*

*gctggatgaacgaccccaacggcctgtggtacgacgagaaggacgccaagtggcacctgtacttccagtacaacccgaacg*

*acaccgtctgggggacgcccttgttctggggccacgccacgtccgacgacctgaccaactgggaggaccagcccatcgccatc*

*gccccgaagcgcaacgactccggcgccttctccggctccatggtggtggactacaacaacacctccggcttcttcaacgacacc*

*atcgacccgcgccagcgctgcgtggccatctggacctacaacaccccggagtccgaggagcagtacatctcctacagcctgga*

*cggcggctacaccttcaccgagtaccagaagaaccccgtgctggccgccaactccacccagttccgcgacccgaaggtcttctg*

*gtacgagccctcccagaagtggatcatgaccgcggccaagtcccaggactacaagatcgagatctactcctccgacgacctga*

*agtcctggaagctggagtccgcgttcgccaacgagggcttcctcggctaccagtacgagtgccccggcctgatcgaggtcccc*

*accgagcaggaccccagcaagtcctactgggtgatgttcatctccatcaaccccggcgccccggccggcggctccttcaaccag*

*tacttcgtcggcagcttcaacggcacccacttcgaggccttcgacaaccagtcccgcgtggtggacttcggcaaggactactac*

*gccctgcagaccttcttcaacaccgacccgacctacgggagcgccctgggcatcgcgtgggcctccaactgggagtactccgcc*

*ttcgtgcccaccaacccctggcgctcctccatgtccctcgtgcgcaagttctccctcaacaccgagtaccaggccaacccggaga*

*cggagctgatcaacctgaaggccgagccgatcctgaacatcagcaacgccggcccctggagccggttcgccaccaacaccac*

*gttgacgaaggccaacagctacaacgtcgacctgtccaacagcaccggcaccctggagttcgagctggtgtacgccgtcaac*

*accacccagacgatctccaagtccgtgttcgcggacctctccctctggttcaagggcctggaggaccccgaggagtacctccgc*

*atgggcttcgaggtgtccgcgtcctccttcttcctggaccgcgggaacagcaaggtgaagttcgtgaaggagaacccctacttc*

*accaaccgcatgagcgtgaacaaccagcccttcaagagcgagaacgacctgtcctactacaaggtgtacggcttgctggacc*

*agaacatcctggagctgtacttcaacgacggcgacgtcgtgtccaccaacacctacttcatgaccaccgggaacgccctgggc*

*tccgtgaacatgacgacgggggtggacaacctgttctacatcgacaagttccaggtgcgcgaggtcaagTGA*caattgGCA

GCAGCAGCTCGGATAGTATCGACACACTCTGGACGCTGGTCGTGTGATGGACTGTTGCCGCCACACT

TGCTGCCTTGACCTGTGAATATCCCTGCCGCTTTTATCAAACAGCCTCAGTGTGTTTGATCTTGTGTGT

ACGCGCTTTTGCGAGTTGCTAGCTGCTTGTGCTATTTGCGAATACCACCCCCAGCATCCCCTTCCCTC

GTTTCATATCGCTTGCATCCCAACCGCAACTTATCTACGCTGTCCTGCTATCCCTCAGCGCTGCTCCTG

-continued

CTCCTGCTCACTGCCCCTCGCACAGCCTTGGTTTGGGCTCCGCCTGTATTCTCCTGGTACTGCAACCT

GTAAACCAGCACTGCAATGCTGATGCACGGGAAGTAGTGGGATGGGAACACAAATGGAggatcccgc gtctcgaacagagcgcgcagaggaacgctgaaggtctcgcctctgtcgcacctcagcgcggcatacaccacaataaccacctgacg aatgcgcttggttcttcgtccattagcgaagcgtccggttcacacacgtgccacgttggcgaggtggcaggtgacaatgatcggtgg atgctgatggtcgaaacgttcacagcctagggatatcgaattcggccgacaggacgcgcgtcaaaggtgctggtcgtgtatgccctg gccggcaggtcgttgctgctgctggttagtgattccgcaaccctgatttggcgtcttattttggcgtggcaaacgctggcgcccgcga gccgggccggcggcgatgcggtgccccacggctgccggaatccaagggaggcaagagcgcccgggtcagttgaagggctttacgc gcaaggtacagccgctcctgcaaggctgcgtggtggaattggacgtgcaggtcctgctgaagttcctccaccgcctcaccagcgga caaagcaccggtgtatcaggtccgtgtcatccactctaaagaactcgactacgacctactgatggccctagattcttcatcaaaaac caaagcaccggtgtatcaggtccgtgtcatccactctaaagaactcgactacgacctactgatggccctagattcttcatcaaaaac gcctgagacacttgcccaggattgaaactccctgaagggaccaccaggggccctgagttgttccttcccccgtggcgagctgccag ccaggctgtacctgtgatcgaggctggcgggaaaataggcttcgtgtgctcaggtcatgggaggtgcaggacagctcatgaaacgc caacaatcgcacaattcatgtcaagctaatcagctatttcctcttcacgagctgtaattgtcccaaaattctggtctaccggggtgat ccttcgtgtacgggccttccctcaaccctaggtatgcgcgcatgcggtcgccgcgcaactcgcgcgagggccgagggtttgggacg ggccgtcccgaaatgcagttgcacccggatgcgtggcaccttttttgcgataatttatgcaatggactgctctgcaaaattctggctct gtcgccaaccctaggatcagcggcgtaggatttcgtaatcattcgtcctgatggggagctaccgactaccctaatatcagcccgact gcctgacgccagcgtccacttttgtgcacacattccattcgtgcccaagacatttcattgtggtgcgaagcgtccccagttacgctcac ctgtttcccgacctccttactgttctgtcgacagagcgggcccacaggccggtcgcagccactagt*ATGGCCACCGCATCCAC*

*TTTCTCGGCGTTCAATGCCCGCTGCGGCGACCTGCGTCGCTCGGCGGGCTCCGGGCCCCGGCGCCCA*

*GCGAGGCCCCTCCCCGTGCGCG*ggcgcgcc*GCCGCCGCCGCCGACGCCAACCCCGCCCGCCCCGAGCG*

*CCGCGTGGTGATCACCGGCCAGGGCGTGGTGACCTCCCTGGGCCAGACCATCGAGCAGTTCTACTC*

*CCGCGTGGTGATCACCGGCCAGGGCGTGGTGACCTCCCTGGGCCAGACCATCGAGCAGTTCTACTC*

*CTCCCTGCTGGAGGGCGTGTCCGGCATCTCCCAGATCCAGAAGTTCGACACCACCGGCTACACCACC*

*CTCCCTGCTGGAGGGCGTGTCCGGCATCTCCCAGATCCAGAAGTTCGACACCACCGGCTACACCACC*

*ACCATCGCCGGCGAGATCAAGTCCCTGCAGCTGGACCCCTACGTGCCCAAGCGCTGGGCCAAGCGC*

*GTGGACGACGTGATCAAGTACGTGTACATCGCCGGCAAGCAGGCCCTGGAGTCCGCCGGCCTGCC*

*CATCGAGGCCGCCGGCCTGGCCGGCGCCGGCCTGGACCCCGCCCTGTGCGGCGTGCTGATCGGCAC*

*CGCCATGGCCGGCATGACCTCCTTCGCCGCCGGCGTGGAGGCCCTGACCCGCGGCGGCGTGCGCAA*

*GATGAACCCCTTCTGCATCCCCTTCTCCATCTCCAACATGGGCGGCGCCATGCTGGCCATGGACATC*

*GGCTTCATGGGCCCCAACTACTCCATCTCCACCGCCTGCGCCACCGGCAACTACTGCATCCTGGGCG*

*CCGCCGACCACATCCGCCGCGGCGACGCCAACGTGATGCTGGCCGGCGGCGCCGACGCCGCCATCA*

-continued

*TCCCTCCGGCATCGGCTTCATCGCCTGCAAGGCCCTGTCCAAGCGCAACGACGAGCCCGAGC*

*GCGCCTCCCGCCCCTGGGACGCCGACCGCGACGGCTTCGTGATGGGCGAGGGCGCCGGCGTGCTG*

*GTGCTGGAGGAGCTGGAGCACGCCAAGCGCCGCGGCGCCACCATCCTGGCCGAGCTGGTGGGCG*

*GCGCCGCCACCTCCGACGCCCACCACATGACCGAGCCCGACCCCCAGGGCGGCGGCGTGCGCCTGT*

*GCCTGGAGCGCGCCCTGGAGCGCGCCCGCCTGGCCCCCGAGCGCGTGGGCTACGTGAACGCCCAC*

*GGCACCTCCACCCCCGCCGGCGACGTGGCCGAGTACCGCGCCATCCGCGCCGTGATCCCCCAGGACT*

*CCCTGCGCATCAACTCCACCAAGTCCATGATCGGCCACCTGCTGGGCGGCGCCGGCGCCGTGGAGG*

*CCGTGGCCGCCATCCAGGCCCTGCGCACCGGCTGGCTGCACCCCAACCTGAACCTGGAGAACCCCG*

*CCCCCGGCGTGGACCCCGTGGTGCTGGTGGGCCCCCGCAAGGAGCGCGCCGAGGACCTGGACGTG*

*GTGCTGTCCAACTCCTTCGGCTTCGGCGGCCACAACTCCTGCGTGATCTTCCGCAAGTACGACGAGA*

*TGGACTACAAGGACCACGACGGCGACTACAAGGACCACGACATCGACTACAAGGACGACGACGAC*

*AAGTGA*atcgatagatctcttaagGCAGCAGCAGCTCGGATAGTATCGACACACTCTGGACGCTGGTCGT

GTGATGGACTGTTGCCGCCACACTTGCTGCCTTGACCTGTGAATATCCCTGCCGCTTTTATCAAACAG

CCTCAGTGTGTTTGATCTTGTGTGTACGCGCTTTTGCGAGTTGCTAGCTGCTTGTGCTATTTGCGAAT

ACCACCCCCAGCATCCCCTTCCCTCGTTTCATATCGCTTGCATCCCAACCGCAACTTATCTACGCTGTC

CTGCTATCCCTCAGCGCTGCTCCTGCTCCTGCTCACTGCCCCTCGCACAGCCTTGGTTTGGGCTCCGC

CTGTATTCTCCTGGTACTGCAACCTGTAAACCAGCACTGCAATGCTGATGCACGGGAAGTAGTGGGA

TGGGAACACAAATGGAaagcttaattaagagctcctttcttgcgctatgacacttccagcaaaaggtagggcgggctgcga gacggcttcccggcgctgcatgcaacaccgatgatgcttcgacccccgaagctccttcggggctgcatgggcgctccgatgccgct ccagggcgagcgctgtttaaatagccaggcccccgattgcaagacattatagcgagctaccaagccatattcaaacacctagat cactaccacttctacacaggccactcgagcttgtgatcgcactccgctaagggggcgcctcttcctcttcgtttcagtcacaacccgc aaac**actagt*ATGGCTATCAAGACGAACAGGCAGCCTGTGGAGAAGCCTCCGTTCACGATCGGGACG***

*CTGCGCAAGGCCATCCCCGCGCACTGTTTCGAGCGCTCGGCGCTTCGTAGCAGCATGTACCTGGCCT*

*TTGACATCGCGGTCATGTCCCTGCTCTACGTCGCGTCGACGTACATCGACCCTGCACCGGTGCCTAC*

*GTGGGTCAAGTACGGCATCATGTGGCCGCTCTACTGGTTCTTCCAG**GTGTGTTTGAGGGTTTTGGTT*

*GCCCGTATTGAGGTCCTGGTGGCGCGCATGGAGGAGAAGGCGCCTGTCCCGCTGACCCCCCCGGCT*

*ACCCTCCCGGCACCTTCCAGGGCGCGTACG**GGAAGAACCAGTAGAGCGGCCACATGATGCCGTACT*

*TGACCCACGTAGGCACCGGTGCAGGGTCGATGTACGTCGACGCGACGTAGAGCAGGGACATGACC*

*GCGATGTCAAAGGCCAGGTACATGCTGCTACGAAGCGCCGAGCGCTCGAAACAGTGCGCGGGGA*

*TGGCCTTGCGCAGCGTCCCGATCGTGAACGGAGGCTTCTCCACAGGCTGCCTGTTCGTCTTGATAGC*

-continued

***CAT*ctcgag**GCAGCAGCAGCTCGGATAGTATCGACACACTCTGGACGCTGGTCGTGTGATGGACTGTT

GCCGCCACACTTGCTGCCTTGACCTGTGAATATCCCTGCCGCTTTTATCAAACAGCCTCAGTGTGTTT

GATCTTGTGTGTACGCGCTTTTGCGAGTTGCTAGCTGCTTGTGCTATTTGCGAATACCACCCCCAGCA

TCCCCTTCCCTCGTTTCATATCGCTTGCATCCCAACCGCAACTTATCTACGCTGTCCTGCTATCCCTCAG

CGCTGCTCCTGCTCCTGCTCACTGCCCCTCGCACAGCCTTGGTTTGGGCTCCGCCTGTATTCTCCTGGT

ACTGCAACCTGTAAACCAGCACTGCAATGCTGATGCACGGGAAGTAGTGGGATGGGAACACAAATG

GAaagctgtattgttttccagaaggagttgctccttgagcctttcattctcagcctcgataacctccaaagccgctctaattgtggagg gggttcgaagacagggtggttggctggatggggaaacgctggtcgcgggattcgatcctgctgcttatatcctccctggaagcacac ccacgactctgaagaagaaaacgtgcacacacacaacccaaccggccgaatatttgcttccttatcccgggtccaagagagactgc gatgccccctcaatcagcatcctcctccctgccgcttcaatcttccctgcttgcctgcgcccgcggtgcgccgtctgcccgcccagtc agtcactcctgcacaggccccttgtgcgcagtgctcctgtaccctttaccgctccttccattctgcgaggccccctattgaatgtattcg ttgcctgtgtggccaagcgggctgctgggcgcgccgccgtcgggcagtgctcggcgactttggcggaagccgattgttcttctgtaag ccacgcgcttgctgctttgggaagagaagggggggggtactgaatggatgaggaggagaaggaggggtattggtattatctgagtt gggtgaagagc

Identification and Analysis of FATA-1 Knockout, KASII Over-Expression and FAD2 RNAi Strains:

Construct D1358, derived from pSZ2419, was transformed into S1920 as described previously. Primary transformants were clonally purified and grown under standard lipid production conditions at pH 5. The resulting fatty acid profiles from representative clones arising from transformation of S1920 with D1358 are summarized in Table 45, below. The *P. moriformis* AMT3 promoter is repressed at pH 5 so the observed phenotypes did not reflect over-expression of *P. moriformis* KASII. Nevertheless, we observed that multiple strains had substantially reduced levels of C16:0 and 10-15% increases in C18:1, suggesting that the construct had disrupted the FATA-1 target gene, increasing the amount of palmitoyl-ACP available for extension by endogenous KASII. One line, D1358-13, was selected for further analysis. D1358-13 accumulated ~17% C16:0, ~75% C18:1 and less than 2% C18:2, indicating that we had successfully integrated at FATA-1 and down-regulated activity of the FAD2 $\Delta^{12}$-desaturase in this strain.

In Table 45, Oleate (C18:1) levels greater than the wild-type level are highlighted with bold text. Palmitate (C16:0) levels less than the wild-type are highlighted with bold text. Levels of linoleate (C18:2) reduced by 1% or more compared to the S1920 parent are highlighted with bold text.

The fatty acid profiles of strains derived from transformant D1358-13 were determined to be stable after more than 60 generations of growth in the absence of selection (growth on sucrose). The performance of selected strains in shake flask assays was then evaluated, and the fatty acid profiles and lipid titers are presented in Table 46, below. Flask experiments were performed at pH 7, enabling activation of the PmAMT3 promoter driving expression of the KASII transgene. The combination of KASII over-expression and FATA-1 knock-out leads to further reductions in palmitate levels and enhanced oleate accumulation compared to the phenotypes observed at pH 5 (Table 45). With more than 82% C18:1, less than 11% C16:0, less than 2% C18:2 and ~83% of the wild-type lipid titer, S5003 was determined to be the most appropriate strain from this set to serve as a host strain for subsequent modifications to elevate stearate levels. DNA blot analysis showed that S5003 has a simple insertion of construct D1358 [pSZ2419] at the FATA-1 locus.

TABLE 45

Fatty acid profiles of D1358 [pSZ2419] primary transformants, compared to the wild-type parental strain, S1920.

| | | Strain | | | | | | | | | | |
|---|---|---|---|---|---|---|---|---|---|---|---|---|
| | | S1920 | D1358-13 | D1358-19 | D1358-11 | D1358-9 | D1358-30 | D1358-28 | D1358-6 | D1358-8 | D1358-10 | D1358-3 |
| Fatty Acid Area % | C12:0 | 0.08 | 0.08 | 0.06 | 0.08 | 0.06 | 0.07 | 0.07 | 0.09 | 0.07 | 0.08 | 0.10 |
| | C14:0 | 1.32 | 0.79 | 0.83 | 0.85 | 0.87 | 0.84 | 0.91 | 0.86 | 0.89 | 0.92 | 0.60 |
| | C16:0 | 26.66 | **17.43** | **18.84** | **20.03** | **16.27** | **18.4** | **19.1** | **18.18** | **15.6** | **16.42** | **11.24** |
| | C16:1 | 0.84 | 0.74 | 0.79 | 0.97 | 0.60 | 0.77 | 1.17 | 0.75 | 0.58 | 0.61 | 0.57 |
| | C18:0 | 3.10 | 2.87 | 2.97 | 2.36 | 3.20 | 2.67 | 2.10 | 2.82 | 3.22 | 3.18 | 2.80 |
| | C18:1 | 50.07 | **74.78** | **69.54** | **68.78** | **71.48** | **69.55** | **69.02** | **68.93** | **70.44** | **69.64** | **75.27** |
| | C18:2 | 7.39 | 1.97 | 5.47 | 5.01 | 6.22 | 6.31 | 6.42 | 6.8 | 7.68 | 7.78 | 8.51 |
| | C18:3α | 0.55 | 0.28 | 0.59 | 0.51 | 0.26 | 0.39 | 0.46 | 0.38 | 0.24 | 0.27 | 0.24 |
| | C20:0 | 0.24 | 0.22 | 0.20 | 0.18 | 0.32 | 0.20 | 0.03 | 0.20 | 0.33 | 0.31 | 0.22 |
| | C20:1 | 0.11 | 0.40 | 0.29 | 0.37 | 0.23 | 0.33 | 0.33 | 0.39 | 0.36 | 0.27 | 0.40 |
| | C22:0 | 0.11 | 0.09 | 0.08 | 0.07 | 0.09 | 0.08 | 0.08 | 0.08 | 0.09 | 0.11 | 0.11 |
| sum C18 | | 70.11 | 79.85 | 78.57 | 77.26 | 81.16 | 78.92 | 78.00 | 78.93 | 81.58 | 80.88 | 86.32 |
| saturates | | 31.48 | 21.48 | 22.98 | 23.52 | 20.81 | 22.26 | 22.29 | 22.23 | 20.20 | 21.03 | 14.57 |
| unsaturates | | 67.96 | 78.12 | 76.68 | 76.24 | 78.79 | 77.35 | 77.4 | 77.25 | 79.28 | 78.57 | 84.99 |

TABLE 46

Fatty acid profiles and lipid titers of FATA-1 knockout, KASII over-expressing, FAD2 RNAi lines derived from D1358-13 primary transformants, compared to the wild-type parental strain, S1920.

| | | | Primary T389, D1358-13 Strain | | | | | | | | | | | | |
|---|---|---|---|---|---|---|---|---|---|---|---|---|---|---|---|
| | | S1920 | S5003 | S5004 | S5005 | S5006 | S5007 | S5008 | S5009 | S5010 | S5011 | S5012 | S5013 | S5101 | S5102 |
| Fatty | C12:0 | 0.05 | 0.08 | 0.09 | 0.11 | 0.19 | 0.11 | 0.14 | 0.10 | 0.12 | 0.08 | 0.11 | 0.09 | 0.20 | 0.20 |
| Acid | C14:0 | 1.34 | 0.96 | 0.98 | 1.03 | 1.04 | 0.96 | 1.02 | 0.98 | 1.03 | 0.98 | 1.01 | 1.00 | 1.03 | 1.02 |
| Area | C16:0 | 20.60 | **10.72** | **10.47** | **8.90** | **6.99** | **9.53** | **9.27** | **10.13** | **8.99** | **10.76** | **9.58** | **10.00** | **6.84** | **6.38** |
| % | C16:1 | 0.88 | 0.42 | 0.39 | 0.31 | 0.29 | 0.39 | 0.37 | 0.41 | 0.32 | 0.40 | 0.35 | 0.35 | 0.27 | 0.27 |
| | C18:0 | 2.78 | 2.92 | 3.00 | 3.16 | 2.71 | 2.88 | 2.85 | 2.81 | 3.21 | 3.03 | 3.10 | 3.20 | 2.77 | 2.71 |
| | C18:1 | 58.49 | **82.08** | **82.24** | **83.66** | **85.49** | **83.28** | **83.38** | **82.57** | **83.51** | **82.12** | **83.10** | **82.63** | **85.88** | **86.13** |
| | C18:2 | 5.83 | 1.89 | 1.88 | 1.80 | 2.01 | 1.87 | 1.89 | 1.89 | 1.77 | 1.73 | 1.75 | 1.76 | 1.94 | 1.95 |
| | C18:3α | 0.42 | 0.23 | 0.23 | 0.25 | 0.35 | 0.27 | 0.29 | 0.27 | 0.28 | 0.22 | 0.24 | 0.28 | 0.34 | 0.36 |
| | C20:0 | 0.17 | 0.10 | 0.16 | 0.17 | 0.15 | 0.15 | 0.16 | 0.16 | 0.17 | 0.14 | 0.16 | 0.16 | 0.15 | 0.15 |
| | C20:1 | 0.05 | 0.23 | 0.24 | 0.27 | 0.36 | 0.28 | 0.29 | 0.26 | 0.27 | 0.21 | 0.25 | 0.24 | 0.38 | 0.39 |
| sum C18 | | 67.48 | 87.12 | 87.35 | 88.87 | 90.56 | 88.26 | 88.41 | 87.64 | 88.74 | 87.10 | 88.19 | 87.82 | 90.93 | 91.16 |
| saturates | | 34.03 | 14.83 | 14.70 | 13.37 | 11.08 | 13.03 | 13.44 | 14.28 | 13.52 | 14.99 | 13.96 | 14.45 | 10.79 | 10.40 |
| unsaturates | | 65.83 | 84.85 | 84.98 | 86.29 | 88.50 | 86.05 | 86.22 | 85.40 | 86.12 | 84.68 | 85.69 | 86.21 | 88.81 | 89.11 |
| lipid titer (% parent) | | 100.0 | 82.8 | 81.1 | 72.8 | 54.4 | 58.3 | 53.7 | 70.6 | 72.2 | 106.9 | 76.5 | 77.5 | 56.7 | 54.6 |

In Table 46, Stearate (C18:1) levels greater than the wild-type level are highlighted with bold text. Palmitate (C16:0) levels lower than the wild-type are highlighted with bold text. Linoleate (C18:2) levels that are lower than the wild-type are indicated with bold text.

Constructs Used for SAD2 Knockout/RNAi in S5003:

Two DNA constructs, pSZ2283 and pSZ2697, were made to simultaneously disrupt the SAD2-1 allele and express a SAD2 hairpin construct in S5003. In each construct, the neoR gene from transposon Tn5, conferring resistance to aminoglycoside antibiotics, was used as a selectable marker for transformation. The sequence of the transforming DNA derived from pSZ2283 is provided immediately below. Relevant restriction sites are indicated in lowercase, bold, and are from 5'-3' BspQI, KpnI, XbaI, MfeI, BamHI, AvrII, EcoRV, EcoRI, SpeI, BamHI, HinDIII, and SacI, respectively. BspQI sites delimit the 5' and 3' ends of the transforming DNA. Underlined sequences at the 5' and 3' flanks of the construct represent genomic DNA from *P. moriformis* that enable targeted integration of the transforming DNA via homologous recombination at the SAD2-1 locus. Proceeding in the 5' to 3' direction, the *Chlamydomonas reinhardtii* TUB2 promoter driving the expression of neoR (encoding aminoglycoside phosphotransferase activity, thereby permitting the strain to grow on G418) is indicated by lowercase, boxed text. The initiator ATG and terminator TGA for neoR are indicated by uppercase italics, while the coding region is indicated with lowercase italics. The 3' UTR of the *C. vulgaris* NR gene is indicated by small capitals, followed by a spacer region indicated by lowercase text. A second *C. reinhardtii* TUB2 promoter sequence, indicated by lowercase boxed text, drives expression of the SAD2 hairpin C sequence. The sense and antisense strands are indicated with uppercase, bold italics, and are separated by the *P. moriformis* FAD2 intron and the first 10 bases of the FAD2 second exon (uppercase italics). A second *C. vulgaris* NR 3' UTR is indicated by small capitals.

Nucleotide sequence of the the transforming DNA from pSZ2283:

(SEQ ID NO: 97)

gctcttcgggtcgccgcgctgcctcgcgtcccctggtggtgcgcgcggtcgccagcgaggccccgctgggcgttccgccctcggtgca gcgcccctcccccgtggtctactccaagctggacaagcagcaccgcctgacgcccgagcgcctggagctggtgcagagcatggggc agtttgcggaggagagggtgctgcccgtgctgcaccccgtggacaagctgtggcagccgcaggacttttgcccgaccccgagtcgc ccgacttcgaggatcaggtggcggagctgcgcgcgcgcgccaaggacctgcccgacgagtactttgtggtgctggtgggggacatg atcacggaggaggcgctgccgacctacatggccatgctcaacacgctggacggcgtgcgcgacgacacgggcgcggccgaccacc cgtgggcgcgctggacgcggcagtgggtggccgaggagaaccggcacggcgacctgctgaacaagtactgctggctgacggggc gcgtcaacatgcgggccgtggaggtgaccatcaacaacctgatcaagagcggcatgaacccgcagacggacaacaacccttattt ggggttcgtctacacctccttccaggagcgcgccaccaagtaggtaccctttcttgcgctatgacacttccagcaaaaggtagggcg ggctgcgagacggcttcccggcgctgcatgcaacaccgatgatgcttcgacccccccgaagctccttcggggctgcatgggcgctccg atgccgctccagggcgagcgctgtttaaatagccaggcccccgattgcaaagacattatagcgagctaccaaagccatattcaaac acctagatcactaccacttctacacaggccactcgagcttgtgatcgcactccgctaagggggcgcctcctcctcttcgtttcagtcac -continued aacccgcaaactctagaatatcaATGatcgagcaggacggcctccacgccggctcccccgccgcctgggtggagcgcctgttc ggctacgactgggcccagcagaccatcggctgctccgacgccgccgtgttccgcctgtccgcccagggccgccccgtgctgttc gtgaagaccgacctgtccggcgccctgaacgagctgcaggacgaggccgcccgcctgtcctggctggccaccaccggcgtgc cctgcgccgccgtgctggacgtggtgaccgaggccggccgcgactggctgctgctgggcgaggtgcccggccaggacctgct gtcctcccacctggcccccgccgagaaggtgtccatcatggccgacgccatgcgccgcctgcacaccctggaccccgccacctg ccccttcgaccaccaggccaagcaccgcatcgagcgcgcccgcacccgcatggaggccggcctggtggaccaggacgacctg gacgaggagcaccagggcctggcccccgccgagctgttcgcccgcctgaaggcccgcatgcccgacggcgaggacctggtg gtgacccacggcgacgcctgcctgcccaacatcatggtggagaacggccgcttctccggcttcatcgactgcggccgcctgggc gtggccgaccgctaccaggacatcgccctggccacccgcgacatcgccgaggagctgggcggcgagtgggccgaccgcttcc tggtgctgtacggcatcgccgcccccgactcccagcgcatcgccttctaccgcctgctggacgagttcttcTGAcaattgGCAG

CAGCAGCTCGGATAGTATCGACACACTCTGGACGCTGGTCGTGTGATGGACTGTTGCCGCCACACTT

GCTGCCTTGACCTGTGAATATCCCTGCCGCTTTTATCAAACAGCCTCAGTGTGTTTGATCTTGTGTGT

ACGCGGCTTTTGCGAGTTGCTAGCTGCTTGTGCTATTTGCGAATACCACCCCCAGCATCCCCTTCCCTC

GTTTCATATCGCTTGCATCCCAACCGCAACTTATCTACGCTGTCCTGCTATCCCTCAGCGCTGCTCCTG

CTCCTGCTCACTGCCCCTCGCACAGCCTTGGTTTGGGCTCCGCCTGTATTCTCCTGGTACTGCAACCT

GTAAACCAGCACTGCAATGCTGATGCACGGGAAGTAGTGGGATGGGAACACAAATGGAggatcccgc gtctcgaacagagcgcgcagaggaacgctgaaggtctcgcctctgtcgcacctcagcgcggcatacaccacaataaccacctgacg aatgcgcttggttcttcgtccattagcgaagcgtccggttcacacacgtgccacgttggcgaggtggcaggtgacaatgatcggtgg agctgatggtcgaaacgttcacagcctagggatatcgaattcctttcttgcgctatgacacttccagcaaaaggtagggcgggctgc gagacggcttcccggcgctgcatgcaacaccgatgatgcttcgaccccccgaagctccttcggggctgcatgggcgctccgatgccg ctccagggcgagcgctgtttaaatagccaggcccccgattgcaaagacattatagcgagctaccaaagccatattcaaacacctag atcactaccacttctacacaggccactcgagcttgtgatcgcactccgctaagggggcgcctcttcctcttcgtttcagtcacaacccg caaacactagtGCGCTGGACGCGGCAGTGGGTGGCCGAGGAGAACCGGCACGGCGACCTGCTGAAC

AAGTACTGTTGGCTGACGGGGCGCGTCAACATGCGGGCCGTGGAGGTGACCATCAACAACCTGAT

CAAGAGCGGCATGAACCCGCAGACGGACAACAACCCTTACTTGGGCTTCGTCTACACCTCCTTCCAG

GAGCGCGCGACCAAGTACAGCCACGGCAACACCGCGCGCCTTGCGGCCGAGCAGTGTGTTTGAGG

GTTTTGGTTGCCCGTATCGAGGTCCTGGTGGCGCGCATGGGGGAGAAGGCGCCTGTCCCGCTGACC

CCCCCGGCTACCCTCCCGGCACCTTCCAGGGCGCGTACGggatccTGCTCGGCCGCAAGGCGCGCGGT

GTTGCCGTGGCTGTACTTGGTCGCGCGCTCCTGGAAGGAGGTGTACACGAAGCCCAAGTAAGGGT

TGTTGTCCGTCTGCGGGTTCATGCCGCTCTTGATCAGGTTGTTGATGGTCACCTCCACGGCCCGCAT

GTTGACGCGCCCGTCAGCCAACAGTACTTGTTCAGCAGGTCGCCGTGCCGGTTCTCCTCGGCCACC

CACTGCCGCGTCCAGAGCaagcttGCAGCAGCAGCTCGGATAGTATCGACACACTCTGGACGCTGGTC

GTGTGATGGACTGTTGCCGCCACACTTGCTGCCTTGACCTGTGAATATCCCTGCCGCTTTTATCAAAC

AGCCTCAGTGTGTTTGATCTTGTGTGTACGCGCTTTTGCGAGTTGCTAGCTGCTTGTGCTATTTGCGA

ATACCACCCCCAGCATCCCCTTCCCTCGTTTCATATCGCTTGCATCCCAACCGCAACTTATCTACGCTG

-continued

TCCTGCTATCCCTCAGCGCTGCTCCTGCTCCTGCTCACTGCCCCTCGCACAGCCTTGGTTTGGGCTCCG

CCTGTATTCTCCTGGTACTGCAACCTGTAAACCAGCACTGCAATGCTGATGCACGGGAAGTAGTGGG

ATGGGAACACAAATGGAaagctggagctccagccacggcaacaccgcgcgccttgcggccgagcacggcgacaagaacc tgagcaagatctgcgggctgatcgccagcgacgagggccggcacgagatcgcctacacgcgcatcgtggacgagttcttccgcctc gaccccgagggcgccgtcgccgcctacgccaacatgatgcgcaagcagatcaccatgcccgcgcacctcatggacgacatgggcc acggcgaggccaacccgggccgcaacctcttcgccgacttctccgcggtcgccgagaagatcgacgtctacgacgccgaggactac tgccgcatcctggagcacctcaacgcgcgctggaaggtggacgagcgccaggtcagcggccaggccgccgcggaccaggagtac gtcctgggcctgccccagcgcttccggaaactcgccgagaagaccgccgccaagcgcaagcgcgtcgcgcgcaggcccgtcgcctt ctcctggatctccgggcgcgagatcatggtctagggagcgacgagtgtgcgtgcggggctggcgggagtgggacgccctcctcgct cctctctgttctgaacggaacaatcggccaccccgcgctacgcgccacgcatcgagcaacgaagaaaacccccgatgataggttg cggtggctgccgggatatagatccggccgcacatcaaagggcccctccgccagagaagaagctcctttcccagcagactcctgaag agc

The sequence of the transforming DNA derived from pSZ2697 is provided immediately below. Relevant restriction sites are indicated in lowercase, bold, and are from 5'-3' NsiI, SpeI, BamHI, HinDIII, SacII, EcoRV, KpnI, XbaI, MfeI, BamHI, AvrII, EcoRV, EcoRI and XbaI, respectively. Underlined sequences at the 5' and 3' flanks of the construct represent genomic DNA from *P. moriformis* that enable targeted integration of the transforming DNA via homologous recombination at the SAD2-1 locus. Proceeding in the 5' to 3' direction, the SAD2 hairpin C sense and antisense strands are indicated with uppercase, bold italics, and are separated by the *P. moriformis* FAD2 intron and the first 10 bases of the FAD2 second exon (uppercase italics). The 3' UTR of the *C. vulgaris* NR gene is indicated by small capitals. The *Chlorella sorokiniana* Glutamate Dehydrogenase (GDH) promoter, driving the expression of neoR (encoding aminoglycoside phosphotransferase activity, thereby permitting the strain to grow on G418) is indicated by lowercase, boxed text. The initiator ATG and terminator TGA for neoR are indicated by uppercase italics, while the coding region is indicated with lowercase italics. A second *C. vulgaris* NR 3' UTR is indicated by small capitals, followed by a spacer region indicated by lowercase text.

Nucleotide sequence of the the transforming DNA from pSZ2697:

(SEQ ID NO: 98)

atgcatgccggtcaccacccgcatgctcgtactacagcgcacgcaccgcttcgtgatccaccgggtgaacgtagtcctcgacggaa acatctggttcgggcctcctgcttgcactcccgcccatgccgacaacctttctgctgttaccacgacccacaatgcaacgcgacacga ccgtgtgggactgatcggttcactgcacctgcatgcaattgtcacaagcgcttactccaattgtattcgtttgttttctgggagcagttg ctcgaccgcccgcgtcccgcaggcagcgatgacgtgtgcgtggcctgggtgtttcgtcgaaaggccagcaaccctaaatcgcaggc gatccggagattgggatctgatccgagtttggaccagatccgccccgatgcggcacgggaactgcatcgactcggcgcggaaccca gctttcgtaaatgccagattggtgtccgatacctggatttgccatcagcgaaacaagacttcagcagcgagcgtatttggcgggcgt gctaccagggttgcatacattgcccatttctgtctggaccgctttactggcgcagagggtgagttgatggggttggcaggcatcgaaa cgcgcgtgcatggtgtgcgtgtctgttttcggctgcacgaattcaatagtcggatgggcgacggtagaattgggtgtggcgctcgcgt gcatgcctcgccccgtcgggtgtcatgaccgggactggaatcccccctcgcgaccatcttgctaacgctcccgactctcccgactagt

*GCGCTGGACGGCGGCAGTGGGTGGCCGAGGAGAACCGGCACGGCGACCTGCTGAACAAGTACTGT*

*TGGCTGACGGGGCGCGTCAACATGCGGGCCGTGGAGGTGACCATCAACAACCTGATCAAGAGCG*

*GCATGAACCCGCAGACGGACAACAACCCTTACTTGGGCTTCGTCTACACCTCCTTCCACCAGCGCGC*

*GACCAAGTACAGCCACGGCAACACCGCGCGCCTTGCGGCCGAGCA*_GTGTGTTTGAGGGTTTTGGTT_

_GCCCGTATCGAGGTCCTGGTGGCGCGCATGGGGGAGAAGGCGCCTGTCCCGCTGACCCCCCCGGCT_

_ACCCTCCCGGCACCTTCCAGGGCGCGTACG_ggatcc*TGCTCGGCCGCAAGGCGCGCGGTGTTGCCGTG*

-continued

*GCTGTACTTGGTCGCGCGCTCCTGGAAGGAGGTGTAGACGAAGCCCAAGTAAGGGTTGTTGTCCG*

*TCTGCGGGTTCATGCCGCTCTTGATCAGGTTGTTGATGGTCACCTCCACGGCCCGCATGTTGACGCG*

*CCCCGTCAGCCAACAGTACTTGTTCAGCAGGTCGCCGTGCCGGTTCTCCTCGGCCACCCACTGCCGC*

*GTCCAGCGC*aagcttGCAGCAGCAGCTCGGATAGTATCGACACACTCTGGACGCTGGTCGTGTGATG

GACTGTTGCCGCCACACTTGCTGCCTTGACCTGTGAATATCCCTGCCGCTTTTATCAAACAGCCTCAG

TGTGTTTGATCTTGTGTGTACGCGCTTTTGCGAGTTGCTAGCTGCTTGTGCTATTTGCGAATACCACC

CCCAGCATCCCCTTCCCTCGTTTCATATCGCTTGCATCCCAACCGCAACTTATCTACGCTGTCCTGCTA

TCCCTCAGCGCTGCTCCTGCTCCTGCTCACTGCCCCTCGCACAGCCTTGGTTTGGGCTCCGCCTGTATT

CTCCTGGTACTGCAACCTGTAAACCAGCACTGCAATGCTGATGCACGGGAAGTAGTGGGATGGGAA

CACAAATGGAAAGCTGgagctcaaagatatcaacttaattaaccaaggtacccgcctgcaacgcaagggcagccacagcc gctcccacccgccgctgaaccgacacgtgctgggcgcctgccgcctgcctgcctgccgcatgcttgtgctggtgaggctgggcagtgctg ccatgctgattgaggcttggttcatcgggtggaagcttatgtgtgtgctgggcttgcatgccgggcaatgcgcatggtggcaagagg gcggcagcacttgctggagctgccgcggtgcctccaggtggttcaatcgcggcagccagagggatttcagatgatcgcgcgtacag gttgagcagcagtgtcagcaaaggtagcagtttgccagaatgatcggttcagctgttaatcaatgccagcaagagaaggggtcaag tgcaaacacgggcatgccacagcacgggcaccggggagtggaatggcaccaccaagtgtgtgcgagccagcatcgccgcctggct gtttcagctacaacggcaggagtcatccaacgtaaccatgagctgatcaacactgcaatgcatcgggcgggcgtgatgcagcatgc ctggcgaagacacatggtgtgcggatgctgccggctgctgcctgctgcgcacgccgttgagttggcagcaggctcagccatgcactg gatggcagctgggctgccactgcaatgtggtggataggatgcaagtggagcgaataccaaaccctctggctgcttgctgggttgcat ggcatcgcaccatcagcaggagcgcatgcgaagggactggccccatgcacgccatgccaaaccggagcgcaccgagtgtccaca ctgtcaccaggcccgcaagctttgcagaaccatgctcatggacgcatgtagcgctgacgtcccttgacggcgctcctctcgggtgtg ggaaacgcaatgcagcacaggcagcagaggcggcggcagcagagcggcggcagcagcggcgggggccacccttgttgcggggt cgcgccccagccagcggtgatgcgctgatcccaaacgagttcacattcatttgcatgcctggagaagcgaggctggggcctttgggc tggtgcagcccgcaatggaatgcgggaccgccaggctagcagcaaaggcgcctcccctactccgcatcgatgttccatagtgcatt ggactgcatttgggtggggcggccggctgtttctttcgtgttgcaaacgcgccagctcagcaacctgtcccgtgggtccccgtgcc gatgaaatcgtgtgcacgccgatcagctgattgcccggctcgcgaagtaggcgccctcctttctgctcgccctctctccgtcccgcctc tagaatatca*ATGatcgagcaggacggcctccacgccggctcccccgccgcctgggtggagcgcctgttcggctacgactggg*

*cccagcagaccatcggctgctccgacgccgccgtgttccgcctgtccgcccagggccgccccgtgctgttcgtgaagaccgacct*

*gtccggcgccctgaacgagctgcaggacgaggccgcccgcctgtcctggctggccaccaccggcgtgccctgcgccgccgtgc*

*tggacgtggtgaccgaggccggccgcgactggctgctgctgggcgaggtgcccggccaggacctgctgtcctcccacctggcc*

*cccgccgagaaggtgtccatcatggccgacgccatgcgccgcctgcacaccctggaccccgccacctgccccttcgaccaccag*

*gccaagcaccgcatcgagcgcgcccgcacccgcatggaggccggcctggtggaccaggacgacctggacgaggagcacca*

*gggcctggcccccgccgagctgttcgcccgcctgaaggcccgcatgcccgacggcgaggacctggtggtgacccacggcgac*

-continued

*gcctgcctgcccaacatcatggtggagaacggccgcttctccggcttcatcgactgcggccgcctgggcgtggccgaccgctac*

*caggacatcgccctggccacccgcgacatcgccgaggagctgggcggcgagtgggccgaccgcttcctggtgctgtacggca*

*tcgccgcccccgactcccagcgcatcgccttctaccgcctgctggacgagttcttcTGA*caattgGCAGCAGCAGCTCGGA

TAGTATCGACACACTCTGGACGCTGGTCGTGTGATGGACTGTTGCCGCCACACTTGCTGCCTTGACC

TGTGAATATCCCTGCCGCTTTTATCAAACAGCCTCAGTGTGTTTGATCTTGTGTGTACGCGCTTTTGC

GAGTTGCTAGCTGCTTGTGCTATTTGCGAATACCACCCCCAGCATCCCCTTCCCTCGTTTCATATCGCT

TGCATCCCAACCGCAACTTATCTACGCTGTCCTGCTATCCCTCAGCGCTGCTCCTGCTCCTGCTCACTG

CCCCTCGCACAGCCTTGGTTTGGGCTCCGCCTGTATTCTCCTGGTACTGCAACCTGTAAACCAGCACT

GCAATGCTGATGCACGGGAAGTAGTGGGATGGGAACACAAATGGAggatcccgcgtctcgaacagagcgcg cagaggaacgctgaaggtctcgcctctgtcgcacctcagcgcggcatacaccacaataaccacctgacgaatgcgcttggttcttcg tccattagcgaagcgtccggttcacacacgtgccacgttggcgaggtggcaggtgacaatgatcggtggagctgatggtcgaaacg ttcacagcctagggatatcgaattccgggtcgccgcgctgcctcgcgtcccctggtggtgcgcgcggtcgccagcgaggccccgctg ggcgttccgccctcggtgcagcgcccctcccccgtggtctactccaagctggacaagcagcaccgcctgacgcccgagcgcctgga gctggtgcagagcatggggcagtttgcggaggagagggtgctgcccgtgctgcaccccgtggacaagctgtggcagccgcaggac tttttgcccgaccccgagtcgcccgacttcgaggatcaggtggcggagctgcgcgcgcgcgccaaggacctgcccgacgagtacttt gtggtgctggtgggggacatgatcacggaggaggcgctgccgacctacatggccatgctcaacacgctggacggcgtgcgcgacg acacgggcgcggccgaccacccgtgggcgcgctggacgcggcagtgggtggccgaggagaaccggcacggcgacctgctgaaca agtactgctggctgacggggcgcgtcaacatgcgggccgtggaggtgaccatcaacaacctgatcaagagcggcatgaacccgca gacggacaacaacccttatttggggttcgtctacacctccttccaggagcgcgccaccaagtatctaga

Identification and Analysis of SAD2 Knockout/Knockdown Strains in the S5003 Background:

Constructs D1639, derived from pSZ2697, and D1682, derived from pSZ2283, were transformed into S5003 as described previously. Primary transformants were clonally purified and grown under standard lipid production conditions at pH 7. The resulting fatty acid profiles from representative clones arising from transformation are summarized in Table 47, below. D1639 transformants accumulated up to 56% C18:0, and D1682 transformants accumulated a maximum of about 35% C18:0. Most of the increases in stearate came at the expense of C18:1, indicating that SAD activity was significantly reduced by the SAD2 knockout/RNAi constructs in these strains. C16:0 levels varied from 6% to 14%; C18:2 ranged from 2-5%. Most strains maintained the low C16:0 and C18:2 phenotypes of the S5003 parent. These fatty acid profiles demonstrate that down-regulating SAD2 expression using knockout/RNAi constructs, in a background with disrupted FATA-1, KASII over-expression and FAD2 RNAi, produces strains with high C18:0, low C16:0 and low C18:2 phenotypes. These strains will be useful for production of high stability, high stearate, high oleic oils, and oils which have high SOS content.

TABLE 47

Fatty acid profiles of D1639 [pSZ2697] and D1682 [pSZ2283] primary transformants, compared to the wild-type strain, S1920, and the S5003 parental base strain.

| | | Strain | | | | | | | | | |
|---|---|---|---|---|---|---|---|---|---|---|---|
| | | S1920 | S5003 | D1682-4 | D1682-17 | D1682-7 | D1682-6 | D1639-2 | D1639-5 | D1639-10 | D1639-19 |
| Fatty Acid | C12:0 | 0.04 | 0.11 | 0.14 | 0.10 | 0.32 | 0.31 | 0.00 | 0.19 | 0.17 | 0.00 |
| Area % | C14:0 | 1.29 | 0.98 | 1.03 | 0.94 | 1.11 | 1.15 | 1.64 | 1.39 | 1.61 | 1.02 |
| | C16:0 | 27.50 | **7.75** | **8.68** | **10.41** | **5.70** | **5.96** | **7.54** | **9.90** | **14.39** | **12.02** |
| | C16:1 | 0.71 | 0.30 | 0.06 | 0.07 | 0.07 | 0.10 | 0.00 | 0.00 | 0.00 | 0.00 |
| | C18:0 | 3.28 | 3.60 | 35.46 | 29.92 | 24.66 | 22.30 | 55.96 | 53.38 | 48.46 | 37.30 |
| | C18:1 | 57.80 | **84.14** | 48.39 | 52.49 | 61.04 | 68.60 | 23.70 | 26.79 | 32.93 | 42.81 |
| | C18:2 | 7.90 | 2.09 | 2.37 | 2.36 | 3.03 | 2.88 | 5.09 | 3.50 | 3.22 | 2.79 |
| | C18:3α | 0.57 | 0.32 | 0.50 | 0.65 | 0.66 | 0.58 | 1.59 | 0.98 | 1.01 | 0.85 |
| | C20:0 | 0.28 | 0.23 | 2.07 | 1.87 | 1.75 | 1.51 | 3.04 | 2.73 | 2.29 | 2.22 |
| | C20:1 | 0.18 | 0.35 | 0.54 | 0.49 | 0.78 | 0.83 | 0.37 | 0.33 | 0.30 | 0.40 |
| | C22:0 | 0.06 | 0.02 | 0.27 | 0.27 | 0.23 | 0.20 | 0.43 | 0.30 | 0.29 | 0.29 |
| | C24:0 | 0.09 | 0.02 | 0.33 | 0.26 | 0.34 | 0.26 | 0.64 | 0.45 | 0.32 | 0.31 |
| sum C18 | | 69.55 | 90.14 | 86.72 | 85.42 | 89.39 | 89.36 | 86.34 | 84.65 | 80.62 | 83.75 |
| saturates | | 32.54 | 12.70 | 47.98 | 48.77 | 34.11 | 31.69 | 69.25 | 68.40 | 62.53 | 53.16 |
| unsaturates | | 67.16 | 87.21 | 51.86 | 56.06 | 65.58 | 67.99 | 30.75 | 31.60 | 37.46 | 46.86 |

In Table 47, Stearate (C18:0) levels greater than the wild-type level are highlighted with bold text. Oleate (C18:1) levels that are higher than in the wild-type are indicated with bold text. Palmitate (C16:0) levels less than the wild-type level are highlighted with bold. Reduced levels of linoleate (C18:2) compared to the wild-type are highlighted with bold text.

Stable lines were isolated from a number of D1639 and D1682 transformants. Shake flask assays were carried out to evaluate the performance of four lines derived from D1639-5. Fatty acid profiles and relative lipid titers from the biomass are shown in Table 48, below.

TABLE 48

Shake flask assays of strains derived from D1639-5, expressing SAD2hpC, driven by the CrTUB2 promoter, targeted to the SAD2-1 locus.

| | | Primary T530; D1639-5 Strain | | | | | |
|---|---|---|---|---|---|---|---|
| | | S1920 | S5003 | S5774 | S5775 | S5776 | S5777 |
| Fatty Acid Area % | C10:0 | 0.01 | 0.00 | 0.07 | 0.08 | 0.05 | 0.04 |
| | C12:0 | 0.02 | 0.11 | 0.19 | 0.22 | 0.25 | 0.23 |
| | C14:0 | 1.52 | 1.10 | 1.35 | 1.32 | 1.30 | 1.43 |
| | C16:0 | 31.61 | **9.59** | **9.28** | **8.44** | **7.74** | **9.46** |
| | C16:1 | 1.04 | 0.34 | 0.03 | 0.02 | 0.01 | 0.01 |
| | C17:0 | 0.10 | 0.11 | 0.10 | 0.10 | 0.10 | 0.09 |
| | C18:0 | 2.98 | 4.36 | 53.01 | 53.52 | 55.32 | 52.09 |
| | C18:1 | 54.81 | **80.84** | 27.26 | 27.52 | 27.42 | 28.06 |
| | C18:2 | 6.88 | 2.42 | 3.55 | 3.52 | 2.38 | 3.45 |
| | C18:3α | 0.53 | 0.33 | 0.97 | 1.03 | 0.82 | 1.06 |
| | C20:0 | 0.26 | 0.31 | 2.88 | 2.94 | 3.15 | 2.72 |
| | C20:1 | 0.05 | 0.34 | 0.38 | 0.38 | 0.40 | 0.37 |
| | C22:0 | 0.03 | 0.06 | 0.36 | 0.37 | 0.39 | 0.35 |
| | C24:0 | 0.07 | 0.08 | 0.53 | 0.54 | 0.53 | 0.60 |
| sum C18 | | 65.19 | 87.95 | 84.79 | 85.58 | 85.94 | 84.66 |
| saturates | | 36.59 | 15.70 | 67.76 | 67.52 | 68.82 | 66.99 |
| unsaturates | | 63.30 | 84.26 | 32.19 | 32.46 | 31.02 | 32.95 |
| % wilt-type lipid titer | | 100.0 | 70.3 | 34.8 | 33.7 | 31.04 | 35.3 |

In Table 48, S5003 is the parent strain; S1920 is the wild-type base strain. Stearate (C18:0) levels higher than in the wild-type strain are indicated with bold. Bold text indicates the increased level of oleate (C18:1) in S5003 compared to the wild-type. Palmitate (C16:0) levels that are less than in the wild-type are highlighted bold. Linoleate (C18:2) levels that are less than in the wild-type are indicated with bold.

Figure 21:
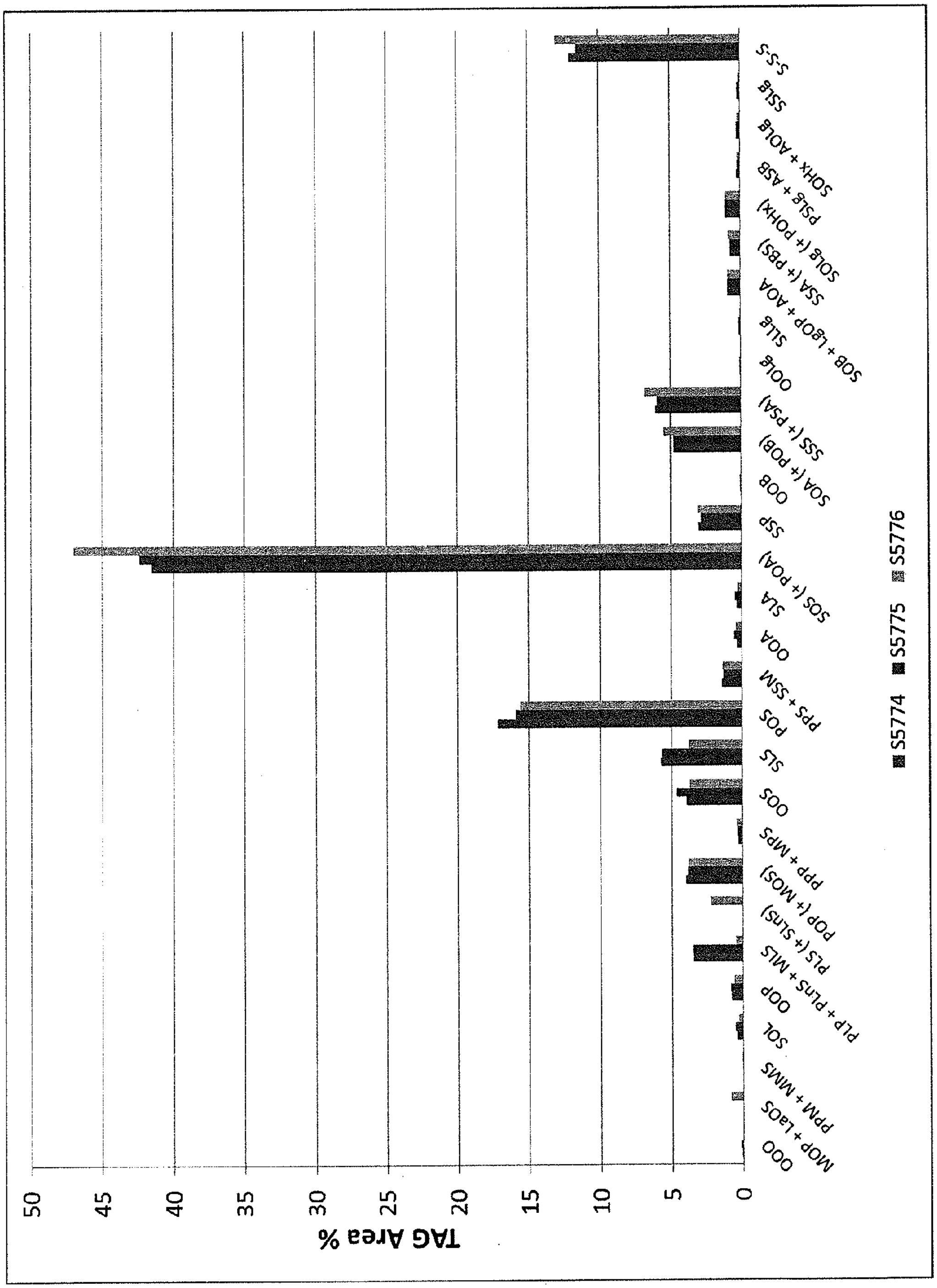
FIG. 21 shows TAG composition of S5774, S5775 and S5776 oils from shake flask biomass. La=laurate (C12:0), M=myristate (C14:0), P=palmitate (C16:0), Po=palmitoleate (C16:1), S=stearate (C18:0), O=oleate (C18:1), L=linoleate (C18:2), Ln=α-linolenate (C18:3), A=arachidate (C20:0), B=behenate (C22:0), Lg=lignocerate (C24:0), Hx=hexacosanoate (C26:0). S—S—S refers to the sum of TAGs in which all three fatty acids are saturated. In each block of bars, the strains are shown in the order illustrated at the bottom of the figure.

Lab scale oils were prepared from biomass collected from the S5774, S5775 and S5776 shake flasks. The TAG compositions of these oils were determined by LC/MS, and are shown in FIG. 21. SOS accumulation ranged from 42-47% in these strains. POS was the next most abundant TAG, at 16-17%. Linoleate-containing TAGs were reduced by more than 50% compared to the S5665 and S5675 oils, described above. S5774-S5776 oils contained 12-13% trisaturated TAGs (S—S—S), similar to the amounts that accumulated in the S5665 and S5775 oils. Modulation of SAD activity during oil production to prevent overproduction of saturated fatty acids may help to reduce accumulation of trisaturates.

Example 49

Properties of Methyl Oleate from High Oleic Microalgal Oils

Esterified oils high in methyl oleate are useful in a variety of applications such as cleaning and lubrication of machinery. For some of these applications, high thermal stability is desired. Thermal stability testing was performed on methylated oil prepared from high-oleic and high-stability-high oleic triglyceride oils prepared from heterotrophically grown oleaginous microalgae as described above. The oils were bleached and deodorized prior to methylation. Commerically available soya methyl ester was used as a control.

High Oleic (HO) oil was prepared from a high oil-yielding strain of *Prototheca moriformis* transformed with a plasmid that can be described as FatA1_Btub:inv:nr::amt03-CwTE2:nr_FatA1. This plasmid was designed to homologously recombine in the FATA1 chromosomal site, thus ablating a FATA acyl-ACP thioesterase choromosomal allele, while expressing an exogenous acyl-ACP thioesterase from *Cuphea. wrightii* (CwTE2, SEQ ID NO: 11) under control of the pH-regulatable amt3 promoter. The CwTE2 gene can be downregulated by cultivation at pH 5 during oil production to further elevate oleate production. Sucrose invertase was also expressed as a selection marker and to allow for cultivation of the strain on sucrose as a sole carbon source. The 3' UTR sequences are from the *Chlorella vulgaris* nitrate reductase gene. The resulting HO strain is denoted Stain Q. The fatty acid profile of the oil produced by Strain Q is listed below in Table 49.

TABLE 49

Fatty acid profile of high oleic oil from Strain Q.

| Fatty Acid | Area % |
|---|---|
| C10 | 0.01 |
| C12:0 | 0.03 |
| C14:0 | 0.43 |
| C15:0 | 0.03 |
| C16:0 | 7.27 |
| C16:1 iso | 0.81 |
| C16:1 | 0.689 |
| C17:0 | 0.06 |
| C18:0 | 1.198 |
| C18:1 | 80.15 |
| C18:1 iso | 0.08 |
| C18:2 | 8.38 |
| C18:3 ALPHA | 0.25 |

TABLE 49-continued

| Fatty acid profile of high oleic oil from Strain Q. | |
|---|---|
| Fatty Acid | Area % |
| C20:0 | 0.02 |
| C20:1 | 0.38 |
| C22:0 | 0.04 |
| C24:0 | 0.03 |

A high-stability-high-oleic oil (HSAO) was also prepared from a high oil-yielding strain of *Prototheca moriformis* transformed with a plasmid that can be described as FADc5'_Btub:inv:nr::btub-CpSAD_CtOTE:nr_FADc3'. The resulting strain (Strain R) expresses sucrose invertase as a selection marker and to allow for cultivation on sucrose as a sole carbon source. In addition, a FAD allele (encoding fatty acid desaturase responsible for the conversion of oleate to linoleate) is disrupted and an oleate-specific acy-ACP thioesterase (*Carthamus tinctorius* OTE, see example 5) fused to the transit peptide from the SAD gene of *Chlorella protothecoides* is expressed under control of the beta tubulin promoter. The 3' UTR sequences are from the *Chlorella vulgaris* nitrate reductase gene. The fatty acid profile of the oil produced by Strain R after heterotrophic cultivation is listed below in Table 50. The fatty acid profile has greater than 85% oleate yet almost none of the major polyunsaturates, linoeic and linolenic acids.

TABLE 50

| Fatty acid profile of high oleic oil from Strain R. | |
|---|---|
| Fatty Acid | Area % |
| C10 | 0.02 |
| C12:0 | 0.07 |
| C14:0 | 0.09 |
| C15:0 | 0.05 |
| C16:0 | 7.28 |
| C16:1 | 0.70 |
| C17:0 | 0.08 |
| C18:0 | 2.15 |
| C18:1 | 86.32 |
| C20:0 | 0.30 |
| C20:1 | 0.46 |
| C22:0 | 0.08 |
| C23:0 | 0.01 |
| C24:0 | 0.06 |

The HO and HSAO oils were methylated by known biodiesel production techniques to make methyl-HO and methyl-HSAO esters. These methyl esters where then subjection to thermal testing according to the following procedure:

1. Prepare equipment as shown in FIG. 1.
2. Add 1 liter of water to test vessel and bring to an active boil on the hotplate.
3. To each test product add 50 ppm Cobalt (0.083 g of 6% Cobalt Napthenate in 100.0 gram sample) and mix thoroughly.
4. Weigh out, in a watch glass, 7.0 g of 100% cotton gauze, (#50 Cheese Cloth).
5. Evenly distribute 14.0 g of test product, as prepared in step 3, onto the gauze.
6. Place thermocouple (thermometer) through the center of #15 stopper. Wrap cotton around the thermocouple.
7. Place wrapped cotton into 24 mesh wire frame cylinder so that it occupies the upper 4½ inches.
8. Position cylinder with wrapped gauze into the 1 L tall form beaker. Secure the beaker in the boiling water and begin recording the temperature increase with time.
9. Continue monitoring the temperature for 2 hours or until a 10 degree temperature drop in observed.
10. Plot temperature vs time on a graph.
11. Any sample which shows a temperature exceeding 100 degrees C. in 1 hour or 200 degrees C. in 2 hours should be regarded as a dangerous oxidation risk or one that is likely to spontaneously combust.

Figure 18:
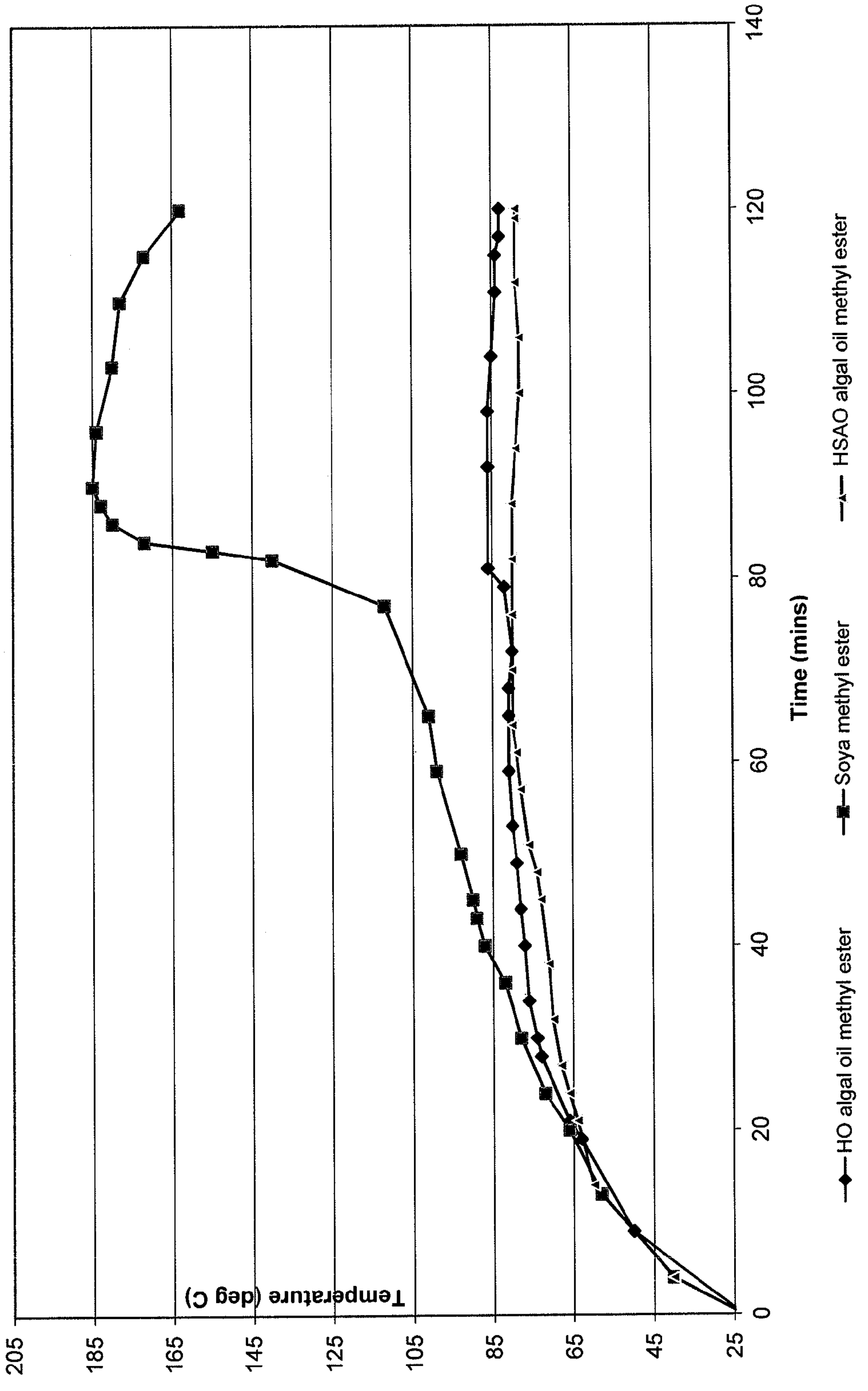
FIG. 18 shows the results of thermal stability testing performed on methylated oil prepared from high-oleic (HO) and high-stability high-oleic (HSAO) triglyceride oils prepared from heterotrophically grown oleaginous microalgae, in comparison to a soya methyl ester control sample.
Figure 20:
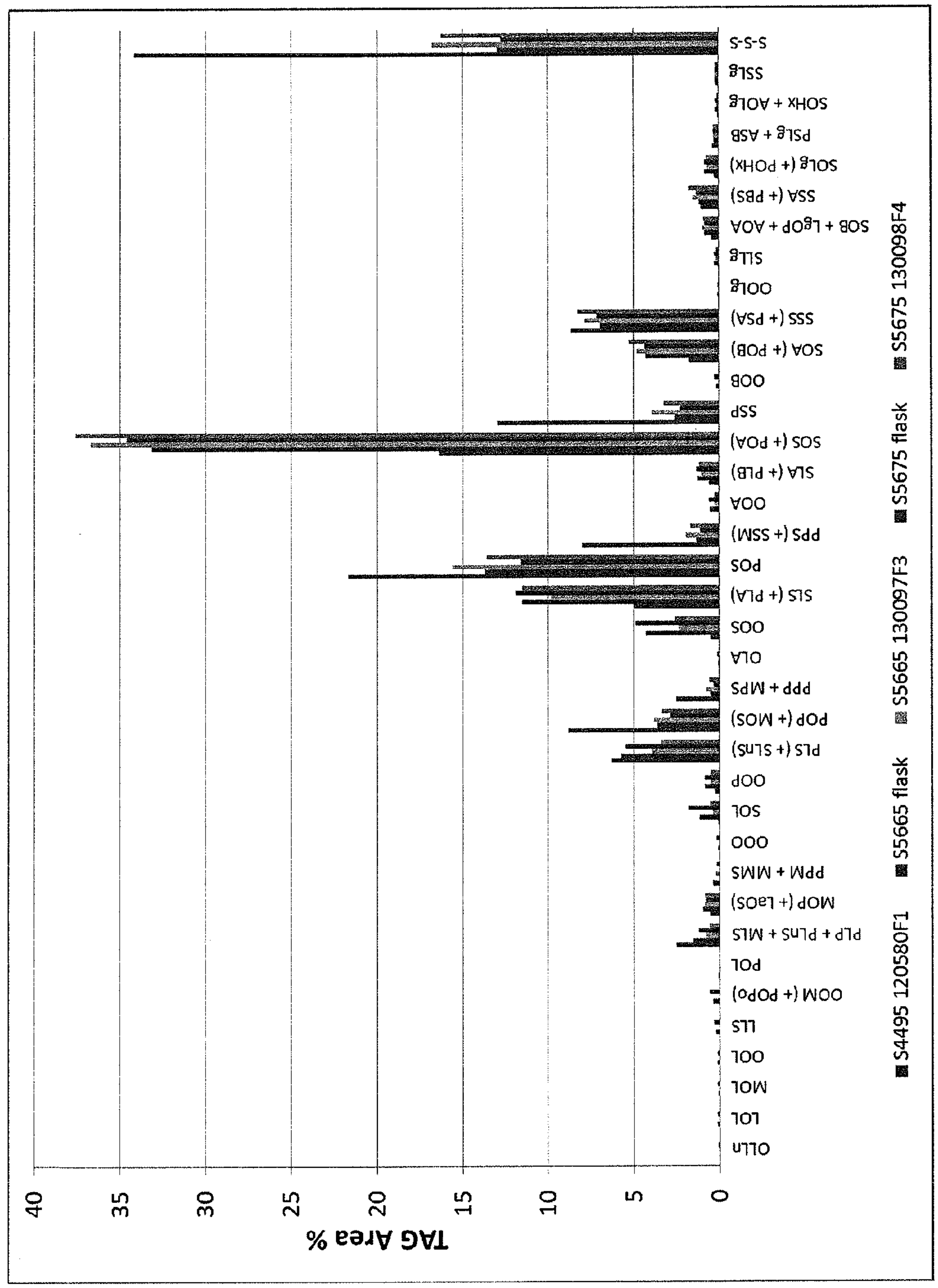
FIG. 20 shows TAG composition of S4495, S5665 and S5675 oils from flask and fermentor biomass. La=laurate (C12:0), M=myristate (C14:0), P=palmitate (C16:0), Po=palmitoleate (C16:1), S=stearate (C18:0), O=oleate (C18:1), L=linoleate (C18:2), Ln=α-linolenate (C18:3), A=arachidate (C20:0), B=behenate (C22:0), Lg=lignocerate (C24:0), Hx=hexacosanoate (C26:0) S—S—S refers to the sum of TAGs in which all three fatty acids are saturated. In each block of bars, the strains are shown in the order illustrated at the bottom of the figure.

Results: The HO and HSAO methyl ester did not exhibit auto-oxidation as evidenced by a temperature rise. The control soya methyl ester sample did exhibit the potential for auto-oxidation. The time-temperature profiles are shown in FIG. 18.

In addition, methylated fatty acid from oil produced by Strain Q was found to have the following characteristics:

Flash Point (ASTM D93) of 182° C.
Non-VOC
Kauri Butanol value (ASTM D1133) of 53.5
Viscosity at 40° C. (ASTM D445) of 4.57 mm2/s
Acid Number (ASTM D664) of 0.17 mg KOH/g
Boiling range distribution (ASTM D2887) 325-362° C.

Example 50

Further Properties of High Oleic (HO) and High-Stability-High-Oleic (HSAO) Microalgal Oils The high oleic oil and the high-stability high-oleic algal oils can have the properties shown in FIG. 19 or these values ±20% for the measured parameters.

In one experiment, HSAO microalgal oil showed 512 hour stability measured by OSI at 110° C. (estimated using 130° C. data) with antioxidants of 0.5% phenyl-alpha-naphthylamine (PANA) and 500 ppm ascorbyl palmitate (AP).

Example 51

Production of Low Saturate Oil by Conversion of Palmitic to Palmitoleate

As described in the examples above, genetic manipulation of microalgae can decrease saturated fat levels, especially by increasing the production of oleic acid. However, in some cases, the acyl-ACP thioesterases expressed in the oleaginous cell liberate more than desirable amounts of palmitate. Here, we describe methods for converting palmitate (16:0) to palmitoleate (16:1) by overexpressing a palmitoyl-ACP desaturase (PAD) gene. The PAD gene can be obtained from natural sources such as Macfadyena unguis (Cat's claw), *Macadamia integrifolia* (Macadamia nut), *Hippophae rhamnoides* (sea buckthorn), or by creating a PAD via mutation of a stearoyl-ACP desaturase to have 16:1 activity. The Macfadyena unguis desaturase is denoted (MuPAD).

A high-oil-producing strain of *Prototheca moriformis* (Strain Z) is biolistically transformed with plasmid DNA constructs with a PAD gene. For example, one of the high oleic strains described in the Examples 6, 36, or 49 can further comprise an exogenous PAD gene. The constructs comprises sucrose invertase as a selectable marker and either the MuPAD or a SAD gene (e.g., *Olea europaea* stearoyl-ACP desaturase, GenBank Accession No. AAB67840.1) having the L118W mutation to shift substrate-specificity toward palmitate. See Cahoon, et al., *Plant Physoil* (1998) 117:593-598. Both the amt3 and beta tubulin (Btub) promoters are used. In addition, the native transit peptide of a plant PAD gene can be swapped with one known to be effective in microalgae (e.g., the transit peptide from the *Chlorella vularis* SAD gene).

The PAD gene can be expressed in a variety of strains including those with a FATA knockout or knockdown and/or a KASII knockin to produce high-oleic oil. Optionally, these strains can also produce high-stability (low polyunsaturate) oil by virtue of a FAD (delta 12 fatty acid desaturase) knockout, knockdown, or by placing FAD expression under control of a regulatable promoter and producing oil under conditions that downregulate FAD. In addition, useful base strains for the introduction of PAD gene activities might also include strains possessing KASII knockouts, and FATA Knockins, whereby levels of C16:0 palmitate are elevated.

As a result, lower levels of palmitic acid are found in the fatty acid profile of the microalgal oil as this is converted into cis-palmitoleic and cis-vaccenic acids. In some cases the total area percent of saturated fatty acids is less than equal to 3.5%, 3% or 2.5%.

Constructs for over expression of Macfadyena unguis C16:0 desaturase (MuPAD) follow:

1) pSZ3142: 6S::CrTUB2:ScSUC2:CvNR::PmAMT3:CpSADtp:MuPAD:CvNR::6S

Relevant Restriction Sites in the Construct pSZ3142 6S::CrTUB2:ScSUC2:CvNR::PmAMT3:CpSADtp:MuPAD:CvNR::6S are indicated in lowercase, bold and underlining and are 5'-3' BspQ 1, Kpn I, Xba I, Mfe I, BamH I, EcoR I, Spe I, Asc I, Cla I, Sac I, BspQ I, respectively. BspQI sites delimit the 5' and 3' ends of the transforming DNA. Bold, lowercase sequences represent genomic DNA from that permit targeted integration at 6s locus via homologous recombination. Proceeding in the 5' to 3' direction, the *C. reinhardtii* β-tubulin promoter driving the expression of the yeast sucrose invertase gene (conferring the ability of Strain Z to metabolize sucrose) is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by an endogenous amt03 promoter of *Prototheca moriformis*, indicated by boxed italics text. The Initiator ATG and terminator TGA codons of the MuPAD are indicated by uppercase, bold italics, while the remainder of the coding region is indicated by bold italics. The *Chlorella protothecoides* S106 stearoyl-ACP desaturase transit peptide is located between initiator ATG and the Asc I site. The *C. vulgaris* nitrate reductase 3' UTR is again indicated by lowercase underlined text followed by the 6S genomic region indicated by bold, lowercase text.

Nucleotide sequence of transforming DNA contained in pSZ3142:

(SEQ ID NO: 99)

gctcttcgccgccgccactggtgctcgagcgcgcccgcgcgtgcgccgccagcgccttggccttttcgccgcgctcgtgcgcgtcgct gatgtccatcaccaggtccatgaggtctgccttgcgccggctgagccactgcttcgtccgggcggccaagaggagcatgagggag gactcctggtccagggtcctgacgtggtcgcggctctgggagcgggccagcatcatctggctctgccgcaccgaggccgcctccaa ctggtcctccagcagccgcagtcgccgccgaccctggcagaggaagacaggtgaggggggtatgaattgtacagaacaaccacg agccttgtctaggcagaatccctaccagtcatggctttacctggatgacggcctgcgaacagctgtccagcgaccctcgctgccgcc gcttctcccgcacgcttctttccagcaccgtgatggcgcgagccagcgccgcacgctggcgctgcgcttcgccgatctgaggacagt cggggaactctgatcagtctaaacccccttgcgcgttagtgttgccatcctttgcagaccggtgagagccgacttgttgtgcgccac cccccacaccacctcctcccagaccaattctgtcacctttttggcgaaggcatcggcctcggcctgcagagaggacagcagtgccc agccgctggggggttggcggatgcacgctcaggtaccctttcttgcgctatgacacttccagcaaaaggtagggcgggctgcgagac ggcttcccggcgctgcatgcaacaccgatgatgcttcgacccccgaagctccttcggggctgcatgggcgctccgatgccgctcca gggcgagcgctgtttaaatagccaggcccccgattgcaaagacattatagcgagctaccaaagccatattcaacacctagatcac taccacttctacacaggccactcgagcttgtgatcgcactccgctaagggggcgcctcttcctcttcgttcagtcacaacccgcaaa ctctagaatatca*ATG**ctgctgcaggccttcctgttcctgctggccggcttcgccgccaagatcagcgcctccatgacgaacga*

*gacgtccgaccgcccctggtgcacttcacccccaacaagggctggatgaacgaccccaacggcctgtggtacgacgagaag*

*gacgccaagtggcacctgtacttccagtacaacccgaacgacaccgtctgggggacgcccttgttctggggccacgccacgtc*

*cgacgacctgaccaactgggaggaccagcccatcgccatcgccccgaagcgcaacgactccggcgccttctccggctccatgg*

*tggtggactacaacaacacctccggcttcttcaacgacaccatcgacccgcgccagcgctgcgtggccatctggacctacaaca*

*ccccggagtccgaggagcagtacatctcctacagcctggacggcggctacaccttcaccgagtaccagaagaaccccgtgctg*

*gccgccaactccacccagttccgcgacccgaaggtcttctggtacgagccctcccagaagtggatcatgaccgcggccaagtc*

*ccaggactacaagatcgagatctactcctccgacgacctgaagtcctggaagctggagtccgcgttcgccaacgagggcttcc*

*tcggctaccagtacgagtgccccggcctgatcgaggtccccaccgagcaggaccccagcaagtcctactgggtgatgttcatct*

*ccatcaaccccggcgccccggccggcggctccttcaaccagtacttcgtcggcagcttcaacggcacccacttcgaggccttcga*

*caaccagtcccgcgtggtggacttcggcaaggactactacgccctgcagaccttcttcaacaccgacccgacctacgggagcg*

-continued

*ccctgggcatcgcgtgggcctccaactgggagtactccgccttcgtgcccaccaacccctggcgctcctccatgtccctcgtgcgc*

*aagttctccctcaacaccgagtaccaggccaacccggagacggagctgatcaacctgaaggccgagccgatcctgaacatca*

*gcaacgccggcccctggagccggttcgccaccaacaccacgttgacgaaggccaacagctacaacgtcgacctgtccaacag*

*caccggcaccctggagttcgagctggtgtacgccgtcaacaccacccagacgatctccaagtccgtgttcgcggacctctccctc*

*tggttcaagggcctggaggaccccgaggagtacctccgcatgggcttcgaggtgtccgcgtcctccttcttcctggaccgcggg*

*aacagcaaggtgaagttcgtgaaggagaacccctacttcaccaaccgcatgagcgtgaacaaccagcccttcaagagcgag*

*aacgacctgtcctactacaaggtgtacggcttgctggaccagaacatcctggagctgtacttcaacgacggcgacgtcgtgtcc*

*accaacacctacttcatgaccaccgggaacgccctgggctccgtgaacatgacgacgggggtggacaacctgttctacatcga*

*caagttccaggtgcgcgaggtcaag* *TGA* caattggcagcagcagctcggatagtatcgacacactctggacgctggtcgtgtga tggactgttgccgccacacttgctgccttgacctgtgaatatccctgccgcttttatcaaacagcctcagtgtgtttgatcttgtgtgtac gcgcttttgcgagttgctagctgcttgtgctatttgcgaataccacccccagcatccccttccctcgtttcatatcgcttgcatcccaacc gcaacttatctacgctgtcctgctatccctcagcgctgctcctgctcctgctcactgcccctcgcacagccttggtttgggctccgcctgt attctcctggtactgcaacctgtaaaccagcactgcaatgctgatgcacgggaagtagtgggatgggaacacaaatggaggatccc gcgtctcgaacagagcgcgcagaggaacgctgaaggtctcgcctctgtcgcacctcagcgcggcatacaccacaataaccacctga cgaatgcgcttggttcttcgtccattagcgaagcgtccggttcacacacgtgccacgttggcgaggtggcaggtgacaatgatcggt ggagctgatggtcgaaacgttcacagcctagggatatcgaattcggccgacaggacgcgcgtcaaaggtgctggtcgtgtatgc cctggccggcaggtcgttgctgctgctggttagtgattccgcaaccctgattttggcgtcttattttggcgtggcaaacgctggcg cccgcgagccgggccggcggcgatgcggtgccccacggctgccggaatccaagggaggcaagagcgcccgggtcagttga agggctttacgcgcaaggtacagccgctcctgcaaggctgcgtggtggaattggacgtgcaggtcctgctgaagttcctccac cgcctcaccagcggacaaagcaccggtgtatcaggtccgtgtcatccactctaaagaactcgactacgacctactgatggccct agattcttcatcaaaaacgcctgagacacttgcccaggattgaaactccctgaagggaccaccaggggccctgagttgttcctt ccccccgtggcgagctgccagccaggctgtacctgtgatcgaggctggcgggaaaataggcttcgtgtgctcaggtcatggg aggtgcaggacagctcatgaaacgccaacaatcgcacaattcatgtcaagctaatcagctatttcctcttcacgagctgtaatt gtcccaaaattctggtctaccgggggtgatccttcgtgtacgggcccttccctcaaccctaggtatgcgcgcatgcggtcgccgc gcaactcgcgcggagggccgagggtttgggacgggccgtcccgaaatgcagttgcacccggatgcgtggcacctttttt gcgat aatttatgcaatggactgctctgcaaaattctggctctgtcgccaaccctaggatcagcggcgtaggatttcgtaatcattcgtc ctgatggggagctaccgactaccctaatatcagcccgactgcctgacgccagcgtccacttttgtgcacacattccattcgtgcc caagacatttcattgtggtgcgaagcgtccccagttacgctcacctgtttcccgacctccttactgttctgtcgacagagcgggcc cacaggccggtcgcagccactagt *ATGgccaccgcatccactttctcggcgttcaatgcccgctgcggcgacctgcgtcgctc*

*ggcgggctccgggccccggcgcccagcgaggcccctccccgtgcgcgggcgcgccgccaccctgcgctccggcctgcgcgac*

*gtggagaccgtgaagaagaccttctcccccgcccgcgaggtgcacgtgcaggtgacccactccatggccccccagaagatc*

*gagatcttcaaggccatggaggactgggccgagaacaacatcctggtgcacctgaagaacgtggagaagtgcccccagc*

-continued cccaggacttcctgcccgaccccgcctccgacgagttccacgaccagatcaaggagctgcgcgagcgcgccaaggagatcc ccgacgactacttcgtggtgctggtgggcgacatgatcaccgaggaggccctgcccacctaccagaccatgctgaacacctg ggacggcgtgcgcgacgagaccggcgcctccccacctcctgggccatctggacccgcgcctggaccgccgaggagaaccg ccacggcgacctcctgaacaagtacctgtacctgtccggccgcgtggacatgaagcagatcgagaagaccatccagtaacct gatcggctccggcatggaccccgcaccgagaactcccctacctgggcttcatctacacctccttccaggagcgcgccacctt catctcccacggcaacaccgcccgcctggcccgcgaccacggcgacttcaagctggcccagatctgcggcaccatcgcctccg acgagaagcgccacgagaccgcctacaccaagatcgtggagaagctgttcgagatcgaccccgacggcaccgtgctggcc ttcggcgacatgatgaagaagaagatctccatgcccgaccacttcatgtacgacggccgcgacgacaacctgttcgaccact tctcctccgtggcccagcgcctgggcgtgtacaccgccaaggactacgccgacatcctggagcacctggtgggccgctggaa ggtggagaagctgaccggcctgtccgccgagggccagaaggcccaggactacgtgtgcggcctgcccccgcatccgccg cctggaggagcgcgcccagatccgcgccaagcattcccccgcctgcccttctcctggatctacgaccgcgaggtgcagctg

*atggactacaaggaccacgacggcgactacaaggaccacgacatcgactacaaggacgacgacgacaagTGA*atcgat agatctcttaaggcagcagcagctcggatagtatcgacacactctggacgctggtcgtgtgatggactgttgccgccacacttgctgc cttgacctgtgaatatccctgccgcttttatcaaacagcctcagtgtgtttgatcttgtgtgtacgcgcttttgcgagttgctagctgctt gtgctatttgcgaataccacccccagcatccccttccctcgtttcatatcgcttgcatcccaaccgcaacttatctacgctgtcctgcta tccctcagcgctgctcctgctcctgctcactgcccctcgcacagccttggtttgggctccgcctgtattctcctggtactgcaacctgta aaccagcactgcaatgctgatgcacgggaagtagtgggatgggaacacaaatggaaagcttaattaagagctcttgttttccagaa ggagttgctccttgagcctttcattctcagcctcgataacctccaaagccgctctaattgtggaggggttcgaatttaaaagcttgg aatgttggttcgtgcgtctggaacaagcccagacttgttgctcactgggaaaaggaccatcagctccaaaaaacttgccgctcaaa ccgcgtacctctgctttcgcgcaatctgccctgttgaaatcgccaccacattcatattgtgacgcttgagcagtctgtaattgcctca gaatgtggaatcatctgccccctgtgcgagcccatgccaggcatgtcgcgggcgaggacacccgccactcgtacagcagaccatt atgctacctcacaatagttcataacagtgaccatatttctcgaagctccccaacgagcacctccatgctctgagtggccaccccccg gccctggtgcttgcggagggcaggtcaaccggcatggggctaccgaaatccccgaccggatcccaccacccccgcgatgggaag aatctctccccgggatgtgggcccaccaccagcacaacctgctggcccaggcgagcgtcaaaccataccacacaaatatccttgg catcggccctgaattccttctgccgctctgctacccggtgcttctgtccgaagcaggggttgctagggatcgctccgagtccgcaaa cccttgtcgcgtggcggggcttgttcgagcttgaagagc

2) pSZ3145: 6S::CrTUB2:ScSUC2:CvNR::PmAMT3:MuPAD:CvNR::6S:

Relevant restriction sites in the construct pSZ3145 6S::CrTUB2:ScSUC2:CvNR::PmAMT3:MuPAD:CvNR::6S are indicated in lowercase, bold and underlining and are 5'-3' BspQ 1, Kpn I, Xba I, Mfe I, BamH I, EcoR I, Spe I, Cla I, Sac I, BspQ I, respectively. BspQI sites delimit the 5' and 3' ends of the transforming DNA. Bold, lowercase sequences represent genomic DNA from that permit targeted integration at 6s locus via homologous recombination. Proceeding in the 5' to 3' direction, the *C. reinhardtii* β-tubulin promoter driving the expression of the yeast sucrose invertase gene (conferring the ability of Strain Z to metabolize sucrose) is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by an endogenous amt03 promoter of *Prototheca moriformis*, indicated by boxed italics text. The Initiator ATG and terminator TGA codons of the MuPAD are indicated by uppercase, bold italics, while the remainder of the coding region is indicated by bold italics. The *C. vulgaris* nitrate reductase 3' UTR is again indicated by lowercase underlined text followed by the 6S genomic region indicated by bold, lowercase text.

Nucleotide sequence of transforming DNA contained in pSZ3145:

(SEQ ID NO: 100)

gctcttcgccgccgccactcctgctcgagcgcgcccgcgcgctgcgccgccagcgccttggccttttcgccgcgctcgtgcgcgtcgct gatgtccatcaccaggtccatgaggtctgccttgcgccggctgagccactgcttcgtccgggcggccaagaggagcatgagggag gactcctggtccagggtcctgacgtggtcgcggctctgggagcgggccagcatcatctggctctgccgcaccgaggccgcctccaa ctggtcctccagcagccgcagtcgccgccgaccctggcagaggaagacaggtgaggggggtatgaattgtacagaacaaccacg agccttgtctaggcagaatccctaccagtcatggctttacctggatgacggcctgcgaacagctgtccagcgaccctcgctgccgcc gcttctcccgcacgcttctttccagcaccgtgatggcgcgagccagcgccgcacgctggcgctgcgcttcgccgatctgaggacagt cggggaactctgatcagtctaaaccccccttgcgcgttagtgttgccatcctttgcagaccggtgagagccgacttgttgtgcgccac cccccacaccacctcctcccagaccaattctgtcaccttttttggcgaaggcatcggcctcggcctgcagagaggacagcagtgccc agccgctgggggttggcggatgcacgctcaggtaccctttcttgcgctatgacacttccagcaaaaggtagggcgggctgcgagac ggcttcccggcgctgcatgcaacaccgatgatgcttcgacccccccgaagctccttcggggctgcatgggcgctccgatgccgctcca gggcgagcgctgtttaaatagccaggcccccgattgcaaagacattatagcgagctaccaaagccatattcaaacacctagatcac taccacttctacacaggccactcgagcttgtgatcgcactccgctaagggggcgcctcttcctcttcgtttcagtcacaacccgcaaa gtctagaatatcaATGctgctgcaggccttcctgttcctgctggccggcttcgccgccaagatcagcgcctccatgacgaacga gacgtccgaccgccccctggtgcacttcacccccaacaagggctggatgaacgaccccaacggcctgtggtacgacgagaag gacgccaagtggcacctgtacttccagtacaacccgaacgacaccgtctgggggacgcccttgttctggggccacgccacgtc cgacgacctgaccaactgggaggaccagcccatcgccatcgccccgaagcgcaacgactccggcgccttctccggctccatgg tggtggactacaacaacacctccggcttcttcaacgacaccatcgacccgcgccagcgctgcgtggccatctggacctacaaca ccccggagtccgaggagcagtacatctcctacagcctggacggcggctacaccttcaccgagtaccagaagaaccccgtgctg gccgccaactccacccagttccgcgacccgaaggtcttctggtacgagccctcccagaagtggatcatgaccgcggccaagtc ccaggactacaagatcgagatctactcctccgacgacctgaagtcctggaagctggagtccgcgttcgccaacgagggcttcc tcggctaccagtacgagtgccccggcctgatcgaggtccccaccgagcaggaccccagcaagtcctactgggtgatgttcatct ccatcaaccccggcgccccggccggcggctccttcaaccagtacttcgtcggcagcttcaacggcacccacttcgaggccttcga caaccagtcccgcgtggtggacttcggcaaggactactacgccctgcagaccttcttcaacaccgacccgacctacgggagcg ccctgggcatcgcgtgggcctccaactgggagtactccgccttcgtgcccaccaacccctggcgctcctccatgtccctcgtgcgc aagttctccctcaacaccgagtaccaggccaacccggagacggagctgatcaacctgaaggccgagccgatcctgaacatca gcaacgccggccccctggagccggttcgccaccaacaccacgttgacgaaggccaacagctacaacgtcgacctgtccaacag caccggcaccctggagttcgagctggtgtacgccgtcaacaccacccagacgatctccaagtccgtgttcgcggacctctccctc tggttcaagggcctggaggaccccgaggagtacctccgcatgggcttcgaggtgtccgcgtcctccttcttcctggaccgcggg aacagcaaggtgaagttcgtgaaggagaacccctacttcaccaaccgcatgagcgtgaacaaccagcccttcaagagcgag aacgacctgtcctactacaaggtgtacggcttgctggaccagaacatcctggagctgtacttcaacgacggcgacgtcgtgtcc accaacacctacttcatgaccaccgggaacgccctgggctccgtgaacatgacgacgggggtggacaacctgttctacatcga caagttccaggtgcgcgaggtcaagTGAcaattggcagcagcagctcggatagtatcgacacactctggacgctggtcgtgtga tggactgttgccgccacacttgctgccttgacctgtgaatatccctgccgcttttatcaaacagcctcagtgtgtttgatcttgtgtgtac gcgcttttgcgagttgctagctgcttgtgctatttgcgaataccacccccagcatccccttccctcgtttcatatcgcttgcatcccaacc gcaacttatctacgctgtcctgctatccctcagcgctgctcctgctcctgctcactgcccctcgcacagccttggtttgggctccgcctgt attctcctggtactgcaacctgtaaaccagcactgcaatgctgatgcacgggaagtagtgggatgggaacacaaatggaggatccc gcgtctcgaacagagcgcgcagaggaacgctgaaggtctcgcctctgtcgcacctcagcgcggcatacaccacaataaccacctga cgaatgcgcttggttcttcgtccattagcgaagcgtccggttcacacacgtgccacgttggcgaggtggcaggtgacaatgatcggt ggagctgatggtcgaaacgttcacagcctagggatatcgaattcggccgacaggacgcgcgtcaaaggtgctggtcgtgtatgc -continued

*cctggccggcaggtcgttgctgctgctggttagtgattccgcaaccctgattttggcgtcttattttggcgtggcaaacgctggcg*

*cccgcgagccgggccggcggcgatgcggtgccccacggctgccggaatccaagggaggcaagagcgcccgggtcagttga*

*agggctttacgcgcaaggtacagccgctcctgcaaggctgctggtggaattggacgtgcaggtcctgctgaagttcctccac*

*cgcctcaccagcggacaaagcaccggtgtatcaggtccgtgtcatccactctaaagaactcgactacgacctactgatggccct*

*agattcttcatcaaaaacgcctgagacacttgcccaggattgaaactccctgaagggaccaccaggggccctgagttgttcctt*

*cccccgtggcgagctgccagccaggctgtacctgtgatcgaggctggcgggaaaataggcttcgtgtgctcaggtcattggg*

*aggtgcaggacagctcatgaaacgccaacaatcgcacaattcatgtcaagctaatcagctatttcctcttcacgagctgtaatt*

*gtcccaaaattctggtctaccgggggtgatccttcgtgtacgggcccttccctcaaccctaggtatgcgcgcatgcggtcgccgc*

*gcaactcgcgcgagggccgagggtttgggacgggccgtcccgaaatgcagttgcacccggatgcgtggcaccttttttgcgat*

*aatttatgcaatggactgctctgcaaaattctggctctgtcgccaaccctaggatcagcggcgtaggatttcgtaatcattcgtc*

*ctgatggggagctaccgactaccctaatatcagcccgactgcctgacgccagcgtccacttttgtgcacacattccattcgtgcc*

*caagacatttcattgtggtgcgaagcgtccccagttacgctcacctgtttcccgacctccttactgttctgtcgacagagcgggcc*

*cacaggccggtcgcagcc*actagt*ATGgccctgaagctgaacgccatcaacttccagtcccccaagtgctcctccttcggcct*

*gcccccgtggtgtccctgcgctcccccaagctgtccgtggccgccaccctgcgctccggcctgcgcgacgtggagaccgtga*

*agaagaccttctcccccgcccgcgaggtgcacgtgcaggtgacccactccatggcccccagaagatcgagatcttcaaggc*

*catggaggactgggccgagaacaacatcctggtgcacctgaagaacgtggagaagtgcccccagccccaggacttcctgc*

*ccgaccccgcctccgacgagttccacgaccagatcaaggagctgcgcgagcgcgccaaggagatccccgacgactacttcg*

*tggtgctggtgggcgacatgatcaccgaggaggccctgcccacctaccagaccatgctgaacacctgggacggcgtgcgcg*

*acgagaccggcgcctcccccacctcctgggccatctggacccgcgcctggaccgccgaggagaaccgccacggcgacccccct*

*gaacaagtacctgtacctgtccggccgcgtggacatgaagcagatcgagaagaccatccagtacctgatcggctccggcat*

*ggacccccgcaccgagaactcccccctacctgggcttcatctacacctccttccaggagcgcgccacctcatctcccacggcaa*

*caccgcccgcctggcccgcgaccacggcgacttcaagctggcccagatctgcggcaccatcgcctccgacgagaagcgccac*

*gagaccgcctacaccaagatcgtggagaagctgttcgagatcgaccccgacggcaccgtgctggccttcggcgacatgatg*

*aagaagaagatctccatgcccgaccacttcatgtacgacggccgcgacgacaacctgttcgaccacttctcctccgtggccca*

*gcgcctgggcgtgtacaccgccaaggactacgccgacatcctggagcacctggtgggccgctggaagtggagaagctga*

*ccggcctgtccgccgagggccagaaggcccaggactacgtgtgcggcctgcccccccgcatccgccgcctggaggagcgcg*

*cccagatccgcgccaagcaggccccccgcctgcccttctcctggatctacgaccgcgaggtgcagctgatggactacaagga*

*ccacgacggcgactacaaggaccacgacatcgactacaaggacgacgacgacaagTGA*atcgatagatctcttaaggcag cagcagctcggatagtatcgacacactctggacgctggtcgtgtgatggactgttgccgccacacttgctgccttgacctgtgaatat ccctgccgcttttatcaaacagcctcagtgtgtttgatcttgtgtgtacgcgcttttgcgagttgctagctgcttgtgctatttgcgaata ccacccccagcatccccttccctcgtttcatatcgcttgcatcccaaccgcaacttatctacgctgtcctgctatccctcagcgctgctc ctgctcctgctcactgcccctcgcacagccttggtttgggctccgcctgtattctcctggtactgcaacctgtaaaccagcactgcaat gctgatgcacgggaagtagtgggatgggaacacaaatggaaagcttaattaagagctcttgttttccagaaggagttgctccttga gcctttcattctcagcctcgataacctccaaagccgctctaattgtggagggggttcgaatttaaaagcttggaatgttggttcgtgc gtctggaacaagcccagacttgttgctcactgggaaaaggaccatcagctccaaaaaacttgccgctcaaaccgcgtacctctgct ttcgcgcaatctgccctgttgaaatcgccaccacattcatattgtgacgcttgagcagtctgtaattgcctcagaatgtggaatcatc tgcccccctgtgcgagcccatgccaggcatgtcgcgggcgaggacacccgccactcgtacagcagaccattatgctacctcacaata gttcataacagtgaccatatttctcgaagctccccaacgagcacctccatgctctgagtggccaccccccggccctggtgcttgcgg

-continued agggcaggtcaaccggcatggggctaccgaaatccccgaccggatcccaccacccccgcgatgggaagaatctctccccgggat gtgggcccaccaccagcacaacctgctggcccaggcgagcgtcaaaccataccacacaaatatccttggcatcggccctgaattc cttctgccgctctgctacccggtgcttctgtccgaagcaggggttgctagggatcgctccgagtccgcaaacccttgtcgcgtggcg gggcttgttcgagcttgaagagc

3) pSZ3137: 6S::CrTUB2:ScSUC2:CvNR::CrTUB2:CpSADtp:MuPAD:CvNR::6S

Relevant Restriction Sites in the Construct pSZ3137 6S::CrTUB2:ScSUC2:CvNR::CrTUB2:CpSADtp:MuPAD:CvNR::6S are indicated in lowercase, bold and underlining and are 5'-3' BspQ 1, Kpn I, Xba I, Mfe I, BamH I, EcoR I, Spe I, Asc I, Cla I, Sac I, BspQ I, respectively. BspQI sites delimit the 5' and 3' ends of the transforming DNA. Bold, lowercase sequences represent genomic DNA from that permit targeted integration at 6s locus via homologous recombination. Proceeding in the 5' to 3' direction, the *C. reinhardtii* β-tubulin promoter driving the expression of the yeast sucrose invertase gene (conferring the ability of Strain Z to metabolize sucrose) is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by *C. reinhardtii* 3-tubulin promoter, indicated by boxed italics text. The Initiator ATG and terminator TGA codons of the MuPAD are indicated by uppercase, bold italics, while the remainder of the coding region is indicated by bold italics. The *Chlorella protothecoides* S106 stearoyl-ACP desaturase transit peptide is located between initiator ATG and the Asc I site. The *C. vulgaris* nitrate reductase 3' UTR is again indicated by lowercase underlined text followed by the 6S genomic region indicated by bold, lowercase text.

Nucleotide sequence of transforming DNA contained in pSZ3137:

(SEQ ID NO: 101)

gctcttcgccgccgccactcctgctcgagcgcgcccgcgcgtgcgccgccagcgccttggccttttcgccgcgctcgtgcgcgtcgct gatgtccatcaccaggtccatgaggtctgccttgcgccggctgagccactgcttcgtccgggcggccaagaggagcatgagggag gactcctggtccagggtcctgacgtggtcgcggctctgggagcgggccagcatcatctggctctgccgcaccgaggccgcctccaa ctggtcctccagcagccgcagtcgccgccgaccctggcagaggaagacaggtgaggggggtatgaattgtacagaacaaccacg agccttgtctaggcagaatccctaccagtcatggctttacctggatgacggcctgcgaacagctgtccagcgaccctcgctgccgcc gcttctcccgcacgcttctttccagcaccgtgatggcgcgagccagcgccgcacgctggcgctgcgcttcgccgatctgaggacagt cggggaactctgatcagtctaaacccccttgcgcgttagtgttgccatcctttgcagaccggtgagagccgacttgttgtgcgccac cccccacaccacctcctcccagaccaattctgtcacctttttggcgaaggcatcggcctcggcctgcagagaggacagcagtgccc agccgctggggggttggcggatgcacgctcaggtaccctttcttgcgctatgacacttccagcaaaaggtagggcgggctgcgagac ggcttcccggcgctgcatgcaacaccgatgatgcttcgacccccgaagctccttcggggctgcatgggcgctccgatgccgctcca gggcgagcgctgtttaaatagccaggcccccgattgcaaagacattatagcgagctaccaaagccatattcaaacacctagatcac taccacttctacacaggccactcgagcttgtgatcgcactccgctaagggggcgcctcttcctcttcgtttcagtcacaacccgcaaa ctctagaatatca*ATG**ctgctgcaggccttcctgttcctgctggccggcttcgccgccaagatcagcgcctccatgacgaacga*

*gacgtccgaccgccccctggtgcacttcacccccaacaagggctggatgaacgaccccaacggcctgtggtacgacgagaag*

*gacgccaagtggcacctgtacttccagtacaacccgaacgacaccgtctgggggacgcccttgttctggggccacgccacgtc*

*cgacgacctgaccaactgggaggaccagcccatcgccatcgccccgaagcgcaacgactccggcgccttctccggctccatgg*

*tggtggactacaacaacacctccggcttcttcaacgacaccatcgacccgcgccagcgctgcgtggccatctggacctacaaca*

*ccccggagtccgaggagcagtacatctcctacagcctggacggcggctacaccttcaccgagtaccagaagaaccccgtgctg*

*gccgccaactccacccagttccgcgacccgaaggtcttctggtacgagccctcccagaagtggatcatgaccgcggccaagtc*

*ccaggactacaagatcgagatctactcctccgacgacctgaagtcctggaagctggagtccgcgttcgccaacgagggcttcc*

*tcggctaccagtacgagtgccccggcctgatcgaggtccccaccgagcaggaccccagcaagtcctactgggtgatgttcatct*

*ccatcaaccccggcgccccggccggcggctccttcaaccagtacttcgtcggcagcttcaacggcacccacttcgaggccttcga*

*caaccagtcccgcgtggtggacttcggcaaggactactacgccctgcagaccttcttcaacaccgacccgacctacgggagcg*

*ccctgggcatcgcgtgggcctccaactgggagtactccgccttcgtgcccaccaacccctggcgctcctccatgtccctcgtgcgc*

*aagttctccctcaacaccgagtaccaggccaacccggagacggagctgatcaacctgaaggccgagccgatcctgaacatca*

-continued gcaacgccggcccctggagccggttcgccaccaacaccacgttgacgaaggccaacagctacaacgtcgacctgtccaacag caccggcaccctggagttcgagctggtgtacgccgtcaacaccacccagacgatctccaagtccgtgttcgcggacctctccctc tggttcaagggcctggaggaccccgaggagtacctccgcatgggcttcgaggtgtccgcgtcctccttcttcctggaccgcggg aacagcaaggtgaagttcgtgaaggagaacccctacttcaccaaccgcatgagcgtgaacaaccagcccttcaagagcgag aacgacctgtcctactacaaggtgtacggcttgctggaccagaacatcctggagctgtacttcaacgacggcgacgtcgtgtcc accaacacctacttcatgaccaccgggaacgccctgggctccgtgaacatgacgacgggggtggacaacctgttctacatcga caagttccaggtgcgcgaggtcaagTGAcaattggcagcagcagctcggatagtatcgacacactctggacgctggtcgtgtga tggactgttgccgccacacttgctgccttgacctgtgaatatccctgccgcttttatcaaacagcctcagtgtgtttgatcttgtgtgtac gcgcttttgcgagttgctagctgcttgtgctatttgcgaataccacccccagcatccccttccctcgtttcatatcgcttgcatcccaacc gcaacttatctacgctgtcctgctatccctcagcgctgctcctgctcctgctcactgcccctcgcacagccttggtttgggctccgcctgt attctcctggtactgcaacctgtaaaccagcactgcaatgctgatgcacgggaagtagtgggatgggaacacaaatggaggatccc gcgtctcgaacagagcgcgcagaggaacgctgaaggtctcgcctctgtcgcacctcagcgcggcatacaccacaataaccacctga cgaatgcgcttggttcttcgtccattagcgaagcgtccggttcacacacgtgccacgttggcgaggtggcaggtgacaatgatcggt ggagctgatggtcgaaacgttcacagcctagggatatcgaattcctttcttgcgctatgacacttccagcaaaaggtagggcggg ctgcgagacggcttcccggcgctgcatgcaacaccgatgatgcttcgacccccccgaagctccttcggggctgcatgggcgctcc gatgccgctccagggcgagcgctgtttaaatagccaggcccccgattgcaaagacattatagcgagctaccaaagccatattc aaacacctagatcactaccacttctacacaggccactcgagcttgtgatcgcactccgctaagggggcgcctcttcctcttcgttt cagtcacaacccgcaaacactagtATGgccaccgcatccactttctcggcgttcaatgcccgctgcggcgacctgcgtcgctc ggcgggctccgggccccggcgcccagcgaggcccctccccgtgcgcgggcgcgccgccaccctgcgctccggcctgcgcgac gtggagaccgtgaagaagaccttctcccccgcccgcgaggtgcacgtgcaggtgacccactccatggcccccagaagatc gagatcttcaaggccatggaggactgggccgagaacaacatcctggtgcacctgaagaacgtggagaagtgcccccagc cccaggacttcctgcccgaccccgcctccgacgagttccacgaccagatcaaggagctgcgcgagcgcgccaaggagatcc ccgacgactacttcgtggtgctggtgggcgacatgatcaccgaggaggccctgcccacctaccagaccatgctgaacacctg ggacggcgtgcgcgacgagaccggcgcctcccccacctcctgggccatctggacccgcgcctggaccgccgaggagaaccg ccacggcgacccccctgaacaagtacctgtacctgtccggccgcgtggacatgaagcagatcgagaagaccatccagtacct gatcggctccggcatggacccccgcaccgagaactcccccctacctgggcttcatctacacctccttccaggagcgcgccacctt catctcccacggcaacaccgcccgcctggcccgcgaccacggcgacttcaagctggcccagatctgcggcaccatcgcctccg acgagaagcgccacgagaccgcctacaccaagatcgtggagaagctgttcgagatcgaccccgacggcaccgtgctggcc ttcggcgacatgatgaagaagaagatctccatgcccgaccacttcatgtacgacggccgcgacgacaacctgttcgaccact tctcctccgtggcccagcgcctgggcgtgtacaccgccaaggactacgccgacatcctggagcacctggtgggccgctggaa ggtggagaagctgaccggcctgtccgccgagggccagaaggcccaggactacgtgtgcggcctgcccccccgcatccgccg cctggaggagcgcgcccagatccgcgccaagcaggcccccgcctgcccttctcctggatctacgaccgcgaggtgcagctg atggactacaaggaccacgacggcgactacaaggaccacgacatcgactacaaggacgacgacgacaagTGAatcgat agatctcttaaggcagcagcagctcggatagtatcgacacactctggacgctggtcgtgtgatggactgttgccgccacacttgctgc cttgacctgtgaatatccctgccgcttttatcaaacagcctcagtgtgtttgatcttgtgtgtacgcgcttttgcgagttgctagctgctt gtgctatttgcgaataccacccccagcatccccttccctcgtttcatatcgcttgcatcccaaccgcaacttatctacgctgtcctgcta tccctcagcgctgctcctgctcctgctcactgcccctcgcacagccttggtttgggctccgcctgtattctcctggtactgcaacctgta aaccagcactgcaatgctgatgcacgggaagtagtgggatgggaacacaaatggaaagcttaattaagagctcttgttttccagaa ggagttgctccttgagcctttcattctcagcctcgataacctccaaagccgctctaattgtggaggggttcgaatttaaaagcttgg -continued

```
aatgttggttcgtgcgtctggaacaagcccagacttgttgctcactgggaaaggaccatcagctccaaaaaacttgccgctcaaa

ccgcgtacctctgctttcgcgcaatctgccctgttgaaatcgccaccacattcatattgtgacgcttgagcagtctgtaattgcctca

gaatgtggaatcatctgcccctgtgcgagcccatgccaggcatgtcgcgggcgaggacacccgccactcgtacagcagaccatt

atgctacctcacaatagttcataacagtgaccatatttctcgaagctccccaacgagcacctccatgctctgagtggccaccccccg

gccctggtgcttgcggagggcaggtcaaccggcatggggctaccgaaatccccgaccggatcccaccacccccgcgatgggaag

aatctctccccgggatgtgggcccaccaccagcacaacctgctggcccaggcgagcgtcaaaccataccacacaaatatccttgg

catcggccctgaattccttctgccgctctgctacccggtgcttctgtccgaagcaggggttgctagggatcgctccgagtccgcaaa

cccttgtcgcgtggcggggcttgttcgagcttgaagagc
```

Example 52

Myristate Rich Oil Produced by Overexpressing a *Cuphea palustris* Thioesterase Here, we demonstrate that over expression of a *Cuphea palustris* thioesterase (Cpal FATB1, accession AAC49180) UTEX1435 results in a large increase in C14:0.

Constructs used for the overexpression of the Cpal FATB1 gene were codon optimized for expression in *P. moriformis* as described herein. The construct can be written as 6SA::CrTUB2-ScSUC2-CvNR:PmAMT3-CpSAD1tpExt_CpalFATB2FLAG_ExtA-CvNR::6SB.

In this high-myristate strain, the myristate content was 65.70 percent, as shown in Table 51, below. This is a very large increase from the myristate content of the wild-type oil produced by the base strain which has a myristate content of approximately 1%.

TABLE 51

| The fatty acid profile of the high myristate strain. | |
|---|---|
| C10:0 | 0.04 |
| C12:0 | 1.19 |
| C14:0 | 65.7 |
| C16:0 | 13.55 |
| C18:0 | 0.57 |
| C18:1 | 12.2 |
| C18:2 | 5.13 |
| C20:0 | 0.05 |
| C22:0 | 0.01 |
| C24:0 | 0.01 |

Figure 4:
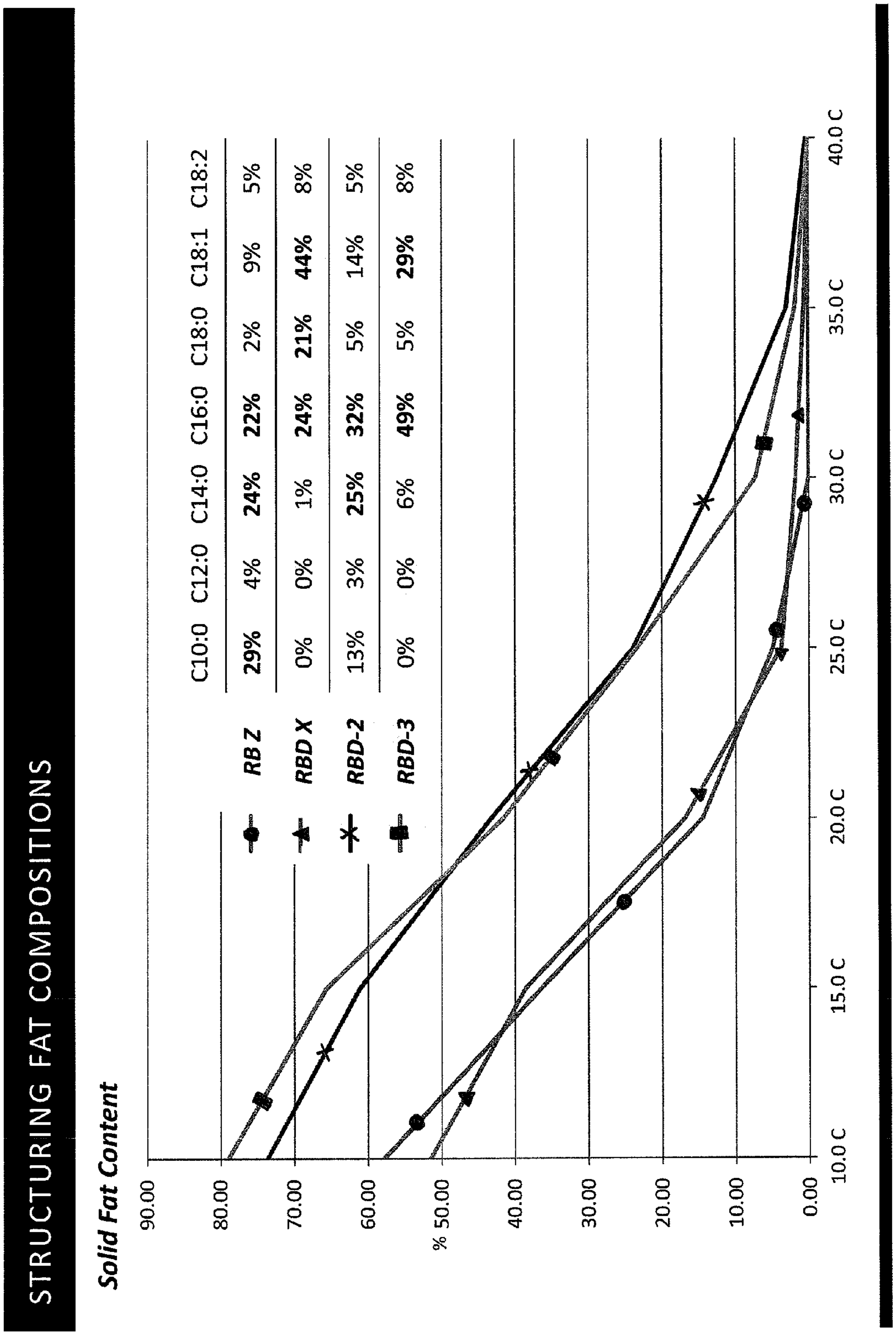
Figure 5:
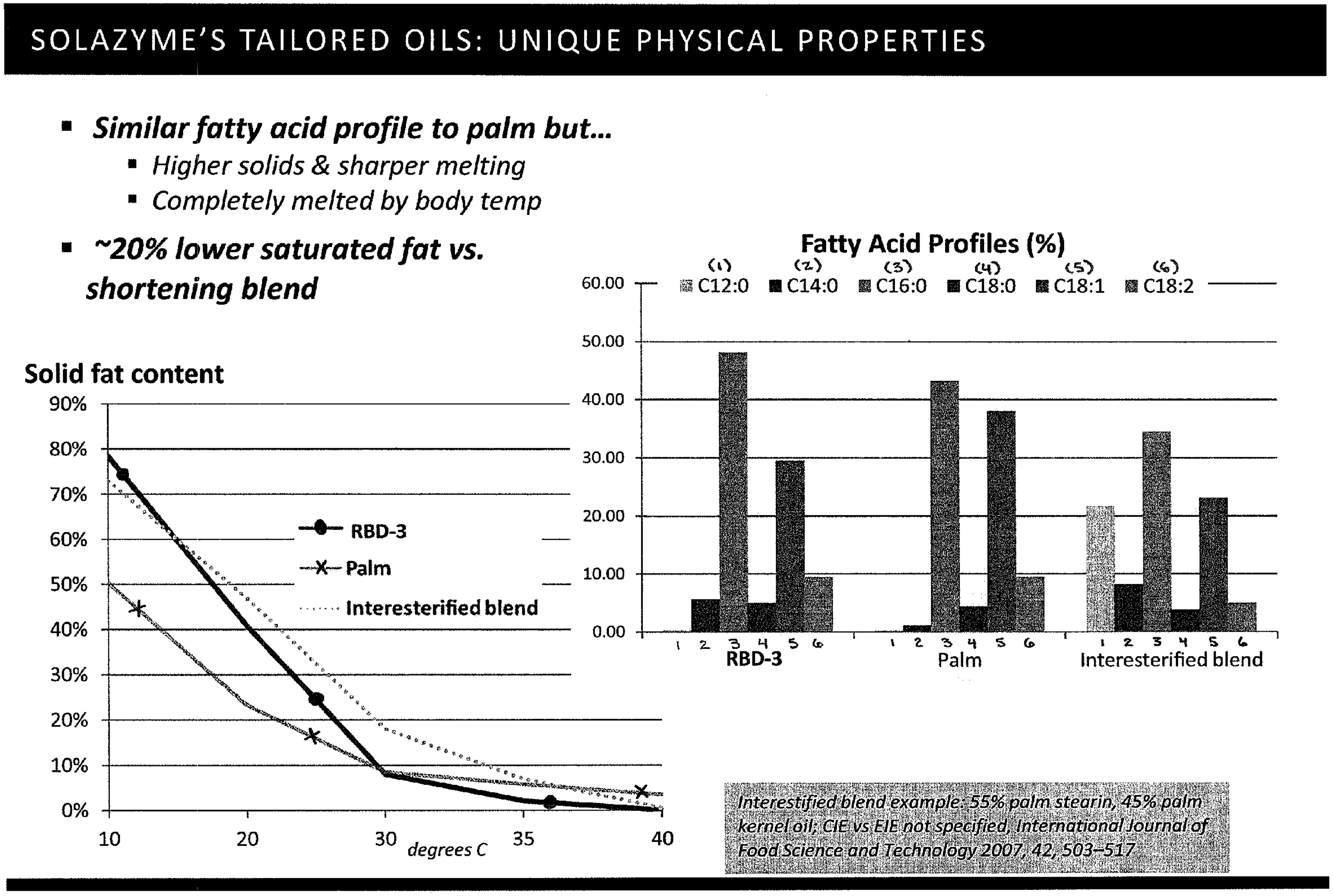
Figure 6:
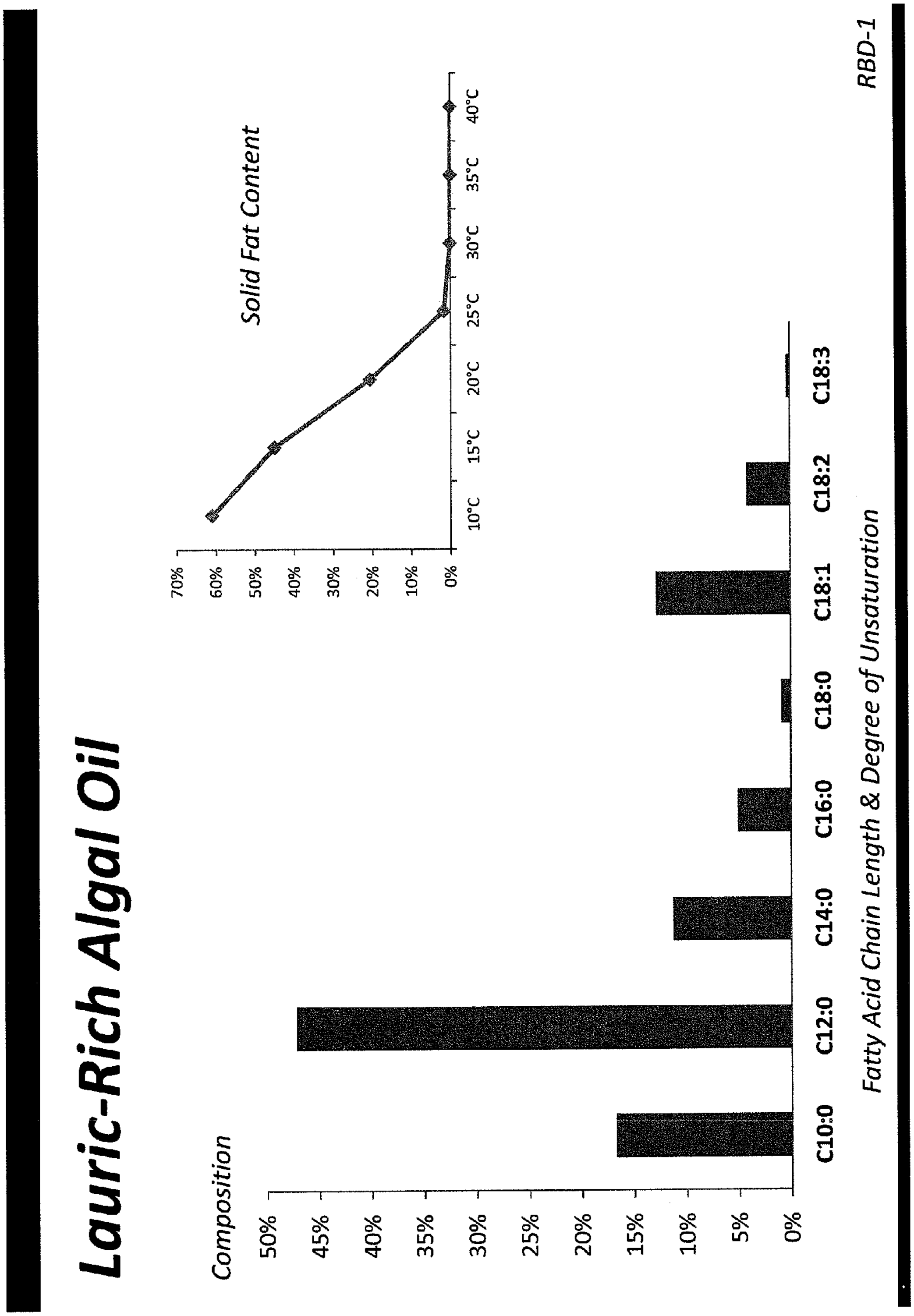
Figure 7:
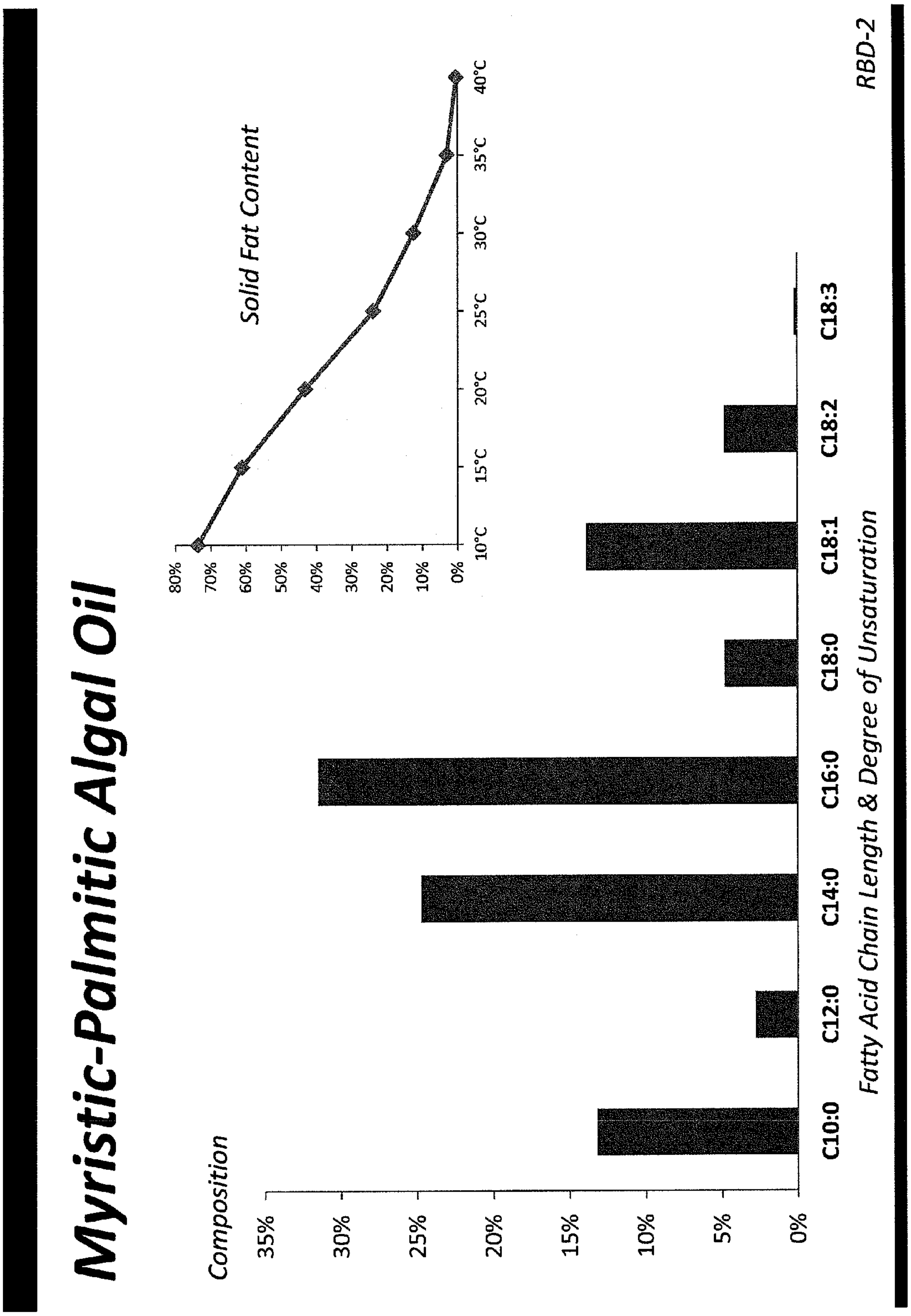
Figure 8:
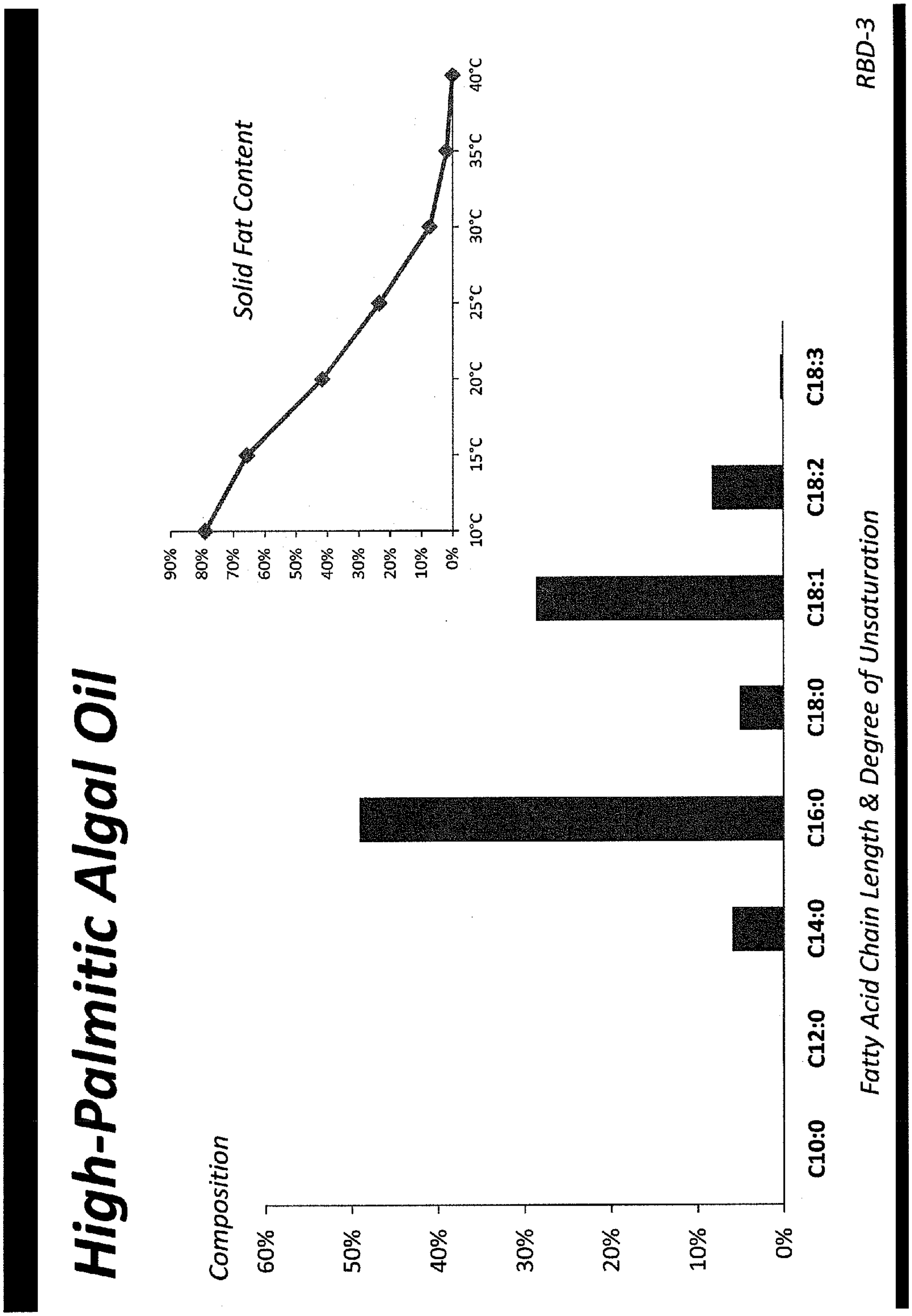
Figure 9:
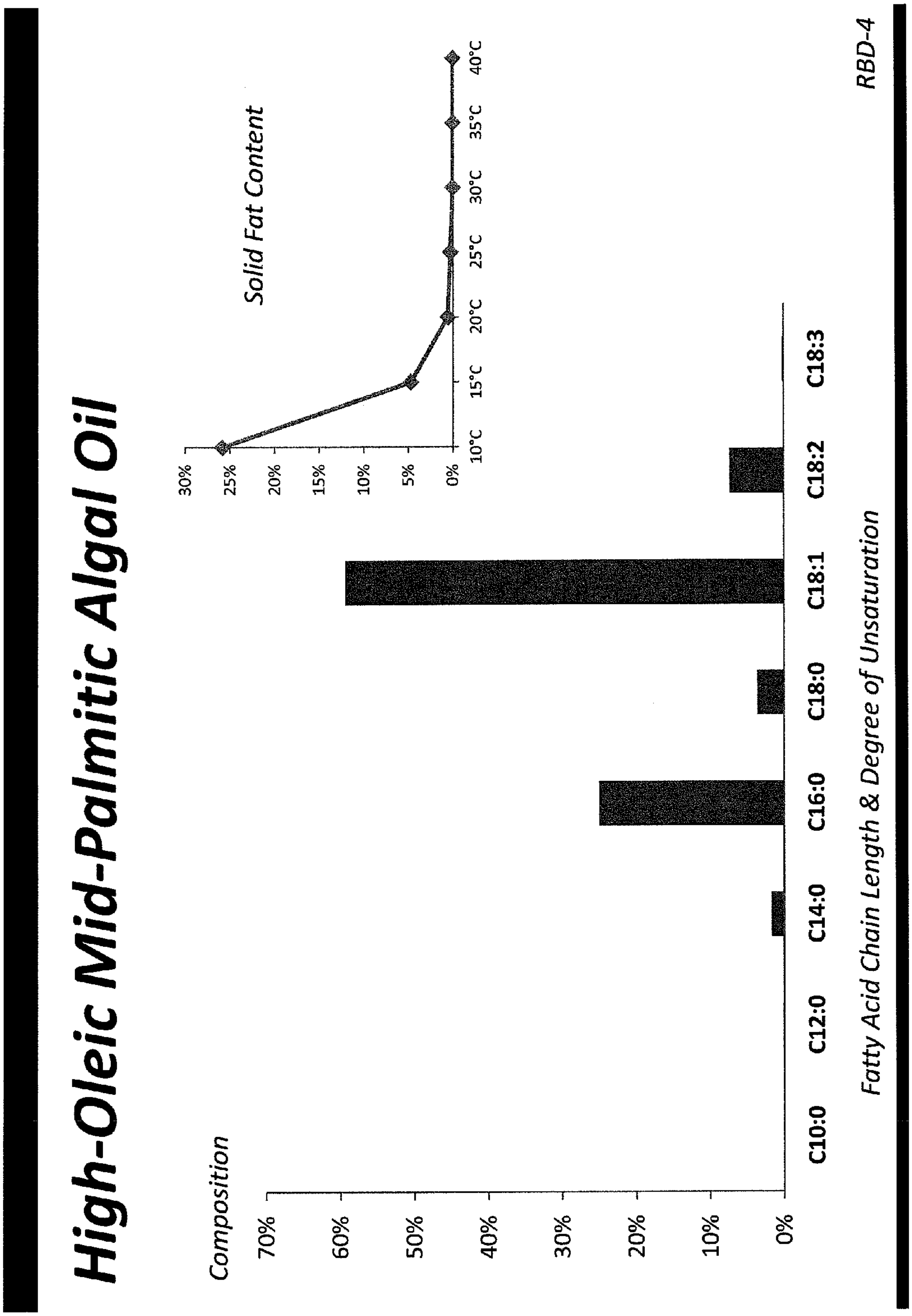
Figure 22:
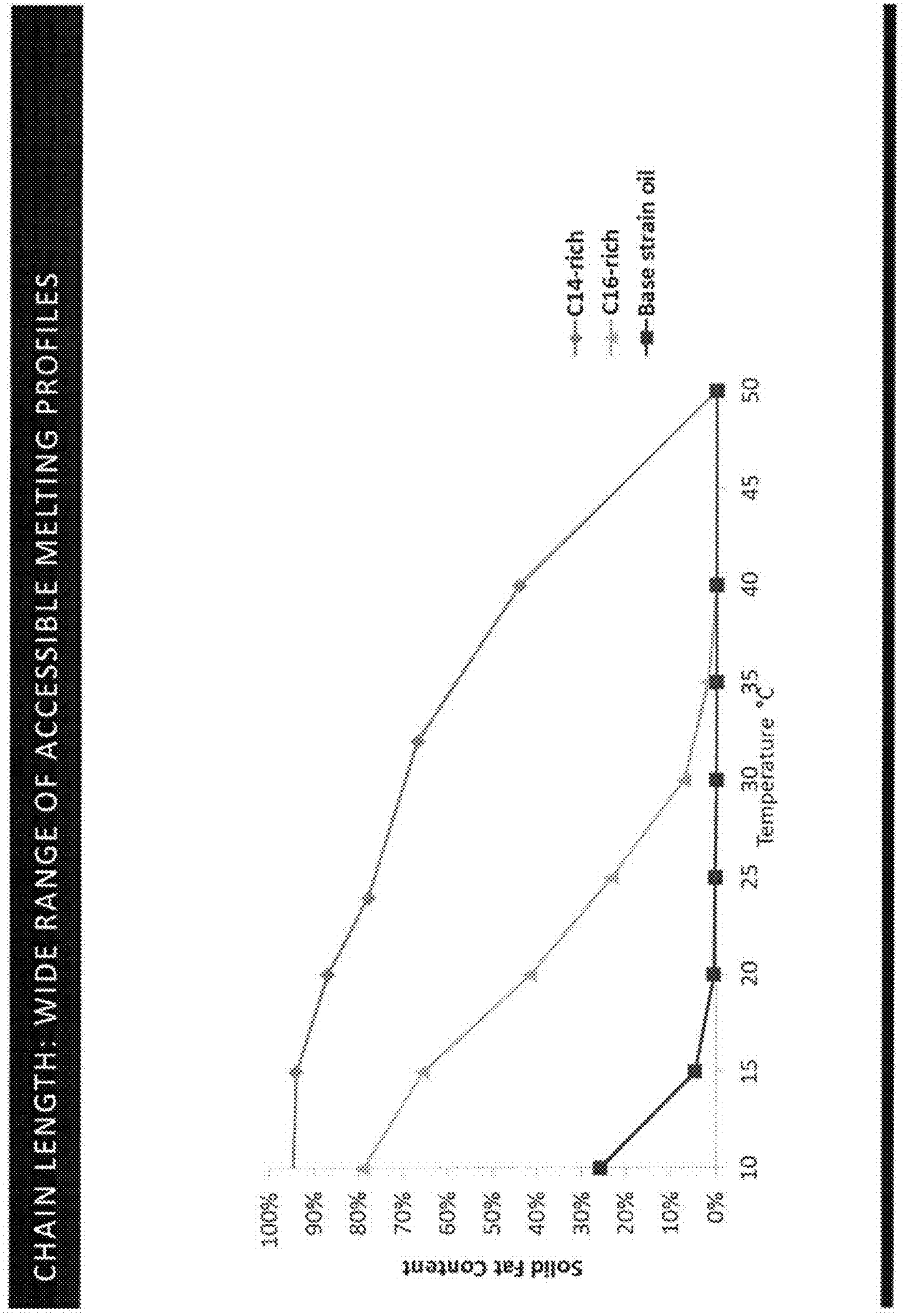
FIG. 22 shows the fatty acid profile and solid fat content of a refined, bleached and deodorized myristate rich oil from a genetically engineered *Prototheca morformis* strain as discussed in Example 52.

FIG. 22 shows that at 25° C., the solid fat content is over 80%. At 25° C., the base strain oil has no or negligible solid fat. As a comparison, the solid fat content of a refined, bleached, deodorized oil (RBD-3), as shown in FIG. 4, is reproduced. RBD-3 is oil from a *P. moriformis* strain engineered to produce high amounts of C16:0. The construct for the high C16:0 producing strain can be written as 6SA-bTub-Inv-nr::Amt03-Native Ch16TE-nr-6SB. This construct encodes for a C16:0 preferring *Cuphea hookeriana* thioesterase.

Example 53

Myristate Rich Oil Produced by Overexpressing a *Cuphea palustris* Thioesterase Here, we demonstrate that over expression of a *Cuphea palustris* thioesterase (Cpal FATB2, accession AAC49180) in UTEX1435 results in a large increase in C14:0 production (over 60% of the fatty acid profile).

Constructs used for the overexpression of the Cpal FATB2 gene were codon optimized for expression in *P. moriformis* as described herein. *Cuphea palustris* FATB2 is a C14 preferring thioesterase. Two constructs, both encoding the Cpal FATB2 gene, were prepared. The first construct, pSZ2479, can be written as 6SA::CrTUB2-ScSUC2-CvNR:PmAMT3-CpSAD1tpExt_CpalFATB2ExtA-CvNR::6SB. The FatB2 coding sequence is given as SEQ ID NO: 86 and the amino acid sequence is given as SEQ ID NO: 87. The second construct, pSZ2480 can be written as 6SA::CrTUB2-ScSUC2-CvNR:PmAMT3-CpSAD1tpExt_CpalFATB2FLAG_ExtA-CvNR::6SB. The nucleic acid sequence and amino acid sequence are given as SEQ ID NO: 88 and SEQ ID NO: 89.

*P. moriformis* transformed with pSZ2480 produced high levels of myristic acid. The myristate content was 65.70 percent. This is a very large increase when compared to the myristate content of the wild-type oil produced by the base strain, which has a myristate content of approximately 1%.

The fatty acid profile of the high myristate strain is shown in the Table 52 below.

TABLE 52

| Fatty acid profile of high myristate strain. | |
|---|---|
| Fatty Acid | % |
| C10:0 | 0.04 |
| C12:0 | 1.19 |
| C14:0 | 65.7 |
| C16:0 | 13.55 |
| C18:0 | 0.57 |
| C18:1 | 12.2 |
| C18:2 | 5.13 |
| C20:0 | 0.05 |
| C22:0 | 0.01 |
| C24:0 | 0.01 |

Example 54

Production of Eicosenoic and Erucic Fatty Acids

In this example we demonstrate that expression of heterologous fatty acid elongase (FAE), also known as 3-ketoacyl-CoA synthase (KCS), genes from *Cramble abyssinica* (CaFAE, Accession No: AY793549), *Lunaria annua* (LaFAE, ACJ61777), and *Cardamine graeca* (CgFAE, ACJ61778) leads to production of very long chain monounsaturated fatty acids such as eicosenoic ($20:1^{\Delta 11}$) and erucic ($22:1^{\Delta 13}$) acids in classically mutagenized derivative of UTEX 1435, Strain Z. On the other hand a putative FAE gene from *Tropaeolum majus* (TmFAE, ABD77097) and two FAE genes from *Brassica napus* (BnFAE1, AAA96054 and BnFAE2, AAT65206), while resulting in modest increase in eicosenoic (20:1$^{\Delta 11}$), produced no detectable erucic acid in STRAIN Z. Interestingly the unsaturated fatty acid profile obtained with heterologous expression of BnFAE1 in STRAIN Z resulted in noticeable increase in Docosadienoic acid (22:2n6). All the genes were codon optimized to reflect UTEX 1435 codon usage. These results suggest that CaFAE, LaFAE or CgFAE genes encode condensing enzymes involved in the biosynthesis of very long-chain utilizing monounsaturated and saturated acyl substrates, with specific capability for improving the eicosenoic and erucic acid content.

Construct Used for the Expression of the *Cramble abyssinica* Fatty Acid Elongase (CaFAE) in *P. moriformis* (UTEX 1435 Strain STRAIN Z)-[pSZ3070]:

In this example STRAIN Z strains, transformed with the construct pSZ3070, were generated, which express sucrose invertase (allowing for their selection and growth on medium containing sucrose) and *C. abyssinica* FAE gene. Construct pSZ3070 introduced for expression in STRAIN Z can be written as 6S::CrTUB2-ScSUC2-Cvnr:PmAmt03-CaFAE-Cvnr::6S.

The sequence of the transforming DNA is provided below. Relevant restriction sites in the construct are indicated in lowercase, bold, and are from 5'-3' BspQI, KpnI, XbaI, MfeI, BamHI, EcoRI, SpeI, AflII, SacI, BspQI, respectively. BspQI sites delimit the 5' and 3' ends of the transforming DNA. Bold, lowercase sequences represent genomic DNA from STRAIN Z that permit targeted integration at the 6S locus via homologous recombination. Proceeding in the 5' to 3' direction, the *C. reinhardtii* β-tubulin promoter driving the expression of the *Saccharomyces cerevisiae* SUC2 gene (encoding sucrose hydrolyzing activity, thereby permitting the strain to grow on sucrose) is indicated by lowercase, boxed text. The initiator ATG and terminator TGA for SUC2 are indicated by uppercase italics, while the coding region is indicated with lowercase italics. The *Chlorella vulgaris* nitrate reductase (NR) gene 3' UTR is indicated by lowercase underlined text followed by an endogenous AMT3 promoter of *P. moriformis*, indicated by boxed italicized text. The Initiator ATG and terminator TGA codons of the CaFAE are indicated by uppercase, bold italics, while the remainder of the gene is indicated by bold italics. The *C. vulgaris* nitrate reductase 3' UTR is again indicated by lowercase underlined text followed by the STRAIN Z 6S genomic region indicated by bold, lowercase text. The final construct was sequenced to ensure correct reading frames and targeting sequences.

Nucleotide sequence of transforming DNA contained in plasmid pSZ3070:

(SEQ ID NO: 102)

gctcttcgccgccgccactcctgctcgagcgcgcccgcgcgtgcgccgccagcgccttggccttttcgccgcgctcgtgcgcgtcgctgatgt ccatcaccaggtccatgaggtagccttgcgccggctgagccactgcttcgtccgggcggccaagaggagcatgagggaggactcctggt ccagggtcctgacgtggtcgcggctctgggagcgggccagcatcatctggctagccgcaccgaggccgcctccaactggtcctccagca gccgcagtcgccgccgaccaggcagaggaagacaggtgagggggtatgaattgtacagaacaaccacgagccttgtctaggcagaa tccctaccagtcatggctttacctggatgacggcctgcgaacagctgtccagcgaccctcgagccgccgcttctcccgcacgcttctttcca gcaccgtgatggcgcgagccagcgccgcacgctggcgagcgcttcgccgatctgaggacagtcggggaactctgatcagtctaaacccc cttgcgcgttagtgttgccatcctttgcagaccggtgagagccgacttgttgtgcgccacccccacaccacctcctcccagaccaattagt caccttttggcgaaggcatcggcctcggcctgcagagaggacagcagtgcccagccgctggggttggcggatgcacgctcaggtaccc tttcttgcgctatgacacttccagcaaaaggtagggcgggctgcgagacggcttcccggcgctgcatgcaacaccgatgatgcttcgacccccg aagctccttcggggctgcatgggcgctccgatgccgctccagggcgagcgctgtttaaatagccaggcccccgattgcaaagacattatagcgag ctaccaaagccatattcaaacacctagatcactaccacttctacacaggccactcgagcttgtgatcgcactccgctaagggggcgcctcttcctctt cgtttcagtcacaacccgcaaactctagaatatca*ATG**ctgctgcaggccttcctgttcctgctggccggcttcgccgccaagatcagcgcctcc*

*atgacgaacgagacgtccgaccgccccctggtgcacttcacccccaacaagggctggatgaacgaccccaacggcctgtggtacgacgag*

*aaggacgccaagtggcacctgtacttccagtacaacccgaacgacaccgtctgggggacgcccttgttctggggccacgccacgtccgacg*

*acctgaccaactgggaggaccagcccatcgccatcgccccgaagcgcaacgactccggcgccttctccggctccatggtggtggactacaa*

*caacacctccggcttcttcaacgacaccatcgacccgcgccagcgctgcgtggccatctggacctacaacaccccggagtccgaggagcagt*

*acatctcctacagcctggacggcggctacaccttcaccgagtaccagaagaaccccgtgctggccgccaactccacccagttccgcgacccg*

*aaggtcttctggtacgagccctcccagaagtggatcatgaccgcggccaagtcccaggactacaagatcgagatctactcctccgacgacctg*

*aagtcctggaagctggagtccgcgttcgccaacgagggcttcctcggctaccagtacgagtgccccggcctgatcgaggtccccaccgagca*

*ggaccccagcaagtcctactgggtgatgttcatctccatcaaccccggcgccccggccggcggctccttcaaccagtacttcgtcggcagcttc*

*aacggcacccacttcgaggccttcgacaaccagtcccgcgtggtggacttcggcaaggactactacgccctgcagaccttcttcaacaccgac*

*ccgacctacgggagcgccctgggcatcgcgtgggcctccaactgggagtactccgccttcgtgcccaccaacccctggcgctcctccatgtcc*

*ctcgtgcgcaagttctccctcaacaccgagtaccaggccaacccggagacggagctgatcaacctgaaggccgagccgatcctgaacatca*

*gcaacgccggcccctggagccggttcgccaccaacaccacgttgacgaaggccaacagctacaacgtcgacctgtccaacagcaccggca*

-continued ccctggagttcgagctggtgtacgccgtcaacaccacccagacgatctccaagtccgtgttcgcggacctctccctctggttcaagggcctgga ggaccccgaggagtacctccgcatgggcttcgaggtgtccgcgtcctccttcttcctggaccgcgggaacagcaaggtgaagttcgtgaagga gaacccctacttcaccaaccgcatgagcgtgaacaaccagcccttcaagagcgagaacgacctgtcctactacaaggtgtacggcttgctgg accagaacatcctggagctgtacttcaacgacggcgacgtcgtgtccaccaacacctacttcatgaccaccgggaacgccctgggctccgtg aacatgacgacgggggtggacaacctgttctacatcgacaagttccaggtgcgcgaggtcaagTGAcaattggcagcagcagctcggata gtatcgacacactctggacgctggtcgtgtgatggactgttgccgccacacttgctgccttgacctgtgaatatccctgccgcttttatcaaacagcctc agtgtgtagatcttgtgtgtacgcgcttttgcgagttgctagctgcttgtgctatttgcgaataccacccccagcatccccttccctcgtttcatatcgctt gcatcccaaccgcaacttatctacgctgtcctgctatccctcagcgctgctcctgctcctgctcactgcccctcgcacagccttggtttgggctccgcc tgtattctcctaatactacaacctataaaccaacactacaatgctgatgcacgggaagtagtgggatgggaacacaaatggaggatcccgcgtctc gaacagagcgcgcagaggaacgctgaaggtctcgcctctgtcgcacctcagcgcggcatacaccacaataaccacctgacgaatgcgcttggtt cttcgtccattagcgaagcgtccggttcacacacgtgccacgttggcgaggtggcaggtgacaatgatcggtggagctgatggtcgaaacgttcac agcctagggatatcgaattcggccgacaggacgcgcgtcaaaggtgctggtcgtgtatgccctggccggcaggtcgttgctgctgctggttagt gattccgcaaccctgattttggcgtcttattttggcgtggcaaacgctggcgcccgcgagccgggccggcggcgatgcggtgccccacggctg ccggaatccaagggaggcaagagcgcccgggtcagttgaagggctttacgcgcaaggtacagccgctcctgcaaggctgctggtggaatt ggacgtgcaggtcctgctgaagttcctccaccgcctcaccagcggacaaagcaccggtgtatcaggtccgtgtcatccactctaaagaactcg actacgacctactgatggccctagattcttcatcaaaaacgcctgagacacttgcccaggattgaaactccctgaagggaccaccaggggcc ctgagttgttccttcccccgtggcgagctgccagccaggctgtacctgtgatcgaggctggcgggaaaataggcttcgtgtgctcaggtcatgg gaggtgcaggacagctcatgaaacgccaacaatcgcacaattcatgtcaagctaatcagctatttcctcttcacgagctgtaattgtcccaaaa ttctggtctaccgggggtgatccttcgtgtacgggcccttccctcaaccctaggtatgcgcgcatgcggtcgccgcgcaactcgcgcgagggcc gagggtttgggacgggccgtcccgaaatgcagttgcacccggatgcgtggcacctttttgcgataatttatgcaatggactgctctgcaaaatt ctggctcgtcgccaaccctaggatcagcggcgtaggatttcgtaatcattcgtcctgatggggagctaccgactaccctaatatcagcccgact gcctgacgccagcgtccacttttgtgcacacattccattcgtgcccaagacatttcattgtggtgcgaagcgtccccagttacgctcacctgtttcc cgacctccttactgttctgtcgacagagcgggcccacaggccggtcgcagccactagtATGacctccatcaacgtgaagctgctgtacc actacgtgatcaccaacctgttcaacctgtgcttcttcccccctgaccgccatcgtggccggcaaggcctcccgcctgaccatcgacg acctgcaccacctgtactactcctacctgcagcacaacgtgatcaccatcgcccccctgttcgccttcaccgtgttcggctccatcct gtacatcgtgacccgccccaagcccgtgtacctggtggagtactcctgctacctgccccccacccagtgccgctcctccatctccaa ggtgatggacatcttctaccaggtgcgcaaggccgacccccttccgcaacggcacctgcgacgactcctcctggctggacttcctgc gcaagatccaggagcgctccggcctgggcgacgagacccacggccccgagggcctgctgcaggtgccccccgcaagacctt cgccgcgcccgcgaggagaccgagcaggtgatcgtgggcgccctgaagaacctgttcgagaacaccaaggtgaaccccaa ggacatcggcatcctggtggtgaactcctccatgttcaacccccacccctccctgtccgccatggtggtgaacaccttcaagctgcg ctccaacgtgcgctccttcaacctgggcggcatgggctgctccgccggcgtgatcgccatcgacctggccaaggacctgctgcac gtgcacaagaacacctacgccctggtggtgtccaccgagaacatcacctacaacatctacgccggcgacaaccgctccatgatg gtgtccaactgcctgttccgcgtgggcggcgccgccatcctgctgtccaacaagccccgcgaccgccgccgctccaagtacgagc tggtgcacaccgtgcgcacccacaccggcgccgacgacaagtccttccgctgcgtgcagcagggcgacgacgagaacggcaa gaccggcgtgtccctgtccaaggacatcaccgaggtggccggccgcaccgtgaagaagaacatcgccaccctgggcccccctga tcctgcccctgtccgagaagctgctgttcttcgtgaccttcatggccaagaagctgttcaaggacaaggtgaagcactactacgtgc ccgacttcaagctggccatcgaccacttctgcatccacgccggcggccgcgccgtgatcgacgtgctggagaagaacctgggcc -continued tggcccccatcgacgtggaggcctcccgctccaccctgcaccgcttcggcaacacctcctcctcctccatctggtacgagctggcct acatcgaggccaagggccgcatgaagaagggcaacaaggtgtggcagatcgccctgggctccggcttcaagtgcaactccgc cgtgtgggtggccctgtccaacgtgaaggcctccaccaactcccccctgggagcatcgaccgctaccccgtgaagatcgac tccgactccgccaagtccgagacccagaacggccgctccTGActtaaggcagcagcagctcggatagtatcgacacactct ggacgctggtcgtgtgatggactgttgccgccacacttgctgccttgacctgtgaatatccctgccgcttttatcaaacagcctcagtgtgtttgatcttg tgtgtacgcgcttttgcgagttgctagctgcttgtgctatttgcgaataccacccccagcatccccaccctcgatcatatcgcttgcatcccaaccgca acttatctacgctgtcctgctatccctcagcgctgctcctgctcctgctcactgcccctcgcacagccaggtagggctccgcctgtattctcctggtac tgcaacctataaaccaacactacaatactaatacacgggaagtagtgggatgggaacacaaatggaaagcttaattaagagctcttgttttccaga aggagttgctccttgagcctttcattctcagcctcgataacctccaaagccgctctaattgtggaggggggttcgaatttaaaagcttggaatg ttggttcgtgcgtctggaacaagcccagacttgttgctcactgggaaaaggaccatcagctccaaaaaacttgccgctcaaaccgcgtacc tctgctttcgcgcaatctgccctgttgaaatcgccaccacattcatattgtgacgcttgagcagtctgtaattgcctcagaatgtggaatcatc tgcccccctgtgcgagcccatgccaggcatgtcgcgggcgaggacacccgccactcgtacagcagaccattatgctacctcacaatagttca taacagtgaccatatttctcgaagctccccaacgagcacctccatgctctgagtggccaccccccggccctggtgcttgcggagggcaggt caaccggcatggggctaccgaaatccccgaccggatcccaccacccccgcgatgggaagaatctctccccgggatgtgggcccaccacc agcacaacctgctggcccaggcgagcgtcaaaccataccacacaaatatccttggcatcggccctgaattccttctgccgctctgctacccg gtgcttctgtccgaagcaggggttgctagggatcgctccgagtccgcaaacccttgtcgcgtggcggggcttgttcgagcttgaagagc Constructs Used for the Expression of the FAE Genes from Higher Plants in STRAIN Z:

In addition to the CaFAE gene (pSZ3070), LaFAE (pSZ3071) from *Lunaria annua*, CgFAE (pSZ3072) from *Cardamine graeca*, TmFAE (pSZ3067) *Tropaeolum majus* and BnFAE1 (pSZ3068) and BnFAE2 (pSZ3069) genes from *Brassica napus* have been constructed for expression in STRAIN Z. These constructs can be described as:

pSZ3071-6S::CrTUB2-ScSUC2-Cvnr:PmAmt03-LaFAE-Cvnr::6S pSZ3072-6S::CrTUB2-ScSUC2-Cvnr:PmAmt03-Cg-FAE-Cvnr::6S pSZ3067-6S::CrTUB2-ScSUC2-Cvnr:PmAmt03-Tm-FAE-Cvnr::6S pSZ3068-6S::CrTUB2-ScSUC2-Cvnr:PmAmt03-Bn-FAE1-Cvnr::6S pSZ3069-6S::CrTUB2-ScSUC2-Cvnr:PmAmt03-Bn-FAE2-Cvnr::6S All these constructs have the same vector backbone; selectable marker, promoters, and 3' utr as pSZ3070, differing only in the respective FAE genes. Relevant restriction sites in these constructs are also the same as in pSZ3070. The sequences of LaFAE, CgFAE, TmFAE, BnFAE1 and BnFAE2 are shown below. Relevant restriction sites as bold text including SpeI and NM are shown 5'-3' respectively.

Nucleotide sequence of LaFAE contained in pSZ3071:

(SEQ ID NO: 103)

actagtATGacctccatcaacgtgaagctgctgtaccactacgtgatcaccaacttcttcaacctgtgcttcttcccccctgaccgccat cctggccggcaaggcctcccgcctgaccaccaacgacctgcaccacttctactcctacctgcagcacaacctgatcaccctgacc ctgctgttcgccttcaccgtgttcggctccgtgctgtacttcgtgacccgccccaagcccgtgtacctggtggactactcctgctacctg cccccccagcacctgtccgccggcatctccaagaccatggagatcttctaccagatccgcaagtccgacccccctgcgcaacgtgg ccctggacgactcctcctccctggacttcctgcgcaagatccaggagcgctccggcctgggcgacgagacctacggccccgagg gcctgttcgagatcccccccccgcaagaacctggcctccgcccgcgaggagaccgagcaggtgatcaacggcgccctgaagaa cctgttcgagaacaccaaggtgaaccccaaggagatcggcatcctggtggtgaactcctccatgttcaacccccacccccctccctgt ccgccatggtggtgaacaccttcaagctgcgctccaacatcaagtccttcaacctgggcggcatgggctgctccgccggcgtgatc gccatcgacctggccaaggacctgctgcacgtgcacaagaacacctacgccctggtggtgtccaccgagaacatcacccagaa catctacaccggcgacaaccgctccatgatggtgtccaactgcctgttccgcgtgggcggcgccgccatcctgctgtccaacaagc ccggcgaccgccgccgctccaagtaccgcctggcccacaccgtgcgcacccacaccggcgccgacgacaagtccttcggctgc gtgcgccaggaggaggacgactccggcaagaccggcgtgtccctgtccaaggacatcaccggcgtggccggcatcaccgtgc -continued

*agaagaacatcaccaccctgggccccctggtgctgcccctgtccgagaagatcctgttcgtggtgaccttcgtggccaagaagct*

*gctgaaggacaagatcaagcactactacgtgcccgacttcaagctggccgtggaccacttctgcatccacgccggcggccgcgc*

*cgtgatcgacgtgctggagaagaacctgggcctgtcccccatcgacgtggaggcctcccgctccaccctgcaccgcttcggcaac*

*acctcctcctcctccatctggtacgagctggcctacatcgaggccaagggccgcatgaagaagggcaacaaggcctggcagatc*

*gccgtgggctccggcttcaagtgcaactccgccgtgtgggtggccctgcgcaacgtgaaggcctccgccaactccccctgggagc*

*actgcatccacaagtaccccgtgcagatgtactccggctcctccaagtccgagacccgcgcccagaacggccgctcc*TGA*ctta*

*ag*

Nucleotide sequence of CgFAE contained in pSZ3072:

(SEQ ID NO: 104)

*actagt*ATG*acctccatcaacgtgaagctgctgtaccactacgtgctgaccaacttcttcaacctgtgcctgttccccctgaccgcctt*

*ccccgccggcaaggcctcccagctgaccaccaacgacctgcaccacctgtactcctacctgcaccacaacctgatcaccgtgac*

*cctgctgttcgccttcaccgtgttcggctccatcctgtacatcgtgacccgccccaagcccgtgtacctggtggactactcctgctacc*

*tgccccccccgccacctgtcctgcggcatctcccgcgtgatggagatcttctacgagatccgcaagtccgacccctcccgcgaggtg*

*cccttcgacgacccctcctccctggagttcctgcgcaagatccaggagcgctccggcctgggcgacgagacctacggcccccag*

*ggcctggtgcacgacatgtcccctgcgcatgaacttcgccgccgcccgcgaggagaccgagcaggtgatcaacggcgccctgga*

*gaagctgttcgagaacaccaaggtgaaccccccgcgagatcggcatcctggtggtgaactcctccatgttcaaccccacccccctcc*

*ctgtccgccatggtggtgaacaccttcaagctgcgctccaacatcaagtccttctccctgggcggcatgggctgctccgccggcatc*

*atcgccatcgacctggccaaggacctgctgcacgtgcacaagaacacctacgccctggtggtgtccaccgagaacatcacccac*

*tccacctacaccggcgacaaccgctccatgatggtgtccaactgcctgttccgcatgggcggcgccgccatcctgctgtccaacaa*

*ggccggcgaccgccgccgctccaagtacaagctggcccacaccgtgcgcacccacaccggcgccgacgaccagtccttccgct*

*gcgtgcgccaggaggacgacgaccgcggcaagatcggcgtgtgcctgtccaaggacatcaccgccgtggccggcaagaccgt*

*gaccaagaacatcgccaccctgggccccctggtgctgcccctgtccgagaagttcctgtacgtggtgtccctgatggccaagaag*

*ctgttcaagaacaagatcaagcacacctacgtgcccgacttcaagctggccatcgaccacttctgcatccacgccggcggccgcg*

*ccgtgatcgacgtgctggagaagaacctggccctgtcccccgtggacgtggaggcctcccgctccaccctgcaccgcttcggcaa*

*cacctcctcctcctccatctggtacgagctggcctacatcgaggccaagggccgcatgaagaagggcaacaaggtgtggcagat*

*cgccatcggctccggcttcaagtgcaactccgccgtgtgggtggccctgtgcaacgtgaagccctccgtgaactccccctgggag*

*cactgcatcgaccgctaccccgtggagatcaactacggctcctccaagtccgagacccgcgcccagaacggccgctcc*TGA*ctt*

*aag*

Nucleotide sequence of TmFAE contained in pSZ3067:

(SEQ ID NO: 105)

*actagt*ATG*tccggcaccaaggccacctccgtgtccgtgcccctgcccgacttcaagcagtccgtgaacctgaagtacgtgaagc*

*tgggctaccactactccatcacccacgccatgtacctgttcctgacccccctgctgctgatcatgtccgcccagatctccaccttctcc*

*atccaggacttccaccacctgtacaaccacctgatcctgcacaacctgtcctccctgatcctgtgcatcgccctgctgctgttcgtgct*

*gaccctgtacttcctgacccgccccacccccgtgtacctgctgaacttctcctgctacaagcccgacgccatccacaagtgcgacc*

*gccgccgcttcatggacaccatccgcggcatgggcacctacaccgaggagaacatcgagttccagcgcaaggtgctggagcgc*

*tccggcatcggcgagtcctcctacctgccccccaccgtgttcaagatcccccccccgcgtgtacgacgccgaggagcgcgccgag*

*gccgagatgctgatgttcggcgccgtggacggcctgttcgagaagatctccgtgaagcccaaccagatcggcgtgctggtggtga*

*actgcggcctgttcaaccccatcccctccctgtcctccatgatcgtgaaccgctacaagatgcgcggcaacgtgttctcctacaacct*

*gggcggcatgggctgctccgccggcgtgatctccatcgacctggccaaggacctgctgcaggtgcgccccaactcctacgccctg*

-continued gtggtgtccctggagtgcatctccaagaacctgtacctgggcgagcagcgctccatgctggtgtccaactgcctgttccgcatgggc ggcgccgccatcctgctgtccaacaagatgtccgaccgctggcgctccaagtaccgcctggtgcacaccgtgcgcacccacaag ggcaccgaggacaactgcttctcctgcgtgacccgcaaggaggactccgacggcaagatcggcatctccctgtccaagaacctg atggccgtggccggcgacgccctgaagaccaacatcaccaccctgggcccccctggtgctgcccatgtccgagcagctgctgttctt cgccaccctggtgggcaagaaggtgttcaagatgaagctgcagccctacatccccgacttcaagctggccttcgagcacttctgc atccacgccggcggccgcgccgtgctggacgagctggagaagaacctgaagctgtcctcctggcacatggagccctcccgcat gtccctgtaccgcttcggcaacacctcctcctcctccctgtggtacgagctggcctactccgaggccaagggccgcatcaagaagg gcgaccgcgtgtggcagatcgccttcggctccggcttcaagtgcaactccgccgtgtggaaggccctgcgcaacgtgaaccccg ccgaggagaagaacccctggatggacgagatccacctgttccccgtggaggtgcccctgaacTGActtaag Nucleotide sequence of BnFAE1 contained in pSZ3068:

(SEQ ID NO: 106)

actagtATGacctccatcaacgtgaagctgctgtaccactacgtgatcaccaacctgttcaacctgtgcttcttccccctgaccgcc atcgtggccggcaaggcctacctgaccatcgacgacctgcaccacctgtactactcctacctgcagcacaacctgatcaccatcg ccccccctgctggccttcaccgtgttcggctccgtgctgtacatcgccacccgccccaagcccgtgtacctggtggagtactcctgcta cctgcccccccacccactgccgctcctccatctccaaggtgatggacatcttcttccaggtgcgcaaggccgacccctcccgcaacg gcacctgcgacgactcctcctggctggacttcctgcgcaagatccaggagcgctccggcctgggcgacgagacccacggcccc gagggcctgctgcaggtgcccccccgcaagaccttcgcccgcgcccgcgaggagaccgagcaggtgatcatcggcgccctgg agaacctgttcaagaacaccaacgtgaaccccaaggacatcggcatcctggtggtgaactcctccatgttcaacccaccccctc cctgtccgccatggtggtgaacaccttcaagctgcgctccaacgtgcgctccttcaacctgggcggcatgggctgctccgccggcg tgatcgccatcgacctggccaaggacctgctgcacgtgcacaagaacacctacgccctggtggtgtccaccgagaacatcacct acaacatctacgccggcgacaaccgctccatgatggtgtccaactgcctgttccgcgtgggcggcgccgccatcctgctgtccaac aagccccgcgaccgccgccgctccaagtacgagctggtgcacaccgtgcgcacccacaccggcgccgacgacaagtggttcc gctgcgtgcagcagggcgacgacgagaacggccagaccggcgtgtccctgtccaaggacatcaccgacgtggccggccgcac cgtgaagaagaacatcgccaccctgggcccccctgatcctgcccctgtccgagaagctgctgttcttcgtgaccttcatgggcaaga agctgttcaaggacgagatcaagcactactacgtgcccgacttcaagctggccatcgaccacttctgcatccacgccggcggcaa ggccgtgatcgacgtgctggagaagaacctgggcctggcccccatcgacgtggaggcctcccgctccaccctgcaccgcttcgg caacacctcctcctcctccatctggtacgagctggcctacatcgagcccaagggccgcatgaagaagggcaacaaggtgtggca gatcgccctgggctccggcttcaagtgcaactccgccgtgtgggtggccctgaacaacgtgaaggcctccaccaactcccccctgg gagcactgcatcgaccgctaccccgtgaagatcgactccgactccggcaagtccgagacccgcgtgcccaacggccgctccTG Acttaag Nucleotide sequence of BnFAE2 contained in pSZ3069:

(SEQ ID NO: 107)

actagATGgagcgcaccaactccatcgagatggaccaggagcgcctgaccgccgagatggccttcaaggactcctcctccgc cgtgatccgcatccgccgccgcctgcccgacttcctgacctccgtgaagctgaagtacgtgaagctgggcctgcacaactccttca acttcaccaccttcctgttcctgctgatcatcctgcccctgaccggcaccgtgctggtgcagctgaccggcctgaccttcgagaccttc tccgagctgtggtacaaccacgccgcccagctggacggcgtgacccgcctggcctgcctggtgtccctgtgcttcgtgctgatcatc tacgtgaccaaccgctccaagcccgtgtacctggtggacttctcctgctacaagcccgaggacgagcgcaagatgtccgtggact ccttcctgaagatgaccgagcagaacggcgcctcaccgacgacaccgtgcagttccagcagcgcatctccaaccgcgccggc ctgggcgacgagacctacctgccccgcggcatcacctccaccccccccaagctgaacatgtccgaggcccgcgccgaggccga -continued

```
ggccgtgatgttcggcgccctggactccctgttcgagaagaccggcataagcccgccgaggtgggcatcctgatcgtgtcctgct

ccctgttcaaccccaccccctccctgtccgccatgatcgtgaaccactacaagatgcgcgaggacatcaagtcctacaacctggg

cggcatgggctgctccgccggcctgatctccatcgacctggccaacaacctgctgaaggccaaccccaactcctacgccgtggtg

gtgtccaccgagaacatcaccctgaactggtacttcggcaacgaccgctccatgctgctgtgcaactgcatcttccgcatgggcgg

cgccgccatcctgctgtccaaccgccgccaggaccgctccaagtccaagtacgagctggtgaacgtggtgcgcacccacaagg

gctccgacgacaagaactacaactgcgtgtaccagaaggaggacgagcgcggcaccatcggcgtgtccctggcccgcgagct

gatgtccgtggccggcgacgccctgaagaccaacatcaccaccctgggccccatggtgctgcccctgtccggccagctgatgttct

ccgtgtccctggtgaagcgcaagctgctgaagctgaaggtgaagccctacatccccgacttcaagctggccttcgagcacttctgc

atccacgccggcggccgcgccgtgctggacgaggtgcagaagaacctggacctggaggactggcacatggagccctcccgca

tgaccctgcaccgcttcggcaacacctcctcctcctccctgtggtacgagatggcctacaccgaggccaagggccgcgtgaaggc

cggcgaccgcctgtggcagatcgccttcggctccggcttcaagtgcaactccgccgtgtggaaggccctgcgcgtggtgtccacc

gaggagctgaccggcaacgcctgggccggctccatcgagaactaccccgtgaagatcgtgcagTGActtaag
```

To determine their impact on fatty acid profiles, the above constructs containing various heterologous FAE genes, driven by the PmAMT3 promoter, were transformed independently into STRAIN Z.

Primary transformants were clonally purified and grown under standard lipid production conditions at pH7.0 (all the plasmids require growth at pH 7.0 to allow for maximal FAE gene expression when driven by the pH regulated PmAMT03 promoter). The resulting profiles from a set of representative clones arising from transformations with pSZ3070, pSZ3071, pSZ3072, pSZ3067, pSZ3068 and pSZ3069 into STRAIN Z are shown in Tables 53-58, respectively, below.

All the transgenic STRAIN Z strains expressing heterologous FAE genes show an increased accumulation of C20:1 and C22:1 fatty acid (see Tables 53-58). The increase in eicosenoic ($20:1^{\Delta 11}$) and erucic ($22:1^{\Delta 13}$) acids levels over the wildtype is consistently higher than the wildtype levels. Additionally, the unsaturated fatty acid profile obtained with heterologous expression of BnFAE1 in STRAIN Z resulted in noticeable increase in Docosadienoic acid (C22:2n6). Protein alignment of aforementioned FAE expressed in STRAIN Z is shown in FIG. 23.

TABLE 53

Unsaturated fatty acid profile in STRAIN Z and representative derivative transgenic lines transformed with pSZ3070 (CaFAE) DNA.

| Sample ID | C18:1 | C18:2 | C18:3a | C20:1 | C22:1 | C22:2n6 | C22:5 |
|---|---|---|---|---|---|---|---|
| STRAIN Z; T588; D1828-20 | 51.49 | 9.13 | 0.65 | 4.35 | 1.24 | 0.11 | 0.00 |
| STRAIN Z; T588; D1828-23 | 55.59 | 7.65 | 0.50 | 3.78 | 0.85 | 0.00 | 0.13 |
| STRAIN Z; T588; D1828-43 | 54.70 | 7.64 | 0.50 | 3.44 | 0.85 | 0.09 | 0.00 |
| STRAIN Z; T588; D1828-12 | 52.43 | 7.89 | 0.59 | 2.72 | 0.73 | 0.00 | 0.00 |
| STRAIN Z; T588; D1828-19 | 56.02 | 7.12 | 0.52 | 3.04 | 0.63 | 0.10 | 0.11 |
| Cntrl STRAIN Z pH 7 | 57.99 | 6.62 | 0.56 | 0.19 | 0.00 | 0.06 | 0.05 |
| Cntrl STRAIN Z pH 5 | 57.70 | 7.08 | 0.54 | 0.11 | 0.00 | 0.05 | 0.05 |

TABLE 54

Unsaturated fatty acid profile in STRAIN Z and representative derivative transgenic lines transformed with pSZ3071 (LaFAE) DNA.

| Sample ID | C18:1 | C18:2 | C18:3a | C20:1 | C22:1 | C22:2n6 | C22:5 |
|---|---|---|---|---|---|---|---|
| STRAIN Z; T588; D1829-36 | 54.66 | 7.04 | 0.52 | 1.82 | 0.84 | 0.12 | 0.09 |
| STRAIN Z; T588; D1829-24 | 56.27 | 6.72 | 0.51 | 1.70 | 0.72 | 0.09 | 0.00 |

TABLE 54-continued

Unsaturated fatty acid profile in STRAIN Z and representative derivative transgenic lines transformed with pSZ3071 (LaFAE) DNA.

| Sample ID | C18:1 | C18:2 | C18:3a | C20:1 | C22:1 | C22:2n6 | C22:5 |
|---|---|---|---|---|---|---|---|
| STRAIN Z; T588; D1829-11 | 56.65 | 8.36 | 0.54 | 2.04 | 0.67 | 0.00 | 0.00 |
| STRAIN Z; T588; D1829-35 | 55.57 | 7.71 | 0.53 | 0.10 | 0.66 | 0.00 | 0.00 |
| STRAIN Z; T588; D1829-42 | 56.03 | 7.06 | 0.54 | 1.54 | 0.51 | 0.06 | 0.08 |
| Cntrl STRAIN Z pH 7 | 57.70 | 7.08 | 0.54 | 0.11 | 0.00 | 0.06 | 0.05 |
| Cntrl STRAIN Z pH 5 | 57.99 | 6.62 | 0.56 | 0.19 | 0.00 | 0.05 | 0.05 |

TABLE 55

Unsaturated fatty acid profile in STRAIN Z and representative derivative transgenic lines transformed with pSZ3072 (CgFAE) DNA.

| Sample ID | C18:1 | C18:2 | C18:3a | C20:1 | C22:1 | C22:2n6 | C22:5 |
|---|---|---|---|---|---|---|---|
| STRAIN Z; T588; D1830-47 | 57.74 | 7.79 | 0.52 | 1.61 | 0.25 | 0.11 | 0.05 |
| STRAIN Z; T588; D1830-16 | 58.06 | 7.39 | 0.55 | 1.64 | 0.22 | 0.07 | 0.06 |
| STRAIN Z; T588; D1830-12 | 57.77 | 6.86 | 0.51 | 1.34 | 0.19 | 0.09 | 0.00 |
| STRAIN Z; T588; D1830-37 | 58.45 | 7.54 | 0.49 | 1.65 | 0.19 | 0.06 | 0.00 |
| STRAIN Z; T588; D1830-44 | 57.10 | 7.28 | 0.56 | 1.43 | 0.19 | 0.07 | 0.00 |
| Cntrl STRAIN Z pH 7 | 57.70 | 7.08 | 0.54 | 0.11 | 0.00 | 0.06 | 0.05 |
| Cntrl STRAIN Z pH 5 | 57.99 | 6.62 | 0.56 | 0.19 | 0.00 | 0.05 | 0.05 |

TABLE 56

Unsaturated fatty acid profile in S3067 and representative derivative transgenic lines transformed with pSZ3070 (TmFAE) DNA. No detectable Erucic (22:1) acid peaks were reported for these transgenic lines.

| Sample ID | C18:1 | C18:2 | C18:3a | C20:1 | C22:2n6 | C22:5 |
|---|---|---|---|---|---|---|
| STRAIN Z; T588; D1825-47 | 59.97 | 7.44 | 0.56 | 0.57 | 0.00 | 0.00 |
| STRAIN Z; T588; D1825-35 | 58.77 | 7.16 | 0.51 | 0.50 | 0.09 | 0.11 |
| STRAIN Z; T588; D1825-27 | 60.40 | 7.82 | 0.47 | 0.44 | 0.07 | 0.07 |
| STRAIN Z; T588; D1825-14 | 58.07 | 7.32 | 0.54 | 0.41 | 0.05 | 0.05 |
| STRAIN Z; T588; D1825-40 | 58.66 | 7.74 | 0.46 | 0.39 | 0.08 | 0.00 |
| Cntrl STRAIN Z pH 7 | 57.99 | 6.62 | 0.56 | 0.19 | 0.05 | 0.05 |
| Cntrl STRAIN Z pH 5 | 57.70 | 7.08 | 0.54 | 0.11 | 0.06 | 0.05 |

TABLE 57

Unsaturated fatty acid profile in STRAIN Z and representative derivative transgenic lines transformed with pSZ3068 (BnFAE1) DNA. No detectable Erucic (22:1) acid peaks were reported for these transgenic lines.

| Sample ID | C18:1 | C18:2 | C18:3a | C20:1 | C22:2n6 | C22:5 |
|---|---|---|---|---|---|---|
| STRAIN Z; T588; D1826-30 | 59.82 | 7.88 | 0.55 | 0.32 | 0.17 | 0.10 |
| STRAIN Z; T588; D1826-23 | 59.32 | 8.02 | 0.58 | 0.27 | 0.18 | 0.07 |
| STRAIN Z; T588; D1826-45 | 59.63 | 7.49 | 0.55 | 0.27 | 0.19 | 0.08 |
| STRAIN Z; T588; D1826-24 | 59.35 | 7.78 | 0.57 | 0.26 | 0.23 | 0.00 |
| STRAIN Z; T588; D1826-34 | 59.14 | 7.61 | 0.57 | 0.25 | 0.22 | 0.05 |
| Cntrl STRAIN Z pH 7 | 57.81 | 7.15 | 0.59 | 0.19 | 0.04 | 0.06 |
| Cntrl STRAIN Z pH 5 | 58.23 | 6.70 | 0.58 | 0.18 | 0.05 | 0.06 |

TABLE 58

Unsaturated fatty acid profile in STRAIN Z and representative derivative transgenic lines transformed with pSZ3069 (BnFAE2) DNA. No detectable Erucic (22:1) acid peaks were reported for these transgenic lines.

| Sample ID | C18:1 | C18:2 | C18:3a | C20:1 | C22:2n6 | C22:5 |
|---|---|---|---|---|---|---|
| STRAIN Z; T588; D1827-6 | 60.59 | 8.20 | 0.57 | 0.34 | 0.00 | 0.07 |
| STRAIN Z; T588; D1827-42 | 59.62 | 6.44 | 0.52 | 0.30 | 0.07 | 0.00 |
| STRAIN Z; T588; D1827-48 | 59.71 | 7.99 | 0.59 | 0.30 | 0.06 | 0.00 |
| STRAIN Z; T588; D1827-43 | 60.66 | 8.21 | 0.59 | 0.29 | 0.04 | 0.00 |
| STRAIN Z; T588; D1827-3 | 60.26 | 7.99 | 0.57 | 0.28 | 0.04 | 0.00 |
| Cntrl STRAIN Z pH 7 | 57.81 | 7.15 | 0.59 | 0.19 | 0.04 | 0.06 |
| Cntrl STRAIN Z pH 5 | 58.23 | 6.70 | 0.58 | 0.18 | 0.05 | 0.06 |

Example 55

Elevating Total Unsaturated Fatty Acids Level by Expressing Heterologous Desaturase Genes One of the approaches to generate a “zero SAT FAT” (e.g., total unsaturated fatty acids target at 97% or more/less than or equal to 3% saturated fat) strain is to express desaturase genes in a high oleic strain such as Strain N, which we found to produce about 85% C18:1 with total un-saturates around 93% in multiple fermentation runs. We expect the total saturates will be further diminished by expressing desaturase genes in Strain N.

In the examples below, we demonstrated the ability to reduce stearic and palmitic levels in wild type strain UTEX1435 by over expression of heterologous stearoyl-ACP desaturase genes, including desaturases from *Olea europaea, Ricinus communis*, and *Chlorella protothecoides.*

Construct Used for the Expression of the *Olea europaea* Stearoyl-ACP Desaturase:

To introduce the *O. europaea* stearoyl-ACP desaturase (Accession No: AAB67840.1) into UTEX1435, Strain A, the *Saccharomyces cerevisiae* invertase gene was utilized as the selectable marker to confer the ability of growing on sucrose media. The construct that has been expressed in UTEX1435, Strain A can be written as 6SA::CrTUB2:ScSUC2:CvNR::CrTUB2:CpSADtp:OeSAD:CvNR::65B and is termed pSZ1377.

Relevant restriction sites in the construct pSZ1377 are indicated in lowercase, bold and underlining and are 5'-3' BspQ 1, Kpn I, Xba I, Mfe I, BamH I, EcoR I, Spe I, Asc I, Cla I, Sac I, BspQ I, respectively. BspQI sites delimit the 5' and 3' ends of the transforming DNA. Bold, lowercase sequences represent genomic DNA that permit targeted integration at 6s locus via homologous recombination. Proceeding in the 5' to 3' direction, the *C. reinhardtii* β-tubulin promoter driving the expression of the yeast sucrose invertase gene is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by the second *C. reinhardtii* β-tubulin promoter driving the expression of the OeSAD, indicated by boxed italics text. The Initiator ATG and terminator TGA codons of the OeSAD are indicated by uppercase, bold italics, while the remainder of the stearoyl-ACP desaturase coding region is indicated by bold italics. The *Chlorella protothecoides* stearoyl-ACP desaturase transit peptide is located between initiator ATG and the Asc I site. The *C. vulgaris* nitrate reductase 3' UTR is again indicated by lowercase underlined text followed by the 6S genomic region indicated by bold, lowercase text.

Nucleotide sequence of transforming DNA contained in pSZ 1377:

(SEQ ID NO: 108)

gctcttcgccgccactcctgctcgagcgcgcccgcgcgtgcgccgccagcgccttggccttttcgccgcgctcgtgcgcgtcgctgatgtcca tcaccaggtccatgaggtctgccttgcgccggctgagccactgcttcgtccgggcggccaagaggagcatgagggaggactcctggtccaggg tcctgacgtggtcgcggctctgggagcgggccagcatcatctggctctgccgcaccgaggccgcctccaactggtcctccagcagccgcagtcg ccgccgaccctggcagaggaagacaggtgaggggggtatgaattgtacagaacaaccacgagccttgtctaggcagaatccctaccagtcat ggctttacctggatgacggcctgcgaacagctgtccagcgaccctcgctgccgccgcttctcccgcacgcttctttccagcaccgtgatggcgcg agccagcgccgcacgctggcgctgcgcttcgccgatctgaggacagtcggggaactctgatcagtctaaaccccttgcgcgttagtgttgcca tcctttgcagaccggtgagagccgacttgttgtgcgccacccccacaccacctcctcccagaccaattctgtcacctttttggcgaaggcatcgg cctcggcctgcagagaggacagcagtgcccagccgctggggttggcggatgcacgctcaggtaccctttcttgcgctatgacacttccagcaa aaggtagggcgggctgcgagacggcttcccggcgctgcatgcaacaccgatgatgcttcgacccccccgaagctccttcggggctgcatgggcgc tccgatgccgctccagggcgagcgctgtttaaatagccaggcccccgattgcaaagacattatagcgagctaccaaagccatatttcaaacacct agatcactaccacttctacacaggccactcgagcttgtgatcgcactccgctaagggggcgcctcttcctcttcgtttcagtcacaacccgcaaac tctagaatatca*ATG**ctgctgcaggccttcctgttcctgctggccggcttcgccgccaagatcagcgcctccatgacgaacgagacgtccga*

*ccgccccctggtgcacttcacccccaacaagggctggatgaacgaccccaacggcctgtggtacgacgagaaggacgccaagtggcacc*

*tgtacttccagtacaacccgaacgacaccgtctgggggacgcccttgttctggggccacgccacgtccgacgacctgaccaactgggagg*

*accagcccatcgccatcgccccgaagcgcaacgactccggcgccttctccggctccatggtggtggactacaacaacacctccggcttcttc*

*aacgacaccatcgacccgcgccagcgctgcgtggccatctggacctacaacaccccggagtccgaggagcagtacatctcctacagcctg*

*gacggcggctacaccttcaccgagtaccagaagaaccccgtgctggccgccaactccacccagttccgcgacccgaaggtcttctggtacg*

*agccctcccagaagtggatcatgaccgcggccaagtcccaggactacaagatcgagatctactcctccgacgacctgaagtcctggaagc*

*tggagtccgcgttcgccaacgagggcttcctcggctaccagtacgagtgccccggcctgatcgaggtccccaccgagcaggaccccagca*

*agtcctactgggtgatgttcatctccatcaaccccggcgccccggccggcggctccttcaaccagtacttcgtcggcagcttcaacggcaccc*

*acttcgaggccttcgacaaccagtcccgcgtggtggacttcggcaaggactactacgccctgcagaccttcttcaacaccgacccgacctac*

*gggagcgccctgggcatcgcgtgggcctccaactgggagtactccgccttcgtgcccaccaacccctggcgctcctccatgtccctcgtgcgc*

*aagttctccctcaacaccgagtaccaggccaacccggagacggagctgatcaacctgaaggccgagccgatcctgaacatcagcaacgc*

*cggcccctggagccggttcgccaccaacaccacgttgacgaaggccaacagctacaacgtcgacctgtccaacagcaccggcaccctgga*

*gttcgagctggtgtacgccgtcaacaccacccagacgatctccaagtccgtgttcgcggacctctccctctggttcaagggcctggaggacc*

*ccgaggagtacctccgcatgggcttcgaggtgtccgcgtcctccttcttcctggaccgcgggaacagcaaggtgaagttcgtgaaggaga*

*acccctacttcaccaaccgcatgagcgtgaacaaccagcccttcaagagcgagaacgacctgtcctactacaaggtgtacggcttgctgga*

*ccagaacatcctggagctgtacttcaacgacggcgacgtcgtgtccaccaacacctacttcatgaccaccgggaacgccctgggctccgtg*

*aacatgacgacgggggtggacaacctgttctacatcgacaagttccaggtgcgcgaggtcaag**TGA*caattggcagcagcagctcggat agtatcgacacactctggacgctggtcgtgtgatggactgttgccgccacacttgctgccttgacctgtgaatatccctgccgcttttatcaaacag cctcagtgtgtttgatcttgtgtgtacgcgcttttgcgagttgctagctgcttgtgctatttgcgaataccacccccagcatccccttccctcgtttcat atcgcttgcatcccaaccgcaacttatctacgctgtcctgctatccctcagcgctgctcctgctcctgctcactgcccctcgcacagccttggtttgg gctccgcctgtattctcctggtactgcaacctgtaaaccagcactgcaatgctgatgcacgggaagtagtgggatgggaacacaaatggaggat cccgcgtctcgaacagagcgcgcagaggaacgctgaaggtctcgcctctgtcgcacctcagcgcggcatacaccacaataaccacctgacgaa tgcgcttggttcttcgtccattagcgaagcgtccggttcacacacgtgccacgttggcgaggtggcaggtgacaatgatcggtggagctgatggtc gaaacgttcacagcctagggatatcgaattc*ctttcttgcgctatgacacttccagcaaaaggtagggcgggctgcgagacggcttcccggc*

*gctgcatgcaacaccgatgatgcttcgacccccccgaagctccttcggggctgcatgggcgctccgatgccgctccagggcgagcgctgttta*

*aatagccaggcccccgattgcaaagacattatagcgagctaccaaagccatattcaaacacctagatcactaccacttctacacaggcca*

-continued ctcgagcttgtgatcgcactccgctaagggggcgcctcttcctcttcgtttcagtcacaacccgcaaacactagtATGgccaccgcatccact ttctcggcgttcaatgcccgctgcggcgacctgcgtcgctcggcgggctccgggccccggcgcccagcgaggcccctccccgtgcgcgggc gcgccgaggtgcacgtgcaggtgacccactccctggcccccgagaagcgcgagatcttcaactccctgaacaactgggcccaggagaa catcctggtgctgctgaaggacgtggacaagtgctggcagccctccgacttcctgcccgactccgcctccgagggcttcgacgagcaggt gatggagctgcgcaagcgctgcaaggagatccccgacgactacttcatcgtgctggtgggcgacatgatcaccgaggaggccctgccc acctaccagaccatgctgaacaccctggacggcgtgcgcgacgagaccggcgcctccctgacccccctgggccatctggacccgcgcctg gaccgccgaggagaaccgccacggcgacctgctgaacaagtacctgtacctgtccggccgcgtggacatgaagcagatcgagaagac catccagtacctgatcggctccggcatggacccccgcaccgagaacaacccctacctgggcttcatctacacctccttccaggagcgcgcc accttcatctcccacggcaacaccgcccgcctggccaaggagcacggcgacctgaagctggcccagatctgcggcatcatcgccgccga cgagaagcgccacgagaccgcctacaccaagatcgtggagaagctgttcgagatcgaccccgacggcaccgtgctggccctggccgac atgatgcgcaagaaggtgtccatgcccgcccacctgatgtacgacggccaggacgacaacctgttcgagaacttctcctccgtggccca gcgcctgggcgtgtacaccgccaaggactacgccgacatcctggagttcctggtgggccgctgggacatcgagaagctgaccggcctgt ccggcgagggccgcaaggcccaggactacgtgtgcaccctgcccccccgcatccgccgcctggaggagcgcgcccagtcccgcgtgaa gaaggcctccgccacccccttctcctggatcttcggccgcgagatcaacctgatggactacaaggaccacgacggcgactacaaggacc acgacatcgactacaaggacgacgacgacaagTGAatcgatagatctcttaaggcagcagcagctcggatagtatcgacacactctggac gctggtcgtgtgatggactgttgccgccacacttgctgccttgacctgtgaatatccctgccgcttttatcaaacagcctcagtgtgtttgatcttgtg tgtacgcgcttttgcgagttgctagctgcttgtgctatttgcgaataccacccccagcatccccttccctcgtttcatatcgcttgcatcccaaccgca acttatctacgctgtcctgctatccctcagcgctgctcctgctcctgctcactgcccctcgcacagccttggtttgggctccgcctgtattctcctggt actgcaacctgtaaaccagcactgcaatgctgatgcacgggaagtagtgggatgggaacacaaatggaaagcttaattaagagctcttgttttc cagaaggagttgctccttgagcctttcattctcagcctcgataacctccaaagccgctctaattgtggaggggggttcgaatttaaaagcttggaa tgttggttcgtgcgtctggaacaagcccagacttgttgctcactgggaaaaggaccatcagctccaaaaaacttgccgctcaaaccgcgtacct ctgctttcgcgcaatctgccctgttgaaatcgccaccacattcatattgtgacgcttgagcagtctgtaattgcctcagaatgtggaatcatctgc cccctgtgcgagcccatgccaggcatgtcgcgggcgaggacacccgccactcgtacagcagaccattatgctacctcacaatagttcataaca gtgaccatatttctcgaagctccccaacgagcacctccatgctctgagtggccaccccccggccctggtgcttgcggagggcaggtcaaccggc atggggctaccgaaatccccgaccggatcccaccacccccgcgatgggaagaatctctccccgggatgtgggcccaccaccagcacaacctgc tggcccaggcgagcgtcaaaccataccacacaaatatccttggcatcggccctgaattccttctgccgctctgctacccggtgcttctgtccgaa gcaggggttgctagggatcgctccgagtccgcaaacccttgtcgcgtggcggggcttgttcgagcttgaagagc Construct Used for the Expression of the *Ricinus communis* Stearoyl-ACP Desaturase:

To introduce the *Ricinus communis* stearoyl-ACP desaturase (Accession No: AAA74692.1) into UTEX1435, Strain A, the *Saccharomyces cerevisiae* invertase gene was utilized as the selectable marker to confer the ability of growing on sucrose media. The construct that has been expressed in UTEX1435, Strain A can be written as 6SA::CrTUB2:ScSUC2:CvNR::PmAMT03:CpSADtp:RcSAD:CvNR::6SB and is termed pSZ1454.

Relevant restriction sites in the construct pSZ1454 are indicated in lowercase, bold and underlining and are 5'-3' BspQ 1, Kpn I, Xba I, Mfe I, BamH I, EcoR I, Spe I, Asc I, Cla I, Sac I, BspQ I, respectively. BspQI sites delimit the 5' and 3' ends of the transforming DNA. Bold, lowercase sequences represent genomic DNA that permit targeted integration at 6s locus via homologous recombination. Proceeding in the 5' to 3' direction, the *C. reinhardtii* β-tubulin promoter driving the expression of the yeast sucrose invertase gene is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by the endogenous AMT03 promoter driving the expression of the RcSAD, indicated by boxed italics text. The Initiator ATG and terminator TGA codons of the RcSAD are indicated by uppercase, bold italics, while the remainder of the stearoyl-ACP desaturase coding region is indicated by bold italics. The *Chlorella protothecoides* stearoyl-ACP desaturase transit peptide is located between initiator ATG and the Asc I site. The *C. vulgaris* nitrate reductase 3' UTR is again indicated by lowercase underlined text followed by the 6S genomic region indicated by bold, lowercase text.

Nucleotide sequence of transforming DNA contained in pSZ1454:

(SEQ ID NO: 109)

gctcttcgccgccgccactcctgctcgagcgcgcccgcgcgtgcgccgccagcgccttggccttttcgccgcgctcgtgcgcgtcgctgatgtcca tcaccaggtccatgaggtctgccttgcgccggctgagccactgcttcgtccgggcggccaagaggagcatgagggaggactcctggtccaggg tcctgacgtggtcgcggctctgggagcgggccagcatcatctggctctgccgcaccgaggccgcctccaactggtcctccagcagccgcagtcg ccgccgaccctggcagaggaagacaggtgaggggggtatgaattgtacagaacaaccacgagccttgtctaggcagaatccctaccagtcat ggctttacctggatgacggcctgcgaacagctgtccagcgaccctcgctgccgccgcttctcccgcacgcttattccagcaccgtgatggcgcg agccagcgccgcacgctggcgctgcgcttcgccgatctgaggacagtcggggaactctgatcagtctaaacccccttgcgcgttagtgttgcca tcctttgcagaccggtgagagccgacttgttgtgcgccaccccccacaccacctcctcccagaccaattctgtcacctttttggcgaaggcatcgg cctcggcctgcagagaggacagcagtgcccagccgctggggggttggcggatgcacgctcaggtaccctttcttgcgctatgacacttccagcaa aaggtagggcgggctgcgagacggcttcccggcgctgcatgcaacaccgatgatgcttcgacccccccgaagctccttcggggctgcatgggcgc tccgatgccgctccagggcgagcgctgtttaaatagccaggcccccgattgcaaagacattatagcgagctaccaaagccatattcaaacacct agatcactaccacttctacacaggccactcgagcttgtgatcgcactccgctaagggggcgcctcttcctcttcgtttcagtcacaacccgcaaac tctagaatatcaATGctgctgcaggccttcctgttcctgctggccggcttcgccgccaagatcagcgcctccatgacgaacgagacgtccga ccgcccccctggtgcacttcacccccaacaagggctggatgaacgaccccaacggcctgtggtacgacgagaaggacgccaagtggcacc tgtacttccagtacaacccgaacgacaccgtctgggggacgcccttgttctggggccacgccacgtccgacgacctgaccaactgggagg accagcccatcgccatcgccccgaagcgcaacgactccggcgccttctccggctccatggtggtggactacaacaacacctccggcttcttc aacgacaccatcgacccgcgccagcgctgcgtggccatctggacctacaacaccccggagtccgaggagcagtacatctcctacagcctg gacggcggctacaccttcaccgagtaccagaagaaccccgtgctggccgccaactccacccagttccgcgacccgaaggtcttctggtacg agccctcccagaagtggatcatgaccgcggccaagtcccaggactacaagatcgagatctactcctccgacgacctgaagtcctggaagc tggagtccgcgttcgccaacgagggcttcctcggctaccagtacgagtgccccggcctgatcgaggtccccaccgagcaggaccccagca agtcctactgggtgatgttcatctccatcaaccccggcgccccggccggcggctccttcaaccagtacttcgtcggcagcttcaacggcaccc acttcgaggccttcgacaaccagtcccgcgtggtggacttcggcaaggactactacgccctgcagaccttcttcaacaccgacccgacctac gggagcgccctgggcatcgcgtgggcctccaactgggagtactccgccttcgtgcccaccaacccctggcgctcctccatgtccctcgtgcgc aagttctccctcaacaccgagtaccaggccaacccggagacggagctgatcaacctgaaggccgagccgatcctgaacatcagcaacgc cggcccctggagccggttcgccaccaacaccacgttgacgaaggccaacagctacaacgtcgacctgtccaacagcaccggcaccctgga gttcgagctggtgtacgccgtcaacaccacccagacgatctccaagtccgtgttcgcggacctctccctctggttcaagggcctggaggacc ccgaggagtacctccgcatgggcttcgaggtgtccgcgtcctccttcttcctggaccgcgggaacagcaaggtgaagttcgtgaaggaga acccctacttcaccaaccgcatgagcgtgaacaaccagcccttcaagagcgagaacgacctgtcctactacaaggtgtacggcttgctgga ccagaacatcctggagctgtacttcaacgacggcgacgtcgtgtccaccaacacctacttcatgaccaccgggaacgccctgggctccgtg aacatgacgacgggggtggacaacctgttctacatcgacaagttccaggtgcgcgaggtcaagTGAcaattggcagcagcagctcggat agtatcgacacactctggacgctggtcgtgtgatggactgttgccgccacacttgctgccttgacctgtgaatatccctgccgcttttatcaaacag cctcagtgtgtttgatcttgtgtgtacgcgcttttgcgagttgctagctgcttgtgctatttgcgaataccacccccagcatccccttccctcgtttcat atcgcttgcatcccaaccgcaacttatctacgctgtcctgctatccctcagcgctgctcctgctcctgctcactgcccctcgcacagccttggtttgg gctccgcctgtattctcctggtactgcaacctgtaaaccagcactgcaatgctgatgcacgggaagtagtgggatgggaacacaaatggaggat cccgcgtctcgaacagagcgcgcagaggaacgctgaaggtctcgcctctgtcgcacctcagcgcggcatacaccacaataaccacctgacgaa tgcgcttggttcttcgtccattagcgaagcgtccggttcacacacgtgccacgttggcgaggtggcaggtgacaatgatcggtggagctgatggtc gaaacgttcacagcctagggatatcgaattcggccgacaggacgcgcgtcaaaggtgctggtcgtgtatgccctggccggcaggtcgttgc tgctgctggttagtgattccgcaaccctgattttggcgtcttattttggcgtggcaaacgctggcgcccgcgagccgggccggcggcgatgc ggtgccccacggctgccggaatccaagggaggcaagagcgcccgggtcagttgaagggctttacgcgcaaggtacagccgctcctgca -continued aggctgcgtggtggaattggacgtgcaggtcctgctgaagttcctccaccgcctcaccagcggacaaagcaccggtgtatcaggtccgtgt catccactctaaagaactcgactacgacctactgatggccctagattcttcatcaaaaacgcctgagacacttgcccaggattgaaactccc tgaagggaccaccaggggccctgagttgttccttccccccgtggcgagctgccagccaggctgtacctgtgatcgaggctggcgggaaaa taggcttcgtgtgctcaggtcatgggaggtgcaggacagctcatgaaacgccaacaatcgcacaattcatgtcaagctaatcagctatttc ctcttcacgagctgtaattgtcccaaaattctggtctaccgggggtgatccttcgtgtacgggcccttccctcaaccctaggtatgcgcgcatg cggtcgccgcgcaactcgcgcgagggccgagggtttgggacgggccgtcccgaaatgcagttgcacccggatgcgtggcacctttttttgc gataatttatgcaatggactgctctgcaaaattctggctctgtcgccaaccctaggatcagcggcgtaggatttcgtaatcattcgtcctgat ggggagctaccgactaccctaatatcagcccgactgcctgacgccagcgtccacttttgtgcacacattccattcgtgcccaagacatttcat tgtggtgcgaagcgtccccagttacgctcacctgtttcccgacctccttactgttctgtcgacagagcgggcccacaggccggtcgcagccac tagtATGgccaccgcatccactttctcggcgttcaatgcccgctgcggcgacctgcgtcgctcggcgggctccgggccccggcgcccagc gaggcccctccccgtgcgcgggcgcgccgcctccaccctgaagtccggctccaaggaggtggagaacctgaagaagcccttcatgccccc ccgcgaggtgcacgtgcaggtgacccactccatgcccccccagaagatcgagatcttcaagtccctggacaactgggccgaggagaac atcctggtgcacctgaagcccgtggagaagtgctggcagccccaggacttcctgcccgaccccgcctccgacggcttcgacgagcaggt gcgcgagctgcgcgagcgcgccaaggagatccccgacgactacttcgtggtgctggtgggcgacatgatcaccgaggaggccctgccc acctaccagaccatgctgaacaccctggacggcgtgcgcgacgagaccggcgcctcccccacctcctgggccatctggacccgcgcctgg accgccgaggagaaccgccacggcgacctgctgaacaagtacctgtacctgtccggccgcgtggacatgcgccagatcgagaagacc atccagtacctgatcggctccgcatggacccccgcaccgagaactcccccctacctgggcttcatctacacctccttccaggagcgcgccac cttcatctcccacggcaacaccgcccgccaggccaaggagcacggcgacatcaagctggcccagatctgcggcaccatcgccgccgacg agaagcgccacgagaccgcctacaccaagatcgtggagaagctgttcgagatcgaccccgacggcaccgtgctggccttcgccgacat gatgcgcaagaagatctccatgcccgcccacctgatgtacgacggccgcgacgacaacctgttcgaccacttctccgccgtggcccagcg cctgggcgtgtacaccgccaaggactacgccgacatcctggagttcctggtgggccgctggaaggtggacaagctgaccggcctgtccg ccgagggccagaaggcccaggactacgtgtgccgcctgcccccccgcatccgccgcctggaggagcgcgcccagggccgcgccaagg aggcccccaccatgcccttctcctggatcttcgaccgccaggtgaagctgatggactacaaggaccacgacggcgactacaaggaccac gacatcgactacaaggacgacgacgacaagTGAatcgatagatctcttaaggcagcagcagctcggatagtatcgacacactctggacgc tggtcgtgtgatggactgttgccgccacacttgctgccttgacctgtgaatatccctgccgcttttatcaaacagcctcagtgtgtttgatcttgtgtg tacgcgcttttgcgagttgctagctgcttgtgctatttgcgaataccacccccagcatccccttccctcgtttcatatcgcttgcatcccaaccgcaa cttatctacgctgtcctgctatccctcagcgctgctcctgctcctgctcactgcccctcgcacagccttggtttgggctccgcctgtattctcctggtac tgcaacctgtaaaccagcactgcaatgctgatgcacgggaagtagtgggatgggaacacaaatggaaagcttaattaagagctcttgttttcca gaaggagttgctccttgagcctttcattctcagcctcgataacctccaaagccgctctaattgtggaggggttcgaatttaaaagcttggaatg ttggttcgtgcgtctggaacaagcccagacttgttgctcactgggaaaaggaccatcagctccaaaaaacttgccgctcaaaccgcgtacctct gctttcgcgcaatctgccctgttgaaatcgccaccacattcatattgtgacgcttgagcagtctgtaattgcctcagaatgtggaatcatctgccc cctgtgcgagcccatgccaggcatgtcgcgggcgaggacacccgccactcgtacagcagaccattatgctacctcacaatagttcataacagt gaccatatttctcgaagctccccaacgagcacctccatgctctgagtggccacccccggccctggtgcttgcggagggcaggtcaaccggcat ggggctaccgaaatccccgaccggatcccaccacccccgcgatgggaagaatctctccccgggatgtgggcccaccaccagcacaacctgctg gcccaggcgagcgtcaaaccataccacacaaatatccttggcatcggccctgaattccttctgccgctctgctacccggtgcttctgtccgaagc aggggttgctagggatcgctccgagtccgcaaacccttgtcgcgtggcggggcttgttcgagcttgaagagc Construct Used for the Expression of the *Chlorella protothecoides* Stearoyl-ACP Desaturase:

To introduce the *Chlorella protothecoides* stearoyl-ACP desaturase into UTEX1435, Strain Z, the *Saccharomyces cerevisiae* invertase gene was utilized as the selectable marker to confer the ability of growing on sucrose media. The construct that has been expressed in UTEX1435, Strain Z can be written as 6SA::CrTUB2:ScSUC2:CvNR::PmAMT03:CpSAD1:CvNR::6SB and is termed pSZ3144.

Relevant restriction sites in the construct pSZ3144 are indicated in lowercase, bold and underlining and are 5'-3' BspQ 1, Kpn I, Xba I, Mfe I, BamH I, EcoR I, Spe I, Cla I, Sac I, BspQ I, respectively. BspQI sites delimit the 5' and 3' ends of the transforming DNA. Bold, lowercase sequences represent genomic DNA that permit targeted integration at 6s locus via homologous recombination. Proceeding in the 5' to 3' direction, the *C. reinhardtii* β-tubulin promoter driving the expression of the yeast sucrose invertase gene is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by the endogenous AMT03 promoter driving the expression of the CpSAD1, indicated by boxed italics text. The Initiator ATG and terminator TGA codons of the CpSAD1 are indicated by uppercase, bold italics, while the remainder of the stearoyl-ACP desaturase coding region is indicated by bold italics. The *C. vulgaris* nitrate reductase 3' UTR is again indicated by lowercase underlined text followed by the 6S genomic region indicated by bold, lowercase text.

Nucleotide sequence of transforming DNA contained in pSZ3144:

(SEQ ID NO: 110)

gctcttcgccgccgccactcctgctcgagcgcgcccgcgcgtgcgccgccagcgccttggccttttcgccgcgctcgtgcgcgtcgctgatgtcca tcaccaggtccatgaggtctgccttgcgccggctgagccactgcttcgtccgggcggccaagaggagcatgagggaggactcctggtccaggg tcctgacgtggtcgcggctctgggagcgggccagcatcatctggctctgccgcaccgaggccgcctccaactggtcctccagcagccgcagtcg ccgccgaccctggcagaggaagacaggtgaggggggtatgaattgtacagaacaaccacgagccttgtctaggcagaatccctaccagtcat ggctttacctggatgacggcctgcgaacagctgtccagcgaccctcgctgccgccgcttctcccgcacgcttctttccagcaccgtgatggcgcg agccagcgccgcacgctggcgctgcgcttcgccgatctgaggacagtcggggaactctgatcagtctaaacccccttgcgcgttagtgttgcca tcctttgcagaccggtgagagccgacttgttgtgcgccacccccacaccacctcctcccagaccaattctgtcaccttttggcgaaggcatcgg cctcggcctgcagagaggacagcagtgcccagccgctggggttggcggatgcacgctcaggtaccctttcttgcgctatgacacttccagcaa aaggtagggcgggctgcgagacggcttcccggcgctgcatgcaacaccgatgatgcttcgacccccgaagctccttcggggctgcatgggcgc tccgatgccgctccagggcgagcgctgtttaaatagccaggcccccgattgcaaagacattatagcgagctaccaaagccatattcaaacacct agatcactaccacttctacacaggccactcgagcttgtgatcgcactccgctaagggggcgcctcttcctcttcgtttcagtcacaacccgcaaac tctagaatatca*ATG**ctgctgcaggccttcctgttcctgctggccggcttcgccgccaagatcagcgcctccatgacgaacgagacgtccga*

*ccgccccctggtgcacttcacccccaacaagggctggatgaacgaccccaacggcctgtggtacgacgagaaggacgccaagtggcacc*

*tgtacttccagtacaacccgaacgacaccgtctgggggacgcccttgttctggggccacgccacgtccgacgacctgaccaactgggagg*

*accagcccatcgccatcgccccgaagcgcaacgactccggcgccttctccggctccatggtggtggactacaacaacacctccggcttcttc*

*aacgacaccatcgacccgcgccagcgctgcgtggccatctggacctacaacaccccggagtccgaggagcagtacatctcctacagcctg*

*gacggcggctacaccttcaccgagtaccagaagaaccccgtgctggccgccaactccacccagttccgcgacccgaaggtcttctggtacg*

*agccctcccagaagtggatcatgaccgcggccaagtcccaggactacaagatcgagatctactcctccgacgacctgaagtcctggaagc*

*tggagtccgcgttcgccaacgagggcttcctcggctaccagtacgagtgccccggcctgatcgaggtccccaccgagcaggaccccagca*

*agtcctactgggtgatgttcatctccatcaaccccggcgccccggccggcggctccttcaaccagtacttcgtcggcagcttcaacggcaccc*

*acttcgaggccttcgacaaccagtcccgcgtggtggacttcggcaaggactactacgccctgcagaccttcttcaacaccgacccgacctac*

*gggagcgccctgggcatcgcgtgggcctccaactgggagtactccgccttcgtgcccaccaacccctggcgctcctccatgtccctcgtgcgc*

*aagttctccctcaacaccgagtaccaggccaacccggagacggagctgatcaacctgaaggccgagccgatcctgaacatcagcaacgc*

*cggccccctggagccggttcgccaccaacaccacgttgacgaaggccaacagctacaacgtcgacctgtccaacagcaccggcaccctgga*

*gttcgagctggtgtacgccgtcaacaccacccagacgatctccaagtccgtgttcgcggacctctccctctggttcaagggcctggaggacc*

*ccgaggagtacctccgcatgggcttcgaggtgtccgcgtcctccttcttcctggaccgcgggaacagcaaggtgaagttcgtgaaggaga*

*acccctacttcaccaaccgcatgagcgtgaacaaccagcccttcaagagcgagaacgacctgtcctactacaaggtgtacggcttgctgga*

*ccagaacatcctggagctgtacttcaacgacggcgacgtcgtgtccaccaacacctacttcatgaccaccgggaacgccctgggctccgtg*

*aacatgacgacgggggtggacaacctgttctacatcgacaagttccaggtgcgcgaggtcaag**TGA*caattggcagcagcagctcggat -continued agtatcgacacactctggacgctggtcgtgtgatggactgttgccgccacacttgctgccttgacctgtgaatatccctgccgcttttatcaaacag cctcagtgtgtttgatcttgtgtgtacgcgcttttgcgagttgctagctgcttgtgctatttgcgaataccacccccagcatccccttccctcgtttcat atcgcttgcatcccaaccgcaacttatctacgctgtcctgctatccctcagcgctgctcctgctcctgctcactgcccctcgcacagccttggtttgg gctccgcctgtattctcctggtactgcaacctgtaaaccagcactgcaatgctgatgcacgggaagtagtgggatgggaacacaaatggaggat cccgcgtctcgaacagagcgcgcagaggaacgctgaaggtctcgcctctgtcgcacctcagcgcggcatacaccacaataaccacctgacgaa tgcgcttggttcttcgtccattagcgaagcgtccggttcacacacgtgccacgttggcgaggtggcaggtgacaatgatcggtggagctgatggtc gaaacgttcacagcctagggatatcgaattc*ggccgacaggacgcgcgtcaaaggtgctggtcgtgtatgccctggccggcaggtcgttgc*

*tgctgctggttagtgattccgcaaccctgattttggcgtcttattttggcgtggcaaacgctggcgcccgcgagccgggccggcggcgatgc*

*ggtgccccacggctgccggaatccaagggaggcaagagcgcccgggtcagttgaagggctttacgcgcaaggtacagccgctcctgca*

*aggctgcgtggtggaattggacgtgcaggtcctgctgaagttcctccaccgcctcaccagcggacaaagcaccggtgtatcaggtccgtgt*

*catccactctaaagaactcgactacgacctactgatggccctagattcttcatcaaaaacgcctgagacacttgcccaggattgaaactccc*

*tgaagggaccaccaggggccctgagttgttccttcccccgtggcgagctgccagccaggctgtacctgtgatcgaggctggcgggaaaa*

*taggcttcgtgtgctcaggtcatgggaggtgcaggacagctcatgaaacgccaacaatcgcacaattcatgtcaagctaatcagctatttc*

*ctcttcacgagctgtaattgtcccaaaattctggtctaccgggggtgatccttcgtgtacgggcccttccctcaaccctaggtatgcgcgcatg*

*cggtcgccgcgcaactcgcgcgagggccgagggtttgggacgggccgtcccgaaatgcagttgcacccggatgcgtggcaccttttttgc*

*gataatttatgcaatggactgctctgcaaaattctggctctgtcgccaaccctaggatcagcggcgtaggatttcgtaatcattcgtcctgat*

*ggggagctaccgactaccctaatatcagcccgactgcctgacgccagcgtccacttttgtgcacacattccattcgtgcccaagacatttcat*

*tgtggtgcgaagcgtccccagttacgctcacctgtttcccgacctccttactgttctgtcgacagagcgggcccacaggccggtcgcagcc*ac

**tagt*ATGgccaccgcctccaccttctccgccttcaacgcccgctgcggcgacctgcgccgctccgccggctccggcccccgccgcccccgccc***

*gccccctgcccgtgcgcgccgccatcgcctccgaggtgcccgtggccaccacctcccccgccccggccccaccgtgtactccaagctggac*

*aaggcccacaccctgacccccgagcgcatggagctgatcaacggcatgtccgccttcgccgaggagcgcatcctgcccgtgctgcagccc*

*gtggagaagctgtggcagccccaggacctgctgcccgaccccgagtcccccgacttcctggaccaggtggccgagctgcgcgcccgcgc*

*cgccaacgtgcccgacgactacttcgtggtgctggtgggcgacatgatcaccgaggaggccctgcccacctacatggccatgctgaaca*

*ccctggacggcgtgcgcgacgagaccggcgccgccgaccacccctggggccgctggacccgccagtgggtggccgaggagaaccgcc*

*acggcgacctgctgaacaagtactgctggctgaccggccgcgtgaacatgaaggccatcgaggtgaccatccagaacctgatcggctc*

*gccgatgaaccccaagaccgagaacaacccctacctgggcttcgtgtacacctccttccaggagcgcgccaccaagtactcccacggca*

*acaccgcccgcctggccgcccagtacggcgacgccaccctgtccaaggtgtgcggcgtgatcgccgccgacgagggccgccacgagat*

*cgcctacacccgcatcgtggaggagttcttccgcctggaccccgagggcgccatgtccgcctacgccgacatgatgcgcaagcagatcac*

*catgcccgcccacctgatggacgaccagcagcacggcacccgcaacaccggccgcaacctgttcgccgacttctccgccgtgaccgaga*

*agctggacgtgtacgacgccgaggactactgcaagatcctggagcacctgaactcccgctggaagatcgccgaccgcaccgtgtccgg*

*cgacgccggcgccgaccaggagtacgtgctgcgcctgccctcccgcttccgcaagctggccgagaagtccgccgccaagcgcgccaag*

*accaagcccaagcccgtggccttctcctggctgtccggccgcgaggtgatggtgTGA*atcgatagatctcttaaggcagcagcagctcgga tagtatcgacacactctggacgctggtcgtgtgatggactgttgccgccacacttgctgccttgacctgtgaatatccctgccgcttttatcaaaca gcctcagtgtgtttgatcttgtgtgtacgcgcttttgcgagttgctagctgcttgtgctatttgcgaataccacccccagcatccccttccctcgtttca tatcgcttgcatcccaaccgcaacttatctacgctgtcctgctatccctcagcgctgctcctgctcctgctcactgcccctcgcacagccttggtttgg gctccgcctgtattctcctggtactgcaacctgtaaaccagcactgcaatgctgatgcacgggaagtagtgggatgggaacacaaatggaaagc ttaattaagagctcttgttttccagaaggagttgctccttgagcctttcattctcagcctcgataacctccaaagccgctctaattgtggagggggg ttcgaatttaaaagcttggaatgttggttcgtgcgtctggaacaagcccagacttgttgctcactgggaaaaggaccatcagctccaaaaaact tgccgctcaaaccgcgtacctctgattcgcgcaatctgccctgttgaaatcgccaccacattcatattgtgacgcttgagcagtctgtaattgcc

-continued

```
tcagaatgtggaatcatctgccccctgtgcgagcccatgccaggcatgtcgcgggcgaggacacccgccactcgtacagcagaccattatgct
acctcacaatagttcataacagtgaccatatttctcgaagctccccaacgagcacctccatgctctgagtggccaccccccggccctggtgcttg
cggagggcaggtcaaccggcatggggctaccgaaatccccgaccggatcccaccacccccgcgatgggaagaatctctccccgggatgtggg
cccaccaccagcacaacctgctggcccaggcgagcgtcaaaccataccacacaaatatccttggcatcggccctgaattccttctgccgctctg
ctacccggtgcttctgtccgaagcaggggttgctagggatcgctccgagtccgcaaacccttgtcgcgtggcggggcttgttcgagcttgaaga
gc
```

Results:

Primary transformants were clonally purified and grown under low-nitrogen lipid production conditions at either pH5.0 or pH7.0, depending on the promoters that drive the expression of the desaturase genes. Transgenic lines arising from the transformations with pSZ1377 (D583) were assayed in lipid production media at pH5.0, because of the nature of the promoters and the fact that *P. moriformis* produces more lipid at pH5.0. Transgenic lines generated from the transformation of pSZ1454 (D648) and pSZ3144 (D1923) are assayed at pH 7.0 to allow for maximal desaturase gene expression when driven by the pH regulated PmAMT3 promoter. The resulting profiles from representative clones arising from transformations with D583, D648, and D1923 are shown in Tables 59, 60 and 61, respectively, below. The expression of OeSAD and CpSAD1 genes is a clear diminution of C18:0 chain lengths with an increase in C18:1. Also we noticed that there is a subtle increase in the level of C16:1, indicating these stearoyl-ACP desaturases may have broad specificity. The transformants resulted from the expression of RcSAD gene also diminishes in the level of C18:0, and elevation in C16:1. However, there is also a drop in the level of C18:1 fatty acid and increase in C18:2, which may be caused by the growth defect of these transgenic lines. The impact of these desaturase genes in the high oleic strain S5587 will be determined.

TABLE 59

Lipid profile of representative clones arising from transformation with D583 (pSZ1377) DNA

| Sample ID | C16:0 | C16:1 | C18:0 | C18:1 | C18:2 |
|---|---|---|---|---|---|
| D583-25 | 19.20 | 1.53 | 1.15 | 64.08 | 11.76 |
| D583-10 | 21.86 | 0.99 | 1.77 | 61.43 | 11.42 |
| D583-3 | 21.94 | 0.95 | 1.85 | 62.22 | 10.53 |
| D583-33 | 20.76 | 0.95 | 1.85 | 61.76 | 12.17 |
| D583-26 | 20.18 | 0.92 | 1.89 | 62.56 | 11.97 |
| D583-1 | 21.28 | 0.95 | 1.90 | 62.63 | 10.94 |
| S1331 | 25.48 | 0.71 | 3.23 | 59.70 | 8.25 |

TABLE 60

Lipid profile of representative clones arising from transformation with D648 (pSZ1454) DNA

| Sample ID | C16:0 | C16:1 | C18:0 | C18:1 | C18:2 |
|---|---|---|---|---|---|
| D648-9 | 26.92 | 2.30 | 1.12 | 54.27 | 11.30 |
| D648-28 | 26.54 | 2.50 | 1.32 | 52.58 | 12.90 |
| D648-15 | 29.47 | 1.68 | 1.48 | 51.74 | 11.48 |
| D648-12 | 27.39 | 1.41 | 1.66 | 54.45 | 11.58 |
| D648-43 | 29.74 | 1.52 | 1.68 | 52.59 | 10.85 |
| D648-7 | 26.98 | 1.62 | 1.69 | 54.51 | 11.39 |
| S1331-pH 7 | 25.86 | 0.96 | 2.84 | 58.33 | 9.16 |

TABLE 61

Lipid profile of representative clones arising from transformation with D1923 (pSZ3144) DNA

| Sample ID | C14:0 | C14:1 | C16:0 | C16:1 | C18:0 | C18:1 | C18:2 |
|---|---|---|---|---|---|---|---|
| Block 2; E2; pH7; STRAIN Z; T613; D1923-2 | 1.46 | 0.11 | 20.74 | 2.54 | 0.86 | 63.99 | 9.03 |
| Block 2; G12; pH7; STRAIN Z; T613; D1923-36 | 1.52 | 0.10 | 25.20 | 1.97 | 1.67 | 61.10 | 7.38 |
| Block 2; E8; pH7; STRAIN Z; T613; D1923-8 | 1.48 | 0.09 | 26.41 | 1.78 | 1.54 | 60.54 | 7.01 |
| Block 2; F3; pH7STRAIN Z; T613; D1923-15 | 1.50 | 0.07 | 25.87 | 1.75 | 1.62 | 61.25 | 6.94 |
| Block 2; F9; pH7; STRAIN Z; T613; D1923-21 | 1.47 | 0.07 | 27.02 | 1.73 | 1.84 | 60.15 | 6.55 |
| Block 2; F4; pH7; STRAIN Z; T613; D1923-16 | 1.44 | 0.07 | 24.30 | 1.71 | 1.41 | 62.79 | 7.29 |
| pH7 STRAIN Z | 1.47 | 0.00 | 28.25 | 0.82 | 3.16 | 58.27 | 6.72 |

The described embodiments of the invention are intended to be merely exemplary and numerous variations and modifications will be apparent to those skilled in the art. All such variations and modifications are intended to be within the scope of the present invention. For example, the various triglyceride oils can be tailored in for a mixture of midchain and long chain fatty acids in order to adjust parameters such as polarity, solvency, and foam-height of the oils or chemicals made from the oils. In addition, where a knockout of a gene is called for, an equivalent result may be reached using knockdown techniques including mutation and expression of inhibitory substances such as RNAi or antisense.

SEQUENCE LISTING

SEQ ID NO: 1
6*S* 5' genomic donor sequence
GCTCTTCGCCGCCGCCACTCCTGCTCGAGCGCGCCCGCGCGTGCGCCGCCAGCGCCTTGGCCTTTTCG
CCGCGCTCGTGCGCGTCGCTGATGTCCATCACCAGGTCCATGAGGTCTGCCTTGCGCCGGCTGAGCCA
CTGCTTCGTCCGGGCGGCCAAGAGGAGCATGAGGGAGGACTCCTGGTCCAGGGTCCTGACGTGGTCGC
GGCTCTGGGAGCGGGCCAGCATCATCTGGCTCTGCCGCACCGAGGCCGCCTCCAACTGGTCCTCCAGC
AGCCGCAGTCGCCGCCGACCCTGGCAGAGGAAGACAGGTGAGGGGGGTATGAATTGTACAGAACAACC
ACGAGCCTTGTCTAGGCAGAATCCCTACCAGTCATGGCTTTACCTGGATGACGGCCTGCGAACAGCTG
TCCAGCGACCCTCGCTGCCGCCGCTTCTCCCGCACGCTTCTTTCCAGCACCGTGATGGCGCGAGCCAG
CGCCGCACGCTGGCGCTGCGCTTCGCCGATCTGAGGACAGTCGGGGAACTCTGATCAGTCTAAACCCC
CTTGCGCGTTAGTGTTGCCATCCTTTGCAGACCGGTGAGAGCCGACTTGTTGTGCGCCACCCCCCACA
CCACCTCCTCCCAGACCAATTCTGTCACCTTTTTGGCGAAGGCATCGGCCTCGGCCTGCAGAGAGGAC
AGCAGTGCCCAGCCGCTGGGGGTTGGCGGATGCACGCTCAGGTACC SEQ ID NO: 2
6*S* 3' genomic donor sequence
GAGCTCCTTGTTTTCCAGAAGGAGTTGCTCCTTGAGCCTTTCATTCTCAGCCTCGATAACCTCCAAAG
CCGCTCTAATTGTGGAGGGGGTTCGAATTTAAAAGCTTGGAATGTTGGTTCGTGCGTCTGGAACAAGC
CCAGACTTGTTGCTCACTGGGAAAAGGACCATCAGCTCCAAAAAACTTGCCGCTCAAACCGCGTACCT
CTGCTTTCGCGCAATCTGCCCTGTTGAAATCGCCACCACATTCATATTGTGACGCTTGAGCAGTCTGT
AATTGCCTCAGAATGTGGAATCATCTGCCCCCTGTGCGAGCCCATGCCAGGCATGTCGCGGGCGAGGA
CACCCGCCACTCGTACAGCAGACCATTATGCTACCTCACAATAGTTCATAACAGTGACCATATTTCTC
GAAGCTCCCCAACGAGCACCTCCATGCTCTGAGTGGCCACCCCCCGGCCCTGGTGCTTGCGGAGGGCA
GGTCAACCGGCATGGGGCTACCGAAATCCCCGACCGGATCCCACCACCCCCGCGATGGGAAGAATCTC
TCCCCGGGATGTGGGCCCACCACCAGCACAACCTGCTGGCCCAGGCGAGCGTCAAACCATACCACACA
AATATCCTTGGCATCGGCCCTGAATTCCTTCTGCCGCTCTGCTACCCGGTGCTTCTGTCCGAAGCAGG
GGTTGCTAGGGATCGCTCCGAGTCCGCAAACCCTTGTCGCGTGGCGGGGCTTGTTCGAGCTTGAAGAG
C SEQ ID NO: 3
*S. cereviseae* invertase protein sequence
MLLQAFLFLLAGFAAKISASMTNETSDRPLVHFTPNKGWMNDPNGLWYDEKDAKWHLYFQYNPNDTVW
GTPLFWGHATSDDLTNWEDQPIAIAPKRNDSGAFSGSMVVDYNNTSGFFNDTIDPRQRCVAIWTYNTP
ESEEQYISYSLDGGYTFTEYQKNPVLAANSTQFRDPKVFWYEPSQKWIMTAAKSQDYKIEIYSSDDLK
SWKLESAFANEGFLGYQYECPGLIEVPTEQDPSKSYWVMFISINPGAPAGGSFNQYFVGSFNGTHFEA
FDNQSRVVDFGKDYYALQTFFNTDPTYGSALGIAWASNWEYSAFVPTNPWRSSMSLVRKFSLNTEYQA
NPETELINLKAEPILNISNAGPWSRFATNTTLTKANSYNVDLSNSTGTLEFELVYAVNTTQTISKSVF
ADLSLWFKGLEDPEEYLRMGFEVSASSFFLDRGNSKVKFVKENPYFTNRMSVNNQPFKSENDLSYYKV
YGLLDQNILELYFNDGDVVSTNTYFMTTGNALGSVNMTTGVDNLFYIDKFQVREVK SEQ ID NO: 4
*S. cereviseae* invertase protein coding sequence codon optimized for expression in *P. moriformis* (UTEX 1435)
ATGctgctgcaggccttcctgttcctgctggccggcttcgccgccaagatcagcgcctccatgacgaa
cgagacgtccgaccgccccctggtgcacttcacccccaacaagggctggatgaacgaccccaacggcc
tgtggtacgacgagaaggacgccaagtggcacctgtacttccagtacaacccgaacgacaccgtctgg
gggacgcccttgttctggggccacgccacgtccgacgacctgaccaactgggaggaccagcccatcgc
catcgccccgaagcgcaacgactccggcgccttctccggctccatggtggtggactacaacaacacct
ccggcttcttcaacgacaccatcgacccgcgccagcgctgcgtggccatctggacctacaacaccccg
gagtccgaggagcagtacatctcctacagcctggacggcggctacaccttcaccgagtaccagaagaa
ccccgtgctggccgccaactccacccagttccgcgacccgaaggtcttctggtacgagccctcccaga
agtggatcatgaccgcggccaagtcccaggactacaagatcgagatctactcctccgacgacctgaag
tcctggaagctggagtccgcgttcgccaacgagggcttcctcggctaccagtacgagtgccccggcct
gatcgaggtccccaccgagcaggaccccagcaagtcctactgggtgatgttcatctccatcaaccccg
gcgccccggccggcggctccttcaaccagtacttcgtcggcagcttcaacggcacccacttcgaggcc
ttcgacaaccagtcccgcgtggtggacttcggcaaggactactacgccctgcagaccttcttcaacac
cgacccgacctacgggagcgccctgggcatcgcgtgggcctccaactgggagtactccgccttcgtgc
ccaccaacccctggcgctcctccatgtccctcgtgcgcaagttctccctcaacaccgagtaccaggcc
aacccggagacggagctgatcaacctgaaggccgagccgatcctgaacatcagcaacgccggcccctg
gagccggttcgccaccaacaccacgttgacgaaggccaacagctacaacgtcgacctgtccaacagca
ccggcaccctggagttcgagctggtgtacgccgtcaacaccacccagacgatctccaagtccgtgttc
gcggacctctccctctggttcaagggcctggaggaccccgaggagtacctccgcatgggcttcgaggt
gtccgcgtcctccttcttcctggaccgcgggaacagcaaggtgaagttcgtgaaggagaacccctact
tcaccaaccgcatgagcgtgaacaaccagcccttcaagagcgagaacgacctgtcctactacaaggtg
tacggcttgctggaccagaacatcctggagctgtacttcaacgacggcgacgtcgtgtccaccaacac
ctacttcatgaccaccgggaacgccctgggctccgtgaacatgacgacgggggtggacaacctgttct
acatcgacaagttccaggtgcgcgaggtcaagTGA -continued

SEQUENCE LISTING

SEQ ID NO: 5
*Chlamydomonas reinhardtii* TUB2 (B-tub) promoter/5' UTR
CTTTCTTGCGCTATGACACTTCCAGCAAAAGGTAGGGCGGGCTGCGAGACGGCTTCCCGGCGCTGCAT
GCAACACCGATGATGCTTCGACCCCCCGAAGCTCCTTCGGGGCTGCATGGGCGCTCCGATGCCGCTCC
AGGGCGAGCGCTGTTTAAATAGCCAGGCCCCCGATTGCAAAGACATTATAGCGAGCTACCAAAGCCAT
ATTCAAACACCTAGATCACTACCACTTCTACACAGGCCACTCGAGCTTGTGATCGCACTCCGCTAAGG
GGGCGCCTCTTCCTCTTCGTTTCAGTCACAACCCGCAAAC SEQ ID NO: 6
*Chlorella vulgaris* nitrate reductase 3' UTR
GCAGCAGCAGCTCGGATAGTATCGACACACTCTGGACGCTGGTCGTGTGATGGACTGTTGCCGCCACA
CTTGCTGCCTTGACCTGTGAATATCCCTGCCGCTTTTATCAAACAGCCTCAGTGTGTTTGATCTTGTG
TGTACGCGCTTTTGCGAGTTGCTAGCTGCTTGTGCTATTTGCGAATACCACCCCCAGCATCCCCTTCC
CTCGTTTCATATCGCTTGCATCCCAACCGCAACTTATCTACGCTGTCCTGCTATCCCTCAGCGCTGCT
CCTGCTCCTGCTCACTGCCCCTCGCACAGCCTTGGTTTGGGCTCCGCCTGTATTCTCCTGGTACTGCA
ACCTGTAAACCAGCACTGCAATGCTGATGCACGGGAAGTAGTGGGATGGGAACACAAATGGAAAGCTT SEQ ID NO: 7
Nucleotide sequence of the codon-optimized expression cassette of
*S. cerevisiae* suc2 gene with *C. reinhardtii* β-tubulin promoter/5'
UTR and *C. vulgaris* nitrate reductase 3' UTR
CTTTCTTGCGCTATGACACTTCCAGCAAAAGGTAGGGCGGGCTGCGAGACGGCTTCCCGGCGCTGCAT
GCAACACCGATGATGCTTCGACCCCCCGAAGCTCCTTCGGGGCTGCATGGGCGCTCCGATGCCGCTCC
AGGGCGAGCGCTGTTTAAATAGCCAGGCCCCCGATTGCAAAGACATTATAGCGAGCTACCAAAGCCAT
ATTCAAACACCTAGATCACTACCACTTCTACACAGGCCACTCGAGCTTGTGATCGCACTCCGCTAAGG
GGGCGCCTCTTCCTCTTCGTTTCAGTCACAACCCGCAAACGGCGCGCCATGCTGCTGCAGGCCTTCCT
GTTCCTGCTGGCCGGCTTCGCCGCCAAGATCAGCGCCTCCATGACGAACGAGACGTCCGACCGCCCCC
TGGTGCACTTCACCCCCAACAAGGGCTGGATGAACGACCCCAACGGCCTGTGGTACGACGAGAAGGAC
GCCAAGTGGCACCTGTACTTCCAGTACAACCCGAACGACACCGTCTGGGGGACGCCCTTGTTCTGGGG
CCACGCCACGTCCGACGACCTGACCAACTGGGAGGACCAGCCCATCGCCATCGCCCCGAAGCGCAACG
ACTCCGGCGCCTTCTCCGGCTCCATGGTGGTGGACTACAACAACACCTCCGGCTTCTTCAACGACACC
ATCGACCCGCGCCAGCGCTGCGTGGCCATCTGGACCTACAACACCCCGGAGTCCGAGGAGCAGTACAT
CTCCTACAGCCTGGACGGCGGCTACACCTTCACCGAGTACCAGAAGAACCCCGTGCTGGCCGCCAACT
CCACCCAGTTCCGCGACCCGAAGGTCTTCTGGTACGAGCCCTCCCAGAAGTGGATCATGACCGCGGCC
AAGTCCCAGGACTACAAGATCGAGATCTACTCCTCCGACGACCTGAAGTCCTGGAAGCTGGAGTCCGC
GTTCGCCAACGAGGGCTTCCTCGGCTACCAGTACGAGTGCCCCGGCCTGATCGAGGTCCCCACCGAGC
AGGACCCCAGCAAGTCCTACTGGGTGATGTTCATCTCCATCAACCCCGGCGCCCCGGCCGGCGGCTCC
TTCAACCAGTACTTCGTCGGCAGCTTCAACGGCACCCACTTCGAGGCCTTCGACAACCAGTCCCGCGT
GGTGGACTTCGGCAAGGACTACTACGCCCTGCAGACCTTCTTCAACACCGACCCGACCTACGGGAGCG
CCCTGGGCATCGCGTGGGCCTCCAACTGGGAGTACTCCGCCTTCGTGCCCACCAACCCCTGGCGCTCC
TCCATGTCCCTCGTGCGCAAGTTCTCCCTCAACACCGAGTACCAGGCCAACCCGGAGACGGAGCTGAT
CAACCTGAAGGCCGAGCCGATCCTGAACATCAGCAACGCCGGCCCCTGGAGCCGGTTCGCCACCAACA
CCACGTTGACGAAGGCCAACAGCTACAACGTCGACCTGTCCAACAGCACCGGCACCCTGGAGTTCGAG
CTGGTGTACGCCGTCAACACCACCCAGACGATCTCCAAGTCCGTGTTCGCGGACCTCTCCCTCTGGTT
CAAGGGCCTGGAGGACCCCGAGGAGTACCTCCGCATGGGCTTCGAGGTGTCCGCGTCCTCCTTCTTCC
TGGACCGCGGGAACAGCAAGGTGAAGTTCGTGAAGGAGAACCCCTACTTCACCAACCGCATGAGCGTG
AACAACCAGCCCTTCAAGAGCGAGAACGACCTGTCCTACTACAAGGTGTACGGCTTGCTGGACCAGAA
CATCCTGGAGCTGTACTTCAACGACGGCGACGTCGTGTCCACCAACACCTACTTCATGACCACCGGGA
ACGCCCTGGGCTCCGTGAACATGACGACGGGGGTGGACAACCTGTTCTACATCGACAAGTTCCAGGTG
CGCGAGGTCAAGTGACAATTGGCAGCAGCAGCTCGGATAGTATCGACACACTCTGGACGCTGGTCGTG
TGATGGACTGTTGCCGCCACACTTGCTGCCTTGACCTGTGAATATCCCTGCCGCTTTTATCAAACAGC
CTCAGTGTGTTTGATCTTGTGTGTACGCGCTTTTGCGAGTTGCTAGCTGCTTGTGCTATTTGCGAATA
CCACCCCCAGCATCCCCTTCCCTCGTTTCATATCGCTTGCATCCCAACCGCAACTTATCTACGCTGTC
CTGCTATCCCTCAGCGCTGCTCCTGCTCCTGCTCACTGCCCCTCGCACAGCCTTGGTTTGGGCTCCGC
CTGTATTCTCCTGGTACTGCAACCTGTAAACCAGCACTGCAATGCTGATGCACGGGAAGTAGTGGGAT
GGGAACACAAATGGAGGATCC SEQ ID NO: 8
*Prototheca moriformis* (UTEX 1435) Amt03 promoter
GGCCGACAGGACGCGCGTCAAAGGTGCTGGTCGTGTATGCCCTGGCCGGCAGGTCGTTGCTGCTGCTG
GTTAGTGATTCCGCAACCCTGATTTTGGCGTCTTATTTTGGCGTGGCAAACGCTGGCGCCCGCGAGCC
GGGCCGGCGGCGATGCGGTGCCCCACGGCTGCCGGAATCCAAGGGAGGCAAGAGCGCCCGGGTCAGTT
GAAGGGCTTTACGCGCAAGGTACAGCCGCTCCTGCAAGGCTGCGTGGTGGAATTGGACGTGCAGGTCC
TGCTGAAGTTCCTCCACCGCCTCACCAGCGGACAAAGCACCGGTGTATCAGGTCCGTGTCATCCACTC
TAAAGAGCTCGACTACGACCTACTGATGGCCCTAGATTCTTCATCAAAAACGCCTGAGACACTTGCCC
AGGATTGAAACTCCCTGAAGGGACCACCAGGGGCCCTGAGTTGTTCCTTCCCCCCGTGGCGAGCTGCC
AGCCAGGCTGTACCTGTGATCGAGGCTGGCGGGAAAATAGGCTTCGTGTGCTCAGGTCATGGGAGGTG
CAGGACAGCTCATGAAACGCCAACAATCGCACAATTCATGTCAAGCTAATCAGCTATTTCCTCTTCAC
GAGCTGTAATTGTCCCAAAATTCTGGTCTACCGGGGGTGATCCTTCGTGTACGGGCCCTTCCCTCAAC
CCTAGGTATGCGCGCATGCGGTCGCCGCGCAACTCGCGCGAGGGCCGAGGGTTTGGGACGGGCCGTCC
CGAAATGCAGTTGCACCCGGATGCGTGGCACCTTTTTTGCGATAATTTATGCAATGGACTGCTCTGCA
AAATTCTGGCTCTGTCGCCAACCCTAGGATCAGCGGCGTAGGATTTCGTAATCATTCGTCCTGATGGG
GAGCTACCGACTACCCTAATATCAGCCCGACTGCCTGACGCCAGCGTCCACTTTTGTGCACACATTCC
ATTCGTGCCCAAGACATTTCATTGTGGTGCGAAGCGTCCCCAGTTACGCTCACCTGTTTCCCGACCTC
CTTACTGTTCTGTCGACAGAGCGGGCCCACAGGCCGGTCGCAGCC -continued

SEQUENCE LISTING

SEQ ID NO: 9
*Chlorella protothecoides* (UTEX 250) stearoyl ACP desaturase transit peptide cDNA sequence codon optimized for expression in *P. moriformis*.
ACTAGTATGGCCACCGCATCCACTTTCTCGGCGTTCAATGCCCGCTGCGGCGACCTGCGTCGCTCGGC
GGGCTCCGGGCCCCGGCGCCCAGCGAGGCCCCTCCCCGTGCGCGGGCGCGCC SEQ ID NO: 10
*Cuphea wrightii* FatB2 thioesterase nucleic acid sequence; Gen Bank Accession No. U56104
ATGGTGGTGGCCGCCGCCGCCAGCAGCGCCTTCTTCCCCGTGCCCGCCCCCCGCCCCACCCCCAAGCC
CGGCAAGTTCGGCAACTGGCCCAGCAGCCTGAGCCAGCCCTTCAAGCCCAAGAGCAACCCCAACGGCC
GCTTCCAGGTGAAGGCCAACGTGAGCCCCCACGGGCGCGCCCCCAAGGCCAACGGCAGCGCCGTGAGC
CTGAAGTCCGGCAGCCTGAACACCCTGGAGGACCCCCCCAGCAGCCCCCCCCCCCGCACCTTCCTGAA
CCAGCTGCCCGACTGGAGCCGCCTGCGCACCGCCATCACCACCGTGTTCGTGGCCGCCGAGAAGCAGT
TCACCCGCCTGGACCGCAAGAGCAAGCGCCCCGACATGCTGGTGGACTGGTTCGGCAGCGAGACCATC
GTGCAGGACGGCCTGGTGTTCCGCGAGCGCTTCAGCATCCGCAGCTACGAGATCGGCGCCGACCGCAC
CGCCAGCATCGAGACCCTGATGAACCACCTGCAGGACACCAGCCTGAACCACTGCAAGAGCGTGGGCC
TGCTGAACGACGGCTTCGGCCGCACCCCCGAGATGTGCACCCGCGACCTGATCTGGGTGCTGACCAAG
ATGCAGATCGTGGTGAACCGCTACCCCACCTGGGGCGACACCGTGGAGATCAACAGCTGGTTCAGCCA
GAGCGGCAAGATCGGCATGGGCCGCGAGTGGCTGATCAGCGACTGCAACACCGGCGAGATCCTGGTGC
GCGCCACCAGCGCCTGGGCCATGATGAACCAGAAGACCCGCCGCTTCAGCAAGCTGCCCTGCGAGGTG
CGCCAGGAGATCGCCCCCCACTTCGTGGACGCCCCCCCCGTGATCGAGGACAACGACCGCAAGCTGCA
CAAGTTCGACGTGAAGACCGGCGACAGCATCTGCAAGGGCCTGACCCCCGGCTGGAACGACTTCGACG
TGAACCAGCACGTGAGCAACGTGAAGTACATCGGCTGGATTCTGGAGAGCATGCCCACCGAGGTGCTG
GAGACCCAGGAGCTGTGCAGCCTGACCCTGGAGTACCGCCGCGAGTGCGGCCGCGAGAGCGTGGTGGA
GAGCGTGACCAGCATGAACCCCAGCAAGGTGGGCGACCGCAGCCAGTACCAGCACCTGCTGCGCCTGG
AGGACGGCGCCGACATCATGAAGGGCCGCACCGAGTGGCGCCCCAAGAACGCCGGCACCAACCGCGCC
ATCAGCACCTGA SEQ ID NO: 11
*Cuphea wrightii* FatB2 thioesterase amino acid sequence; Gen Bank Accession No. U56104
MVVAAAASSAFFPVPAPRPTPKPGKFGNWPSSLSQPFKPKSNPNGRFQVKANVSPHPKANGSAVSLKS
GSLNTLEDPPSSPPPRTFLNQLPDWSRLRTAITTVFVAAEKQFTRLDRKSKRPDMLVDWFGSETIVQD
GLVFRERFSIRSYEIGADRTASIETLMNHLQDTSLNHCKSVGLLNDGFGRTPEMCTRDLIWVLTKMQI
VVNRYPTWGDTVEINSWFSQSGKIGMGREWLISDCNTGEILVRATSAWAMMNQKTRRFSKLPCEVRQE
IAPHFVDAPPVIEDNDRKLHKFDVKTGDSICKGLTPGWNDFDVNQHVSNVKYIGWILESMPTEVLETQ
ELCSLTLEYRRECGRESVVESVTSMNPSKVGDRSQYQHLLRLEDGADIMKGRTEWRPKNAGTNRAIST SEQ ID NO: 12
Codon-optimized coding region of *Cocus nucifera* C12:0-preferring LPAAT from pSZ2046
ATGGACGCCTCCGGCGCCTCCTCCTTCCTGCGCGGCCGCTGCCTGGAGTCCTGCTTCAAGGCCTCCTT
CGGCTACGTAATGTCCCAGCCCAAGGACGCCGCCGGCCAGCCCTCCCGCCGCCCCGCCGACGCCGACG
ACTTCGTGGACGACGACCGCTGGATCACCGTGATCCTGTCCGTGGTGCGCATCGCCGCCTGCTTCCTG
TCCATGATGGTGACCACCATCGTGTGGAACATGATCATGCTGATCCTGCTGCCCTGGCCCTACGCCCG
CATCCGCCAGGGCAACCTGTACGGCCACGTGACCGGCCGCATGCTGATGTGGATTCTGGGCAACCCCA
TCACCATCGAGGGCTCCGAGTTCTCCAACACCCGCGCCATCTACATCTGCAACCACGCCTCCCTGGTG
GACATCTTCCTGATCATGTGGCTGATCCCCAAGGGCACCGTGACCATCGCCAAGAAGGAGATCATCTG
GTATCCCCTGTTCGGCCAGCTGTACGTGCTGGCCAACCACCAGCGCATCGACCGCTCCAACCCCTCCG
CCGCCATCGAGTCCATCAAGGAGGTGGCCCGCGCCGTGGTGAAGAAGAACCTGTCCCTGATCATCTTC
CCCGAGGGCACCCGCTCCAAGACCGGCCGCCTGCTGCCCTTCAAGAAGGGCTTCATCCACATCGCCCT
CCAGACCCGCCTGCCCATCGTGCCGATGGTGCTGACCGGCACCCACCTGGCCTGGCGCAAGAACTCCC
TGCGCGTGCGCCCCGCCCCCATCACCGTGAAGTACTTCTCCCCCATCAAGACCGACGACTGGGAGGAG
GAGAAGATCAACCACTACGTGGAGATGATCCACGCCCTGTACGTGGACCACCTGCCCGAGTCCCAGAA
GCCCCTGGTGTCCAAGGGCCGCGACGCCTCCGGCCGCTCCAACTCCTGA SEQ ID NO: 13
pLoop 5' genomic donor sequence
gctcttcgctaacggaggtctgtcaccaaatggaccccgtctattgcgggaaaccacggcgatggcac
gtttcaaaacttgatgaaatacaatattcagtatgtcgcgggcggcgacggcggggagctgatgtcgc
gctgggtattgcttaatcgccagcttcgcccccgtcttggcgcgaggcgtgaacaagccgaccgatgt
gcacgagcaaatcctgacactagaagggctgactcgcccggcacggctgaattacacaggcttgcaaa
aataccagaatttgcacgcaccgtattcgcggtattttgttggacagtgaatagcgatgcggcaatgg
cttgtggcgttagaaggtgcgacgaaggtggtgccaccactgtgccagccagtcctggcggctcccag
ggccccgatcaagagccaggacatccaaactacccacagcatcaacgccccggcctatactcgaaccc
cacttgcactctgcaatggtatgggaaccacggggcagtcttgtgtgggtcgcgcctatcgcggtcgg
cgaagaccgggaaggtacc SEQ ID NO: 14
pLoop 3' genomic donor sequence
gagctcagcggcgacggtcctgctaccgtacgacgttgggcacgcccatgaaagtttgtataccgagc
ttgttgagcgaactgcaagcgcggctcaaggatacttgaactcctggattgatatcggtccaataatg
gatggaaaatccgaacctcgtgcaagaactgagcaaacctcgttacatggatgcacagtcgccagtcc
aatgaacattgaagtgagcgaactgttcgcttcggtggcagtactactcaaagaatgagctgctgtta
aaaatgcactctcgttctctcaagtgagtggcagatgagtgctcacgccttgcacttcgctgcccgtg -continued

SEQUENCE LISTING tcatgccctgcgccccaaaatttgaaaaaagggatgagattattgggcaatggacgacgtcgtcgctc
cgggagtcaggaccggcggaaaataagaggcaacacactccgcttcttagctcttcc SEQ ID NO: 15
NeoR expression cassette including *C. reinhardtii* (β-tubulin
promoter/5' UTR and *C. vulgaris* nitrate reductase 3' UTR
ctttcttgcgctatgacacttccagcaaaaggtagggcgggctgcgagacggcttcccggcgctgcat
gcaacaccgatgatgcttcgaccccccgaagctccttcggggctgcatgggcgctccgatgccgctcc
agggcgagcgctgtttaaatagccaggcccccgattgcaaagacattatagcgagctaccaaagccat
attcaaacacctagatcactaccacttctacacaggccactcgagcttgtgatcgcactccgctaagg
gggcgcctcttcctcttcgtttcagtcacaacccgcaaactctagaatatcaATGatcgagcaggacg
gcctccacgccggctcccccgccgcctgggtggagcgcctgttcggctacgactgggcccagcagacc
atcggctgctccgacgccgccgtgttccgcctgtccgcccagggccgccccgtgctgttcgtgaagac
cgacctgtccggcgccctgaacgagctgcaggacgaggccgcccgcctgtcctggctggccaccaccg
gcgtgccctgcgccgccgtgctggacgtggtgaccgaggccggccgcgactggctgctgctgggcgag
gtgcccggccaggacctgctgtcctcccacctggcccccgccgagaaggtgtccatcatggccgacgc
catgcgccgcctgcacaccctggaccccgccacctgccccttcgaccaccaggccaagcaccgcatcg
agcgcgcccgcacccgcatggaggccggcctggtggaccaggacgacctggacgaggagcaccagggc
ctggcccccgccgagctgttcgcccgcctgaaggcccgcatgcccgacggcgaggacctggtggtgac
ccacggcgacgcctgcctgcccaacatcatggtggagaacggccgcttctccggcttcatcgactgcg
gccgcctgggcgtggccgaccgctaccaggacatcgccctggccacccgcgacatcgccgaggagctg
ggcggcgagtgggccgaccgcttcctggtgctgtacggcatcgccgcccccgactcccagcgcatcgc
cttctaccgcctgctggacgagttcttcTGAcaattggcagcagcagctcggatagtatcgacacact
ctggacgctggtcgtgtgatggactgttgccgccacacttgctgccttgacctgtgaatatccctgcc
gcttttatcaaacagcctcagtgtgtttgatcttgtgtgtacgcgcttttgcgagttgctagctgctt
gtgctatttgcgaataccacccccagcatccccttccctcgtttcatatcgcttgcatcccaaccgca
acttatctacgctgtcctgctatccctcagcgctgctcctgctcctgctcactgcccctcgcacagcc
ttggtttgggctccgcctgtattctcctggtactgcaacctgtaaaccagcactgcaatgctgatgca
cgggaagtagtgggatgggaacacaaatggaggatcc SEQ ID NO: 16
*Cocos nucifera* 1-acyl-sn-glycerol-3-phosphate acyltransferase
(LPAAT)
MDASGASSFLRGRCLESCFKASFGYVMSQPKDAAGQPSRRPADADDFVDDDRWITVILSV
VRIAACFLSMMVTTIVWNMIMLILLPWPYARIRQGNLYGHVTGRMLMWILGNPITIEGSE
FSNTRAIYICNHASLVDIFLIMWLIPKGTVTIAKKEIIWYPLFGQLYVLANHQRIDRSNP
SAAIESIKEVARAVVKKNLSLIIFPEGTRSKTGRLLPFKKGFIHIALQTRLPIVPMVLTG
THLAWRKNSLRVRPAPITVKYFSPIKTDDWEEEKINHYVEMIHALYVDHLPESQKPLVSK
GRDASGRSNS SEQ ID NO: 17
pSZ1500
GGGCTGGTCTGAATCCTTCAGGCGGGTGTTACCCGAGAAAGAAAGGGTGCCGATTTCAAAGCAGACCC
ATGTGCCGGGCCCTGTGGCCTGTGTTGGCGCCTATGTAGTCACCCCCCCTCACCCAATTGTCGCCAGT
TTGCGCACTCCATAAACTCAAAACAGCAGCTTCTGAGCTGCGCTGTTCAAGAACACCTCTGGGGTTTG
CTCACCCGCGAGGTCGACGCCCAGCATGGCTATCAAGACGAACAGGCAGCCTGTGGAGAAGCCTCCGT
TCACGATCGGGACGCTGCGCAAGGCCATCCCCGCGCACTGTTTCGAGCGCTCGGCGCTTCGTAGCAGC
ATGTACCTGGCCTTTGACATCGCGGTCATGTCCCTGCTCTACGTCGCGTCGACGTACATCGACCCTGC
ACCGGTGCCTACGTGGGTCAAGTACGGCATCATGTGGCCGCTCTACTGGTTCTTCCAGGTGTGTTTGA
GGGTTTTGGTTGCCCGTATTGAGGTCCTGGTGGCGCGCATGGAGGAGAAGGCGCCTGTCCCGCTGACC
CCCCCGGCTACCCTCCCGGCACCTTCCAGGGCGCCTTCGGCACGGGTGTCTGGGTGTGCGCGCACGAG
TGCGGCCACCAGGCCTTTTCCTCCAGCCAGGCCATCAACGACGGCGTGGGCCTGGTGTTCCACAGCCT
GCTGCTGGTGCCCTACTACTCCTGGAAGCACTCGCACCGGGTACCCTTTCTTGCGCTATGACACTTCC
AGCAAAAGGTAGGGCGGGCTGCGAGACGGCTTCCCGGCGCTGCATGCAACACCGATGATGCTTCGACC
CCCCGAAGCTCCTTCGGGGCTGCATGGGCGCTCCGATGCCGCTCCAGGGCGAGCGCTGTTTAAATAGC
CAGGCCCCCGATTGCAAAGACATTATAGCGAGCTACCAAAGCCATATTCAAACACCTAGATCACTACC
ACTTCTACACAGGCCACTCGAGCTTGTGATCGCACTCCGCTAAGGGGGCGCCTCTTCCTCTTCGTTTC
AGTCACAACCCGCAAACTCTAGAATATCAATGCTGCTGCAGGCCTTCCTGTTCCTGCTGGCCGGCTTC
GCCGCCAAGATCAGCGCCTCCATGACGAACGAGACGTCCGACCGCCCCCTGGTGCACTTCACCCCCAA
CAAGGGCTGGATGAACGACCCCAACGGCCTGTGGTACGACGAGAAGGACGCCAAGTGGCACCTGTACT
TCCAGTACAACCCGAACGACACCGTCTGGGGGACGCCCTTGTTCTGGGGCCACGCCACGTCCGACGAC
CTGACCAACTGGGAGGACCAGCCCATCGCCATCGCCCCGAAGCGCAACGACTCCGGCGCCTTCTCCGG
CTCCATGGTGGTGGACTACAACAACACCTCCGGCTTCTTCAACGACACCATCGACCCGCGCCAGCGCT
GCGTGGCCATCTGGACCTACAACACCCCGGAGTCCGAGGAGCAGTACATCTCCTACAGCCTGGACGGC
GGCTACACCTTCACCGAGTACCAGAAGAACCCCGTGCTGGCCGCCAACTCCACCCAGTTCCGCGACCC
GAAGGTCTTCTGGTACGAGCCCTCCCAGAAGTGGATCATGACCGCGGCCAAGTCCCAGGACTACAAGA
TCGAGATCTACTCCTCCGACGACCTGAAGTCCTGGAAGCTGGAGTCCGCGTTCGCCAACGAGGGCTTC
CTCGGCTACCAGTACGAGTGCCCCGGCCTGATCGAGGTCCCCACCGAGCAGGACCCCAGCAAGTCCTA
CTGGGTGATGTTCATCTCCATCAACCCCGGCGCCCCGGCCGGCGGCTCCTTCAACCAGTACTTCGTCG
GCAGCTTCAACGGCACCCACTTCGAGGCCTTCGACAACCAGTCCCGCGTGGTGGACTTCGGCAAGGAC
TACTACGCCCTGCAGACCTTCTTCAACACCGACCCGACCTACGGGAGCGCCCTGGGCATCGCGTGGGC
CTCCAACTGGGAGTACTCCGCCTTCGTGCCCACCAACCCCTGGCGCTCCTCCATGTCCCTCGTGCGCA
AGTTCTCCCTCAACACCGAGTACCAGGCCAACCCGGAGACGGAGCTGATCAACCTGAAGGCCGAGCCG -continued

SEQUENCE LISTING

ATCCTGAACATCAGCAACGCCGGCCCCTGGAGCCGGTTCGCCACCAACACCACGTTGACGAAGGCCAA
CAGCTACAACGTCGACCTGTCCAACAGCACCGGCACCCTGGAGTTCGAGCTGGTGTACGCCGTCAACA
CCACCCAGACGATCTCCAAGTCCGTGTTCGCGGACCTCTCCCTCTGGTTCAAGGGCCTGGAGGACCCC
GAGGAGTACCTCCGCATGGGCTTCGAGGTGTCCGCGTCCTCCTTCTTCCTGGACCGCGGGAACAGCAA
GGTGAAGTTCGTGAAGGAGAACCCCTACTTCACCAACCGCATGAGCGTGAACAACCAGCCCTTCAAGA
GCGAGAACGACCTGTCCTACTACAAGGTGTACGGCTTGCTGGACCAGAACATCCTGGAGCTGTACTTC
AACGACGGCGACGTCGTGTCCACCAACACCTACTTCATGACCACCGGGAACGCCCTGGGCTCCGTGAA
CATGACGACGGGGGTGGACAACCTGTTCTACATCGACAAGTTCCAGGTGCGCGAGGTCAAGTGACAAT
TGGCAGCAGCAGCTCGGATAGTATCGACACACTCTGGACGCTGGTCGTGTGATGGACTGTTGCCGCCA
CACTTGCTGCCTTGACCTGTGAATATCCCTGCCGCTTTTATCAAACAGCCTCAGTGTGTTTGATCTTG
TGTGTACGCGCTTTTGCGAGTTGCTAGCTGCTTGTGCTATTTGCGAATACCACCCCCAGCATCCCCTT
CCCTCGTTTCATATCGCTTGCATCCCAACCGCAACTTATCTACGCTGTCCTGCTATCCCTCAGCGCTG
CTCCTGCTCCTGCTCACTGCCCCTCGCACAGCCTTGGTTTGGGCTCCGCCTGTATTCTCCTGGTACTG
CAACCTGTAAACCAGCACTGCAATGCTGATGCACGGGAAGTAGTGGGATGGGAACACAAATGGAGGAT
CCCGCGTCTCGAACAGAGCGCGCAGAGGAACGCTGAAGGTCTCGCCTCTGTCGCACCTCAGCGCGGCA
TACACCACAATAACCACCTGACGAATGCGCTTGGTTCTTCGTCCATTAGCGAAGCGTCCGGTTCACAC
ACGTGCCACGTTGGCGAGGTGGCAGGTGACAATGATCGGTGGAGCTGATGGTCGAAACGTTCACAGCC
TAGGGATATCGAATTCGGCCGACAGGACGCGCGTCAAAGGTGCTGGTCGTGTATGCCCTGGCCGGCAG
GTCGTTGCTGCTGCTGGTTAGTGATTCCGCAACCCTGATTTTGGCGTCTTATTTTGGCGTGGCAAACG
CTGGCGCCCGCGAGCCGGGCCGGCGGCGATGCGGTGCCCCACGGCTGCCGGAATCCAAGGGAGGCAAG
AGCGCCCGGGTCAGTTGAAGGGCTTTACGCGCAAGGTACAGCCGCTCCTGCAAGGCTGCGTGGTGGAA
TTGGACGTGCAGGTCCTGCTGAAGTTCCTCCACCGCCTCACCAGCGGACAAAGCACCGGTGTATCAGG
TCCGTGTCATCCACTCTAAAGAACTCGACTACGACCTACTGATGGCCCTAGATTCTTCATCAAAAACG
CCTGAGACACTTGCCCAGGATTGAAACTCCCTGAAGGGACCACCAGGGGCCCTGAGTTGTTCCTTCCC
CCCGTGGCGAGCTGCCAGCCAGGCTGTACCTGTGATCGAGGCTGGCGGGAAAATAGGCTTCGTGTGCT
CAGGTCATGGGAGGTGCAGGACAGCTCATGAAACGCCAACAATCGCACAATTCATGTCAAGCTAATCA
GCTATTTCCTCTTCACGAGCTGTAATTGTCCCAAAATTCTGGTCTACCGGGGGTGATCCTTCGTGTAC
GGGCCCTTCCCTCAACCCTAGGTATGCGCGCATGCGGTCGCCGCGCAACTCGCGCGAGGGCCGAGGGT
TTGGGACGGGCCGTCCCGAAATGCAGTTGCACCCGGATGCGTGGCACCTTTTTTGCGATAATTTATGC
AATGGACTGCTCTGCAAAATTCTGGCTCTGTCGCCAACCCTAGGATCAGCGGCGTAGGATTTCGTAAT
CATTCGTCCTGATGGGGAGCTACCGACTACCCTAATATCAGCCCGACTGCCTGACGCCAGCGTCCACT
TTTGTGCACACATTCCATTCGTGCCCAAGACATTTCATTGTGGTGCGAAGCGTCCCCAGTTACGCTCA
CCTGTTTCCCGACCTCCTTACTGTTCTGTCGACAGAGCGGGCCCACAGGCCGGTCGCAGCCACTAGTA
TGGCCACCGCATCCACTTTCTCGGCGTTCAATGCCCGCTGCGGCGACCTGCGTCGCTCGGCGGGCTCC
GGGCCCCGGCGCCCAGCGAGGCCCCTCCCCGTGCGCGGGCGCGCCGCCACCGGCGAGCAGCCCTCCGG
CGTGGCCTCCCTGCGCGAGGCCGACAAGGAGAAGTCCCTGGGCAACCGCCTGCGCCTGGGCTCCCTGA
CCGAGGACGGCCTGTCCTACAAGGAGAAGTTCGTGATCCGCTGCTACGAGGTGGGCATCAACAAGACC
GCCACCATCGAGACCATCGCCAACCTGCTGCAGGAGGTGGGCGGCAACCACGCCCAGGGCGTGGGCTT
CTCCACCGACGGCTTCGCCACCACCACCACCATGCGCAAGCTGCACCTGATCTGGGTGACCGCCCGCA
TGCACATCGAGATCTACCGCTACCCCGCCTGGTCCGACGTGATCGAGATCGAGACCTGGGTGCAGGGC
GAGGGCAAGGTGGGCACCCGCCGCGACTGGATCCTGAAGGACTACGCCAACGGCGAGGTGATCGGCCG
CGCCACCTCCAAGTGGGTGATGATGAACGAGGACACCCGCCGCCTGCAGAAGGTGTCCGACGACGTGC
GCGAGGAGTACCTGGTGTTCTGCCCCCGCACCCTGCGCCTGGCCTTCCCCGAGGAGAACAACAACTCC
ATGAAGAAGATCCCCAAGCTGGAGGACCCCGCCGAGTACTCCCGCCTGGGCCTGGTGCCCCGCCGCTC
CGACCTGGACATGAACAAGCACGTGAACAACGTGACCTACATCGGCTGGGCCCTGGAGTCCATCCCCC
CCGAGATCATCGACACCCACGAGCTGCAGGCCATCACCCTGGACTACCGCCGCGAGTGCCAGCGCGAC
GACATCGTGGACTCCCTGACCTCCCGCGAGCCCCTGGGCAACGCCGCCGGCGTGAAGTTCAAGGAGAT
CAACGGCTCCGTGTCCCCCAAGAAGGACGAGCAGGACCTGTCCCGCTTCATGCACCTGCTGCGCTCCG
CCGGCTCCGGCCTGGAGATCAACCGCTGCCGCACCGAGTGGCGCAAGAAGCCCGCCAAGCGCATGGAC
TACAAGGACCACGACGGCGACTACAAGGACCACGACATCGACTACAAGGACGACGACGACAAGTGAAT
CGATAGATCTCTTAAGGCAGCAGCAGCTCGGATAGTATCGACACACTCTGGACGCTGGTCGTGTGATG
GACTGTTGCCGCCACACTTGCTGCCTTGACCTGTGAATATCCCTGCCGCTTTTATCAAACAGCCTCAG
TGTGTTTGATCTTGTGTGTACGCGCTTTTGCGAGTTGCTAGCTGCTTGTGCTATTTGCGAATACCACC
CCCAGCATCCCCTTCCCTCGTTTCATATCGCTTGCATCCCAACCGCAACTTATCTACGCTGTCCTGCT
ATCCCTCAGCGCTGCTCCTGCTCCTGCTCACTGCCCCTCGCACAGCCTTGGTTTGGGCTCCGCCTGTA
TTCTCCTGGTACTGCAACCTGTAAACCAGCACTGCAATGCTGATGCACGGGAAGTAGTGGGATGGGAA
CACAAATGGAAAGCTTAATTAAGAGCTCCCGCCACCACTCCAACACGGGGTGCCTGGACAAGGACGAG
GTGTTTGTGCCGCCGCACCGCGCAGTGGCGCACGAGGGCCTGGAGTGGGAGGAGTGGCTGCCCATCCG
CATGGGCAAGGTGCTGGTCACCCTGACCCTGGGCTGGCCGCTGTACCTCATGTTCAACGTCGCCTCGC
GGCCGTACCCGCGCTTCGCCAACCACTTTGACCCGTGGTCGCCCATCTTCAGCAAGCGCGAGCGCATC
GAGGTGGTCATCTCCGACCTGGCGCTGGTGGCGGTGCTCAGCGGGCTCAGCGTGCTGGGCCGCACCAT
GGGCTGGGCCTGGCTGGTCAAGACCTACGTGGTGCCCTACCTGATCGTGAACATGTGGCTCGTGCTCA
TCACGCTGCTCCAGCACACGCACCCGGCGCTGCCGCACTACTTCGAGAAGGACTGGGACTGGCTGCGC
GGCGCCATGGCCACCGTGGACCGCTCCATGGGCCCGCCCTTCATGGACAACATCCTGCACCACATCTC
CGACACCCACGTGCTGCACCACCTCTTCAGCACCATCCCGCACTACCACGCCGAGGAGGCCTCCGCCG
CCATCAGGCCCATCCTGGGCAAGTACTACCAGTCCGACAGCCGCTGGGTCGGCCGCGCCCTGTGGGAG
GACTGGCGCGACTGCCGCTACGTCGTCCCGGACGCGCCCGAGGACGACTCCGCGCTCTGGTTCCACAA
GTGAGTGAGTGA

SEQ ID NO: 18
5' FADc genomic region donor DNA
GGGCTGGTCTGAATCCTTCAGGCGGGTGTTACCCGAGAAAGAAAGGGTGCCGATTTCAAAGCAGACCC
ATGTGCCGGGCCCTGTGGCCTGTGTTGGCGCCTATGTAGTCACCCCCCCTCACCCAATTGTCGCCAGT
TTGCGCACTCCATAAACTCAAAACAGCAGCTTCTGAGCTGCGCTGTTCAAGAACACCTCTGGGGTTTG
CTCACCCGCGAGGTCGACGCCCAGCATGGCTATCAAGACGAACAGGCAGCCTGTGGAGAAGCCTCCGT
TCACGATCGGGACGCTGCGCAAGGCCATCCCCGCGCACTGTTTCGAGCGCTCGGCGCTTCGTAGCAGC
ATGTACCTGGCCTTTGACATCGCGGTCATGTCCCTGCTCTACGTCGCGTCGACGTACATCGACCCTGC -continued

SEQUENCE LISTING

ACCGGTGCCTACGTGGGTCAAGTACGGCATCATGTGGCCGCTCTACTGGTTCTTCCAGGTGTGTTTGA
GGGTTTTGGTTGCCCGTATTGAGGTCCTGGTGGCGCGCATGGAGGAGAAGGCGCCTGTCCCGCTGACC
CCCCCGGCTACCCTCCCGGCACCTTCCAGGGCGCCTTCGGCACGGGTGTCTGGGTGTGCGCGCACGAG
TGCGGCCACCAGGCCTTTTCCTCCAGCCAGGCCATCAACGACGGCGTGGGCCTGGTGTTCCACAGCCT
GCTGCTGGTGCCCTACTACTCCTGGAAGCACTCGCACCG

SEQ ID NO: 19
3' FADc genomic region donor DNA
CCGCCACCACTCCAACACGGGGTGCCTGGACAAGGACGAGGTGTTTGTGCCGCCGCACCGCGCAGTGG
CGCACGAGGGCCTGGAGTGGAGGAGTGGCTGCCCATCCGCATGGGCAAGGTGCTGGTCACCCTGACC
CTGGGCTGGCCGCTGTACCTCATGTTCAACGTCGCCTCGCGGCCGTACCCGCGCTTCGCCAACCACTT
TGACCCGTGGTCGCCCATCTTCAGCAAGCGCGAGCGCATCGAGGTGGTCATCTCCGACCTGGCGCTGG
TGGCGGTGCTCAGCGGGCTCAGCGTGCTGGGCCGCACCATGGGCTGGGCCTGGCTGGTCAAGACCTAC
GTGGTGCCCTACCTGATCGTGAACATGTGGCTCGTGCTCATCACGCTGCTCCAGCACACGCACCCGGC
GCTGCCGCACTACTTCGAGAAGGACTGGGACTGGCTGCGCGGCGCCATGGCCACCGTGGACCGCTCCA
TGGGCCCGCCCTTCATGGACAACATCCTGCACCACATCTCCGACACCCACGTGCTGCACCACCTCTTC
AGCACCATCCCGCACTACCACGCCGAGGAGGCCTCCGCCGCCATCAGGCCCATCCTGGGCAAGTACTA
CCAGTCCGACAGCCGCTGGGTCGGCCGCGCCCTGTGGGAGGACTGGCGCGACTGCCGCTACGTCGTCC
CGGACGCGCCCGAGGACGACTCCGCGCTCTGGTTCCACAAGTGAGTGAGTGA SEQ ID NO: 20
5' donor DNA sequence of *Prototheca moriformis* FATA1 knockout
homologous recombination targeting construct
GCTCTTCGGAGTCACTGTGCCACTGAGTTCGACTGGTAGCTGAATGGAGTCGCTGCTCCACTAAACGA
ATTGTCAGCACCGCCAGCCGGCCGAGGACCCGAGTCATAGCGAGGGTAGTAGCGCGCCATGGCACCGA
CCAGCCTGCTTGCCAGTACTGGCGTCTCTTCCGCTTCTCTGTGGTCCTCTGCGCGCTCCAGCGCGTGC
GCTTTTCCGGTGGATCATGCGGTCCGTGGCGCACCGCAGCGGCCGCTGCCCATGCAGCGCCGCTGCTT
CCGAACAGTGGCGGTCAGGGCCGCACCCGCGGTAGCCGTCCGTCCGGAACCCGCCCAAGAGTTTTGGG
AGCAGCTTGAGCCCTGCAAGATGGCGGAGGACAAGCGCATCTTCCTGGAGGAGCACCGGTGCGTGGAG
GTCCGGGGCTGACCGGCCGTCGCATTCAACGTAATCAATCGCATGATGATCAGAGGACACGAAGTCTT
GGTGGCGGTGGCCAGAAACACTGTCCATTGCAAGGGCATAGGGATGCGTTCCTTCACCTCTCATTTCT
CATTTCTGAATCCCTCCCTGCTCACTCTTTCTCCTCCTCCTTCCCGTTCACGCAGCATTCGGGGTACC SEQ ID NO: 21
3' donor DNA sequence of *Prototheca moriformis* FATA1 knockout
homologous recombination targeting construct
GACAGGGTGGTTGGCTGGATGGGGAAACGCTGGTCGCGGGATTCGATCCTGCTGCTTATATCCTCCCT
GGAAGCACACCCACGACTCTGAAGAAGAAAACGTGCACACACACAACCCAACCGGCCGAATATTTGCT
TCCTTATCCCGGGTCCAAGAGAGACTGCGATGCCCCCCTCAATCAGCATCCTCCTCCCTGCCGCTTCA
ATCTTCCCTGCTTGCCTGCGCCCGCGGTGCGCCGTCTGCCCGCCCAGTCAGTCACTCCTGCACAGGCC
CCTTGTGCGCAGTGCTCCTGTACCCTTTACCGCTCCTTCCATTCTGCGAGGCCCCCTATTGAATGTAT
TCGTTGCCTGTGTGGCCAAGCGGGCTGCTGGGCGCGCCGCCGTCGGGCAGTGCTCGGCGACTTTGGCG
GAAGCCGATTGTTCTTCTGTAAGCCACGCGCTTGCTGCTTTGGGAAGAGAAGGGGGGGGGTACTGAAT
GGATGAGGAGGAGAAGGAGGGGTATTGGTATTATCTGAGTTGGGTGAAGAGC SEQ ID NO: 22
*Chlorella protothecoides* actin promoter/5' UTR
agtttaggtccagcgtccgtggggggggacgggctgggagcttgggccgggaagggcaagacgatgca
gtccctctggggagtcacagccgactgtgtgtgttgcactgtgcggcccgcagcactcacacgcaaaa
tgcctggccgacaggcaggccctgtccagtgcaacatccacggtccctctcatcaggctcaccttgct
cattgacataacggaatgcgtaccgctctttcagatctgtccatccagagaggggagcaggctcccca
ccgacgctgtcaaacttgcttcctgcccaaccgaaaacattattgtttgaggggggggggggggggggc
agattgcatggcgggatatctcgtgaggaacatcactgggacactgtggaacacagtgagtgcagtat
gcagagcatgtatgctaggggtcagcgcaggaaggggggcctttcccagtctcccatgccactgcaccg
tatccacgactcaccaggaccagcttcttgatcggcttccgctcccgtggacaccagtgtgtagcctc
tggactccaggtatgcgtgcaccgcaaaggccagccgatcgtgccgattcctggggtggaggatatga
gtcagccaacttggggctcagagtgcacactggggcacgatacgaaacaacatctacaccgtgtcctc
catgctgacacaccacagcttcgctccacctgaatgtgggcgcatgggcccgaatcacagccaatgtc
gctgctgccataatgtgatccagaccctctccgcccagatgccgagcggatcgtgggcgctgaataga
ttcctgtttcgatcactgtttgggtcctttccttttcgtctcggatgcgcgtctcgaaacaggctgcg
tcgggctttcggatcccttttgctccctccgtcaccatcctgcgcgcgggcaagttgcttgaccctgg
gctgtaccagggttggagggtattaccgcgtcaggccattcccagcccggattcaattcaaagtctgg
gccaccaccctccgccgctctgtctgatcactccacattcgtgcatacactacgttcaagtcctgatc
caggcgtgtctcgggacaaggtgtgcttgagtttgaatctcaaggacccactccagcacagctgctgg
ttgaccccgccctcgcaa SEQ ID NO: 23
AtTHIC expression cassette comprising *Chlorella protothecoides*
actin promoter/5' UTR, *Arabidopsis thaliana* THIC protein coding
sequence codon-optimized for expression in *Prototheca moriformis*,
and *Chlorella vulgaris* nitrate reductase 3' UTR
agtttaggtccagcgtccgtggggggggacgggctgggagcttgggccgggaagggcaagacgatgca
gtccctctggggagtcacagccgactgtgtgtgttgcactgtgcggcccgcagcactcacacgcaaaa
tgcctggccgacaggcaggccctgtccagtgcaacatccacggtccctctcatcaggctcaccttgct
cattgacataacggaatgcgtaccgctctttcagatctgtccatccagagaggggagcaggctcccca
ccgacgctgtcaaacttgcttcctgcccaaccgaaaacattattgtttgaggggggggggggggggggc
agattgcatggcgggatatctcgtgaggaacatcactgggacactgtggaacacagtgagtgcagtat -continued

SEQUENCE LISTING gcagagcatgtatgctaggggtcagcgcaggaaggggcctttcccagtctcccatgccactgcaccg
tatccacgactcaccaggaccagcttcttgatcggcttccgctcccgtggacaccagtgtgtagcctc
tggactccaggtatgcgtgcaccgcaaaggccagccgatcgtgccgattcctggggtggaggatatga
gtcagccaacttggggctcagagtgcacactggggcacgatacgaaacaacatctacaccgtgtcctc
catgctgacacaccacagcttcgctccacctgaatgtgggcgcatgggcccgaatcacagccaatgtc
gctgctgccataatgtgatccagaccctctccgcccagatgccgagcggatcgtgggcgctgaataga
ttcctgtttcgatcactgtttgggtcctttccttttcgtctcggatgcgcgtctcgaaacaggctgcg
tcgggctttcggatcccttttgctccctccgtcaccatcctgcgcgcgggcaagttgcttgaccctgg
gctgtaccagggttggagggtattaccgcgtcaggccattcccagcccggattcaattcaaagtctgg
gccaccaccctccgccgctctgtctgatcactccacattcgtgcatacactacgttcaagtcctgate
caggcgtgtctcgggacaaggtgtgcttgagtttgaatctcaaggacccactccagcacagctgctgg
ttgaccccgccctcgcaatctagaATGgccgcgtccgtccactgcaccctgatgtccgtggtctgcaa
caacaagaaccactccgcccgccccaagctgcccaactcctccctgctgcccggcttcgacgtggtgg
tccaggccgcggccacccgcttcaagaaggagacgacgaccacccgcgccacgctgacgttcgacccc
cccacgaccaactccgagcgcgccaagcagcgcaagcacaccatcgacccctcctcccccgacttcca
gcccatcccctccttcgaggagtgcttccccaagtccacgaaggagcacaaggaggtggtgcacgagg
agtccggccacgtcctgaaggtgcccttccgccgcgtgcacctgtccggcggcgagcccgccttcgac
aactacgacacgtccggcccccagaacgtcaacgcccacatcggcctggcgaagctgcgcaaggagtg
gatcgaccgccgcgagaagctgggcacgccccgctacacgcagatgtactacgcgaagcagggcatca
tcacggaggagatgctgtactgcgcgacgcgcgagaagctggaccccgagttcgtccgctccgaggtc
gcgcggggccgcgccatcatcccctccaacaagaagcacctggagctggagcccatgatcgtgggccg
caagttcctggtgaaggtgaacgcgaacatcggcaactccgccgtggcctcctccatcgaggaggagg
tctacaaggtgcagtgggccaccatgtggggcgccgacaccatcatggacctgtccacgggccgccac
atccacgagacgcgcgagtggatcctgcgcaactccgcggtccccgtgggcaccgtccccatctacca
ggcgctggagaaggtggacggcatcgcggagaacctgaactgggaggtgttccgcgagacgctgatcg
agcaggccgagcagggcgtggactacttcacgatccacgcgggcgtgctgctgcgctacatcccccctg
accgccaagcgcctgacgggcatcgtgtcccgcggcggctccatccacgcgaagtggtgcctggccta
ccacaaggagaacttcgcctacgagcactgggacgacatcctggacatctgcaaccagtacgacgtcg
ccctgtccatcggcgacggcctgcgccccggctccatctacgacgccaacgacacggcccagttcgcc
gagctgctgacccagggcgagctgacgcgccgcgcgtgggagaaggacgtgcaggtgatgaacgaggg
ccccggccacgtgcccatgcacaagatccccgagaacatgcagaagcagctggagtggtgcaacgagg
cgcccttctacaccctgggccccctgacgaccgacatcgcgcccggctacgaccacatcacctccgcc
atcggcgcggccaacatcggcgccctgggcaccgccctgctgtgctacgtgacgcccaaggagcacct
gggcctgcccaaccgcgacgacgtgaaggcgggcgtcatcgcctacaagatcgccgcccacgcggccg
acctggccaagcagcacccccacgcccaggcgtgggacgacgcgctgtccaaggcgcgcttcgagttc
cgctggatggaccagttcgcgctgtccctggaccccatgacggcgatgtccttccacgacgagacgct
gcccgcggacggcgcgaaggtcgcccacttctgctccatgtgcggccccaagttctgctccatgaaga
tcacggaggacatccgcaagtacgccgaggagaacggctacggctccgccgaggaggccatccgccag
ggcatggacgccatgtccgaggagttcaacatcgccaagaagacgatctccggcgagcagcacggcga
ggtcggcggcgagatctacctgcccgagtcctacgtcaaggccgcgcagaagTGAcaattggcagcag
cagctcggatagtatcgacacactctggacgctggtcgtgtgatggactgttgccgccacacttgctg
ccttgacctgtgaatatccctgccgcttttatcaaacagcctcagtgtgtttgatcttgtgtgtacgc
gcttttgcgagttgctagctgcttgtgctatttgcgaataccacccccagcatccccttccctcgttt
catatcgcttgcatcccaaccgcaacttatctacgctgtcctgctatccctcagcgctgctcctgctc
ctgctcactgcccctcgcacagccttggtttgggctccgcctgtattctcctggtactgcaacctgta
aaccagcactgcaatgctgatgcacgggaagtagtgggatgggaacacaaatggaggatcc SEQ ID NO: 24
ATGgccaccgcatccactttctcggcgttcaatgcccgctgcggcgacctgcgtcgctcggcgggctc
cgggccccggcgcccagcgaggcccctccccgtgcgcggcgcgccgccgccgccgccgacgccaacc
ccgcccgccccgagcgccgcgtggtgatcaccggccagggcgtggtgacctccctgggccagaccatc
gagcagttctactcctccctgctggagggcgtgtccggcatctcccagatccagaagttcgacaccac
cggctacaccaccaccatcgccggcgagatcaagtccctgcagctggacccctacgtgcccaagcgct
gggccaagcgcgtggacgacgtgatcaagtacgtgtacatcgccggcaagcaggccctggagtccgcc
ggcctgcccatcgaggccgccggcctggccggcgccggcctggacccgccctgtgcggcgtgctgat
cggcaccgccatggccggcatgacctccttcgccgccggcgtggaggccctgacccgcggcggcgtgc
gcaagatgaaccccttctgcatccccttctccatctccaacatgggcggcgccatgctggccatggac
atcggcttcatgggccccaactactccatctccaccgcctgcgccaccggcaactactgcatcctggg
cgccgccgaccacatccgccgcggcgacgccaacgtgatgctggccggcggcgccgacgccgccatca
tcccctccggcatcggcggcttcatcgcctgcaaggccctgtccaagcgcaacgacgagcccgagcgc
gcctcccgcccctgggacgccgaccgcgacggcttcgtgatgggcgagggcgccggcgtgctggtgct
ggaggagctggagcacgccaagcgccgcggcgccaccatcctggccgagctggtgggcggcgccgcca
cctccgacgcccaccacatgaccgagcccgacccccagggccgcggcgtgcgcctgtgcctggagcgc
gccctggagcgcgcccgcctggcccccgagcgcgtgggctacgtgaacgcccacggcacctccacccc
cgccggcgacgtggccgagtaccgcgccatccgcgccgtgatcccccaggactccctgcgcatcaact
ccaccaagtccatgatcggccacctgctgggcggcgccggcgccgtggaggccgtggccgccatccag
gccctgcgcaccggctggctgcaccccaacctgaacctggagaaccccgcccccggcgtggaccccgt
ggtgctggtgggcccccgcaaggagcgcgccgaggacctggacgtggtgctgtccaactccttcggct
tcggcggccacaactcctgcgtgatcttccgcaagtacgacgagatggactacaaggaccacgacggc
gactacaaggaccacgacatcgactacaaggacgacgacgacaagTGA SEQ ID NO: 25
MATASTFSAFNARCGDLRRSAGSGPRRPARPLPVRGRAAAAADANPARPERRVVITGQGVVTSLGQTI
EQFYSSLLEGVSGISQIQKFDTTGYTTTIAGEIKSLQLDPYVPKRWAKRVDDVIKYVYIAGKQALESA
GLPIEAAGLAGAGLDPALCGVLIGTAMAGMTSFAAGVEALTRGGVRKMNPFCIPFSISNMGGAMLAMD
IGFMGPNYSISTACATGNYCILGAADHIRRGDANVMLAGGADAAIIPSGIGGFIACKALSKRNDEPER
ASRPWDADRDGFVMGEGAGVLVLEELEHAKRRGATILAELVGGAATSDAHHMTEPDPQGRGVRLCLER -continued

SEQUENCE LISTING

ALERARLAPERVGYVNAHGTSTPAGDVAEYRAIRAVIPQDSLRINSTKSMIGHLLGGAGAVEAVAAIQ
ALRTGWLHPNLNLENPAPGVDPVVLVGPRKERAEDLDVVLSNSFGFGGHNSCVIFRKYDEMDYKDHDG
DYKDHDIDYKDDDDK

SEQ ID NO: 26
Codon-optimized *Protetheca moriformis* (UTEX 1435) FAD2 protein-coding sequence
ATGgccatcaagaccaaccgccagcccgtggagaagccccccttcaccatcggcaccctgcgcaaggc
catccccgcccactgcttcgagcgctccgccctgcgctcctccatgtacctggccttcgacatcgccg
tgatgtccctgctgtacgtggcctccacctacatcgaccccgcccccgtgcccacctgggtgaagtac
ggcgtgatgtggcccctgtactggttcttccagggcgccttcggcaccggcgtgtgggtgtgcgccca
cgagtgcggccaccaggccttctcctcctcccaggccatcaacgacggcgtgggcctggtgttccact
ccctgctgctggtgccctactactcctggaagcactcccaccgccgccaccactccaacaccggctgc
ctggacaaggacgaggtgttcgtgcccccccaccgcgccgtggcccacgagggcctggagtgggagga
gtggctgcccatccgcatgggcaaggtgctggtgaccctgaccctgggctggcccctgtacctgatgt
tcaacgtggcctcccgcccctacccccgcttcgccaaccacttcgacccctggtcccccatcttctcc
aagcgcgagcgcatcgaggtggtgatctccgacctggccctggtggccgtgctgtccggcctgtccgt
gctgggccgcaccatgggctgggcctggctggtgaagacctacgtggtgccctacctgatcgtgaaca
tgtggctggtgctgatcaccctgctgcagcacacccaccccgccctgccccactacttcgagaaggac
tgggactggctgcgcggcgccatggccaccgtggaccgctccatgggcccccccttcatggacaacat
cctgcaccacatctccgacacccacgtgctgcaccacctgttctccaccatcccccactaccacgccg
aggaggcctccgccgccatccgccccatcctgggcaagtactaccagtccgactcccgctgggtgggc
cgcgccctgtgggaggactggcgcgactgccgctacgtggtgcccgacgcccccgaggacgactccgc
cctgtggttccacaagTAG SEQ ID NO: 27
Amino acid sequence of *Prototheca moriformis* FAD2
MAIKTNRQPVEKPPFTIGTLRKAIPAHCFERSALRSSMYLAFDIAVMSLLYVASTYIDPAPVPTWVKY
GVMWPLYWFFQGAFGTGVWVCAHECGHQAFSSSQAINDGVGLVFHSLLLVPYYSWKHSHRRHHSNTGC
LDKDEVFVPPHRAVAHEGLEWEEWLPIRMGKVLVTLTLGWPLYLMFNVASRPYPRFANHFDPWSPIFS
KRERIEVVISDLALVAVLSGLSVLGRTMGWAWLVKTYVVPYLIVNMWLVLITLLQHTHPALPHYFEKD
WDWLRGAMATVDRSMGPPFMDNILHHISDTHVLHHLFSTIPHYHAEEASAAIRPILGKYYQSDSRWVG
RALWEDWRDCRYVVPDAPEDDSALWFHK SEQ ID NO: 28
Codon-optimized coding region of *Brassica napus* C18:0-preferring thioesterase from pSZ1358
ACTAGTATGCTGAAGCTGTCCTGCAACGTGACCAACAACCTGCACACCTTCTCCTTCTTCTCCGACTC
CTCCCTGTTCATCCCCGTGAACCGCCGCACCATCGCCGTGTCCTCCGGGCGCGCCTCCCAGCTGCGCA
AGCCCGCCCTGGACCCCCTGCGCGCCGTGATCTCCGCCGACCAGGGCTCCATCTCCCCCGTGAACTCC
TGCACCCCCGCCGACCGCCTGCGCGCCGGCCGCCTGATGGAGGACGGCTACTCCTACAAGGAGAAGTT
CATCGTGCGCTCCTACGAGGTGGGCATCAACAAGACCGCCACCGTGGAGACCATCGCCAACCTGCTGC
AGGAGGTGGCCTGCAACCACGTGCAGAAGTGCGGCTTCTCCACCGACGGCTTCGCCACCACCCTGACC
ATGCGCAAGCTGCACCTGATCTGGGTGACCGCCCGCATGCACATCGAGATCTACAAGTACCCCGCCTG
GTCCGACGTGGTGGAGATCGAGACCTGGTGCCAGTCCGAGGGCCGCATCGGCACCCGCCGCGACTGGA
TCCTGCGCGACTCCGCCACCAACGAGGTGATCGGCCGCGCCACCTCCAAGTGGGTGATGATGAACCAG
GACACCCGCCGCCTGCAGCGCGTGACCGACGAGGTGCGCGACGAGTACCTGGTGTTCTGCCCCCGCGA
GCCCCGCCTGGCCTTCCCCGAGGAGAACAACTCCTCCCTGAAGAAGATCCCCAAGCTGGAGGACCCCG
CCCAGTACTCCATGCTGGAGCTGAAGCCCCGCCGCGCCGACCTGGACATGAACCAGCACGTGAACAAC
GTGACCTACATCGGCTGGGTGCTGGAGTCCATCCCCCAGGAGATCATCGACACCCACGAGCTGCAGGT
GATCACCCTGGACTACCGCCGCGAGTGCCAGCAGGACGACATCGTGGACTCCCTGACCACCTCCGAGA
TCCCCGACGACCCCATCTCCAAGTTCACCGGCACCAACGGCTCCGCCATGTCCTCCATCCAGGGCCAC
AACGAGTCCCAGTTCCTGCACATGCTGCGCCTGTCCGAGAACGGCCAGGAGATCAACCGCGGCCGCAC
CCAGTGGCGCAAGAAGTCCTCCCGCATGGACTACAAGGACCACGACGGCGACTACAAGGACCACGACA
TCGACTACAAGGACGACGACGACAAGTGAATCGAT SEQ ID NO: 29
Amino acid sequence of *Brassica napus* C18:0-preferring thioesterase (Accession No. CAA52070.1)
MLKLSCNVTNNLHTFSFFSDSSLFIPVNRRTIAVSSSQLRKPALDPLRAVISADQGSISPVNSCTPAD
RLRAGRLMEDGYSYKEKFIVRSYEVGINKTATVETIANLLQEVACNHVQKCGFSTDGFATTLTMRKLH
LIWVTARMHIEIYKYPAWSDVVEIETWCQSEGRIGTRRDWILRDSATNEVIGRATSKWVMMNQDTRRL
QRVTDEVRDEYLVFCPREPRLAFPEENNSSLKKIPKLEDPAQYSMLELKPRRADLDMNQHVNNVTYIG
WVLESIPQEIIDTHELQVITLDYRRECQQDDIVDSLTTSEIPDDPISKFTGTNGSAMSSIQGHNESQF
LHMLRLSENGGQEINRGRTQWRKKSSR SEQ ID NO: 30
*Prototheca moriformis* FATA1 allele 1 5' homology donor region
GGAGTCACTGTGCCACTGAGTTCGACTGGTAGCTGAATGGAGTCGCTGCTCCACTAAACGAATTGTCA
GCACCGCCAGCCGGCCGAGGACCCGAGTCATAGCGAGGGTAGTAGCGCGCCATGGCACCGACCAGCCT
GCTTGCCAGTACTGGCGTCTCTTCCGCTTCTCTGTGGTCCTCTGCGCGCTCCAGCGCGTGCGCTTTTC
CGGTGGATCATGCGGTCCGTGGCGCACCGCAGCGGCCGCTGCCCATGCAGCGCCGCTGCTTCCGAACA
GTGGCGGTCAGGGCCGCACCCGCGGTAGCCGTCCGTCCGGAACCCGCCCAAGAGTTTTGGGAGCAGCT
TGAGCCCTGCAAGATGGCGGAGGACAAGCGCATCTTCCTGGAGGAGCACCGGTGCGTGGAGGTCCGGG
GCTGACCGGCCGTCGCATTCAACGTAATCAATCGCATGATGATCAGAGGACACGAAGTCTTGGTGGCG
GTGGCCAGAAACACTGTCCATTGCAAGGGCATAGGGATGCGTTCCTTCACCTCTCATTTCTCATTTCT
GAATCCCTCCCTGCTCACTCTTTCTCCTCCTCCTTCCCGTTCACGCAGCATTCGG -continued

SEQUENCE LISTING

SEQ ID NO: 31
*Prototheca moriformis* FATA1 allele 1 3' homology donor region
GACAGGGTGGTTGGCTGGATGGGGAAACGCTGGTCGCGGGATTCGATCCTGCTGCTTATATCCTCCCT
GGAAGCACACCCACGACTCTGAAGAAGAAAACGTGCACACACACAACCCAACCGGCCGAATATTTGCT
TCCTTATCCCGGGTCCAAGAGAGACTGCGATGCCCCCCTCAATCAGCATCCTCCTCCCTGCCGCTTCA
ATCTTCCCTGCTTGCCTGCGCCCGCGGTGCGCCGTCTGCCCGCCCAGTCAGTCACTCCTGCACAGGCC
CCTTGTGCGCAGTGCTCCTGTACCCTTTACCGCTCCTTCCATTCTGCGAGGCCCCCTATTGAATGTAT
TCGTTGCCTGTGTGGCCAAGCGGGCTGCTGGGCGCGCCGCCGTCGGGCAGTGCTCGGCGACTTTGGCG
GAAGCCGATTGTTCTTCTGTAAGCCACGCGCTTGCTGCTTTGGGAAGAGAAGGGGGGGGGTACTGAAT
GGATGAGGAGGAGAAGGAGGGGTATTGGTATTATCTGAGTTGGGT SEQ ID NO: 32
*Prototheca moriformis* FATA1 allele 2 5' homology donor region
AATGGAGTCGCTGCTCCACTAATCGAATTGTCAGCACCGCCAGCCGGCCGAGGACCCGAGTCATAGCG
AGGGTAGTAGCGCGCCATGGCACCGACCAGCCTGCTTGCCCGTACTGGCGTCTCTTCCGCTTCTCTGT
GCTCCTCTACGCGCTCCGGCGCGTGCGCTTTTCCGGTGGATCATGCGGTCCGTGGCGCACCGCAGCGG
CCGCTGCCCATGCAGCGCCGCTGCTTCCGAACAGTGGCTGTCAGGGCCGCACCCGCAGTAGCCGTCCG
TCCGGAACCCGCCCAAGAGTTTTGGGAGCAGCTTGAGCCCTGCAAGATGGCGGAGGACAAGCGCATCT
TCCTGGAGGAGCACCGGTGCGCGGAGGTCCGGGGCTGACCGGCCGTCGCATTCAACGTAATCAATCGC
ATGATGATCACAGGACGCGACGTCTTGGTGGCGGTGGCCAGGGACACTGCCCATTGCACAGGCATAGG
AATGCGTTCCTTCTCATTTCTCAGTTTTCTGAGCCCCTCCCTCTTCACTCTTTCTCCTCCTCCTCCCC
TCTCACGCAGCATTCGTGG SEQ ID NO: 33
*Prototheca moriformis* FATA1 allele 2 3' homology donor region
CACTAGTATCGATTTCGAACAGAGGAGAGGGTGGCTGGTAGTTGCGGGATGGCTGGTCGCCCGTCGAT
CCTGCTGCTGCTATTGTCTCCTCCTGCACAAGCCCACCCACGACTCCGAAGAAGAAGAAGAAAACGCG
CACACACACAACCCAACCGGCCGAATATTTGCTTCCTTATCCCGGGTCCAAGAGAGACGGCGATGCCC
CCCTCAATCAGCCTCCTCCTCCCTGCCGCTCCAATCTTCCCTGCTTGCATGCGCCCGCGAGAGGCTGT
CTGCGCGCCCCGTCAGTCACTCCCCGTGCAGACGCCTCGTGCTCGGTGCTCCTGTATCCTTTACCGCT
CCTTTCATTCTGCGAGGCCCCCTGTTGAATGTATTCGTTGCCTGTGTGGCCAAGCGCGCTGCTGGGCG
CGCCGCCGTCGGGCGGTGCTCGGCGACTCTGGCGGAAGCCGGTTGTTCTTCTGTAAGCCACGCGCTTG
CTGCTTTTGGAAAAGAGGGGGGTTTACTGAATGGAGGAGGAGCAGGATAATTGGTAGTATCTGAGTTG
TTG SEQ ID NO: 34
SAD2 hairpin C
actagtGCGCTGGACGCGGCAGTGGGTGGCCGAGGAGAACCGGCACGGCGACCTGCTGAACAAGTACT
GTTGGCTGACGGGGCGCGTCAACATGCGGGCCGTGGAGGTGACCATCAACAACCTGATCAAGAGCGGC
ATGAACCCGCAGACGGACAACAACCCTTACTTGGGCTTCGTCTACACCTCCTTCCAGGAGCGCGCGAC
CAAGTACAGCCACGGCAACACCGCGCGCCTTGCGGCCGAGCAGTGTGTTTGAGGGTTTTGGTTGCCCG
TATCGAGGTCCTGGTGGCGCGCATGGGGGAGAAGGCGCCTGTCCCGCTGACCCCCCCGGCTACCCTCC
CGGCACCTTCCAGGGCGCGTACGggatccTGCTCGGCCGCAAGGCGCGCGGTGTTGCCGTGGCTGTAC
TTGGTCGCGCGCTCCTGGAAGGAGGTGTAGACGAAGCCCAAGTAAGGGTTGTTGTCCGTCTGCGGGTT
CATGCCGCTCTTGATCAGGTTGTTGATGGTCACCTCCACGGCCCGCATGTTGACGCGCCCCGTCAGCC
AACAGTACTTGTTCAGCAGGTCGCCGTGCCGGTTCTCCTCGGCCACCCACTGCCGCGTCCAGCGCaag
ctt SEQ ID NO: 35
MSIQFALRAAYIKGTCQRLSGRGAALGLSRDWTPGWTLPRCWPASAAATAPPRARHQERAIHLTSGRR
RHSALASDADERALPSNAPGLVMASQANYFRVRLLPEQEEGELESWSPNVRHTTLLCKPRAMLSKLQM
RVMVGDRVIVTAIDPVNMTVHAPPFDPLPATRFLVAGEAADMDITVVLNKADLVPEEESAALAQEVAS
WGPVVLTSTLTGRGLQELERQLGSTTAVLAGPSGAGKSSIINALARAARERPSDASVSNVPEEQVVGE
DGRALANPPPFTLADIRNAIPKDCFRKSAAKSLAYLGDLSITGMAVLAYKINSPWLWPLYWFAQGTMF
WALFVVGHDCGHQSFSTSKRLNDALAWLGALAAGTWTWALGVLPMLNLYLAPYVWLLVTYLHHHGPSD
PREEMPWYRGREWSYMRGGLTTIDRDYGLFNKVHHDIGTHVVHH SEQ ID NO: 36
MFWALFVVGHDCGHQSFSTSKRLNDAVGLFVHSIIGVPYHGWRISHRTHHNNHGHVENDESWYPPTES
GLKAMTDMGRQGRFHFPSMLFVYPFYLFWRSPGKTGSHFSPATDLFALWEAPLIRTSNACQLAWLGAL
AAGTWALGVLPMLNLYLAPYVISVAWLDLVTYLHHHGPSDPREEMPWYRGREWSYMRGGLTTIDRDYG
LFNKVHHDIGTHVVHHLFPQIPHYNLCRATKAAKKVLGPYYREPERCPLGLLPVHLLAPLLRSLGQDH
FVDDAGSVLFYRRAEGINPWIQKLLPWLGGARRGADAQRDAAQ SEQ ID NO: 37
Camelina sativa omega-3 FAD7-2
MANLVLSECGIRPLPRIYTTPRSNFVSNNNKPIFKFRPFTSYKTSSSPLACSRDGFGKNWSLNVSVPL
TTTTPIVDESPLKEEEEEKQRFDPGAPPPFNLADIRAAIPKHCWVKNPWKSMSYVLRDVAIVFALAAG
ASYLNNWIVWPLYWLAQGTMFWALFVLGHDCGHGSFSNNPRLNNVVGHLLHSSILVPYHGWRISHRTH
HQNHGHVENDESWHPMSEKIYQSLDKPTRFFRFTLPLVMLAYPFYLWARSPGKKGSHYHPESDLFLPK
EKTDVLTSTACWTAMAALLICLNFVVGPVQMLKLYGIPYWINVMWLDFVTYLHHHGHEDKLPWYRGKE
WSYLRGGLTTLDRDYGVINNIHHDIGTHVIHHLFPQIPHYHLVEATEAVKPVLGKYYREPDKSGPLPL
HLLGILAKSIKEDHYVSDEGDVVYYKADPNMYGEIKVGAD -continued

SEQUENCE LISTING

SEQ ID NO: 38
*Prototheca moriformis* delta 12 desaturase allele 2
MAIKTNRQPVEKPPFTIGTLRKAIPAHCFERSALRSSMYLAFDIAVMSLLYVASTYIDPAPVPTWVKY
GIMWPLYWFFQGAFGTGVWVCAHECGHQAFSSSQAINDGVGLVFHSLLLVPYYSWKHSHRRHHSNTGC
LDKDEVFVPPHRAVAHEGLEWEEWLPIRMGKVLVTLTLGWPLYLMFNVASRPYPRFANHFDPWSPIFS
KRERIEVVISDLALVAVLSGLSVLGRTMGWAWLVKTYVVPYMIVNMWLVLITLLQHTHPALPHYFEKD
WDWLRGAMATVDRSMGPPFMDSILHHISDTHVLHHLFSTIPHYHAEEASAAIRPILGKYYQSDSRWVG
RALWEDWRDCRYVVPDAPEDDSALWFHK SEQ ID NO: 39
Camelina sativa omega-3 FAD7-1
MANLVLSECGIRPLPRIYTTPRSNFVSNNNKPIFKFRPLTSYKTSSPLFCSRDGFGRNWSLNVSVPLA
TTTPIVDESPLEEEEEEEKQRFDPGAPPPFNLADIRAAIPKHCWVKNPWKSMSYVLRDVAIVFALAAG
AAYLNNWIVWPLYWLAQGTMFWALFVLGHDCGHGSFSNNPRLNNVVGHLLHSSILVPYHGWRISHRTH
HQNHGHVENDESWHPMSEKIYQSLDKPTRFFRFTLPLVMLAYPFYLWARSPGKKGSHYHPESDLFLPK
EKTDVLTSTACWTAMAALLICLNFVVGPVQMLKLYGIPYWINVMWLDFVTYLHHHGHEDKLPWYRGKE
WSYLRGGLTTLDRDYGVINNIHHDIGTHVIHHLFPQIPHYHLVEATEAVKPVLGKYYREPDKSGPLPL
HLLGILAKSIKEDHYVSDEGDVVYYKADPNMYGEIKVGAD SEQ ID NO: 40
PmFATA-hpB
actagtCATTCGGGGCAACGAGGTGGGCCCCTCGCAGCGGCTGACGATCACGGCGGTGGCCAACATCC
TGCAGGAGGCGGCGGGCAACCACGCGGTGGCCATGTGGGGCCGGAGCGTGTGTTTGAGGGTTTTGGTT
GCCCGTATTGAGGTCCTGGTGGCGCGCATGGGGGAGAAGGCGCCTGTCCCGCTGACCCCCCCGGCTAC
CCTCCCGGCACCTTCCAGGGCGCGTACGggatccGCTCCGGCCCCACATGGCCACCGCGTGGTTGCCC
GCCGCCTCCTGCAGGATGTTGGCCACCGCCGTGATCGTCAGCCGCTGCGAGGGGCCCACCTCGTTGCC
CCGAATGaagctt SEQ ID NO: 41
PmFATA-hpC
actagtGGAGGGTTTCGCGACGGACCCGGAGCTGCAGGAGGCGGGTCTCATCTTTGTGATGACGCGCA
TGCAGATCCAGATGTACCGCTACCCGCGCTGGGGCGACCTGATGCAGGTGGAGACCTGGTTCCAGAGT
GTGTTTGAGGGTTTTGGTTGCCCGTATTGAGGTCCTGGTGGCGCGCATGGGGGAGAAGGCGCCTGTCC
CGCTGACCCCCCCGGCTACCCTCCCGGCACCTTCCAGGGCGCGTACGggatccTCTGGAACCAGGTCT
CCACCTGCATCAGGTCGCCCCAGCGCGGGTAGCGGTACATCTGGATCTGCATGCGCGTCATCACAAAG
ATGAGACCCGCCTCCTGCAGCTCCGGGTCCGTCGCGAAACCCTCCaagctt SEQ ID NO: 42
PmFATA-hpD
actagtCGGCGGGCAAGCTGGGCGCGCAGCGCGAGTGGGTGCTGCGCGACAAGCTGACCGGCGAGGCG
CTGGGCGCGGCCACCTCGAGCTGGGTCATGATCAACATCCGCACGCGCCGGCCGTGCCGCATGCCGGG
TGTGTTTGAGGGTTTTGGTTGCCCGTATCGAGGTCCTGGTGGCGCGCATGGGGGAGAAGGCGCCTGTC
CCGCTGACCCCCCCGGCTACCCTCCCGGCACCTTCCAGGGCGCGTACGggatccCCGGCATGCGGCAC
GGCCGGCGCGTGCGGATGTTGATCATGACCCAGCTCGAGGTGGCCGCGCCCAGCGCCTCGCCGGTCAG
CTTGTCGCGCAGCACCCACTCGCGCTGCGCGCCCAGCTTGCCCGCCGaagctt SEQ ID NO: 43
PmFATA-hpE
actagtGTCCGCGTCAAGTCGGCCTTCTTCGCGCGCGAGCCGCCGCGCCTGGCGCTGCCGCCCGCGGT
CACGCGTGCCAAGCTGCCCAACATCGCGACGCCGGCGCCGCTGCGCGGGCACCGCCAGGTCGCGCGCC
GCACCGACATGGACATGAACGGGCACGTGAACAACGTGGCCTACCTGGCCTGGTGCCTGGAGTGTGTT
TGAGGGTTTTGGTTGCCCGTATTGAGGTCCTGGTGGCGCGCATGGGGGAGAAGGCGCCTGTCCCGCTG
ACCCCCCCGGCTACCCTCCCGGCACCTTCCAGGGCGCGTACGggatccTCCAGGCACCAGGCCAGGTA
GGCCACGTTGTTCACGTGCCCGTTCATGTCCATGTCGGTGCGGCGCGCGACCTGGCGGTGCCCGCGCA
GCGGCGCCGGCGTCGCGATGTTGGGCAGCTTGGCACGCGTGACCGCGGGCGGCAGCGCCAGGCGCGGC
GGCTCGCGCGCGAAGAAGGCCGACTTGACGCGGACaagctt SEQ ID NO: 44
PmFATA-hpF
actagtCCGTGCCCGAGCACGTCTTCAGCGACTACCACCTCTACCAGATGGAGATCGACTTCAAGGCC
GAGTGCCACGCGGGCGACGTCATCTCCTCCCAGGCCGAGCAGATCCCGCCCCAGGAGGCGCTCACGCA
CAACGGCGCCGGCCGCAACCCCTCCTGCTTCGTCCATAGCATTCTGCGCGCCGAGACCGAGCGTGTGT
TTGAGGGTTTTGGTTGCCCGTATCGAGGTCCTGGTGGCGCGCATGGGGGAGAAGGCGCCTGTCCCGCT
GACCCCCCCGGCTACCCTCCCGGCACCTTCCAGGGCGCGTACGggatccGCTCGGTCTCGGCGCGCAG
AATGCTATGGACGAAGCAGGAGGGGTTGCGGCCGGCGCCGTTGTGCGTGAGCGCCTCCTGGGGCGGGA
TCTGCTCGGCCTGGGAGGAGATGACGTCGCCCGCGTGGCACTCGGCCTTGAAGTCGATCTCCATCTGG
TAGAGGTGGTAGTCGCTGAAGACGTGCTCGGGCACGGaagctt SEQ ID NO: 45
PmFATA-hpG
actagtTCGTCCGCGCGCGAACCACATGGTCGGCCCCCATCGACGCGCCCGCCGCCAAGCCGCCCAAG
GCGAGCCACTGAGGACAGGGTGGTTGGCTGGATGGGGAAACGCTGGTCGCGGGATTCGATCCTGCTGC
TTATATCCTCGTGTGTTTGAGGGTTTTGGTTGCCCGTATTGAGGTCCTGGTGGCGCGCATGGGGGAGA
AGGCGCCTGTCCCGCTGACCCCCCCGGCTACCCTCCCGGCACCTTCCAGGGCGCGTACGggatccGAG -continued

SEQUENCE LISTING

GATATAAGCAGCAGGATCGAATCCCGCGACCAGCGTTTCCCCATCCAGCCAACCACCCTGTCCTCAGT
GGCTCGCCTTGGGCGGCTTGGCGGCGGGCGCGTCGATGGGGGCCGACCATGTGGTTCGCGCGCGGACG
Aaagctt SEQ ID NO: 46
Codon-optimized *Cuphea wrightii* KASAI
ATGGCCGCCGCCGCCAGCATGGTGGCCAGCCCCTTCTGCACCTGGCTGGTGGCCAGCTGCATGAGCAC
CAGCTTCGACAACGACCCCCGCAGCCCCAGCGTGAAGCGCTTCCCCCGCCGCAAGCGCGTGCTGAGCC
AGCGCGGCAGCACCTACGTATTCCAGTGCCTGGTGGCCAGCTGCATCGACCCCTGCGACCAGTACCGC
AGCAGCGCCAGCCTGAGCTTCCTGGGCGACAACGGCTTCGCCAGCCTGTTCGGCAGCAAGCCCTTCAT
GAGCAACCGCGGCCACCGCCGCCTGCGCCGCGCCAGCCACAGCGGCGAGGCCATGGCCGTGGCCCTGC
AGCCCGCCCAGGAGGCCGGCACCAAGAAGAAGCCCGTGATCAAGCAGCGCCGCGTGGTGGTGACCGGC
ATGGGCGTGGTGACCCCCCTGGGCCACGAGCCCGACGTGTTCTACAACAACCTGCTGGACGGCGTGAG
CGGCATCAGCGAGATCGAGACCTTCGACTGCACCCAGTTCCCCACCCGCATCGCCGGCGAGATCAAGA
GCTTCAGCACCGACGGCTGGGTGGCCCCCAAGCTGAGCAAGCGCATGGACAAGTTCATGCTGTACCTG
CTGACCGCCGGCAAGAAGGCCCTGGCCGACGGCGGCATCACCGACGAGGTGATGAAGGAGCTGGACAA
GCGCAAGTGCGGCGTGCTGATCGGCAGCGGCATGGGCGGCATGAAGGTGTTCAACGACGCCATCGAGG
CCCTGCGCGTGAGCTACAAGAAGATGAACCCCTTCTGCGTGCCCTTCGCCACCACCAACATGGGCAGC
GCCATGCTGGCCATGGACCTGGGCTGGATGGGCCCCAACTACAGCATCAGCACCGCCTGCGCCACCAG
CAACTTCTGCATCCTGAACGCCGCCAACCACATCATCCGCGGCGAGGCCGACATGATGCTGTGCGGCG
GCAGCGACGCCGTGATCATCCCCATCGGCCTGGGCGGCTTCGTGGCCTGCCGCGCCCTGAGCCAGCGC
AACAGCGACCCCACCAAGGCCAGCCGCCCCTGGGACAGCAACCGCGACGGCTTCGTGATGGGCGAGGG
CGCCGGCGTGCTGCTGCTGGAGGAGCTGGAGCACGCCAAGAAGCGCGGCGCCACCATCTACGCCGAGT
TCCTGGGCGGCAGCTTCACCTGCGACGCCTACCACATGACCGAGCCCCACCCCGAGGGCGCCGGCGTG
ATCCTGTGCATCGAGAAGGCCCTGGCCCAGGCCGGCGTGAGCAAGGAGGACGTGAACTACATCAACGC
CCACGCCACCAGCACCAGCGCCGGCGACATCAAGGAGTACCAGGCCCTGGCCCGCTGCTTCGGCCAGA
ACAGCGAGCTGCGCGTGAACAGCACCAAGAGCATGATCGGCCACCTGCTGGGCGCCGCCGGCGGCGTG
GAGGCCGTGACCGTGGTGCAGGCCATCCGCACCGGCTGGATTCACCCCAACCTGAACCTGGAGGACCC
CGACAAGGCCGTGGACGCCAAGCTGCTGGTGGGCCCCAAGAAGGAGCGCCTGAACGTGAAGGTGGGCC
TGAGCAACAGCTTCGGCTTCGGCGGCCACAACAGCAGCATCCTGTTCGCCCCCTGCAACGTGTGA SEQ ID NO: 47
Codon-optimized *Cuphea wrightii* KASAI with *P. moriformis* SAD
transit peptide
ATGGGCCGCGGTGTCTCCCTTCCCCGGCCCAGGGTCGCGGTGCGCGCCCAGTCGGCGAGTCAGGTTTT
GGAGAGCTGTATTCCAGTGCCTGGTGGCCAGCTGCATCGACCCCTGCGACCAGTACCGCAGCAGCGCC
AGCCTGAGCTTCCTGGGCGACAACGGCTTCGCCAGCCTGTTCGGCAGCAAGCCCTTCATGAGCAACCG
CGGCCACCGCCGCCTGCGCCGCGCCAGCCACAGCGGCGAGGCCATGGCCGTGGCCCTGCAGCCCGCCC
AGGAGGCCGGCACCAAGAAGAAGCCCGTGATCAAGCAGCGCCGCGTGGTGGTGACCGGCATGGGCGTG
GTGACCCCCCTGGGCCACGAGCCCGACGTGTTCTACAACAACCTGCTGGACGGCGTGAGCGGCATCAG
CGAGATCGAGACCTTCGACTGCACCCAGTTCCCCACCCGCATCGCCGGCGAGATCAAGAGCTTCAGCA
CCGACGGCTGGGTGGCCCCCAAGCTGAGCAAGCGCATGGACAAGTTCATGCTGTACCTGCTGACCGCC
GGCAAGAAGGCCCTGGCCGACGGCGGCATCACCGACGAGGTGATGAAGGAGCTGGACAAGCGCAAGTG
CGGCGTGCTGATCGGCAGCGGCATGGGCGGCATGAAGGTGTTCAACGACGCCATCGAGGCCCTGCGCG
TGAGCTACAAGAAGATGAACCCCTTCTGCGTGCCCTTCGCCACCACCAACATGGGCAGCGCCATGCTG
GCCATGGACCTGGGCTGGATGGGCCCCAACTACAGCATCAGCACCGCCTGCGCCACCAGCAACTTCTG
CATCCTGAACGCCGCCAACCACATCATCCGCGGCGAGGCCGACATGATGCTGTGCGGCGGCAGCGACG
CCGTGATCATCCCCATCGGCCTGGGCGGCTTCGTGGCCTGCCGCGCCCTGAGCCAGCGCAACAGCGAC
CCCACCAAGGCCAGCCGCCCCTGGGACAGCAACCGCGACGGCTTCGTGATGGGCGAGGGCGCCGGCGT
GCTGCTGCTGGAGGAGCTGGAGCACGCCAAGAAGCGCGGCGCCACCATCTACGCCGAGTTCCTGGGCG
GCAGCTTCACCTGCGACGCCTACCACATGACCGAGCCCCACCCCGAGGGCGCCGGCGTGATCCTGTGC
ATCGAGAAGGCCCTGGCCCAGGCCGGCGTGAGCAAGGAGGACGTGAACTACATCAACGCCCACGCCAC
CAGCACCAGCGCCGGCGACATCAAGGAGTACCAGGCCCTGGCCCGCTGCTTCGGCCAGAACAGCGAGC
TGCGCGTGAACAGCACCAAGAGCATGATCGGCCACCTGCTGGGCGCCGCCGGCGGCGTGGAGGCCGTG
ACCGTGGTGCAGGCCATCCGCACCGGCTGGATTCACCCCAACCTGAACCTGGAGGACCCCGACAAGGC
CGTGGACGCCAAGCTGCTGGTGGGCCCCAAGAAGGAGCGCCTGAACGTGAAGGTGGGCCTGAGCAACA
GCTTCGGCTTCGGCGGCCACAACAGCAGCATCCTGTTCGCCCCCTGCAACGTGTGA SEQ ID NO: 48
Codon-optimized *Cuphea pulcherrima* KASIV
ATGCCCGCGGCCAGCTCGCTGCTGGCGTCCCCCCTGTGCACCTGGCTGCTGGCCGCGTGCATGAGCAC
CTCGTTCCACCCCTCCGACCCCCTGCCCCCCAGCATCTCGTCCCCCCGCCGCCGCCTGAGCCGCCGCC
GCATCCTGTCGCAGTGCGCCCCCCTGCCCTCCGCGAGCTCGGCCCTGCGCGGCTCCAGCTTCCACACC
CTGGTGACCTCGTATCTGGCGTGCTTCGAGCCCTGCCACGACTATTATACCAGCGCCTCCCTGTTCGG
CTCGCGCCCCATCCGCACCACCCGCCGCCACCGCCGCCTGAACCGCGCGAGCCCCTCGCGCGAGGCGA
TGGCGGTCGCCCTGCAGCCCGAGCAGGAGGTGACCACCAAGAAGAAGCCCTCCATCAAGCAGCGCCGC
GTCGTGGTCACCGGCATGGGCGTGGTCACCCCCCTGGGCCACGACCCCGACGTGTTCTATAACAACCT
GCTGGACGGCACCAGCGGCATCTCGGAGATCGAGACCTTCGACTGCGCGCAGTTCCCCACCCGCATCG
CCGGCGAGATCAAGTCCTTCAGCACCGACGGCTGGGTCGCGCCCAAGCTGTCGAAGCGCATGGACAAG
TTCATGCTGTATATGCTGACCGCCGGCAAGAAGGCGCTGACCGACGGCGGCATCACCGAGGACGTGAT
GAAGGAGCTGGACAAGCGCAAGTGCGGCGTCCTGATCGGCTCCGCGATGGGCGGCATGAAGGTGTTCA
ACGACGCGATCGAGGCCCTGCGCATCAGCTATAAGAAGATGAACCCCTTCTGCGTGCCCTTCGCGACC
ACCAACATGGGCTCGGCCATGCTGGCGATGGACCTGGGCTGGATGGGCCCCAACTATTCCATCAGCAC
CGCCTGCGCGACCTCGAACTTCTGCATCATGAACGCGGCCAACCACATCATCCGCGGCGAGGCGGACG
TCATGCTGTGCGGCGGCTCCGACGCCGTGATCATCCCCATCGGCATGGGCGGCTTCGTCGCGTGCCGC
GCCCTGAGCCAGCGCAACTCGGACCCCACCAAGGCGTCCCGCCCCTGGGACAGCAACCGCGACGGCTT
CGTGATGGGCGAGGGCGCCGGCGTCCTGCTGCTGGAGGAGCTGGAGCACGCGAAGAAGCGCGGCGCCA -continued

SEQUENCE LISTING

CCATCTATGCGGAGTTCCTGGGCGGCTCGTTCACCTGCGACGCCTATCACATGACCGAGCCCCACCCC
GACGGCGCCGGCGTGATCCTGTGCATCGAGAAGGCGCTGGCCCAGTCCGGCGTCAGCCGCGAGGACGT
GAACTATATCAACGCGCACGCCACCTCGACCCCCGCGGGCGACATCAAGGAGTATCAGGCCCTGATCC
ACTGCTTCGGCCAGAACCGCGAGCTGAAGGTCAACTCCACCAAGAGCATGATCGGCCACCTGCTGGGC
GCGGCGGGCGGCGTGGAGGCGGTCTCGGTGGTCCAGGCCATCCGCACCGGCTGGATCCACCCCAACAT
CAACCTGGAGAACCCCGACGAGGGCGTGGACACCAAGCTGCTGGTGGGCCCCAAGAAGGAGCGCCTGA
ACGTCAAGGTGGGCCTGTCCAACAGCTTCGGCTTCGGCGGCCACAACTCGTCCATCCTGTTCGCGCCC
TATATCTGA

SEQ ID NO: 49
Codon-optimized *Cuphea hookeriana* KASIV
ATGGTGGCCGCCGCCGCCTCCAGCGCCTTCTTCCCCGTGCCCGCCCCCGGCGCCTCCCCCAAGCCCGG
CAAGTTCGGCAACTGGCCCTCCAGCCTGAGCCCCTCCTTCAAGCCCAAGTCCATCCCCAACGGCGGCT
TCCAGGTGAAGGCCAACGACAGCGCCCACCCCAAGGCCAACGGCTCCGCCGTGAGCCTGAAGAGCGGC
AGCCTGAACACCCAGGAGGACACCTCCTCCAGCCCCCCCCCCCGCACCTTCCTGCACCAGCTGCCCGA
CTGGAGCCGCCTGCTGACCGCCATCACCACCGTGTTCGTGAAGTCCAAGCGCCCCGACATGCACGACC
GCAAGTCCAAGCGCCCCGACATGCTGGTGGACAGCTTCGGCCTGGAGTCCACCGTGCAGGACGGCCTG
GTGTTCCGCCAGTCCTTCTCCATCCGCTCCTACGAGATCGGCACCGACCGCACCGCCAGCATCGAGAC
CCTGATGAACCACCTGCAGGAGACCTCCCTGAACCACTGCAAGAGCACCGGCATCCTGCTGGACGGCT
TCGGCCGCACCCTGGAGATGTGCAAGCGCGACCTGATCTGGGTGGTGATCAAGATGCAGATCAAGGTG
AACCGCTACCCCGCCTGGGGCGACACCGTGGAGATCAACACCCGCTTCAGCCGCCTGGGCAAGATCGG
CATGGGCCGCGACTGGCTGATCTCCGACTGCAACACCGGCGAGATCCTGGTGCGCGCCACCAGCGCCT
ACGCCATGATGAACCAGAAGACCCGCCGCCTGTCCAAGCTGCCCTACGAGGTGCACCAGGAGATCGTG
CCCCTGTTCGTGGACAGCCCCGTGATCGAGGACTCCGACCTGAAGGTGCACAAGTTCAAGGTGAAGAC
CGGCGACAGCATCCAGAAGGGCCTGACCCCCGGCTGGAACGACCTGGACGTGAACCAGCACGTGTCCA
ACGTGAAGTACATCGGCTGGATCCTGGAGAGCATGCCCACCGAGGTGCTGGAGACCCAGGAGCTGTGC
TCCCTGGCCCTGGAGTACCGCCGCGAGTGCGGCCGCGACTCCGTGCTGGAGAGCGTGACCGCCATGGA
CCCCAGCAAGGTGGGCGTGCGCTCCCAGTACCAGCACCTGCTGCGCCTGGAGGACGGCACCGCCATCG
TGAACGGCGCCACCGAGTGGCGCCCCAAGAACGCCGGCGCCAACGGCGCCATCTCCACCGGCAAGACC
AGCAACGGCAACTCCGTGTCCATGTGA SEQ ID NO: 50
*Protheca moriformis* (UTEX 1435) KAS1 allele 1 5' donor sequence
gctcttcctcaccgcgtgaattgctgtcccaaacgtaagcatcatcgtggctcggtcacgcgatcctg
gatccggggatcctagaccgctggtggagagcgctgccgtcggattggtggcaagtaagattgcgcag
gttggcgaagggagagaccaaaaccggaggctggaagcgggcacaacatcgtattattgcgtatagta
gagcagtggcagtcgcatttcgaggtccgcaacggatctcgcaagctcgctacgctcacagtaggaga
aaggggaccactgcccctgccagaatggtcgcgaccctctccctcgccggccccgcctgcaacacgca
gtgcgtatccggcaagcgggctgtcgccttcaaccgcccccatgttggcgtccgggctcgatcaggtg
cgctgaggggggtttggtgtgcccgcgcctctgggcccgtgtcggccgtgcggacgtggggccctggg
cagtggatcagcagggtttgcgtgcaaatgcctataccggcgattgaatagcgatgaacgggatacgg
ttgcgctcactccatgcccatgcgaccccgtttctgtccgccagccgtggtcgcccgggctgcgaagc
gggaccccacccagcgcattgtgatcaccggaatgggcgtgggtacc SEQ ID NO: 51
*Protheca moriformis* (UTEX 1435) KAS1 allele 1 3' donor sequence
gagctccacctgcatccgcctggcgctcgaggacgccggcgtctcgcccgacgaggtcaactacgtca
acgcgcacgccacctccaccctggtgggcgacaaggccgaggtgcgcgcggtcaagtcggtctttggc
gacatgaagggcatcaagatgaacgccaccaagtccatgatcgggcactgcctgggcgccgccggcgg
catggaggccgtcgccacgctcatggccatccgcaccggctgggtgcaccccaccatcaaccacgaca
accccatcgccgaggtcgacggcctggacgtcgtcgccaacgccaaggcccagcacaaaatcaacgtc
gccatctccaactccttcggcttcggcgggcacaactccgtcgtcgcctttgcgcccttccgcgagta
ggcggagcgagcgcgcttggctgaggagggaggcggggtgcgagccctttggctgcgcgcgatactct
ccccgcacgagcagactccacgcgcctgaatctacttgtcaacgagcaaccgtgtgttttgtccgtgg
ccattcttattatttctccgactgtggccgtactctgtttggctgtgcaagcaccgaagagcc SEQ ID NO: 52
*Protheca moriformis* (UTEX 1435) KAS1 allele 2 5' donor sequence
gctcttcgcgcaagctcgctacgctcacagtaggagataggggaccactgcccctgccagaatggtcg
cgaccctgtccctcgccggccccgcctgcaacacgcagtgcgtatccagcaagcgggttgtcgccttc
aaccgcccccatgttggcgtccgggctcgatcaggtgcgctgaggggggtttggtgggcccgcgcctc
tgggcccgtgtcggccgtgcggacgtggggcccggggtagtggatcagcaggggttgcatgcaaatgc
ctataccggcgattgaatagcgatgaacgggatacggttgcgctcactccatgcccatgcgaccccgt
ttctgtccgccagccgtggtcgcccgagctgcgaagcgggaccccacccagcgcattgtgatcaccgg
aatgggcgtggcctccgtgtttggcaacgatgtcgagaccttttacgacaagcttctggaaggaacga
gcggcgtggacctgatttccaggtgcgtaggtccttggatgaatgcgtctaggttgcgaggtgactgg
ccaggaagcagcaggcttggggtttggtgttctgatttctggtaatttgaggtttcattataagattc
tgtacggtcttgtttcggggtacc SEQ ID NO: 53
*Protheca moriformis* (UTEX 1435) KAS1 allele 2 3' donor sequence
gagctccacctgcatccgcctggcgctcgaggacgccggcgtctcgcccgacgaggtcaactacgtca
acgcgcacgccacctccaccctggtgggcgacaaggccgaggtgcgcgcggtcaagtcggtctttggc
gacatgaagggcatcaagatgaacgccaccaagtccatgatcgggcactgcctgggcgccgccggcgg
catggaggccgtcgccacgctcatggccatccgcaccggctgggtgcaccccaccatcaaccacgaca
accccatcgccgaggtcgacggcctggacgtcgtcgccaacgccaaggcccagcacaaaatcaacgtc
gccatctccaactccttcggcttcggcgggcacaactccgtcgtcgcctttgcgcccttccgcgagta -continued

SEQUENCE LISTING ggcggagcgagcgcgcttggctgaggagggaggcggggtgcgagccctttggctgcgcgcgatactct
ccccgcacgagcagactccacgcgcctgaatctacttgtcaacgagcaaccgtgtgttttgtccgtgg
ccattcttattatttctccgactgtggccgtactctgtttggctgtgcaagcaccgaagagcc SEQ ID NO: 54
*Prototheca moriformis* (UTEX 1435) KASI-hairpin B
actagtcaTGGTCGCCCGGGCTGCGAAGCGGGACCCCACCCAGCGCATTGTGATCACCGGAATGGGCG
TGGCCTCCGTGTTTGGCAACGATGTCGAGACCTTTTACAgtgtgtttgagggttttggttgcccgtat
tgaggtcctggtggcgcgcatggaggagaaggcgcctgtcccgctgacccccccggctaccctcccgg
caccttccagggcgcgtacgggatccTGTAAAAGGTCTCGACATCGTTGCCAAACACGGAGGCCACGC
CCATTCCGGTGATCACAATGCGCTGGGTGGGGTCCCGCTTCGCAGCCCGGGCGACCAaagctt SEQ ID NO: 55
*Prototheca moriformis* (UTEX 1435) KASI-hairpin C
actagtcaTTGACATCTCCGAGTTCCCGACCAAGTTTGCGGCGCAGATCACCGGCTTCTCCGTGGAGG
ACTGCGTGGACAAGAAGAACGCGCGGCGGTACGACGACGCGCTGTCGTACGCGATGGTGGCCTCCAAG
AAGGCCCTGCGCCAGGCGGGACTGGAGAAGGACAAGTGCCCCGAGGGCTACGGAGgtgtgtttgaggg
ttttggttgcccgtattgaggtcctggtggcgcgcatggaggagaaggcgcctgtcccgctgaccccc
ccggctaccctcccggcaccttccagggcgcgtacgggatccCTCCGTAGCCCTCGGGGCACTTGTCC
TTCTCCAGTCCCGCCTGGCGCAGGGCCTTCTTGGAGGCCACCATCGCGTACGACAGCGCGTCGTCGTA
CCGCCGCGCGTTCTTCTTGTCCACGCAGTCCTCCACGGAGAAGCCGGTGATCTGCGCCGCAAACTTGG
TCGGGAACTCGGAGATGTCAAaagctt SEQ ID NO: 56
*Prototheca moriformis* (UTEX 1435) KASI-hairpin D
actagtcaTGGGCGTGAGCACCTGCATCCGCCTGGCGCTCGAGGACGCCGGCGTCTCGCCCGACGAGG
TCAACTACGTCAACGCGCACGCCACCTCCACCCTGGTGGGCGACAAGGCCGAGGTGCGCGCGGTCAAG
TCGGTCTTTGGCGACATGAAGGGCATCAAGATgtgtgtttgagggttttggttgcccgtattgaggtc
ctggtggcgcgcatggaggagaaggcgcctgtcccgctgacccccccggctaccctcccggcaccttc
cagggcgcgtacgggatccATCTTGATGCCCTTCATGTCGCCAAAGACCGACTTGACCGCGCGCACCT
CGGCCTTGTCGCCCACCAGGGTGGAGGTGGCGTGCGCGTTGACGTAGTTGACCTCGTCGGGCGAGACG
CCGGCGTCCTCGAGCGCCAGGCGGATGCAGGTGCTCACGCCCAaagctt SEQ ID NO: 57
*Prototheca moriformis* (UTEX 1435) KASI-hairpin E
actagtcaCAACCATCAACCACGACAACCCCATCGCCGAGGTCGACGGCCTGGACGTCGTCGCCAACG
CCAAGGCCCAGCACAAAATCAACGTCGCCATCTCCAACTCCTTCGgtgtgtttgagggttttggttgc
ccgtattgaggtcctggtggcgcgcatggaggagaaggcgcctgtcccgctgacccccccggctaccc
tcccggcaccttccagggcgcgtacgggatccCGAAGGAGTTGGAGATGGCGACGTTGATTTTGTGCT
GGGCCTTGGCGTTGGCGACGACGTCCAGGCCGTCGACCTCGGCGATGGGGTTGTCGTGGTTGATGGTa
agctt SEQ ID NO: 58
Codon optimized *M. polymorpha* FAE3 (GenBank Accession No. AAP74370)
ATGgactcccgcgcccagaaccgcgacggcggcgaggacgtgaagcaggagctgctgtccgccggcga
cgacggcaaggtgccctgccccaccgtggccatcggcatccgccagcgcctgcccgacttcctgcagt
ccgtgaacatgaagtacgtgaagctgggctaccactacctgatcacccacgccatgttcctgctgacc
ctgcccgccttcttcctggtggccgccgagatcggccgcctgggccacgagcgcatctaccgcgagct
gtggacccacctgcacctgaacctggtgtccatcatggcctgctcctccgccctggtggccggcgcca
ccctgtacttcatgtcccgcccccgccccgtgtacctggtggagttcgcctgctaccgccccgacgag
cgcctgaaggtgtccaaggacttcttcctggacatgtcccgccgcaccggcctgttctcctcctcctc
catggacttccagaccaagatcacccagcgctccggcctgggcgacgagacctacctgcccccgcca
tcctggcctcccccccaacccctgcatgcgcgaggcccgcgaggaggccgccatggtgatgttcggc
gccctggacgagctgttcgagcagaccggcgtgaagcccaaggagatcggcgtgctggtggtgaactg
ctccctgttcaaccccacccctccatgtccgccatgatcgtgaaccactaccacatgcgcggcaaca
tcaagtccctgaacctgggcggcatgggctgctccgccggcctgatctccatcgacctggcccgcgac
ctgctgcaggtgcacggcaacacctacgccgtggtggtgtccaccgagaacatcaccctgaactggta
cttcggcgacgaccgctccaagctgatgtccaactgcatcttccgcatgggcggcgccgccgtgctgc
tgtccaacaagcgccgcgagcgccgccgcgccaagtacgagctgctgcacaccgtgcgcacccacaag
ggcgccgacgacaagtgcttccgctgcgtgtaccaggaggaggactccaccggctccctgggcgtgtc
cctgtcccgcgagctgatggccgtggccggcaacgccctgaaggccaacatcaccaccctgggccccc
tggtgctgcccctgtccgagcagatcctgttcttcgcctccctggtggcccgcaagttcctgaacatg
aagatgaagccctacatccccgacttcaagctggccttcgagcacttctgcatccacgccggcggccg
cgccgtgctggacgagctggagaagaacctggacctgaccgagtggcacatggagccctcccgcatga
ccctgtaccgcttcggcaacacctcctcctcctccctgtggtacgagctggcctacaccgaggcccag
ggccgcgtgaagcgcggcgaccgcctgtggcagatcgccttcggctccggcttcaagtgcaactccgc
cgtgtggcgcgcgctgcgcaccgtgaagcccccgtgaacaacgcctggtccgacgtgatcgaccgct
tccccgtgaagctgccccagttcTGA

SEQ ID NO: 59
*M. polymorpha* FAE3 (GenBank Accession No. AAP74370)
MDSRAQNRDGGEDVKQELLSAGDDGKVPCPTVAIGIRQRLPDFLQSVNMKYVKLGYHYLITHAMFLLT
LPAFFLVAAEIGRLGHERIYRELWTHLHLNLVSIMACSSALVAGATLYFMSRPRPVYLVEFACYRPDE
RLKVSKDFFLDMSRRTGLFSSSSMDFQTKITQRSGLGDETYLPPAILASPPNPCMREAREEAAMVMFG
ALDELFEQTGVKPKEIGVLVVNCSLFNPTPSMSAMIVNHYHMRGNIKSLNLGGMGCSAGLISIDLARD
LLQVHGNTYAVVVSTENITLNWYFGDDRSKLMSNCIFRMGGAAVLLSNKRRERRRAKYELLHTVRTHK
GADDKCFRCVYQEEDSTGSLGVSLSRELMAVAGNALKANITTLGPLVLPLSEQILFFASLVARKFLNM -continued

SEQUENCE LISTING

KMKPYIPDFKLAFEHFCIHAGGRAVLDELEKNLDLTEWHMEPSRMTLYRFGNTSSSSLWYELAYTEAQ
GRVKRGDRLWQTAFGSGFKCNSAVWRALRTVKPPVNNAWSDVIDRFPVKLPQF

SEQ ID NO: 60
*Trypanosoma brucei* ELO3 (GenBank Accession No. AAX70673)
*ATG**ctgatgaacttcggcggctcctacgacgcctacatcaacaacttccagggcaccttcctggccga*
*gtggatgctggaccacccctccgtgccctacatcgccggcgtgatgtacctgatcctggtgctgtacg*
*tgcccaagtccatcatggcctcccagccccccctgaacctgcgcgccgccaacatcgtgtggaacctg*
*ttcctgaccctgttctccatgtgcggcgcctactacaccgtgccctacctggtgaaggccttcatgaa*
*ccccgagatcgtgatggccgcctccggcatcaagctggacgccaacacctcccccatcatcacccact*
*ccggcttctacaccaccacctgcgccctggccgactccttctacttcaacggcgacgtgggcttctgg*
*gtggccctgttcgccctgtccaagatccccgagatgatcgacaccgccttcctggtgttccagaagaa*
*gcccgtgatcttcctgcactggtaccaccacctgaccgtgatgctgttctgctggttcgcctacgtgc*
*agaagatctcctccggcctgtggttcgcctccatgaactactccgtgcactccatcatgtacctgtac*
*tacttcgtgtgcgcctgcggccaccgccgcctggtgcgccccttcgcccccatcatcaccttcgtgca*
*gatcttccagatggtggtgggcaccatcgtggtgtgctacacctacaccgtgaagcacgtgctgggcc*
*gctcctgcaccgtgaccgacttctccctgcacaccggcctggtgatgtacgtgtcctacctgctgctg*
*ttctcccagctgttctaccgctcctacctgtcccccgcgacaaggcctccatcccccacgtggccgc*
*cgagatcaagaagaaggag**TGA*

SEQ ID NO: 61
*Trypanosoma brucei* ELO3 (GenBank Accession No. AAX70673)
MYPTHRDLILNNYSDIYRSPTCHYHTWHILIHTPINELLFPNLPRECDFGYDIPYFRGQIDVFDGWSM
IHFISSNWCIPITVCLCYIMMIAGLKKYMGPRDGGRAPIQAKNYIIAWNLFLSFFSFAGVYYTVPYHL
FDPENGLFAQGFYSTVCNNGAYYGNGNVGFFVWLFIYSKIFELVDIFFLLIRKNPVIFLHWYHHLTVL
LYCWHAYSVRIGIGIWFATMNYSVHSVMYLYFAMTQYGPSTKKFAKKFSKFITTIQILQMVVGIIVIF
AAMLYVTFDVPCYTSLANSVLGLMMYASYFVLFVQLYVSHYVSPKHVKQE SEQ ID NO: 62
Codon optimized *Saccharomyces cerevisiae* ELO1 (GenBank Accession
No. P39540)
*ATG**gtgtccgactggaagaacttctgcctggagaaggcctcccgcttccgccccaccatcgaccgccc*
*cttcttcaacatctacctgtgggactacttcaaccgcgccgtgggctgggccaccgccggccgcttcc*
*agcccaaggacttcgagttcaccgtgggcaagcagcccctgtccgagccccgccccgtgctgctgttc*
*atcgccatgtactacgtggtgatcttcggcggccgctccctggtgaagtcctgcaagcccctgaagct*
*gcgcttcatctcccaggtgcacaacctgatgctgacctccgtgtccttcctgtggctgatcctgatgg*
*tggagcagatgctgcccatcgtgtaccgccacggcctgtacttcgccgtgtgcaacgtggagtcctgg*
*acccagcccatggagaccctgtactacctgaactacatgaccaagttcgtggagttcgccgacaccgt*
*gctgatggtgctgaagcaccgcaagctgaccttcctgcacacctaccaccacggcgccaccgccctgc*
*tgtgctacaaccagctggtgggctacaccgccgtgacctgggtgcccgtgaccctgaacctggccgtg*
*cacgtgctgatgtactggtactacttcctgtccgcctccggcatccgcgtgtggtggaaggcctgggt*
*gacccgcctgcagatcgtgcagttcatgctggacctgatcgtggtgtactacgtgctgtaccagaaga*
*tcgtggccgcctacttcaagaacgcctgcacccccagtgcgaggactgcctgggctccatgaccgcc*
*atcgccgccggcgccgccatcctgacctcctacctgttcctgttcatctccttctacatcgaggtgta*
*caagcgcggctccgcctccggcaagaagaagatcaacaagaacaac**TGA*

SEQ ID NO: 63
*Saccharomyces cerevisiae* ELO1 (GenBank Accession No. P39540)
MVSDWKNFCLEKASRFRPTIDRPFFNIYLWDYFNRAVGWATAGRFQPKDFEFTVGKQPLSEPRPVLLF
IAMYYVVIFGGRSLVKSCKPLKLRFISQVHNLMLTSVSFLWLILMVEQMLPIVYRHGLYFAVCNVESW
TQPMETLYYLNYMTKFVEFADTVLMVLKHRKLTFLHTYHHGATALLCYNQLVGYTAVTWVPVTLNLAV
HVLMYWYYFLSASGIRVWWKAWVIRLQIVQFMLDLIVVYYVLYQKIVAAYFKNACTPQCEDCLGSMTA
IAAGAAILTSYLFLFISFYIEVYKRGSASGKKKINKNN SEQ ID NO: 64
Codon optimized *Brassica napus* acyl-ACP thioesterase (GenBank
Accession No. CAA52070) with 3X FLAG Tag
ATGctgaagctgtcctgcaacgtgaccaacaacctgcacaccttctccttcttctccgactcctccct
gttcatccccgtgaaccgccgcaccatcgccgtgtcctccgggcgcgcctcccagctgcgcaagcccg
ccctggacccccctgcgcgccgtgatctccgccgaccagggctccatctcccccgtgaactcctgcacc
cccgccgaccgcctgcgcgccggccgcctgatggaggacggctactcctacaaggagaagttcatcgt
gcgctcctacgaggtgggcatcaacaagaccgccaccgtggagaccatcgccaacctgctgcaggagg
tggcctgcaaccacgtgcagaagtgcggcttctccaccgacggcttcgccaccaccctgaccatgcgc
aagctgcacctgatctgggtgaccgcccgcatgcacatcgagatctacaagtaccccgcctggtccga
cgtggtggagatcgagacctggtgccagtccgagggccgcatcggcacccgccgcgactggatcctgc
gcgactccgccaccaacgaggtgatcggccgcgccacctccaagtgggtgatgatgaaccaggacacc
cgccgcctgcagcgcgtgaccgacgaggtgcgcgacgagtacctggtgttctgcccccgcgagccccg
cctggccttccccgaggagaacaactcctccctgaagaagatccccaagctggaggaccccgcccagt
actccatgctggagctgaagccccgccgcgccgacctggacatgaaccagcacgtgaacaacgtgacc
tacatcggctgggtgctggagtccatcccccaggagatcatcgacacccacgagctgcaggtgatcac
cctggactaccgccgcgagtgccagcaggacgacatcgtggactccctgaccacctccgagatccccg
acgaccccatctccaagttcaccggcaccaacggctccgccatgtcctccatccagggccacaacgag
tcccagttcctgcacatgctgcgcctgtccgagaacggccaggagatcaaccgcggccgcacccagtg
gcgcaagaagtcctcccgcATGGACTACAAGGACCACGACGGCGACTACAAGGACCACGACATCGACT
ACAAGGACGACGACGACAAGTGA -continued

SEQUENCE LISTING

SEQ ID NO: 65
*Brassica napus* acyl-ACP thioesterase (Genbank Accession No. CAA52070) with 3X FLAG Tag
MLKLSCNVTNNLHTFSFFSDSSLFIPVNRRTIAVSS*GRA*SQLRKPALDPLRAVISADQGSISPVNSCT
PADRLRAGRLMEDGYSYKEKFIVRSYEVGINKTATVETIANLLQEVACNHVQKCGFSTDGFATTLTMR
KLHLIWVTARMHIEIYKYPAWSDVVEIETWCQSEGRIGTRRDWILRDSATNEVIGRATSKWVMMNQDT
RRLQRVTDEVRDEYLVFCPREPRLAFPEENNSSLKKIPKLEDPAQYSMLELKPRRADLDMNQHVNNVT
YIGWVLESIPQEIIDTHELQVITLDYRRECQQDDIVDSLTTSEIPDDPISKFTGTNGSAMSSIQGHNE
SQFLHMLRLSENGQEINRGRTQWRKKSSRMDYKDHDGDYKDHDIDYKDDDDK

SEQ ID NO: 66
Codon optimized *Brassica napus* acyl-ACP thioesterase (GenBank Accession No. CAA52070), with UTEX 250 stearoyl-ACP desaturase (SAD) chloroplast transit peptide and 3X FLAG Tag
ATGgccaccgcatccactttctcggcgttcaatgcccgctgcggcgacctgcgtcgctcggcgggctc
cgggccccggcgcccagcgaggcccctccccgtgcgcgggcgcgcctcccagctgcgcaagcccgccc
tggacccccctgcgcgccgtgatctccgccgaccagggctccatctcccccgtgaactcctgcaccccc
gccgaccgcctgcgcgccggccgcctgatggaggacggctactcctacaaggagaagttcatcgtgcg
ctcctacgaggtgggcatcaacaagaccgccaccgtggagaccatcgccaacctgctgcaggaggtgg
cctgcaaccacgtgcagaagtgcggcttctccaccgacggcttcgccaccaccctgaccatgcgcaag
ctgcacctgatctgggtgaccgcccgcatgcacatcgagatctacaagtaccccgcctggtccgacgt
ggtggagatcgagacctggtgccagtccgagggccgcatcggcacccgccgcgactggatcctgcgcg
actccgccaccaacgaggtgatcggccgcgccacctccaagtgggtgatgatgaaccaggacacccgc
cgcctgcagcgcgtgaccgacgaggtgcgcgacgagtacctggtgttctgcccccgcgagccccgcct
ggccttccccgaggagaacaactcctccctgaagaagatccccaagctggaggaccccgcccagtact
ccatgctggagctgaagcccgccgcgccgacctggacatgaaccagcacgtgaacaacgtgacctac
atcggctgggtgctggagtccatcccccaggagatcatcgacacccacgagctgcaggtgatcaccct
ggactaccgccgcgagtgccagcaggacgacatcgtggactccctgaccacctccgagatccccgacg
accccatctccaagttcaccggcaccaacggctccgccatgtcctccatccagggccacaacgagtcc
cagttcctgcacatgctgcgcctgtccgagaacggccaggagatcaaccgcggccgcacccagtggcg
caagaagtcctcccgcATGGACTACAAGGACCACGACGGCGACTACAAGGACCACGACATCGACTACA
AGGACGACGACGACAAGTGA SEQ ID NO: 67
*Brassica napus* acyl-ACP thioesterase (GenBank Accession No. CAA52070) with UTEX 250 stearoyl-ACP desaturase (SAD) chloroplast transit peptide and 3X FLAG ® Tag
MATASTFSAFNARCGDLRRSAGSGPRRPARPLPVR*GRA*SQLRKPALDPLRAVISADQGSISPVNSCTP
ADRLRAGRLMEDGYSYKEKFIVRSYEVGINKTATVETIANLLQEVACNHVQKCGFSTDGFATTLTMRK
LHLIWVTARMHIEIYKYPAWSDVVEIETWCQSEGRIGTRRDWILRDSATNEVIGRATSKWVMMNQDTR
RLQRVTDEVRDEYLVFCPREPRLAFPEENNSSLKKIPKLEDPAQYSMLELKPRRADLDMNQHVNNVTY
IGWVLESIPQEIIDTHELQVITLDYRRECQQDDIVDSLTTSEIPDDPISKFTGTNGSAMSSIQGHNES
QFLHMLRLSENGQEINRGRTQWRKKSSRMDYKDHDGDYKDHDIDYKDDDDK

SEQ ID NO: 68
Codon optimized C. tinctorius FATA (GenBank Accession No. AAA33019) with UTEX 250 stearoyl-ACP desaturase (SAD) chloroplast transit peptide and 3X FLAG ® Tag
*ATG**gccaccgcatccactttctcggcgttcaatgcccgctgcggcgacctgcgtcgctcggcgggctc*
*cgggccccggcgcccagcgaggcccctccccgtgcgcg**ggcgcgcc**gccaccggcgagcagccctccg*
*gcgtggcctccctgcgcgaggccgacaaggagaagtccctgggcaaccgcctgcgcctgggctccctg*
*accgaggacggcctgtcctacaaggagaagttcgtgatccgctgctacgaggtgggcatcaacaagac*
*cgccaccatcgagaccatcgccaacctgctgcaggaggtgggcggcaaccacgcccagggcgtgggct*
*tctccaccgacggcttcgccaccaccaccaccatgcgcaagctgcacctgatctgggtgaccgcccgc*
*atgcacatcgagatctaccgctaccccgcctggtccgacgtgatcgagatcgagacctgggtgcaggg*
*cgagggcaaggtgggcacccgccgcgactggatcctgaaggactacgccaacggcgaggtgatcggcc*
*gcgccacctccaagtgggtgatgatgaacgaggacacccgccgcctgcagaaggtgtccgacgacgtg*
*cgcgaggagtacctggtgttctgcccccgcaccctgcgcctggccttccccgaggagaacaacaactc*
*catgaagaagatccccaagctggaggaccccgccgagtactcccgcctgggcctggtgccccgccgct*
*ccgacctggacatgaacaagcacgtgaacaacgtgacctacatcggctgggccctggagtccatcccc*
*cccgagatcatcgacacccacgagctgcaggccatcaccctggactaccgccgcgagtgccagcgcga*
*cgacatcgtggactccctgacctcccgcgagcccctgggcaacgccgccggcgtgaagttcaaggaga*
*tcaacggctccgtgtcccccaagaaggacgagcaggacctgtcccgcttcatgcacctgctgcgctcc*
*gccggctccggcctggagatcaaccgctgccgcaccgagtggcgcaagaagcccgccaagcgcATGGA*
CTACAAGGACCACGACGGCGACTACAAGGACCACGACATCGACTACAAGGACGACGACGACAAG*TGA*

SEQ ID NO: 69
*C. tinctorius* FATA (GenBank Accession No. AAA33019) with UTEX 250 stearoyl-ACP desaturase (SAD) chloroplast transit peptide
MATASTFSAFNARCGDLRRSAGSGPRRPARPLPVR*GRA*ATGEQPSGVASLREADKEKSLGNRLRLGSL
TEDGLSYKEKFVIRCYEVGINKTATIETIANLLQEVGGNHAQGVGFSTDGFATTTTMRKLHLIWVTAR
MHIEIYRYPAWSDVIEIETWVQGEGKVGTRRDWILKDYANGEVIGRATSKWVMMNEDTRRLQKVSDDV
REEYLVFCPRTLRLAFPEENNNSMKKIPKLEDPAEYSRLGLVPRRSDLDMNKHVNNVTYIGWALESIP
PEIIDTHELQAITLDYRRECQRDDIVDSLTSREPLGNAAGVKFKEINGSVSPKKDEQDLSRFMHLLRS
AGSGLEINRCRTEWRKKPAKRMDYKDHDGDYKDHDIDYKDDDDK

-continued

SEQUENCE LISTING

SEQ ID NO: 70
Codon optimized *R. communis* FATA (Genbank Accession No. ABS30422) with a 3xFLAG epitope tag

*ATG**ctgaaggtgccctgctgcaacgccaccgaccccatccagtccctgtcctcccagtgccgcttcct gacccacttcaacaaccgcccctacttcacccgccgcccctccatccccaccttcttctcctccaaga actcctccgcctccctgcaggccgtggtgtccgacatctcctccgtggagtccgccgcctgcgactcc ctggccaaccgcctgcgcctgggcaagctgaccgaggacggcttctcctacaaggagaagttcatcgt ggggcgcgcccgctcctacgaggtgggcatcaacaagaccgccaccgtggagaccatcgccaacctgc tgcaggaggtgggctgcaaccacgcccagtccgtgggcttctccaccgacggcttcgccaccaccacc tccatgcgcaagatgcacctgatctgggtgaccgcccgcatgcacatcgagatctacaagtaccccgc ctggtccgacgtggtggaggtggagacctggtgccagtccgagggccgcatcggcacccgccgcgact ggatcctgaccgactacgccaccggccagatcatcggccgcgccacctccaagtgggtgatgatgaac caggacacccgccgcctgcagaaggtgaccgacgacgtgcgcgaggagtacctggtgttctgcccccg cgagctgcgcctggccttccccgaggagaacaaccgctcctccaagaagatctccaagctggaggacc ccgcccagtactccaagctgggcctggtgccccgccgcgccgacctggacatgaaccagcacgtgaac aacgtgacctacatcggctgggtgctggagtccatcccccaggagatcatcgacacccacgagctgca gaccatcaccctggactaccgccgcgagtgccagcacgacgacatcgtggactccctgacctccgtgg agccctccgagaacctggaggccgtgtccgagctgcgcggcaccaacggctccgccaccaccaccgcc ggcgacgaggactgccgcaacttcctgcacctgctgcgcctgtccggcgacggcctggagatcaaccg cggccgcaccgagtggcgcaagaagtccgcccgc*ATGGACTACAAGGACCACGACGGCGACTACAAGG ACCACGACATCGACTACAAGGACGACGACGACAAG*TGA*

SEQ ID NO: 71
*R. communis* FATA (Genbank Accession No. ABS30422) with a 3xFLAG ® epitope tag MLKVPCCNATDPIQSLSSQCRFLTHFNNRPYFTRRPSIPTFFSSKNSSASLQAVVSDISSVESAACDS LANRLRLGKLTEDGFSYKEKFIV*GRA*RSYEVGINKTATVETIANLLQEVGCNHAQSVGFSTDGFATTT SMRKMHLIWVTARMHIEIYKYPAWSDVVEVETWCQSEGRIGTRRDWILTDYATGQIIGRATSKWVMMN QDTRRLQKVTDDVREEYLVFCPRELRLAFPEENNRSSKKISKLEDPAQYSKLGLVPRRADLDMNQHVN NVTYIGWVLESIPQEIIDTHELQTITLDYRRECQHDDIVDSLTSVEPSENLEAVSELRGTNGSATTTA GDEDCRNFLHLLRLSGDGLEINRGRTEWRKKSARMDYKDHDGDYKDHDIDYKDDDDK

SEQ ID NO: 72
Codon optimized *G. mangostana* FATA1 (GenBank Accession No. AAB51523) with 3X FLAG ® epitope tag

*ATG**ctgaagctgtcctcctcccgctccccccctggcccgcatccccacccgcccccgccccaactccat cccccccccgcatcatcgtggtgtcctcctcctcctccaaggtgaacccccctgaagaccgaggccgtgg tgtcctccggcctggccgaccgcctgcgcctgggctccctgaccgaggacggcctgtcctacaaggag aagttcatcgtgcgctgctacgaggtgggcatcaacaagaccgccaccgtggagaccatcgccaacct gctgcaggaggtgggctgcaaccacgcccagtccgtgggctactccaccggcggcttctccaccaccc ccaccatgcgcaagctgcgcctgatctgggtgaccgcccgcatgcacatcgagatctacaagtacccc gcctggtccgacgtggtggagatcgagtcctggggccagggcgagggcaagatcggcacccgccgcga ctggatcctgcgcgactacgccaccggccaggtgatcggccgcgccacctccaagtgggtgatgatga accaggacacccgccgcctgcagaaggtggacgtggacgtgcgcgacgagtacctggtgcactgcccc cgcgagctgcgcctggccttccccgaggagaacaactcctccctgaagaagatctccaagctggagga cccctcccagtactccaagctgggcctggtgccccgccgcgccgacctggacatgaaccagcacgtga acaacgtgacctacatcggctgggtgctggagtccatgccccaggagatcatcgacacccacgagctg cagaccatcaccctggactaccgccgcgagtgccagcacgacgacgtggtggactccctgacctcccc cgagccctccgaggacgccgaggccgtgttcaaccacaacggcaccaacggctccgccaacgtgtccg ccaacgaccacggctgccgcaacttcctgcacctgctgcgcctgtccggcaacggcctggagatcaac cgcggccgcaccgagtggcgcaagaagcccacccgc*ATGGACTACAAGGACCACGACGGCGACTACAA GGACCACGACATCGACTACAAGGACGACGACGACAAG*TGA*

SEQ ID NO: 73
*G. mangostana* FATA1 (GenBank Accession No. AAB51523) with 3X FLAG ® epitope tag MLKLSSSRSPLARIPTRPRPNSIPPRIIVVSSSSSKVNPLKTEAVVSSGLADRLRLGSLTEDGLSYKE KFIVRCYEVGINKTATVETIANLLQEVGCNHAQSVGYSTGGFSTTPTMRKLRLIWVTARMHIEIYKYP AWSDVVEIESWGQGEGKIGTRRDWILRDYATGQVIGRATSKWVMMNQDTRRLQKVDVDVRDEYLVHCP RELRLAFPEENNSSLKKISKLEDPSQYSKLGLVPRRADLDMNQHVNNVTYIGWVLESMPQEIIDTHEL QTITLDYRRECQHDDVVDSLTSPEPSEDAEAVFNHNGTNGSANVSANDHGCRNFLHLLRLSGNGLEIN RGRTEWRKKPTRMDYKDHDGDYKDHDIDYKDDDDK

SEQ ID NO: 74
Codon optimized *Theobroma cacao* FATA1 with 3X FLAG ® epitope tag

*ATG**ctgaagctgtcctcctgcaacgtgaccgaccagcgccaggccctggcccagtgccgcttcctggc ccccccgccccccttctccttccgctggcgcaccccgtggtggtgtcctgctcccccctcctcccgcc ccaacctgtccccccctgcaggtggtgctgtccggccagcagcaggccggcatggagctggtggagtcc ggctccggctccctggccgaccgcctgcgcctgggctccctgaccgaggacggcctgtcctacaagga gaagttcatcgtgcgctgctacgaggtgggcatcaacaagaccgccaccgtggagaccatcgccaacc tgctgcaggaggtgggctgcaaccacgcccagtccgtgggctactccaccgacggcttcgccaccacc cgcaccatgcgcaagctgcacctgatctgggtgaccgcccgcatgcacatcgagatctacaagtaccc cgcctggtccgacgtgatcgagatcgagacctggtgccagtccgagggccgcatcggcacccgccgcg actggatcctgaaggacttcggcaccggcgaggtgatcggccgcgccacctccaagtgggtgatgatg aaccaggacacccgccgcctgcagaaggtgtccgacgacgtgcgcgaggagtacctggtgttctgccc ccgcgagctgcgcctggccttccccgaggagaacaacaactccctgaagaagatcgccaagctggacg actccttccagtactcccgcctgggcctgatgccccgccgcgccgacctggacatgaaccagcacgtg*

-continued

SEQUENCE LISTING

*aacaacgtgacctacatcggctgggtgctggagtccatgccccaggagatcatcgacacccacgagct*
*gcagaccatcaccctggactaccgccgcgagtgccagcaggacgacgtggtggactccctgacctccc*
*ccgagcaggtggagggcaccgagaaggtgtccgccatccacggcaccaacggctccgccgccgcccgc*
*gaggacaagcaggactgccgccagttcctgcacctgctgcgcctgtcctccgacggccaggagatcaa*
*ccgcggccgcaccgagtggcgcaagaagcccgcccgcATGGACTACAAGGACCACGACGGCGACTACA*
*AGGACCACGACATCGACTACAAGGACGACGACGACAAG*TGA

SEQ ID NO: 75
*Theobroma cacao* FATA1 with 3X FLAG ® epitope tag
MLKLSSCNVTDQRQALAQCRFLAPPAPFSFRWRTPVVVSCSPSSRPNLSPLQVVLSGQQQAGMELVES
GSGSLADRLRLGSLTEDGLSYKEKFIVRCYEVGINKTATVETIANLLQEVGCNHAQSVGYSTDGFATT
RTMRKLHLIWVTARMHIEIYKYPAWSDVIEIETWCQSEGRIGTRRDWILKDFGTGEVIGRATSKWVMM
NQDTRRLQKVSDDVREEYLVFCPRELRLAFPEENNNSLKKIAKLDDSFQYSRLGLMPRRADLDMNQHV
NNVTYIGWVLESMPQEIIDTHELQTITLDYRRECQQDDVVDSLTSPEQVEGTEKVSAIHGTNGSAAAR
EDKQDCRQFLHLLRLSSDGQEINRGRTEWRKKPARMDYKDHDGDYKDHDIDYKDDDDK

SEQ ID NO: 76
UTEX 1439, UTEX 1441, UTEX 1435, UTEX 1437 *Prototheca moriformis*
TGTTGAAGAATGAGCCGGCGACTTAAAATAAATGGCAGGCTAAGAGAATTAATAACTCGAAACCTAAG
CGAAAGCAAGTCTTAATAGGGCGCTAATTTAACAAAACATTAAATAAAATCTAAAGTCATTTATTTTA
GACCCGAACCTGAGTGATCTAACCATGGTCAGGATGAAACTTGGGTGACACCAAGTGGAAGTCCGAAC
CGACCGATGTTGAAAAATCGGCGGATGAACTGTGGTTAGTGGTGAAATACCAGTCGAACTCAGAGCTA
GCTGGTTCTCCCCGAAATGCGTTGAGGCGCAGCAATATATCTCGTCTATCTAGGGGTAAAGCACTGTT
TCGGTGCGGGCTATGAAAATGGTACCAAATCGTGGCAAACTCTGAATACTAGAAATGACGATATATTA
GTGAGACTATGGGGGATAAGCTCCATAGTCGAGAGGGAAACAGCCCAGACCACCAGTTAAGGCCCCAA
AATGATAATGAAGTGGTAAAGGAGGTGAAAATGCAAATACAACCAGGAGGTTGGCTTAGAAGCAGCCA
TCCTTTAAAGAGTGCGTAATAGCTCACTG SEQ ID NO: 77
Cu PSR23 LPAAT2-1
MAIAAAAVIFLFGLIFFASGLIINLFQALCFVLIRPLSKNAYRRINRVFAELLLSELLCLFDWWAGAK
LKLFTDPETFRLMGKEHALVIINHMTELDWMVGWVMGQHFGCLGSIISVAKKSTKFLPVLGWSMWFSE
YLYLERSWAKDKSTLKSHIERLIDYPLPFWLVIFVEGTRFTRTKLLAAQQYAVSSGLPVPRNVLIPRT
KGFVSCVSHMRSFVPAVYDVTVAFPKTSPPPTLLNLFEGQSIMLHVHIKRHAMKDLPESDDAVAEWCR
DKFVEKDALLDKHNAEDTFSGQEVCHSGSRQLKSLLVVISWVVVTTFGALKFLQWSSWKGKAFSAIGL
GIVTLLMHVLILSSQAERSNPAEVAQAKLKTGLSISKKVTDKEN SEQ ID NO: 78
CuPSR23 LPAAT3-1
MAIAAAAVIVPLSLLFFVSGLIVNLVQAVCFVLIRPLSKNTYRRINRVVAELLWLELVWLIDWWAGVK
IKVFTDHETFHLMGKEHALVICNHKSDIDWLVGWVLGQRSGCLGSTLAVMKKSSKFLPVLGWSMWFSE
YLFLERSWAKDEITLKSGLNRLKDYPLPFWLALFVEGTRFTRAKLLAAQQYAASSGLPVPRNVLIPRT
KGFVSSVSHMRSFVPAIYDVTVAIPKTSPPPTLIRMFKGQSSVLHVHLKRHLMKDLPESDDAVAQWCR
DIFVEKDALLDKHNAEDTFSGQELQETGRPIKSLLVVISWAVLEVFGAVKFLQWSSLLSSWKGLAFSG
IGLGVITLLMHILILFSQSERSTPAKVAPAKPKNEGESSKTEMEKEK SEQ ID NO: 79
Amino acid sequence for CuPSR23 LPPATx:
MEIPPHCLCSPSPAPSQLYYKKKKHAILQTQTPYRYRVSPTCFAPPRLRKQHPYPLPVLCYPKLLHFS
QPRYPLVRSHLAEAGVAYRPGYELLGKIRGVCFYAVTAAVALLLFQCMLLLHPFVLLFDPFPRKAHHT
IAKLWSICSVSLFYKIHIKGLENLPPPHSPAVYVSNHQSFLDIYTLLTLGRTFKFISKTEIFLYPIIG
WAMYMLGTIPLKRLDSRSQLDTLKRCMDLIKKGASVFFFPEGTRSKDGKLGAFKKGAFSIAAKSKVPV
VPITLIGTGKIMPPGSELTVNPGTVQVIIHKPIEGSDAEAMCNEARATISHSLDD SEQ ID NO: 80
cDNA sequence for CuPSR23 LPAATx coding region
ATGGAGATCCCGCCTCACTGTCTCTGTTCGCCTTCGCCTGCGCCTTCGCAATTGTA
TTACAAGAAGAAGAAGCATGCCATTCTCCAAACTCAAACTCCCTATAGATATAG
AGTTTCCCCGACATGCTTTGCCCCCCCCCGATTGAGGAAGCAGCATCCTTACCCT
CTCCCTGTCCTCTGCTATCCAAAACTCCTCCACTTCAGCCAGCCTAGGTACCCTCT
GGTTAGATCTCATTTGGCTGAAGCTGGTGTTGCTTATCGTCCAGGATACGAATTA
TTAGGAAAAATAAGGGGAGTGTGTTTCTATGCTGTCACTGCTGCCGTTGCCTTGC
TTCTATTTCAGTGCATGCTCCTCCTCCATCCCTTTGTGCTCCTCTTCGATCCATTTC
CAAGAAAGGCTCACCATACCATCGCCAAACTCTGGTCTATCTGCTCTGTTTCTCTT
TTTTACAAGATTCACATCAAGGGTTTGGAAAATCTTCCCCCACCCCACTCTCCTGC
CGTCTATGTCTCTAATCATCAGAGTTTTCTCGACATCTATACTCTCCTCACTCTCG
GTAGAACCTTCAAGTTCATCAGCAAGACTGAGATCTTTCTCTATCCAATTATCGG
TTGGGCCATGTATATGTTGGGTACCATTCCTCTCAAGCGGTTGGACAGCAGAAGC
CAATTGGACACTCTTAAGCGATGTATGGATCTCATCAAGAAGGGAGCATCCGTCT
TTTTCTTCCCAGAGGGAACACGAAGTAAAGATGGGAAACTGGGTGCTTTCAAGA
AAGGTGCATTCAGCATCGCAGCAAAAAGCAAGGTTCCTGTTGTGCCGATCACCCT
TATTGGAACTGGCAAGATTATGCCACCTGGGAGCGAACTTACTGTCAATCCAGGA
ACTGTGCAAGTAATCATACATAAACCTATCGAAGGAAGTGATGCAGAAGCAATG
TGCAATGAAGCTAGAGCCACGATTTCTCACTCACTTGATGATTAA -continued

SEQUENCE LISTING

SEQ ID NO: 81
cDNA sequence for CuPSR23 LPAAT 2-1 coding region
ATGGCGATTGCAGCGGCAGCTGTCATCTTCCTCTTCGGCCTTATCTTCTTCGCCTC
CGGCCTCATAATCAATCTCTTCCAGGCGCTTTGCTTTGTCCTTATTCGGCCTCTTT
CGAAAAACGCCTACMGGAGAATAAACAGAGTTTTTGCAGAATTGTTGTTGTCGG
AGCTTTTATGCCTATTCGATTGGTGGGCTGGTGCTAAGCTCAAATTATTTACCGAC
CCTGAAACCTTTCGCCTTATGGGCAAGGAACATGCTCTTGTCATAATTAATCACA
TGACTGAACTTGACTGGATGGTTGGATGGGTTATGGGTCAGCATTTTGGTTGCCT
TGGGAGCATAATATCTGTTGCGAAGAAATCAACAAAATTTCTTCCGGTATTGGGG
TGGTCAATGTGGTTTTCAGAGTACCTATATCTTGAGAGAAGCTGGGCCAAGGATA
AAAGTACATTAAAGTCACATATCGAGAGGCTGATAGACTACCCCCTGCCCTTCTG
GTTGGTAATTTTTGTGGAAGGAACTCGGTTTACTCGGACAAAACTCTTGGCAGCC
CAGCAGTATGCTGTCTCATCTGGGCTACCAGTGCCGAGAAATGTTTTGATCCCAC
GTACTAAGGGTTTTGTTTCATGTGTAAGTCACATGCGATCATTTGTTCCAGCAGTA
TATGATGTCACAGTGGCATTCCCTAAGACTTCACCTCCACCAACGTTGCTAAATC
TTTTCGAGGGTCAGTCCATAATGCTTCACGTTCACATCAAGCGACATGCAATGAA
AGATTTACCAGAATCCGATGATGCAGTAGCAGAGTGGTGTAGAGACAAATTTGT
GGAAAAGGATGCTTTGTTGGACAAGCATAATGCTGAGGACACTTTCAGTGGTCA
AGAAGTTTGTCATAGCGGCAGCCGCCAGTTAAAGTCTCTTCTGGTGGTAATATCT
TGGGTGGTTGTAACAACATTTGGGGCTCTAAAGTTCCTTCAGTGGTCATCATGGA
AGGGGAAAGCATTTTCAGCTATCGGGCTGGGCATCGTCACTCTACTTATGCACGT
ATTGATTCTATCCTCACAAGCAGAGCGGTCTAACCCTGCGGAGGTGGCACAGGC
AAAGCTAAAGACCGGGTTGTCGATCTCAAAGAAGGTAACGGACAAGGAAAACTAG SEQ ID NO: 82
cDNA sequence for CuPSR23 LPAAx 3-1 coding region
ATGGCGATTGCTGCGGCAGCTGTCATCGTCCCGCTCAGCCTCCTCTTCTTCGTCTC
CGGCCTCATCGTCAATCTCGTACAGGCAGTTTGCTTTGTACTGATTAGGCCTCTGT
CGAAAAACACTTACAGAAGAATAAACAGAGTGGTTGCAGAATTGTTGTGGTTGG
AGTTGGTATGGCTGATTGATTGGTGGGCTGGTGTCAAGATAAAAGTATTCACGGA
TCATGAAACCTTTCACCTTATGGGCAAAGAACATGCTCTTGTCATTTGTAATCAC
AAGAGTGACATAGACTGGCTGGTTGGGTGGGTTCTGGGACAGCGGTCAGGTTGC
CTTGGAAGCACATTAGCTGTTATGAAGAAATCATCAAAGTTTCTCCCGGTATTAG
GGTGGTCAATGTGGTTCTCAGAGTATCTATTCCTTGAAAGAAGCTGGGCCAAGGA
TGAAATTACATTAAAGTCAGGTTTGAATAGGCTGAAAGACTATCCCTTACCCTTC
TGGTTGGCACTTTTTGTGGAAGGAACTCGGTTCACTCGAGCAAAACTCTTGGCAG
CCCAGCAGTATGCTGCCTCTTCGGGGCTACCTGTGCCGAGAAATGTTCTGATCCC
GCGTACTAAGGGTTTTGTTTCTTCTGTGAGTCACATGCGATCATTTGTTCCAGCCA
TATATGATGTTACAGTGGCAATCCCAAAGACGTCACCTCCACCAACATTGATAAG
AATGTTCAAGGGACAGTCCTCAGTGCTTCACGTCCACCTCAAGCGACACCTAATG
AAAGATTTACCTGAATCAGATGATGCTGTTGCTCAGTGGTGCAGAGATATATTCG
TCGAGAAGGATGCTTTGTTGGATAAGCATAATGCTGAGGACACTTTCAGTGGCCA
AGAACTTCAAGAAACTGGCCGCCCAATAAAGTCTCTTCTGGTTGTAATCTCTTGG
GCGGTGTTGGAGGTATTTGGAGCTGTGAAGTTTCTTCAATGGTCATCGCTGTTAT
CATCATGGAAGGGACTTGCATTTTCGGGAATAGGACTGGGTGTCATCACGCTACT
CATGCACATACTGATTTTATTCTCACAATCCGAGCGGTCTACCCCTGCAAAAGTG
GCACCAGCAAAGCCAAAGAATGAGGGAGAGTCCTCCAAGACGGAAATGGAAAA
GGAAAAGTAG SEQ ID NO: 83
cDNA sequence for CuPSR23 LPAATx coding region codon optimized
for *Prototheca moriformis*
*ATGgagatcccccccactgcctgtgctccccctcccccgccccctcccagctgtactacaagaaga*
*agaagcacgccatcctgcagacccagacccccctaccgctaccgcgtgtcccccacctgcttcgcccc*
*cccccgcctgcgcaagcagcacccctacccccctgcccgtgctgtgctaccccaagctgctgcacttc*
*tcccagccccgctacccccctggtgcgctcccacctggccgaggccggcgtggcctaccgccccggc*
*tacgagctgctgggcaagatccgcggcgtgtgcttctacgccgtgaccgccgccgtggccctgctg*
*ctgttccagtgcatgctgctgctgcaccccttcgtgctgctgttcgaccccttcccccgcaaggccc*
*accacaccatcgccaagctgtggtccatctgctccgtgtccctgttctacaagatccacatcaaggg*
*cctggagaacctgcccccccccactcccccgccgtgtacgtgtccaaccaccagtccttcctggac*
*atctacaccctgctgaccctgggccgcaccttcaagttcatctccaagaccgagatcttcctgtaccc*
*catcatcggctgggccatgtacatgctgggcaccatcccccctgaagcgcctggactcccgctcccag*
*ctggacaccctgaagcgctgcatggacctgatcaagaagggcgcctccgtgttcttcttccccgagg*
*gcacccgctccaaggacggcaagctgggcgccttcaagaagggcgccttctccatcgccgccaagtc*
*caaggtgcccgtggtgcccatcaccctgatcggcaccggcaagatcatgcccccggctccgagctg*
*accgtgaaccccggcaccgtgcaggtgatcatccacaagcccatcgagggctccgacgccgaggcca*
*tgtgcaacgaggcccgcgccaccatctcccactccctggacgacTGA*

SEQ ID NO: 84
cDNA sequence for CuPSR23 LPAAT 2-1 coding region codon optimized
for *Prototheca moriformis*

-continued

SEQUENCE LISTING

*ATGgcgatcgcggccgcggcggtgatcttcctgttcggcctgatcttcttcgcctccggcctga*
*tcatcaacctgttccaggcgctgtgcttcgtcctgatccgcccctgtccaagaacgcctaccgc*
*cgcatcaaccgcgtgttcgcggagctgctgctgtccgagctgctgtgcctgttcgactggtggg*
*cgggcgcgaagctgaagctgttcaccgaccccgagacgttccgcctgatgggcaaggagcacgc*
*cctggtcatcatcaaccacatgaccgagctggactggatggtgggctgggtgatgggccagcac*
*ttcggctgcctgggctccatcatctccgtcgccaagaagtccacgaagttcctgcccgtgctggg*
*ctggtccatgtggttctccgagtacctgtacctggagcgctcctgggccaaggacaagtccaccc*
*tgaagtcccacatcgagcgcctgatcgactacccccctgcccttctggctggtcatcttcgtcgag*
*ggcacccgcttcacgcgcacgaagctgctggcggcccagcagtacgcggtctcctccggcctgc*
*ccgtcccccgcaacgtcctgatcccccgcacgaagggcttcgtctcctgcgtgtcccacatgcgc*
*tccttcgtccccgcggtgtacgacgtcacggtggcgttccccaagacgtcccccccccccacgct*
*gctgaacctgttcgagggccagtccatcatgctgcacgtgcacatcaagcgccacgccatgaagg*
*acctgcccgagtccgacgacgccgtcgcggagtggtgccgcgacaagttcgtcgagaaggacgc*
*cctgctggacaagcacaacgcggaggacacgttctccggccaggaggtgtgccactccggctcc*
*cgccagctgaagtccctgctggtcgtgatctcctgggtcgtggtgacgacgttcggcgccctga*
*agttcctgcagtggtcctcctggaagggcaaggcgttctccgccatcggcctgggcatcgtcac*
*cctgctgatgcacgtgctgatcctgtcctcccaggccgagcgctccaaccccgccgaggtggcc*
*caggccaagctgaagaccggcctgtccatctccaagaaggtgacggacaaggagaacTGA*

SEQ ID NO: 85
cDNA sequence for CuPSR23 LPAAx 3-1 coding region codon optimized for *Prototheca moriformis*

*ATGgccatcgcggcggccgcggtgatcgtgcccctgtccctgctgttcttcgtgtccggcctga*
*tcgtcaacctggtgcaggccgtctgcttcgtcctgatccgcccctgtccaagaacacgtaccgc*
*cgcatcaaccgcgtggtcgcggagctgctgtggctggagctggtgtggctgatcgactggtggg*
*cgggcgtgaagatcaaggtcttcacggaccacgagacgttccacctgatgggcaaggagcacgc*
*cctggtcatctgcaaccacaagtccgacatcgactggctggtcggctgggtcctgggccagcgc*
*tccggctgcctgggctccaccctggcggtcatgaagaagtcctccaagttcctgcccgtcctgg*
*gctggtccatgtggttctccgagtacctgttcctggagcgctcctgggccaaggacgagatcac*
*gctgaagtccggcctgaaccgcctgaaggactacccccctgcccttctggctggcgctgttcgtg*
*gagggcacgcgcttcacccgcgcgaagctgctggcggcgcagcagtacgccgcgtcctccggcc*
*tgcccgtgccccgcaacgtgctgatcccccgcacgaagggcttcgtgtcctccgtgtcccacatg*
*cgctccttcgtgcccgcgatctacgacgtcaccgtggccatccccaagacgtcccccccccccac*
*gctgatccgcatgttcaagggccagtcctccgtgctgcacgtgcacctgaagcgccacctgatga*
*aggacctgcccgagtccgacgacgccgtcgcgcagtggtgccgcgacatcttcgtggagaagga*
*cgcgctgctggacaagcacaacgccgaggacaccttctccggccaggagctgcaggagaccggc*
*cgccccatcaagtccctgctggtcgtcatctcctggccgtcctggaggtgttcggcgccgtca*
*agttcctgcagtggtcctccctgctgtcctcctggaagggcctggcgttctccggcatcggcct*
*gggcgtgatcaccctgctgatgcacatcctgatcctgttctcccagtccgagcgctccaccccccg*
*ccaaggtggcccccgcgaagcccaagaacgagggcgagtcctccaagaccgagatggagaagga*
*gaagTGA*

SEQ ID NO: 86
Nucleic acid sequence encoding 14:0-ACP thioesterase, *Cuphea palustris* (Cpal FATB2, accession AAC49180) containing an extended heterologous transit peptide from *C. protothecoides* and a 41 amino acid N-terminal extension derived from the native Cpal FATB2 sequence in construct D1481 [pSZ2479]

GCGCACCCCAAGGCGAACGGCAGCGCGGTGTCGCTGAAGTCGGGCTCCCTGGAGACCCAGGAGGACAA
GACGAGCAGCTCGTCCCCCCCCCCCCGCACGTTCATCAACCAGCTGCCCGTGTGGAGCATGCTGCTGT
CGGCGGTGACCACGGTCTTCGGCGTGGCCGAGAAGCAGTGGCCCATGCTGGACCGCAAGTCCAAGCGC
CCCGACATGCTGGTCGAGCCCCTGGGCGTGGACCGCATCGTCTACGACGGCGTGAGCTTCCGCCAGTC
GTTCTCCATCCGCAGCTACGAGATCGGCGCCGACCGCACCGCCTCGATCGAGACGCTGATGAACATGT
TCCAGGAGACCTCCCTGAACCACTGCAAGATCATCGGCCTGCTGAACGACGGCTTCGGCCGCACGCCC
GAGATGTGCAAGCGCGACCTGATCTGGGTCGTGACCAAGATGCAGATCGAGGTGAACCGCTACCCCAC
GTGGGGCGACACCATCGAGGTCAACACGTGGGTGAGCGCCTCGGGCAAGCACGGCATGGGCCGCGACT
GGCTGATCTCCGACTGCCACACCGGCGAGATCCTGATCCGCGCGACGAGCGTCTGGGCGATGATGAAC
CAGAAGACCCGCCGCCTGTCGAAGATCCCCTACGAGGTGCGCCAGGAGATCGAGCCCCAGTTCGTCGA
CTCCGCCCCCGTGATCGTGGACGACCGCAAGTTCCACAAGCTGGACCTGAAGACGGGCGACAGCATCT
GCAACGGCCTGACCCCCCGCTGGACGGACCTGGACGTGAACCAGCACGTCAACAACGTGAAGTACATC
GGCTGGATCCTGCAGTCGGTCCCCACCGAGGTGTTCGAGACGCAGGAGCTGTGCGGCCTGACCCTGGA
GTACCGCCGCGAGTGCGGCCGCGACTCCGTGCTGGAGAGCGTCACGGCCATGGACCCCTCGAAGGAGG
GCGACCGCTCCCTGTACCAGCACCTGCTGCGCCTGGAGGACGGCGCGGACATCGTGAAGGGCCGCACC
GAGTGGCGCCCCAAGAACGCCGGCGCCAAGGGCGCCATCCTGACGGGCAAGACCAGCAACGGCAACTC
GATCTCCTGA

SEQ ID NO: 87
Amino acid sequence of 14:0-ACP thioesterase, *Cuphea palustris* (Cpal FATB2, accession AAC49180) containing an extended heterologous transit peptide from *C. protothecoides* and a 41 amino acid N-terminal extension derived from the native Cpal FATB2 sequence encoded by construct D1481 [pSZ2479]

AHPKANGSAVSLKSGSLETQEDKTSSSSPPPRTFINQLPVWSMLLSAVTTVFGVAEKQWP
MLDRKSKRPDMLVEPLGVDRIVYDGVSFRQSFSIRSYEIGADRTASIETLMNMFQETSLN
HCKIIGLLNDGFGRTPEMCKRDLIWVVTKMQIEVNRYPTWGDTIEVNTWVSASGKHGMGR
DWLISDCHTGEILIRATSVWAMMNQKTRRLSKIPYEVRQEIEPQFVDSAPVIVDDRKFHK
LDLKTGDSICNGLTPRWTDLDVNQHVNNVKYIGWILQSVPTEVFETQELCGLTLEYRREC

-continued

SEQUENCE LISTING

GRDSVLESVTAMDPSKEGDRSLYQHLLRLEDGADIVKGRTEWRPKNAGAKGAILTGKTSN
GNSIS

SEQ ID No: 88
Nucleic acid sequence encoding 14:0-ACP thioesterase, Cuphea palustris (Cpal FATB2, accession AAC49180) containing an extended heterologous transit peptide from C. protothecoides, a 41 amino acid N-terminal extension derived from the native Cpal FATB2 sequence,and a C-terminal FLAG epitope tag in construct D1482
GCGCACCCCAAGGCGAACGGCAGCGCGGTGTCGCTGAAGTCGGGCTCCCTGGAGACCCAGGAGGACAA
GACGAGCAGCTCGTCCCCCCCCCCCCGCACGTTCATCAACCAGCTGCCCGTGTGGAGCATGCTGCTGT
CGGCGGTGACCACGGTCTTCGGCGTGGCCGAGAAGCAGTGGCCCATGCTGGACCGCAAGTCCAAGCGC
CCCGACATGCTGGTCGAGCCCCTGGGCGTGGACCGCATCGTCTACGACGGCGTGAGCTTCCGCCAGTC
GTTCTCCATCCGCAGCTACGAGATCGGCGCCGACCGCACCGCCTCGATCGAGACGCTGATGAACATGT
TCCAGGAGACCTCCCTGAACCACTGCAAGATCATCGGCCTGCTGAACGACGGCTTCGGCCGCACGCCC
GAGATGTGCAAGCGCGACCTGATCTGGGTCGTGACCAAGATGCAGATCGAGGTGAACCGCTACCCCAC
GTGGGGCGACACCATCGAGGTCAACACGTGGGTGAGCGCCTCGGGCAAGCACGGCATGGGCCGCGACT
GGCTGATCTCCGACTGCCACACCGGCGAGATCCTGATCCGCGCGACGAGCGTCTGGGCGATGATGAAC
CAGAAGACCCGCCGCCTGTCGAAGATCCCCTACGAGGTGCGCCAGGAGATCGAGCCCCAGTTCGTCGA
CTCCGCCCCCGTGATCGTGGACGACCGCAAGTTCCACAAGCTGGACCTGAAGACGGGCGACAGCATCT
GCAACGGCCTGACCCCCCGCTGGACGGACCTGGACGTGAACCAGCACGTCAACAACGTGAAGTACATC
GGCTGGATCCTGCAGTCGGTCCCCACCGAGGTGTTCGAGACGCAGGAGCTGTGCGGCCTGACCCTGGA
GTACCGCCGCGAGTGCGGCCGCGACTCCGTGCTGGAGAGCGTCACGGCCATGGACCCCTCGAAGGAGG
GCGACCGCTCCCTGTACCAGCACCTGCTGCGCCTGGAGGACGGCGCGGACATCGTGAAGGGCCGCACC
GAGTGGCGCCCCAAGAACGCCGGCGCCAAGGGCGCCATCCTGACGGGCAAGACCAGCAACGGCAACTC
GATCTCCatggactacaaggaccacgacggcgactacaaggaccacgacatcgactacaaggacgacg
acgacaagtga SEQ ID NO: 89
Amino acid sequence of 14:0-ACP thioesterase, *Cuphea palustris* (Cpal FATB2, accession AAC49180) containing an extended heterologous transit peptide from *C. protothecoides*, a 41 amino acid N-terminal extension derived from the native Cpal FATB2 sequence,and a C-terminal FLAG epitope tag encoded by construct D1482 [pSZ2480]
AHPKANGSAVSLKSGSLETQEDKTSSSSPPPRTFINQLPVWSMLLSAVTTVFGVAEKQWP
MLDRKSKRPDMLVEPLGVDRIVYDGVSFRQSFSIRSYEIGADRTASIETLMNMFQETSLN
HCKIIGLLNDGFGRTPEMCKRDLIWVVTKMQIEVNRYPTWGDTIEVNTWVSASGKHGMGR
DWLISDCHTGEILIRATSVWAMMNQKTRRLSKIPYEVRQEIEPQFVDSAPVIVDDRKFHK
LDLKTGDSICNGLTPRWTDLDVNQHVNNVKYIGWILQSVPTEVFETQELCGLTLEYRREC
GRDSVLESVTAMDPSKEGDRSLYQHLLRLEDGADIVKGRTEWRPKNAGAKGAILTGKTSN
GNSISMDYKDHDGDYKDHDIDYKDDDDK

What is claimed is:

1. A recombinant vector or isolated host cell comprising recombinant nucleic acids encoding a protein having at least 90% identity to SEQ ID NO: 77, wherein the protein has lysophosphatidic acid acyltransferase (LPAAT) activity.

2. A recombinant vector or isolated host cell comprising recombinant nucleic acids encoding a protein having at least 90% identity to SEQ ID NO: 78, wherein the protein has lysophosphatidic acid acyltransferase (LPAAT) activity.

3. A recombinant vector or isolated host cell comprising recombinant nucleic acids encoding a protein having at least 90% identity to SEQ ID NO: 79, wherein the protein has lysophosphatidic acid acyltransferase (LPAAT) activity.

* * * * *

SEQUENCE LISTING

<160> NUMBER OF SEQ ID NOS: 117

<210> SEQ ID NO 1
<211> LENGTH: 726
<212> TYPE: DNA
<213> ORGANISM: Cuphea wrightii

<400> SEQUENCE: 1
gctcttcgcc gccgccactc ctgctcgagc gcgcccgcgc gtgcgccgcc agcgccttgg 60
ccttttcgcc gcgctcgtgc gcgtcgctga tgtccatcac caggtccatg aggtctgcct 120
tgcgccggct gagccactgc ttcgtccggg cggccaagag gagcatgagg gaggactcct 180
ggtccagggt cctgacgtgg tcgcggctct gggagcgggc cagcatcatc tggctctgcc 240
gcaccgaggc cgcctccaac tggtcctcca gcagccgcag tcgccgccga ccctggcaga 300
ggaagacagg tgaggggggt atgaattgta cagaacaacc acgagccttg tctaggcaga 360
atccctacca gtcatggctt tacctggatg acggcctgcg aacagctgtc cagcgaccct 420
cgctgccgcc gcttctcccg cacgcttctt tccagcaccg tgatggcgcg agccagcgcc 480
gcacgctggc gctgcgcttc gccgatctga ggacagtcgg ggaactctga tcagtctaaa 540 ccccttgcg cgttagtgtt gccatccttt gcagaccggt gagagccgac ttgttgtgcg 600
ccacccccca caccacctcc tcccagacca attctgtcac ctttttggcg aaggcatcgg 660
cctcggcctg cagagaggac agcagtgccc agccgctggg ggttggcgga tgcacgctca 720
ggtacc 726

<210> SEQ ID NO 2
<211> LENGTH: 749
<212> TYPE: DNA
<213> ORGANISM: Cuphea wrightii

<400> SEQUENCE: 2
gagctccttg ttttccagaa ggagttgctc cttgagcctt tcattctcag cctcgataac 60
ctccaaagcc gctctaattg tggagggggt tcgaatttaa aagcttggaa tgttggttcg 120
tgcgtctgga acaagcccag acttgttgct cactgggaaa aggaccatca gctccaaaaa 180
acttgccgct caaaccgcgt acctctgctt tcgcgcaatc tgccctgttg aaatcgccac 240
cacattcata ttgtgacgct tgagcagtct gtaattgcct cagaatgtgg aatcatctgc 300
cccctgtgcg agcccatgcc aggcatgtcg cgggcgagga cacccgccac tcgtacagca 360
gaccattatg ctacctcaca atagttcata acagtgacca tatttctcga agctccccaa 420
cgagcacctc catgctctga gtggccaccc cccggccctg gtgcttgcgg agggcaggtc 480
aaccggcatg gggctaccga aatccccgac cggatcccac cacccccgcg atgggaagaa 540
tctctccccg ggatgtgggc ccaccaccag cacaacctgc tggcccaggc gagcgtcaaa 600
ccataccaca caaatatcct tggcatcggc cctgaattcc ttctgccgct ctgctacccg 660
gtgcttctgt ccgaagcagg ggttgctagg gatcgctccg agtccgcaaa cccttgtcgc 720
gtggcggggc ttgttcgagc ttgaagagc 749

<210> SEQ ID NO 3
<211> LENGTH: 532
<212> TYPE: PRT
<213> ORGANISM: Saccharomyces cereviseae

<400> SEQUENCE: 3

Met Leu Leu Gln Ala Phe Leu Phe Leu Leu Ala Gly Phe Ala Ala Lys
1 5 10 15

Ile Ser Ala Ser Met Thr Asn Glu Thr Ser Asp Arg Pro Leu Val His
20 25 30

Phe Thr Pro Asn Lys Gly Trp Met Asn Asp Pro Asn Gly Leu Trp Tyr
35 40 45

Asp Glu Lys Asp Ala Lys Trp His Leu Tyr Phe Gln Tyr Asn Pro Asn
50 55 60

Asp Thr Val Trp Gly Thr Pro Leu Phe Trp Gly His Ala Thr Ser Asp
65 70 75 80

Asp Leu Thr Asn Trp Glu Asp Gln Pro Ile Ala Ile Ala Pro Lys Arg
85 90 95

Asn Asp Ser Gly Ala Phe Ser Gly Ser Met Val Val Asp Tyr Asn Asn
100 105 110

Thr Ser Gly Phe Phe Asn Asp Thr Ile Asp Pro Arg Gln Arg Cys Val
115 120 125

Ala Ile Trp Thr Tyr Asn Thr Pro Glu Ser Glu Glu Gln Tyr Ile Ser
130 135 140

Tyr Ser Leu Asp Gly Gly Tyr Thr Phe Thr Glu Tyr Gln Lys Asn Pro
145 150 155 160

Val Leu Ala Ala Asn Ser Thr Gln Phe Arg Asp Pro Lys Val Phe Trp

```
                165                 170                 175

Tyr Glu Pro Ser Gln Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
        195                 200                 205

Glu Ser Ala Phe Ala Asn Glu Gly Phe Leu Gly Tyr Gln Tyr Glu Cys
    210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
            260                 265                 270

Phe Asp Asn Gln Ser Arg Val Val Asp Phe Gly Lys Asp Tyr Tyr Ala
        275                 280                 285

Leu Gln Thr Phe Phe Asn Thr Asp Pro Thr Tyr Gly Ser Ala Leu Gly
    290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335

Glu Tyr Gln Ala Asn Pro Glu Thr Glu Leu Ile Asn Leu Lys Ala Glu
            340                 345                 350

Pro Ile Leu Asn Ile Ser Asn Ala Gly Pro Trp Ser Arg Phe Ala Thr
        355                 360                 365

Asn Thr Thr Leu Thr Lys Ala Asn Ser Tyr Asn Val Asp Leu Ser Asn
    370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
                405                 410                 415

Gly Leu Glu Asp Pro Glu Glu Tyr Leu Arg Met Gly Phe Glu Val Ser
            420                 425                 430

Ala Ser Ser Phe Phe Leu Asp Arg Gly Asn Ser Lys Val Lys Phe Val
        435                 440                 445

Lys Glu Asn Pro Tyr Phe Thr Asn Arg Met Ser Val Asn Asn Gln Pro
    450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Thr Gly Asn Ala Leu Gly Ser Val Asn
            500                 505                 510

Met Thr Thr Gly Val Asp Asn Leu Phe Tyr Ile Asp Lys Phe Gln Val
        515                 520                 525

Arg Glu Val Lys
    530


<210> SEQ ID NO 4
<211> LENGTH: 1599
<212> TYPE: DNA
<213> ORGANISM: Saccharomyces cereviseae

<400> SEQUENCE: 4
```

```
atgctgctgc aggccttcct gttcctgctg gccggcttcg ccgccaagat cagcgcctcc     60
atgacgaacg agacgtccga ccgcccccctg gtgcacttca cccccaacaa gggctggatg    120
aacgacccca acggcctgtg gtacgacgag aaggacgcca agtggcacct gtacttccag    180
tacaacccga acgacaccgt ctgggggacg ccccttgttct ggggccacgc cacgtccgac    240
gacctgacca actgggagga ccagcccatc gccatcgccc cgaagcgcaa cgactccggc    300
gccttctccg gctccatggt ggtggactac aacaacacct ccggcttctt caacgacacc    360
atcgacccgc gccagcgctg cgtggccatc tggacctaca acaccccgga gtccgaggag    420
cagtacatct cctacagcct ggacggcggc tacaccttca ccgagtacca gaagaacccc    480
gtgctggccg ccaactccac ccagttccgc gacccgaagg tcttctggta cgagccctcc    540
cagaagtgga tcatgaccgc ggccaagtcc caggactaca agatcgagat ctactcctcc    600
gacgacctga agtcctggaa gctggagtcc gcgttcgcca acgagggctt cctcggctac    660
cagtacgagt gccccggcct gatcgaggtc cccaccgagc aggaccccag caagtcctac    720
tgggtgatgt tcatctccat caaccccggc gccccggccg gcggctcctt caaccagtac    780
ttcgtcggca gcttcaacgg cacccacttc gaggccttcg acaaccagtc ccgcgtggtg    840
gacttcggca aggactacta cgccctgcag accttcttca acaccgaccc gacctacggg    900
agcgccctgg gcatcgcgtg ggcctccaac tgggagtact ccgccttcgt gcccaccaac    960
ccctggcgct cctccatgtc cctcgtgcgc aagttctccc tcaacaccga gtaccaggcc   1020
aacccggaga cggagctgat caacctgaag gccgagccga tcctgaacat cagcaacgcc   1080
ggcccctgga gccggttcgc caccaacacc acgttgacga aggccaacag ctacaacgtc   1140
gacctgtcca acagcaccgg caccctggag ttcgagctgg tgtacgccgt caacaccacc   1200
cagacgatct ccaagtccgt gttcgcggac ctctccctct ggttcaaggg cctggaggac   1260
cccgaggagt acctccgcat gggcttcgag gtgtccgcgt cctccttctt cctggaccgc   1320
gggaacagca aggtgaagtt cgtgaaggag aacccctact tcaccaaccg catgagcgtg   1380
aacaaccagc ccttcaagag cgagaacgac ctgtcctact acaaggtgta cggcttgctg   1440
gaccagaaca tcctggagct gtacttcaac gacggcgacg tcgtgtccac caacacctac   1500
ttcatgacca ccgggaacgc cctgggctcc gtgaacatga cgacgggggt ggacaacctg   1560
ttctacatcg acaagttcca ggtgcgcgag gtcaagtga                           1599
```

<210> SEQ ID NO 5
<211> LENGTH: 312
<212> TYPE: DNA
<213> ORGANISM: Chlamydomonas reinhardtii

<400> SEQUENCE: 5

```
ctttcttgcg ctatgacact tccagcaaaa ggtagggcgg gctgcgagac ggcttcccgg     60
cgctgcatgc aacaccgatg atgcttcgac cccccgaagc tccttcgggg ctgcatgggc    120
gctccgatgc cgctccaggg cgagcgctgt ttaaatagcc aggcccccga ttgcaaagac    180
attatagcga gctaccaaag ccatattcaa acacctagat cactaccact tctacacagg    240
ccactcgagc ttgtgatcgc actccgctaa gggggcgcct cttcctcttc gtttcagtca    300
caacccgcaa ac                                                        312
```

<210> SEQ ID NO 6
<211> LENGTH: 408
<212> TYPE: DNA
<213> ORGANISM: Chlorella vulgaris

<400> SEQUENCE: 6

```
gcagcagcag ctcggatagt atcgacacac tctggacgct ggtcgtgtga tggactgttg     60

ccgccacact tgctgccttg acctgtgaat atccctgccg cttttatcaa acagcctcag    120

tgtgtttgat cttgtgtgta cgcgcttttg cgagttgcta gctgcttgtg ctatttgcga    180

ataccacccc cagcatcccc ttccctcgtt tcatatcgct tgcatcccaa ccgcaactta    240

tctacgctgt cctgctatcc ctcagcgctg ctcctgctcc tgctcactgc ccctcgcaca    300

gccttggttt gggctccgcc tgtattctcc tggtactgca acctgtaaac cagcactgca    360

atgctgatgc acgggaagta gtgggatggg aacacaaatg gaaagctt                 408
```

<210> SEQ ID NO 7
<211> LENGTH: 2333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
ctttcttgcg ctatgacact tccagcaaaa ggtagggcgg gctgcgagac ggcttcccgg     60

cgctgcatgc aacaccgatg atgcttcgac cccccgaagc tccttcgggg ctgcatgggc    120

gctccgatgc cgctccaggg cgagcgctgt ttaaatagcc aggcccccga ttgcaaagac    180

attatagcga gctaccaaag ccatattcaa acacctagat cactaccact tctacacagg    240

ccactcgagc ttgtgatcgc actccgctaa gggggcgcct cttcctcttc gtttcagtca    300

caacccgcaa acggcgcgcc atgctgctgc aggccttcct gttcctgctg gccggcttcg    360

ccgccaagat cagcgcctcc atgacgaacg agacgtccga ccgcccctg gtgcacttca    420

cccccaacaa gggctggatg aacgacccca acggcctgtg gtacgacgag aaggacgcca    480

agtggcacct gtacttccag tacaacccga acgacaccgt ctgggggacg cccttgttct    540

ggggccacgc cacgtccgac gacctgacca actgggagga ccagcccatc gccatcgccc    600

cgaagcgcaa cgactccggc gccttctccg gctccatggt ggtggactac aacaacacct    660

ccggcttctt caacgacacc atcgacccgc gccagcgctg cgtggccatc tggacctaca    720

acaccccgga gtccgaggag cagtacatct cctacagcct ggacggcggc tacaccttca    780

ccgagtacca gaagaacccc gtgctggccg ccaactccac ccagttccgc gacccgaagg    840

tcttctggta cgagccctcc cagaagtgga tcatgaccgc ggccaagtcc caggactaca    900

agatcgagat ctactcctcc gacgacctga agtcctggaa gctggagtcc gcgttcgcca    960

acgagggctt cctcggctac cagtacgagt gccccggcct gatcgaggtc cccaccgagc   1020

aggaccccag caagtcctac tgggtgatgt tcatctccat caaccccggc gccccggccg   1080

gcggctcctt caaccagtac ttcgtcggca gcttcaacgg cacccacttc gaggccttcg   1140

acaaccagtc ccgcgtggtg gacttcggca aggactacta cgccctgcag accttcttca   1200

acaccgaccc gacctacggg agcgccctgg gcatcgcgtg ggcctccaac tgggagtact   1260

ccgccttcgt gcccaccaac ccctggcgct cctccatgtc cctcgtgcgc aagttctccc   1320

tcaacaccga gtaccaggcc aacccggaga cggagctgat caacctgaag gccgagccga   1380

tcctgaacat cagcaacgcc ggcccctgga gccggttcgc caccaacacc acgttgacga   1440

aggccaacag ctacaacgtc gacctgtcca acagcaccgg caccctggag ttcgagctgg   1500

tgtacgccgt caacaccacc cagacgatct ccaagtccgt gttcgcggac ctctccctct   1560
```

ggttcaaggg cctggaggac cccgaggagt acctccgcat gggcttcgag gtgtccgcgt 1620
cctccttctt cctggaccgc gggaacagca aggtgaagtt cgtgaaggag aacccctact 1680
tcaccaaccg catgagcgtg aacaaccagc ccttcaagag cgagaacgac ctgtcctact 1740
acaaggtgta cggcttgctg gaccagaaca tcctggagct gtacttcaac gacggcgacg 1800
tcgtgtccac caacacctac ttcatgacca ccgggaacgc cctgggctcc gtgaacatga 1860
cgacgggggt ggacaacctg ttctacatcg acaagttcca ggtgcgcgag gtcaagtgac 1920
aattggcagc agcagctcgg atagtatcga cacactctgg acgctggtcg tgtgatggac 1980
tgttgccgcc acacttgctg ccttgacctg tgaatatccc tgccgctttt atcaaacagc 2040
ctcagtgtgt ttgatcttgt gtgtacgcgc ttttgcgagt tgctagctgc ttgtgctatt 2100
tgcgaatacc acccccagca tccccttccc tcgtttcata tcgcttgcat cccaaccgca 2160
acttatctac gctgtcctgc tatccctcag cgctgctcct gctcctgctc actgcccctc 2220
gcacagcctt ggtttgggct ccgcctgtat tctcctggta ctgcaacctg taaaccagca 2280
ctgcaatgct gatgcacggg aagtagtggg atgggaacac aaatggagga tcc 2333

<210> SEQ ID NO 8
<211> LENGTH: 1065
<212> TYPE: DNA
<213> ORGANISM: Prototheca moriformis

<400> SEQUENCE: 8
ggccgacagg acgcgcgtca aaggtgctgg tcgtgtatgc cctggccggc aggtcgttgc 60
tgctgctggt tagtgattcc gcaaccctga ttttggcgtc ttattttggc gtggcaaacg 120
ctggcgcccg cgagccgggc cggcggcgat gcggtgcccc acggctgccg gaatccaagg 180
gaggcaagag cgcccgggtc agttgaaggg ctttacgcgc aaggtacagc cgctcctgca 240
aggctgcgtg gtggaattgg acgtgcaggt cctgctgaag ttcctccacc gcctcaccag 300
cggacaaagc accggtgtat caggtccgtg tcatccactc taaagagctc gactacgacc 360
tactgatggc cctagattct tcatcaaaaa cgcctgagac acttgcccag gattgaaact 420
ccctgaaggg accaccaggg gccctgagtt gttccttccc cccgtggcga gctgccagcc 480
aggctgtacc tgtgatcgag gctggcggga aaataggctt cgtgtgctca ggtcatggga 540
ggtgcaggac agctcatgaa acgccaacaa tcgcacaatt catgtcaagc taatcagcta 600
tttcctcttc acgagctgta attgtcccaa aattctggtc taccgggggt gatccttcgt 660
gtacgggccc ttccctcaac cctaggtatg cgcgcatgcg gtcgccgcgc aactcgcgcg 720
agggccgagg gtttgggacg ggccgtcccg aaatgcagtt gcacccggat gcgtggcacc 780
ttttttgcga taatttatgc aatggactgc tctgcaaaat tctggctctg tcgccaaccc 840
taggatcagc ggcgtaggat ttcgtaatca ttcgtcctga tggggagcta ccgactaccc 900
taatatcagc ccgactgcct gacgccagcg tccacttttg tgcacacatt ccattcgtgc 960
ccaagacatt tcattgtggt gcgaagcgtc cccagttacg ctcacctgtt tcccgacctc 1020
cttactgttc tgtcgacaga gcgggcccac aggccggtcg cagcc 1065

<210> SEQ ID NO 9
<211> LENGTH: 120
<212> TYPE: DNA
<213> ORGANISM: Chlorella protothecoides

<400> SEQUENCE: 9

-continued

```
actagtatgg ccaccgcatc cactttctcg gcgttcaatg cccgctgcgg cgacctgcgt      60

cgctcggcgg gctccgggcc ccggcgccca gcgaggcccc tccccgtgcg cgggcgcgcc     120
```

<210> SEQ ID NO 10
<211> LENGTH: 1236
<212> TYPE: DNA
<213> ORGANISM: Cuphea wrightii

<400> SEQUENCE: 10

```
atggtggtgg ccgccgccgc cagcagcgcc ttcttccccg tgcccgcccc ccgccccacc      60

cccaagcccg gcaagttcgg caactggccc agcagcctga gccagccctt caagcccaag     120

agcaacccca acggccgctt ccaggtgaag gccaacgtga gcccccacgg gcgcgccccc     180

aaggccaacg gcagcgccgt gagcctgaag tccggcagcc tgaacaccct ggaggacccc     240

cccagcagcc cccccccccg caccttcctg aaccagctgc ccgactggag ccgcctgcgc     300

accgccatca ccaccgtgtt cgtggccgcc gagaagcagt tcacccgcct ggaccgcaag     360

agcaagcgcc ccgacatgct ggtggactgg ttcggcagcg agaccatcgt gcaggacggc     420

ctggtgttcc gcgagcgctt cagcatccgc agctacgaga tcggcgccga ccgcaccgcc     480

agcatcgaga ccctgatgaa ccacctgcag gacaccagcc tgaaccactg caagagcgtg     540

ggcctgctga acgacggctt cggccgcacc cccgagatgt gcacccgcga cctgatctgg     600

gtgctgacca agatgcagat cgtggtgaac cgctacccca cctggggcga caccgtggag     660

atcaacagct ggttcagcca gagcggcaag atcggcatgg gccgcgagtg gctgatcagc     720

gactgcaaca ccggcgagat cctggtgcgc gccaccagcg cctgggccat gatgaaccag     780

aagacccgcc gcttcagcaa gctgccctgc gaggtgcgcc aggagatcgc cccccacttc     840

gtggacgccc cccccgtgat cgaggacaac gaccgcaagc tgcacaagtt cgacgtgaag     900

accggcgaca gcatctgcaa gggcctgacc cccggctgga acgacttcga cgtgaaccag     960

cacgtgagca acgtgaagta catcggctgg attctggaga gcatgcccac cgaggtgctg    1020

gagacccagg agctgtgcag cctgaccctg gagtaccgcc gcgagtgcgg ccgcgagagc    1080

gtggtggaga gcgtgaccag catgaacccc agcaaggtgg gcgaccgcag ccagtaccag    1140

cacctgctgc gcctggagga cggcgccgac atcatgaagg gccgcaccga gtggcgcccc    1200

aagaacgccg gcaccaaccg cgccatcagc acctga                              1236
```

<210> SEQ ID NO 11
<211> LENGTH: 408
<212> TYPE: PRT
<213> ORGANISM: Cuphea wrightii

<400> SEQUENCE: 11

```
Met Val Val Ala Ala Ala Ala Ser Ser Ala Phe Phe Pro Val Pro Ala
1               5                   10                  15

Pro Arg Pro Thr Pro Lys Pro Gly Lys Phe Gly Asn Trp Pro Ser Ser
            20                  25                  30

Leu Ser Gln Pro Phe Lys Pro Lys Ser Asn Pro Asn Gly Arg Phe Gln
        35                  40                  45

Val Lys Ala Asn Val Ser Pro His Pro Lys Ala Asn Gly Ser Ala Val
    50                  55                  60

Ser Leu Lys Ser Gly Ser Leu Asn Thr Leu Glu Asp Pro Pro Ser Ser
65                  70                  75                  80

Pro Pro Pro Arg Thr Phe Leu Asn Gln Leu Pro Asp Trp Ser Arg Leu
                85                  90                  95
```

```
Arg Thr Ala Ile Thr Thr Val Phe Val Ala Ala Glu Lys Gln Phe Thr
            100                 105                 110

Arg Leu Asp Arg Lys Ser Lys Arg Pro Asp Met Leu Val Asp Trp Phe
        115                 120                 125

Gly Ser Glu Thr Ile Val Gln Asp Gly Leu Val Phe Arg Glu Arg Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Thr
            180                 185                 190

Arg Asp Leu Ile Trp Val Leu Thr Lys Met Gln Ile Val Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Glu Trp Leu Ile Ser Asp Cys Asn
225                 230                 235                 240

Thr Gly Glu Ile Leu Val Arg Ala Thr Ser Ala Trp Ala Met Met Asn
                245                 250                 255

Gln Lys Thr Arg Arg Phe Ser Lys Leu Pro Cys Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Gly Trp Asn Asp Phe Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Glu Ser Val Val Glu Ser Val Thr Ser Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Arg Ala Ile Ser Thr
                405
```

<210> SEQ ID NO 12
<211> LENGTH: 933
<212> TYPE: DNA
<213> ORGANISM: Cocus nucifera

<400> SEQUENCE: 12

```
atggacgcct ccggcgcctc ctccttcctg cgcggccgct gcctggagtc ctgcttcaag     60

gcctccttcg gctacgtaat gtcccagccc aaggacgccg ccggccagcc ctcccgccgc    120

cccgccgacg ccgacgactt cgtggacgac gaccgctgga tcaccgtgat cctgtccgtg    180

gtgcgcatcg ccgcctgctt cctgtccatg atggtgacca ccatcgtgtg gaacatgatc    240

atgctgatcc tgctgccctg gccctacgcc cgcatccgcc agggcaacct gtacggccac    300
```

-continued gtgaccggcc gcatgctgat gtggattctg ggcaacccca tcaccatcga gggctccgag 360
ttctccaaca cccgcgccat ctacatctgc aaccacgcct ccctggtgga catcttcctg 420
atcatgtggc tgatccccaa gggcaccgtg accatcgcca agaaggagat catctggtat 480
cccctgttcg gccagctgta cgtgctggcc aaccaccagc gcatcgaccg ctccaacccc 540
tccgccgcca tcgagtccat caaggaggtg gcccgcgccg tggtgaagaa gaacctgtcc 600
ctgatcatct tccccgaggg cacccgctcc aagaccggcc gcctgctgcc cttcaagaag 660
ggcttcatcc acatcgccct ccagacccgc ctgcccatcg tgccgatggt gctgaccggc 720
acccacctgg cctggcgcaa gaactccctg cgcgtgcgcc ccgcccccat caccgtgaag 780
tacttctccc ccatcaagac cgacgactgg gaggaggaga agatcaacca ctacgtggag 840
atgatccacg ccctgtacgt ggaccacctg cccgagtccc agaagcccct ggtgtccaag 900
ggccgcgacg cctccggccg ctccaactcc tga 933

<210> SEQ ID NO 13
<211> LENGTH: 563
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 13
gctcttcgct aacggaggtc tgtcaccaaa tggaccccgt ctattgcggg aaaccacggc 60
gatggcacgt ttcaaaactt gatgaaatac aatattcagt atgtcgcggg cggcgacggc 120
ggggagctga tgtcgcgctg ggtattgctt aatcgccagc ttcgcccccg tcttggcgcg 180
aggcgtgaac aagccgaccg atgtgcacga gcaaatcctg acactagaag ggctgactcg 240
cccggcacgg ctgaattaca caggcttgca aaaataccag aatttgcacg caccgtattc 300
gcggtatttt gttggacagt gaatagcgat gcggcaatgg cttgtggcgt tagaaggtgc 360
gacgaaggtg gtgccaccac tgtgccagcc agtcctggcg gctcccaggg ccccgatcaa 420
gagccaggac atccaaacta cccacagcat caacgccccg gcctatactc gaaccccact 480
tgcactctgc aatggtatgg gaaccacggg gcagtcttgt gtgggtcgcg cctatcgcgg 540
tcggcgaaga ccgggaaggt acc 563

<210> SEQ ID NO 14
<211> LENGTH: 465
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14
gagctcagcg gcgacggtcc tgctaccgta cgacgttggg cacgcccatg aaagtttgta 60
taccgagctt gttgagcgaa ctgcaagcgc ggctcaagga tacttgaact cctggattga 120
tatcggtcca ataatggatg gaaaatccga acctcgtgca agaactgagc aaacctcgtt 180
acatggatgc acagtcgcca gtccaatgaa cattgaagtg agcgaactgt tcgcttcggt 240
ggcagtacta ctcaaagaat gagctgctgt taaaaatgca ctctcgttct ctcaagtgag 300
tggcagatga gtgctcacgc cttgcacttc gctgcccgtg tcatgccctg cgccccaaaa 360
tttgaaaaaa gggatgagat tattgggcaa tggacgacgt cgtcgctccg ggagtcagga 420
ccggcggaaa ataagaggca acacactccg cttcttagct cttcc 465

<210> SEQ ID NO 15
<211> LENGTH: 1533
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15
ctttcttgcg ctatgacact tccagcaaaa ggtagggcgg gctgcgagac ggcttcccgg 60
cgctgcatgc aacaccgatg atgcttcgac cccccgaagc tccttcgggg ctgcatgggc 120
gctccgatgc cgctccaggg cgagcgctgt ttaaatagcc aggcccccga ttgcaaagac 180
attatagcga gctaccaaag ccatattcaa acacctagat cactaccact tctacacagg 240
ccactcgagc ttgtgatcgc actccgctaa gggggcgcct cttcctcttc gtttcagtca 300
caacccgcaa actctagaat atcaatgatc gagcaggacg gcctccacgc cggctccccc 360
gccgcctggg tggagcgcct gttcggctac gactgggccc agcagaccat cggctgctcc 420
gacgccgccg tgttccgcct gtccgcccag ggccgccccg tgctgttcgt gaagaccgac 480
ctgtccggcg ccctgaacga gctgcaggac gaggccgccc gcctgtcctg gctggccacc 540
accggcgtgc cctgcgccgc cgtgctggac gtggtgaccg aggccggccg cgactggctg 600
ctgctgggcg aggtgcccgg ccaggacctg ctgtcctccc acctggcccc cgccgagaag 660
gtgtccatca tggccgacgc catgcgccgc ctgcacaccc tggaccccgc cacctgcccc 720
ttcgaccacc aggccaagca ccgcatcgag cgcgcccgca cccgcatgga ggccggcctg 780
gtggaccagg acgacctgga cgaggagcac cagggcctgg cccccgccga gctgttcgcc 840
cgcctgaagg cccgcatgcc cgacggcgag gacctggtgg tgacccacgg cgacgcctgc 900
ctgcccaaca tcatggtgga gaacggccgc ttctccggct tcatcgactg cggccgcctg 960
ggcgtggccg accgctacca ggacatcgcc ctggccaccc gcgacatcgc cgaggagctg 1020
ggcggcgagt gggccgaccg cttcctggtg ctgtacggca tcgccgcccc cgactcccag 1080
cgcatcgcct tctaccgcct gctggacgag ttcttctgac aattggcagc agcagctcgg 1140
atagtatcga cacactctgg acgctggtcg tgtgatggac tgttgccgcc acacttgctg 1200
ccttgacctg tgaatatccc tgccgctttt atcaaacagc ctcagtgtgt ttgatcttgt 1260
gtgtacgcgc ttttgcgagt tgctagctgc ttgtgctatt tgcgaatacc acccccagca 1320
tccccttccc tcgtttcata tcgcttgcat cccaaccgca acttatctac gctgtcctgc 1380
tatccctcag cgctgctcct gctcctgctc actgcccctc gcacagcctt ggtttgggct 1440
ccgcctgtat tctcctggta ctgcaacctg taaaccagca ctgcaatgct gatgcacggg 1500
aagtagtggg atgggaacac aaatggagga tcc 1533

<210> SEQ ID NO 16
<211> LENGTH: 310
<212> TYPE: PRT
<213> ORGANISM: Cocos nucifera

<400> SEQUENCE: 16

Met Asp Ala Ser Gly Ala Ser Ser Phe Leu Arg Gly Arg Cys Leu Glu
1 5 10 15

Ser Cys Phe Lys Ala Ser Phe Gly Tyr Val Met Ser Gln Pro Lys Asp
20 25 30

Ala Ala Gly Gln Pro Ser Arg Arg Pro Ala Asp Ala Asp Asp Phe Val

-continued

```
        35                  40                  45

Asp Asp Asp Arg Trp Ile Thr Val Ile Leu Ser Val Val Arg Ile Ala
    50                  55                  60

Ala Cys Phe Leu Ser Met Met Val Thr Thr Ile Val Trp Asn Met Ile
65                  70                  75                  80

Met Leu Ile Leu Leu Pro Trp Pro Tyr Ala Arg Ile Arg Gln Gly Asn
                85                  90                  95

Leu Tyr Gly His Val Thr Gly Arg Met Leu Met Trp Ile Leu Gly Asn
            100                 105                 110

Pro Ile Thr Ile Glu Gly Ser Glu Phe Ser Asn Thr Arg Ala Ile Tyr
        115                 120                 125

Ile Cys Asn His Ala Ser Leu Val Asp Ile Phe Leu Ile Met Trp Leu
    130                 135                 140

Ile Pro Lys Gly Thr Val Thr Ile Ala Lys Lys Glu Ile Ile Trp Tyr
145                 150                 155                 160

Pro Leu Phe Gly Gln Leu Tyr Val Leu Ala Asn His Gln Arg Ile Asp
                165                 170                 175

Arg Ser Asn Pro Ser Ala Ala Ile Glu Ser Ile Lys Glu Val Ala Arg
            180                 185                 190

Ala Val Val Lys Lys Asn Leu Ser Leu Ile Ile Phe Pro Glu Gly Thr
        195                 200                 205

Arg Ser Lys Thr Gly Arg Leu Leu Pro Phe Lys Lys Gly Phe Ile His
    210                 215                 220

Ile Ala Leu Gln Thr Arg Leu Pro Ile Val Pro Met Val Leu Thr Gly
225                 230                 235                 240

Thr His Leu Ala Trp Arg Lys Asn Ser Leu Arg Val Arg Pro Ala Pro
                245                 250                 255

Ile Thr Val Lys Tyr Phe Ser Pro Ile Lys Thr Asp Asp Trp Glu Glu
            260                 265                 270

Glu Lys Ile Asn His Tyr Val Glu Met Ile His Ala Leu Tyr Val Asp
        275                 280                 285

His Leu Pro Glu Ser Gln Lys Pro Leu Val Ser Lys Gly Arg Asp Ala
    290                 295                 300

Ser Gly Arg Ser Asn Ser
305                 310


<210> SEQ ID NO 17
<211> LENGTH: 6676
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

gggctggtct gaatccttca ggcgggtgtt acccgagaaa gaaagggtgc cgatttcaaa      60

gcagacccat gtgccgggcc ctgtggcctg tgttggcgcc tatgtagtca cccccccctca    120

cccaattgtc gccagtttgc gcactccata aactcaaaac agcagcttct gagctgcgct    180

gttcaagaac acctctgggg tttgctcacc cgcgaggtcg acgcccagca tggctatcaa    240

gacgaacagg cagcctgtgg agaagcctcc gttcacgatc gggacgctgc gcaaggccat    300

ccccgcgcac tgtttcgagc gctcggcgct tcgtagcagc atgtacctgg cctttgacat    360

cgcggtcatg tccctgctct acgtcgcgtc gacgtacatc gaccctgcac cggtgcctac    420

gtgggtcaag tacggcatca tgtggccgct ctactggttc ttccaggtgt gtttgagggt    480
```

-continued

```
tttggttgcc cgtattgagg tcctggtggc gcgcatggag gagaaggcgc ctgtcccgct    540
gacccccccg gctaccctcc cggcaccttc cagggcgcct tcggcacggg tgtctgggtg    600
tgcgcgcacg agtgcggcca ccaggccttt tcctccagcc aggccatcaa cgacggcgtg    660
ggcctggtgt tccacagcct gctgctggtg ccctactact cctggaagca ctcgcaccgg    720
gtacccttc ttgcgctatg acacttccag caaaaggtag ggcgggctgc gagacggctt    780
cccggcgctg catgcaacac cgatgatgct tcgacccccc gaagctcctt cggggctgca    840
tgggcgctcc gatgccgctc cagggcgagc gctgtttaaa tagccaggcc cccgattgca    900
aagacattat agcgagctac caaagccata ttcaaacacc tagatcacta ccacttctac    960
acaggccact cgagcttgtg atcgcactcc gctaaggggg cgcctcttcc tcttcgtttc   1020
agtcacaacc cgcaaactct agaatatcaa tgctgctgca ggccttcctg ttcctgctgg   1080
ccggcttcgc cgccaagatc agcgcctcca tgacgaacga gacgtccgac cgcccccctgg  1140
tgcacttcac ccccaacaag ggctggatga acgaccccaa cggcctgtgg tacgacgaga   1200
aggacgccaa gtggcacctg tacttccagt acaacccgaa cgacaccgtc tgggggacgc   1260
ccttgttctg ggccacgcc acgtccgacg acctgaccaa ctgggaggac cagcccatcg    1320
ccatcgcccc gaagcgcaac gactccggcg ccttctccgg ctccatggtg gtggactaca   1380
acaacacctc cggcttcttc aacgacacca tcgacccgcg ccagcgctgc gtggccatct   1440
ggacctacaa caccccggag tccgaggagc agtacatctc ctacagcctg gacggcggct   1500
acaccttcac cgagtaccag aagaaccccg tgctggccgc caactccacc cagttccgcg   1560
acccgaaggt cttctggtac gagccctccc agaagtggat catgaccgcg gccaagtccc   1620
aggactacaa gatcgagatc tactcctccg acgacctgaa gtcctggaag ctggagtccg   1680
cgttcgccaa cgagggcttc ctcggctacc agtacgagtg ccccggcctg atcgaggtcc   1740
ccaccgagca ggaccccagc aagtcctact gggtgatgtt catctccatc aaccccggcg   1800
ccccggccgg cggctccttc aaccagtact tcgtcggcag cttcaacggc acccacttcg   1860
aggccttcga caaccagtcc cgcgtggtgg acttcggcaa ggactactac gccctgcaga   1920
ccttcttcaa caccgacccg acctacggga gcgccctggg catcgcgtgg gcctccaact   1980
gggagtactc cgccttcgtg cccaccaacc cctggcgctc ctccatgtcc ctcgtgcgca   2040
agttctccct caacaccgag taccaggcca acccggagac ggagctgatc aacctgaagg   2100
ccgagccgat cctgaacatc agcaacgccg gcccctggag ccggttcgcc accaacacca   2160
cgttgacgaa ggccaacagc tacaacgtcg acctgtccaa cagcaccggc accctggagt   2220
tcgagctggt gtacgccgtc aacaccaccc agacgatctc caagtccgtg ttcgcggacc   2280
tctccctctg gttcaagggc ctggaggacc ccgaggagta cctccgcatg ggcttcgagg   2340
tgtccgcgtc ctccttcttc ctggaccgcg ggaacagcaa ggtgaagttc gtgaaggaga   2400
acccctactt caccaaccgc atgagcgtga acaaccagcc cttcaagagc gagaacgacc   2460
tgtcctacta caaggtgtac ggcttgctgg accagaacat cctggagctg tacttcaacg   2520
acggcgacgt cgtgtccacc aacacctact tcatgaccac cgggaacgcc ctgggctccg   2580
tgaacatgac gacgggggtg gacaacctgt tctacatcga caagttccag gtgcgcgagg   2640
tcaagtgaca attggcagca gcagctcgga tagtatcgac acactctgga cgctggtcgt   2700
gtgatggact gttgccgcca cacttgctgc cttgacctgt gaatatccct gccgctttta   2760
tcaaacagcc tcagtgtgtt tgatcttgtg tgtacgcgct tttgcgagtt gctagctgct   2820
```

```
tgtgctattt gcgaatacca cccccagcat ccccttccct cgtttcatat cgcttgcatc   2880
ccaaccgcaa cttatctacg ctgtcctgct atccctcagc gctgctcctg ctcctgctca   2940
ctgcccctcg cacagccttg gtttgggctc cgcctgtatt ctcctggtac tgcaacctgt   3000
aaaccagcac tgcaatgctg atgcacggga agtagtggga tgggaacaca aatggaggat   3060
cccgcgtctc gaacagagcg cgcagaggaa cgctgaaggt ctcgcctctg tcgcacctca   3120
gcgcggcata caccacaata accacctgac gaatgcgctt ggttcttcgt ccattagcga   3180
agcgtccggt tcacacacgt gccacgttgg cgaggtggca ggtgacaatg atcggtggag   3240
ctgatggtcg aaacgttcac agcctaggga tatcgaattc ggccgacagg acgcgcgtca   3300
aaggtgctgg tcgtgtatgc cctggccggc aggtcgttgc tgctgctggt tagtgattcc   3360
gcaaccctga ttttggcgtc ttattttggc gtggcaaacg ctggcgcccg cgagccgggc   3420
cggcggcgat gcggtgcccc acggctgccg gaatccaagg gaggcaagag cgcccgggtc   3480
agttgaaggg ctttacgcgc aaggtacagc cgctcctgca aggctgcgtg gtggaattgg   3540
acgtgcaggt cctgctgaag ttcctccacc gcctcaccag cggacaaagc accggtgtat   3600
caggtccgtg tcatccactc taaagaactc gactacgacc tactgatggc cctagattct   3660
tcatcaaaaa cgcctgagac acttgcccag gattgaaact ccctgaaggg accaccaggg   3720
gccctgagtt gttccttccc cccgtggcga gctgccagcc aggctgtacc tgtgatcgag   3780
gctggcggga aaataggctt cgtgtgctca ggtcatggga ggtgcaggac agctcatgaa   3840
acgccaacaa tcgcacaatt catgtcaagc taatcagcta tttcctcttc acgagctgta   3900
attgtcccaa aattctggtc taccgggggt gatccttcgt gtacgggccc ttccctcaac   3960
cctaggtatg cgcgcatgcg gtcgccgcgc aactcgcgcg agggccgagg gtttgggacg   4020
ggccgtcccg aaatgcagtt gcacccggat gcgtggcacc ttttttgcga taatttatgc   4080
aatggactgc tctgcaaaat tctggctctg tcgccaaccc taggatcagc ggcgtaggat   4140
ttcgtaatca ttcgtcctga tggggagcta ccgactaccc taatatcagc ccgactgcct   4200
gacgccagcg tccacttttg tgcacacatt ccattcgtgc ccaagacatt tcattgtggt   4260
gcgaagcgtc cccagttacg ctcacctgtt tcccgacctc cttactgttc tgtcgacaga   4320
gcgggcccac aggccggtcg cagccactag tatggccacc gcatccactt tctcggcgtt   4380
caatgcccgc tgcggcgacc tgcgtcgctc ggcgggctcc gggcccccggc gcccagcgag   4440
gcccctcccc gtgcgcgggc gcgccgccac cggcgagcag ccctccggcg tggcctccct   4500
gcgcgaggcc gacaaggaga agtccctggg caaccgcctg cgcctgggct ccctgaccga   4560
ggacggcctg tcctacaagg agaagttcgt gatccgctgc tacgaggtgg gcatcaacaa   4620
gaccgccacc atcgagacca tcgccaacct gctgcaggag gtgggcggca accacgccca   4680
gggcgtgggc ttctccaccg acggcttcgc caccaccacc accatgcgca agctgcacct   4740
gatctgggtg accgcccgca tgcacatcga gatctaccgc taccccgcct ggtccgacgt   4800
gatcgagatc gagacctggg tgcagggcga gggcaaggtg ggcacccgcc gcgactggat   4860
cctgaaggac tacgccaacg gcgaggtgat cggccgcgcc acctccaagt gggtgatgat   4920
gaacgaggac acccgccgcc tgcagaaggt gtccgacgac gtgcgcgagg agtacctggt   4980
gttctgcccc cgcaccctgc gcctggcctt ccccgaggag aacaacaact ccatgaagaa   5040
gatccccaag ctggaggacc ccgccgagta ctcccgcctg ggcctggtgc cccgccgctc   5100
cgacctggac atgaacaagc acgtgaacaa cgtgacctac atcggctggg ccctggagtc   5160
catccccccc gagatcatcg acacccacga gctgcaggcc atcaccctgg actaccgccg   5220
```

```
cgagtgccag cgcgacgaca tcgtggactc cctgacctcc cgcgagcccc tgggcaacgc   5280

cgccggcgtg aagttcaagg agatcaacgg ctccgtgtcc cccaagaagg acgagcagga   5340

cctgtcccgc ttcatgcacc tgctgcgctc cgccggctcc ggcctggaga tcaaccgctg   5400

ccgcaccgag tggcgcaaga agcccgccaa gcgcatggac tacaaggacc acgacggcga   5460

ctacaaggac cacgacatcg actacaagga cgacgacgac aagtgaatcg atagatctct   5520

taaggcagca gcagctcgga tagtatcgac acactctgga cgctggtcgt gtgatggact   5580

gttgccgcca cacttgctgc cttgacctgt gaatatccct gccgctttta tcaaacagcc   5640

tcagtgtgtt tgatcttgtg tgtacgcgct tttgcgagtt gctagctgct tgtgctattt   5700

gcgaatacca cccccagcat ccccttccct cgtttcatat cgcttgcatc ccaaccgcaa   5760

cttatctacg ctgtcctgct atccctcagc gctgctcctg ctcctgctca ctgcccctcg   5820

cacagccttg gtttgggctc cgcctgtatt ctcctggtac tgcaacctgt aaaccagcac   5880

tgcaatgctg atgcacggga agtagtggga tgggaacaca aatggaaagc ttaattaaga   5940

gctcccgcca ccactccaac acggggtgcc tggacaagga cgaggtgttt gtgccgccgc   6000

accgcgcagt ggcgcacgag ggcctggagt gggaggagtg gctgcccatc cgcatgggca   6060

aggtgctggt caccctgacc ctgggctggc cgctgtacct catgttcaac gtcgcctcgc   6120

ggccgtaccc gcgcttcgcc aaccactttg acccgtggtc gcccatcttc agcaagcgcg   6180

agcgcatcga ggtggtcatc tccgacctgg cgctggtggc ggtgctcagc gggctcagcg   6240

tgctgggccg caccatgggc tgggcctggc tggtcaagac ctacgtggtg ccctacctga   6300

tcgtgaacat gtggctcgtg ctcatcacgc tgctccagca cacgcacccg gcgctgccgc   6360

actacttcga gaaggactgg gactggctgc gcggcgccat ggccaccgtg gaccgctcca   6420

tgggcccgcc cttcatggac aacatcctgc accacatctc cgacacccac gtgctgcacc   6480

acctcttcag caccatcccg cactaccacg ccgaggaggc ctccgccgcc atcaggccca   6540

tcctgggcaa gtactaccag tccgacagcc gctgggtcgg ccgcgccctg tgggaggact   6600

ggcgcgactg ccgctacgtc gtcccggacg cgcccgagga cgactccgcg ctctggttcc   6660

acaagtgagt gagtga                                                   6676
```

<210> SEQ ID NO 18
<211> LENGTH: 719
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 18

```
gggctggtct gaatccttca ggcgggtgtt acccgagaaa gaaagggtgc cgatttcaaa     60

gcagacccat gtgccgggcc ctgtggcctg tgttggcgcc tatgtagtca cccccccctca   120

cccaattgtc gccagtttgc gcactccata aactcaaaac agcagcttct gagctgcgct    180

gttcaagaac acctctgggg tttgctcacc cgcgaggtcg acgcccagca tggctatcaa    240

gacgaacagg cagcctgtgg agaagcctcc gttcacgatc gggacgctgc gcaaggccat    300

ccccgcgcac tgtttcgagc gctcggcgct tcgtagcagc atgtacctgg cctttgacat    360

cgcggtcatg tccctgctct acgtcgcgtc gacgtacatc gaccctgcac cggtgcctac    420

gtgggtcaag tacggcatca tgtggccgct ctactggttc ttccaggtgt gtttgagggt    480

tttggttgcc cgtattgagg tcctggtggc gcgcatggag gagaaggcgc ctgtcccgct    540
```

-continued gacccccccg gctaccctcc cggcaccttc cagggcgcct tcggcacggg tgtctgggtg 600
tgcgcgcacg agtgcggcca ccaggccttt tcctccagcc aggccatcaa cgacggcgtg 660
ggcctggtgt tccacagcct gctgctggtg ccctactact cctggaagca ctcgcaccg 719

<210> SEQ ID NO 19
<211> LENGTH: 732
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19
ccgccaccac tccaacacgg ggtgcctgga caaggacgag gtgtttgtgc cgccgcaccg 60
cgcagtggcg cacgagggcc tggagtggga ggagtggctg cccatccgca tgggcaaggt 120
gctggtcacc ctgaccctgg gctggccgct gtacctcatg ttcaacgtcg cctcgcggcc 180
gtacccgcgc ttcgccaacc actttgaccc gtggtcgccc atcttcagca agcgcgagcg 240
catcgaggtg gtcatctccg acctggcgct ggtggcggtg ctcagcgggc tcagcgtgct 300
gggccgcacc atgggctggg cctggctggt caagacctac gtggtgccct acctgatcgt 360
gaacatgtgg ctcgtgctca tcacgctgct ccagcacacg cacccggcgc tgccgcacta 420
cttcgagaag gactgggact ggctgcgcgg cgccatggcc accgtggacc gctccatggg 480
cccgcccttc atggacaaca tcctgcacca catctccgac acccacgtgc tgcaccacct 540
cttcagcacc atcccgcact accacgccga ggaggcctcc gccgccatca ggcccatcct 600
gggcaagtac taccagtccg acagccgctg ggtcggccgc gccctgtggg aggactggcg 660
cgactgccgc tacgtcgtcc cggacgcgcc cgaggacgac tccgcgctct ggttccacaa 720
gtgagtgagt ga 732

<210> SEQ ID NO 20
<211> LENGTH: 612
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20
gctcttcgga gtcactgtgc cactgagttc gactggtagc tgaatggagt cgctgctcca 60
ctaaacgaat tgtcagcacc gccagccggc cgaggacccg agtcatagcg agggtagtag 120
cgcgccatgg caccgaccag cctgcttgcc agtactggcg tctcttccgc ttctctgtgg 180
tcctctgcgc gctccagcgc gtgcgctttt ccggtggatc atgcggtccg tggcgcaccg 240
cagcggccgc tgcccatgca gcgccgctgc ttccgaacag tggcggtcag ggccgcaccc 300
gcggtagccg tccgtccgga acccgcccaa gagttttggg agcagcttga gccctgcaag 360
atggcggagg acaagcgcat cttcctggag gagcaccggt gcgtggaggt ccggggctga 420
ccggccgtcg cattcaacgt aatcaatcgc atgatgatca gaggacacga agtcttggtg 480
gcggtggcca gaaacactgt ccattgcaag ggcataggga tgcgttcctt cacctctcat 540
ttctcatttc tgaatccctc cctgctcact ctttctcctc ctccttcccg ttcacgcagc 600
attcggggta cc 612

<210> SEQ ID NO 21

<211> LENGTH: 528
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
gacagggtgg ttggctggat ggggaaacgc tggtcgcggg attcgatcct gctgcttata     60

tcctccctgg aagcacaccc acgactctga agaagaaaac gtgcacacac acaacccaac    120

cggccgaata tttgcttcct tatcccgggt ccaagagaga ctgcgatgcc cccctcaatc    180

agcatcctcc tccctgccgc ttcaatcttc cctgcttgcc tgcgcccgcg gtgcgccgtc    240

tgcccgccca gtcagtcact cctgcacagg ccccttgtgc gcagtgctcc tgtacccttt    300

accgctcctt ccattctgcg aggcccccta ttgaatgtat tcgttgcctg tgtggccaag    360

cgggctgctg ggcgcgccgc cgtcgggcag tgctcggcga ctttggcgga agccgattgt    420

tcttctgtaa gccacgcgct tgctgctttg ggaagagaag gggggggta ctgaatggat    480

gaggaggaga aggaggggta ttggtattat ctgagttggg tgaagagc                 528
```

<210> SEQ ID NO 22
<211> LENGTH: 1174
<212> TYPE: DNA
<213> ORGANISM: Chlorella protothecoides

<400> SEQUENCE: 22

```
agtttaggtc cagcgtccgt ggggggggac gggctgggag cttgggccgg gaagggcaag     60

acgatgcagt ccctctgggg agtcacagcc gactgtgtgt gttgcactgt gcggcccgca    120

gcactcacac gcaaaatgcc tggccgacag gcaggccctg tccagtgcaa catccacggt    180

ccctctcatc aggctcacct tgctcattga cataacggaa tgcgtaccgc tctttcagat    240

ctgtccatcc agagagggga gcaggctccc caccgacgct gtcaaacttg cttcctgccc    300

aaccgaaaac attattgttt gaggggggggg ggggggggc agattgcatg gcgggatatc    360

tcgtgaggaa catcactggg acactgtgga acacagtgag tgcagtatgc agagcatgta    420

tgctaggggt cagcgcagga agggggcctt tcccagtctc ccatgccact gcaccgtatc    480

cacgactcac caggaccagc ttcttgatcg gcttccgctc ccgtggacac cagtgtgtag    540

cctctggact ccaggtatgc gtgcaccgca aaggccagcc gatcgtgccg attcctgggg    600

tggaggatat gagtcagcca acttggggct cagagtgcac actggggcac gatacgaaac    660

aacatctaca ccgtgtcctc catgctgaca caccacagct tcgctccacc tgaatgtggg    720

cgcatgggcc cgaatcacag ccaatgtcgc tgctgccata atgtgatcca gaccctctcc    780

gcccagatgc cgagcggatc gtgggcgctg aatagattcc tgtttcgatc actgtttggg    840

tcctttcctt ttcgtctcgg atgcgcgtct cgaaacaggc tgcgtcgggc tttcggatcc    900

cttttgctcc ctccgtcacc atcctgcgcg cgggcaagtt gcttgaccct gggctgtacc    960

agggttggag ggtattaccg cgtcaggcca ttcccagccc ggattcaatt caaagtctgg   1020

gccaccaccc tccgccgctc tgtctgatca ctccacattc gtgcatacac tacgttcaag   1080

tcctgatcca ggcgtgtctc gggacaaggt gtgcttgagt ttgaatctca aggacccact   1140

ccagcacagc tgctggttga ccccgccctc gcaa                               1174
```

<210> SEQ ID NO 23
<211> LENGTH: 3529
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 23

agtttaggtc cagcgtccgt gggggggac gggctgggag cttgggccgg gaagggcaag     60

acgatgcagt ccctctgggg agtcacagcc gactgtgtgt gttgcactgt gcggcccgca    120

gcactcacac gcaaaatgcc tggccgacag gcaggccctg tccagtgcaa catccacggt    180

ccctctcatc aggctcacct tgctcattga cataacggaa tgcgtaccgc tctttcagat    240

ctgtccatcc agagagggga gcaggctccc caccgacgct gtcaaacttg cttcctgccc    300

aaccgaaaac attattgttt gaggggggggg gggggggggc agattgcatg gcgggatatc    360

tcgtgaggaa catcactggg acactgtgga acacagtgag tgcagtatgc agagcatgta    420

tgctaggggt cagcgcagga agggggcctt tcccagtctc ccatgccact gcaccgtatc    480

cacgactcac caggaccagc ttcttgatcg gcttccgctc ccgtggacac cagtgtgtag    540

cctctggact ccaggtatgc gtgcaccgca aaggccagcc gatcgtgccg attcctgggg    600

tggaggatat gagtcagcca acttggggct cagagtgcac actggggcac gatacgaaac    660

aacatctaca ccgtgtcctc catgctgaca caccacagct tcgctccacc tgaatgtggg    720

cgcatgggcc cgaatcacag ccaatgtcgc tgctgccata atgtgatcca gaccctctcc    780

gcccagatgc cgagcggatc gtgggcgctg aatagattcc tgtttcgatc actgtttggg    840

tcctttcctt ttcgtctcgg atgcgcgtct cgaaacaggc tgcgtcgggc tttcggatcc    900

cttttgctcc ctccgtcacc atcctgcgcg cgggcaagtt gcttgaccct gggctgtacc    960

agggttggag ggtattaccg cgtcaggcca ttcccagccc ggattcaatt caaagtctgg   1020

gccaccaccc tccgccgctc tgtctgatca ctccacattc gtgcatacac tacgttcaag   1080

tcctgatcca ggcgtgtctc gggacaaggt gtgcttgagt ttgaatctca aggacccact   1140

ccagcacagc tgctggttga ccccgccctc gcaatctaga atggccgcgt ccgtccactg   1200

caccctgatg tccgtggtct gcaacaacaa gaaccactcc gcccgcccca agctgcccaa   1260

ctcctccctg ctgcccggct tcgacgtggt ggtccaggcc gcggccaccc gcttcaagaa   1320

ggagacgacg accacccgcg ccacgctgac gttcgacccc cccacgacca actccgagcg   1380

cgccaagcag cgcaagcaca ccatcgaccc ctcctccccc gacttccagc ccatcccctc   1440

cttcgaggag tgcttcccca agtccacgaa ggagcacaag gaggtggtgc acgaggagtc   1500

cggccacgtc ctgaaggtgc ccttccgccg cgtgcacctg tccggcggcg agcccgcctt   1560

cgacaactac gacacgtccg gcccccagaa cgtcaacgcc cacatcggcc tggcgaagct   1620

gcgcaaggag tggatcgacc gccgcgagaa gctgggcacg ccccgctaca cgcagatgta   1680

ctacgcgaag cagggcatca tcacggagga gatgctgtac tgcgcgacgc gcgagaagct   1740

ggaccccgag ttcgtccgct ccgaggtcgc gcggggccgc gccatcatcc cctccaacaa   1800

gaagcacctg gagctggagc ccatgatcgt gggccgcaag ttcctggtga aggtgaacgc   1860

gaacatcggc aactccgccg tggcctcctc catcgaggag gaggtctaca aggtgcagtg   1920

ggccaccatg tggggcgccg acaccatcat ggacctgtcc acgggccgcc acatccacga   1980

gacgcgcgag tggatcctgc gcaactccgc ggtccccgtg ggcaccgtcc ccatctacca   2040

ggcgctggag aaggtggacg gcatcgcgga gaacctgaac tgggaggtgt tccgcgagac   2100

gctgatcgag caggccgagc agggcgtgga ctacttcacg atccacgcgg gcgtgctgct   2160
```

```
gcgctacatc cccctgaccg ccaagcgcct gacgggcatc gtgtcccgcg gcggctccat   2220

ccacgcgaag tggtgcctgg cctaccacaa ggagaacttc gcctacgagc actgggacga   2280

catcctggac atctgcaacc agtacgacgt cgccctgtcc atcggcgacg gcctgcgccc   2340

cggctccatc tacgacgcca acgacacggc ccagttcgcc gagctgctga cccagggcga   2400

gctgacgcgc cgcgcgtggg agaaggacgt gcaggtgatg aacgagggcc ccggccacgt   2460

gcccatgcac aagatccccg agaacatgca gaagcagctg gagtggtgca acgaggcgcc   2520

cttctacacc ctgggccccc tgacgaccga catcgcgccc ggctacgacc acatcacctc   2580

cgccatcggc gcggccaaca tcggcgccct gggcaccgcc ctgctgtgct acgtgacgcc   2640

caaggagcac ctgggcctgc ccaaccgcga cgacgtgaag gcgggcgtca tcgcctacaa   2700

gatcgccgcc cacgcggccg acctggccaa gcagcacccc cacgcccagg cgtgggacga   2760

cgcgctgtcc aaggcgcgct tcgagttccg ctggatggac cagttcgcgc tgtccctgga   2820

ccccatgacg gcgatgtcct tccacgacga gacgctgccc gcggacggcg cgaaggtcgc   2880

ccacttctgc tccatgtgcg gccccaagtt ctgctccatg aagatcacgg aggacatccg   2940

caagtacgcc gaggagaacg gctacggctc cgccgaggag gccatccgcc agggcatgga   3000

cgccatgtcc gaggagttca acatcgccaa gaagacgatc tccggcgagc agcacggcga   3060

ggtcggcggc gagatctacc tgcccgagtc ctacgtcaag gccgcgcaga agtgacaatt   3120

ggcagcagca gctcggatag tatcgacaca ctctggacgc tggtcgtgtg atggactgtt   3180

gccgccacac ttgctgcctt gacctgtgaa tatccctgcc gcttttatca aacagcctca   3240

gtgtgtttga tcttgtgtgt acgcgctttt gcgagttgct agctgcttgt gctatttgcg   3300

aataccaccc ccagcatccc cttccctcgt ttcatatcgc ttgcatccca accgcaactt   3360

atctacgctg tcctgctatc cctcagcgct gctcctgctc ctgctcactg cccctcgcac   3420

agccttggtt tgggctccgc ctgtattctc ctggtactgc aacctgtaaa ccagcactgc   3480

aatgctgatg cacgggaagt agtgggatgg gaacacaaat ggaggatcc                3529
```

```
<210> SEQ ID NO 24
<211> LENGTH: 1476
<212> TYPE: DNA
<213> ORGANISM: Protetheca moriformis

<400> SEQUENCE: 24

atggccaccg catccacttt ctcggcgttc aatgcccgct gcggcgacct gcgtcgctcg     60

gcgggctccg ggcccggcg cccagcgagg cccctccccg tgcgcgggcg cgccgccgcc     120

gccgccgacg ccaaccccgc ccgccccgag cgccgcgtgg tgatcaccgg ccagggcgtg    180

gtgacctccc tgggccagac catcgagcag ttctactcct ccctgctgga gggcgtgtcc    240

ggcatctccc agatccagaa gttcgacacc accggctaca ccaccaccat cgccggcgag    300

atcaagtccc tgcagctgga cccctacgtg cccaagcgct gggccaagcg cgtggacgac    360

gtgatcaagt acgtgtacat cgccggcaag caggccctgg agtccgccgg cctgcccatc    420

gaggccgccg gcctggccgg cgccggcctg gaccccgccc tgtgcggcgt gctgatcggc    480

accgccatgg ccggcatgac ctccttcgcc gccggcgtgg aggccctgac ccgcggcggc    540

gtgcgcaaga tgaacccctt ctgcatcccc ttctccatct ccaacatggg cggcgccatg    600

ctggccatgg acatcggctt catgggcccc aactactcca tctccaccgc ctgcgccacc    660

ggcaactact gcatcctggg cgccgccgac cacatccgcc gcggcgacgc caacgtgatg    720

ctggccggcg gcgccgacgc cgccatcatc ccctccggca tcggcggctt catcgcctgc    780
```

```
aaggccctgt ccaagcgcaa cgacgagccc gagcgcgcct cccgcccctg ggacgccgac    840

cgcgacggct tcgtgatggg cgagggcgcc ggcgtgctgg tgctggagga gctggagcac    900

gccaagcgcc gcggcgccac catcctggcc gagctggtgg gcggcgccgc cacctccgac    960

gcccaccaca tgaccgagcc cgacccccag ggccgcggcg tgcgcctgtg cctggagcgc   1020

gccctggagc gcgcccgcct ggcccccgag cgcgtgggct acgtgaacgc ccacggcacc   1080

tccacccccg ccggcgacgt ggccgagtac cgcgccatcc gcgccgtgat cccccaggac   1140

tccctgcgca tcaactccac caagtccatg atcggccacc tgctgggcgg cgccggcgcc   1200

gtggaggccg tggccgccat ccaggccctg cgcaccggct ggctgcaccc caacctgaac   1260

ctggagaacc ccgcccccgg cgtggacccc gtggtgctgg tgggcccccg caaggagcgc   1320

gccgaggacc tggacgtggt gctgtccaac tccttcggct tcggcggcca caactcctgc   1380

gtgatcttcc gcaagtacga cgagatggac tacaaggacc acgacggcga ctacaaggac   1440

cacgacatcg actacaagga cgacgacgac aagtga                             1476
```

<210> SEQ ID NO 25
<211> LENGTH: 491
<212> TYPE: PRT
<213> ORGANISM: Protetheca moriformis

<400> SEQUENCE: 25

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ala Ala Ala Ala Asp Ala Asn Pro Ala Arg
        35                  40                  45

Pro Glu Arg Arg Val Val Ile Thr Gly Gln Gly Val Val Thr Ser Leu
    50                  55                  60

Gly Gln Thr Ile Glu Gln Phe Tyr Ser Ser Leu Leu Glu Gly Val Ser
65                  70                  75                  80

Gly Ile Ser Gln Ile Gln Lys Phe Asp Thr Thr Gly Tyr Thr Thr Thr
                85                  90                  95

Ile Ala Gly Glu Ile Lys Ser Leu Gln Leu Asp Pro Tyr Val Pro Lys
            100                 105                 110

Arg Trp Ala Lys Arg Val Asp Asp Val Ile Lys Tyr Val Tyr Ile Ala
        115                 120                 125

Gly Lys Gln Ala Leu Glu Ser Ala Gly Leu Pro Ile Glu Ala Ala Gly
    130                 135                 140

Leu Ala Gly Ala Gly Leu Asp Pro Ala Leu Cys Gly Val Leu Ile Gly
145                 150                 155                 160

Thr Ala Met Ala Gly Met Thr Ser Phe Ala Ala Gly Val Glu Ala Leu
                165                 170                 175

Thr Arg Gly Gly Val Arg Lys Met Asn Pro Phe Cys Ile Pro Phe Ser
            180                 185                 190

Ile Ser Asn Met Gly Gly Ala Met Leu Ala Met Asp Ile Gly Phe Met
        195                 200                 205

Gly Pro Asn Tyr Ser Ile Ser Thr Ala Cys Ala Thr Gly Asn Tyr Cys
    210                 215                 220

Ile Leu Gly Ala Ala Asp His Ile Arg Arg Gly Asp Ala Asn Val Met
225                 230                 235                 240

Leu Ala Gly Gly Ala Asp Ala Ala Ile Ile Pro Ser Gly Ile Gly Gly
```

```
                245                 250                 255

Phe Ile Ala Cys Lys Ala Leu Ser Lys Arg Asn Asp Glu Pro Glu Arg
            260                 265                 270

Ala Ser Arg Pro Trp Asp Ala Asp Arg Asp Gly Phe Val Met Gly Glu
        275                 280                 285

Gly Ala Gly Val Leu Val Leu Glu Glu Leu Glu His Ala Lys Arg Arg
    290                 295                 300

Gly Ala Thr Ile Leu Ala Glu Leu Val Gly Gly Ala Ala Thr Ser Asp
305                 310                 315                 320

Ala His His Met Thr Glu Pro Asp Pro Gln Gly Arg Gly Val Arg Leu
                325                 330                 335

Cys Leu Glu Arg Ala Leu Glu Arg Ala Arg Leu Ala Pro Glu Arg Val
            340                 345                 350

Gly Tyr Val Asn Ala His Gly Thr Ser Thr Pro Ala Gly Asp Val Ala
        355                 360                 365

Glu Tyr Arg Ala Ile Arg Ala Val Ile Pro Gln Asp Ser Leu Arg Ile
    370                 375                 380

Asn Ser Thr Lys Ser Met Ile Gly His Leu Leu Gly Gly Ala Gly Ala
385                 390                 395                 400

Val Glu Ala Val Ala Ala Ile Gln Ala Leu Arg Thr Gly Trp Leu His
                405                 410                 415

Pro Asn Leu Asn Leu Glu Asn Pro Ala Pro Gly Val Asp Pro Val Val
            420                 425                 430

Leu Val Gly Pro Arg Lys Glu Arg Ala Glu Asp Leu Asp Val Val Leu
        435                 440                 445

Ser Asn Ser Phe Gly Phe Gly Gly His Asn Ser Cys Val Ile Phe Arg
    450                 455                 460

Lys Tyr Asp Glu Met Asp Tyr Lys Asp His Asp Gly Asp Tyr Lys Asp
465                 470                 475                 480

His Asp Ile Asp Tyr Lys Asp Asp Asp Asp Lys
                485                 490


<210> SEQ ID NO 26
<211> LENGTH: 1107
<212> TYPE: DNA
<213> ORGANISM: Protetheca moriformis

<400> SEQUENCE: 26

atggccatca agaccaaccg ccagcccgtg gagaagcccc ccttcaccat cggcaccctg      60

cgcaaggcca tccccgccca ctgcttcgag cgctccgccc tgcgctcctc catgtacctg     120

gccttcgaca tcgccgtgat gtccctgctg tacgtggcct ccacctacat cgaccccgcc     180

cccgtgccca cctgggtgaa gtacggcgtg atgtggcccc tgtactggtt cttccagggc     240

gccttcggca ccggcgtgtg ggtgtgcgcc cacgagtgcg gccaccaggc cttctcctcc     300

tcccaggcca tcaacgacgg cgtgggcctg gtgttccact ccctgctgct ggtgccctac     360

tactcctgga agcactccca ccgccgccac cactccaaca ccggctgcct ggacaaggac     420

gaggtgttcg tgcccccca ccgcgccgtg gcccacgagg gcctggagtg ggaggagtgg     480

ctgcccatcc gcatgggcaa ggtgctggtg accctgaccc tgggctggcc cctgtacctg     540

atgttcaacg tggcctcccg cccctacccc cgcttcgcca accacttcga cccctggtcc     600

cccatcttct ccaagcgcga gcgcatcgag gtggtgatct ccgacctggc cctggtggcc     660

gtgctgtccg gcctgtccgt gctgggccgc accatgggct gggcctggct ggtgaagacc     720
```

-continued

```
tacgtggtgc cctacctgat cgtgaacatg tggctggtgc tgatcaccct gctgcagcac    780

acccaccccg ccctgcccca ctacttcgag aaggactggg actggctgcg cggcgccatg    840

gccaccgtgg accgctccat gggccccccc ttcatggaca acatcctgca ccacatctcc    900

gacacccacg tgctgcacca cctgttctcc accatccccc actaccacgc cgaggaggcc    960

tccgccgcca tccgccccat cctgggcaag tactaccagt ccgactcccg ctgggtgggc   1020

cgcgccctgt gggaggactg gcgcgactgc cgctacgtgg tgcccgacgc ccccgaggac   1080

gactccgccc tgtggttcca caagtag                                       1107
```

<210> SEQ ID NO 27
<211> LENGTH: 368
<212> TYPE: PRT
<213> ORGANISM: Protetheca moriformis

<400> SEQUENCE: 27

```
Met Ala Ile Lys Thr Asn Arg Gln Pro Val Glu Lys Pro Pro Phe Thr
1               5                   10                  15

Ile Gly Thr Leu Arg Lys Ala Ile Pro Ala His Cys Phe Glu Arg Ser
            20                  25                  30

Ala Leu Arg Ser Ser Met Tyr Leu Ala Phe Asp Ile Ala Val Met Ser
        35                  40                  45

Leu Leu Tyr Val Ala Ser Thr Tyr Ile Asp Pro Ala Pro Val Pro Thr
    50                  55                  60

Trp Val Lys Tyr Gly Val Met Trp Pro Leu Tyr Trp Phe Phe Gln Gly
65                  70                  75                  80

Ala Phe Gly Thr Gly Val Trp Val Cys Ala His Glu Cys Gly His Gln
                85                  90                  95

Ala Phe Ser Ser Ser Gln Ala Ile Asn Asp Gly Val Gly Leu Val Phe
            100                 105                 110

His Ser Leu Leu Leu Val Pro Tyr Tyr Ser Trp Lys His Ser His Arg
        115                 120                 125

Arg His His Ser Asn Thr Gly Cys Leu Asp Lys Asp Glu Val Phe Val
    130                 135                 140

Pro Pro His Arg Ala Val Ala His Glu Gly Leu Glu Trp Glu Glu Trp
145                 150                 155                 160

Leu Pro Ile Arg Met Gly Lys Val Leu Val Thr Leu Thr Leu Gly Trp
                165                 170                 175

Pro Leu Tyr Leu Met Phe Asn Val Ala Ser Arg Pro Tyr Pro Arg Phe
            180                 185                 190

Ala Asn His Phe Asp Pro Trp Ser Pro Ile Phe Ser Lys Arg Glu Arg
        195                 200                 205

Ile Glu Val Val Ile Ser Asp Leu Ala Leu Val Ala Val Leu Ser Gly
    210                 215                 220

Leu Ser Val Leu Gly Arg Thr Met Gly Trp Ala Trp Leu Val Lys Thr
225                 230                 235                 240

Tyr Val Val Pro Tyr Leu Ile Val Asn Met Trp Leu Val Leu Ile Thr
                245                 250                 255

Leu Leu Gln His Thr His Pro Ala Leu Pro His Tyr Phe Glu Lys Asp
            260                 265                 270

Trp Asp Trp Leu Arg Gly Ala Met Ala Thr Val Asp Arg Ser Met Gly
        275                 280                 285

Pro Pro Phe Met Asp Asn Ile Leu His His Ile Ser Asp Thr His Val
    290                 295                 300
```

-continued

Leu His His Leu Phe Ser Thr Ile Pro His Tyr His Ala Glu Glu Ala
305 310 315 320

Ser Ala Ala Ile Arg Pro Ile Leu Gly Lys Tyr Tyr Gln Ser Asp Ser
325 330 335

Arg Trp Val Gly Arg Ala Leu Trp Glu Asp Trp Arg Asp Cys Arg Tyr
340 345 350

Val Val Pro Asp Ala Pro Glu Asp Asp Ser Ala Leu Trp Phe His Lys
355 360 365

<210> SEQ ID NO 28
<211> LENGTH: 1191
<212> TYPE: DNA
<213> ORGANISM: Brassica napus

<400> SEQUENCE: 28
actagtatgc tgaagctgtc ctgcaacgtg accaacaacc tgcacacctt ctccttcttc 60
tccgactcct ccctgttcat ccccgtgaac cgccgcacca tcgccgtgtc ctccgggcgc 120
gcctcccagc tgcgcaagcc cgccctggac cccctgcgcg ccgtgatctc cgccgaccag 180
ggctccatct cccccgtgaa ctcctgcacc cccgccgacc gcctgcgcgc cggccgcctg 240
atggaggacg gctactccta caaggagaag ttcatcgtgc gctcctacga ggtgggcatc 300
aacaagaccg ccaccgtgga gaccatcgcc aacctgctgc aggaggtggc ctgcaaccac 360
gtgcagaagt gcggcttctc caccgacggc ttcgccacca ccctgaccat gcgcaagctg 420
cacctgatct gggtgaccgc ccgcatgcac atcgagatct acaagtaccc cgcctggtcc 480
gacgtggtgg agatcgagac ctggtgccag tccgagggcc gcatcggcac ccgccgcgac 540
tggatcctgc gcgactccgc caccaacgag gtgatcggcc gcgccacctc caagtgggtg 600
atgatgaacc aggacacccg ccgcctgcag cgcgtgaccg acgaggtgcg cgacgagtac 660
ctggtgttct gcccccgcga gccccgcctg gccttccccg aggagaacaa ctcctccctg 720
aagaagatcc ccaagctgga ggaccccgcc cagtactcca tgctggagct gaagccccgc 780
cgcgccgacc tggacatgaa ccagcacgtg aacaacgtga cctacatcgg ctgggtgctg 840
gagtccatcc cccaggagat catcgacacc cacgagctgc aggtgatcac cctggactac 900
cgccgcgagt gccagcagga cgacatcgtg gactccctga ccacctccga gatccccgac 960
gaccccatct ccaagttcac cggcaccaac ggctccgcca tgtcctccat ccagggccac 1020
aacgagtccc agttcctgca catgctgcgc ctgtccgaga acggccagga gatcaaccgc 1080
ggccgcaccc agtggcgcaa gaagtcctcc cgcatggact acaaggacca cgacggcgac 1140
tacaaggacc acgacatcga ctacaaggac gacgacgaca agtgaatcga t 1191

<210> SEQ ID NO 29
<211> LENGTH: 366
<212> TYPE: PRT
<213> ORGANISM: Brassica napus

<400> SEQUENCE: 29

Met Leu Lys Leu Ser Cys Asn Val Thr Asn Asn Leu His Thr Phe Ser
1 5 10 15

Phe Phe Ser Asp Ser Ser Leu Phe Ile Pro Val Asn Arg Arg Thr Ile
20 25 30

Ala Val Ser Ser Ser Gln Leu Arg Lys Pro Ala Leu Asp Pro Leu Arg
35 40 45

Ala Val Ile Ser Ala Asp Gln Gly Ser Ile Ser Pro Val Asn Ser Cys
50 55 60

Thr Pro Ala Asp Arg Leu Arg Ala Gly Arg Leu Met Glu Asp Gly Tyr
65 70 75 80

Ser Tyr Lys Glu Lys Phe Ile Val Arg Ser Tyr Glu Val Gly Ile Asn
85 90 95

Lys Thr Ala Thr Val Glu Thr Ile Ala Asn Leu Leu Gln Glu Val Ala
100 105 110

Cys Asn His Val Gln Lys Cys Gly Phe Ser Thr Asp Gly Phe Ala Thr
115 120 125

Thr Leu Thr Met Arg Lys Leu His Leu Ile Trp Val Thr Ala Arg Met
130 135 140

His Ile Glu Ile Tyr Lys Tyr Pro Ala Trp Ser Asp Val Val Glu Ile
145 150 155 160

Glu Thr Trp Cys Gln Ser Glu Gly Arg Ile Gly Thr Arg Arg Asp Trp
165 170 175

Ile Leu Arg Asp Ser Ala Thr Asn Glu Val Ile Gly Arg Ala Thr Ser
180 185 190

Lys Trp Val Met Met Asn Gln Asp Thr Arg Arg Leu Gln Arg Val Thr
195 200 205

Asp Glu Val Arg Asp Glu Tyr Leu Val Phe Cys Pro Arg Glu Pro Arg
210 215 220

Leu Ala Phe Pro Glu Glu Asn Asn Ser Ser Leu Lys Lys Ile Pro Lys
225 230 235 240

Leu Glu Asp Pro Ala Gln Tyr Ser Met Leu Glu Leu Lys Pro Arg Arg
245 250 255

Ala Asp Leu Asp Met Asn Gln His Val Asn Asn Val Thr Tyr Ile Gly
260 265 270

Trp Val Leu Glu Ser Ile Pro Gln Glu Ile Ile Asp Thr His Glu Leu
275 280 285

Gln Val Ile Thr Leu Asp Tyr Arg Arg Glu Cys Gln Gln Asp Asp Ile
290 295 300

Val Asp Ser Leu Thr Thr Ser Glu Ile Pro Asp Asp Pro Ile Ser Lys
305 310 315 320

Phe Thr Gly Thr Asn Gly Ser Ala Met Ser Ser Ile Gln Gly His Asn
325 330 335

Glu Ser Gln Phe Leu His Met Leu Arg Leu Ser Glu Asn Gly Gln Glu
340 345 350

Ile Asn Arg Gly Arg Thr Gln Trp Arg Lys Lys Ser Ser Arg
355 360 365

<210> SEQ ID NO 30
<211> LENGTH: 599
<212> TYPE: DNA
<213> ORGANISM: Prototheca moriformis

<400> SEQUENCE: 30
ggagtcactg tgccactgag ttcgactggt agctgaatgg agtcgctgct ccactaaacg 60
aattgtcagc accgccagcc ggccgaggac ccgagtcata gcgagggtag tagcgcgcca 120
tggcaccgac cagcctgctt gccagtactg gcgtctcttc cgcttctctg tggtcctctg 180
cgcgctccag cgcgtgcgct tttccggtgg atcatgcggt ccgtggcgca ccgcagcggc 240
cgctgcccat gcagcgccgc tgcttccgaa cagtggcggt cagggccgca cccgcggtag 300
ccgtccgtcc ggaacccgcc caagagtttt gggagcagct tgagccctgc aagatggcgg 360
aggacaagcg catcttcctg gaggagcacc ggtgcgtgga ggtccggggc tgaccggccg 420

```
tcgcattcaa cgtaatcaat cgcatgatga tcagaggaca cgaagtcttg gtggcggtgg    480

ccagaaacac tgtccattgc aagggcatag ggatgcgttc cttcacctct catttctcat    540

ttctgaatcc ctccctgctc actctttctc ctcctccttc ccgttcacgc agcattcgg     599


<210> SEQ ID NO 31
<211> LENGTH: 521
<212> TYPE: DNA
<213> ORGANISM: Prototheca moriformis

<400> SEQUENCE: 31

gacagggtgg ttggctggat ggggaaacgc tggtcgcggg attcgatcct gctgcttata     60

tcctccctgg aagcacaccc acgactctga agaagaaaac gtgcacacac acaacccaac    120

cggccgaata tttgcttcct tatcccgggt ccaagagaga ctgcgatgcc cccctcaatc    180

agcatcctcc tccctgccgc ttcaatcttc cctgcttgcc tgcgcccgcg gtgcgccgtc    240

tgcccgccca gtcagtcact cctgcacagg ccccttgtgc gcagtgctcc tgtacccttt    300

accgctcctt ccattctgcg aggcccccta ttgaatgtat tcgttgcctg tgtggccaag    360

cgggctgctg ggcgcgccgc cgtcgggcag tgctcggcga ctttggcgga agccgattgt    420

tcttctgtaa gccacgcgct tgctgctttg ggaagagaag gggggggggta ctgaatggat   480

gaggaggaga aggaggggta ttggtattat ctgagttggg t                        521


<210> SEQ ID NO 32
<211> LENGTH: 563
<212> TYPE: DNA
<213> ORGANISM: Prototheca moriformis

<400> SEQUENCE: 32

aatggagtcg ctgctccact aatcgaattg tcagcaccgc cagccggccg aggacccgag     60

tcatagcgag ggtagtagcg cgccatggca ccgaccagcc tgcttgcccg tactggcgtc    120

tcttccgctt ctctgtgctc ctctacgcgc tccggcgcgt gcgcttttcc ggtggatcat    180

gcggtccgtg gcgcaccgca gcggccgctg cccatgcagc gccgctgctt ccgaacagtg    240

gctgtcaggg ccgcacccgc agtagccgtc cgtccggaac ccgcccaaga gttttgggag    300

cagcttgagc cctgcaagat ggcggaggac aagcgcatct tcctggagga gcaccggtgc    360

gcggaggtcc ggggctgacc ggccgtcgca ttcaacgtaa tcaatcgcat gatgatcaca    420

ggacgcgacg tcttggtggc ggtggccagg gacactgccc attgcacagg cataggaatg    480

cgttccttct catttctcag ttttctgagc cctccctct tcactctttc tcctcctcct    540

cccctctcac gcagcattcg tgg                                             563


<210> SEQ ID NO 33
<211> LENGTH: 547
<212> TYPE: DNA
<213> ORGANISM: Prototheca moriformis

<400> SEQUENCE: 33

cactagtatc gatttcgaac agaggagagg gtggctggta gttgcgggat ggctggtcgc     60

ccgtcgatcc tgctgctgct attgtctcct cctgcacaag cccacccacg actccgaaga    120

agaagaagaa aacgcgcaca cacacaaccc aaccggccga atatttgctt ccttatcccg    180

ggtccaagag agacggcgat gccccccctca atcagcctcc tcctccctgc cgctccaatc   240

ttccctgctt gcatgcgccc gcgagaggct gtctgcgcgc cccgtcagtc actccccgtg    300
```

-continued

```
cagacgcctc gtgctcggtg ctcctgtatc ctttaccgct cctttcattc tgcgaggccc    360

cctgttgaat gtattcgttg cctgtgtggc caagcgcgct gctgggcgcg ccgccgtcgg    420

gcggtgctcg gcgactctgg cggaagccgg ttgttcttct gtaagccacg cgcttgctgc    480

ttttggaaaa gagggggtt tactgaatgg aggaggagca ggataattgg tagtatctga    540

gttgttg                                                              547


<210> SEQ ID NO 34
<211> LENGTH: 615
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

actagtgcgc tggacgcggc agtgggtggc cgaggagaac cggcacggcg acctgctgaa     60

caagtactgt tggctgacgg ggcgcgtcaa catgcgggcc gtggaggtga ccatcaacaa    120

cctgatcaag agcggcatga acccgcagac ggacaacaac ccttacttgg gcttcgtcta    180

cacctccttc caggagcgcg cgaccaagta cagccacggc aacaccgcgc gccttgcggc    240

cgagcagtgt gtttgagggt tttggttgcc cgtatcgagg tcctggtggc gcgcatgggg    300

gagaaggcgc ctgtcccgct gacccccccg gctaccctcc cggcaccttc cagggcgcgt    360

acgggatcct gctcggccgc aaggcgcgcg gtgttgccgt ggctgtactt ggtcgcgcgc    420

tcctggaagg aggtgtagac gaagcccaag taagggttgt tgtccgtctg cgggttcatg    480

ccgctcttga tcaggttgtt gatggtcacc tccacggccc gcatgttgac gcgccccgtc    540

agccaacagt acttgttcag caggtcgccg tgccggttct cctcggccac ccactgccgc    600

gtccagcgca agctt                                                     615


<210> SEQ ID NO 35
<211> LENGTH: 452
<212> TYPE: PRT
<213> ORGANISM: Prototheca moriformis

<400> SEQUENCE: 35

Met Ser Ile Gln Phe Ala Leu Arg Ala Ala Tyr Ile Lys Gly Thr Cys
1               5                   10                  15

Gln Arg Leu Ser Gly Arg Gly Ala Ala Leu Gly Leu Ser Arg Asp Trp
            20                  25                  30

Thr Pro Gly Trp Thr Leu Pro Arg Cys Trp Pro Ala Ser Ala Ala Ala
        35                  40                  45

Thr Ala Pro Pro Arg Ala Arg His Gln Glu Arg Ala Ile His Leu Thr
    50                  55                  60

Ser Gly Arg Arg Arg His Ser Ala Leu Ala Ser Asp Ala Asp Glu Arg
65                  70                  75                  80

Ala Leu Pro Ser Asn Ala Pro Gly Leu Val Met Ala Ser Gln Ala Asn
                85                  90                  95

Tyr Phe Arg Val Arg Leu Leu Pro Glu Gln Glu Glu Gly Glu Leu Glu
            100                 105                 110

Ser Trp Ser Pro Asn Val Arg His Thr Thr Leu Leu Cys Lys Pro Arg
        115                 120                 125

Ala Met Leu Ser Lys Leu Gln Met Arg Val Met Val Gly Asp Arg Val
    130                 135                 140

Ile Val Thr Ala Ile Asp Pro Val Asn Met Thr Val His Ala Pro Pro
```

-continued

```
145                 150                 155                 160

Phe Asp Pro Leu Pro Ala Thr Arg Phe Leu Val Ala Gly Glu Ala Ala
                165                 170                 175

Asp Met Asp Ile Thr Val Val Leu Asn Lys Ala Asp Leu Val Pro Glu
            180                 185                 190

Glu Glu Ser Ala Ala Leu Ala Gln Glu Val Ala Ser Trp Gly Pro Val
        195                 200                 205

Val Leu Thr Ser Thr Leu Thr Gly Arg Gly Leu Gln Glu Leu Glu Arg
    210                 215                 220

Gln Leu Gly Ser Thr Thr Ala Val Leu Ala Gly Pro Ser Gly Ala Gly
225                 230                 235                 240

Lys Ser Ser Ile Ile Asn Ala Leu Ala Arg Ala Ala Arg Glu Arg Pro
                245                 250                 255

Ser Asp Ala Ser Val Ser Asn Val Pro Glu Glu Gln Val Val Gly Glu
            260                 265                 270

Asp Gly Arg Ala Leu Ala Asn Pro Pro Pro Phe Thr Leu Ala Asp Ile
        275                 280                 285

Arg Asn Ala Ile Pro Lys Asp Cys Phe Arg Lys Ser Ala Ala Lys Ser
    290                 295                 300

Leu Ala Tyr Leu Gly Asp Leu Ser Ile Thr Gly Met Ala Val Leu Ala
305                 310                 315                 320

Tyr Lys Ile Asn Ser Pro Trp Leu Trp Pro Leu Tyr Trp Phe Ala Gln
                325                 330                 335

Gly Thr Met Phe Trp Ala Leu Phe Val Val Gly His Asp Cys Gly His
            340                 345                 350

Gln Ser Phe Ser Thr Ser Lys Arg Leu Asn Asp Ala Leu Ala Trp Leu
        355                 360                 365

Gly Ala Leu Ala Ala Gly Thr Trp Thr Trp Ala Leu Gly Val Leu Pro
    370                 375                 380

Met Leu Asn Leu Tyr Leu Ala Pro Tyr Val Trp Leu Leu Val Thr Tyr
385                 390                 395                 400

Leu His His His Gly Pro Ser Asp Pro Arg Glu Glu Met Pro Trp Tyr
                405                 410                 415

Arg Gly Arg Glu Trp Ser Tyr Met Arg Gly Gly Leu Thr Thr Ile Asp
            420                 425                 430

Arg Asp Tyr Gly Leu Phe Asn Lys Val His His Asp Ile Gly Thr His
        435                 440                 445

Val Val His His
    450
```

<210> SEQ ID NO 36
<211> LENGTH: 315
<212> TYPE: PRT
<213> ORGANISM: Prototheca moriformis

<400> SEQUENCE: 36

```
Met Phe Trp Ala Leu Phe Val Val Gly His Asp Cys Gly His Gln Ser
1               5                   10                  15

Phe Ser Thr Ser Lys Arg Leu Asn Asp Ala Val Gly Leu Phe Val His
            20                  25                  30

Ser Ile Ile Gly Val Pro Tyr His Gly Trp Arg Ile Ser His Arg Thr
        35                  40                  45

His His Asn Asn His Gly His Val Glu Asn Asp Glu Ser Trp Tyr Pro
    50                  55                  60
```

Pro Thr Glu Ser Gly Leu Lys Ala Met Thr Asp Met Gly Arg Gln Gly
65 70 75 80

Arg Phe His Phe Pro Ser Met Leu Phe Val Tyr Pro Phe Tyr Leu Phe
85 90 95

Trp Arg Ser Pro Gly Lys Thr Gly Ser His Phe Ser Pro Ala Thr Asp
100 105 110

Leu Phe Ala Leu Trp Glu Ala Pro Leu Ile Arg Thr Ser Asn Ala Cys
115 120 125

Gln Leu Ala Trp Leu Gly Ala Leu Ala Ala Gly Thr Trp Ala Leu Gly
130 135 140

Val Leu Pro Met Leu Asn Leu Tyr Leu Ala Pro Tyr Val Ile Ser Val
145 150 155 160

Ala Trp Leu Asp Leu Val Thr Tyr Leu His His His Gly Pro Ser Asp
165 170 175

Pro Arg Glu Glu Met Pro Trp Tyr Arg Gly Arg Glu Trp Ser Tyr Met
180 185 190

Arg Gly Gly Leu Thr Thr Ile Asp Arg Asp Tyr Gly Leu Phe Asn Lys
195 200 205

Val His His Asp Ile Gly Thr His Val Val His His Leu Phe Pro Gln
210 215 220

Ile Pro His Tyr Asn Leu Cys Arg Ala Thr Lys Ala Ala Lys Lys Val
225 230 235 240

Leu Gly Pro Tyr Tyr Arg Glu Pro Glu Arg Cys Pro Leu Gly Leu Leu
245 250 255

Pro Val His Leu Leu Ala Pro Leu Leu Arg Ser Leu Gly Gln Asp His
260 265 270

Phe Val Asp Asp Ala Gly Ser Val Leu Phe Tyr Arg Arg Ala Glu Gly
275 280 285

Ile Asn Pro Trp Ile Gln Lys Leu Leu Pro Trp Leu Gly Gly Ala Arg
290 295 300

Arg Gly Ala Asp Ala Gln Arg Asp Ala Ala Gln
305 310 315

<210> SEQ ID NO 37
<211> LENGTH: 448
<212> TYPE: PRT
<213> ORGANISM: Camelina sativa

<400> SEQUENCE: 37

Met Ala Asn Leu Val Leu Ser Glu Cys Gly Ile Arg Pro Leu Pro Arg
1 5 10 15

Ile Tyr Thr Thr Pro Arg Ser Asn Phe Val Ser Asn Asn Asn Lys Pro
20 25 30

Ile Phe Lys Phe Arg Pro Phe Thr Ser Tyr Lys Thr Ser Ser Ser Pro
35 40 45

Leu Ala Cys Ser Arg Asp Gly Phe Gly Lys Asn Trp Ser Leu Asn Val
50 55 60

Ser Val Pro Leu Thr Thr Thr Thr Pro Ile Val Asp Glu Ser Pro Leu
65 70 75 80

Lys Glu Glu Glu Glu Glu Lys Gln Arg Phe Asp Pro Gly Ala Pro Pro
85 90 95

Pro Phe Asn Leu Ala Asp Ile Arg Ala Ala Ile Pro Lys His Cys Trp
100 105 110

Val Lys Asn Pro Trp Lys Ser Met Ser Tyr Val Leu Arg Asp Val Ala
115 120 125

```
Ile Val Phe Ala Leu Ala Ala Gly Ala Ser Tyr Leu Asn Asn Trp Ile
    130                 135                 140

Val Trp Pro Leu Tyr Trp Leu Ala Gln Gly Thr Met Phe Trp Ala Leu
145                 150                 155                 160

Phe Val Leu Gly His Asp Cys Gly His Gly Ser Phe Ser Asn Asn Pro
                165                 170                 175

Arg Leu Asn Asn Val Val Gly His Leu Leu His Ser Ser Ile Leu Val
            180                 185                 190

Pro Tyr His Gly Trp Arg Ile Ser His Arg Thr His His Gln Asn His
        195                 200                 205

Gly His Val Glu Asn Asp Glu Ser Trp His Pro Met Ser Glu Lys Ile
    210                 215                 220

Tyr Gln Ser Leu Asp Lys Pro Thr Arg Phe Phe Arg Phe Thr Leu Pro
225                 230                 235                 240

Leu Val Met Leu Ala Tyr Pro Phe Tyr Leu Trp Ala Arg Ser Pro Gly
                245                 250                 255

Lys Lys Gly Ser His Tyr His Pro Glu Ser Asp Leu Phe Leu Pro Lys
            260                 265                 270

Glu Lys Thr Asp Val Leu Thr Ser Thr Ala Cys Trp Thr Ala Met Ala
        275                 280                 285

Ala Leu Leu Ile Cys Leu Asn Phe Val Val Gly Pro Val Gln Met Leu
    290                 295                 300

Lys Leu Tyr Gly Ile Pro Tyr Trp Ile Asn Val Met Trp Leu Asp Phe
305                 310                 315                 320

Val Thr Tyr Leu His His His Gly His Glu Asp Lys Leu Pro Trp Tyr
                325                 330                 335

Arg Gly Lys Glu Trp Ser Tyr Leu Arg Gly Gly Leu Thr Thr Leu Asp
            340                 345                 350

Arg Asp Tyr Gly Val Ile Asn Asn Ile His His Asp Ile Gly Thr His
        355                 360                 365

Val Ile His His Leu Phe Pro Gln Ile Pro His Tyr His Leu Val Glu
    370                 375                 380

Ala Thr Glu Ala Val Lys Pro Val Leu Gly Lys Tyr Tyr Arg Glu Pro
385                 390                 395                 400

Asp Lys Ser Gly Pro Leu Pro Leu His Leu Leu Gly Ile Leu Ala Lys
                405                 410                 415

Ser Ile Lys Glu Asp His Tyr Val Ser Asp Glu Gly Asp Val Val Tyr
            420                 425                 430

Tyr Lys Ala Asp Pro Asn Met Tyr Gly Glu Ile Lys Val Gly Ala Asp
        435                 440                 445


<210> SEQ ID NO 38
<211> LENGTH: 368
<212> TYPE: PRT
<213> ORGANISM: Prototheca moriformis

<400> SEQUENCE: 38

Met Ala Ile Lys Thr Asn Arg Gln Pro Val Glu Lys Pro Pro Phe Thr
1               5                   10                  15

Ile Gly Thr Leu Arg Lys Ala Ile Pro Ala His Cys Phe Glu Arg Ser
            20                  25                  30

Ala Leu Arg Ser Ser Met Tyr Leu Ala Phe Asp Ile Ala Val Met Ser
        35                  40                  45

Leu Leu Tyr Val Ala Ser Thr Tyr Ile Asp Pro Ala Pro Val Pro Thr
```

```
    50                  55                  60

Trp Val Lys Tyr Gly Ile Met Trp Pro Leu Tyr Trp Phe Phe Gln Gly
65                  70                  75                  80

Ala Phe Gly Thr Gly Val Trp Val Cys Ala His Glu Cys Gly His Gln
                85                  90                  95

Ala Phe Ser Ser Ser Gln Ala Ile Asn Asp Gly Val Gly Leu Val Phe
            100                 105                 110

His Ser Leu Leu Leu Val Pro Tyr Tyr Ser Trp Lys His Ser His Arg
        115                 120                 125

Arg His His Ser Asn Thr Gly Cys Leu Asp Lys Asp Glu Val Phe Val
    130                 135                 140

Pro Pro His Arg Ala Val Ala His Glu Gly Leu Glu Trp Glu Glu Trp
145                 150                 155                 160

Leu Pro Ile Arg Met Gly Lys Val Leu Val Thr Leu Thr Leu Gly Trp
                165                 170                 175

Pro Leu Tyr Leu Met Phe Asn Val Ala Ser Arg Pro Tyr Pro Arg Phe
            180                 185                 190

Ala Asn His Phe Asp Pro Trp Ser Pro Ile Phe Ser Lys Arg Glu Arg
        195                 200                 205

Ile Glu Val Val Ile Ser Asp Leu Ala Leu Val Ala Val Leu Ser Gly
    210                 215                 220

Leu Ser Val Leu Gly Arg Thr Met Gly Trp Ala Trp Leu Val Lys Thr
225                 230                 235                 240

Tyr Val Val Pro Tyr Met Ile Val Asn Met Trp Leu Val Leu Ile Thr
                245                 250                 255

Leu Leu Gln His Thr His Pro Ala Leu Pro His Tyr Phe Glu Lys Asp
            260                 265                 270

Trp Asp Trp Leu Arg Gly Ala Met Ala Thr Val Asp Arg Ser Met Gly
        275                 280                 285

Pro Pro Phe Met Asp Ser Ile Leu His His Ile Ser Asp Thr His Val
    290                 295                 300

Leu His His Leu Phe Ser Thr Ile Pro His Tyr His Ala Glu Glu Ala
305                 310                 315                 320

Ser Ala Ala Ile Arg Pro Ile Leu Gly Lys Tyr Tyr Gln Ser Asp Ser
                325                 330                 335

Arg Trp Val Gly Arg Ala Leu Trp Glu Asp Trp Arg Asp Cys Arg Tyr
            340                 345                 350

Val Val Pro Asp Ala Pro Glu Asp Asp Ser Ala Leu Trp Phe His Lys
        355                 360                 365


<210> SEQ ID NO 39
<211> LENGTH: 448
<212> TYPE: PRT
<213> ORGANISM: Camelina sativa

<400> SEQUENCE: 39

Met Ala Asn Leu Val Leu Ser Glu Cys Gly Ile Arg Pro Leu Pro Arg
1               5                   10                  15

Ile Tyr Thr Thr Pro Arg Ser Asn Phe Val Ser Asn Asn Asn Lys Pro
            20                  25                  30

Ile Phe Lys Phe Arg Pro Leu Thr Ser Tyr Lys Thr Ser Ser Pro Leu
        35                  40                  45

Phe Cys Ser Arg Asp Gly Phe Gly Arg Asn Trp Ser Leu Asn Val Ser
    50                  55                  60
```

```
Val Pro Leu Ala Thr Thr Thr Pro Ile Val Asp Glu Ser Pro Leu Glu
65                  70                  75                  80

Glu Glu Glu Glu Glu Glu Lys Gln Arg Phe Asp Pro Gly Ala Pro Pro
                85                  90                  95

Pro Phe Asn Leu Ala Asp Ile Arg Ala Ala Ile Pro Lys His Cys Trp
            100                 105                 110

Val Lys Asn Pro Trp Lys Ser Met Ser Tyr Val Leu Arg Asp Val Ala
        115                 120                 125

Ile Val Phe Ala Leu Ala Ala Gly Ala Ala Tyr Leu Asn Asn Trp Ile
    130                 135                 140

Val Trp Pro Leu Tyr Trp Leu Ala Gln Gly Thr Met Phe Trp Ala Leu
145                 150                 155                 160

Phe Val Leu Gly His Asp Cys Gly His Gly Ser Phe Ser Asn Asn Pro
                165                 170                 175

Arg Leu Asn Asn Val Val Gly His Leu Leu His Ser Ser Ile Leu Val
            180                 185                 190

Pro Tyr His Gly Trp Arg Ile Ser His Arg Thr His His Gln Asn His
        195                 200                 205

Gly His Val Glu Asn Asp Glu Ser Trp His Pro Met Ser Glu Lys Ile
    210                 215                 220

Tyr Gln Ser Leu Asp Lys Pro Thr Arg Phe Phe Arg Phe Thr Leu Pro
225                 230                 235                 240

Leu Val Met Leu Ala Tyr Pro Phe Tyr Leu Trp Ala Arg Ser Pro Gly
                245                 250                 255

Lys Lys Gly Ser His Tyr His Pro Glu Ser Asp Leu Phe Leu Pro Lys
            260                 265                 270

Glu Lys Thr Asp Val Leu Thr Ser Thr Ala Cys Trp Thr Ala Met Ala
        275                 280                 285

Ala Leu Leu Ile Cys Leu Asn Phe Val Val Gly Pro Val Gln Met Leu
    290                 295                 300

Lys Leu Tyr Gly Ile Pro Tyr Trp Ile Asn Val Met Trp Leu Asp Phe
305                 310                 315                 320

Val Thr Tyr Leu His His His Gly His Glu Asp Lys Leu Pro Trp Tyr
                325                 330                 335

Arg Gly Lys Glu Trp Ser Tyr Leu Arg Gly Gly Leu Thr Thr Leu Asp
            340                 345                 350

Arg Asp Tyr Gly Val Ile Asn Asn Ile His His Asp Ile Gly Thr His
        355                 360                 365

Val Ile His His Leu Phe Pro Gln Ile Pro His Tyr His Leu Val Glu
    370                 375                 380

Ala Thr Glu Ala Val Lys Pro Val Leu Gly Lys Tyr Tyr Arg Glu Pro
385                 390                 395                 400

Asp Lys Ser Gly Pro Leu Pro Leu His Leu Leu Gly Ile Leu Ala Lys
                405                 410                 415

Ser Ile Lys Glu Asp His Tyr Val Ser Asp Glu Gly Asp Val Val Tyr
            420                 425                 430

Tyr Lys Ala Asp Pro Asn Met Tyr Gly Glu Ile Lys Val Gly Ala Asp
        435                 440                 445
```

<210> SEQ ID NO 40
<211> LENGTH: 353
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

```
actagtcatt cggggcaacg aggtgggccc ctcgcagcgg ctgacgatca cggcggtggc     60
caacatcctg caggaggcgg cgggcaacca cgcggtggcc atgtggggcc ggagcgtgtg    120
tttgagggtt ttggttgccc gtattgaggt cctggtggcg cgcatggggg agaaggcgcc    180
tgtcccgctg accccccccgg ctaccctccc ggcaccttcc agggcgcgta cgggatccgc    240
tccggcccca catggccacc gcgtggttgc ccgccgcctc ctgcaggatg ttggccaccg    300
ccgtgatcgt cagccgctgc gaggggccca cctcgttgcc ccgaatgaag ctt           353
```

<210> SEQ ID NO 41
<211> LENGTH: 391
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41

```
actagtggag ggtttcgcga cggacccgga gctgcaggag gcgggtctca tctttgtgat     60
gacgcgcatg cagatccaga tgtaccgcta cccgcgctgg ggcgacctga tgcaggtgga    120
gacctggttc cagagtgtgt ttgagggttt tggttgcccg tattgaggtc ctggtggcgc    180
gcatggggga gaaggcgcct gtcccgctga cccccccggc taccctcccg gcaccttcca    240
gggcgcgtac gggatcctct ggaaccaggt ctccacctgc atcaggtcgc cccagcgcgg    300
gtagcggtac atctggatct gcatgcgcgt catcacaaag atgagacccg cctcctgcag    360
ctccgggtcc gtcgcgaaac cctccaagct t                                   391
```

<210> SEQ ID NO 42
<211> LENGTH: 393
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42

```
actagtcggc gggcaagctg ggcgcgcagc gcgagtgggt gctgcgcgac aagctgaccg     60
gcgaggcgct gggcgcggcc acctcgagct gggtcatgat caacatccgc acgcgccggc    120
cgtgccgcat gccgggtgtg tttgagggtt ttggttgccc gtatcgaggt cctggtggcg    180
cgcatggggg agaaggcgcc tgtcccgctg accccccccgg ctaccctccc ggcaccttcc    240
agggcgcgta cgggatcccc ggcatgcggc acggccggcg cgtgcggatg ttgatcatga    300
cccagctcga ggtggccgcg cccagcgcct cgccggtcag cttgtcgcgc agcacccact    360
cgcgctgcgc gcccagcttg cccgccgaag ctt                                 393
```

<210> SEQ ID NO 43
<211> LENGTH: 517
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

```
actagtgtcc gcgtcaagtc ggccttcttc gcgcgcgagc cgccgcgcct ggcgctgccg     60
```

cccgcggtca cgcgtgccaa gctgcccaac atcgcgacgc cggcgccgct gcgcgggcac 120
cgccaggtcg cgcgccgcac cgacatggac atgaacgggc acgtgaacaa cgtggcctac 180
ctggcctggt gcctggagtg tgtttgaggg ttttggttgc ccgtattgag gtcctggtgg 240
cgcgcatggg ggagaaggcg cctgtcccgc tgaccccccc ggctaccctc ccggcacctt 300
ccagggcgcg tacgggatcc tccaggcacc aggccaggta ggccacgttg ttcacgtgcc 360
cgttcatgtc catgtcggtg cggcgcgcga cctggcggtg cccgcgcagc ggcgccggcg 420
tcgcgatgtt gggcagcttg gcacgcgtga ccgcgggcgg cagcgccagg cgcggcggct 480
cgcgcgcgaa gaaggccgac ttgacgcgga caagctt 517

<210> SEQ ID NO 44
<211> LENGTH: 519
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44
actagtccgt gcccgagcac gtcttcagcg actaccacct ctaccagatg gagatcgact 60
tcaaggccga gtgccacgcg ggcgacgtca tctcctccca ggccgagcag atcccgcccc 120
aggaggcgct cacgcacaac ggcgccggcc gcaacccctc ctgcttcgtc catagcattc 180
tgcgcgccga gaccgagcgt gtgtttgagg gttttggttg cccgtatcga ggtcctggtg 240
gcgcgcatgg gggagaaggc gcctgtcccg ctgacccccc cggctaccct cccggcacct 300
tccagggcgc gtacgggatc cgctcggtct cggcgcgcag aatgctatgg acgaagcagg 360
aggggttgcg gccggcgccg ttgtgcgtga gcgcctcctg ggcgggatc tgctcggcct 420 gggaggagat gacgtcgccc gcgtggcact cggccttgaa gtcgatctcc atctggtaga 480
ggtggtagtc gctgaagacg tgctcgggca cggaagctt 519

<210> SEQ ID NO 45
<211> LENGTH: 415
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45
actagttcgt ccgcgcgcga accacatggt cggcccccat cgacgcgccc gccgccaagc 60
cgcccaaggc gagccactga ggacagggtg gttggctgga tggggaaacg ctggtcgcgg 120
gattcgatcc tgctgcttat atcctcgtgt gtttgagggt tttggttgcc cgtattgagg 180
tcctggtggc gcgcatgggg gagaaggcgc ctgtcccgct gaccccccg gctaccctcc 240 cggcaccttc cagggcgcgt acgggatccg aggatataag cagcaggatc gaatcccgcg 300
accagcgttt ccccatccag ccaaccaccc tgtcctcagt ggctcgcctt gggcggcttg 360
gcggcgggcg cgtcgatggg ggccgaccat gtggttcgcg cgcggacgaa agctt 415

<210> SEQ ID NO 46
<211> LENGTH: 1629
<212> TYPE: DNA
<213> ORGANISM: Cuphea wrightii

<400> SEQUENCE: 46
atggccgccg ccgccagcat ggtggccagc cccttctgca cctggctggt ggccagctgc 60

-continued atgagcacca gcttcgacaa cgacccccgc agccccagcg tgaagcgctt cccccgccgc 120
aagcgcgtgc tgagccagcg cggcagcacc tacgtattcc agtgcctggt ggccagctgc 180
atcgacccct gcgaccagta ccgcagcagc gccagcctga gcttcctggg cgacaacggc 240
ttcgccagcc tgttcggcag caagcccttc atgagcaacc gcggccaccg ccgcctgcgc 300
cgcgccagcc acagcggcga ggccatggcc gtggccctgc agcccgccca ggaggccggc 360
accaagaaga agcccgtgat caagcagcgc cgcgtggtgg tgaccggcat gggcgtggtg 420
acccccctgg gccacgagcc cgacgtgttc tacaacaacc tgctggacgg cgtgagcggc 480
atcagcgaga tcgagacctt cgactgcacc cagttcccca cccgcatcgc cggcgagatc 540
aagagcttca gcaccgacgg ctgggtggcc cccaagctga gcaagcgcat ggacaagttc 600
atgctgtacc tgctgaccgc cggcaagaag gccctggccg acggcggcat caccgacgag 660
gtgatgaagg agctggacaa gcgcaagtgc ggcgtgctga tcggcagcgg catgggcggc 720
atgaaggtgt tcaacgacgc catcgaggcc ctgcgcgtga gctacaagaa gatgaacccc 780
ttctgcgtgc ccttcgccac caccaacatg ggcagcgcca tgctggccat ggacctgggc 840
tggatgggcc ccaactacag catcagcacc gcctgcgcca ccagcaactt ctgcatcctg 900
aacgccgcca accacatcat ccgcggcgag gccgacatga tgctgtgcgg cggcagcgac 960
gccgtgatca tccccatcgg cctgggcggc ttcgtggcct gccgcgccct gagccagcgc 1020
aacagcgacc ccaccaaggc cagccgcccc tgggacagca accgcgacgg cttcgtgatg 1080
ggcgagggcg ccggcgtgct gctgctggag gagctggagc acgccaagaa gcgcggcgcc 1140
accatctacg ccgagttcct gggcggcagc ttcacctgcg acgcctacca catgaccgag 1200
ccccaccccg agggcgccgg cgtgatcctg tgcatcgaga aggccctggc ccaggccggc 1260
gtgagcaagg aggacgtgaa ctacatcaac gcccacgcca ccagcaccag cgccggcgac 1320
atcaaggagt accaggccct ggcccgctgc ttcggccaga acagcgagct gcgcgtgaac 1380
agcaccaaga gcatgatcgg ccacctgctg ggcgccgccg gcggcgtgga ggccgtgacc 1440
gtggtgcagg ccatccgcac cggctggatt caccccaacc tgaacctgga ggaccccgac 1500
aaggccgtgg acgccaagct gctggtgggc cccaagaagg agcgcctgaa cgtgaaggtg 1560
ggcctgagca acagcttcgg cttcggcggc cacaacagca gcatcctgtt cgcccccctgc 1620 aacgtgtga 1629

<210> SEQ ID NO 47
<211> LENGTH: 1552
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 47
atgggccgcg gtgtctccct tccccggccc agggtcgcgg tgcgcgccca gtcggcgagt 60
caggttttgg agagctgtat tccagtgcct ggtggccagc tgcatcgacc cctgcgacca 120
gtaccgcagc agcgccagcc tgagcttcct gggcgacaac ggcttcgcca gcctgttcgg 180
cagcaagccc ttcatgagca accgcggcca ccgccgcctg cgccgcgcca gccacagcgg 240
cgaggccatg gccgtggccc tgcagcccgc ccaggaggcc ggcaccaaga agaagcccgt 300
gatcaagcag cgccgcgtgg tggtgaccgg catgggcgtg gtgacccccc tgggccacga 360
gcccgacgtg ttctacaaca acctgctgga cggcgtgagc ggcatcagcg agatcgagac 420

```
cttcgactgc acccagttcc ccacccgcat cgccggcgag atcaagagct tcagcaccga    480
cggctgggtg gcccccaagc tgagcaagcg catggacaag ttcatgctgt acctgctgac    540
cgccggcaag aaggccctgg ccgacggcgg catcaccgac gaggtgatga aggagctgga    600
caagcgcaag tgcggcgtgc tgatcggcag cggcatgggc ggcatgaagg tgttcaacga    660
cgccatcgag gccctgcgcg tgagctacaa gaagatgaac cccttctgcg tgcccttcgc    720
caccaccaac atgggcagcg ccatgctggc catggacctg ggctggatgg gccccaacta    780
cagcatcagc accgcctgcg ccaccagcaa cttctgcatc ctgaacgccg ccaaccacat    840
catccgcggc gaggccgaca tgatgctgtg cggcggcagc gacgccgtga tcatccccat    900
cggcctgggc ggcttcgtgg cctgccgcgc cctgagccag cgcaacagcg accccaccaa    960
ggccagccgc ccctgggaca gcaaccgcga cggcttcgtg atgggcgagg gcgccggcgt   1020
gctgctgctg gaggagctgg agcacgccaa gaagcgcggc gccaccatct acgccgagtt   1080
cctgggcggc agcttcacct gcgacgccta ccacatgacc gagccccacc ccgagggcgc   1140
cggcgtgatc ctgtgcatcg agaaggccct ggcccaggcc ggcgtgagca aggaggacgt   1200
gaactacatc aacgcccacg ccaccagcac cagcgccggc gacatcaagg agtaccaggc   1260
cctggcccgc tgcttcggcc agaacagcga gctgcgcgtg aacagcacca agagcatgat   1320
cggccacctg ctgggcgccg ccggcggcgt ggaggccgtg accgtggtgc aggccatccg   1380
caccggctgg attcacccca acctgaacct ggaggacccc gacaaggccg tggacgccaa   1440
gctgctggtg ggccccaaga aggagcgcct gaacgtgaag gtgggcctga gcaacagctt   1500
cggcttcggc ggccacaaca gcagcatcct gttcgccccc tgcaacgtgt ga           1552
```

<210> SEQ ID NO 48
<211> LENGTH: 1641
<212> TYPE: DNA
<213> ORGANISM: Cuphea pulcherrima

<400> SEQUENCE: 48

```
atgcccgcgg ccagctcgct gctggcgtcc cccctgtgca cctggctgct ggccgcgtgc     60
atgagcacct cgttccaccc ctccgacccc ctgcccccca gcatctcgtc cccccgccgc    120
cgcctgagcc gccgccgcat cctgtcgcag tgcgcccccc tgccctccgc gagctcggcc    180
ctgcgcggct ccagcttcca caccctggtg acctcgtatc tggcgtgctt cgagccctgc    240
cacgactatt ataccagcgc ctccctgttc ggctcgcgcc ccatccgcac cacccgccgc    300
caccgccgcc tgaaccgcgc gagcccctcg cgcgaggcga tggcggtcgc cctgcagccc    360
gagcaggagg tgaccaccaa gaagaagccc tccatcaagc agcgccgcgt cgtggtcacc    420
ggcatgggcg tggtcacccc cctgggccac gaccccgacg tgttctataa caacctgctg    480
gacggcacca gcggcatctc ggagatcgag accttcgact gcgcgcagtt ccccacccgc    540
atcgccggcg agatcaagtc cttcagcacc gacggctggg tcgcgcccaa gctgtcgaag    600
cgcatggaca agttcatgct gtatatgctg accgccggca agaaggcgct gaccgacggc    660
ggcatcaccg aggacgtgat gaaggagctg gacaagcgca agtgcggcgt cctgatcggc    720
tccgcgatgg gcggcatgaa ggtgttcaac gacgcgatcg aggccctgcg catcagctat    780
aagaagatga accccttctg cgtgcccttc gcgaccacca acatgggctc ggccatgctg    840
gcgatggacc tgggctggat gggccccaac tattccatca gcaccgcctg cgcgacctcg    900
aacttctgca tcatgaacgc ggccaaccac atcatccgcg gcgaggcgga cgtcatgctg    960
```

-continued

```
tgcggcggct ccgacgccgt gatcatcccc atcggcatgg gcggcttcgt cgcgtgccgc   1020

gccctgagcc agcgcaactc ggaccccacc aaggcgtccc gcccctggga cagcaaccgc   1080

gacggcttcg tgatgggcga gggcgccggc gtcctgctgc tggaggagct ggagcacgcg   1140

aagaagcgcg gcgccaccat ctatgcggag ttcctgggcg gctcgttcac ctgcgacgcc   1200

tatcacatga ccgagcccca ccccgacggc gccggcgtga tcctgtgcat cgagaaggcg   1260

ctggcccagt ccggcgtcag ccgcgaggac gtgaactata tcaacgcgca cgccacctcg   1320

acccccgcgg gcgacatcaa ggagtatcag gccctgatcc actgcttcgg ccagaaccgc   1380

gagctgaagg tcaactccac caagagcatg atcggccacc tgctgggcgc ggcgggcggc   1440

gtggaggcgg tctcggtggt ccaggccatc cgcaccggct ggatccaccc caacatcaac   1500

ctggagaacc ccgacgaggg cgtggacacc aagctgctgg tgggccccaa gaaggagcgc   1560

ctgaacgtca aggtgggcct gtccaacagc ttcggcttcg gcggccacaa ctcgtccatc   1620

ctgttcgcgc cctatatctg a                                              1641
```

<210> SEQ ID NO 49
<211> LENGTH: 1251
<212> TYPE: DNA
<213> ORGANISM: Cuphea hookeriana

<400> SEQUENCE: 49

```
atggtggccg ccgccgcctc cagcgccttc ttccccgtgc ccgcccccgg cgcctccccc     60

aagcccggca agttcggcaa ctggccctcc agcctgagcc cctccttcaa gcccaagtcc    120

atccccaacg gcggcttcca ggtgaaggcc aacgacagcg cccaccccaa ggccaacggc    180

tccgccgtga gcctgaagag cggcagcctg aacacccagg aggacacctc ctccagcccc    240

cccccccgca ccttcctgca ccagctgccc gactggagcc gcctgctgac cgccatcacc    300

accgtgttcg tgaagtccaa gcgccccgac atgcacgacc gcaagtccaa gcgccccgac    360

atgctggtgg acagcttcgg cctggagtcc accgtgcagg acggcctggt gttccgccag    420

tccttctcca tccgctccta cgagatcggc accgaccgca ccgccagcat cgagaccctg    480

atgaaccacc tgcaggagac ctccctgaac cactgcaaga gcaccggcat cctgctggac    540

ggcttcggcc gcaccctgga gatgtgcaag cgcgacctga tctgggtggt gatcaagatg    600

cagatcaagg tgaaccgcta ccccgcctgg ggcgacaccg tggagatcaa cacccgcttc    660

agccgcctgg gcaagatcgg catgggccgc gactggctga tctccgactg caacaccggc    720

gagatcctgg tgcgcgccac cagcgcctac gccatgatga accagaagac ccgccgcctg    780

tccaagctgc cctacgaggt gcaccaggag atcgtgcccc tgttcgtgga cagccccgtg    840

atcgaggact ccgacctgaa ggtgcacaag ttcaaggtga agaccggcga cagcatccag    900

aagggcctga cccccggctg gaacgacctg gacgtgaacc agcacgtgtc caacgtgaag    960

tacatcggct ggatcctgga gagcatgccc accgaggtgc tggagaccca ggagctgtgc   1020

tccctggccc tggagtaccg ccgcgagtgc ggccgcgact ccgtgctgga gagcgtgacc   1080

gccatggacc ccagcaaggt gggcgtgcgc tcccagtacc agcacctgct gcgcctggag   1140

gacggcaccg ccatcgtgaa cggcgccacc gagtggcgcc ccaagaacgc cggcgccaac   1200

ggcgccatct ccaccggcaa gaccagcaac ggcaactccg tgtccatgtg a            1251
```

<210> SEQ ID NO 50
<211> LENGTH: 659
<212> TYPE: DNA
<213> ORGANISM: Protheca moriformis -continued

<400> SEQUENCE: 50
gctcttcctc accgcgtgaa ttgctgtccc aaacgtaagc atcatcgtgg ctcggtcacg 60
cgatcctgga tccggggatc ctagaccgct ggtggagagc gctgccgtcg gattggtggc 120
aagtaagatt gcgcaggttg gcgaagggag agaccaaaac cggaggctgg aagcgggcac 180
aacatcgtat tattgcgtat agtagagcag tggcagtcgc atttcgaggt ccgcaacgga 240
tctcgcaagc tcgctacgct cacagtagga gaaaggggac cactgcccct gccagaatgg 300
tcgcgaccct ctccctcgcc ggccccgcct gcaacacgca gtgcgtatcc ggcaagcggg 360
ctgtcgcctt caaccgcccc catgttggcg tccgggctcg atcaggtgcg ctgagggggg 420
tttggtgtgc ccgcgcctct gggcccgtgt cggccgtgcg gacgtggggc cctgggcagt 480
ggatcagcag ggtttgcgtg caaatgccta taccggcgat tgaatagcga tgaacgggat 540
acggttgcgc tcactccatg cccatgcgac cccgtttctg tccgccagcc gtggtcgccc 600
gggctgcgaa gcgggacccc acccagcgca ttgtgatcac cggaatgggc gtgggtacc 659

<210> SEQ ID NO 51
<211> LENGTH: 607
<212> TYPE: DNA
<213> ORGANISM: Protheca moriformis

<400> SEQUENCE: 51
gagctccacc tgcatccgcc tggcgctcga ggacgccggc gtctcgcccg acgaggtcaa 60
ctacgtcaac gcgcacgcca cctccaccct ggtgggcgac aaggccgagg tgcgcgcggt 120
caagtcggtc tttggcgaca tgaagggcat caagatgaac gccaccaagt ccatgatcgg 180
gcactgcctg ggcgccgccg gcggcatgga ggccgtcgcc acgctcatgg ccatccgcac 240
cggctgggtg caccccacca tcaaccacga caaccccatc gccgaggtcg acggcctgga 300
cgtcgtcgcc aacgccaagg cccagcacaa aatcaacgtc gccatctcca actccttcgg 360
cttcggcggg cacaactccg tcgtcgcctt tgcgcccttc cgcgagtagg cggagcgagc 420
gcgcttggct gaggagggag gcggggtgcg agccctttgg ctgcgcgcga tactctcccc 480
gcacgagcag actccacgcg cctgaatcta cttgtcaacg agcaaccgtg tgttttgtcc 540
gtggccattc ttattatttc tccgactgtg gccgtactct gtttggctgt gcaagcaccg 600
aagagcc 607

<210> SEQ ID NO 52
<211> LENGTH: 636
<212> TYPE: DNA
<213> ORGANISM: Protheca moriformis

<400> SEQUENCE: 52
gctcttcgcg caagctcgct acgctcacag taggagatag ggaccactg ccccctgccag 60 aatggtcgcg accctgtccc tcgccggccc cgcctgcaac acgcagtgcg tatccagcaa 120
gcgggttgtc gccttcaacc gcccccatgt tggcgtccgg gctcgatcag gtgcgctgag 180
gggggtttgg tgggcccgcg cctctgggcc cgtgtcggcc gtgcggacgt ggggcccggg 240
gtagtggatc agcaggggtt gcatgcaaat gcctataccg gcgattgaat agcgatgaac 300
gggatacggt tgcgctcact ccatgcccat gcgaccccgt ttctgtccgc cagccgtggt 360
cgcccgagct gcgaagcggg accccaccca gcgcattgtg atcaccggaa tgggcgtggc 420
ctccgtgttt ggcaacgatg tcgagacctt ttacgacaag cttctggaag gaacgagcgg 480
cgtggacctg atttccaggt gcgtaggtcc ttggatgaat gcgtctaggt tgcgaggtga 540
ctggccagga agcagcaggc ttggggtttg gtgttctgat ttctggtaat ttgaggtttc 600
attataagat tctgtacggt cttgtttcgg ggtacc 636

<210> SEQ ID NO 53
<211> LENGTH: 607
<212> TYPE: DNA
<213> ORGANISM: Protheca moriformis

<400> SEQUENCE: 53
gagctccacc tgcatccgcc tggcgctcga ggacgccggc gtctcgcccg acgaggtcaa 60
ctacgtcaac gcgcacgcca cctccaccct ggtgggcgac aaggccgagg tgcgcgcggt 120
caagtcggtc tttggcgaca tgaagggcat caagatgaac gccaccaagt ccatgatcgg 180
gcactgcctg ggcgccgccg gcggcatgga ggccgtcgcc acgctcatgg ccatccgcac 240
cggctgggtg caccccacca tcaaccacga caaccccatc gccgaggtcg acggcctgga 300
cgtcgtcgcc aacgccaagg cccagcacaa aatcaacgtc gccatctcca actccttcgg 360
cttcggcggg cacaactccg tcgtcgcctt tgcgcccttc cgcgagtagg cggagcgagc 420
gcgcttggct gaggagggag gcggggtgcg agccctttgg ctgcgcgcga tactctcccc 480
gcacgagcag actccacgcg cctgaatcta cttgtcaacg agcaaccgtg tgttttgtcc 540
gtggccattc ttattatttc tccgactgtg gccgtactct gtttggctgt gcaagcaccg 600
aagagcc 607

<210> SEQ ID NO 54
<211> LENGTH: 335
<212> TYPE: DNA
<213> ORGANISM: Protheca moriformis

<400> SEQUENCE: 54
actagtcatg gtcgcccggg ctgcgaagcg ggaccccacc cagcgcattg tgatcaccgg 60
aatgggcgtg gcctccgtgt ttggcaacga tgtcgagacc ttttacagtg tgtttgaggg 120
ttttggttgc ccgtattgag gtcctggtgg cgcgcatgga ggagaaggcg cctgtcccgc 180
tgaccccccc ggctaccctc ccggcacctt ccagggcgcg tacgggatcc tgtaaaaggt 240
ctcgacatcg ttgccaaaca cggaggccac gcccattccg gtgatcacaa tgcgctgggt 300
ggggtcccgc ttcgcagccc gggcgaccaa agctt 335

<210> SEQ ID NO 55
<211> LENGTH: 503
<212> TYPE: DNA
<213> ORGANISM: Protheca moriformis

<400> SEQUENCE: 55
actagtcatt gacatctccg agttcccgac caagtttgcg gcgcagatca ccggcttctc 60
cgtggaggac tgcgtggaca agaagaacgc gcggcggtac gacgacgcgc tgtcgtacgc 120
gatggtggcc tccaagaagg ccctgcgcca ggcgggactg gagaaggaca agtgccccga 180
gggctacgga ggtgtgtttg agggttttgg ttgcccgtat tgaggtcctg gtggcgcgca 240
tggaggagaa ggcgcctgtc ccgctgaccc ccccggctac cctcccggca ccttccaggg 300
cgcgtacggg atccctccgt agccctcggg gcacttgtcc ttctccagtc ccgcctggcg 360
cagggccttc ttggaggcca ccatcgcgta cgacagcgcg tcgtcgtacc gccgcgcgtt 420
cttcttgtcc acgcagtcct ccacggagaa gccggtgatc tgcgccgcaa acttggtcgg 480
gaactcggag atgtcaaaag ctt 503

<210> SEQ ID NO 56
<211> LENGTH: 457
<212> TYPE: DNA
<213> ORGANISM: Protheca moriformis

<400> SEQUENCE: 56
actagtcatg ggcgtgagca cctgcatccg cctggcgctc gaggacgccg gcgtctcgcc 60
cgacgaggtc aactacgtca acgcgcacgc cacctccacc ctggtgggcg acaaggccga 120
ggtgcgcgcg gtcaagtcgg tctttggcga catgaagggc atcaagatgt gtgtttgagg 180
gttttggttg cccgtattga ggtcctggtg gcgcgcatgg aggagaaggc gcctgtcccg 240
ctgacccccc cggctaccct cccggcacct tccagggcgc gtacgggatc catcttgatg 300
cccttcatgt cgccaaagac cgacttgacc gcgcgcacct cggccttgtc gcccaccagg 360
gtggaggtgg cgtgcgcgtt gacgtagttg acctcgtcgg gcgagacgcc ggcgtcctcg 420
agcgccaggc ggatgcaggt gctcacgccc aaagctt 457

<210> SEQ ID NO 57
<211> LENGTH: 345
<212> TYPE: DNA
<213> ORGANISM: Protheca moriformis

<400> SEQUENCE: 57
actagtcaca accatcaacc acgacaaccc catcgccgag gtcgacggcc tggacgtcgt 60
cgccaacgcc aaggcccagc acaaaatcaa cgtcgccatc tccaactcct tcggtgtgtt 120
tgagggtttt ggttgcccgt attgaggtcc tggtggcgcg catggaggag aaggcgcctg 180
tcccgctgac ccccccggct accctcccgg caccttccag ggcgcgtacg ggatcccgaa 240
ggagttggag atggcgacgt tgattttgtg ctgggccttg gcgttggcga cgacgtccag 300
gccgtcgacc tcggcgatgg ggttgtcgtg gttgatggta agctt 345

<210> SEQ ID NO 58
<211> LENGTH: 1590
<212> TYPE: DNA
<213> ORGANISM: Marchantia polymorpha

<400> SEQUENCE: 58
atggactccc gcgcccagaa ccgcgacggc ggcgaggacg tgaagcagga gctgctgtcc 60
gccggcgacg acggcaaggt gccctgcccc accgtggcca tcggcatccg ccagcgcctg 120
cccgacttcc tgcagtccgt gaacatgaag tacgtgaagc tgggctacca ctacctgatc 180
acccacgcca tgttcctgct gaccctgccc gccttcttcc tggtggccgc cgagatcggc 240
cgcctgggcc acgagcgcat ctaccgcgag ctgtggaccc acctgcacct gaacctggtg 300
tccatcatgg cctgctcctc cgccctggtg gccggcgcca ccctgtactt catgtcccgc 360
ccccgccccg tgtacctggt ggagttcgcc tgctaccgcc ccgacgagcg cctgaaggtg 420
tccaaggact tcttcctgga catgtcccgc cgcaccggcc tgttctcctc ctcctccatg 480
gacttccaga ccaagatcac ccagcgctcc ggcctgggcg acgagaccta cctgcccccc 540
gccatcctgg cctccccccc caacccctgc atgcgcgagg cccgcgagga ggccgccatg 600
gtgatgttcg gcgccctgga cgagctgttc gagcagaccg gcgtgaagcc caaggagatc 660
ggcgtgctgg tggtgaactg ctccctgttc aaccccaccc cctccatgtc cgccatgatc 720

-continued

```
gtgaaccact accacatgcg cggcaacatc aagtccctga acctgggcgg catgggctgc    780

tccgccggcc tgatctccat cgacctggcc cgcgacctgc tgcaggtgca cggcaacacc    840

tacgccgtgg tggtgtccac cgagaacatc accctgaact ggtacttcgg cgacgaccgc    900

tccaagctga tgtccaactg catcttccgc atgggcggcg ccgccgtgct gctgtccaac    960

aagcgccgcg agcgccgccg cgccaagtac gagctgctgc acaccgtgcg cacccacaag   1020

ggcgccgacg acaagtgctt ccgctgcgtg taccaggagg aggactccac cggctccctg   1080

ggcgtgtccc tgtcccgcga gctgatggcc gtggccggca acgccctgaa ggccaacatc   1140

accaccctgg gccccctggt gctgcccctg tccgagcaga tcctgttctt cgcctccctg   1200

gtggcccgca agttcctgaa catgaagatg aagccctaca tccccgactt caagctggcc   1260

ttcgagcact tctgcatcca cgccggcggc cgcgccgtgc tggacgagct ggagaagaac   1320

ctggacctga ccgagtggca catggagccc tcccgcatga ccctgtaccg cttcggcaac   1380

acctcctcct cctccctgtg gtacgagctg gcctacaccg aggcccaggg ccgcgtgaag   1440

cgcggcgacc gcctgtggca gatcgccttc ggctccggct tcaagtgcaa ctccgccgtg   1500

tggcgcgcgc tgcgcaccgt gaagcccccc gtgaacaacg cctggtccga cgtgatcgac   1560

cgcttccccg tgaagctgcc ccagttctga                                    1590
```

<210> SEQ ID NO 59
<211> LENGTH: 529
<212> TYPE: PRT
<213> ORGANISM: Marchantia polymorpha

<400> SEQUENCE: 59

```
Met Asp Ser Arg Ala Gln Asn Arg Asp Gly Gly Glu Asp Val Lys Gln
1               5                   10                  15

Glu Leu Leu Ser Ala Gly Asp Asp Gly Lys Val Pro Cys Pro Thr Val
            20                  25                  30

Ala Ile Gly Ile Arg Gln Arg Leu Pro Asp Phe Leu Gln Ser Val Asn
        35                  40                  45

Met Lys Tyr Val Lys Leu Gly Tyr His Tyr Leu Ile Thr His Ala Met
    50                  55                  60

Phe Leu Leu Thr Leu Pro Ala Phe Phe Leu Val Ala Ala Glu Ile Gly
65                  70                  75                  80

Arg Leu Gly His Glu Arg Ile Tyr Arg Glu Leu Trp Thr His Leu His
                85                  90                  95

Leu Asn Leu Val Ser Ile Met Ala Cys Ser Ser Ala Leu Val Ala Gly
            100                 105                 110

Ala Thr Leu Tyr Phe Met Ser Arg Pro Arg Pro Val Tyr Leu Val Glu
        115                 120                 125

Phe Ala Cys Tyr Arg Pro Asp Glu Arg Leu Lys Val Ser Lys Asp Phe
    130                 135                 140

Phe Leu Asp Met Ser Arg Arg Thr Gly Leu Phe Ser Ser Ser Ser Met
145                 150                 155                 160

Asp Phe Gln Thr Lys Ile Thr Gln Arg Ser Gly Leu Gly Asp Glu Thr
                165                 170                 175

Tyr Leu Pro Pro Ala Ile Leu Ala Ser Pro Pro Asn Pro Cys Met Arg
            180                 185                 190

Glu Ala Arg Glu Glu Ala Ala Met Val Met Phe Gly Ala Leu Asp Glu
        195                 200                 205

Leu Phe Glu Gln Thr Gly Val Lys Pro Lys Glu Ile Gly Val Leu Val
    210                 215                 220
```

Val Asn Cys Ser Leu Phe Asn Pro Thr Pro Ser Met Ser Ala Met Ile
225 230 235 240

Val Asn His Tyr His Met Arg Gly Asn Ile Lys Ser Leu Asn Leu Gly
245 250 255

Gly Met Gly Cys Ser Ala Gly Leu Ile Ser Ile Asp Leu Ala Arg Asp
260 265 270

Leu Leu Gln Val His Gly Asn Thr Tyr Ala Val Val Val Ser Thr Glu
275 280 285

Asn Ile Thr Leu Asn Trp Tyr Phe Gly Asp Asp Arg Ser Lys Leu Met
290 295 300

Ser Asn Cys Ile Phe Arg Met Gly Gly Ala Ala Val Leu Leu Ser Asn
305 310 315 320

Lys Arg Arg Glu Arg Arg Arg Ala Lys Tyr Glu Leu Leu His Thr Val
325 330 335

Arg Thr His Lys Gly Ala Asp Asp Lys Cys Phe Arg Cys Val Tyr Gln
340 345 350

Glu Glu Asp Ser Thr Gly Ser Leu Gly Val Ser Leu Ser Arg Glu Leu
355 360 365

Met Ala Val Ala Gly Asn Ala Leu Lys Ala Asn Ile Thr Thr Leu Gly
370 375 380

Pro Leu Val Leu Pro Leu Ser Glu Gln Ile Leu Phe Phe Ala Ser Leu
385 390 395 400

Val Ala Arg Lys Phe Leu Asn Met Lys Met Lys Pro Tyr Ile Pro Asp
405 410 415

Phe Lys Leu Ala Phe Glu His Phe Cys Ile His Ala Gly Gly Arg Ala
420 425 430

Val Leu Asp Glu Leu Glu Lys Asn Leu Asp Leu Thr Glu Trp His Met
435 440 445

Glu Pro Ser Arg Met Thr Leu Tyr Arg Phe Gly Asn Thr Ser Ser Ser
450 455 460

Ser Leu Trp Tyr Glu Leu Ala Tyr Thr Glu Ala Gln Gly Arg Val Lys
465 470 475 480

Arg Gly Asp Arg Leu Trp Gln Ile Ala Phe Gly Ser Gly Phe Lys Cys
485 490 495

Asn Ser Ala Val Trp Arg Ala Leu Arg Thr Val Lys Pro Pro Val Asn
500 505 510

Asn Ala Trp Ser Asp Val Ile Asp Arg Phe Pro Val Lys Leu Pro Gln
515 520 525

Phe

<210> SEQ ID NO 60
<211> LENGTH: 906
<212> TYPE: DNA
<213> ORGANISM: Trypanosoma brucei

<400> SEQUENCE: 60
atgctgatga acttcggcgg ctcctacgac gcctacatca acaacttcca gggcaccttc 60
ctggccgagt ggatgctgga ccacccctcc gtgccctaca tcgccggcgt gatgtacctg 120
atcctggtgc tgtacgtgcc caagtccatc atggcctccc agcccccct gaacctgcgc 180 gccgccaaca tcgtgtggaa cctgttcctg accctgttct ccatgtgcgg cgcctactac 240
accgtgccct acctggtgaa ggccttcatg aaccccgaga tcgtgatggc cgcctccggc 300
atcaagctgg acgccaacac ctcccccatc atcacccact ccggcttcta caccaccacc 360

-continued

```
tgcgccctgg ccgactcctt ctacttcaac ggcgacgtgg gcttctgggt ggccctgttc    420

gccctgtcca agatccccga gatgatcgac accgccttcc tggtgttcca gaagaagccc    480

gtgatcttcc tgcactggta ccaccacctg accgtgatgc tgttctgctg gttcgcctac    540

gtgcagaaga tctcctccgg cctgtggttc gcctccatga actactccgt gcactccatc    600

atgtacctgt actacttcgt gtgcgcctgc ggccaccgcc gcctggtgcg ccccttcgcc    660

cccatcatca ccttcgtgca gatcttccag atggtggtgg gcaccatcgt ggtgtgctac    720

acctacaccg tgaagcacgt gctgggccgc tcctgcaccg tgaccgactt ctccctgcac    780

accggcctgg tgatgtacgt gtcctacctg ctgctgttct cccagctgtt ctaccgctcc    840

tacctgtccc cccgcgacaa ggcctccatc cccacgtgg ccgccgagat caagaagaag     900

gagtga                                                                906
```

<210> SEQ ID NO 61
<211> LENGTH: 322
<212> TYPE: PRT
<213> ORGANISM: Trypanosoma brucei

<400> SEQUENCE: 61

```
Met Tyr Pro Thr His Arg Asp Leu Ile Leu Asn Asn Tyr Ser Asp Ile
1               5                   10                  15

Tyr Arg Ser Pro Thr Cys His Tyr His Thr Trp His Thr Leu Ile His
            20                  25                  30

Thr Pro Ile Asn Glu Leu Leu Phe Pro Asn Leu Pro Arg Glu Cys Asp
        35                  40                  45

Phe Gly Tyr Asp Ile Pro Tyr Phe Arg Gly Gln Ile Asp Val Phe Asp
    50                  55                  60

Gly Trp Ser Met Ile His Phe Thr Ser Ser Asn Trp Cys Ile Pro Ile
65                  70                  75                  80

Thr Val Cys Leu Cys Tyr Ile Met Met Ile Ala Gly Leu Lys Lys Tyr
                85                  90                  95

Met Gly Pro Arg Asp Gly Gly Arg Ala Pro Ile Gln Ala Lys Asn Tyr
            100                 105                 110

Ile Ile Ala Trp Asn Leu Phe Leu Ser Phe Phe Ser Phe Ala Gly Val
        115                 120                 125

Tyr Tyr Thr Val Pro Tyr His Leu Phe Asp Pro Glu Asn Gly Leu Phe
    130                 135                 140

Ala Gln Gly Phe Tyr Ser Thr Val Cys Asn Asn Gly Ala Tyr Tyr Gly
145                 150                 155                 160

Asn Gly Asn Val Gly Phe Phe Val Trp Leu Phe Ile Tyr Ser Lys Ile
                165                 170                 175

Phe Glu Leu Val Asp Thr Phe Phe Leu Leu Ile Arg Lys Asn Pro Val
            180                 185                 190

Ile Phe Leu His Trp Tyr His His Leu Thr Val Leu Leu Tyr Cys Trp
        195                 200                 205

His Ala Tyr Ser Val Arg Ile Gly Thr Gly Ile Trp Phe Ala Thr Met
    210                 215                 220

Asn Tyr Ser Val His Ser Val Met Tyr Leu Tyr Phe Ala Met Thr Gln
225                 230                 235                 240

Tyr Gly Pro Ser Thr Lys Lys Phe Ala Lys Lys Phe Ser Lys Phe Ile
                245                 250                 255

Thr Thr Ile Gln Ile Leu Gln Met Val Val Gly Ile Ile Val Thr Phe
            260                 265                 270
```

```
Ala Ala Met Leu Tyr Val Thr Phe Asp Val Pro Cys Tyr Thr Ser Leu
        275                 280                 285

Ala Asn Ser Val Leu Gly Leu Met Met Tyr Ala Ser Tyr Phe Val Leu
    290                 295                 300

Phe Val Gln Leu Tyr Val Ser His Tyr Val Ser Pro Lys His Val Lys
305                 310                 315                 320

Gln Glu


<210> SEQ ID NO 62
<211> LENGTH: 933
<212> TYPE: DNA
<213> ORGANISM: Saccharomyces cerevisiae

<400> SEQUENCE: 62

atggtgtccg actggaagaa cttctgcctg gagaaggcct cccgcttccg ccccaccatc      60

gaccgcccct tcttcaacat ctacctgtgg gactacttca accgcgccgt gggctgggcc     120

accgccggcc gcttccagcc caaggacttc gagttcaccg tgggcaagca gcccctgtcc     180

gagccccgcc ccgtgctgct gttcatcgcc atgtactacg tggtgatctt cggcggccgc     240

tccctggtga agtcctgcaa gcccctgaag ctgcgcttca tctcccaggt gcacaacctg     300

atgctgacct ccgtgtcctt cctgtggctg atcctgatgg tggagcagat gctgcccatc     360

gtgtaccgcc acggcctgta cttcgccgtg tgcaacgtgg agtcctggac ccagcccatg     420

gagaccctgt actacctgaa ctacatgacc aagttcgtgg agttcgccga caccgtgctg     480

atggtgctga agcaccgcaa gctgaccttc ctgcacacct accaccacgg cgccaccgcc     540

ctgctgtgct acaaccagct ggtgggctac accgccgtga cctgggtgcc cgtgaccctg     600

aacctggccg tgcacgtgct gatgtactgg tactacttcc tgtccgcctc cggcatccgc     660

gtgtggtgga aggcctgggt gacccgcctg cagatcgtgc agttcatgct ggacctgatc     720

gtggtgtact acgtgctgta ccagaagatc gtggccgcct acttcaagaa cgcctgcacc     780

ccccagtgcg aggactgcct gggctccatg accgccatcg ccgccggcgc cgccatcctg     840

acctcctacc tgttcctgtt catctccttc tacatcgagg tgtacaagcg cggctccgcc     900

tccggcaaga agaagatcaa caagaacaac tga                                   933


<210> SEQ ID NO 63
<211> LENGTH: 310
<212> TYPE: PRT
<213> ORGANISM: Saccharomyces cerevisiae

<400> SEQUENCE: 63

Met Val Ser Asp Trp Lys Asn Phe Cys Leu Glu Lys Ala Ser Arg Phe
1               5                   10                  15

Arg Pro Thr Ile Asp Arg Pro Phe Phe Asn Ile Tyr Leu Trp Asp Tyr
            20                  25                  30

Phe Asn Arg Ala Val Gly Trp Ala Thr Ala Gly Arg Phe Gln Pro Lys
        35                  40                  45

Asp Phe Glu Phe Thr Val Gly Lys Gln Pro Leu Ser Glu Pro Arg Pro
    50                  55                  60

Val Leu Leu Phe Ile Ala Met Tyr Tyr Val Val Ile Phe Gly Gly Arg
65                  70                  75                  80

Ser Leu Val Lys Ser Cys Lys Pro Leu Lys Leu Arg Phe Ile Ser Gln
                85                  90                  95

Val His Asn Leu Met Leu Thr Ser Val Ser Phe Leu Trp Leu Ile Leu
```

```
            100                 105                 110

Met Val Glu Gln Met Leu Pro Ile Val Tyr Arg His Gly Leu Tyr Phe
        115                 120                 125

Ala Val Cys Asn Val Glu Ser Trp Thr Gln Pro Met Glu Thr Leu Tyr
    130                 135                 140

Tyr Leu Asn Tyr Met Thr Lys Phe Val Glu Phe Ala Asp Thr Val Leu
145                 150                 155                 160

Met Val Leu Lys His Arg Lys Leu Thr Phe Leu His Thr Tyr His His
                165                 170                 175

Gly Ala Thr Ala Leu Leu Cys Tyr Asn Gln Leu Val Gly Tyr Thr Ala
            180                 185                 190

Val Thr Trp Val Pro Val Thr Leu Asn Leu Ala Val His Val Leu Met
        195                 200                 205

Tyr Trp Tyr Tyr Phe Leu Ser Ala Ser Gly Ile Arg Val Trp Trp Lys
    210                 215                 220

Ala Trp Val Thr Arg Leu Gln Ile Val Gln Phe Met Leu Asp Leu Ile
225                 230                 235                 240

Val Val Tyr Tyr Val Leu Tyr Gln Lys Ile Val Ala Ala Tyr Phe Lys
                245                 250                 255

Asn Ala Cys Thr Pro Gln Cys Glu Asp Cys Leu Gly Ser Met Thr Ala
            260                 265                 270

Ile Ala Ala Gly Ala Ala Ile Leu Thr Ser Tyr Leu Phe Leu Phe Ile
        275                 280                 285

Ser Phe Tyr Ile Glu Val Tyr Lys Arg Gly Ser Ala Ser Gly Lys Lys
    290                 295                 300

Lys Ile Asn Lys Asn Asn
305                 310
```

<210> SEQ ID NO 64
<211> LENGTH: 1179
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
atgctgaagc tgtcctgcaa cgtgaccaac aacctgcaca ccttctcctt cttctccgac     60

tcctccctgt tcatccccgt gaaccgccgc accatcgccg tgtcctccgg gcgcgcctcc    120

cagctgcgca agcccgccct ggaccccctg cgcgccgtga tctccgccga ccagggctcc    180

atctcccccg tgaactcctg cacccccgcc gaccgcctgc gcgccggccg cctgatggag    240

gacggctact cctacaagga gaagttcatc gtgcgctcct acgaggtggg catcaacaag    300

accgccaccg tggagaccat cgccaacctg ctgcaggagg tggcctgcaa ccacgtgcag    360

aagtgcggct tctccaccga cggcttcgcc accaccctga ccatgcgcaa gctgcacctg    420

atctgggtga ccgcccgcat gcacatcgag atctacaagt accccgcctg gtccgacgtg    480

gtggagatcg agacctggtg ccagtccgag ggccgcatcg gcacccgccg cgactggatc    540

ctgcgcgact ccgccaccaa cgaggtgatc ggccgcgcca cctccaagtg ggtgatgatg    600

aaccaggaca cccgccgcct gcagcgcgtg accgacgagg tgcgcgacga gtacctggtg    660

ttctgccccc gcgagccccg cctggccttc cccgaggaga acaactcctc cctgaagaag    720

atccccaagc tggaggaccc cgcccagtac tccatgctgg agctgaagcc ccgccgcgcc    780

gacctggaca tgaaccagca cgtgaacaac gtgacctaca tcggctgggt gctggagtcc    840
```

```
atcccccagg agatcatcga cacccacgag ctgcaggtga tcaccctgga ctaccgccgc    900

gagtgccagc aggacgacat cgtggactcc ctgaccacct ccgagatccc cgacgacccc    960

atctccaagt tcaccggcac caacggctcc gccatgtcct ccatccaggg ccacaacgag   1020

tcccagttcc tgcacatgct gcgcctgtcc gagaacggcc aggagatcaa ccgcggccgc   1080

acccagtggc gcaagaagtc ctcccgcatg gactacaagg accacgacgg cgactacaag   1140

gaccacgaca tcgactacaa ggacgacgac gacaagtga                          1179
```

<210> SEQ ID NO 65
<211> LENGTH: 392
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Met Leu Lys Leu Ser Cys Asn Val Thr Asn Asn Leu His Thr Phe Ser
1               5                   10                  15

Phe Phe Ser Asp Ser Ser Leu Phe Ile Pro Val Asn Arg Arg Thr Ile
            20                  25                  30

Ala Val Ser Ser Gly Arg Ala Ser Gln Leu Arg Lys Pro Ala Leu Asp
        35                  40                  45

Pro Leu Arg Ala Val Ile Ser Ala Asp Gln Gly Ser Ile Ser Pro Val
    50                  55                  60

Asn Ser Cys Thr Pro Ala Asp Arg Leu Arg Ala Gly Arg Leu Met Glu
65                  70                  75                  80

Asp Gly Tyr Ser Tyr Lys Glu Lys Phe Ile Val Arg Ser Tyr Glu Val
                85                  90                  95

Gly Ile Asn Lys Thr Ala Thr Val Glu Thr Ile Ala Asn Leu Leu Gln
            100                 105                 110

Glu Val Ala Cys Asn His Val Gln Lys Cys Gly Phe Ser Thr Asp Gly
        115                 120                 125

Phe Ala Thr Thr Leu Thr Met Arg Lys Leu His Leu Ile Trp Val Thr
    130                 135                 140

Ala Arg Met His Ile Glu Ile Tyr Lys Tyr Pro Ala Trp Ser Asp Val
145                 150                 155                 160

Val Glu Ile Glu Thr Trp Cys Gln Ser Glu Gly Arg Ile Gly Thr Arg
                165                 170                 175

Arg Asp Trp Ile Leu Arg Asp Ser Ala Thr Asn Glu Val Ile Gly Arg
            180                 185                 190

Ala Thr Ser Lys Trp Val Met Met Asn Gln Asp Thr Arg Arg Leu Gln
        195                 200                 205

Arg Val Thr Asp Glu Val Arg Asp Glu Tyr Leu Val Phe Cys Pro Arg
    210                 215                 220

Glu Pro Arg Leu Ala Phe Pro Glu Glu Asn Asn Ser Ser Leu Lys Lys
225                 230                 235                 240

Ile Pro Lys Leu Glu Asp Pro Ala Gln Tyr Ser Met Leu Glu Leu Lys
                245                 250                 255

Pro Arg Arg Ala Asp Leu Asp Met Asn Gln His Val Asn Asn Val Thr
            260                 265                 270

Tyr Ile Gly Trp Val Leu Glu Ser Ile Pro Gln Glu Ile Ile Asp Thr
        275                 280                 285

His Glu Leu Gln Val Ile Thr Leu Asp Tyr Arg Arg Glu Cys Gln Gln
```

```
    290                 295                 300

Asp Asp Ile Val Asp Ser Leu Thr Thr Ser Glu Ile Pro Asp Asp Pro
305                 310                 315                 320

Ile Ser Lys Phe Thr Gly Thr Asn Gly Ser Ala Met Ser Ser Ile Gln
                325                 330                 335

Gly His Asn Glu Ser Gln Phe Leu His Met Leu Arg Leu Ser Glu Asn
            340                 345                 350

Gly Gln Glu Ile Asn Arg Gly Arg Thr Gln Trp Arg Lys Lys Ser Ser
        355                 360                 365

Arg Met Asp Tyr Lys Asp His Asp Gly Asp Tyr Lys Asp His Asp Ile
    370                 375                 380

Asp Tyr Lys Asp Asp Asp Asp Lys
385                 390
```

<210> SEQ ID NO 66
<211> LENGTH: 1176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

```
atggccaccg catccacttt ctcggcgttc aatgcccgct gcggcgacct gcgtcgctcg     60

gcgggctccg ggccccggcg cccagcgagg cccctccccg tgcgcgggcg cgcctcccag    120

ctgcgcaagc ccgccctgga ccccctgcgc gccgtgatct ccgccgacca gggctccatc    180

tcccccgtga actcctgcac ccccgccgac cgcctgcgcg ccggccgcct gatggaggac    240

ggctactcct acaaggagaa gttcatcgtg cgctcctacg aggtgggcat caacaagacc    300

gccaccgtgg agaccatcgc caacctgctg caggaggtgg cctgcaacca cgtgcagaag    360

tgcggcttct ccaccgacgg cttcgccacc accctgacca tgcgcaagct gcacctgatc    420

tgggtgaccg cccgcatgca catcgagatc tacaagtacc ccgcctggtc cgacgtggtg    480

gagatcgaga cctggtgcca gtccgagggc cgcatcggca cccgccgcga ctggatcctg    540

cgcgactccg ccaccaacga ggtgatcggc cgcgccacct ccaagtgggt gatgatgaac    600

caggacaccc gccgcctgca gcgcgtgacc gacgaggtgc gcgacgagta cctggtgttc    660

tgcccccgcg agccccgcct ggccttcccc gaggagaaca actcctccct gaagaagatc    720

cccaagctgg aggaccccgc ccagtactcc atgctggagc tgaagccccg ccgcgccgac    780

ctggacatga accagcacgt gaacaacgtg acctacatcg gctgggtgct ggagtccatc    840

cccaggaga tcatcgacac ccacgagctg caggtgatca ccctggacta ccgccgcgag    900

tgccagcagg acgacatcgt ggactccctg accacctccg agatccccga cgaccccatc    960

tccaagttca ccggcaccaa cggctccgcc atgtcctcca tccagggcca caacgagtcc   1020

cagttcctgc acatgctgcg cctgtccgag aacggccagg agatcaaccg cggccgcacc   1080

cagtggcgca agaagtcctc ccgcatggac tacaaggacc acgacggcga ctacaaggac   1140

cacgacatcg actacaagga cgacgacgac aagtga                              1176
```

<210> SEQ ID NO 67
<211> LENGTH: 391
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ser Gln Leu Arg Lys Pro Ala Leu Asp Pro
        35                  40                  45

Leu Arg Ala Val Ile Ser Ala Asp Gln Gly Ser Ile Ser Pro Val Asn
    50                  55                  60

Ser Cys Thr Pro Ala Asp Arg Leu Arg Ala Gly Arg Leu Met Glu Asp
65                  70                  75                  80

Gly Tyr Ser Tyr Lys Glu Lys Phe Ile Val Arg Ser Tyr Glu Val Gly
                85                  90                  95

Ile Asn Lys Thr Ala Thr Val Glu Thr Ile Ala Asn Leu Leu Gln Glu
            100                 105                 110

Val Ala Cys Asn His Val Gln Lys Cys Gly Phe Ser Thr Asp Gly Phe
        115                 120                 125

Ala Thr Thr Leu Thr Met Arg Lys Leu His Leu Ile Trp Val Thr Ala
    130                 135                 140

Arg Met His Ile Glu Ile Tyr Lys Tyr Pro Ala Trp Ser Asp Val Val
145                 150                 155                 160

Glu Ile Glu Thr Trp Cys Gln Ser Glu Gly Arg Ile Gly Thr Arg Arg
                165                 170                 175

Asp Trp Ile Leu Arg Asp Ser Ala Thr Asn Glu Val Ile Gly Arg Ala
            180                 185                 190

Thr Ser Lys Trp Val Met Met Asn Gln Asp Thr Arg Arg Leu Gln Arg
        195                 200                 205

Val Thr Asp Glu Val Arg Asp Glu Tyr Leu Val Phe Cys Pro Arg Glu
    210                 215                 220

Pro Arg Leu Ala Phe Pro Glu Glu Asn Asn Ser Ser Leu Lys Lys Ile
225                 230                 235                 240

Pro Lys Leu Glu Asp Pro Ala Gln Tyr Ser Met Leu Glu Leu Lys Pro
                245                 250                 255

Arg Arg Ala Asp Leu Asp Met Asn Gln His Val Asn Asn Val Thr Tyr
            260                 265                 270

Ile Gly Trp Val Leu Glu Ser Ile Pro Gln Glu Ile Ile Asp Thr His
        275                 280                 285

Glu Leu Gln Val Ile Thr Leu Asp Tyr Arg Arg Glu Cys Gln Gln Asp
    290                 295                 300

Asp Ile Val Asp Ser Leu Thr Thr Ser Glu Ile Pro Asp Asp Pro Ile
305                 310                 315                 320

Ser Lys Phe Thr Gly Thr Asn Gly Ser Ala Met Ser Ser Ile Gln Gly
                325                 330                 335

His Asn Glu Ser Gln Phe Leu His Met Leu Arg Leu Ser Glu Asn Gly
            340                 345                 350

Gln Glu Ile Asn Arg Gly Arg Thr Gln Trp Arg Lys Lys Ser Ser Arg
        355                 360                 365

Met Asp Tyr Lys Asp His Asp Gly Asp Tyr Lys Asp His Asp Ile Asp
    370                 375                 380

Tyr Lys Asp Asp Asp Asp Lys
385                 390
```

<210> SEQ ID NO 68
<211> LENGTH: 1155
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 68
atggccaccg catccacttt ctcggcgttc aatgcccgct gcggcgacct gcgtcgctcg 60
gcgggctccg ggccccggcg cccagcgagg cccctccccg tgcgcgggcg cgccgccacc 120
ggcgagcagc cctccggcgt ggcctccctg cgcgaggccg acaaggagaa gtccctgggc 180
aaccgcctgc gcctgggctc cctgaccgag gacggcctgt cctacaagga gaagttcgtg 240
atccgctgct acgaggtggg catcaacaag accgccacca tcgagaccat cgccaacctg 300
ctgcaggagg tgggcggcaa ccacgcccag ggcgtgggct tctccaccga cggcttcgcc 360
accaccacca ccatgcgcaa gctgcacctg atctgggtga ccgcccgcat gcacatcgag 420
atctaccgct accccgcctg gtccgacgtg atcgagatcg agacctgggt gcagggcgag 480
ggcaaggtgg gcacccgccg cgactggatc ctgaaggact acgccaacgg cgaggtgatc 540
ggccgcgcca cctccaagtg ggtgatgatg aacgaggaca cccgccgcct gcagaaggtg 600
tccgacgacg tgcgcgagga gtacctggtg ttctgccccc gcaccctgcg cctggccttc 660
cccgaggaga acaacaactc catgaagaag atccccaagc tggaggaccc cgccgagtac 720
tcccgcctgg gcctggtgcc ccgccgctcc gacctggaca tgaacaagca cgtgaacaac 780
gtgacctaca tcggctgggc cctggagtcc atcccccccg agatcatcga cacccacgag 840
ctgcaggcca tcaccctgga ctaccgccgc gagtgccagc gcgacgacat cgtggactcc 900
ctgacctccc gcgagcccct gggcaacgcc gccggcgtga agttcaagga gatcaacggc 960
tccgtgtccc ccaagaagga cgagcaggac ctgtcccgct tcatgcacct gctgcgctcc 1020
gccggctccg gcctggagat caaccgctgc cgcaccgagt ggcgcaagaa gcccgccaag 1080
cgcatggact acaaggacca cgacggcgac tacaaggacc acgacatcga ctacaaggac 1140
gacgacgaca agtga 1155

<210> SEQ ID NO 69
<211> LENGTH: 384
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 69

Met Ala Thr Ala Ser Thr Phe Ser Ala Phe Asn Ala Arg Cys Gly Asp
1 5 10 15

Leu Arg Arg Ser Ala Gly Ser Gly Pro Arg Arg Pro Ala Arg Pro Leu
20 25 30

Pro Val Arg Gly Arg Ala Ala Thr Gly Glu Gln Pro Ser Gly Val Ala
35 40 45

Ser Leu Arg Glu Ala Asp Lys Glu Lys Ser Leu Gly Asn Arg Leu Arg
50 55 60

Leu Gly Ser Leu Thr Glu Asp Gly Leu Ser Tyr Lys Glu Lys Phe Val
65 70 75 80

Ile Arg Cys Tyr Glu Val Gly Ile Asn Lys Thr Ala Thr Ile Glu Thr
85 90 95

```
Ile Ala Asn Leu Leu Gln Glu Val Gly Gly Asn His Ala Gln Gly Val
            100                 105                 110

Gly Phe Ser Thr Asp Gly Phe Ala Thr Thr Thr Thr Met Arg Lys Leu
        115                 120                 125

His Leu Ile Trp Val Thr Ala Arg Met His Ile Glu Ile Tyr Arg Tyr
    130                 135                 140

Pro Ala Trp Ser Asp Val Ile Glu Ile Glu Thr Trp Val Gln Gly Glu
145                 150                 155                 160

Gly Lys Val Gly Thr Arg Arg Asp Trp Ile Leu Lys Asp Tyr Ala Asn
                165                 170                 175

Gly Glu Val Ile Gly Arg Ala Thr Ser Lys Trp Val Met Met Asn Glu
            180                 185                 190

Asp Thr Arg Arg Leu Gln Lys Val Ser Asp Asp Val Arg Glu Glu Tyr
        195                 200                 205

Leu Val Phe Cys Pro Arg Thr Leu Arg Leu Ala Phe Pro Glu Glu Asn
    210                 215                 220

Asn Asn Ser Met Lys Lys Ile Pro Lys Leu Glu Asp Pro Ala Glu Tyr
225                 230                 235                 240

Ser Arg Leu Gly Leu Val Pro Arg Arg Ser Asp Leu Asp Met Asn Lys
                245                 250                 255

His Val Asn Asn Val Thr Tyr Ile Gly Trp Ala Leu Glu Ser Ile Pro
            260                 265                 270

Pro Glu Ile Ile Asp Thr His Glu Leu Gln Ala Ile Thr Leu Asp Tyr
        275                 280                 285

Arg Arg Glu Cys Gln Arg Asp Asp Ile Val Asp Ser Leu Thr Ser Arg
    290                 295                 300

Glu Pro Leu Gly Asn Ala Ala Gly Val Lys Phe Lys Glu Ile Asn Gly
305                 310                 315                 320

Ser Val Ser Pro Lys Lys Asp Glu Gln Asp Leu Ser Arg Phe Met His
                325                 330                 335

Leu Leu Arg Ser Ala Gly Ser Gly Leu Glu Ile Asn Arg Cys Arg Thr
            340                 345                 350

Glu Trp Arg Lys Lys Pro Ala Lys Arg Met Asp Tyr Lys Asp His Asp
        355                 360                 365

Gly Asp Tyr Lys Asp His Asp Ile Asp Tyr Lys Asp Asp Asp Asp Lys
    370                 375                 380
```

<210> SEQ ID NO 70
<211> LENGTH: 1194
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 70

```
atgctgaagg tgccctgctg caacgccacc gaccccatcc agtccctgtc ctcccagtgc      60

cgcttcctga cccacttcaa caaccgcccc tacttcaccc gccgcccctc catccccacc     120

ttcttctcct ccaagaactc ctccgcctcc ctgcaggccg tggtgtccga catctcctcc     180

gtggagtccg ccgcctgcga ctccctggcc aaccgcctgc gcctgggcaa gctgaccgag     240

gacggcttct cctacaagga gaagttcatc gtggggcgcg cccgctccta cgaggtgggc     300

atcaacaaga ccgccaccgt ggagaccatc gccaacctgc tgcaggaggt gggctgcaac     360

cacgcccagt ccgtgggctt ctccaccgac ggcttcgcca ccaccacctc catgcgcaag     420
```

-continued

```
atgcacctga tctgggtgac cgcccgcatg cacatcgaga tctacaagta ccccgcctgg    480

tccgacgtgg tggaggtgga gacctggtgc cagtccgagg gccgcatcgg cacccgccgc    540

gactggatcc tgaccgacta cgccaccggc cagatcatcg gccgcgccac ctccaagtgg    600

gtgatgatga accaggacac ccgccgcctg cagaaggtga ccgacgacgt gcgcgaggag    660

tacctggtgt tctgcccccg cgagctgcgc ctggccttcc ccgaggagaa caaccgctcc    720

tccaagaaga tctccaagct ggaggacccc gcccagtact ccaagctggg cctggtgccc    780

cgccgcgccg acctggacat gaaccagcac gtgaacaacg tgacctacat cggctgggtg    840

ctggagtcca tcccccagga gatcatcgac acccacgagc tgcagaccat caccctggac    900

taccgccgcg agtgccagca cgacgacatc gtggactccc tgacctccgt ggagccctcc    960

gagaacctgg aggccgtgtc cgagctgcgc ggcaccaacg gctccgccac caccaccgcc   1020

ggcgacgagg actgccgcaa cttcctgcac ctgctgcgcc tgtccggcga cggcctggag   1080

atcaaccgcg gccgcaccga gtggcgcaag aagtccgccc gcatggacta caaggaccac   1140

gacggcgact acaaggacca cgacatcgac tacaaggacg acgacgacaa gtga         1194
```

<210> SEQ ID NO 71
<211> LENGTH: 397
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Met Leu Lys Val Pro Cys Cys Asn Ala Thr Asp Pro Ile Gln Ser Leu
1               5                   10                  15

Ser Ser Gln Cys Arg Phe Leu Thr His Phe Asn Asn Arg Pro Tyr Phe
            20                  25                  30

Thr Arg Arg Pro Ser Ile Pro Thr Phe Phe Ser Ser Lys Asn Ser Ser
        35                  40                  45

Ala Ser Leu Gln Ala Val Val Ser Asp Ile Ser Ser Val Glu Ser Ala
    50                  55                  60

Ala Cys Asp Ser Leu Ala Asn Arg Leu Arg Leu Gly Lys Leu Thr Glu
65                  70                  75                  80

Asp Gly Phe Ser Tyr Lys Glu Lys Phe Ile Val Gly Arg Ala Arg Ser
                85                  90                  95

Tyr Glu Val Gly Ile Asn Lys Thr Ala Thr Val Glu Thr Ile Ala Asn
            100                 105                 110

Leu Leu Gln Glu Val Gly Cys Asn His Ala Gln Ser Val Gly Phe Ser
        115                 120                 125

Thr Asp Gly Phe Ala Thr Thr Thr Ser Met Arg Lys Met His Leu Ile
    130                 135                 140

Trp Val Thr Ala Arg Met His Ile Glu Ile Tyr Lys Tyr Pro Ala Trp
145                 150                 155                 160

Ser Asp Val Val Glu Val Glu Thr Trp Cys Gln Ser Glu Gly Arg Ile
                165                 170                 175

Gly Thr Arg Arg Asp Trp Ile Leu Thr Asp Tyr Ala Thr Gly Gln Ile
            180                 185                 190

Ile Gly Arg Ala Thr Ser Lys Trp Val Met Met Asn Gln Asp Thr Arg
        195                 200                 205

Arg Leu Gln Lys Val Thr Asp Asp Val Arg Glu Glu Tyr Leu Val Phe
    210                 215                 220
```

```
Cys Pro Arg Glu Leu Arg Leu Ala Phe Pro Glu Glu Asn Asn Arg Ser
225                 230                 235                 240

Ser Lys Lys Ile Ser Lys Leu Glu Asp Pro Ala Gln Tyr Ser Lys Leu
                245                 250                 255

Gly Leu Val Pro Arg Arg Ala Asp Leu Asp Met Asn Gln His Val Asn
            260                 265                 270

Asn Val Thr Tyr Ile Gly Trp Val Leu Glu Ser Ile Pro Gln Glu Ile
        275                 280                 285

Ile Asp Thr His Glu Leu Gln Thr Ile Thr Leu Asp Tyr Arg Arg Glu
    290                 295                 300

Cys Gln His Asp Asp Ile Val Asp Ser Leu Thr Ser Val Glu Pro Ser
305                 310                 315                 320

Glu Asn Leu Glu Ala Val Ser Glu Leu Arg Gly Thr Asn Gly Ser Ala
                325                 330                 335

Thr Thr Thr Ala Gly Asp Glu Asp Cys Arg Asn Phe Leu His Leu Leu
            340                 345                 350

Arg Leu Ser Gly Asp Gly Leu Glu Ile Asn Arg Gly Arg Thr Glu Trp
        355                 360                 365

Arg Lys Lys Ser Ala Arg Met Asp Tyr Lys Asp His Asp Gly Asp Tyr
    370                 375                 380

Lys Asp His Asp Ile Asp Tyr Lys Asp Asp Asp Asp Lys
385                 390                 395


<210> SEQ ID NO 72
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

atgctgaagc tgtcctcctc ccgctccccc ctggcccgca tccccacccg cccccgcccc     60

aactccatcc ccccccgcat catcgtggtg tcctcctcct cctccaaggt gaacccccctg   120

aagaccgagg ccgtggtgtc ctccggcctg gccgaccgcc tgcgcctggg ctccctgacc    180

gaggacggcc tgtcctacaa ggagaagttc atcgtgcgct gctacgaggt gggcatcaac    240

aagaccgcca ccgtggagac catcgccaac ctgctgcagg aggtgggctg caaccacgcc    300

cagtccgtgg gctactccac cggcggcttc tccaccaccc ccaccatgcg caagctgcgc    360

ctgatctggg tgaccgcccg catgcacatc gagatctaca agtaccccgc ctggtccgac    420

gtggtggaga tcgagtcctg ggccagggc gagggcaaga tcggcacccg ccgcgactgg     480

atcctgcgcg actacgccac cggccaggtg atcggccgcg ccacctccaa gtgggtgatg    540

atgaaccagg acacccgccg cctgcagaag gtggacgtgg acgtgcgcga cgagtacctg    600

gtgcactgcc cccgcgagct gcgcctggcc ttccccgagg agaacaactc ctccctgaag    660

aagatctcca agctggagga cccctcccag tactccaagc tgggcctggt gccccgccgc    720

gccgacctgg acatgaacca gcacgtgaac aacgtgacct acatcggctg ggtgctggag    780

tccatgcccc aggagatcat cgacacccac gagctgcaga ccatcaccct ggactaccgc    840

cgcgagtgcc agcacgacga cgtggtggac tccctgacct cccccgagcc ctccgaggac    900

gccgaggccg tgttcaacca caacggcacc aacggctccg ccaacgtgtc cgccaacgac    960

cacggctgcc gcaacttcct gcacctgctg cgcctgtccg gcaacggcct ggagatcaac   1020

cgcggccgca ccgagtggcg caagaagccc acccgcatgg actacaagga ccacgacggc   1080
```

```
gactacaagg accacgacat cgactacaag gacgacgacg acaagtga              1128


<210> SEQ ID NO 73
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Leu Lys Leu Ser Ser Ser Arg Ser Pro Leu Ala Arg Ile Pro Thr
1               5                   10                  15

Arg Pro Arg Pro Asn Ser Ile Pro Pro Arg Ile Ile Val Val Ser Ser
            20                  25                  30

Ser Ser Ser Lys Val Asn Pro Leu Lys Thr Glu Ala Val Val Ser Ser
        35                  40                  45

Gly Leu Ala Asp Arg Leu Arg Leu Gly Ser Leu Thr Glu Asp Gly Leu
    50                  55                  60

Ser Tyr Lys Glu Lys Phe Ile Val Arg Cys Tyr Glu Val Gly Ile Asn
65                  70                  75                  80

Lys Thr Ala Thr Val Glu Thr Ile Ala Asn Leu Leu Gln Glu Val Gly
                85                  90                  95

Cys Asn His Ala Gln Ser Val Gly Tyr Ser Thr Gly Gly Phe Ser Thr
            100                 105                 110

Thr Pro Thr Met Arg Lys Leu Arg Leu Ile Trp Val Thr Ala Arg Met
        115                 120                 125

His Ile Glu Ile Tyr Lys Tyr Pro Ala Trp Ser Asp Val Val Glu Ile
    130                 135                 140

Glu Ser Trp Gly Gln Gly Glu Gly Lys Ile Gly Thr Arg Arg Asp Trp
145                 150                 155                 160

Ile Leu Arg Asp Tyr Ala Thr Gly Gln Val Ile Gly Arg Ala Thr Ser
                165                 170                 175

Lys Trp Val Met Met Asn Gln Asp Thr Arg Arg Leu Gln Lys Val Asp
            180                 185                 190

Val Asp Val Arg Asp Glu Tyr Leu Val His Cys Pro Arg Glu Leu Arg
        195                 200                 205

Leu Ala Phe Pro Glu Glu Asn Asn Ser Ser Leu Lys Lys Ile Ser Lys
    210                 215                 220

Leu Glu Asp Pro Ser Gln Tyr Ser Lys Leu Gly Leu Val Pro Arg Arg
225                 230                 235                 240

Ala Asp Leu Asp Met Asn Gln His Val Asn Asn Val Thr Tyr Ile Gly
                245                 250                 255

Trp Val Leu Glu Ser Met Pro Gln Glu Ile Ile Asp Thr His Glu Leu
            260                 265                 270

Gln Thr Ile Thr Leu Asp Tyr Arg Arg Glu Cys Gln His Asp Asp Val
        275                 280                 285

Val Asp Ser Leu Thr Ser Pro Glu Pro Ser Glu Asp Ala Glu Ala Val
    290                 295                 300

Phe Asn His Asn Gly Thr Asn Gly Ser Ala Asn Val Ser Ala Asn Asp
305                 310                 315                 320

His Gly Cys Arg Asn Phe Leu His Leu Leu Arg Leu Ser Gly Asn Gly
                325                 330                 335

Leu Glu Ile Asn Arg Gly Arg Thr Glu Trp Arg Lys Lys Pro Thr Arg
            340                 345                 350
```

Met Asp Tyr Lys Asp His Asp Gly Asp Tyr Lys Asp His Asp Ile Asp
355 360 365

Tyr Lys Asp Asp Asp Asp Lys
370 375

<210> SEQ ID NO 74
<211> LENGTH: 1197
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 74
atgctgaagc tgtcctcctg caacgtgacc gaccagcgcc aggccctggc ccagtgccgc 60
ttcctggccc cccccgcccc cttctccttc cgctggcgca cccccgtggt ggtgtcctgc 120
tccccctcct cccgccccaa cctgtccccc ctgcaggtgg tgctgtccgg ccagcagcag 180
gccggcatgg agctggtgga gtccggctcc ggctccctgg ccgaccgcct gcgcctgggc 240
tccctgaccg aggacggcct gtcctacaag gagaagttca tcgtgcgctg ctacgaggtg 300
ggcatcaaca agaccgccac cgtggagacc atcgccaacc tgctgcagga ggtgggctgc 360
aaccacgccc agtccgtggg ctactccacc gacggcttcg ccaccacccg caccatgcgc 420
aagctgcacc tgatctgggt gaccgcccgc atgcacatcg agatctacaa gtaccccgcc 480
tggtccgacg tgatcgagat cgagacctgg tgccagtccg agggccgcat cggcacccgc 540
cgcgactgga tcctgaagga cttcggcacc ggcgaggtga tcggccgcgc cacctccaag 600
tgggtgatga tgaaccagga cacccgccgc ctgcagaagg tgtccgacga cgtgcgcgag 660
gagtacctgg tgttctgccc ccgcgagctg cgcctggcct tccccgagga gaacaacaac 720
tccctgaaga agatcgccaa gctggacgac tccttccagt actcccgcct gggcctgatg 780
ccccgccgcg ccgacctgga catgaaccag cacgtgaaca acgtgaccta catcggctgg 840
gtgctggagt ccatgcccca ggagatcatc gacacccacg agctgcagac catcaccctg 900
gactaccgcc gcgagtgcca gcaggacgac gtggtggact ccctgacctc ccccgagcag 960
gtggagggca ccgagaaggt gtccgccatc cacggcacca acggctccgc cgccgcccgc 1020
gaggacaagc aggactgccg ccagttcctg cacctgctgc gcctgtcctc cgacggccag 1080
gagatcaacc gcggccgcac cgagtggcgc aagaagcccg cccgcatgga ctacaaggac 1140
cacgacggcg actacaagga ccacgacatc gactacaagg acgacgacga caagtga 1197

<210> SEQ ID NO 75
<211> LENGTH: 398
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

Met Leu Lys Leu Ser Ser Cys Asn Val Thr Asp Gln Arg Gln Ala Leu
1 5 10 15

Ala Gln Cys Arg Phe Leu Ala Pro Pro Ala Pro Phe Ser Phe Arg Trp
20 25 30

Arg Thr Pro Val Val Val Ser Cys Ser Pro Ser Ser Arg Pro Asn Leu
35 40 45

Ser Pro Leu Gln Val Val Leu Ser Gly Gln Gln Gln Ala Gly Met Glu

```
    50                  55                  60

Leu Val Glu Ser Gly Ser Gly Ser Leu Ala Asp Arg Leu Arg Leu Gly
65                  70                  75                  80

Ser Leu Thr Glu Asp Gly Leu Ser Tyr Lys Glu Lys Phe Ile Val Arg
                85                  90                  95

Cys Tyr Glu Val Gly Ile Asn Lys Thr Ala Thr Val Glu Thr Ile Ala
            100                 105                 110

Asn Leu Leu Gln Glu Val Gly Cys Asn His Ala Gln Ser Val Gly Tyr
        115                 120                 125

Ser Thr Asp Gly Phe Ala Thr Thr Arg Thr Met Arg Lys Leu His Leu
    130                 135                 140

Ile Trp Val Thr Ala Arg Met His Ile Glu Ile Tyr Lys Tyr Pro Ala
145                 150                 155                 160

Trp Ser Asp Val Ile Glu Ile Glu Thr Trp Cys Gln Ser Glu Gly Arg
                165                 170                 175

Ile Gly Thr Arg Arg Asp Trp Ile Leu Lys Asp Phe Gly Thr Gly Glu
            180                 185                 190

Val Ile Gly Arg Ala Thr Ser Lys Trp Val Met Met Asn Gln Asp Thr
        195                 200                 205

Arg Arg Leu Gln Lys Val Ser Asp Asp Val Arg Glu Glu Tyr Leu Val
    210                 215                 220

Phe Cys Pro Arg Glu Leu Arg Leu Ala Phe Pro Glu Glu Asn Asn Asn
225                 230                 235                 240

Ser Leu Lys Lys Ile Ala Lys Leu Asp Asp Ser Phe Gln Tyr Ser Arg
                245                 250                 255

Leu Gly Leu Met Pro Arg Arg Ala Asp Leu Asp Met Asn Gln His Val
            260                 265                 270

Asn Asn Val Thr Tyr Ile Gly Trp Val Leu Glu Ser Met Pro Gln Glu
        275                 280                 285

Ile Ile Asp Thr His Glu Leu Gln Thr Ile Thr Leu Asp Tyr Arg Arg
    290                 295                 300

Glu Cys Gln Gln Asp Asp Val Val Asp Ser Leu Thr Ser Pro Glu Gln
305                 310                 315                 320

Val Glu Gly Thr Glu Lys Val Ser Ala Ile His Gly Thr Asn Gly Ser
                325                 330                 335

Ala Ala Ala Arg Glu Asp Lys Gln Asp Cys Arg Gln Phe Leu His Leu
            340                 345                 350

Leu Arg Leu Ser Ser Asp Gly Gln Glu Ile Asn Arg Gly Arg Thr Glu
        355                 360                 365

Trp Arg Lys Lys Pro Ala Arg Met Asp Tyr Lys Asp His Asp Gly Asp
    370                 375                 380

Tyr Lys Asp His Asp Ile Asp Tyr Lys Asp Asp Asp Asp Lys
385                 390                 395
```

<210> SEQ ID NO 76
<211> LENGTH: 573
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76

```
tgttgaagaa tgagccggcg acttaaaata aatggcaggc taagagaatt aataactcga     60

aacctaagcg aaagcaagtc ttaatagggc gctaatttaa caaaacatta aataaaatct    120
```

```
aaagtcattt attttagacc cgaacctgag tgatctaacc atggtcagga tgaaacttgg    180

gtgacaccaa gtggaagtcc gaaccgaccg atgttgaaaa atcggcggat gaactgtggt    240

tagtggtgaa ataccagtcg aactcagagc tagctggttc tccccgaaat gcgttgaggc    300

gcagcaatat atctcgtcta tctaggggta aagcactgtt tcggtgcggg ctatgaaaat    360

ggtaccaaat cgtggcaaac tctgaatact agaaatgacg atatattagt gagactatgg    420

gggataagct ccatagtcga gagggaaaca gcccagacca ccagttaagg ccccaaaatg    480

ataatgaagt ggtaaaggag gtgaaaatgc aaatacaacc aggaggttgg cttagaagca    540

gccatccttt aaagagtgcg taatagctca ctg                                 573
```

```
<210> SEQ ID NO 77
<211> LENGTH: 384
<212> TYPE: PRT
<213> ORGANISM: Cuphea wrightii

<400> SEQUENCE: 77

Met Ala Ile Ala Ala Ala Ala Val Ile Phe Leu Phe Gly Leu Ile Phe
1               5                   10                  15

Phe Ala Ser Gly Leu Ile Ile Asn Leu Phe Gln Ala Leu Cys Phe Val
            20                  25                  30

Leu Ile Arg Pro Leu Ser Lys Asn Ala Tyr Arg Arg Ile Asn Arg Val
        35                  40                  45

Phe Ala Glu Leu Leu Leu Ser Glu Leu Leu Cys Leu Phe Asp Trp Trp
    50                  55                  60

Ala Gly Ala Lys Leu Lys Leu Phe Thr Asp Pro Glu Thr Phe Arg Leu
65                  70                  75                  80

Met Gly Lys Glu His Ala Leu Val Ile Ile Asn His Met Thr Glu Leu
                85                  90                  95

Asp Trp Met Val Gly Trp Val Met Gly Gln His Phe Gly Cys Leu Gly
            100                 105                 110

Ser Ile Ile Ser Val Ala Lys Lys Ser Thr Lys Phe Leu Pro Val Leu
        115                 120                 125

Gly Trp Ser Met Trp Phe Ser Glu Tyr Leu Tyr Leu Glu Arg Ser Trp
    130                 135                 140

Ala Lys Asp Lys Ser Thr Leu Lys Ser His Ile Glu Arg Leu Ile Asp
145                 150                 155                 160

Tyr Pro Leu Pro Phe Trp Leu Val Ile Phe Val Glu Gly Thr Arg Phe
                165                 170                 175

Thr Arg Thr Lys Leu Leu Ala Ala Gln Gln Tyr Ala Val Ser Ser Gly
            180                 185                 190

Leu Pro Val Pro Arg Asn Val Leu Ile Pro Arg Thr Lys Gly Phe Val
        195                 200                 205

Ser Cys Val Ser His Met Arg Ser Phe Val Pro Ala Val Tyr Asp Val
    210                 215                 220

Thr Val Ala Phe Pro Lys Thr Ser Pro Pro Pro Thr Leu Leu Asn Leu
225                 230                 235                 240

Phe Glu Gly Gln Ser Ile Met Leu His Val His Ile Lys Arg His Ala
                245                 250                 255

Met Lys Asp Leu Pro Glu Ser Asp Asp Ala Val Ala Glu Trp Cys Arg
            260                 265                 270

Asp Lys Phe Val Glu Lys Asp Ala Leu Leu Asp Lys His Asn Ala Glu
        275                 280                 285
```

-continued

```
Asp Thr Phe Ser Gly Gln Glu Val Cys His Ser Gly Ser Arg Gln Leu
    290                 295                 300

Lys Ser Leu Leu Val Val Ile Ser Trp Val Val Val Thr Thr Phe Gly
305                 310                 315                 320

Ala Leu Lys Phe Leu Gln Trp Ser Ser Trp Lys Gly Lys Ala Phe Ser
                325                 330                 335

Ala Ile Gly Leu Gly Ile Val Thr Leu Leu Met His Val Leu Ile Leu
            340                 345                 350

Ser Ser Gln Ala Glu Arg Ser Asn Pro Ala Glu Val Ala Gln Ala Lys
        355                 360                 365

Leu Lys Thr Gly Leu Ser Ile Ser Lys Lys Val Thr Asp Lys Glu Asn
    370                 375                 380


<210> SEQ ID NO 78
<211> LENGTH: 387
<212> TYPE: PRT
<213> ORGANISM: Cuphea wrightii

<400> SEQUENCE: 78

Met Ala Ile Ala Ala Ala Ala Val Ile Val Pro Leu Ser Leu Leu Phe
1               5                   10                  15

Phe Val Ser Gly Leu Ile Val Asn Leu Val Gln Ala Val Cys Phe Val
            20                  25                  30

Leu Ile Arg Pro Leu Ser Lys Asn Thr Tyr Arg Arg Ile Asn Arg Val
        35                  40                  45

Val Ala Glu Leu Leu Trp Leu Glu Leu Val Trp Leu Ile Asp Trp Trp
    50                  55                  60

Ala Gly Val Lys Ile Lys Val Phe Thr Asp His Glu Thr Phe His Leu
65                  70                  75                  80

Met Gly Lys Glu His Ala Leu Val Ile Cys Asn His Lys Ser Asp Ile
                85                  90                  95

Asp Trp Leu Val Gly Trp Val Leu Gly Gln Arg Ser Gly Cys Leu Gly
            100                 105                 110

Ser Thr Leu Ala Val Met Lys Lys Ser Ser Lys Phe Leu Pro Val Leu
        115                 120                 125

Gly Trp Ser Met Trp Phe Ser Glu Tyr Leu Phe Leu Glu Arg Ser Trp
    130                 135                 140

Ala Lys Asp Glu Ile Thr Leu Lys Ser Gly Leu Asn Arg Leu Lys Asp
145                 150                 155                 160

Tyr Pro Leu Pro Phe Trp Leu Ala Leu Phe Val Glu Gly Thr Arg Phe
                165                 170                 175

Thr Arg Ala Lys Leu Leu Ala Ala Gln Gln Tyr Ala Ala Ser Ser Gly
            180                 185                 190

Leu Pro Val Pro Arg Asn Val Leu Ile Pro Arg Thr Lys Gly Phe Val
        195                 200                 205

Ser Ser Val Ser His Met Arg Ser Phe Val Pro Ala Ile Tyr Asp Val
    210                 215                 220

Thr Val Ala Ile Pro Lys Thr Ser Pro Pro Pro Thr Leu Ile Arg Met
225                 230                 235                 240

Phe Lys Gly Gln Ser Ser Val Leu His Val His Leu Lys Arg His Leu
                245                 250                 255

Met Lys Asp Leu Pro Glu Ser Asp Asp Ala Val Ala Gln Trp Cys Arg
            260                 265                 270

Asp Ile Phe Val Glu Lys Asp Ala Leu Leu Asp Lys His Asn Ala Glu
        275                 280                 285
```

```
Asp Thr Phe Ser Gly Gln Glu Leu Gln Glu Thr Gly Arg Pro Ile Lys
    290                 295                 300

Ser Leu Leu Val Val Ile Ser Trp Ala Val Leu Glu Val Phe Gly Ala
305                 310                 315                 320

Val Lys Phe Leu Gln Trp Ser Ser Leu Leu Ser Ser Trp Lys Gly Leu
                325                 330                 335

Ala Phe Ser Gly Ile Gly Leu Gly Val Ile Thr Leu Leu Met His Ile
            340                 345                 350

Leu Ile Leu Phe Ser Gln Ser Glu Arg Ser Thr Pro Ala Lys Val Ala
        355                 360                 365

Pro Ala Lys Pro Lys Asn Glu Gly Glu Ser Ser Lys Thr Glu Met Glu
    370                 375                 380

Lys Glu Lys
385


<210> SEQ ID NO 79
<211> LENGTH: 327
<212> TYPE: PRT
<213> ORGANISM: Cuphea wrightii

<400> SEQUENCE: 79

Met Glu Ile Pro Pro His Cys Leu Cys Ser Pro Ser Pro Ala Pro Ser
1               5                   10                  15

Gln Leu Tyr Tyr Lys Lys Lys Lys His Ala Ile Leu Gln Thr Gln Thr
            20                  25                  30

Pro Tyr Arg Tyr Arg Val Ser Pro Thr Cys Phe Ala Pro Pro Arg Leu
        35                  40                  45

Arg Lys Gln His Pro Tyr Pro Leu Pro Val Leu Cys Tyr Pro Lys Leu
    50                  55                  60

Leu His Phe Ser Gln Pro Arg Tyr Pro Leu Val Arg Ser His Leu Ala
65                  70                  75                  80

Glu Ala Gly Val Ala Tyr Arg Pro Gly Tyr Glu Leu Leu Gly Lys Ile
                85                  90                  95

Arg Gly Val Cys Phe Tyr Ala Val Thr Ala Ala Val Ala Leu Leu Leu
            100                 105                 110

Phe Gln Cys Met Leu Leu Leu His Pro Phe Val Leu Leu Phe Asp Pro
        115                 120                 125

Phe Pro Arg Lys Ala His His Thr Ile Ala Lys Leu Trp Ser Ile Cys
    130                 135                 140

Ser Val Ser Leu Phe Tyr Lys Ile His Ile Lys Gly Leu Glu Asn Leu
145                 150                 155                 160

Pro Pro Pro His Ser Pro Ala Val Tyr Val Ser Asn His Gln Ser Phe
                165                 170                 175

Leu Asp Ile Tyr Thr Leu Leu Thr Leu Gly Arg Thr Phe Lys Phe Ile
            180                 185                 190

Ser Lys Thr Glu Ile Phe Leu Tyr Pro Ile Ile Gly Trp Ala Met Tyr
        195                 200                 205

Met Leu Gly Thr Ile Pro Leu Lys Arg Leu Asp Ser Arg Ser Gln Leu
    210                 215                 220

Asp Thr Leu Lys Arg Cys Met Asp Leu Ile Lys Lys Gly Ala Ser Val
225                 230                 235                 240

Phe Phe Phe Pro Glu Gly Thr Arg Ser Lys Asp Gly Lys Leu Gly Ala
                245                 250                 255

Phe Lys Lys Gly Ala Phe Ser Ile Ala Ala Lys Ser Lys Val Pro Val
```

-continued

```
            260                 265                 270

Val Pro Ile Thr Leu Ile Gly Thr Gly Lys Ile Met Pro Pro Gly Ser
        275                 280                 285

Glu Leu Thr Val Asn Pro Gly Thr Val Gln Val Ile Ile His Lys Pro
    290                 295                 300

Ile Glu Gly Ser Asp Ala Glu Ala Met Cys Asn Glu Ala Arg Ala Thr
305                 310                 315                 320

Ile Ser His Ser Leu Asp Asp
                325


<210> SEQ ID NO 80
<211> LENGTH: 984
<212> TYPE: DNA
<213> ORGANISM: Cuphea wrightii

<400> SEQUENCE: 80

atggagatcc cgcctcactg tctctgttcg ccttcgcctg cgccttcgca attgtattac      60

aagaagaaga agcatgccat tctccaaact caaactccct atagatatag agtttccccg     120

acatgctttg cccccccccg attgaggaag cagcatcctt accctctccc tgtcctctgc     180

tatccaaaac tcctccactt cagccagcct aggtaccctc tggttagatc tcatttggct     240

gaagctggtg ttgcttatcg tccaggatac gaattattag gaaaaataag gggagtgtgt     300

ttctatgctg tcactgctgc cgttgccttg cttctatttc agtgcatgct cctcctccat     360

ccctttgtgc tcctcttcga tccatttcca agaaaggctc accataccat cgccaaactc     420

tggtctatct gctctgtttc tctttttac aagattcaca tcaagggttt ggaaaatctt     480

cccccacccc actctcctgc cgtctatgtc tctaatcatc agagttttct cgacatctat     540

actctcctca ctctcggtag aaccttcaag ttcatcagca agactgagat ctttctctat     600

ccaattatcg gttgggccat gtatatgttg ggtaccattc ctctcaagcg gttggacagc     660

agaagccaat tggacactct taagcgatgt atggatctca tcaagaaggg agcatccgtc     720

tttttcttcc cagagggaac acgaagtaaa gatgggaaac tgggtgcttt caagaaaggt     780

gcattcagca tcgcagcaaa aagcaaggtt cctgttgtgc cgatcaccct tattggaact     840

ggcaagatta tgccacctgg gagcgaactt actgtcaatc caggaactgt gcaagtaatc     900

atacataaac ctatcgaagg aagtgatgca gaagcaatgt gcaatgaagc tagagccacg     960

atttctcact cacttgatga ttaa                                            984


<210> SEQ ID NO 81
<211> LENGTH: 1155
<212> TYPE: DNA
<213> ORGANISM: Cuphea wrightii

<400> SEQUENCE: 81

atggcgattg cagcggcagc tgtcatcttc ctcttcggcc ttatcttctt cgcctccggc      60

ctcataatca atctcttcca ggcgctttgc tttgtcctta ttcggcctct ttcgaaaaac     120

gcctacmgga gaataaacag agtttttgca gaattgttgt tgtcggagct tttatgccta     180

ttcgattggt gggctggtgc taagctcaaa ttatttaccg accctgaaac ctttcgcctt     240

atgggcaagg aacatgctct tgtcataatt aatcacatga ctgaacttga ctggatggtt     300

ggatgggtta tgggtcagca ttttggttgc cttgggagca taatatctgt tgcgaagaaa     360

tcaacaaaat ttcttccggt attggggtgg tcaatgtggt tttcagagta cctatatctt     420

gagagaagct gggccaagga taaaagtaca ttaaagtcac atatcgagag gctgatagac     480
```

```
taccccctgc ccttctggtt ggtaattttt gtggaaggaa ctcggtttac tcggacaaaa    540

ctcttggcag cccagcagta tgctgtctca tctgggctac cagtgccgag aaatgttttg    600

atcccacgta ctaagggttt tgtttcatgt gtaagtcaca tgcgatcatt tgttccagca    660

gtatatgatg tcacagtggc attccctaag acttcacctc caccaacgtt gctaaatctt    720

ttcgagggtc agtccataat gcttcacgtt cacatcaagc gacatgcaat gaaagattta    780

ccagaatccg atgatgcagt agcagagtgg tgtagagaca aatttgtgga aaaggatgct    840

ttgttggaca agcataatgc tgaggacact ttcagtggtc aagaagtttg tcatagcggc    900

agccgccagt taaagtctct tctggtggta atatcttggg tggttgtaac aacatttggg    960

gctctaaagt tccttcagtg gtcatcatgg aaggggaaag cattttcagc tatcgggctg   1020

ggcatcgtca ctctacttat gcacgtattg attctatcct cacaagcaga gcggtctaac   1080

cctgcggagg tggcacaggc aaagctaaag accgggttgt cgatctcaaa gaaggtaacg   1140

gacaaggaaa actag                                                    1155
```

<210> SEQ ID NO 82
<211> LENGTH: 1164
<212> TYPE: DNA
<213> ORGANISM: Cuphea wrightii

<400> SEQUENCE: 82

```
atggcgattg ctgcggcagc tgtcatcgtc ccgctcagcc tcctcttctt cgtctccggc     60

ctcatcgtca atctcgtaca ggcagtttgc tttgtactga ttaggcctct gtcgaaaaac    120

acttacagaa gaataaacag agtggttgca gaattgttgt ggttggagtt ggtatggctg    180

attgattggt gggctggtgt caagataaaa gtattcacgg atcatgaaac ctttcacctt    240

atgggcaaag aacatgctct tgtcatttgt aatcacaaga gtgacataga ctggctggtt    300

gggtgggttc tgggacagcg gtcaggttgc cttggaagca cattagctgt tatgaagaaa    360

tcatcaaagt ttctcccggt attagggtgg tcaatgtggt tctcagagta tctattcctt    420

gaaagaagct gggccaagga tgaaattaca ttaaagtcag gtttgaatag gctgaaagac    480

tatcccttac ccttctggtt ggcacttttt gtggaaggaa ctcggttcac tcgagcaaaa    540

ctcttggcag cccagcagta tgctgcctct tcggggctac ctgtgccgag aaatgttctg    600

atcccgcgta ctaagggttt tgtttcttct gtgagtcaca tgcgatcatt tgttccagcc    660

atatatgatg ttacagtggc aatcccaaag acgtcacctc caccaacatt gataagaatg    720

ttcaagggac agtcctcagt gcttcacgtc cacctcaagc gacacctaat gaaagattta    780

cctgaatcag atgatgctgt tgctcagtgg tgcagagata tattcgtcga gaaggatgct    840

ttgttggata agcataatgc tgaggacact ttcagtggcc aagaacttca agaaactggc    900

cgcccaataa agtctcttct ggttgtaatc tcttgggcgg tgttggaggt atttggagct    960

gtgaagtttc ttcaatggtc atcgctgtta tcatcatgga agggacttgc attttcggga   1020

ataggactgg gtgtcatcac gctactcatg cacatactga ttttattctc acaatccgag   1080

cggtctaccc ctgcaaaagt ggcaccagca aagccaaaga atgagggaga gtcctccaag   1140

acggaaatgg aaaaggaaaa gtag                                          1164
```

<210> SEQ ID NO 83
<211> LENGTH: 984
<212> TYPE: DNA
<213> ORGANISM: Cuphea wrightii

<400> SEQUENCE: 83

```
atggagatcc ccccccactg cctgtgctcc ccctccccccg cccccctccca gctgtactac     60
aagaagaaga agcacgccat cctgcagacc cagaccccct accgctaccg cgtgtccccc    120
acctgcttcg ccccccccccg cctgcgcaag cagcacccct accccctgcc cgtgctgtgc    180
taccccaagc tgctgcactt ctcccagccc cgctaccccc tggtgcgctc ccacctggcc    240
gaggccggcg tggcctaccg ccccggctac gagctgctgg gcaagatccg cggcgtgtgc    300
ttctacgccg tgaccgccgc cgtggccctg ctgctgttcc agtgcatgct gctgctgcac    360
cccttcgtgc tgctgttcga cccccttcccc cgcaaggccc accacaccat cgccaagctg    420
tggtccatct gctccgtgtc cctgttctac aagatccaca tcaagggcct ggagaacctg    480
cccccccccc actcccccgc cgtgtacgtg tccaaccacc agtccttcct ggacatctac    540
accctgctga ccctgggccg caccttcaag ttcatctcca agaccgagat cttcctgtac    600
cccatcatcg gctgggccat gtacatgctg ggcaccatcc ccctgaagcg cctggactcc    660
cgctcccagc tggacaccct gaagcgctgc atggacctga tcaagaaggg cgcctccgtg    720
ttcttcttcc ccgagggcac ccgctccaag gacggcaagc tgggcgcctt caagaagggc    780
gccttctcca tcgccgccaa gtccaaggtg cccgtggtgc ccatcaccct gatcggcacc    840
ggcaagatca tgccccccgg ctccgagctg accgtgaacc ccggcaccgt gcaggtgatc    900
atccacaagc ccatcgaggg ctccgacgcc gaggccatgt gcaacgaggc ccgcgccacc    960
atctcccact ccctggacga ctga                                           984
```

<210> SEQ ID NO 84
<211> LENGTH: 1155
<212> TYPE: DNA
<213> ORGANISM: Cuphea wrightii

<400> SEQUENCE: 84

```
atggcgatcg cggccgcggc ggtgatcttc ctgttcggcc tgatcttctt cgcctccggc     60
ctgatcatca acctgttcca ggcgctgtgc ttcgtcctga tccgcccccct gtccaagaac    120
gcctaccgcc gcatcaaccg cgtgttcgcg gagctgctgc tgtccgagct gctgtgcctg    180
ttcgactggt gggcgggcgc gaagctgaag ctgttcaccg accccgagac gttccgcctg    240
atgggcaagg agcacgccct ggtcatcatc aaccacatga ccgagctgga ctggatggtg    300
ggctgggtga tgggccagca cttcggctgc ctgggctcca tcatctccgt cgccaagaag    360
tccacgaagt tcctgcccgt gctgggctgg tccatgtggt tctccgagta cctgtacctg    420
gagcgctcct gggccaagga caagtccacc ctgaagtccc acatcgagcg cctgatcgac    480
tacccccctgc ccttctggct ggtcatcttc gtcgagggca cccgcttcac gcgcacgaag    540
ctgctggcgg cccagcagta cgcggtctcc tccggcctgc ccgtcccccg caacgtcctg    600
atcccccgca cgaagggctt cgtctcctgc gtgtcccaca tgcgctcctt cgtccccgcg    660
gtgtacgacg tcacggtggc gttccccaag acgtcccccc cccccacgct gctgaacctg    720
ttcgagggcc agtccatcat gctgcacgtg cacatcaagc gccacgccat gaaggacctg    780
cccgagtccg acgacgccgt cgcggagtgg tgccgcgaca agttcgtcga gaaggacgcc    840
ctgctggaca agcacaacgc ggaggacacg ttctccggcc aggaggtgtg ccactccggc    900
tcccgccagc tgaagtccct gctggtcgtg atctcctggg tcgtggtgac gacgttcggc    960
gccctgaagt tcctgcagtg gtcctcctgg aagggcaagg cgttctccgc catcggcctg   1020
ggcatcgtca ccctgctgat gcacgtgctg atcctgtcct cccaggccga gcgctccaac   1080
```

-continued cccgccgagg tggcccaggc caagctgaag accggcctgt ccatctccaa gaaggtgacg 1140
gacaaggaga actga 1155

<210> SEQ ID NO 85
<211> LENGTH: 1164
<212> TYPE: DNA
<213> ORGANISM: Cuphea wrightii

<400> SEQUENCE: 85
atggccatcg cggcggccgc ggtgatcgtg cccctgtccc tgctgttctt cgtgtccggc 60
ctgatcgtca acctggtgca ggccgtctgc ttcgtcctga tccgccccct gtccaagaac 120
acgtaccgcc gcatcaaccg cgtggtcgcg gagctgctgt ggctggagct ggtgtggctg 180
atcgactggt gggcgggcgt gaagatcaag gtcttcacgg accacgagac gttccacctg 240
atgggcaagg agcacgccct ggtcatctgc aaccacaagt ccgacatcga ctggctggtc 300
ggctgggtcc tgggccagcg ctccggctgc ctgggctcca ccctggcggt catgaagaag 360
tcctccaagt tcctgcccgt cctgggctgg tccatgtggt tctccgagta cctgttcctg 420
gagcgctcct gggccaagga cgagatcacg ctgaagtccg gcctgaaccg cctgaaggac 480
taccccctgc ccttctggct ggcgctgttc gtggagggca cgcgcttcac ccgcgcgaag 540
ctgctggcgg cgcagcagta cgccgcgtcc tccggcctgc ccgtgccccg caacgtgctg 600
atcccccgca cgaagggctt cgtgtcctcc gtgtcccaca tgcgctcctt cgtgcccgcg 660
atctacgacg tcaccgtggc catccccaag acgtcccccc cccccacgct gatccgcatg 720
ttcaagggcc agtcctccgt gctgcacgtg cacctgaagc gccacctgat gaaggacctg 780
cccgagtccg acgacgccgt cgcgcagtgg tgccgcgaca tcttcgtgga gaaggacgcg 840
ctgctggaca agcacaacgc cgaggacacc ttctccggcc aggagctgca ggagaccggc 900
cgccccatca agtccctgct ggtcgtcatc tcctgggccg tcctggaggt gttcggcgcc 960
gtcaagttcc tgcagtggtc ctccctgctg tcctcctgga agggcctggc gttctccggc 1020
atcggcctgg gcgtgatcac cctgctgatg cacatcctga tcctgttctc ccagtccgag 1080
cgctccaccc ccgccaaggt ggcccccgcg aagcccaaga acgagggcga gtcctccaag 1140
accgagatgg agaaggagaa gtga 1164

<210> SEQ ID NO 86
<211> LENGTH: 1098
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 86
gcgcacccca aggcgaacgg cagcgcggtg tcgctgaagt cgggctccct ggagacccag 60
gaggacaaga cgagcagctc gtcccccccc ccccgcacgt tcatcaacca gctgcccgtg 120
tggagcatgc tgctgtcggc ggtgaccacg gtcttcggcg tggccgagaa gcagtggccc 180
atgctggacc gcaagtccaa gcgccccgac atgctggtcg agcccctggg cgtggaccgc 240
atcgtctacg acggcgtgag cttccgccag tcgttctcca tccgcagcta cgagatcggc 300
gccgaccgca ccgcctcgat cgagacgctg atgaacatgt tccaggagac ctccctgaac 360
cactgcaaga tcatcggcct gctgaacgac ggcttcggcc gcacgcccga gatgtgcaag 420
cgcgacctga tctgggtcgt gaccaagatg cagatcgagg tgaaccgcta ccccacgtgg 480

```
ggcgacacca tcgaggtcaa cacgtgggtg agcgcctcgg gcaagcacgg catgggccgc    540

gactggctga tctccgactg ccacaccggc gagatcctga tccgcgcgac gagcgtctgg    600

gcgatgatga accagaagac ccgccgcctg tcgaagatcc cctacgaggt gcgccaggag    660

atcgagcccc agttcgtcga ctccgccccc gtgatcgtgg acgaccgcaa gttccacaag    720

ctggacctga agacgggcga cagcatctgc aacggcctga ccccccgctg gacggacctg    780

gacgtgaacc agcacgtcaa caacgtgaag tacatcggct ggatcctgca gtcggtcccc    840

accgaggtgt tcgagacgca ggagctgtgc ggcctgaccc tggagtaccg ccgcgagtgc    900

ggccgcgact ccgtgctgga gagcgtcacg gccatggacc cctcgaagga gggcgaccgc    960

tccctgtacc agcacctgct gcgcctggag gacggcgcgg acatcgtgaa gggccgcacc   1020

gagtggcgcc ccaagaacgc cggcgccaag ggcgccatcc tgacgggcaa gaccagcaac   1080

ggcaactcga tctcctga                                                 1098
```

<210> SEQ ID NO 87
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

```
Ala His Pro Lys Ala Asn Gly Ser Ala Val Ser Leu Lys Ser Gly Ser
1               5                   10                  15

Leu Glu Thr Gln Glu Asp Lys Thr Ser Ser Ser Ser Pro Pro Pro Arg
            20                  25                  30

Thr Phe Ile Asn Gln Leu Pro Val Trp Ser Met Leu Leu Ser Ala Val
        35                  40                  45

Thr Thr Val Phe Gly Val Ala Glu Lys Gln Trp Pro Met Leu Asp Arg
    50                  55                  60

Lys Ser Lys Arg Pro Asp Met Leu Val Glu Pro Leu Gly Val Asp Arg
65                  70                  75                  80

Ile Val Tyr Asp Gly Val Ser Phe Arg Gln Ser Phe Ser Ile Arg Ser
                85                  90                  95

Tyr Glu Ile Gly Ala Asp Arg Thr Ala Ser Ile Glu Thr Leu Met Asn
            100                 105                 110

Met Phe Gln Glu Thr Ser Leu Asn His Cys Lys Ile Ile Gly Leu Leu
        115                 120                 125

Asn Asp Gly Phe Gly Arg Thr Pro Glu Met Cys Lys Arg Asp Leu Ile
    130                 135                 140

Trp Val Val Thr Lys Met Gln Ile Glu Val Asn Arg Tyr Pro Thr Trp
145                 150                 155                 160

Gly Asp Thr Ile Glu Val Asn Thr Trp Val Ser Ala Ser Gly Lys His
                165                 170                 175

Gly Met Gly Arg Asp Trp Leu Ile Ser Asp Cys His Thr Gly Glu Ile
            180                 185                 190

Leu Ile Arg Ala Thr Ser Val Trp Ala Met Met Asn Gln Lys Thr Arg
        195                 200                 205

Arg Leu Ser Lys Ile Pro Tyr Glu Val Arg Gln Glu Ile Glu Pro Gln
    210                 215                 220

Phe Val Asp Ser Ala Pro Val Ile Val Asp Asp Arg Lys Phe His Lys
225                 230                 235                 240
```

```
Leu Asp Leu Lys Thr Gly Asp Ser Ile Cys Asn Gly Leu Thr Pro Arg
                245                 250                 255

Trp Thr Asp Leu Asp Val Asn Gln His Val Asn Asn Val Lys Tyr Ile
            260                 265                 270

Gly Trp Ile Leu Gln Ser Val Pro Thr Glu Val Phe Glu Thr Gln Glu
        275                 280                 285

Leu Cys Gly Leu Thr Leu Glu Tyr Arg Arg Glu Cys Gly Arg Asp Ser
    290                 295                 300

Val Leu Glu Ser Val Thr Ala Met Asp Pro Ser Lys Glu Gly Asp Arg
305                 310                 315                 320

Ser Leu Tyr Gln His Leu Leu Arg Leu Glu Asp Gly Ala Asp Ile Val
                325                 330                 335

Lys Gly Arg Thr Glu Trp Arg Pro Lys Asn Ala Gly Ala Lys Gly Ala
            340                 345                 350

Ile Leu Thr Gly Lys Thr Ser Asn Gly Asn Ser Ile Ser
        355                 360                 365


<210> SEQ ID NO 88
<211> LENGTH: 1167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

gcgcacccca aggcgaacgg cagcgcggtg tcgctgaagt cgggctccct ggagacccag     60

gaggacaaga cgagcagctc gtcccccccc ccccgcacgt tcatcaacca gctgcccgtg    120

tggagcatgc tgctgtcggc ggtgaccacg gtcttcggcg tggccgagaa gcagtggccc    180

atgctggacc gcaagtccaa gcgccccgac atgctggtcg agcccctggg cgtggaccgc    240

atcgtctacg acggcgtgag cttccgccag tcgttctcca tccgcagcta cgagatcggc    300

gccgaccgca ccgcctcgat cgagacgctg atgaacatgt tccaggagac ctccctgaac    360

cactgcaaga tcatcggcct gctgaacgac ggcttcggcc gcacgcccga gatgtgcaag    420

cgcgacctga tctgggtcgt gaccaagatg cagatcgagg tgaaccgcta ccccacgtgg    480

ggcgacacca tcgaggtcaa cacgtgggtg agcgcctcgg gcaagcacgg catgggccgc    540

gactggctga tctccgactg ccacaccggc gagatcctga tccgcgcgac gagcgtctgg    600

gcgatgatga accagaagac ccgccgcctg tcgaagatcc cctacgaggt gcgccaggag    660

atcgagcccc agttcgtcga ctccgccccc gtgatcgtgg acgaccgcaa gttccacaag    720

ctggacctga agacgggcga cagcatctgc aacggcctga ccccccgctg gacggacctg    780

gacgtgaacc agcacgtcaa caacgtgaag tacatcggct ggatcctgca gtcggtcccc    840

accgaggtgt tcgagacgca ggagctgtgc ggcctgaccc tggagtaccg ccgcgagtgc    900

ggccgcgact ccgtgctgga gagcgtcacg gccatggacc cctcgaagga gggcgaccgc    960

tccctgtacc agcacctgct gcgcctggag gacggcgcgg acatcgtgaa gggccgcacc   1020

gagtggcgcc ccaagaacgc cggcgccaag ggcgccatcc tgacgggcaa gaccagcaac   1080

ggcaactcga tctccatgga ctacaaggac cacgacggcg actacaagga ccacgacatc   1140

gactacaagg acgacgacga caagtga                                        1167


<210> SEQ ID NO 89
<211> LENGTH: 388
<212> TYPE: PRT
```

-continued

<213> ORGANISM: Artificial Sequence
<220> FEATURE:
<223> OTHER INFORMATION: Description of Artificial Sequence: Synthetic
      polypeptide

<400> SEQUENCE: 89

```
Ala His Pro Lys Ala Asn Gly Ser Ala Val Ser Leu Lys Ser Gly Ser
1               5                   10                  15

Leu Glu Thr Gln Glu Asp Lys Thr Ser Ser Ser Ser Pro Pro Pro Arg
            20                  25                  30

Thr Phe Ile Asn Gln Leu Pro Val Trp Ser Met Leu Leu Ser Ala Val
        35                  40                  45

Thr Thr Val Phe Gly Val Ala Glu Lys Gln Trp Pro Met Leu Asp Arg
    50                  55                  60

Lys Ser Lys Arg Pro Asp Met Leu Val Glu Pro Leu Gly Val Asp Arg
65                  70                  75                  80

Ile Val Tyr Asp Gly Val Ser Phe Arg Gln Ser Phe Ser Ile Arg Ser
                85                  90                  95

Tyr Glu Ile Gly Ala Asp Arg Thr Ala Ser Ile Glu Thr Leu Met Asn
            100                 105                 110

Met Phe Gln Glu Thr Ser Leu Asn His Cys Lys Ile Ile Gly Leu Leu
        115                 120                 125

Asn Asp Gly Phe Gly Arg Thr Pro Glu Met Cys Lys Arg Asp Leu Ile
    130                 135                 140

Trp Val Val Thr Lys Met Gln Ile Glu Val Asn Arg Tyr Pro Thr Trp
145                 150                 155                 160

Gly Asp Thr Ile Glu Val Asn Thr Trp Val Ser Ala Ser Gly Lys His
                165                 170                 175

Gly Met Gly Arg Asp Trp Leu Ile Ser Asp Cys His Thr Gly Glu Ile
            180                 185                 190

Leu Ile Arg Ala Thr Ser Val Trp Ala Met Met Asn Gln Lys Thr Arg
        195                 200                 205

Arg Leu Ser Lys Ile Pro Tyr Glu Val Arg Gln Glu Ile Glu Pro Gln
    210                 215                 220

Phe Val Asp Ser Ala Pro Val Ile Val Asp Asp Arg Lys Phe His Lys
225                 230                 235                 240

Leu Asp Leu Lys Thr Gly Asp Ser Ile Cys Asn Gly Leu Thr Pro Arg
                245                 250                 255

Trp Thr Asp Leu Asp Val Asn Gln His Val Asn Asn Val Lys Tyr Ile
            260                 265                 270

Gly Trp Ile Leu Gln Ser Val Pro Thr Glu Val Phe Glu Thr Gln Glu
        275                 280                 285

Leu Cys Gly Leu Thr Leu Glu Tyr Arg Arg Glu Cys Gly Arg Asp Ser
    290                 295                 300

Val Leu Glu Ser Val Thr Ala Met Asp Pro Ser Lys Glu Gly Asp Arg
305                 310                 315                 320

Ser Leu Tyr Gln His Leu Leu Arg Leu Glu Asp Gly Ala Asp Ile Val
                325                 330                 335

Lys Gly Arg Thr Glu Trp Arg Pro Lys Asn Ala Gly Ala Lys Gly Ala
            340                 345                 350

Ile Leu Thr Gly Lys Thr Ser Asn Gly Asn Ser Ile Ser Met Asp Tyr
        355                 360                 365

Lys Asp His Asp Gly Asp Tyr Lys Asp His Asp Ile Asp Tyr Lys Asp
    370                 375                 380
```

Asp Asp Asp Lys
385

<210> SEQ ID NO 90
<211> LENGTH: 5428
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 90
gctcttccgc taacggaggt ctgtcaccaa atggaccccg tctattgcgg gaaaccacgg 60
cgatggcacg tttcaaaact tgatgaaata caatattcag tatgtcgcgg gcggcgacgg 120
cggggagctg atgtcgcgct gggtattgct taatcgccag cttcgccccc gtcttggcgc 180
gaggcgtgaa caagccgacc gatgtgcacg agcaaatcct gacactagaa gggctgactc 240
gcccggcacg gctgaattac acaggcttgc aaaaatacca gaatttgcac gcaccgtatt 300
cgcggtattt tgttggacag tgaatagcga tgcggcaatg gcttgtggcg ttagaaggtg 360
cgacgaaggt ggtgccacca ctgtgccagc cagtcctggc ggctcccagg gccccgatca 420
agagccagga catccaaact acccacagca tcaacgcccc ggcctatact cgaaccccac 480
ttgcactctg caatggtatg ggaaccacgg ggcagtcttg tgtgggtcgc gcctatcgcg 540
gtcggcgaag accgggaagg taccctttct tgcgctatga cacttccagc aaaaggtagg 600
gcgggctgcg agacggcttc ccggcgctgc atgcaacacc gatgatgctt cgaccccccg 660
aagctccttc ggggctgcat gggcgctccg atgccgctcc agggcgagcg ctgtttaaat 720
agccaggccc ccgattgcaa agacattata gcgagctacc aaagccatat tcaaacacct 780
agatcactac cacttctaca caggccactc gagcttgtga tcgcactccg ctaagggggc 840
gcctcttcct cttcgtttca gtcacaaccc gcaaactcta gaatatcaat gatcgagcag 900
gacggcctcc acgccggctc cccgccgcc tgggtggagc gcctgttcgg ctacgactgg 960
gcccagcaga ccatcggctg ctccgacgcc gccgtgttcc gcctgtccgc ccagggccgc 1020
cccgtgctgt tcgtgaagac cgacctgtcc ggcgccctga acgagctgca ggacgaggcc 1080
gcccgcctgt cctggctggc caccaccggc gtgccctgcg ccgccgtgct ggacgtggtg 1140
accgaggccg gccgcgactg gctgctgctg ggcgaggtgc ccggccagga cctgctgtcc 1200
tcccacctgg cccccgccga gaaggtgtcc atcatggccg acgccatgcg ccgcctgcac 1260
accctggacc ccgccacctg ccccttcgac caccaggcca agcaccgcat cgagcgcgcc 1320
cgcacccgca tggaggccgg cctggtggac caggacgacc tggacgagga gcaccagggc 1380 ctggccccg ccgagctgtt cgcccgcctg aaggcccgca tgcccgacgg cgaggacctg 1440
gtggtgaccc acggcgacgc ctgcctgccc aacatcatgg tggagaacgg ccgcttctcc 1500
ggcttcatcg actgcggccg cctgggcgtg gccgaccgct accaggacat cgccctggcc 1560
acccgcgaca tcgccgagga gctgggcggc gagtgggccg accgcttcct ggtgctgtac 1620
ggcatcgccg cccccgactc ccagcgcatc gccttctacc gcctgctgga cgagttcttc 1680
tgacaattgg cagcagcagc tcggatagta tcgacacact ctggacgctg gtcgtgtgat 1740
ggactgttgc cgccacactt gctgccttga cctgtgaata tccctgccgc ttttatcaaa 1800
cagcctcagt gtgtttgatc ttgtgtgtac gcgcttttgc gagttgctag ctgcttgtgc 1860
tatttgcgaa taccaccccc agcatcccct tccctcgttt catatcgctt gcatcccaac 1920
cgcaacttat ctacgctgtc ctgctatccc tcagcgctgc tcctgctcct gctcactgcc 1980
cctcgcacag ccttggtttg ggctccgcct gtattctcct ggtactgcaa cctgtaaacc 2040
agcactgcaa tgctgatgca cgggaagtag tgggatggga acacaaatgg aggatcccgc 2100
gtctcgaaca gagcgcgcag aggaacgctg aaggtctcgc ctctgtcgca cctcagcgcg 2160
gcatacacca caataaccac ctgacgaatg cgcttggttc ttcgtccatt agcgaagcgt 2220
ccggttcaca cacgtgccac gttggcgagg tggcaggtga caatgatcgg tggagctgat 2280
ggtcgaaacg ttcacagcct agggatatcg aattcggccg acaggacgcg cgtcaaaggt 2340
gctggtcgtg tatgccctgg ccggcaggtc gttgctgctg ctggttagtg attccgcaac 2400
cctgattttg gcgtcttatt ttggcgtggc aaacgctggc gcccgcgagc cgggccggcg 2460
gcgatgcggt gccccacggc tgccggaatc caagggaggc aagagcgccc gggtcagttg 2520
aagggcttta cgcgcaaggt acagccgctc ctgcaaggct gcgtggtgga attggacgtg 2580
caggtcctgc tgaagttcct ccaccgcctc accagcggac aaagcaccgg tgtatcaggt 2640
ccgtgtcatc cactctaaag agctcgacta cgacctactg atggccctag attcttcatc 2700
aaaaacgcct gagacacttg cccaggattg aaactccctg aagggaccac caggggccct 2760
gagttgttcc ttccccccgt ggcgagctgc cagccaggct gtacctgtga tcgaggctgg 2820
cgggaaaata ggcttcgtgt gctcaggtca tgggaggtgc aggacagctc atgaaacgcc 2880
aacaatcgca caattcatgt caagctaatc agctatttcc tcttcacgag ctgtaattgt 2940
cccaaaattc tggtctaccg ggggtgatcc ttcgtgtacg ggcccttccc tcaaccctag 3000
gtatgcgcgc atgcggtcgc cgcgcaactc gcgcgagggc cgagggtttg ggacgggccg 3060
tcccgaaatg cagttgcacc cggatgcgtg gcaccttttt tgcgataatt tatgcaatgg 3120
actgctctgc aaaattctgg ctctgtcgcc aaccctagga tcagcggcgt aggatttcgt 3180
aatcattcgt cctgatgggg agctaccgac taccctaata tcagcccgac tgcctgacgc 3240
cagcgtccac ttttgtgcac acattccatt cgtgcccaag acatttcatt gtggtgcgaa 3300
gcgtccccag ttacgctcac ctgtttcccg acctccttac tgttctgtcg acagagcggg 3360
cccacaggcc ggtcgcagcc actagtatgg cgatcgcggc cgcggcggtg atcttcctgt 3420
tcggcctgat cttcttcgcc tccggcctga tcatcaacct gttccaggcg ctgtgcttcg 3480
tcctgatccg cccccctgtcc aagaacgcct accgccgcat caaccgcgtg ttcgcggagc 3540
tgctgctgtc cgagctgctg tgcctgttcg actggtgggc gggcgcgaag ctgaagctgt 3600
tcaccgaccc cgagacgttc cgcctgatgg gcaaggagca cgccctggtc atcatcaacc 3660
acatgaccga gctggactgg atggtgggct gggtgatggg ccagcacttc ggctgcctgg 3720
gctccatcat ctccgtcgcc aagaagtcca cgaagttcct gcccgtgctg ggctggtcca 3780
tgtggttctc cgagtacctg tacctggagc gctcctgggc caaggacaag tccaccctga 3840
agtcccacat cgagcgcctg atcgactacc ccctgccctt ctggctggtc atcttcgtcg 3900
agggcacccg cttcacgcgc acgaagctgc tggcggccca gcagtacgcg gtctcctccg 3960
gcctgcccgt cccccgcaac gtcctgatcc cccgcacgaa gggcttcgtc tcctgcgtgt 4020
cccacatgcg ctccttcgtc cccgcggtgt acgacgtcac ggtggcgttc cccaagacgt 4080
cccccccccc cacgctgctg aacctgttcg agggccagtc catcatgctg cacgtgcaca 4140
tcaagcgcca cgccatgaag gacctgcccg agtccgacga cgccgtcgcg gagtggtgcc 4200
gcgacaagtt cgtcgagaag gacgccctgc tggacaagca caacgcggag gacacgttct 4260
ccggccagga ggtgtgccac tccggctccc gccagctgaa gtccctgctg gtcgtgatct 4320

```
cctgggtcgt ggtgacgacg ttcggcgccc tgaagttcct gcagtggtcc tcctggaagg   4380

gcaaggcgtt ctccgccatc ggcctgggca tcgtcaccct gctgatgcac gtgctgatcc   4440

tgtcctccca ggccgagcgc tccaaccccg ccgaggtggc ccaggccaag ctgaagaccg   4500

gcctgtccat ctccaagaag gtgacggaca aggagaactg attaattaac tcgaggcagc   4560

agcagctcgg atagtatcga cacactctgg acgctggtcg tgtgatggac tgttgccgcc   4620

acacttgctg ccttgacctg tgaatatccc tgccgctttt atcaaacagc ctcagtgtgt   4680

ttgatcttgt gtgtacgcgc ttttgcgagt tgctagctgc ttgtgctatt tgcgaatacc   4740

acccccagca tccccttccc tcgtttcata tcgcttgcat cccaaccgca acttatctac   4800

gctgtcctgc tatccctcag cgctgctcct gctcctgctc actgcccctc gcacagcctt   4860

ggtttgggct ccgcctgtat tctcctggta ctgcaacctg taaaccagca ctgcaatgct   4920

gatgcacggg aagtagtggg atgggaacac aaatggaaag cttgagctca gcggcgacgg   4980

tcctgctacc gtacgacgtt gggcacgccc atgaaagttt gtataccgag cttgttgagc   5040

gaactgcaag cgcggctcaa ggatacttga actcctggat tgatatcggt ccaataatgg   5100

atggaaaatc cgaacctcgt gcaagaactg agcaaacctc gttacatgga tgcacagtcg   5160

ccagtccaat gaacattgaa gtgagcgaac tgttcgcttc ggtggcagta ctactcaaag   5220

aatgagctgc tgttaaaaat gcactctcgt tctctcaagt gagtggcaga tgagtgctca   5280

cgccttgcac ttcgctgccc gtgtcatgcc ctgcgcccca aaatttgaaa aaagggatga   5340

gattattggg caatggacga cgtcgtcgct ccgggagtca ggaccggcgg aaaataagag   5400

gcaacacact ccgcttctta gctcttcg                                      5428
```

<210> SEQ ID NO 91
<211> LENGTH: 5437
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91

```
gctcttccgc taacggaggt ctgtcaccaa atggaccccg tctattgcgg gaaaccacgg     60

cgatggcacg tttcaaaact tgatgaaata caatattcag tatgtcgcgg gcggcgacgg    120

cggggagctg atgtcgcgct gggtattgct taatcgccag cttcgccccc gtcttggcgc    180

gaggcgtgaa caagccgacc gatgtgcacg agcaaatcct gacactagaa gggctgactc    240

gcccggcacg gctgaattac acaggcttgc aaaaatacca gaatttgcac gcaccgtatt    300

cgcggtattt tgttggacag tgaatagcga tgcggcaatg gcttgtggcg ttagaaggtg    360

cgacgaaggt ggtgccacca ctgtgccagc cagtcctggc ggctcccagg gccccgatca    420

agagccagga catccaaact acccacagca tcaacgcccc ggcctatact cgaaccccac    480

ttgcactctg caatggtatg ggaaccacgg ggcagtcttg tgtgggtcgc gcctatcgcg    540

gtcggcgaag accgggaagg taccctttct tgcgctatga cacttccagc aaaaggtagg    600

gcgggctgcg agacggcttc ccggcgctgc atgcaacacc gatgatgctt cgaccccccg    660

aagctccttc ggggctgcat gggcgctccg atgccgctcc agggcgagcg ctgtttaaat    720

agccaggccc ccgattgcaa agacattata gcgagctacc aaagccatat tcaaacacct    780

agatcactac cacttctaca caggccactc gagcttgtga tcgcactccg ctaagggggc    840

gcctcttcct cttcgtttca gtcacaaccc gcaaactcta gaatatcaat gatcgagcag    900
```

```
gacggcctcc acgccggctc ccccgccgcc tgggtggagc gcctgttcgg ctacgactgg    960
gcccagcaga ccatcggctg ctccgacgcc gccgtgttcc gcctgtccgc ccagggccgc   1020
cccgtgctgt tcgtgaagac cgacctgtcc ggcgccctga acgagctgca ggacgaggcc   1080
gcccgcctgt cctggctggc caccaccggc gtgccctgcg ccgccgtgct ggacgtggtg   1140
accgaggccg gccgcgactg gctgctgctg ggcgaggtgc ccggccagga cctgctgtcc   1200
tcccacctgg cccccgccga gaaggtgtcc atcatggccg acgccatgcg ccgcctgcac   1260
accctggacc ccgccacctg ccccttcgac caccaggcca agcaccgcat cgagcgcgcc   1320
cgcacccgca tggaggccgg cctggtggac caggacgacc tggacgagga gcaccagggc   1380
ctggcccccg ccgagctgtt cgcccgcctg aaggcccgca tgcccgacgg cgaggacctg   1440
gtggtgaccc acggcgacgc ctgcctgccc aacatcatgg tggagaacgg ccgcttctcc   1500
ggcttcatcg actgcggccg cctgggcgtg gccgaccgct accaggacat cgccctggcc   1560
acccgcgaca tcgccgagga gctgggcggc gagtgggccg accgcttcct ggtgctgtac   1620
ggcatcgccg cccccgactc ccagcgcatc gccttctacc gcctgctgga cgagttcttc   1680
tgacaattgg cagcagcagc tcggatagta tcgacacact ctggacgctg gtcgtgtgat   1740
ggactgttgc cgccacactt gctgccttga cctgtgaata tccctgccgc ttttatcaaa   1800
cagcctcagt gtgtttgatc ttgtgtgtac gcgcttttgc gagttgctag ctgcttgtgc   1860
tatttgcgaa taccaccccc agcatcccct tccctcgttt catatcgctt gcatcccaac   1920
cgcaacttat ctacgctgtc ctgctatccc tcagcgctgc tcctgctcct gctcactgcc   1980
cctcgcacag ccttggtttg ggctccgcct gtattctcct ggtactgcaa cctgtaaacc   2040
agcactgcaa tgctgatgca cgggaagtag tgggatggga acacaaatgg aggatcccgc   2100
gtctcgaaca gagcgcgcag aggaacgctg aaggtctcgc ctctgtcgca cctcagcgcg   2160
gcatacacca caataaccac ctgacgaatg cgcttggttc ttcgtccatt agcgaagcgt   2220
ccggttcaca cacgtgccac gttggcgagg tggcaggtga caatgatcgg tggagctgat   2280
ggtcgaaacg ttcacagcct agggatatcg aattcggccg acaggacgcg cgtcaaaggt   2340
gctggtcgtg tatgccctgg ccggcaggtc gttgctgctg ctggttagtg attccgcaac   2400
cctgattttg gcgtcttatt ttggcgtggc aaacgctggc gcccgcgagc cgggccggcg   2460
gcgatgcggt gccccacggc tgccggaatc caagggaggc aagagcgccc gggtcagttg   2520
aagggcttta cgcgcaaggt acagccgctc ctgcaaggct gcgtggtgga attggacgtg   2580
caggtcctgc tgaagttcct ccaccgcctc accagcggac aaagcaccgg tgtatcaggt   2640
ccgtgtcatc cactctaaag agctcgacta cgacctactg atggccctag attcttcatc   2700
aaaaacgcct gagacacttg cccaggattg aaactccctg aagggaccac caggggccct   2760
gagttgttcc ttcccccgt ggcgagctgc cagccaggct gtacctgtga tcgaggctgg   2820
cgggaaaata ggcttcgtgt gctcaggtca tgggaggtgc aggacagctc atgaaacgcc   2880
aacaatcgca caattcatgt caagctaatc agctatttcc tcttcacgag ctgtaattgt   2940
cccaaaattc tggtctaccg ggggtgatcc ttcgtgtacg ggcccttccc tcaaccctag   3000
gtatgcgcgc atgcggtcgc cgcgcaactc gcgcgagggc cgagggtttg ggacgggccg   3060
tcccgaaatg cagttgcacc cggatgcgtg gcaccttttt tgcgataatt tatgcaatgg   3120
actgctctgc aaaattctgg ctctgtcgcc aaccctagga tcagcggcgt aggatttcgt   3180
aatcattcgt cctgatgggg agctaccgac taccctaata tcagcccgac tgcctgacgc   3240
cagcgtccac ttttgtgcac acattccatt cgtgcccaag acatttcatt gtggtgcgaa   3300
```

-continued

```
gcgtccccag ttacgctcac ctgtttcccg acctccttac tgttctgtcg acagagcggg   3360

cccacaggcc ggtcgcagcc actagtatgg ccatcgcggc ggccgcggtg atcgtgcccc   3420

tgtccctgct gttcttcgtg tccggcctga tcgtcaacct ggtgcaggcc gtctgcttcg   3480

tcctgatccg ccccctgtcc aagaacacgt accgccgcat caaccgcgtg gtcgcggagc   3540

tgctgtggct ggagctggtg tggctgatcg actggtgggc gggcgtgaag atcaaggtct   3600

tcacggacca cgagacgttc cacctgatgg gcaaggagca cgccctggtc atctgcaacc   3660

acaagtccga catcgactgg ctggtcggct gggtcctggg ccagcgctcc ggctgcctgg   3720

gctccaccct ggcggtcatg aagaagtcct ccaagttcct gcccgtcctg ggctggtcca   3780

tgtggttctc cgagtacctg ttcctggagc gctcctgggc caaggacgag atcacgctga   3840

agtccggcct gaaccgcctg aaggactacc ccctgccctt ctggctggcg ctgttcgtgg   3900

agggcacgcg cttcacccgc gcgaagctgc tggcggcgca gcagtacgcc gcgtcctccg   3960

gcctgcccgt gccccgcaac gtgctgatcc cccgcacgaa gggcttcgtg tcctccgtgt   4020

cccacatgcg ctccttcgtg cccgcgatct acgacgtcac cgtggccatc cccaagacgt   4080

cccccccccc cacgctgatc cgcatgttca agggccagtc ctccgtgctg cacgtgcacc   4140

tgaagcgcca cctgatgaag gacctgcccg agtccgacga cgccgtcgcg cagtggtgcc   4200

gcgacatctt cgtggagaag gacgcgctgc tggacaagca caacgccgag gacaccttct   4260

ccggccagga gctgcaggag accggccgcc ccatcaagtc cctgctggtc gtcatctcct   4320

gggccgtcct ggaggtgttc ggcgccgtca agttcctgca gtggtcctcc ctgctgtcct   4380

cctggaaggg cctggcgttc tccggcatcg gcctgggcgt gatcaccctg ctgatgcaca   4440

tcctgatcct gttctcccag tccgagcgct ccacccccgc caaggtggcc cccgcgaagc   4500

ccaagaacga gggcgagtcc tccaagaccg agatggagaa ggagaagtga ttaattaact   4560

cgaggcagca gcagctcgga tagtatcgac acactctgga cgctggtcgt gtgatggact   4620

gttgccgcca cacttgctgc cttgacctgt gaatatccct gccgctttta tcaaacagcc   4680

tcagtgtgtt tgatcttgtg tgtacgcgct tttgcgagtt gctagctgct tgtgctattt   4740

gcgaatacca cccccagcat ccccttccct cgtttcatat cgcttgcatc ccaaccgcaa   4800

cttatctacg ctgtcctgct atccctcagc gctgctcctg ctcctgctca ctgcccctcg   4860

cacagccttg gtttgggctc cgcctgtatt ctcctggtac tgcaacctgt aaaccagcac   4920

tgcaatgctg atgcacggga agtagtggga tgggaacaca aatggaaagc ttgagctcag   4980

cggcgacggt cctgctaccg tacgacgttg ggcacgccca tgaaagtttg tataccgagc   5040

ttgttgagcg aactgcaagc gcggctcaag gatacttgaa ctcctggatt gatatcggtc   5100

caataatgga tggaaaatcc gaacctcgtg caagaactga gcaaacctcg ttacatggat   5160

gcacagtcgc cagtccaatg aacattgaag tgagcgaact gttcgcttcg gtggcagtac   5220

tactcaaaga atgagctgct gttaaaaatg cactctcgtt ctctcaagtg agtggcagat   5280

gagtgctcac gccttgcact tcgctgcccg tgtcatgccc tgcgccccaa aatttgaaaa   5340

aagggatgag attattgggc aatggacgac gtcgtcgctc cgggagtcag gaccggcgga   5400

aaataagagg caacacactc cgcttcttag ctcttcg                            5437
```

<210> SEQ ID NO 92
<211> LENGTH: 5257
<212> TYPE: DNA
<213> ORGANISM: Artificial Sequence
<220> FEATURE:

-continued

<223> OTHER INFORMATION: Description of Artificial Sequence: Synthetic
polynucleotide

<400> SEQUENCE: 92

```
gctcttccgc taacggaggt ctgtcaccaa atggaccccg tctattgcgg gaaaccacgg     60
cgatggcacg tttcaaaact tgatgaaata caatattcag tatgtcgcgg gcggcgacgg    120
cggggagctg atgtcgcgct gggtattgct taatcgccag cttcgccccc gtcttggcgc    180
gaggcgtgaa caagccgacc gatgtgcacg agcaaatcct gacactagaa gggctgactc    240
gcccggcacg gctgaattac acaggcttgc aaaaatacca gaatttgcac gcaccgtatt    300
cgcggtattt tgttggacag tgaatagcga tgcggcaatg gcttgtggcg ttagaaggtg    360
cgacgaaggt ggtgccacca ctgtgccagc cagtcctggc ggctcccagg gccccgatca    420
agagccagga catccaaact acccacagca tcaacgcccc ggcctatact cgaaccccac    480
ttgcactctg caatggtatg ggaaccacgg ggcagtcttg tgtgggtcgc gcctatcgcg    540
gtcggcgaag accgggaagg taccctttct tgcgctatga cacttccagc aaaaggtagg    600
gcgggctgcg agacggcttc ccggcgctgc atgcaacacc gatgatgctt cgaccccccg    660
aagctccttc ggggctgcat gggcgctccg atgccgctcc agggcgagcg ctgtttaaat    720
agccaggccc ccgattgcaa agacattata gcgagctacc aaagccatat tcaaacacct    780
agatcactac cacttctaca caggccactc gagcttgtga tcgcactccg ctaagggggc    840
gcctcttcct cttcgtttca gtcacaaccc gcaaactcta gaatatcaat gatcgagcag    900
gacggcctcc acgccggctc cccgccgcc tgggtggagc gcctgttcgg ctacgactgg    960
gcccagcaga ccatcggctg ctccgacgcc gccgtgttcc gcctgtccgc ccagggccgc   1020
cccgtgctgt tcgtgaagac cgacctgtcc ggcgccctga acgagctgca ggacgaggcc   1080
gcccgcctgt cctggctggc caccaccggc gtgccctgcg ccgccgtgct ggacgtggtg   1140
accgaggccg gccgcgactg gctgctgctg ggcgaggtgc ccggccagga cctgctgtcc   1200
tcccacctgg cccccgccga gaaggtgtcc atcatggccg acgccatgcg ccgcctgcac   1260
accctggacc ccgccacctg ccccttcgac caccaggcca agcaccgcat cgagcgcgcc   1320
cgcacccgca tggaggccgg cctggtggac caggacgacc tggacgagga gcaccagggc   1380
ctggcccccg ccgagctgtt cgcccgcctg aaggcccgca tgcccgacgg cgaggacctg   1440
gtggtgaccc acggcgacgc ctgcctgccc aacatcatgg tggagaacgg ccgcttctcc   1500
ggcttcatcg actgcggccg cctgggcgtg gccgaccgct accaggacat cgccctggcc   1560
acccgcgaca tcgccgagga gctgggcggc gagtgggccg accgcttcct ggtgctgtac   1620
ggcatcgccg cccccgactc ccagcgcatc gccttctacc gcctgctgga cgagttcttc   1680
tgacaattgg cagcagcagc tcggatagta tcgacacact ctggacgctg gtcgtgtgat   1740
ggactgttgc cgccacactt gctgccttga cctgtgaata tccctgccgc ttttatcaaa   1800
cagcctcagt gtgtttgatc ttgtgtgtac gcgcttttgc gagttgctag ctgcttgtgc   1860
tatttgcgaa taccaccccc agcatcccct tccctcgttt catatcgctt gcatcccaac   1920
cgcaacttat ctacgctgtc ctgctatccc tcagcgctgc tcctgctcct gctcactgcc   1980
cctcgcacag ccttggtttg ggctccgcct gtattctcct ggtactgcaa cctgtaaacc   2040
agcactgcaa tgctgatgca cgggaagtag tgggatggga acacaaatgg aggatcccgc   2100
gtctcgaaca gagcgcgcag aggaacgctg aaggtctcgc ctctgtcgca cctcagcgcg   2160
gcatacacca caataaccac ctgacgaatg cgcttggttc ttcgtccatt agcgaagcgt   2220
```

-continued ccggttcaca cacgtgccac gttggcgagg tggcaggtga caatgatcgg tggagctgat 2280
ggtcgaaacg ttcacagcct agggatatcg aattcggccg acaggacgcg cgtcaaaggt 2340
gctggtcgtg tatgccctgg ccggcaggtc gttgctgctg ctggttagtg attccgcaac 2400
cctgattttg gcgtcttatt ttggcgtggc aaacgctggc gcccgcgagc cgggccggcg 2460
gcgatgcggt gccccacggc tgccggaatc caagggaggc aagagcgccc gggtcagttg 2520
aagggcttta cgcgcaaggt acagccgctc ctgcaaggct gcgtggtgga attggacgtg 2580
caggtcctgc tgaagttcct ccaccgcctc accagcggac aaagcaccgg tgtatcaggt 2640
ccgtgtcatc cactctaaag agctcgacta cgacctactg atggccctag attcttcatc 2700
aaaaacgcct gagacacttg cccaggattg aaactccctg aagggaccac caggggccct 2760
gagttgttcc ttccccccgt ggcgagctgc cagccaggct gtacctgtga tcgaggctgg 2820
cgggaaaata ggcttcgtgt gctcaggtca tgggaggtgc aggacagctc atgaaacgcc 2880
aacaatcgca caattcatgt caagctaatc agctatttcc tcttcacgag ctgtaattgt 2940
cccaaaattc tggtctaccg ggggtgatcc ttcgtgtacg ggcccttccc tcaaccctag 3000
gtatgcgcgc atgcggtcgc cgcgcaactc gcgcgagggc cgagggtttg ggacgggccg 3060
tcccgaaatg cagttgcacc cggatgcgtg gcaccttttt tgcgataatt tatgcaatgg 3120
actgctctgc aaaattctgg ctctgtcgcc aaccctagga tcagcggcgt aggatttcgt 3180
aatcattcgt cctgatgggg agctaccgac taccctaata tcagcccgac tgcctgacgc 3240
cagcgtccac ttttgtgcac acattccatt cgtgcccaag acatttcatt gtggtgcgaa 3300
gcgtccccag ttacgctcac ctgtttcccg acctccttac tgttctgtcg acagagcggg 3360
cccacaggcc ggtcgcagcc actagtatgg agatcccccc ccactgcctg tgctcccccct 3420
cccccgcccc ctcccagctg tactacaaga agaagaagca cgccatcctg cagacccaga 3480
ccccctaccg ctaccgcgtg tcccccacct gcttcgcccc cccccgcctg cgcaagcagc 3540
acccctaccc cctgcccgtg ctgtgctacc ccaagctgct gcacttctcc cagccccgct 3600
accccctggt gcgctcccac ctggccgagg ccggcgtggc ctaccgcccc ggctacgagc 3660
tgctgggcaa gatccgcggc gtgtgcttct acgccgtgac cgccgccgtg gccctgctgc 3720
tgttccagtg catgctgctg ctgcacccct tcgtgctgct gttcgacccc ttcccccgca 3780
aggcccacca caccatcgcc aagctgtggt ccatctgctc cgtgtccctg ttctacaaga 3840
tccacatcaa gggcctggag aacctgcccc ccccccactc ccccgccgtg tacgtgtcca 3900
accaccagtc cttcctggac atctacaccc tgctgaccct gggccgcacc ttcaagttca 3960
tctccaagac cgagatcttc ctgtacccca tcatcggctg ggccatgtac atgctgggca 4020
ccatccccct gaagcgcctg gactcccgct cccagctgga caccctgaag cgctgcatgg 4080
acctgatcaa gaagggcgcc tccgtgttct tcttccccga gggcacccgc tccaaggacg 4140
gcaagctggg cgccttcaag aagggcgcct tctccatcgc cgccaagtcc aaggtgcccg 4200
tggtgcccat caccctgatc ggcaccggca agatcatgcc ccccggctcc gagctgaccg 4260
tgaaccccgg caccgtgcag gtgatcatcc acaagcccat cgagggctcc gacgccgagg 4320
ccatgtgcaa cgaggcccgc gccaccatct cccactccct ggacgactga ttaattaact 4380
cgaggcagca gcagctcgga tagtatcgac acactctgga cgctggtcgt gtgatggact 4440
gttgccgcca cacttgctgc cttgacctgt gaatatccct gccgctttta tcaaacagcc 4500
tcagtgtgtt tgatcttgtg tgtacgcgct tttgcgagtt gctagctgct tgtgctattt 4560
gcgaatacca cccccagcat ccccttccct cgtttcatat cgcttgcatc ccaaccgcaa 4620

```
cttatctacg ctgtcctgct atccctcagc gctgctcctg ctcctgctca ctgcccctcg   4680

cacagccttg gtttgggctc cgcctgtatt ctcctggtac tgcaacctgt aaaccagcac   4740

tgcaatgctg atgcacggga agtagtggga tgggaacaca aatggaaagc ttgagctcag   4800

cggcgacggt cctgctaccg tacgacgttg ggcacgccca tgaaagtttg tataccgagc   4860

ttgttgagcg aactgcaagc gcggctcaag gatacttgaa ctcctggatt gatatcggtc   4920

caataatgga tggaaaatcc gaacctcgtg caagaactga gcaaacctcg ttacatggat   4980

gcacagtcgc cagtccaatg aacattgaag tgagcgaact gttcgcttcg gtggcagtac   5040

tactcaaaga atgagctgct gttaaaaatg cactctcgtt ctctcaagtg agtggcagat   5100

gagtgctcac gccttgcact tcgctgcccg tgtcatgccc tgcgccccaa aatttgaaaa   5160

aagggatgag attattgggc aatggacgac gtcgtcgctc cgggagtcag gaccggcgga   5220

aaataagagg caacacactc cgcttcttag ctcttcg                            5257
```

<210> SEQ ID NO 93
<211> LENGTH: 6714
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93

```
gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120

tgcgccggct gagccactgc ttcgtccggg cggccaagag gagcatgagg gaggactcct    180

ggtccagggt cctgacgtgg tcgcggctct gggagcgggc cagcatcatc tggctctgcc    240

gcaccgaggc cgcctccaac tggtcctcca gcagccgcag tcgccgccga ccctggcaga    300

ggaagacagg tgaggggggt atgaattgta cagaacaacc acgagccttg tctaggcaga    360

atccctacca gtcatggctt tacctggatg acggcctgcg aacagctgtc cagcgaccct    420

cgctgccgcc gcttctcccg cacgcttctt tccagcaccg tgatggcgcg agccagcgcc    480

gcacgctggc gctgcgcttc gccgatctga ggacagtcgg ggaactctga tcagtctaaa    540

ccccccttgcg cgttagtgtt gccatccttt gcagaccggt gagagccgac ttgttgtgcg    600

ccaccccccca caccacctcc tcccagacca attctgtcac ctttttggcg aaggcatcgg    660

cctcggcctg cagagaggac agcagtgccc agccgctggg ggttggcgga tgcacgctca    720

ggtacccttt cttgcgctat gacacttcca gcaaaaggta gggcgggctg cgagacggct    780

tcccggcgct gcatgcaaca ccgatgatgc ttcgaccccc cgaagctcct tcggggctgc    840

atgggcgctc cgatgccgct ccagggcgag cgctgtttaa atagccaggc ccccgattgc    900

aaagacatta tagcgagcta ccaaagccat attcaaacac ctagatcact accacttcta    960

cacaggccac tcgagcttgt gatcgcactc cgctaagggg gcgcctcttc ctcttcgttt   1020

cagtcacaac ccgcaaactc tagaatatca atgctgctgc aggccttcct gttcctgctg   1080

gccggcttcg ccgccaagat cagcgcctcc atgacgaacg agacgtccga ccgccccctg   1140

gtgcacttca cccccaacaa gggctggatg aacgacccca acggcctgtg gtacgacgag   1200

aaggacgcca agtggcacct gtacttccag tacaacccga acgacaccgt ctgggggacg   1260

cccttgttct ggggccacgc cacgtccgac gacctgacca actgggagga ccagcccatc   1320

gccatcgccc cgaagcgcaa cgactccggc gccttctccg gctccatggt ggtggactac   1380
```

aacaacacct ccggcttctt caacgacacc atcgacccgc gccagcgctg cgtggccatc 1440
tggacctaca acaccccgga gtccgaggag cagtacatct cctacagcct ggacggcggc 1500
tacaccttca ccgagtacca gaagaacccc gtgctggccg ccaactccac ccagttccgc 1560
gacccgaagg tcttctggta cgagccctcc cagaagtgga tcatgaccgc ggccaagtcc 1620
caggactaca agatcgagat ctactcctcc gacgacctga agtcctggaa gctggagtcc 1680
gcgttcgcca acgagggctt cctcggctac cagtacgagt gccccggcct gatcgaggtc 1740
cccaccgagc aggaccccag caagtcctac tgggtgatgt tcatctccat caaccccggc 1800
gccccggccg gcggctcctt caaccagtac ttcgtcggca gcttcaacgg cacccacttc 1860
gaggccttcg acaaccagtc ccgcgtggtg gacttcggca aggactacta cgccctgcag 1920
accttcttca acaccgaccc gacctacggg agcgccctgg gcatcgcgtg ggcctccaac 1980
tgggagtact ccgccttcgt gcccaccaac ccctggcgct cctccatgtc cctcgtgcgc 2040
aagttctccc tcaacaccga gtaccaggcc aacccggaga cggagctgat caacctgaag 2100
gccgagccga tcctgaacat cagcaacgcc ggcccctgga gccggttcgc caccaacacc 2160
acgttgacga aggccaacag ctacaacgtc gacctgtcca acagcaccgg caccctggag 2220
ttcgagctgg tgtacgccgt caacaccacc cagacgatct ccaagtccgt gttcgcggac 2280
ctctccctct ggttcaaggg cctggaggac cccgaggagt acctccgcat gggcttcgag 2340
gtgtccgcgt cctccttctt cctggaccgc gggaacagca aggtgaagtt cgtgaaggag 2400
aacccctact tcaccaaccg catgagcgtg aacaaccagc ccttcaagag cgagaacgac 2460
ctgtcctact acaaggtgta cggcttgctg gaccagaaca tcctggagct gtacttcaac 2520
gacggcgacg tcgtgtccac caacacctac ttcatgacca ccgggaacgc cctgggctcc 2580
gtgaacatga cgacgggggt ggacaacctg ttctacatcg acaagttcca ggtgcgcgag 2640
gtcaagtgac aattggcagc agcagctcgg atagtatcga cacactctgg acgctggtcg 2700
tgtgatggac tgttgccgcc acacttgctg ccttgacctg tgaatatccc tgccgctttt 2760
atcaaacagc ctcagtgtgt ttgatcttgt gtgtacgcgc ttttgcgagt tgctagctgc 2820
ttgtgctatt tgcgaatacc acccccagca tccccttccc tcgtttcata tcgcttgcat 2880
cccaaccgca acttatctac gctgtcctgc tatccctcag cgctgctcct gctcctgctc 2940
actgcccctc gcacagcctt ggtttgggct ccgcctgtat tctcctggta ctgcaacctg 3000
taaaccagca ctgcaatgct gatgcacggg aagtagtggg atgggaacac aaatggagga 3060
tcccgcgtct cgaacagagc gcgcagagga acgctgaagg tctcgcctct gtcgcacctc 3120
agcgcggcat acaccacaat aaccacctga cgaatgcgct tggttcttcg tccattagcg 3180
aagcgtccgg ttcacacacg tgccacgttg gcgaggtggc aggtgacaat gatcggtgga 3240
gctgatggtc gaaacgttca cagcctaggg atatcgaatt cggccgacag gacgcgcgtc 3300
aaaggtgctg gtcgtgtatg ccctggccgg caggtcgttg ctgctgctgg ttagtgattc 3360
cgcaaccctg attttggcgt cttattttgg cgtggcaaac gctggcgccc gcgagccggg 3420
ccggcggcga tgcggtgccc cacggctgcc ggaatccaag ggaggcaaga gcgcccgggt 3480
cagttgaagg gctttacgcg caaggtacag ccgctcctgc aaggctgcgt ggtggaattg 3540
gacgtgcagg tcctgctgaa gttcctccac cgcctcacca gcggacaaag caccggtgta 3600
tcaggtccgt gtcatccact ctaaagaact cgactacgac ctactgatgg ccctagattc 3660
ttcatcaaaa acgcctgaga cacttgccca ggattgaaac tccctgaagg gaccaccagg 3720

-continued ggccctgagt tgttccttcc ccccgtggcg agctgccagc caggctgtac ctgtgatcga 3780
ggctggcggg aaaataggct tcgtgtgctc aggtcatggg aggtgcagga cagctcatga 3840
aacgccaaca atcgcacaat tcatgtcaag ctaatcagct atttcctctt cacgagctgt 3900
aattgtccca aaattctggt ctaccggggg tgatccttcg tgtacgggcc cttccctcaa 3960
ccctaggtat gcgcgcatgc ggtcgccgcg caactcgcgc gagggccgag ggtttgggac 4020
gggccgtccc gaaatgcagt tgcacccgga tgcgtggcac cttttttgcg ataatttatg 4080
caatggactg ctctgcaaaa ttctggctct gtcgccaacc ctaggatcag cggcgtagga 4140
tttcgtaatc attcgtcctg atggggagct accgactacc ctaatatcag cccgactgcc 4200
tgacgccagc gtccactttt gtgcacacat tccattcgtg cccaagacat ttcattgtgg 4260
tgcgaagcgt ccccagttac gctcacctgt ttcccgacct ccttactgtt ctgtcgacag 4320
agcgggccca caggccggtc gcagccacta gtatggcccc cacctccctg ctggcctcca 4380
ccggcgtgtc ctccgcctcc ctgtggtcct ccgcccgctc ctccgcctgc gccttccccg 4440
tggaccacgc cgtgcgcggc gccccccagc gcccccctgcc catgcagcgc cgctgcttcc 4500
gcaccgtggc cgtgcgcggg cgcgccgccg cccccgccgt ggccgtgcgc cccgagcccg 4560
cccaggagtt ctgggagcag ctggagccct gcaagatggc cgaggacaag cgcatcttcc 4620
tggaggagca ccgcatccgc ggcaacgagg tgggcccctc ccagcgcctg accatcaccg 4680
ccgtggccaa catcctgcag gaggccgccg gcaaccacgc cgtggccatg tggggccgct 4740
cctccgaggg cttcgccacc gaccccgagc tgcaggaggc cggcctgatc ttcgtgatga 4800
cccgcatgca gatccagatg taccgctacc cccgctgggg cgacctgatg caggtggaga 4860
cctggttcca gaccgccggc aagctgggcg cccagcgcga gtgggtgctg cgcgacaagc 4920
tgaccggcga ggccctgggc gccgccacct cctcctgggt gatgatcaac atccgcaccc 4980
gccgcccctg ccgcatgccc gagctggtgc gcgtgaagtc cgccttcttc gcccgcgagc 5040
ccccccgcct ggccctgccc cccgccgtga cccgcgccaa gctgcccaac atcgccaccc 5100 ccgccccct gcgcggccac cgccaggtgg cccgccgcac cgacatggac atgaacggcc 5160
acgtgaacaa cgtggcctac ctggcctggt gcctggaggc cgtgcccgag cacgtgttct 5220
ccgactacca cctgtaccag atggagatcg acttcaaggc cgagtgccac gccggcgacg 5280
tgatctcctc ccaggccgag cagatccccc cccaggaggc cctgacccac aacggcgccg 5340
gccgcaaccc ctcctgcttc gtgcactcca tcctgcgcgc cgagaccgag ctggtgcgcg 5400
cccgcaccac ctggtccgcc cccatcgacg cccccgccgc caagcccccc aaggcctccc 5460
acatggacta caaggaccac gacggcgact acaaggacca cgacatcgac tacaaggacg 5520
acgacgacaa gtgaatcgat agatctctta aggcagcagc agctcggata gtatcgacac 5580
actctggacg ctggtcgtgt gatggactgt tgccgccaca cttgctgcct tgacctgtga 5640
atatccctgc cgcttttatc aaacagcctc agtgtgtttg atcttgtgtg tacgcgcttt 5700
tgcgagttgc tagctgcttg tgctatttgc gaataccacc cccagcatcc ccttccctcg 5760
tttcatatcg cttgcatccc aaccgcaact tatctacgct gtcctgctat ccctcagcgc 5820
tgctcctgct cctgctcact gcccctcgca cagccttggt ttgggctccg cctgtattct 5880
cctggtactg caacctgtaa accagcactg caatgctgat gcacgggaag tagtgggatg 5940
ggaacacaaa tggaaagctt aattaagagc tcttgttttc cagaaggagt tgctccttga 6000
gcctttcatt ctcagcctcg ataacctcca aagccgctct aattgtggag gggttcgaa 6060 tttaaaagct tggaatgttg gttcgtgcgt ctggaacaag cccagacttg ttgctcactg 6120
ggaaaaggac catcagctcc aaaaaacttg ccgctcaaac cgcgtacctc tgctttcgcg 6180
caatctgccc tgttgaaatc gccaccacat tcatattgtg acgcttgagc agtctgtaat 6240
tgcctcagaa tgtggaatca tctgcccct gtgcgagccc atgccaggca tgtcgcgggc 6300
gaggacaccc gccactcgta cagcagacca ttatgctacc tcacaatagt tcataacagt 6360
gaccatattt ctcgaagctc cccaacgagc acctccatgc tctgagtggc cacccccgg 6420 ccctggtgct tgcggagggc aggtcaaccg gcatggggct accgaaatcc ccgaccggat 6480
cccaccaccc ccgcgatggg aagaatctct ccccgggatg tgggcccacc accagcacaa 6540
cctgctggcc caggcgagcg tcaaaccata ccacacaaat atccttggca tcggccctga 6600
attccttctg ccgctctgct acccggtgct tctgtccgaa gcaggggttg ctagggatcg 6660
ctccgagtcc gcaaaccctt gtcgcgtggc ggggcttgtt cgagcttgaa gagc 6714

<210> SEQ ID NO 94
<211> LENGTH: 5279
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 94
gctcttcggg tcgccgcgct gcctcgcgtc ccctggtggt gcgcgcggtc gccagcgagg 60
ccccgctggg cgttccgccc tcggtgcagc gcccctcccc cgtggtctac tccaagctgg 120
acaagcagca ccgcctgacg cccgagcgcc tggagctggt gcagagcatg gggcagtttg 180
cggaggagag ggtgctgccc gtgctgcacc ccgtggacaa gctgtggcag ccgcaggact 240
ttttgcccga ccccgagtcg cccgacttcg aggatcaggt ggcggagctg cgcgcgcgcg 300
ccaaggacct gcccgacgag tactttgtgg tgctggtggg ggacatgatc acggaggagg 360
cgctgccgac ctacatggcc atgctcaaca cgctggacgg cgtgcgcgac gacacgggcg 420
cggccgacca cccgtgggcg cgctggacgc ggcagtgggt ggccgaggag aaccggcacg 480
gcgacctgct gaacaagtac tgctggctga cggggcgcgt caacatgcgg gccgtggagg 540
tgaccatcaa caacctgatc aagagcggca tgaacccgca gacggacaac aacccttatt 600
tggggttcgt ctacacctcc ttccaggagc gcgccaccaa gtaggtaccc tttcttgcgc 660
tatgacactt ccagcaaaag gtagggcggg ctgcgagacg gcttcccggc gctgcatgca 720
acaccgatga tgcttcgacc ccccgaagct ccttcggggc tgcatgggcg ctccgatgcc 780
gctccagggc gagcgctgtt taaatagcca ggcccccgat tgcaaagaca ttatagcgag 840
ctaccaaagc catattcaaa cacctagatc actaccactt ctacacaggc cactcgagct 900
tgtgatcgca ctccgctaag gggcgcctc ttcctcttcg tttcagtcac aacccgcaaa 960
cggcgcgcca tgctgctgca ggccttcctg ttcctgctgg ccggcttcgc cgccaagatc 1020
agcgcctcca tgacgaacga gacgtccgac cgcccctgg tgcacttcac ccccaacaag 1080
ggctggatga acgaccccaa cggcctgtgg tacgacgaga aggacgccaa gtggcacctg 1140
tacttccagt acaacccgaa cgacaccgtc tgggggacgc ccttgttctg ggccacgcc 1200 acgtccgacg acctgaccaa ctgggaggac cagcccatcg ccatcgcccc gaagcgcaac 1260
gactccggcg ccttctccgg ctccatggtg gtggactaca acaacacctc cggcttcttc 1320
aacgacacca tcgacccgcg ccagcgctgc gtggccatct ggacctacaa cacccggag 1380 tccgaggagc agtacatctc ctacagcctg gacggcggct acaccttcac cgagtaccag 1440
aagaaccccg tgctggccgc caactccacc cagttccgcg acccgaaggt cttctggtac 1500
gagccctccc agaagtggat catgaccgcg gccaagtccc aggactacaa gatcgagatc 1560
tactcctccg acgacctgaa gtcctggaag ctggagtccg cgttcgccaa cgagggcttc 1620
ctcggctacc agtacgagtg ccccggcctg atcgaggtcc ccaccgagca ggaccccagc 1680
aagtcctact gggtgatgtt catctccatc aaccccggcg ccccggccgg cggctccttc 1740
aaccagtact tcgtcggcag cttcaacggc acccacttcg aggccttcga caaccagtcc 1800
cgcgtggtgg acttcggcaa ggactactac gccctgcaga ccttcttcaa caccgacccg 1860
acctacggga gcgccctggg catcgcgtgg gcctccaact gggagtactc cgccttcgtg 1920
cccaccaacc cctggcgctc ctccatgtcc ctcgtgcgca agttctccct caacaccgag 1980
taccaggcca acccggagac ggagctgatc aacctgaagg ccgagccgat cctgaacatc 2040
agcaacgccg gcccctggag ccggttcgcc accaacacca cgttgacgaa ggccaacagc 2100
tacaacgtcg acctgtccaa cagcaccggc accctggagt tcgagctggt gtacgccgtc 2160
aacaccaccc agacgatctc caagtccgtg ttcgcggacc tctccctctg gttcaagggc 2220
ctggaggacc ccgaggagta cctccgcatg ggcttcgagg tgtccgcgtc ctccttcttc 2280
ctggaccgcg ggaacagcaa ggtgaagttc gtgaaggaga acccctactt caccaaccgc 2340
atgagcgtga acaaccagcc cttcaagagc gagaacgacc tgtcctacta caaggtgtac 2400
ggcttgctgg accagaacat cctggagctg tacttcaacg acggcgacgt cgtgtccacc 2460
aacacctact tcatgaccac cgggaacgcc ctgggctccg tgaacatgac gacgggggtg 2520
gacaacctgt tctacatcga caagttccag gtgcgcgagg tcaagtgaca attggcagca 2580
gcagctcgga tagtatcgac acactctgga cgctggtcgt gtgatggact gttgccgcca 2640
cacttgctgc cttgacctgt gaatatccct gccgctttta tcaaacagcc tcagtgtgtt 2700
tgatcttgtg tgtacgcgct tttgcgagtt gctagctgct tgtgctattt gcgaatacca 2760
cccccagcat ccccttccct cgtttcatat cgcttgcatc ccaaccgcaa cttatctacg 2820
ctgtcctgct atccctcagc gctgctcctg ctcctgctca ctgcccctcg cacagccttg 2880
gtttgggctc cgcctgtatt ctcctggtac tgcaacctgt aaaccagcac tgcaatgctg 2940
atgcacggga agtagtggga tgggaacaca aatggaggat cccgcgtctc gaacagagcg 3000
cgcagaggaa cgctgaaggt ctcgcctctg tcgcacctca gcgcggcata caccacaata 3060
accacctgac gaatgcgctt ggttcttcgt ccattagcga agcgtccggt tcacacacgt 3120
gccacgttgg cgaggtggca ggtgacaatg atcggtggag ctgatggtcg aaacgttcac 3180
agcctaggga tatcgaattc ctttcttgcg ctatgacact tccagcaaaa ggtagggcgg 3240
gctgcgagac ggcttcccgg cgctgcatgc aacaccgatg atgcttcgac cccccgaagc 3300
tccttcgggg ctgcatgggc gctccgatgc cgctccaggg cgagcgctgt ttaaatagcc 3360
aggcccccga ttgcaaagac attatagcga gctaccaaag ccatattcaa acacctagat 3420
cactaccact tctacacagg ccactcgagc ttgtgatcgc actccgctaa gggggcgcct 3480
cttcctcttc gtttcagtca caacccgcaa acactagtgc gctggacgcg gcagtgggtg 3540
gccgaggaga accggcacgg cgacctgctg aacaagtact gttggctgac ggggcgcgtc 3600
aacatgcggg ccgtggaggt gaccatcaac aacctgatca agagcggcat gaacccgcag 3660
acggacaaca acccttactt gggcttcgtc tacacctcct tccaggagcg cgcgaccaag 3720
tacagccacg gcaacaccgc gcgccttgcg gccgagcagt gtgtttgagg gttttggttg 3780

```
cccgtatcga ggtcctggtg gcgcgcatgg gggagaaggc gcctgtcccg ctgacccccc   3840

cggctaccct cccggcacct tccagggcgc gtacgggatc ctgctcggcc gcaaggcgcg   3900

cggtgttgcc gtggctgtac ttggtcgcgc gctcctggaa ggaggtgtag acgaagccca   3960

agtaagggtt gttgtccgtc tgcgggttca tgccgctctt gatcaggttg ttgatggtca   4020

cctccacggc ccgcatgttg acgcgccccg tcagccaaca gtacttgttc agcaggtcgc   4080

cgtgccggtt ctcctcggcc acccactgcc gcgtccagcg caagcttgca gcagcagctc   4140

ggatagtatc gacacactct ggacgctggt cgtgtgatgg actgttgccg ccacacttgc   4200

tgccttgacc tgtgaatatc cctgccgctt ttatcaaaca gcctcagtgt gtttgatctt   4260

gtgtgtacgc gcttttgcga gttgctagct gcttgtgcta tttgcgaata ccaccccccag  4320

catcccettc cctcgtttca tatcgcttgc atcccaaccg caacttatct acgctgtcct   4380

gctatccctc agcgctgctc ctgctcctgc tcactgcccc tcgcacagcc ttggtttggg   4440

ctccgcctgt attctcctgg tactgcaacc tgtaaaccag cactgcaatg ctgatgcacg   4500

ggaagtagtg ggatgggaac acaaatggaa agctggagct ccagccacgg caacaccgcg   4560

cgccttgcgg ccgagcacgg cgacaagaac ctgagcaaga tctgcgggct gatcgccagc   4620

gacgagggcc ggcacgagat cgcctacacg cgcatcgtgg acgagttctt ccgcctcgac   4680

cccgagggcg ccgtcgccgc ctacgccaac atgatgcgca agcagatcac catgcccgcg   4740

cacctcatgg acgacatggg ccacggcgag gccaacccgg gccgcaacct cttcgccgac   4800

ttctccgcgg tcgccgagaa gatcgacgtc tacgacgccg aggactactg ccgcatcctg   4860

gagcacctca acgcgcgctg gaaggtggac gagcgccagg tcagcggcca ggccgccgcg   4920

gaccaggagt acgtcctggg cctgccccag cgcttccgga aactcgccga gaagaccgcc   4980

gccaagcgca agcgcgtcgc gcgcaggccc gtcgccttct cctggatctc cgggcgcgag   5040

atcatggtct agggagcgac gagtgtgcgt gcggggctgg cgggagtggg acgccctcct   5100

cgctcctctc tgttctgaac ggaacaatcg gccaccccgc gctacgcgcc acgcatcgag   5160

caacgaagaa aacccccccga tgataggttg cggtggctgc cgggatatag atccggccgc  5220

acatcaaagg gcccctccgc cagagaagaa gctcctttcc cagcagactc ctgaagagc    5279
```

<210> SEQ ID NO 95
<211> LENGTH: 6580
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 95

```
gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120

tgcgccggct gagccactgc ttcgtccggg cggccaagag gagcatgagg gaggactcct    180

ggtccagggt cctgacgtgg tcgcggctct gggagcgggc cagcatcatc tggctctgcc    240

gcaccgaggc cgcctccaac tggtcctcca gcagccgcag tcgccgccga ccctggcaga    300

ggaagacagg tgaggggtgt atgaattgta cagaacaacc acgagccttg tctaggcaga    360

atccctacca gtcatggctt tacctggatg acggcctgcg aacagctgtc cagcgaccct    420

cgctgccgcc gcttctcccg cacgcttctt tccagcaccg tgatggcgcg agccagcgcc    480

gcacgctggc gctgcgcttc gccgatctga ggacagtcgg ggaactctga tcagtctaaa    540
```

-continued

```
ccccccttgcg cgttagtgtt gccatccttt gcagaccggt gagagccgac ttgttgtgcg    600
ccaccccccca caccacctcc tcccagacca attctgtcac ctttttggcg aaggcatcgg    660
cctcggcctg cagagaggac agcagtgccc agccgctggg ggttggcgga tgcacgctca    720
ggtacccttt cttgcgctat gacacttcca gcaaaaggta gggcgggctg cgagacggct    780
tcccggcgct gcatgcaaca ccgatgatgc ttcgaccccc cgaagctcct tcggggctgc    840
atgggcgctc cgatgccgct ccagggcgag cgctgtttaa atagccaggc ccccgattgc    900
aaagacatta tagcgagcta ccaaagccat attcaaacac ctagatcact accacttcta    960
cacaggccac tcgagcttgt gatcgcactc cgctaagggg gcgcctcttc ctcttcgttt   1020
cagtcacaac ccgcaaactc tagaatatca atgatcgagc aggacggcct ccacgccggc   1080
tcccccgccg cctgggtgga gcgcctgttc ggctacgact gggcccagca gaccatcggc   1140
tgctccgacg ccgccgtgtt ccgcctgtcc gcccagggcc gccccgtgct gttcgtgaag   1200
accgacctgt ccggcgccct gaacgagctg caggacgagg ccgcccgcct gtcctggctg   1260
gccaccaccg gcgtgccctg cgccgccgtg ctggacgtgg tgaccgaggc cggccgcgac   1320
tggctgctgc tgggcgaggt gcccggccag gacctgctgt cctcccacct ggcccccgcc   1380
gagaaggtgt ccatcatggc cgacgccatg cgccgcctgc acaccctgga ccccgccacc   1440
tgccccttcg accaccaggc caagcaccgc atcgagcgcg cccgcacccg catggaggcc   1500
ggcctggtgg accaggacga cctggacgag gagcaccagg gcctggcccc cgccgagctg   1560
ttcgcccgcc tgaaggcccg catgcccgac ggcgaggacc tggtggtgac ccacggcgac   1620
gcctgcctgc ccaacatcat ggtggagaac ggccgcttct ccggcttcat cgactgcggc   1680
cgcctgggcg tggccgaccg ctaccaggac atcgccctgg ccacccgcga catcgccgag   1740
gagctgggcg gcgagtgggc cgaccgcttc ctggtgctgt acggcatcgc cgcccccgac   1800
tcccagcgca tcgccttcta ccgcctgctg gacgagttct tctgacaatt ggcagcagca   1860
gctcggatag tatcgacaca ctctggacgc tggtcgtgtg atggactgtt gccgccacac   1920
ttgctgcctt gacctgtgaa tatccctgcc gcttttatca aacagcctca gtgtgtttga   1980
tcttgtgtgt acgcgctttt gcgagttgct agctgcttgt gctatttgcg aataccaccc   2040
ccagcatccc cttccctcgt ttcatatcgc ttgcatccca accgcaactt atctacgctg   2100
tcctgctatc cctcagcgct gctcctgctc ctgctcactg cccctcgcac agccttggtt   2160
tgggctccgc ctgtattctc ctggtactgc aacctgtaaa ccagcactgc aatgctgatg   2220
cacgggaagt agtgggatgg gaacacaaat ggaggatccc gcgtctcgaa cagagcgcgc   2280
agaggaacgc tgaaggtctc gcctctgtcg cacctcagcg cggcatacac cacaataacc   2340
acctgacgaa tgcgcttggt tcttcgtcca ttagcgaagc gtccggttca cacacgtgcc   2400
acgttggcga ggtggcaggt gacaatgatc ggtggagctg atggtcgaaa cgttcacagc   2460
ctagggatat cctgaagaat gggaggcagg tgttgttgat tatgagtgtg taaaagaaag   2520
gggtagagag ccgtcctcag atccgactac tatgcaggta gccgctcgcc catgcccgcc   2580
tggctgaata ttgatgcatg cccatcaagg caggcaggca tttctgtgca cgcaccaagc   2640
ccacaatctt ccacaacaca cagcatgtac caacgcacgc gtaaaagttg gggtgctgcc   2700
agtgcgtcat gccaggcatg atgtgctcct gcacatccgc catgatctcc tccatcgtct   2760
cgggtgtttc cggcgcctgg tccgggagcc gttccgccag atacccagac gccacctccg   2820
acctcacggg gtacttttcg agcgtctgcc ggtagtcgac gatcgcgtcc accatggagt   2880
agccgaggcg ccggaactgg cgtgacggag ggaggagagg gaggagagag aggggggggg   2940
```

-continued

```
ggggggggga tgattacacg ccagtctcac aacgcatgca agacccgttt gattatgagt   3000
acaatcatgc actactagat ggatgagcgc caggcataag gcacaccgac gttgatggca   3060
tgagcaactc ccgcatcata tttcctattg tcctcacgcc aagccggtca ccatccgcat   3120
gctcatatta cagcgcacgc accgcttcgt gatccaccgg gtgaacgtag tcctcgacgg   3180
aaacatctgg ctcgggcctc gtgctggcac tccctcccat gccgacaacc tttctgctgt   3240
caccacgacc cacgatgcaa cgcgacacga cccggtggga ctgatcggtt cactgcacct   3300
gcatgcaatt gtcacaagcg catactccaa tcgtatccgt ttgatttctg tgaaaactcg   3360
ctcgaccgcc cgcgtcccgc aggcagcgat gacgtgtgcg tgacctgggt gtttcgtcga   3420
aaggccagca accccaaatc gcaggcgatc cggagattgg gatctgatcc gagcttggac   3480
cagatccccc acgatgcggc acgggaactg catcgactcg gcgcggaacc cagctttcgt   3540
aaatgccaga ttggtgtccg ataccttgat ttgccatcag cgaaacaaga cttcagcagc   3600
gagcgtattt ggcgggcgtg ctaccagggt tgcatacatt gcccatttct gtctggaccg   3660
ctttaccggc gcagagggtg agttgatggg gttggcaggc atcgaaacgc gcgtgcatgg   3720
tgtgtgtgtc tgttttcggc tgcacaattt caatagtcgg atgggcgacg gtagaattgg   3780
gtgttgcgct cgcgtgcatg cctcgccccg tcgggtgtca tgaccgggac tggaatcccc   3840
cctcgcgacc ctcctgctaa cgctcccgac tctcccgccc gcgcgcagga tagactctag   3900
ttcaaccaat cgacaactag tatgcagacc gcccaccagc gcccccccac cgagggccac   3960
tgcttcggcg cccgcctgcc caccgcctcc cgccgcgccg tgcgccgcgc ctggtcccgc   4020
atcgcccgcg ggcgcgccgc cgccgccgcc gacgccaacc ccgcccgccc cgagcgccgc   4080
gtggtgatca ccggccaggg cgtggtgacc tccctgggcc agaccatcga gcagttctac   4140
tcctccctgc tggagggcgt gtccggcatc tcccagatcc agaagttcga caccaccggc   4200
tacaccacca ccatcgccgg cgagatcaag tccctgcagc tggaccccta cgtgcccaag   4260
cgctgggcca agcgcgtgga cgacgtgatc aagtacgtgt acatcgccgg caagcaggcc   4320
ctggagtccg ccggcctgcc catcgaggcc gccggcctgg ccggcgccgg cctggacccc   4380
gccctgtgcg gcgtgctgat cggcaccgcc atggccggca tgacctcctt cgccgccggc   4440
gtggaggccc tgacccgcgg cggcgtgcgc aagatgaacc ccttctgcat ccccttctcc   4500
atctccaaca tgggcggcgc catgctggcc atggacatcg gcttcatggg ccccaactac   4560
tccatctcca ccgcctgcgc caccggcaac tactgcatcc tgggcgccgc cgaccacatc   4620
cgccgcggcg acgccaacgt gatgctggcc ggcggcgccg acgccgccat catcccctcc   4680
ggcatcggcg gcttcatcgc ctgcaaggcc ctgtccaagc gcaacgacga gcccgagcgc   4740
gcctcccgcc cctgggacgc cgaccgcgac ggcttcgtga tgggcgaggg cgccggcgtg   4800
ctggtgctgg aggagctgga gcacgccaag cgccgcggcg ccaccatcct ggccgagctg   4860
gtgggcggcg ccgccacctc cgacgcccac cacatgaccg agcccgaccc ccagggccgc   4920
ggcgtgcgcc tgtgcctgga gcgcgccctg gagcgcgccc gcctggcccc cgagcgcgtg   4980
ggctacgtga acgcccacgg cacctccacc cccgccggcg acgtggccga gtaccgcgcc   5040
atccgcgccg tgatccccca ggactccctg cgcatcaact ccaccaagtc catgatcggc   5100
cacctgctgg gcggcgccgg cgccgtggag gccgtggccg ccatccaggc cctgcgcacc   5160
ggctggctgc accccaacct gaacctggag aaccccgccc ccggcgtgga ccccgtggtg   5220
ctggtgggcc cccgcaagga gcgcgccgag gacctggacg tggtgctgtc caactccttc   5280
```

ggcttcggcg gccacaactc ctgcgtgatc ttccgcaagt acgacgagat ggactacaag 5340
gaccacgacg gcgactacaa ggaccacgac atcgactaca aggacgacga cgacaagtga 5400
atcgatagat ctcttaaggc agcagcagct cggatagtat cgacacactc tggacgctgg 5460
tcgtgtgatg gactgttgcc gccacacttg ctgccttgac ctgtgaatat ccctgccgct 5520
tttatcaaac agcctcagtg tgtttgatct tgtgtgtacg cgcttttgcg agttgctagc 5580
tgcttgtgct atttgcgaat accaccccca gcatcccctt ccctcgtttc atatcgcttg 5640
catcccaacc gcaacttatc tacgctgtcc tgctatccct cagcgctgct cctgctcctg 5700
ctcactgccc ctcgcacagc cttggtttgg gctccgcctg tattctcctg gtactgcaac 5760
ctgtaaacca gcactgcaat gctgatgcac gggaagtagt gggatgggaa cacaaatgga 5820
aagcttaatt aagagctctt gttttccaga aggagttgct ccttgagcct ttcattctca 5880
gcctcgataa cctccaaagc cgctctaatt gtggaggggg ttcgaattta aaagcttgga 5940
atgttggttc gtgcgtctgg aacaagccca gacttgttgc tcactgggaa aaggaccatc 6000
agctccaaaa aacttgccgc tcaaaccgcg tacctctgct ttcgcgcaat ctgccctgtt 6060
gaaatcgcca ccacattcat attgtgacgc ttgagcagtc tgtaattgcc tcagaatgtg 6120
gaatcatctg ccccctgtgc gagcccatgc caggcatgtc gcgggcgagg acacccgcca 6180
ctcgtacagc agaccattat gctacctcac aatagttcat aacagtgacc atatttctcg 6240
aagctcccca acgagcacct ccatgctctg agtggccacc ccccggccct ggtgcttgcg 6300
gagggcaggt caaccggcat ggggctaccg aaatccccga ccggatccca ccacccccgc 6360
gatgggaaga atctctcccc gggatgtggg cccaccacca gcacaacctg ctggcccagg 6420
cgagcgtcaa accataccac acaaatatcc ttggcatcgg ccctgaattc cttctgccgc 6480
tctgctaccc ggtgcttctg tccgaagcag gggttgctag ggatcgctcc gagtccgcaa 6540
acccttgtcg cgtggcgggg cttgttcgag cttgaagagc 6580

<210> SEQ ID NO 96
<211> LENGTH: 8087
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 96
gctcttcgga gtcactgtgc cactgagttc gactggtagc tgaatggagt cgctgctcca 60
ctaaacgaat tgtcagcacc gccagccggc cgaggacccg agtcatagcg agggtagtag 120
cgcgccatgg caccgaccag cctgcttgcc agtactggcg tctcttccgc ttctctgtgg 180
tcctctgcgc gctccagcgc gtgcgctttt ccggtggatc atgcggtccg tggcgcaccg 240
cagcggccgc tgcccatgca gcgccgctgc ttccgaacag tggcggtcag ggccgcaccc 300
gcggtagccg tccgtccgga acccgcccaa gagttttggg agcagcttga gccctgcaag 360
atggcggagg acaagcgcat cttcctggag gagcaccggt gcgtggaggt ccggggctga 420
ccggccgtcg cattcaacgt aatcaatcgc atgatgatca gaggacacga agtcttggtg 480
gcggtggcca gaaacactgt ccattgcaag ggcataggga tgcgttcctt cacctctcat 540
ttctcatttc tgaatccctc cctgctcact ctttctcctc ctccttcccg ttcacgcagc 600
attcggggta ccctttcttg cgctatgaca cttccagcaa aaggtagggc gggctgcgag 660
acggcttccc ggcgctgcat gcaacaccga tgatgcttcg accccccgaa gctccttcgg 720
ggctgcatgg gcgctccgat gccgctccag ggcgagcgct gtttaaatag ccaggccccc 780
gattgcaaag acattatagc gagctaccaa agccatattc aaacacctag atcactacca 840
cttctacaca ggccactcga gcttgtgatc gcactccgct aagggggcgc ctcttcctct 900
tcgtttcagt cacaacccgc aaacggcgcg ccatgctgct gcaggccttc ctgttcctgc 960
tggccggctt cgccgccaag atcagcgcct ccatgacgaa cgagacgtcc gaccgccccc 1020
tggtgcactt cacccccaac aagggctgga tgaacgaccc caacggcctg tggtacgacg 1080
agaaggacgc caagtggcac ctgtacttcc agtacaaccc gaacgacacc gtctggggga 1140
cgcccttgtt ctggggccac gccacgtccg acgacctgac caactgggag gaccagccca 1200
tcgccatcgc cccgaagcgc aacgactccg gcgccttctc cggctccatg gtggtggact 1260
acaacaacac ctccggcttc ttcaacgaca ccatcgaccc gcgccagcgc tgcgtggcca 1320
tctggaccta caacaccccg gagtccgagg agcagtacat ctcctacagc ctggacggcg 1380
gctacacctt caccgagtac cagaagaacc ccgtgctggc cgccaactcc acccagttcc 1440
gcgacccgaa ggtcttctgg tacgagccct cccagaagtg gatcatgacc gcggccaagt 1500
cccaggacta caagatcgag atctactcct ccgacgacct gaagtcctgg aagctggagt 1560
ccgcgttcgc caacgagggc ttcctcggct accagtacga gtgccccggc ctgatcgagg 1620
tccccaccga gcaggacccc agcaagtcct actgggtgat gttcatctcc atcaaccccg 1680
gcgccccggc cggcggctcc ttcaaccagt acttcgtcgg cagcttcaac ggcacccact 1740
tcgaggcctt cgacaaccag tcccgcgtgg tggacttcgg caaggactac tacgccctgc 1800
agaccttctt caacaccgac ccgacctacg ggagcgccct gggcatcgcg tgggcctcca 1860
actgggagta ctccgccttc gtgcccacca acccctggcg ctcctccatg tccctcgtgc 1920
gcaagttctc cctcaacacc gagtaccagg ccaacccgga gacggagctg atcaacctga 1980
aggccgagcc gatcctgaac atcagcaacg ccggcccctg gagccggttc gccaccaaca 2040
ccacgttgac gaaggccaac agctacaacg tcgacctgtc caacagcacc ggcaccctgg 2100
agttcgagct ggtgtacgcc gtcaacacca cccagacgat ctccaagtcc gtgttcgcgg 2160
acctctccct ctggttcaag ggcctggagg accccgagga gtacctccgc atgggcttcg 2220
aggtgtccgc gtcctccttc ttcctggacc gcgggaacag caaggtgaag ttcgtgaagg 2280
agaaccccta cttcaccaac cgcatgagcg tgaacaacca gcccttcaag agcgagaacg 2340
acctgtccta ctacaaggtg tacggcttgc tggaccagaa catcctggag ctgtacttca 2400
acgacggcga cgtcgtgtcc accaacacct acttcatgac caccgggaac gccctgggct 2460
ccgtgaacat gacgacgggg gtggacaacc tgttctacat cgacaagttc caggtgcgcg 2520
aggtcaagtg acaattggca gcagcagctc ggatagtatc gacacactct ggacgctggt 2580
cgtgtgatgg actgttgccg ccacacttgc tgccttgacc tgtgaatatc cctgccgctt 2640
ttatcaaaca gcctcagtgt gtttgatctt gtgtgtacgc gcttttgcga gttgctagct 2700
gcttgtgcta tttgcgaata ccacccccag catccccttc cctcgtttca tatcgcttgc 2760
atcccaaccg caacttatct acgctgtcct gctatccctc agcgctgctc ctgctcctgc 2820
tcactgcccc tcgcacagcc ttggtttggg ctccgcctgt attctcctgg tactgcaacc 2880
tgtaaaccag cactgcaatg ctgatgcacg ggaagtagtg ggatgggaac acaaatggag 2940
gatcccgcgt ctcgaacaga gcgcgcagag gaacgctgaa ggtctcgcct ctgtcgcacc 3000
tcagcgcggc atacaccaca ataaccacct gacgaatgcg cttggttctt cgtccattag 3060
cgaagcgtcc ggttcacaca cgtgccacgt tggcgaggtg gcaggtgaca atgatcggtg 3120

-continued gagctgatgg tcgaaacgtt cacagcctag ggatatcgaa ttcggccgac aggacgcgcg 3180
tcaaaggtgc tggtcgtgta tgccctggcc ggcaggtcgt tgctgctgct ggttagtgat 3240
tccgcaaccc tgattttggc gtcttatttt ggcgtggcaa acgctggcgc ccgcgagccg 3300
ggccggcggc gatgcggtgc cccacggctg ccggaatcca agggaggcaa gagcgcccgg 3360
gtcagttgaa gggctttacg cgcaaggtac agccgctcct gcaaggctgc gtggtggaat 3420
tggacgtgca ggtcctgctg aagttcctcc accgcctcac cagcggacaa agcaccggtg 3480
tatcaggtcc gtgtcatcca ctctaaagaa ctcgactacg acctactgat ggccctagat 3540
tcttcatcaa aaacgcctga gacacttgcc caggattgaa actccctgaa gggaccacca 3600
ggggccctga gttgttcctt ccccccgtgg cgagctgcca gccaggctgt acctgtgatc 3660
gaggctggcg ggaaaatagg cttcgtgtgc tcaggtcatg ggaggtgcag gacagctcat 3720
gaaacgccaa caatcgcaca attcatgtca agctaatcag ctatttcctc ttcacgagct 3780
gtaattgtcc caaaattctg gtctaccggg ggtgatcctt cgtgtacggg cccttccctc 3840
aaccctaggt atgcgcgcat gcggtcgccg cgcaactcgc gcgagggccg agggtttggg 3900
acgggccgtc ccgaaatgca gttgcacccg gatgcgtggc accttttttg cgataattta 3960
tgcaatggac tgctctgcaa aattctggct ctgtcgccaa ccctaggatc agcggcgtag 4020
gatttcgtaa tcattcgtcc tgatggggag ctaccgacta ccctaatatc agcccgactg 4080
cctgacgcca gcgtccactt ttgtgcacac attccattcg tgcccaagac atttcattgt 4140
ggtgcgaagc gtccccagtt acgctcacct gtttcccgac ctccttactg ttctgtcgac 4200
agagcgggcc cacaggccgg tcgcagccac tagtatggcc accgcatcca ctttctcggc 4260
gttcaatgcc cgctgcggcg acctgcgtcg ctcggcgggc tccgggcccc ggcgcccagc 4320
gaggcccctc cccgtgcgcg ggcgcgccgc cgccgccgcc gacgccaacc ccgcccgccc 4380
cgagcgccgc gtggtgatca ccggccaggg cgtggtgacc tccctgggcc agaccatcga 4440
gcagttctac tcctccctgc tggagggcgt gtccggcatc tcccagatcc agaagttcga 4500
caccaccggc tacaccacca ccatcgccgg cgagatcaag tccctgcagc tggaccccta 4560
cgtgcccaag cgctgggcca agcgcgtgga cgacgtgatc aagtacgtgt acatcgccgg 4620
caagcaggcc ctggagtccg ccggcctgcc catcgaggcc gccggcctgg ccggcgccgg 4680
cctggacccc gccctgtgcg gcgtgctgat cggcaccgcc atggccggca tgacctcctt 4740
cgccgccggc gtggaggccc tgacccgcgg cggcgtgcgc aagatgaacc ccttctgcat 4800
ccccttctcc atctccaaca tgggcggcgc catgctggcc atggacatcg gcttcatggg 4860
ccccaactac tccatctcca ccgcctgcgc caccggcaac tactgcatcc tgggcgccgc 4920
cgaccacatc cgccgcggcg acgccaacgt gatgctggcc ggcggcgccg acgccgccat 4980
catcccctcc ggcatcggcg gcttcatcgc ctgcaaggcc ctgtccaagc gcaacgacga 5040
gcccgagcgc gcctcccgcc cctgggacgc cgaccgcgac ggcttcgtga tgggcgaggg 5100
cgccggcgtg ctggtgctgg aggagctgga gcacgccaag cgccgcggcg ccaccatcct 5160
ggccgagctg gtgggcggcg ccgccacctc cgacgcccac cacatgaccg agcccgaccc 5220
ccagggccgc ggcgtgcgcc tgtgcctgga gcgcgccctg gagcgcgccc gcctggcccc 5280
cgagcgcgtg ggctacgtga acgcccacgg cacctccacc cccgccggcg acgtggccga 5340
gtaccgcgcc atccgcgccg tgatccccca ggactccctg cgcatcaact ccaccaagtc 5400
catgatcggc cacctgctgg gcggcgccgg cgccgtggag gccgtggccg ccatccaggc 5460

-continued

```
cctgcgcacc ggctggctgc accccaacct gaacctggag aaccccgccc ccggcgtgga   5520
ccccgtggtg ctggtgggcc cccgcaagga gcgcgccgag gacctggacg tggtgctgtc   5580
caactccttc ggcttcggcg gccacaactc ctgcgtgatc ttccgcaagt acgacgagat   5640
ggactacaag gaccacgacg gcgactacaa ggaccacgac atcgactaca aggacgacga   5700
cgacaagtga atcgatagat ctcttaaggc agcagcagct cggatagtat cgacacactc   5760
tggacgctgg tcgtgtgatg gactgttgcc gccacacttg ctgccttgac ctgtgaatat   5820
ccctgccgct tttatcaaac agcctcagtg tgtttgatct tgtgtgtacg cgcttttgcg   5880
agttgctagc tgcttgtgct atttgcgaat accaccccca gcatcccctt ccctcgtttc   5940
atatcgcttg catcccaacc gcaacttatc tacgctgtcc tgctatccct cagcgctgct   6000
cctgctcctg ctcactgccc ctcgcacagc cttggtttgg gctccgcctg tattctcctg   6060
gtactgcaac ctgtaaacca gcactgcaat gctgatgcac gggaagtagt gggatgggaa   6120
cacaaatgga aagcttaatt aagagctcct ttcttgcgct atgacacttc cagcaaaagg   6180
tagggcgggc tgcgagacgg cttcccggcg ctgcatgcaa caccgatgat gcttcgaccc   6240
cccgaagctc cttcggggct gcatgggcgc tccgatgccg ctccagggcg agcgctgttt   6300
aaatagccag gcccccgatt gcaaagacat tatagcgagc taccaaagcc atattcaaac   6360
acctagatca ctaccacttc tacacaggcc actcgagctt gtgatcgcac tccgctaagg   6420
gggcgcctct tcctcttcgt ttcagtcaca acccgcaaac actagtatgg ctatcaagac   6480
gaacaggcag cctgtggaga agcctccgtt cacgatcggg acgctgcgca aggccatccc   6540
cgcgcactgt ttcgagcgct cggcgcttcg tagcagcatg tacctggcct ttgacatcgc   6600
ggtcatgtcc ctgctctacg tcgcgtcgac gtacatcgac cctgcaccgg tgcctacgtg   6660
ggtcaagtac ggcatcatgt ggccgctcta ctggttcttc caggtgtgtt tgagggtttt   6720
ggttgcccgt attgaggtcc tggtggcgcg catggaggag aaggcgcctg tcccgctgac   6780
ccccccggct accctcccgg caccttccag ggcgcgtacg ggaagaacca gtagagcggc   6840
cacatgatgc cgtacttgac ccacgtaggc accggtgcag ggtcgatgta cgtcgacgcg   6900
acgtagagca gggacatgac cgcgatgtca aaggccaggt acatgctgct acgaagcgcc   6960
gagcgctcga aacagtgcgc ggggatggcc ttgcgcagcg tcccgatcgt gaacggaggc   7020
ttctccacag gctgcctgtt cgtcttgata gccatctcga ggcagcagca gctcggatag   7080
tatcgacaca ctctggacgc tggtcgtgtg atggactgtt gccgccacac ttgctgcctt   7140
gacctgtgaa tatccctgcc gcttttatca aacagcctca gtgtgtttga tcttgtgtgt   7200
acgcgctttt gcgagttgct agctgcttgt gctatttgcg aataccaccc ccagcatccc   7260
cttccctcgt ttcatatcgc ttgcatccca accgcaactt atctacgctg tcctgctatc   7320
cctcagcgct gctcctgctc ctgctcactg cccctcgcac agccttggtt tgggctccgc   7380
ctgtattctc ctggtactgc aacctgtaaa ccagcactgc aatgctgatg cacgggaagt   7440
agtgggatgg gaacacaaat ggaaagctgt attgttttcc agaaggagtt gctccttgag   7500
cctttcattc tcagcctcga taacctccaa agccgctcta attgtggagg gggttcgaag   7560
acagggtggt tggctggatg gggaaacgct ggtcgcggga ttcgatcctg ctgcttatat   7620
cctccctgga agcacaccca cgactctgaa gaagaaaacg tgcacacaca caacccaacc   7680
ggccgaatat ttgcttcctt atcccgggtc caagagagac tgcgatgccc ccctcaatca   7740
gcatcctcct ccctgccgct tcaatcttcc ctgcttgcct gcgcccgcgg tgcgccgtct   7800
gcccgcccag tcagtcactc ctgcacaggc cccttgtgcg cagtgctcct gtacccttta   7860
```

ccgctccttc cattctgcga ggccccctat tgaatgtatt cgttgcctgt gtggccaagc 7920
gggctgctgg gcgcgccgcc gtcgggcagt gctcggcgac tttggcggaa gccgattgtt 7980
cttctgtaag ccacgcgctt gctgctttgg gaagagaagg gggggggtac tgaatggatg 8040
aggaggagaa ggaggggtat tggtattatc tgagttgggt gaagagc 8087

<210> SEQ ID NO 97
<211> LENGTH: 4479
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 97
gctcttcggg tcgccgcgct gcctcgcgtc ccctggtggt gcgcgcggtc gccagcgagg 60
ccccgctggg cgttccgccc tcggtgcagc gcccctcccc cgtggtctac tccaagctgg 120
acaagcagca ccgcctgacg cccgagcgcc tggagctggt gcagagcatg ggcagtttg 180 cggaggagag ggtgctgccc gtgctgcacc ccgtggacaa gctgtggcag ccgcaggact 240
ttttgcccga ccccgagtcg cccgacttcg aggatcaggt ggcggagctg cgcgcgcgcg 300
ccaaggacct gcccgacgag tactttgtgg tgctggtggg ggacatgatc acggaggagg 360
cgctgccgac ctacatggcc atgctcaaca cgctggacgg cgtgcgcgac gacacgggcg 420
cggccgacca cccgtgggcg cgctggacgc ggcagtgggt ggccgaggag aaccggcacg 480
gcgacctgct gaacaagtac tgctggctga cggggcgcgt caacatgcgg gccgtggagg 540
tgaccatcaa caacctgatc aagagcggca tgaacccgca gacggacaac aacccttatt 600
tggggttcgt ctacacctcc ttccaggagc gcgccaccaa gtaggtaccc tttcttgcgc 660
tatgacactt ccagcaaaag gtagggcggg ctgcgagacg gcttcccggc gctgcatgca 720
acaccgatga tgcttcgacc ccccgaagct ccttcggggc tgcatgggcg ctccgatgcc 780
gctccagggc gagcgctgtt taaatagcca ggcccccgat tgcaaagaca ttatagcgag 840
ctaccaaagc catattcaaa cacctagatc actaccactt ctacacaggc cactcgagct 900
tgtgatcgca ctccgctaag gggcgcctc ttcctcttcg tttcagtcac aacccgcaaa 960
ctctagaata tcaatgatcg agcaggacgg cctccacgcc ggctcccccg ccgcctgggt 1020
ggagcgcctg ttcggctacg actgggccca gcagaccatc ggctgctccg acgccgccgt 1080
gttccgcctg tccgcccagg gccgccccgt gctgttcgtg aagaccgacc tgtccggcgc 1140
cctgaacgag ctgcaggacg aggccgcccg cctgtcctgg ctggccacca ccggcgtgcc 1200
ctgcgccgcc gtgctggacg tggtgaccga ggccggccgc gactggctgc tgctgggcga 1260
ggtgcccggc caggacctgc tgtcctccca cctggccccc gccgagaagg tgtccatcat 1320
ggccgacgcc atgcgccgcc tgcacaccct ggaccccgcc acctgcccct tcgaccacca 1380
ggccaagcac cgcatcgagc gcgcccgcac ccgcatggag gccggcctgg tggaccagga 1440
cgacctggac gaggagcacc agggcctggc ccccgccgag ctgttcgccc gcctgaaggc 1500
ccgcatgccc gacggcgagg acctggtggt gacccacggc gacgcctgcc tgcccaacat 1560
catggtggag aacggccgct tctccggctt catcgactgc ggccgcctgg gcgtggccga 1620
ccgctaccag gacatcgccc tggccacccg cgacatcgcc gaggagctgg gcggcgagtg 1680
ggccgaccgc ttcctggtgc tgtacggcat cgccgccccc gactcccagc gcatcgcctt 1740
ctaccgcctg ctggacgagt tcttctgaca attggcagca gcagctcgga tagtatcgac 1800

-continued

```
acactctgga cgctggtcgt gtgatggact gttgccgcca cacttgctgc cttgacctgt   1860
gaatatccct gccgctttta tcaaacagcc tcagtgtgtt tgatcttgtg tgtacgcgct   1920
tttgcgagtt gctagctgct tgtgctattt gcgaatacca cccccagcat ccccttccct   1980
cgtttcatat cgcttgcatc ccaaccgcaa cttatctacg ctgtcctgct atccctcagc   2040
gctgctcctg ctcctgctca ctgcccctcg cacagccttg gtttgggctc cgcctgtatt   2100
ctcctggtac tgcaacctgt aaaccagcac tgcaatgctg atgcacggga agtagtggga   2160
tgggaacaca aatggaggat cccgcgtctc gaacagagcg cgcagaggaa cgctgaaggt   2220
ctcgcctctg tcgcacctca gcgcggcata caccacaata accacctgac gaatgcgctt   2280
ggttcttcgt ccattagcga agcgtccggt tcacacacgt gccacgttgg cgaggtggca   2340
ggtgacaatg atcggtggag ctgatggtcg aaacgttcac agcctaggga tatcgaattc   2400
ctttcttgcg ctatgacact tccagcaaaa ggtagggcgg gctgcgagac ggcttcccgg   2460
cgctgcatgc aacaccgatg atgcttcgac cccccgaagc tccttcgggg ctgcatgggc   2520
gctccgatgc cgctccaggg cgagcgctgt ttaaatagcc aggcccccga ttgcaaagac   2580
attatagcga gctaccaaag ccatattcaa acacctagat cactaccact tctacacagg   2640
ccactcgagc ttgtgatcgc actccgctaa gggggcgcct cttcctcttc gtttcagtca   2700
caacccgcaa acactagtgc gctggacgcg gcagtgggtg gccgaggaga accggcacgg   2760
cgacctgctg aacaagtact gttggctgac ggggcgcgtc aacatgcggg ccgtggaggt   2820
gaccatcaac aacctgatca agagcggcat gaacccgcag acggacaaca acccttactt   2880
gggcttcgtc tacacctcct tccaggagcg cgcgaccaag tacagccacg gcaacaccgc   2940
gcgccttgcg gccgagcagt gtgtttgagg gttttggttg cccgtatcga ggtcctggtg   3000
gcgcgcatgg gggagaaggc gcctgtcccg ctgacccccc cggctaccct cccggcacct   3060
tccagggcgc gtacgggatc ctgctcggcc gcaaggcgcg cggtgttgcc gtggctgtac   3120
ttggtcgcgc gctcctggaa ggaggtgtag acgaagccca agtaagggtt gttgtccgtc   3180
tgcgggttca tgccgctctt gatcaggttg ttgatggtca cctccacggc ccgcatgttg   3240
acgcgccccg tcagccaaca gtacttgttc agcaggtcgc cgtgccggtt ctcctcggcc   3300
acccactgcc gcgtccagcg caagcttgca gcagcagctc ggatagtatc gacacactct   3360
ggacgctggt cgtgtgatgg actgttgccg ccacacttgc tgccttgacc tgtgaatatc   3420
cctgccgctt ttatcaaaca gcctcagtgt gtttgatctt gtgtgtacgc gcttttgcga   3480
gttgctagct gcttgtgcta tttgcgaata ccacccccag catccccttc cctcgtttca   3540
tatcgcttgc atcccaaccg caacttatct acgctgtcct gctatccctc agcgctgctc   3600
ctgctcctgc tcactgcccc tcgcacagcc ttggtttggg ctccgcctgt attctcctgg   3660
tactgcaacc tgtaaaccag cactgcaatg ctgatgcacg ggaagtagtg ggatgggaac   3720
acaaatggaa agctggagct ccagccacgg caacaccgcg cgccttgcgg ccgagcacgg   3780
cgacaagaac ctgagcaaga tctgcgggct gatcgccagc gacgagggcc ggcacgagat   3840
cgcctacacg cgcatcgtgg acgagttctt ccgcctcgac cccgagggcg ccgtcgccgc   3900
ctacgccaac atgatgcgca agcagatcac catgcccgcg cacctcatgg acgacatggg   3960
ccacggcgag gccaacccgg gccgcaacct cttcgccgac ttctccgcgg tcgccgagaa   4020
gatcgacgtc tacgacgccg aggactactg ccgcatcctg gagcacctca acgcgcgctg   4080
gaaggtggac gagcgccagg tcagcggcca ggccgccgcg gaccaggagt acgtcctggg   4140
```

cctgccccag cgcttccgga aactcgccga gaagaccgcc gccaagcgca agcgcgtcgc 4200
gcgcaggccc gtcgccttct cctggatctc cgggcgcgag atcatggtct agggagcgac 4260
gagtgtgcgt gcggggctgg cgggagtggg acgccctcct cgctcctctc tgttctgaac 4320
ggaacaatcg gccaccccgc gctacgcgcc acgcatcgag caacgaagaa aacccccga 4380 tgataggttg cggtggctgc cgggatatag atccggccgc acatcaaagg gcccctccgc 4440
cagagaagaa gctcctttcc cagcagactc ctgaagagc 4479

<210> SEQ ID NO 98
<211> LENGTH: 5243
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98
atgcatgccg gtcaccaccc gcatgctcgt actacagcgc acgcaccgct tcgtgatcca 60
ccgggtgaac gtagtcctcg acggaaacat ctggttcggg cctcctgctt gcactcccgc 120
ccatgccgac aacctttctg ctgttaccac gacccacaat gcaacgcgac acgaccgtgt 180
gggactgatc ggttcactgc acctgcatgc aattgtcaca agcgcttact ccaattgtat 240
tcgtttgttt tctgggagca gttgctcgac cgcccgcgtc ccgcaggcag cgatgacgtg 300
tgcgtggcct gggtgtttcg tcgaaaggcc agcaacccta aatcgcaggc gatccggaga 360
ttgggatctg atccgagttt ggaccagatc cgcccccgatg cggcacggga actgcatcga 420
ctcggcgcgg aacccagctt tcgtaaatgc cagattggtg tccgatacct ggatttgcca 480
tcagcgaaac aagacttcag cagcgagcgt atttggcggg cgtgctacca gggttgcata 540
cattgcccat ttctgtctgg accgctttac tggcgcagag ggtgagttga tggggttggc 600
aggcatcgaa acgcgcgtgc atggtgtgcg tgtctgtttt cggctgcacg aattcaatag 660
tcggatgggc gacggtagaa ttgggtgtgg cgctcgcgtg catgcctcgc cccgtcgggt 720
gtcatgaccg ggactggaat ccccccctcgc gaccatcttg ctaacgctcc cgactctccc 780
gactagtgcg ctggacgcgg cagtgggtgg ccgaggagaa ccggcacggc gacctgctga 840
acaagtactg ttggctgacg gggcgcgtca acatgcgggc cgtggaggtg accatcaaca 900
acctgatcaa gagcggcatg aacccgcaga cggacaacaa cccttacttg ggcttcgtct 960
acacctcctt ccaggagcgc gcgaccaagt acagccacgg caacaccgcg cgccttgcgg 1020
ccgagcagtg tgtttgaggg ttttggttgc ccgtatcgag gtcctggtgg cgcgcatggg 1080
ggagaaggcg cctgtcccgc tgaccccccc ggctaccctc ccggcacctt ccagggcgcg 1140
tacgggatcc tgctcggccg caaggcgcgc ggtgttgccg tggctgtact tggtcgcgcg 1200
ctcctggaag gaggtgtaga cgaagcccaa gtaagggttg ttgtccgtct gcgggttcat 1260
gccgctcttg atcaggttgt tgatggtcac ctccacggcc cgcatgttga cgcgccccgt 1320
cagccaacag tacttgttca gcaggtcgcc gtgccggttc tcctcggcca cccactgccg 1380
cgtccagcgc aagcttgcag cagcagctcg gatagtatcg acacactctg gacgctggtc 1440
gtgtgatgga ctgttgccgc cacacttgct gccttgacct gtgaatatcc ctgccgcttt 1500
tatcaaacag cctcagtgtg tttgatcttg tgtgtacgcg cttttgcgag ttgctagctg 1560
cttgtgctat ttgcgaatac cacccccagc atccccttcc ctcgtttcat atcgcttgca 1620
tcccaaccgc aacttatcta cgctgtcctg ctatccctca gcgctgctcc tgctcctgct 1680

-continued cactgcccct cgcacagcct tggtttgggc tccgcctgta ttctcctggt actgcaacct 1740
gtaaaccagc actgcaatgc tgatgcacgg gaagtagtgg gatgggaaca caaatggaaa 1800
gctggagctc aaagatatca acttaattaa ccaaggtacc cgcctgcaac gcaagggcag 1860
ccacagccgc tcccacccgc cgctgaaccg acacgtgctt gggcgcctgc cgcctgcctg 1920
ccgcatgctt gtgctggtga ggctgggcag tgctgccatg ctgattgagg cttggttcat 1980
cgggtggaag cttatgtgtg tgctgggctt gcatgccggg caatgcgcat ggtggcaaga 2040
gggcggcagc acttgctgga gctgccgcgg tgcctccagg tggttcaatc gcggcagcca 2100
gagggatttc agatgatcgc gcgtacaggt tgagcagcag tgtcagcaaa ggtagcagtt 2160
tgccagaatg atcggttcag ctgttaatca atgccagcaa gagaaggggt caagtgcaaa 2220
cacgggcatg ccacagcacg ggcaccgggg agtggaatgg caccaccaag tgtgtgcgag 2280
ccagcatcgc cgcctggctg tttcagctac aacggcagga gtcatccaac gtaaccatga 2340
gctgatcaac actgcaatca tcgggcgggc gtgatgcaag catgcctggc gaagacacat 2400
ggtgtgcgga tgctgccggc tgctgcctgc tgcgcacgcc gttgagttgg cagcaggctc 2460
agccatgcac tggatggcag ctgggctgcc actgcaatgt ggtggatagg atgcaagtgg 2520
agcgaatacc aaaccctctg gctgcttgct gggttgcatg gcatcgcacc atcagcagga 2580
gcgcatgcga agggactggc cccatgcacg ccatgccaaa ccggagcgca ccgagtgtcc 2640
acactgtcac caggcccgca agctttgcag aaccatgctc atggacgcat gtagcgctga 2700
cgtcccttga cggcgctcct ctcgggtgtg ggaaacgcaa tgcagcacag gcagcagagg 2760
cggcggcagc agagcggcgg cagcagcggc gggggccacc cttcttgcgg ggtcgcgccc 2820
cagccagcgg tgatgcgctg atcccaaacg agttcacatt catttgcatg cctggagaag 2880
cgaggctggg gcctttgggc tggtgcagcc cgcaatggaa tgcgggaccg ccaggctagc 2940
agcaaaggcg cctcccctac tccgcatcga tgttccatag tgcattggac tgcatttggg 3000
tggggcggcc ggctgtttct ttcgtgttgc aaaacgcgcc agctcagcaa cctgtcccgt 3060
gggtcccccg tgccgatgaa atcgtgtgca cgccgatcag ctgattgccc ggctcgcgaa 3120
gtaggcgccc tcctttctgc tcgccctctc tccgtcccgc ctctagaata tcaatgatcg 3180
agcaggacgg cctccacgcc ggctcccccg ccgcctgggt ggagcgcctg ttcggctacg 3240
actgggccca gcagaccatc ggctgctccg acgccgccgt gttccgcctg tccgcccagg 3300
gccgccccgt gctgttcgtg aagaccgacc tgtccggcgc cctgaacgag ctgcaggacg 3360
aggccgcccg cctgtcctgg ctggccacca ccggcgtgcc ctgcgccgcc gtgctggacg 3420
tggtgaccga ggccggccgc gactggctgc tgctgggcga ggtgcccggc caggacctgc 3480
tgtcctccca cctggccccc gccgagaagg tgtccatcat ggccgacgcc atgcgccgcc 3540
tgcacaccct ggaccccgcc acctgcccct tcgaccacca ggccaagcac cgcatcgagc 3600
gcgcccgcac ccgcatggag gccggcctgg tggaccagga cgacctggac gaggagcacc 3660
agggcctggc ccccgccgag ctgttcgccc gcctgaaggc ccgcatgccc gacggcgagg 3720
acctggtggt gacccacggc gacgcctgcc tgcccaacat catggtggag aacggccgct 3780
tctccggctt catcgactgc ggccgcctgg gcgtggccga ccgctaccag gacatcgccc 3840
tggccacccg cgacatcgcc gaggagctgg gcggcgagtg ggccgaccgc ttcctggtgc 3900
tgtacggcat cgccgccccc gactcccagc gcatcgcctt ctaccgcctg ctggacgagt 3960
tcttctgaca attggcagca gcagctcgga tagtatcgac acactctgga cgctggtcgt 4020
gtgatggact gttgccgcca cacttgctgc cttgacctgt gaatatccct gccgctttta 4080

```
tcaaacagcc tcagtgtgtt tgatcttgtg tgtacgcgct tttgcgagtt gctagctgct   4140

tgtgctattt gcgaatacca cccccagcat ccccttccct cgtttcatat cgcttgcatc   4200

ccaaccgcaa cttatctacg ctgtcctgct atccctcagc gctgctcctg ctcctgctca   4260

ctgcccctcg cacagccttg gtttgggctc cgcctgtatt ctcctggtac tgcaacctgt   4320

aaaccagcac tgcaatgctg atgcacggga agtagtggga tgggaacaca aatggaggat   4380

cccgcgtctc gaacagagcg cgcagaggaa cgctgaaggt ctcgcctctg tcgcacctca   4440

gcgcggcata caccacaata accacctgac gaatgcgctt ggttcttcgt ccattagcga   4500

agcgtccggt tcacacacgt gccacgttgg cgaggtggca ggtgacaatg atcggtggag   4560

ctgatggtcg aaacgttcac agcctaggga tatcgaattc cgggtcgccg cgctgcctcg   4620

cgtcccctgg tggtgcgcgc ggtcgccagc gaggccccgc tgggcgttcc gccctcggtg   4680

cagcgcccct cccccgtggt ctactccaag ctggacaagc agcaccgcct gacgcccgag   4740

cgcctggagc tggtgcagag catggggcag tttgcggagg agagggtgct gcccgtgctg   4800

caccccgtgg acaagctgtg gcagccgcag gactttttgc ccgaccccga gtcgcccgac   4860

ttcgaggatc aggtggcgga gctgcgcgcg cgcgccaagg acctgcccga cgagtacttt   4920

gtggtgctgg tgggggacat gatcacggag gaggcgctgc cgacctacat ggccatgctc   4980

aacacgctgg acggcgtgcg cgacgacacg ggcgcggccg accacccgtg ggcgcgctgg   5040

acgcggcagt gggtggccga ggagaaccgg cacggcgacc tgctgaacaa gtactgctgg   5100

ctgacggggc gcgtcaacat gcgggccgtg gaggtgacca tcaacaacct gatcaagagc   5160

ggcatgaacc cgcagacgga caacaaccct tatttggggt tcgtctacac ctccttccag   5220

gagcgcgcca ccaagtatct aga                                           5243
```

<210> SEQ ID NO 99
<211> LENGTH: 6804
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120

tgcgccggct gagccactgc ttcgtccggg cggccaagag gagcatgagg gaggactcct    180

ggtccagggt cctgacgtgg tcgcggctct gggagcgggc cagcatcatc tggctctgcc    240

gcaccgaggc cgcctccaac tggtcctcca gcagccgcag tcgccgccga ccctggcaga    300

ggaagacagg tgagggggt atgaattgta cagaacaacc acgagccttg tctaggcaga     360

atccctacca gtcatggctt tacctggatg acggcctgcg aacagctgtc cagcgaccct    420

cgctgccgcc gcttctcccg cacgcttctt tccagcaccg tgatggcgcg agccagcgcc    480

gcacgctggc gctgcgcttc gccgatctga ggacagtcgg ggaactctga tcagtctaaa    540

ccccttgcg cgttagtgtt gccatccttt gcagaccggt gagagccgac ttgttgtgcg     600

ccaccccca caccacctcc tcccagacca attctgtcac ctttttggcg aaggcatcgg     660

cctcggcctg cagagaggac agcagtgccc agccgctggg ggttggcgga tgcacgctca    720

ggtacccttt cttgcgctat gacacttcca gcaaaaggta gggcgggctg cgagacggct    780

tcccggcgct gcatgcaaca ccgatgatgc ttcgaccccc cgaagctcct tcggggctgc    840
```

atgggcgctc cgatgccgct ccagggcgag cgctgtttaa atagccaggc ccccgattgc 900
aaagacatta tagcgagcta ccaaagccat attcaaacac ctagatcact accacttcta 960
cacaggccac tcgagcttgt gatcgcactc cgctaagggg gcgcctcttc ctcttcgttt 1020
cagtcacaac ccgcaaactc tagaatatca atgctgctgc aggccttcct gttcctgctg 1080
gccggcttcg ccgccaagat cagcgcctcc atgacgaacg agacgtccga ccgcccccctg 1140
gtgcacttca cccccaacaa gggctggatg aacgacccca acggcctgtg gtacgacgag 1200
aaggacgcca agtggcacct gtacttccag tacaacccga acgacaccgt ctgggggacg 1260
cccttgttct ggggccacgc cacgtccgac gacctgacca actgggagga ccagcccatc 1320
gccatcgccc cgaagcgcaa cgactccggc gccttctccg gctccatggt ggtggactac 1380
aacaacacct ccggcttctt caacgacacc atcgacccgc gccagcgctg cgtggccatc 1440
tggacctaca acaccccgga gtccgaggag cagtacatct cctacagcct ggacggcggc 1500
tacaccttca ccgagtacca gaagaacccc gtgctggccg ccaactccac ccagttccgc 1560
gacccgaagg tcttctggta cgagccctcc cagaagtgga tcatgaccgc ggccaagtcc 1620
caggactaca agatcgagat ctactcctcc gacgacctga agtcctggaa gctggagtcc 1680
gcgttcgcca acgagggctt cctcggctac cagtacgagt gccccggcct gatcgaggtc 1740
cccaccgagc aggaccccag caagtcctac tgggtgatgt tcatctccat caaccccggc 1800
gccccggccg gcggctcctt caaccagtac ttcgtcggca gcttcaacgg cacccacttc 1860
gaggccttcg acaaccagtc ccgcgtggtg gacttcggca aggactacta cgccctgcag 1920
accttcttca acaccgaccc gacctacggg agcgccctgg gcatcgcgtg ggcctccaac 1980
tgggagtact ccgccttcgt gcccaccaac ccctggcgct cctccatgtc cctcgtgcgc 2040
aagttctccc tcaacaccga gtaccaggcc aacccggaga cggagctgat caacctgaag 2100
gccgagccga tcctgaacat cagcaacgcc ggcccctgga gccggttcgc caccaacacc 2160
acgttgacga aggccaacag ctacaacgtc gacctgtcca acagcaccgg caccctggag 2220
ttcgagctgg tgtacgccgt caacaccacc cagacgatct ccaagtccgt gttcgcggac 2280
ctctccctct ggttcaaggg cctggaggac cccgaggagt acctccgcat gggcttcgag 2340
gtgtccgcgt cctccttctt cctggaccgc gggaacagca aggtgaagtt cgtgaaggag 2400
aacccctact tcaccaaccg catgagcgtg aacaaccagc ccttcaagag cgagaacgac 2460
ctgtcctact acaaggtgta cggcttgctg gaccagaaca tcctggagct gtacttcaac 2520
gacggcgacg tcgtgtccac caacacctac ttcatgacca ccgggaacgc cctgggctcc 2580
gtgaacatga cgacgggggt ggacaacctg ttctacatcg acaagttcca ggtgcgcgag 2640
gtcaagtgac aattggcagc agcagctcgg atagtatcga cacactctgg acgctggtcg 2700
tgtgatggac tgttgccgcc acacttgctg ccttgacctg tgaatatccc tgccgctttt 2760
atcaaacagc ctcagtgtgt ttgatcttgt gtgtacgcgc ttttgcgagt tgctagctgc 2820
ttgtgctatt tgcgaatacc acccccagca tccccttccc tcgtttcata tcgcttgcat 2880
cccaaccgca acttatctac gctgtcctgc tatccctcag cgctgctcct gctcctgctc 2940
actgcccctc gcacagcctt ggtttgggct ccgcctgtat tctcctggta ctgcaacctg 3000
taaaccagca ctgcaatgct gatgcacggg aagtagtggg atgggaacac aaatggagga 3060
tcccgcgtct cgaacagagc gcgcagagga acgctgaagg tctcgcctct gtcgcacctc 3120
agcgcggcat acaccacaat aaccacctga cgaatgcgct tggttcttcg tccattagcg 3180

-continued

```
aagcgtccgg ttcacacacg tgccacgttg gcgaggtggc aggtgacaat gatcggtgga   3240
gctgatggtc gaaacgttca cagcctaggg atatcgaatt cggccgacag gacgcgcgtc   3300
aaaggtgctg gtcgtgtatg ccctggccgg caggtcgttg ctgctgctgg ttagtgattc   3360
cgcaaccctg attttggcgt cttattttgg cgtggcaaac gctggcgccc gcgagccggg   3420
ccggcggcga tgcggtgccc cacggctgcc ggaatccaag ggaggcaaga gcgcccgggt   3480
cagttgaagg gctttacgcg caaggtacag ccgctcctgc aaggctgcgt ggtggaattg   3540
gacgtgcagg tcctgctgaa gttcctccac cgcctcacca gcggacaaag caccggtgta   3600
tcaggtccgt gtcatccact ctaaagaact cgactacgac ctactgatgg ccctagattc   3660
ttcatcaaaa acgcctgaga cacttgccca ggattgaaac tccctgaagg gaccaccagg   3720
ggccctgagt tgttccttcc ccccgtggcg agctgccagc caggctgtac ctgtgatcga   3780
ggctggcggg aaaataggct tcgtgtgctc aggtcatggg aggtgcagga cagctcatga   3840
aacgccaaca atcgcacaat tcatgtcaag ctaatcagct atttcctctt cacgagctgt   3900
aattgtccca aaattctggt ctaccggggg tgatccttcg tgtacgggcc cttccctcaa   3960
ccctaggtat gcgcgcatgc ggtcgccgcg caactcgcgc gagggccgag ggtttgggac   4020
gggccgtccc gaaatgcagt tgcacccgga tgcgtggcac cttttttgcg ataatttatg   4080
caatggactg ctctgcaaaa ttctggctct gtcgccaacc ctaggatcag cggcgtagga   4140
tttcgtaatc attcgtcctg atggggagct accgactacc ctaatatcag cccgactgcc   4200
tgacgccagc gtccactttt gtgcacacat tccattcgtg cccaagacat ttcattgtgg   4260
tgcgaagcgt ccccagttac gctcacctgt ttcccgacct ccttactgtt ctgtcgacag   4320
agcgggccca caggccggtc gcagccacta gtatggccac cgcatccact ttctcggcgt   4380
tcaatgcccg ctgcggcgac ctgcgtcgct cggcgggctc cgggccccgg cgcccagcga   4440
ggcccctccc cgtgcgcggg cgcgccgcca ccctgcgctc cggcctgcgc gacgtggaga   4500
ccgtgaagaa gaccttctcc cccgcccgcg aggtgcacgt gcaggtgacc cactccatgg   4560
ccccccagaa gatcgagatc ttcaaggcca tggaggactg ggccgagaac aacatcctgg   4620
tgcacctgaa gaacgtggag aagtgccccc agccccagga cttcctgccc gaccccgcct   4680
ccgacgagtt ccacgaccag atcaaggagc tgcgcgagcg cgccaaggag atccccgacg   4740
actacttcgt ggtgctggtg ggcgacatga tcaccgagga ggccctgccc acctaccaga   4800
ccatgctgaa cacctgggac ggcgtgcgcg acgagaccgg cgcctccccc acctcctggg   4860
ccatctggac ccgcgcctgg accgccgagg agaaccgcca cggcgacccc ctgaacaagt   4920
acctgtacct gtccggccgc gtggacatga agcagatcga gaagaccatc cagtacctga   4980
tcggctccgg catggacccc cgcaccgaga actcccccta cctgggcttc atctacacct   5040
ccttccagga gcgcgccacc ttcatctccc acggcaacac cgcccgcctg gcccgcgacc   5100
acggcgactt caagctggcc cagatctgcg gcaccatcgc ctccgacgag aagcgccacg   5160
agaccgccta caccaagatc gtggagaagc tgttcgagat cgaccccgac ggcaccgtgc   5220
tggccttcgg cgacatgatg aagaagaaga tctccatgcc cgaccacttc atgtacgacg   5280
gccgcgacga caacctgttc gaccacttct cctccgtggc ccagcgcctg ggcgtgtaca   5340
ccgccaagga ctacgccgac atcctggagc acctggtggg ccgctggaag gtggagaagc   5400
tgaccggcct gtccgccgag ggccagaagg cccaggacta cgtgtgcggc ctgccccccc   5460
gcatccgccg cctggaggag cgcgcccaga tccgcgccaa gcaggccccc cgcctgccct   5520
tctcctggat ctacgaccgc gaggtgcagc tgatggacta caaggaccac gacggcgact   5580
```

acaaggacca cgacatcgac tacaaggacg acgacgacaa gtgaatcgat agatctctta 5640
aggcagcagc agctcggata gtatcgacac actctggacg ctggtcgtgt gatggactgt 5700
tgccgccaca cttgctgcct tgacctgtga atatccctgc cgcttttatc aaacagcctc 5760
agtgtgtttg atcttgtgtg tacgcgcttt tgcgagttgc tagctgcttg tgctatttgc 5820
gaataccacc cccagcatcc ccttccctcg tttcatatcg cttgcatccc aaccgcaact 5880
tatctacgct gtcctgctat ccctcagcgc tgctcctgct cctgctcact gcccctcgca 5940
cagccttggt ttgggctccg cctgtattct cctggtactg caacctgtaa accagcactg 6000
caatgctgat gcacgggaag tagtgggatg ggaacacaaa tggaaagctt aattaagagc 6060
tcttgttttc cagaaggagt tgctccttga gcctttcatt ctcagcctcg ataacctcca 6120
aagccgctct aattgtggag ggggttcgaa tttaaaagct tggaatgttg gttcgtgcgt 6180
ctggaacaag cccagacttg ttgctcactg ggaaaaggac catcagctcc aaaaaacttg 6240
ccgctcaaac cgcgtacctc tgctttcgcg caatctgccc tgttgaaatc gccaccacat 6300
tcatattgtg acgcttgagc agtctgtaat tgcctcagaa tgtggaatca tctgccccct 6360
gtgcgagccc atgccaggca tgtcgcgggc gaggacaccc gccactcgta cagcagacca 6420
ttatgctacc tcacaatagt tcataacagt gaccatattt ctcgaagctc cccaacgagc 6480
acctccatgc tctgagtggc cacccccgg ccctggtgct tgcggagggc aggtcaaccg 6540
gcatggggct accgaaatcc ccgaccggat cccaccaccc ccgcgatggg aagaatctct 6600
ccccgggatg tgggcccacc accagcacaa cctgctggcc caggcgagcg tcaaaccata 6660
ccacacaaat atccttggca tcggccctga attccttctg ccgctctgct acccggtgct 6720
tctgtccgaa gcaggggttg ctagggatcg ctccgagtcc gcaaaccctt gtcgcgtggc 6780
ggggcttgtt cgagcttgaa gagc 6804

<210> SEQ ID NO 100
<211> LENGTH: 6792
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 100
gctcttcgcc gccgccactc ctgctcgagc gcgcccgcgc gtgcgccgcc agcgccttgg 60
ccttttcgcc gcgctcgtgc gcgtcgctga tgtccatcac caggtccatg aggtctgcct 120
tgcgccggct gagccactgc ttcgtccggg cggccaagag gagcatgagg gaggactcct 180
ggtccagggt cctgacgtgg tcgcggctct gggagcgggc cagcatcatc tggctctgcc 240
gcaccgaggc cgcctccaac tggtcctcca gcagccgcag tcgccgccga ccctggcaga 300
ggaagacagg tgaggggggt atgaattgta cagaacaacc acgagccttg tctaggcaga 360
atccctacca gtcatggctt tacctggatg acggcctgcg aacagctgtc cagcgaccct 420
cgctgccgcc gcttctcccg cacgcttctt tccagcaccg tgatggcgcg agccagcgcc 480
gcacgctggc gctgcgcttc gccgatctga ggacagtcgg ggaactctga tcagtctaaa 540 ccccccttgcg cgttagtgtt gccatccttt gcagaccggt gagagccgac ttgttgtgcg 600 ccaccccccca caccacctcc tcccagacca attctgtcac ctttttggcg aaggcatcgg 660
cctcggcctg cagagaggac agcagtgccc agccgctggg ggttggcgga tgcacgctca 720
ggtacccttt cttgcgctat gacacttcca gcaaaaggta gggcgggctg cgagacggct 780

-continued

```
tcccggcgct gcatgcaaca ccgatgatgc ttcgaccccc cgaagctcct tcggggctgc    840
atgggcgctc cgatgccgct ccagggcgag cgctgtttaa atagccaggc ccccgattgc    900
aaagacatta tagcgagcta ccaaagccat attcaaacac ctagatcact accacttcta    960
cacaggccac tcgagcttgt gatcgcactc cgctaagggg gcgcctcttc ctcttcgttt   1020
cagtcacaac ccgcaaactc tagaatatca atgctgctgc aggccttcct gttcctgctg   1080
gccggcttcg ccgccaagat cagcgcctcc atgacgaacg agacgtccga ccgccccctg   1140
gtgcacttca cccccaacaa gggctggatg aacgacccca acggcctgtg gtacgacgag   1200
aaggacgcca agtggcacct gtacttccag tacaacccga acgacaccgt ctgggggacg   1260
cccttgttct ggggccacgc cacgtccgac gacctgacca actgggagga ccagcccatc   1320
gccatcgccc cgaagcgcaa cgactccggc gccttctccg gctccatggt ggtggactac   1380
aacaacacct ccggcttctt caacgacacc atcgacccgc gccagcgctg cgtggccatc   1440
tggacctaca acaccccgga gtccgaggag cagtacatct cctacagcct ggacggcggc   1500
tacaccttca ccgagtacca gaagaacccc gtgctggccg ccaactccac ccagttccgc   1560
gacccgaagg tcttctggta cgagccctcc cagaagtgga tcatgaccgc ggccaagtcc   1620
caggactaca agatcgagat ctactcctcc gacgacctga agtcctggaa gctggagtcc   1680
gcgttcgcca acgagggctt cctcggctac cagtacgagt gccccggcct gatcgaggtc   1740
cccaccgagc aggaccccag caagtcctac tgggtgatgt tcatctccat caaccccggc   1800
gccccggccg gcggctcctt caaccagtac ttcgtcggca gcttcaacgg cacccacttc   1860
gaggccttcg acaaccagtc ccgcgtggtg gacttcggca aggactacta cgccctgcag   1920
accttcttca acaccgaccc gacctacggg agcgccctgg gcatcgcgtg ggcctccaac   1980
tgggagtact ccgccttcgt gcccaccaac ccctggcgct cctccatgtc cctcgtgcgc   2040
aagttctccc tcaacaccga gtaccaggcc aacccggaga cggagctgat caacctgaag   2100
gccgagccga tcctgaacat cagcaacgcc ggcccctgga gccggttcgc caccaacacc   2160
acgttgacga aggccaacag ctacaacgtc gacctgtcca acagcaccgg caccctggag   2220
ttcgagctgg tgtacgccgt caacaccacc cagacgatct ccaagtccgt gttcgcggac   2280
ctctccctct ggttcaaggg cctggaggac cccgaggagt acctccgcat gggcttcgag   2340
gtgtccgcgt cctccttctt cctggaccgc gggaacagca aggtgaagtt cgtgaaggag   2400
aacccctact tcaccaaccg catgagcgtg aacaaccagc ccttcaagag cgagaacgac   2460
ctgtcctact acaaggtgta cggcttgctg gaccagaaca tcctggagct gtacttcaac   2520
gacggcgacg tcgtgtccac caacacctac ttcatgacca ccgggaacgc cctgggctcc   2580
gtgaacatga cgacgggggt ggacaacctg ttctacatcg acaagttcca ggtgcgcgag   2640
gtcaagtgac aattggcagc agcagctcgg atagtatcga cacactctgg acgctggtcg   2700
tgtgatggac tgttgccgcc acacttgctg ccttgacctg tgaatatccc tgccgctttt   2760
atcaaacagc ctcagtgtgt ttgatcttgt gtgtacgcgc ttttgcgagt tgctagctgc   2820
ttgtgctatt tgcgaatacc acccccagca tccccttccc tcgtttcata tcgcttgcat   2880
cccaaccgca acttatctac gctgtcctgc tatccctcag cgctgctcct gctcctgctc   2940
actgcccctc gcacagcctt ggtttgggct ccgcctgtat tctcctggta ctgcaacctg   3000
taaaccagca ctgcaatgct gatgcacggg aagtagtggg atgggaacac aaatggagga   3060
tcccgcgtct cgaacagagc gcgcagagga acgctgaagg tctcgcctct gtcgcacctc   3120
```

-continued

```
agcgcggcat acaccacaat aaccacctga cgaatgcgct tggttcttcg tccattagcg   3180
aagcgtccgg ttcacacacg tgccacgttg gcgaggtggc aggtgacaat gatcggtgga   3240
gctgatggtc gaaacgttca cagcctaggg atatcgaatt cggccgacag gacgcgcgtc   3300
aaaggtgctg gtcgtgtatg ccctggccgg caggtcgttg ctgctgctgg ttagtgattc   3360
cgcaaccctg attttggcgt cttattttgg cgtggcaaac gctggcgccc gcgagccggg   3420
ccggcggcga tgcggtgccc cacggctgcc ggaatccaag ggaggcaaga gcgcccgggt   3480
cagttgaagg gctttacgcg caaggtacag ccgctcctgc aaggctgcgt ggtggaattg   3540
gacgtgcagg tcctgctgaa gttcctccac cgcctcacca gcggacaaag caccggtgta   3600
tcaggtccgt gtcatccact ctaaagaact cgactacgac ctactgatgg ccctagattc   3660
ttcatcaaaa acgcctgaga cacttgccca ggattgaaac tccctgaagg gaccaccagg   3720
ggccctgagt tgttccttcc ccccgtggcg agctgccagc caggctgtac ctgtgatcga   3780
ggctggcggg aaaataggct tcgtgtgctc aggtcatggg aggtgcagga cagctcatga   3840
aacgccaaca atcgcacaat tcatgtcaag ctaatcagct atttcctctt cacgagctgt   3900
aattgtccca aaattctggt ctaccggggg tgatccttcg tgtacgggcc cttccctcaa   3960
ccctaggtat gcgcgcatgc ggtcgccgcg caactcgcgc gagggccgag ggtttgggac   4020
gggccgtccc gaaatgcagt tgcacccgga tgcgtggcac ctttttgcg ataatttatg   4080
caatggactg ctctgcaaaa ttctggctct gtcgccaacc ctaggatcag cggcgtagga   4140
tttcgtaatc attcgtcctg atggggagct accgactacc ctaatatcag cccgactgcc   4200
tgacgccagc gtccactttt gtgcacacat tccattcgtg cccaagacat ttcattgtgg   4260
tgcgaagcgt ccccagttac gctcacctgt ttcccgacct ccttactgtt ctgtcgacag   4320
agcgggccca caggccggtc gcagccacta gtatggccct gaagctgaac gccatcaact   4380
tccagtcccc caagtgctcc tccttcggcc tgccccccgt ggtgtccctg cgctccccca   4440
agctgtccgt ggccgccacc ctgcgctccg gcctgcgcga cgtggagacc gtgaagaaga   4500
ccttctcccc cgcccgcgag gtgcacgtgc aggtgaccca ctccatggcc ccccagaaga   4560
tcgagatctt caaggccatg gaggactggg ccgagaacaa catcctggtg cacctgaaga   4620
acgtggagaa gtgcccccag ccccaggact tcctgcccga ccccgcctcc gacgagttcc   4680
acgaccagat caaggagctg cgcgagcgcg ccaaggagat ccccgacgac tacttcgtgg   4740
tgctggtggg cgacatgatc accgaggagg ccctgcccac ctaccagacc atgctgaaca   4800
cctgggacgg cgtgcgcgac gagaccggcg cctcccccac ctcctgggcc atctggaccc   4860
gcgcctggac cgccgaggag aaccgccacg gcgacccccct gaacaagtac ctgtacctgt   4920
ccggccgcgt ggacatgaag cagatcgaga agaccatcca gtacctgatc ggctccggca   4980
tggacccccg caccgagaac tccccctacc tgggcttcat ctacacctcc ttccaggagc   5040
gcgccacctt catctcccac ggcaacaccg cccgcctggc ccgcgaccac ggcgacttca   5100
agctggccca gatctgcggc accatcgcct ccgacgagaa gcgccacgag accgcctaca   5160
ccaagatcgt ggagaagctg ttcgagatcg accccgacgg caccgtgctg gccttcggcg   5220
acatgatgaa gaagaagatc tccatgcccg accacttcat gtacgacggc cgcgacgaca   5280
acctgttcga ccacttctcc tccgtggccc agcgcctggg cgtgtacacc gccaaggact   5340
acgccgacat cctggagcac ctggtgggcc gctggaaggt ggagaagctg accggcctgt   5400
ccgccgaggg ccagaaggcc caggactacg tgtgcggcct gccccccgc atccgccgcc   5460
tggaggagcg cgcccagatc cgcgccaagc aggcccccg cctgcccttc tcctggatct   5520
```

-continued

```
acgaccgcga ggtgcagctg atggactaca aggaccacga cggcgactac aaggaccacg   5580

acatcgacta caaggacgac gacgacaagt gaatcgatag atctcttaag gcagcagcag   5640

ctcggatagt atcgacacac tctggacgct ggtcgtgtga tggactgttg ccgccacact   5700

tgctgccttg acctgtgaat atccctgccg cttttatcaa acagcctcag tgtgtttgat   5760

cttgtgtgta cgcgcttttg cgagttgcta gctgcttgtg ctatttgcga ataccacccc   5820

cagcatcccc ttccctcgtt tcatatcgct tgcatcccaa ccgcaactta tctacgctgt   5880

cctgctatcc ctcagcgctg ctcctgctcc tgctcactgc ccctcgcaca gccttggttt   5940

gggctccgcc tgtattctcc tggtactgca acctgtaaac cagcactgca atgctgatgc   6000

acgggaagta gtgggatggg aacacaaatg gaaagcttaa ttaagagctc ttgttttcca   6060

gaaggagttg ctccttgagc ctttcattct cagcctcgat aacctccaaa gccgctctaa   6120

ttgtggaggg ggttcgaatt taaaagcttg gaatgttggt tcgtgcgtct ggaacaagcc   6180

cagacttgtt gctcactggg aaaaggacca tcagctccaa aaaacttgcc gctcaaaccg   6240

cgtacctctg ctttcgcgca atctgccctg ttgaaatcgc caccacattc atattgtgac   6300

gcttgagcag tctgtaattg cctcagaatg tggaatcatc tgccccctgt gcgagcccat   6360

gccaggcatg tcgcgggcga ggacacccgc cactcgtaca gcagaccatt atgctacctc   6420

acaatagttc ataacagtga ccatatttct cgaagctccc caacgagcac ctccatgctc   6480

tgagtggcca ccccccggcc ctggtgcttg cggagggcag gtcaaccggc atggggctac   6540

cgaaatcccc gaccggatcc caccaccccc gcgatgggaa gaatctctcc ccgggatgtg   6600

ggcccaccac cagcacaacc tgctggccca ggcgagcgtc aaaccatacc acacaaatat   6660

ccttggcatc ggccctgaat tccttctgcc gctctgctac ccggtgcttc tgtccgaagc   6720

aggggttgct agggatcgct ccgagtccgc aaacccttgt cgcgtggcgg ggcttgttcg   6780

agcttgaaga gc                                                        6792
```

```
<210> SEQ ID NO 101
<211> LENGTH: 6051
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120

tgcgccggct gagccactgc ttcgtccggg cggccaagag gagcatgagg gaggactcct    180

ggtccagggt cctgacgtgg tcgcggctct gggagcgggc cagcatcatc tggctctgcc    240

gcaccgaggc cgcctccaac tggtcctcca gcagccgcag tcgccgccga ccctggcaga    300

ggaagacagg tgagggggt atgaattgta cagaacaacc acgagccttg tctaggcaga    360

atccctacca gtcatggctt tacctggatg acggcctgcg aacagctgtc cagcgaccct    420

cgctgccgcc gcttctcccg cacgcttctt tccagcaccg tgatggcgcg agccagcgcc    480

gcacgctggc gctgcgcttc gccgatctga ggacagtcgg ggaactctga tcagtctaaa    540

ccccccttgcg cgttagtgtt gccatccttt gcagaccggt gagagccgac ttgttgtgcg    600

ccacccccca caccacctcc tcccagacca attctgtcac ctttttggcg aaggcatcgg    660

cctcggcctg cagagaggac agcagtgccc agccgctggg ggttggcgga tgcacgctca    720
```

-continued

```
ggtacccttt cttgcgctat gacacttcca gcaaaaggta gggcgggctg cgagacggct    780
tcccggcgct gcatgcaaca ccgatgatgc ttcgaccccc cgaagctcct tcggggctgc    840
atgggcgctc cgatgccgct ccagggcgag cgctgtttaa atagccaggc ccccgattgc    900
aaagacatta tagcgagcta ccaaagccat attcaaacac ctagatcact accacttcta    960
cacaggccac tcgagcttgt gatcgcactc cgctaagggg gcgcctcttc ctcttcgttt   1020
cagtcacaac ccgcaaactc tagaatatca atgctgctgc aggccttcct gttcctgctg   1080
gccggcttcg ccgccaagat cagcgcctcc atgacgaacg agacgtccga ccgcccccctg   1140
gtgcacttca cccccaacaa gggctggatg aacgacccca acggcctgtg gtacgacgag   1200
aaggacgcca agtggcacct gtacttccag tacaacccga acgacaccgt ctgggggacg   1260
cccttgttct ggggccacgc cacgtccgac gacctgacca actgggagga ccagcccatc   1320
gccatcgccc cgaagcgcaa cgactccggc gccttctccg gctccatggt ggtggactac   1380
aacaacacct ccggcttctt caacgacacc atcgacccgc gccagcgctg cgtggccatc   1440
tggacctaca acaccccgga gtccgaggag cagtacatct cctacagcct ggacggcggc   1500
tacaccttca ccgagtacca gaagaacccc gtgctggccg ccaactccac ccagttccgc   1560
gacccgaagg tcttctggta cgagccctcc cagaagtgga tcatgaccgc ggccaagtcc   1620
caggactaca agatcgagat ctactcctcc gacgacctga agtcctggaa gctggagtcc   1680
gcgttcgcca acgagggctt cctcggctac cagtacgagt gccccggcct gatcgaggtc   1740
cccaccgagc aggaccccag caagtcctac tgggtgatgt tcatctccat caaccccggc   1800
gccccggccg gcggctcctt caaccagtac ttcgtcggca gcttcaacgg cacccacttc   1860
gaggccttcg acaaccagtc ccgcgtggtg gacttcggca aggactacta cgccctgcag   1920
accttcttca acaccgaccc gacctacggg agcgccctgg gcatcgcgtg ggcctccaac   1980
tgggagtact ccgccttcgt gcccaccaac ccctggcgct cctccatgtc cctcgtgcgc   2040
aagttctccc tcaacaccga gtaccaggcc aacccggaga cggagctgat caacctgaag   2100
gccgagccga tcctgaacat cagcaacgcc ggcccctgga gccggttcgc caccaacacc   2160
acgttgacga aggccaacag ctacaacgtc gacctgtcca acagcaccgg caccctggag   2220
ttcgagctgg tgtacgccgt caacaccacc cagacgatct ccaagtccgt gttcgcggac   2280
ctctccctct ggttcaaggg cctggaggac cccgaggagt acctccgcat gggcttcgag   2340
gtgtccgcgt cctccttctt cctggaccgc gggaacagca aggtgaagtt cgtgaaggag   2400
aacccctact tcaccaaccg catgagcgtg aacaaccagc ccttcaagag cgagaacgac   2460
ctgtcctact acaaggtgta cggcttgctg gaccagaaca tcctggagct gtacttcaac   2520
gacggcgacg tcgtgtccac caacacctac ttcatgacca ccgggaacgc cctgggctcc   2580
gtgaacatga cgacgggggt ggacaacctg ttctacatcg acaagttcca ggtgcgcgag   2640
gtcaagtgac aattggcagc agcagctcgg atagtatcga cacactctgg acgctggtcg   2700
tgtgatggac tgttgccgcc acacttgctg ccttgacctg tgaatatccc tgccgctttt   2760
atcaaacagc ctcagtgtgt ttgatcttgt gtgtacgcgc ttttgcgagt tgctagctgc   2820
ttgtgctatt tgcgaatacc acccccagca tccccttccc tcgtttcata tcgcttgcat   2880
cccaaccgca acttatctac gctgtcctgc tatccctcag cgctgctcct gctcctgctc   2940
actgcccctc gcacagcctt ggtttgggct ccgcctgtat tctcctggta ctgcaacctg   3000
taaaccagca ctgcaatgct gatgcacggg aagtagtggg atgggaacac aaatggagga   3060
```

-continued

```
tcccgcgtct cgaacagagc gcgcagagga acgctgaagg tctcgcctct gtcgcacctc   3120
agcgcggcat acaccacaat aaccacctga cgaatgcgct tggttcttcg tccattagcg   3180
aagcgtccgg ttcacacacg tgccacgttg gcgaggtggc aggtgacaat gatcggtgga   3240
gctgatggtc gaaacgttca cagcctaggg atatcgaatt cctttcttgc gctatgacac   3300
ttccagcaaa aggtagggcg ggctgcgaga cggcttcccg gcgctgcatg caacaccgat   3360
gatgcttcga cccccgaag ctccttcggg gctgcatggg cgctccgatg ccgctccagg   3420
gcgagcgctg tttaaatagc caggcccccg attgcaaaga cattatagcg agctaccaaa   3480
gccatattca aacacctaga tcactaccac ttctacacag gccactcgag cttgtgatcg   3540
cactccgcta agggggcgcc tcttcctctt cgtttcagtc acaacccgca aacactagta   3600
tggccaccgc atccactttc tcggcgttca atgcccgctg cggcgacctg cgtcgctcgg   3660
cgggctccgg gccccggcgc ccagcgaggc ccctccccgt gcgcgggcgc gccgccaccc   3720
tgcgctccgg cctgcgcgac gtggagaccg tgaagaagac cttctccccc gcccgcgagg   3780
tgcacgtgca ggtgacccac tccatggccc cccagaagat cgagatcttc aaggccatgg   3840
aggactgggc cgagaacaac atcctggtgc acctgaagaa cgtggagaag tgcccccagc   3900
cccaggactt cctgcccgac cccgcctccg acgagttcca cgaccagatc aaggagctgc   3960
gcgagcgcgc caaggagatc cccgacgact acttcgtggt gctggtgggc gacatgatca   4020
ccgaggaggc cctgcccacc taccagacca tgctgaacac ctgggacggc gtgcgcgacg   4080
agaccggcgc ctcccccacc tcctgggcca tctggacccg cgcctggacc gccgaggaga   4140
accgccacgg cgacccccctg aacaagtacc tgtacctgtc cggccgcgtg gacatgaagc   4200
agatcgagaa gaccatccag tacctgatcg gctccggcat ggacccccgc accgagaact   4260
cccccctacct gggcttcatc tacacctcct tccaggagcg cgccaccttc atctcccacg   4320
gcaacaccgc ccgcctggcc cgcgaccacg gcgacttcaa gctggcccag atctgcggca   4380
ccatcgcctc cgacgagaag cgccacgaga ccgcctacac caagatcgtg gagaagctgt   4440
tcgagatcga ccccgacggc accgtgctgg ccttcggcga catgatgaag aagaagatct   4500
ccatgcccga ccacttcatg tacgacggcc gcgacgacaa cctgttcgac cacttctcct   4560
ccgtggccca gcgcctgggc gtgtacaccg ccaaggacta cgccgacatc ctggagcacc   4620
tggtgggccg ctggaaggtg gagaagctga ccggcctgtc cgccgagggc cagaaggccc   4680
aggactacgt gtgcggcctg ccccccgca tccgccgcct ggaggagcgc gcccagatcc   4740
gcgccaagca ggcccccgc ctgcccttct cctggatcta cgaccgcgag gtgcagctga   4800
tggactacaa ggaccacgac ggcgactaca aggaccacga catcgactac aaggacgacg   4860
acgacaagtg aatcgataga tctcttaagg cagcagcagc tcggatagta tcgacacact   4920
ctggacgctg gtcgtgtgat ggactgttgc cgccacactt gctgccttga cctgtgaata   4980
tccctgccgc ttttatcaaa cagcctcagt gtgtttgatc ttgtgtgtac gcgcttttgc   5040
gagttgctag ctgcttgtgc tatttgcgaa taccaccccc agcatcccct tccctcgttt   5100
catatcgctt gcatcccaac cgcaacttat ctacgctgtc ctgctatccc tcagcgctgc   5160
tcctgctcct gctcactgcc cctcgcacag ccttggtttg ggctccgcct gtattctcct   5220
ggtactgcaa cctgtaaacc agcactgcaa tgctgatgca cgggaagtag tgggatggga   5280
acacaaatgg aaagcttaat taagagctct tgttttccag aaggagttgc tccttgagcc   5340
tttcattctc agcctcgata acctccaaag ccgctctaat tgtggagggg gttcgaattt   5400
aaaagcttgg aatgttggtt cgtgcgtctg gaacaagccc agacttgttg ctcactggga   5460
```

```
aaaggaccat cagctccaaa aaacttgccg ctcaaaccgc gtacctctgc tttcgcgcaa   5520

tctgccctgt tgaaatcgcc accacattca tattgtgacg cttgagcagt ctgtaattgc   5580

ctcagaatgt ggaatcatct gccccctgtg cgagcccatg ccaggcatgt cgcgggcgag   5640

gacacccgcc actcgtacag cagaccatta tgctacctca caatagttca taacagtgac   5700

catatttctc gaagctcccc aacgagcacc tccatgctct gagtggccac cccccggccc   5760

tggtgcttgc ggagggcagg tcaaccggca tggggctacc gaaatccccg accggatccc   5820

accacccccg cgatgggaag aatctctccc cgggatgtgg gcccaccacc agcacaacct   5880

gctggcccag gcgagcgtca aaccatacca cacaaatatc cttggcatcg gccctgaatt   5940

ccttctgccg ctctgctacc cggtgcttct gtccgaagca ggggttgcta gggatcgctc   6000

cgagtccgca aacccttgtc gcgtggcggg gcttgttcga gcttgaagag c            6051
```

<210> SEQ ID NO 102
<211> LENGTH: 7041
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

```
gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120

tgcgccggct gagccactgc ttcgtccggg cggccaagag gagcatgagg gaggactcct    180

ggtccagggt cctgacgtgg tcgcggctct gggagcgggc cagcatcatc tggctctgcc    240

gcaccgaggc cgcctccaac tggtcctcca gcagccgcag tcgccgccga ccctggcaga    300

ggaagacagg tgagggggt atgaattgta cagaacaacc acgagccttg tctaggcaga    360

atccctacca gtcatggctt tacctggatg acggcctgcg aacagctgtc cagcgaccct    420

cgctgccgcc gcttctcccg cacgcttctt tccagcaccg tgatggcgcg agccagcgcc    480

gcacgctggc gctgcgcttc gccgatctga ggacagtcgg ggaactctga tcagtctaaa    540

ccccccttgcg cgttagtgtt gccatccttt gcagaccggt gagagccgac ttgttgtgcg    600

ccaccccccca caccacctcc tcccagacca attctgtcac ctttttggcg aaggcatcgg    660

cctcggcctg cagagaggac agcagtgccc agccgctggg ggttggcgga tgcacgctca    720

ggtacccttt cttgcgctat gacacttcca gcaaaaggta gggcgggctg cgagacggct    780

tcccggcgct gcatgcaaca ccgatgatgc ttcgaccccc cgaagctcct tcggggctgc    840

atgggcgctc cgatgccgct ccagggcgag cgctgtttaa atagccaggc ccccgattgc    900

aaagacatta tagcgagcta ccaaagccat attcaaacac ctagatcact accacttcta    960

cacaggccac tcgagcttgt gatcgcactc cgctaagggg gcgcctcttc ctcttcgttt   1020

cagtcacaac ccgcaaactc tagaatatca atgctgctgc aggccttcct gttcctgctg   1080

gccggcttcg ccgccaagat cagcgcctcc atgacgaacg agacgtccga ccgccccctg   1140

gtgcacttca cccccaacaa gggctggatg aacgacccca acggcctgtg gtacgacgag   1200

aaggacgcca agtggcacct gtacttccag tacaacccga acgacaccgt ctgggggacg   1260

cccttgttct ggggccacgc cacgtccgac gacctgacca actgggagga ccagcccatc   1320

gccatcgccc cgaagcgcaa cgactccggc gccttctccg gctccatggt ggtggactac   1380

aacaacacct ccggcttctt caacgacacc atcgacccgc gccagcgctg cgtggccatc   1440
```

tggacctaca acaccccgga gtccgaggag cagtacatct cctacagcct ggacggcggc 1500
tacaccttca ccgagtacca gaagaacccc gtgctggccg ccaactccac ccagttccgc 1560
gacccgaagg tcttctggta cgagccctcc cagaagtgga tcatgaccgc ggccaagtcc 1620
caggactaca agatcgagat ctactcctcc gacgacctga agtcctggaa gctggagtcc 1680
gcgttcgcca acgagggctt cctcggctac cagtacgagt gccccggcct gatcgaggtc 1740
cccaccgagc aggaccccag caagtcctac tgggtgatgt tcatctccat caaccccggc 1800
gccccggccg gcggctcctt caaccagtac ttcgtcggca gcttcaacgg cacccacttc 1860
gaggccttcg acaaccagtc ccgcgtggtg gacttcggca aggactacta cgccctgcag 1920
accttcttca acaccgaccc gacctacggg agcgccctgg gcatcgcgtg ggcctccaac 1980
tgggagtact ccgccttcgt gcccaccaac ccctggcgct cctccatgtc cctcgtgcgc 2040
aagttctccc tcaacaccga gtaccaggcc aacccggaga cggagctgat caacctgaag 2100
gccgagccga tcctgaacat cagcaacgcc ggcccctgga gccggttcgc caccaacacc 2160
acgttgacga aggccaacag ctacaacgtc gacctgtcca acagcaccgg caccctggag 2220
ttcgagctgg tgtacgccgt caacaccacc cagacgatct ccaagtccgt gttcgcggac 2280
ctctccctct ggttcaaggg cctggaggac cccgaggagt acctccgcat gggcttcgag 2340
gtgtccgcgt cctccttctt cctggaccgc gggaacagca aggtgaagtt cgtgaaggag 2400
aacccctact tcaccaaccg catgagcgtg aacaaccagc ccttcaagag cgagaacgac 2460
ctgtcctact acaaggtgta cggcttgctg gaccagaaca tcctggagct gtacttcaac 2520
gacggcgacg tcgtgtccac caacacctac ttcatgacca ccgggaacgc cctgggctcc 2580
gtgaacatga cgacgggggt ggacaacctg ttctacatcg acaagttcca ggtgcgcgag 2640
gtcaagtgac aattggcagc agcagctcgg atagtatcga cacactctgg acgctggtcg 2700
tgtgatggac tgttgccgcc acacttgctg ccttgacctg tgaatatccc tgccgctttt 2760
atcaaacagc ctcagtgtgt ttgatcttgt gtgtacgcgc ttttgcgagt tgctagctgc 2820
ttgtgctatt tgcgaatacc acccccagca tccccttccc tcgtttcata tcgcttgcat 2880
cccaaccgca acttatctac gctgtcctgc tatccctcag cgctgctcct gctcctgctc 2940
actgcccctc gcacagcctt ggtttgggct ccgcctgtat tctcctggta ctgcaacctg 3000
taaaccagca ctgcaatgct gatgcacggg aagtagtggg atgggaacac aaatggagga 3060
tcccgcgtct cgaacagagc gcgcagagga acgctgaagg tctcgcctct gtcgcacctc 3120
agcgcggcat acaccacaat aaccacctga cgaatgcgct tggttcttcg tccattagcg 3180
aagcgtccgg ttcacacacg tgccacgttg gcgaggtggc aggtgacaat gatcggtgga 3240
gctgatggtc gaaacgttca cagcctaggg atatcgaatt cggccgacag gacgcgcgtc 3300
aaaggtgctg gtcgtgtatg ccctggccgg caggtcgttg ctgctgctgg ttagtgattc 3360
cgcaaccctg attttggcgt cttattttgg cgtggcaaac gctggcgccc gcgagccggg 3420
ccggcggcga tgcggtgccc cacggctgcc ggaatccaag ggaggcaaga gcgcccgggt 3480
cagttgaagg gctttacgcg caaggtacag ccgctcctgc aaggctgcgt ggtggaattg 3540
gacgtgcagg tcctgctgaa gttcctccac cgcctcacca gcggacaaag caccggtgta 3600
tcaggtccgt gtcatccact ctaaagaact cgactacgac ctactgatgg ccctagattc 3660
ttcatcaaaa acgcctgaga cacttgccca ggattgaaac tccctgaagg gaccaccagg 3720
ggccctgagt tgttccttcc ccccgtggcg agctgccagc caggctgtac ctgtgatcga 3780

-continued ggctggcggg aaaataggct tcgtgtgctc aggtcatggg aggtgcagga cagctcatga 3840
aacgccaaca atcgcacaat tcatgtcaag ctaatcagct atttcctctt cacgagctgt 3900
aattgtccca aaattctggt ctaccggggg tgatccttcg tgtacgggcc cttccctcaa 3960
ccctaggtat gcgcgcatgc ggtcgccgcg caactcgcgc gagggccgag ggtttgggac 4020
gggccgtccc gaaatgcagt tgcacccgga tgcgtggcac ctttttgcg ataatttatg 4080 caatggactg ctctgcaaaa ttctggctct gtcgccaacc ctaggatcag cggcgtagga 4140
tttcgtaatc attcgtcctg atggggagct accgactacc ctaatatcag cccgactgcc 4200
tgacgccagc gtccactttt gtgcacacat tccattcgtg cccaagacat ttcattgtgg 4260
tgcgaagcgt ccccagttac gctcacctgt ttcccgacct ccttactgtt ctgtcgacag 4320
agcgggccca caggccggtc gcagccacta gtatgacctc catcaacgtg aagctgctgt 4380
accactacgt gatcaccaac ctgttcaacc tgtgcttctt ccccctgacc gccatcgtgg 4440
ccggcaaggc ctcccgcctg accatcgacg acctgcacca cctgtactac tcctacctgc 4500
agcacaacgt gatcaccatc gcccccctgt tcgccttcac cgtgttcggc tccatcctgt 4560
acatcgtgac ccgccccaag cccgtgtacc tggtggagta ctcctgctac ctgcccccca 4620
cccagtgccg ctcctccatc tccaaggtga tggacatctt ctaccaggtg cgcaaggccg 4680 acccccttccg caacggcacc tgcgacgact cctcctggct ggacttcctg cgcaagatcc 4740
aggagcgctc cggcctgggc gacgagaccc acggccccga gggcctgctg caggtgcccc 4800
cccgcaagac cttcgccgcc gcccgcgagg agaccgagca ggtgatcgtg ggcgccctga 4860
agaacctgtt cgagaacacc aaggtgaacc ccaaggacat cggcatcctg gtggtgaact 4920
cctccatgtt caaccccacc ccctccctgt ccgccatggt ggtgaacacc ttcaagctgc 4980
gctccaacgt gcgctccttc aacctgggcg gcatgggctg ctccgccggc gtgatcgcca 5040
tcgacctggc caaggacctg ctgcacgtgc acaagaacac ctacgccctg gtggtgtcca 5100
ccgagaacat cacctacaac atctacgccg gcgacaaccg ctccatgatg gtgtccaact 5160
gcctgttccg cgtgggcggc gccgccatcc tgctgtccaa caagccccgc gaccgccgcc 5220
gctccaagta cgagctggtg cacaccgtgc gcacccacac cggcgccgac gacaagtcct 5280
tccgctgcgt gcagcagggc gacgacgaga acggcaagac cggcgtgtcc ctgtccaagg 5340
acatcaccga ggtggccggc cgcaccgtga agaagaacat cgccaccctg ggccccctga 5400
tcctgcccct gtccgagaag ctgctgttct tcgtgacctt catggccaag aagctgttca 5460
aggacaaggt gaagcactac tacgtgcccg acttcaagct ggccatcgac cacttctgca 5520
tccacgccgg cggccgcgcc gtgatcgacg tgctggagaa gaacctgggc ctggccccca 5580
tcgacgtgga ggcctcccgc tccaccctgc accgcttcgg caacacctcc tcctcctcca 5640
tctggtacga gctggcctac atcgaggcca agggccgcat gaagaagggc aacaaggtgt 5700
ggcagatcgc cctgggctcc ggcttcaagt gcaactccgc cgtgtgggtg gccctgtcca 5760
acgtgaaggc ctccaccaac tccccctggg agcactgcat cgaccgctac cccgtgaaga 5820
tcgactccga ctccgccaag tccgagaccc gcgcccagaa cggccgctcc tgacttaagg 5880
cagcagcagc tcggatagta tcgacacact ctggacgctg gtcgtgtgat ggactgttgc 5940
cgccacactt gctgccttga cctgtgaata tccctgccgc ttttatcaaa cagcctcagt 6000
gtgtttgatc ttgtgtgtac gcgcttttgc gagttgctag ctgcttgtgc tatttgcgaa 6060
taccaccccc agcatcccct tccctcgttt catatcgctt gcatcccaac cgcaacttat 6120
ctacgctgtc ctgctatccc tcagcgctgc tcctgctcct gctcactgcc cctcgcacag 6180
ccttggtttg ggctccgcct gtattctcct ggtactgcaa cctgtaaacc agcactgcaa 6240
tgctgatgca cgggaagtag tgggatggga acacaaatgg aaagcttaat taagagctct 6300
tgttttccag aaggagttgc tccttgagcc tttcattctc agcctcgata acctccaaag 6360
ccgctctaat tgtggagggg gttcgaattt aaaagcttgg aatgttggtt cgtgcgtctg 6420
gaacaagccc agacttgttg ctcactggga aaaggaccat cagctccaaa aaacttgccg 6480
ctcaaaccgc gtacctctgc tttcgcgcaa tctgccctgt tgaaatcgcc accacattca 6540
tattgtgacg cttgagcagt ctgtaattgc ctcagaatgt ggaatcatct gccccctgtg 6600
cgagcccatg ccaggcatgt cgcgggcgag gacacccgcc actcgtacag cagaccatta 6660
tgctacctca caatagttca taacagtgac catatttctc gaagctcccc aacgagcacc 6720
tccatgctct gagtggccac cccccggccc tggtgcttgc ggagggcagg tcaaccggca 6780
tggggctacc gaaatccccg accggatccc accacccccg cgatgggaag aatctctccc 6840
cgggatgtgg gcccaccacc agcacaacct gctggcccag gcgagcgtca aaccatacca 6900
cacaaatatc cttggcatcg gccctgaatt ccttctgccg ctctgctacc cggtgcttct 6960
gtccgaagca ggggttgcta gggatcgctc cgagtccgca aacccttgtc gcgtggcggg 7020
gcttgttcga gcttgaagag c 7041

<210> SEQ ID NO 103
<211> LENGTH: 1530
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 103
actagtatga cctccatcaa cgtgaagctg ctgtaccact acgtgatcac caacttcttc 60
aacctgtgct tcttccccct gaccgccatc ctggccggca aggcctcccg cctgaccacc 120
aacgacctgc accacttcta ctcctacctg cagcacaacc tgatcaccct gaccctgctg 180
ttcgccttca ccgtgttcgg ctccgtgctg tacttcgtga cccgccccaa gcccgtgtac 240
ctggtggact actcctgcta cctgcccccc cagcacctgt ccgccggcat ctccaagacc 300
atggagatct tctaccagat ccgcaagtcc gacccccctgc gcaacgtggc cctggacgac 360
tcctcctccc tggacttcct gcgcaagatc caggagcgct ccggcctggg cgacgagacc 420
tacggccccg agggcctgtt cgagatcccc ccccgcaaga acctggcctc cgcccgcgag 480
gagaccgagc aggtgatcaa cggcgccctg aagaacctgt tcgagaacac caaggtgaac 540
cccaaggaga tcggcatcct ggtggtgaac tcctccatgt tcaaccccac cccctccctg 600
tccgccatgg tggtgaacac cttcaagctg cgctccaaca tcaagtcctt caacctgggc 660
ggcatgggct gctccgccgg cgtgatcgcc atcgacctgg ccaaggacct gctgcacgtg 720
cacaagaaca cctacgccct ggtggtgtcc accgagaaca tcacccagaa catctacacc 780
ggcgacaacc gctccatgat ggtgtccaac tgcctgttcc gcgtgggcgg cgccgccatc 840
ctgctgtcca acaagcccgg cgaccgccgc cgctccaagt accgcctggc ccacaccgtg 900
cgcacccaca ccggcgccga cgacaagtcc ttcggctgcg tgcgccagga ggaggacgac 960
tccggcaaga ccggcgtgtc cctgtccaag gacatcaccg gcgtggccgg catcaccgtg 1020
cagaagaaca tcaccaccct gggcccccctg gtgctgcccc tgtccgagaa gatcctgttc 1080
gtggtgacct tcgtggccaa gaagctgctg aaggacaaga tcaagcacta ctacgtgccc 1140

```
gacttcaagc tggccgtgga ccacttctgc atccacgccg gcggccgcgc cgtgatcgac   1200

gtgctggaga agaacctggg cctgtccccc atcgacgtgg aggcctcccg ctccaccctg   1260

caccgcttcg gcaacacctc ctcctcctcc atctggtacg agctggccta catcgaggcc   1320

aagggccgca tgaagaaggg caacaaggcc tggcagatcg ccgtgggctc cggcttcaag   1380

tgcaactccg ccgtgtgggt ggccctgcgc aacgtgaagg cctccgccaa ctccccctgg   1440

gagcactgca tccacaagta ccccgtgcag atgtactccg gctcctccaa gtccgagacc   1500

cgcgcccaga acggccgctc ctgacttaag                                    1530
```

<210> SEQ ID NO 104
<211> LENGTH: 1533
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 104

```
actagtatga cctccatcaa cgtgaagctg ctgtaccact acgtgctgac caacttcttc     60

aacctgtgcc tgttcccccct gaccgccttc cccgccggca aggcctccca gctgaccacc    120

aacgacctgc accacctgta ctcctacctg caccacaacc tgatcaccgt gaccctgctg    180

ttcgccttca ccgtgttcgg ctccatcctg tacatcgtga cccgccccaa gcccgtgtac    240

ctggtggact actcctgcta cctgcccccc cgccacctgt cctgcggcat ctcccgcgtg    300

atggagatct tctacgagat ccgcaagtcc gacccctccc gcgaggtgcc cttcgacgac    360

ccctcctccc tggagttcct gcgcaagatc caggagcgct ccggcctggg cgacgagacc    420

tacggccccc agggcctggt gcacgacatg cccctgcgca tgaacttcgc cgccgcccgc    480

gaggagaccg agcaggtgat caacggcgcc ctggagaagc tgttcgagaa caccaaggtg    540

aacccccgcg agatcggcat cctggtggtg aactcctcca tgttcaaccc cacccccctcc    600

ctgtccgcca tggtggtgaa caccttcaag ctgcgctcca acatcaagtc cttctccctg    660

ggcggcatgg gctgctccgc cggcatcatc gccatcgacc tggccaagga cctgctgcac    720

gtgcacaaga acacctacgc cctggtggtg tccaccgaga acatcaccca ctccacctac    780

accggcgaca accgctccat gatggtgtcc aactgcctgt tccgcatggg cggcgccgcc    840

atcctgctgt ccaacaaggc cggcgaccgc cgccgctcca agtacaagct ggcccacacc    900

gtgcgcaccc acaccggcgc cgacgaccag tccttccgct gcgtgcgcca ggaggacgac    960

gaccgcggca agatcggcgt gtgcctgtcc aaggacatca ccgccgtggc cggcaagacc   1020

gtgaccaaga acatcgccac cctgggcccc ctggtgctgc ccctgtccga gaagttcctg   1080

tacgtggtgt ccctgatggc caagaagctg ttcaagaaca agatcaagca cacctacgtg   1140

cccgacttca agctggccat cgaccacttc tgcatccacg ccggcggccg cgccgtgatc   1200

gacgtgctgg agaagaacct ggccctgtcc cccgtggacg tggaggcctc ccgctccacc   1260

ctgcaccgct tcggcaacac ctcctcctcc tccatctggt acgagctggc ctacatcgag   1320

gccaagggcc gcatgaagaa gggcaacaag gtgtggcaga tcgccatcgg ctccggcttc   1380

aagtgcaact ccgccgtgtg ggtggccctg tgcaacgtga agccctccgt gaactccccc   1440

tgggagcact gcatcgaccg ctaccccgtg gagatcaact acggctcctc caagtccgag   1500

acccgcgccc agaacggccg ctcctgactt aag                                 1533
```

<210> SEQ ID NO 105
<211> LENGTH: 1524
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 105

```
actagtatgt ccggcaccaa ggccacctcc gtgtccgtgc cctgcccgga cttcaagcag     60

tccgtgaacc tgaagtacgt gaagctgggc taccactact ccatcaccca cgccatgtac    120

ctgttcctga cccccctgct gctgatcatg tccgcccaga tctccacctt ctccatccag    180

gacttccacc acctgtacaa ccacctgatc ctgcacaacc tgtcctccct gatcctgtgc    240

atcgccctgc tgctgttcgt gctgaccctg tacttcctga cccgccccac ccccgtgtac    300

ctgctgaact tctcctgcta caagcccgac gccatccaca agtgcgaccg ccgccgcttc    360

atggacacca tccgcggcat gggcacctac accgaggaga acatcgagtt ccagcgcaag    420

gtgctggagc gctccggcat cggcgagtcc tcctacctgc cccccaccgt gttcaagatc    480

ccccccgcg tgtacgacgc cgaggagcgc gccgaggccg agatgctgat gttcggcgcc    540

gtggacggcc tgttcgagaa gatctccgtg aagcccaacc agatcggcgt gctggtggtg    600

aactgcggcc tgttcaaccc catcccctcc ctgtcctcca tgatcgtgaa ccgctacaag    660

atgcgcggca acgtgttctc ctacaacctg ggcggcatgg gctgctccgc cggcgtgatc    720

tccatcgacc tggccaagga cctgctgcag gtgcgcccca actcctacgc cctggtggtg    780

tccctggagt gcatctccaa gaacctgtac ctgggcgagc agcgctccat gctggtgtcc    840

aactgcctgt tccgcatggg cggcgccgcc atcctgctgt ccaacaagat gtccgaccgc    900

tggcgctcca agtaccgcct ggtgcacacc gtgcgcaccc acaagggcac cgaggacaac    960

tgcttctcct gcgtgacccg caaggaggac tccgacggca agatcggcat ctccctgtcc   1020

aagaacctga tggccgtggc cggcgacgcc ctgaagacca acatcaccac cctgggcccc   1080

ctggtgctgc ccatgtccga gcagctgctg ttcttcgcca ccctggtggg caagaaggtg   1140

ttcaagatga agctgcagcc ctacatcccc gacttcaagc tggccttcga gcacttctgc   1200

atccacgccg gcggccgcgc cgtgctggac gagctggaga agaacctgaa gctgtcctcc   1260

tggcacatgg agccctcccg catgtccctg taccgcttcg gcaacacctc ctcctcctcc   1320

ctgtggtacg agctggccta ctccgaggcc aagggccgca tcaagaaggg cgaccgcgtg   1380

tggcagatcg ccttcggctc cggcttcaag tgcaactccg ccgtgtggaa ggccctgcgc   1440

aacgtgaacc ccgccgagga gaagaacccc tggatggacg agatccacct gttccccgtg   1500

gaggtgcccc tgaactgact taag                                          1524
```

<210> SEQ ID NO 106
<211> LENGTH: 1530
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 106

```
actagtatga cctccatcaa cgtgaagctg ctgtaccact acgtgatcac caacctgttc     60

aacctgtgct tcttccccct gaccgccatc gtggccggca aggcctacct gaccatcgac    120

gacctgcacc acctgtacta ctcctacctg cagcacaacc tgatcaccat cgccccccctg   180
```

-continued

```
ctggccttca ccgtgttcgg ctccgtgctg tacatcgcca cccgccccaa gcccgtgtac    240

ctggtggagt actcctgcta cctgcccccc acccactgcc gctcctccat ctccaaggtg    300

atggacatct tcttccaggt gcgcaaggcc gacccctccc gcaacggcac ctgcgacgac    360

tcctcctggc tggacttcct gcgcaagatc caggagcgct ccggcctggg cgacgagacc    420

cacggccccg agggcctgct gcaggtgccc ccccgcaaga ccttcgcccg cgcccgcgag    480

gagaccgagc aggtgatcat cggcgccctg gagaacctgt tcaagaacac caacgtgaac    540

cccaaggaca tcggcatcct ggtggtgaac tcctccatgt tcaaccccac cccctccctg    600

tccgccatgg tggtgaacac cttcaagctg cgctccaacg tgcgctcctt caacctgggc    660

ggcatgggct gctccgccgg cgtgatcgcc atcgacctgg ccaaggacct gctgcacgtg    720

cacaagaaca cctacgccct ggtggtgtcc accgagaaca tcacctacaa catctacgcc    780

ggcgacaacc gctccatgat ggtgtccaac tgcctgttcc gcgtgggcgg cgccgccatc    840

ctgctgtcca acaagccccg cgaccgccgc cgctccaagt acgagctggt gcacaccgtg    900

cgcacccaca ccggcgccga cgacaagtcc ttccgctgcg tgcagcaggg cgacgacgag    960

aacggccaga ccggcgtgtc cctgtccaag gacatcaccg acgtggccgg ccgcaccgtg   1020

aagaagaaca tcgccaccct gggcccccctg atcctgcccc tgtccgagaa gctgctgttc   1080

ttcgtgacct tcatgggcaa gaagctgttc aaggacgaga tcaagcacta ctacgtgccc   1140

gacttcaagc tggccatcga ccacttctgc atccacgccg gcggcaaggc cgtgatcgac   1200

gtgctggaga agaacctggg cctggccccc atcgacgtgg aggcctcccg ctccaccctg   1260

caccgcttcg gcaacacctc ctcctcctcc atctggtacg agctggccta catcgagccc   1320

aagggccgca tgaagaaggg caacaaggtg tggcagatcg ccctgggctc cggcttcaag   1380

tgcaactccg ccgtgtgggt ggccctgaac aacgtgaagg cctccaccaa ctcccccctgg   1440

gagcactgca tcgaccgcta ccccgtgaag atcgactccg actccggcaa gtccgagacc   1500

cgcgtgccca acggccgctc ctgacttaag                                   1530
```

<210> SEQ ID NO 107
<211> LENGTH: 1599
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 107

```
actagtatgg agcgcaccaa ctccatcgag atggaccagg agcgcctgac cgccgagatg     60

gccttcaagg actcctcctc cgccgtgatc cgcatccgcc gccgcctgcc cgacttcctg    120

acctccgtga agctgaagta cgtgaagctg ggcctgcaca actccttcaa cttcaccacc    180

ttcctgttcc tgctgatcat cctgcccctg accggcaccg tgctggtgca gctgaccggc    240

ctgaccttcg agaccttctc cgagctgtgg tacaaccacg ccgcccagct ggacggcgtg    300

acccgcctgg cctgcctggt gtccctgtgc ttcgtgctga tcatctacgt gaccaaccgc    360

tccaagcccg tgtacctggt ggacttctcc tgctacaagc ccgaggacga gcgcaagatg    420

tccgtggact ccttcctgaa gatgaccgag cagaacggcg ccttcaccga cgacaccgtg    480

cagttccagc agcgcatctc caaccgcgcc ggcctgggcg acgagaccta cctgccccgc    540

ggcatcacct ccaccccccc caagctgaac atgtccgagg cccgcgccga ggccgaggcc    600

gtgatgttcg gcgccctgga ctccctgttc gagaagaccg gcatcaagcc cgccgaggtg    660
```

-continued ggcatcctga tcgtgtcctg ctccctgttc aaccccaccc cctccctgtc cgccatgatc 720
gtgaaccact acaagatgcg cgaggacatc aagtcctaca acctgggcgg catgggctgc 780
tccgccggcc tgatctccat cgacctggcc aacaacctgc tgaaggccaa ccccaactcc 840
tacgccgtgg tggtgtccac cgagaacatc accctgaact ggtacttcgg caacgaccgc 900
tccatgctgc tgtgcaactg catcttccgc atgggcggcg ccgccatcct gctgtccaac 960
cgccgccagg accgctccaa gtccaagtac gagctggtga acgtggtgcg cacccacaag 1020
ggctccgacg acaagaacta caactgcgtg taccagaagg aggacgagcg cggcaccatc 1080
ggcgtgtccc tggcccgcga gctgatgtcc gtggccggcg acgccctgaa gaccaacatc 1140
accaccctgg gccccatggt gctgcccctg tccggccagc tgatgttctc cgtgtccctg 1200
gtgaagcgca agctgctgaa gctgaaggtg aagccctaca tccccgactt caagctggcc 1260
ttcgagcact tctgcatcca cgccggcggc cgcgccgtgc tggacgaggt gcagaagaac 1320
ctggacctgg aggactggca catggagccc tcccgcatga ccctgcaccg cttcggcaac 1380
acctcctcct cctccctgtg gtacgagatg gcctacaccg aggccaaggg ccgcgtgaag 1440
gccggcgacc gcctgtggca gatcgccttc ggctccggct tcaagtgcaa ctccgccgtg 1500
tggaaggccc tgcgcgtggt gtccaccgag gagctgaccg gcaacgcctg ggccggctcc 1560
atcgagaact accccgtgaa gatcgtgcag tgacttaag 1599

<210> SEQ ID NO 108
<211> LENGTH: 5988
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 108
gctcttcgcc gccgccactc ctgctcgagc gcgcccgcgc gtgcgccgcc agcgccttgg 60
ccttttcgcc gcgctcgtgc gcgtcgctga tgtccatcac caggtccatg aggtctgcct 120
tgcgccggct gagccactgc ttcgtccggg cggccaagag gagcatgagg gaggactcct 180
ggtccagggt cctgacgtgg tcgcggctct gggagcgggc cagcatcatc tggctctgcc 240
gcaccgaggc cgcctccaac tggtcctcca gcagccgcag tcgccgccga ccctggcaga 300
ggaagacagg tgaggggggt atgaattgta cagaacaacc acgagccttg tctaggcaga 360
atccctacca gtcatggctt tacctggatg acggcctgcg aacagctgtc cagcgaccct 420
cgctgccgcc gcttctcccg cacgcttctt tccagcaccg tgatggcgcg agccagcgcc 480
gcacgctggc gctgcgcttc gccgatctga ggacagtcgg ggaactctga tcagtctaaa 540 ccccccttgcg cgttagtgtt gccatccttt gcagaccggt gagagccgac ttgttgtgcg 600
ccacccccca caccacctcc tcccagacca attctgtcac ctttttggcg aaggcatcgg 660
cctcggcctg cagagaggac agcagtgccc agccgctggg ggttggcgga tgcacgctca 720
ggtacccttt cttgcgctat gacacttcca gcaaaaggta gggcgggctg cgagacggct 780
tcccggcgct gcatgcaaca ccgatgatgc ttcgaccccc cgaagctcct tcggggctgc 840
atgggcgctc cgatgccgct ccagggcgag cgctgtttaa atagccaggc ccccgattgc 900
aaagacatta tagcgagcta ccaaagccat attcaaacac ctagatcact accacttcta 960
cacaggccac tcgagcttgt gatcgcactc cgctaagggg gcgcctcttc ctcttcgttt 1020
cagtcacaac ccgcaaactc tagaatatca atgctgctgc aggccttcct gttcctgctg 1080

-continued

```
gccggcttcg ccgccaagat cagcgcctcc atgacgaacg agacgtccga ccgcccctg    1140
gtgcacttca cccccaacaa gggctggatg aacgacccca acggcctgtg gtacgacgag   1200
aaggacgcca agtggcacct gtacttccag tacaacccga acgacaccgt ctgggggacg   1260
cccttgttct ggggccacgc cacgtccgac gacctgacca actgggagga ccagcccatc   1320
gccatcgccc cgaagcgcaa cgactccggc gccttctccg gctccatggt ggtggactac   1380
aacaacacct ccggcttctt caacgacacc atcgacccgc gccagcgctg cgtggccatc   1440
tggacctaca acaccccgga gtccgaggag cagtacatct cctacagcct ggacggcggc   1500
tacaccttca ccgagtacca gaagaacccc gtgctggccg ccaactccac ccagttccgc   1560
gacccgaagg tcttctggta cgagccctcc cagaagtgga tcatgaccgc ggccaagtcc   1620
caggactaca agatcgagat ctactcctcc gacgacctga agtcctggaa gctggagtcc   1680
gcgttcgcca acgagggctt cctcggctac cagtacgagt gccccggcct gatcgaggtc   1740
cccaccgagc aggaccccag caagtcctac tgggtgatgt tcatctccat caaccccggc   1800
gccccggccg gcggctcctt caaccagtac ttcgtcggca gcttcaacgg cacccacttc   1860
gaggccttcg acaaccagtc ccgcgtggtg gacttcggca aggactacta cgccctgcag   1920
accttcttca acaccgaccc gacctacggg agcgccctgg gcatcgcgtg ggcctccaac   1980
tgggagtact ccgccttcgt gcccaccaac ccctggcgct cctccatgtc cctcgtgcgc   2040
aagttctccc tcaacaccga gtaccaggcc aacccggaga cggagctgat caacctgaag   2100
gccgagccga tcctgaacat cagcaacgcc ggcccctgga gccggttcgc caccaacacc   2160
acgttgacga aggccaacag ctacaacgtc gacctgtcca acagcaccgg caccctggag   2220
ttcgagctgg tgtacgccgt caacaccacc cagacgatct ccaagtccgt gttcgcggac   2280
ctctccctct ggttcaaggg cctggaggac cccgaggagt acctccgcat gggcttcgag   2340
gtgtccgcgt cctccttctt cctggaccgc gggaacagca aggtgaagtt cgtgaaggag   2400
aacccctact tcaccaaccg catgagcgtg aacaaccagc ccttcaagag cgagaacgac   2460
ctgtcctact acaaggtgta cggcttgctg gaccagaaca tcctggagct gtacttcaac   2520
gacggcgacg tcgtgtccac caacacctac ttcatgacca ccgggaacgc cctgggctcc   2580
gtgaacatga cgacgggggt ggacaacctg ttctacatcg acaagttcca ggtgcgcgag   2640
gtcaagtgac aattggcagc agcagctcgg atagtatcga cacactctgg acgctggtcg   2700
tgtgatggac tgttgccgcc acacttgctg ccttgacctg tgaatatccc tgccgctttt   2760
atcaaacagc ctcagtgtgt ttgatcttgt gtgtacgcgc ttttgcgagt tgctagctgc   2820
ttgtgctatt tgcgaatacc acccccagca tccccttccc tcgtttcata tcgcttgcat   2880
cccaaccgca acttatctac gctgtcctgc tatccctcag cgctgctcct gctcctgctc   2940
actgcccctc gcacagcctt ggtttgggct ccgcctgtat tctcctggta ctgcaacctg   3000
taaaccagca ctgcaatgct gatgcacggg aagtagtggg atgggaacac aaatggagga   3060
tcccgcgtct cgaacagagc gcgcagagga acgctgaagg tctcgcctct gtcgcacctc   3120
agcgcggcat acaccacaat aaccacctga cgaatgcgct tggttcttcg tccattagcg   3180
aagcgtccgg ttcacacacg tgccacgttg gcgaggtggc aggtgacaat gatcggtgga   3240
gctgatggtc gaaacgttca cagcctaggg atatcgaatt cctttcttgc gctatgacac   3300
ttccagcaaa aggtagggcg ggctgcgaga cggcttcccg gcgctgcatg caacaccgat   3360
gatgcttcga ccccccgaag ctccttcggg gctgcatggg cgctccgatg ccgctccagg   3420
gcgagcgctg tttaaatagc caggcccccg attgcaaaga cattatagcg agctaccaaa   3480
```

-continued

```
gccatattca aacacctaga tcactaccac ttctacacag gccactcgag cttgtgatcg   3540
cactccgcta agggggcgcc tcttcctctt cgtttcagtc acaacccgca aacactagta   3600
tggccaccgc atccactttc tcggcgttca atgcccgctg cggcgacctg cgtcgctcgg   3660
cgggctccgg gccccggcgc ccagcgaggc ccctccccgt gcgcgggcgc gccgaggtgc   3720
acgtgcaggt gacccactcc ctggccccg agaagcgcga gatcttcaac tccctgaaca    3780
actgggccca ggagaacatc ctggtgctgc tgaaggacgt ggacaagtgc tggcagccct   3840
ccgacttcct gcccgactcc gcctccgagg gcttcgacga gcaggtgatg gagctgcgca   3900
agcgctgcaa ggagatcccc gacgactact tcatcgtgct ggtgggcgac atgatcaccg   3960
aggaggccct gcccacctac cagaccatgc tgaacaccct ggacggcgtg cgcgacgaga   4020
ccggcgcctc cctgaccccc tgggccatct ggacccgcgc ctggaccgcc gaggagaacc   4080
gccacggcga cctgctgaac aagtacctgt acctgtccgg ccgcgtggac atgaagcaga   4140
tcgagaagac catccagtac ctgatcggct ccggcatgga cccccgcacc gagaacaacc   4200
cctacctggg cttcatctac acctccttcc aggagcgcgc caccttcatc tcccacggca   4260
acaccgcccg cctggccaag gagcacggcg acctgaagct ggcccagatc tgcggcatca   4320
tcgccgccga cgagaagcgc cacgagaccg cctacaccaa gatcgtggag aagctgttcg   4380
agatcgaccc cgacggcacc gtgctggccc tggccgacat gatgcgcaag aaggtgtcca   4440
tgcccgccca cctgatgtac gacggccagg acgacaacct gttcgagaac ttctcctccg   4500
tggcccagcg cctgggcgtg tacaccgcca aggactacgc cgacatcctg gagttcctgg   4560
tgggccgctg ggacatcgag aagctgaccg gcctgtccgg cgagggccgc aaggcccagg   4620
actacgtgtg caccctgccc ccccgcatcc gccgcctgga ggagcgcgcc cagtcccgcg   4680
tgaagaaggc ctccgccacc cccttctcct ggatcttcgg ccgcgagatc aacctgatgg   4740
actacaagga ccacgacggc gactacaagg accacgacat cgactacaag gacgacgacg   4800
acaagtgaat cgatagatct cttaaggcag cagcagctcg gatagtatcg acacactctg   4860
gacgctggtc gtgtgatgga ctgttgccgc cacacttgct gccttgacct gtgaatatcc   4920
ctgccgcttt tatcaaacag cctcagtgtg tttgatcttg tgtgtacgcg cttttgcgag   4980
ttgctagctg cttgtgctat ttgcgaatac cacccccagc atccccttcc ctcgtttcat   5040
atcgcttgca tcccaaccgc aacttatcta cgctgtcctg ctatccctca gcgctgctcc   5100
tgctcctgct cactgcccct cgcacagcct tggtttgggc tccgcctgta ttctcctggt   5160
actgcaacct gtaaaccagc actgcaatgc tgatgcacgg gaagtagtgg gatgggaaca   5220
caaatggaaa gcttaattaa gagctcttgt tttccagaag gagttgctcc ttgagccttt   5280
cattctcagc ctcgataacc tccaaagccg ctctaattgt ggagggggtt cgaatttaaa   5340
agcttggaat gttggttcgt gcgtctggaa caagcccaga cttgttgctc actgggaaaa   5400
ggaccatcag ctccaaaaaa cttgccgctc aaaccgcgta cctctgcttt cgcgcaatct   5460
gccctgttga aatcgccacc acattcatat tgtgacgctt gagcagtctg taattgcctc   5520
agaatgtgga atcatctgcc ccctgtgcga gcccatgcca ggcatgtcgc gggcgaggac   5580
acccgccact cgtacagcag accattatgc tacctcacaa tagttcataa cagtgaccat   5640
atttctcgaa gctccccaac gagcacctcc atgctctgag tggccacccc ccggccctgg   5700
tgcttgcgga gggcaggtca accggcatgg ggctaccgaa atccccgacc ggatcccacc   5760
acccccgcga tgggaagaat ctctccccgg gatgtgggcc caccaccagc acaacctgct   5820
```

```
ggcccaggcg agcgtcaaac cataccacac aaatatcctt ggcatcggcc ctgaattcct   5880

tctgccgctc tgctacccgg tgcttctgtc cgaagcaggg gttgctaggg atcgctccga   5940

gtccgcaaac ccttgtcgcg tggcggggct tgttcgagct tgaagagc                5988


<210> SEQ ID NO 109
<211> LENGTH: 6807
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109

gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120

tgcgccggct gagccactgc ttcgtccggg cggccaagag gagcatgagg gaggactcct    180

ggtccagggt cctgacgtgg tcgcggctct gggagcgggc cagcatcatc tggctctgcc    240

gcaccgaggc cgcctccaac tggtcctcca gcagccgcag tcgccgccga ccctggcaga    300

ggaagacagg tgaggggggt atgaattgta cagaacaacc acgagccttg tctaggcaga    360

atccctacca gtcatggctt tacctggatg acggcctgcg aacagctgtc cagcgaccct    420

cgctgccgcc gcttctcccg cacgcttctt tccagcaccg tgatggcgcg agccagcgcc    480

gcacgctggc gctgcgcttc gccgatctga ggacagtcgg ggaactctga tcagtctaaa    540

ccccccttgcg cgttagtgtt gccatccttt gcagaccggt gagagccgac ttgttgtgcg    600

ccaccccccca caccacctcc tcccagacca attctgtcac ctttttggcg aaggcatcgg    660

cctcggcctg cagagaggac agcagtgccc agccgctggg ggttggcgga tgcacgctca    720

ggtacccttt cttgcgctat gacacttcca gcaaaaggta gggcgggctg cgagacggct    780

tcccggcgct gcatgcaaca ccgatgatgc ttcgaccccc cgaagctcct tcggggctgc    840

atgggcgctc cgatgccgct ccagggcgag cgctgtttaa atagccaggc ccccgattgc    900

aaagacatta tagcgagcta ccaaagccat attcaaacac ctagatcact accacttcta    960

cacaggccac tcgagcttgt gatcgcactc cgctaagggg gcgcctcttc ctcttcgttt   1020

cagtcacaac ccgcaaactc tagaatatca atgctgctgc aggccttcct gttcctgctg   1080

gccggcttcg ccgccaagat cagcgcctcc atgacgaacg agacgtccga ccgcccctg   1140

gtgcacttca cccccaacaa gggctggatg aacgacccca acggcctgtg gtacgacgag   1200

aaggacgcca agtggcacct gtacttccag tacaacccga acgacaccgt ctgggggacg   1260

cccttgttct ggggccacgc cacgtccgac gacctgacca actgggagga ccagcccatc   1320

gccatcgccc cgaagcgcaa cgactccggc gccttctccg gctccatggt ggtggactac   1380

aacaacacct ccggcttctt caacgacacc atcgacccgc gccagcgctg cgtggccatc   1440

tggacctaca acaccccgga gtccgaggag cagtacatct cctacagcct ggacggcggc   1500

tacaccttca ccgagtacca gaagaacccc gtgctggccg ccaactccac ccagttccgc   1560

gacccgaagg tcttctggta cgagccctcc cagaagtgga tcatgaccgc ggccaagtcc   1620

caggactaca agatcgagat ctactcctcc gacgacctga agtcctggaa gctggagtcc   1680

gcgttcgcca acgagggctt cctcggctac cagtacgagt gccccggcct gatcgaggtc   1740

cccaccgagc aggaccccag caagtcctac tgggtgatgt tcatctccat caaccccggc   1800

gccccggccg gcggctcctt caaccagtac ttcgtcggca gcttcaacgg cacccacttc   1860
```

-continued

```
gaggccttcg acaaccagtc ccgcgtggtg gacttcggca aggactacta cgccctgcag   1920
accttcttca acaccgaccc gacctacggg agcgccctgg gcatcgcgtg ggcctccaac   1980
tgggagtact ccgccttcgt gcccaccaac ccctggcgct cctccatgtc cctcgtgcgc   2040
aagttctccc tcaacaccga gtaccaggcc aacccggaga cggagctgat caacctgaag   2100
gccgagccga tcctgaacat cagcaacgcc ggcccctgga gccggttcgc caccaacacc   2160
acgttgacga aggccaacag ctacaacgtc gacctgtcca acagcaccgg caccctggag   2220
ttcgagctgg tgtacgccgt caacaccacc cagacgatct ccaagtccgt gttcgcggac   2280
ctctccctct ggttcaaggg cctggaggac cccgaggagt acctccgcat gggcttcgag   2340
gtgtccgcgt cctccttctt cctggaccgc gggaacagca aggtgaagtt cgtgaaggag   2400
aacccctact tcaccaaccg catgagcgtg aacaaccagc ccttcaagag cgagaacgac   2460
ctgtcctact acaaggtgta cggcttgctg gaccagaaca tcctggagct gtacttcaac   2520
gacggcgacg tcgtgtccac caacacctac ttcatgacca ccgggaacgc cctgggctcc   2580
gtgaacatga cgacgggggt ggacaacctg ttctacatcg acaagttcca ggtgcgcgag   2640
gtcaagtgac aattggcagc agcagctcgg atagtatcga cacactctgg acgctggtcg   2700
tgtgatggac tgttgccgcc acacttgctg ccttgacctg tgaatatccc tgccgctttt   2760
atcaaacagc ctcagtgtgt ttgatcttgt gtgtacgcgc ttttgcgagt tgctagctgc   2820
ttgtgctatt tgcgaatacc acccccagca tccccttccc tcgtttcata tcgcttgcat   2880
cccaaccgca acttatctac gctgtcctgc tatccctcag cgctgctcct gctcctgctc   2940
actgcccctc gcacagcctt ggtttgggct ccgcctgtat tctcctggta ctgcaacctg   3000
taaaccagca ctgcaatgct gatgcacggg aagtagtggg atgggaacac aaatggagga   3060
tcccgcgtct cgaacagagc gcgcagagga acgctgaagg tctcgcctct gtcgcacctc   3120
agcgcggcat acaccacaat aaccacctga cgaatgcgct tggttcttcg tccattagcg   3180
aagcgtccgg ttcacacacg tgccacgttg gcgaggtggc aggtgacaat gatcggtgga   3240
gctgatggtc gaaacgttca cagcctaggg atatcgaatt cggccgacag gacgcgcgtc   3300
aaaggtgctg gtcgtgtatg ccctggccgg caggtcgttg ctgctgctgg ttagtgattc   3360
cgcaaccctg attttggcgt cttattttgg cgtggcaaac gctggcgccc gcgagccggg   3420
ccggcggcga tgcggtgccc cacggctgcc ggaatccaag ggaggcaaga gcgcccgggt   3480
cagttgaagg gctttacgcg caaggtacag ccgctcctgc aaggctgcgt ggtggaattg   3540
gacgtgcagg tcctgctgaa gttcctccac cgcctcacca gcggacaaag caccggtgta   3600
tcaggtccgt gtcatccact ctaaagaact cgactacgac ctactgatgg ccctagattc   3660
ttcatcaaaa acgcctgaga cacttgccca ggattgaaac tccctgaagg gaccaccagg   3720
ggccctgagt tgttccttcc ccccgtggcg agctgccagc caggctgtac ctgtgatcga   3780
ggctggcggg aaaataggct tcgtgtgctc aggtcatggg aggtgcagga cagctcatga   3840
aacgccaaca atcgcacaat tcatgtcaag ctaatcagct atttcctctt cacgagctgt   3900
aattgtccca aaattctggt ctaccggggg tgatccttcg tgtacgggcc cttccctcaa   3960
ccctaggtat gcgcgcatgc ggtcgccgcg caactcgcgc gagggccgag ggtttgggac   4020
gggccgtccc gaaatgcagt tgcacccgga tgcgtggcac ctttttttgcg ataatttatg   4080
caatggactg ctctgcaaaa ttctggctct gtcgccaacc ctaggatcag cggcgtagga   4140
tttcgtaatc attcgtcctg atggggagct accgactacc ctaatatcag cccgactgcc   4200
tgacgccagc gtccactttt gtgcacacat tccattcgtg cccaagacat ttcattgtgg   4260
```

-continued

```
tgcgaagcgt ccccagttac gctcacctgt ttcccgacct ccttactgtt ctgtcgacag   4320
agcgggccca caggccggtc gcagccacta gtatggccac cgcatccact ttctcggcgt   4380
tcaatgcccg ctgcggcgac ctgcgtcgct cggcgggctc cgggccccgg cgcccagcga   4440
ggcccctccc cgtgcgcggg cgcgccgcct ccaccctgaa gtccggctcc aaggaggtgg   4500
agaacctgaa gaagcccttc atgccccccc gcgaggtgca cgtgcaggtg acccactcca   4560
tgccccccca gaagatcgag atcttcaagt ccctggacaa ctgggccgag gagaacatcc   4620
tggtgcacct gaagcccgtg gagaagtgct ggcagcccca ggacttcctg cccgaccccg   4680
cctccgacgg cttcgacgag caggtgcgcg agctgcgcga gcgcgccaag gagatccccg   4740
acgactactt cgtggtgctg gtgggcgaca tgatcaccga ggaggccctg cccacctacc   4800
agaccatgct gaacaccctg gacggcgtgc gcgacgagac cggcgcctcc cccacctcct   4860
gggccatctg gacccgcgcc tggaccgccg aggagaaccg ccacggcgac ctgctgaaca   4920
agtacctgta cctgtccggc cgcgtggaca tgcgccagat cgagaagacc atccagtacc   4980
tgatcggctc cggcatggac ccccgcaccg agaactcccc ctacctgggc ttcatctaca   5040
cctccttcca ggagcgcgcc accttcatct cccacggcaa caccgcccgc caggccaagg   5100
agcacggcga catcaagctg gcccagatct gcggcaccat cgccgccgac gagaagcgcc   5160
acgagaccgc ctacaccaag atcgtggaga agctgttcga gatcgacccc gacggcaccg   5220
tgctggcctt cgccgacatg atgcgcaaga agatctccat gcccgcccac ctgatgtacg   5280
acggccgcga cgacaacctg ttcgaccact tctccgccgt ggcccagcgc ctgggcgtgt   5340
acaccgccaa ggactacgcc gacatcctgg agttcctggt gggccgctgg aaggtggaca   5400
agctgaccgg cctgtccgcc gagggccaga aggcccagga ctacgtgtgc cgcctgcccc   5460
cccgcatccg ccgcctggag gagcgcgccc agggccgcgc caaggaggcc cccaccatgc   5520
ccttctcctg gatcttcgac cgccaggtga agctgatgga ctacaaggac cacgacggcg   5580
actacaagga ccacgacatc gactacaagg acgacgacga caagtgaatc gatagatctc   5640
ttaaggcagc agcagctcgg atagtatcga cacactctgg acgctggtcg tgtgatggac   5700
tgttgccgcc acacttgctg ccttgacctg tgaatatccc tgccgctttt atcaaacagc   5760
ctcagtgtgt ttgatcttgt gtgtacgcgc ttttgcgagt tgctagctgc ttgtgctatt   5820
tgcgaatacc acccccagca tccccttccc tcgtttcata tcgcttgcat cccaaccgca   5880
acttatctac gctgtcctgc tatccctcag cgctgctcct gctcctgctc actgcccctc   5940
gcacagcctt ggtttgggct ccgcctgtat tctcctggta ctgcaacctg taaaccagca   6000
ctgcaatgct gatgcacggg aagtagtggg atgggaacac aaatggaaag cttaattaag   6060
agctcttgtt ttccagaagg agttgctcct tgagcctttc attctcagcc tcgataacct   6120
ccaaagccgc tctaattgtg gagggggttc gaatttaaaa gcttggaatg ttggttcgtg   6180
cgtctggaac aagcccagac ttgttgctca ctgggaaaag gaccatcagc tccaaaaaac   6240
ttgccgctca aaccgcgtac ctctgctttc gcgcaatctg ccctgttgaa atcgccacca   6300
cattcatatt gtgacgcttg agcagtctgt aattgcctca gaatgtggaa tcatctgccc   6360
cctgtgcgag cccatgccag gcatgtcgcg ggcgaggaca cccgccactc gtacagcaga   6420
ccattatgct acctcacaat agttcataac agtgaccata tttctcgaag ctccccaacg   6480
agcacctcca tgctctgagt ggccaccccc cggccctggt gcttgcggag ggcaggtcaa   6540
ccggcatggg gctaccgaaa tccccgaccg gatcccacca cccccgcgat gggaagaatc   6600
```

-continued

```
tctccccggg atgtgggccc accaccagca caacctgctg gcccaggcga gcgtcaaacc   6660

ataccacaca aatatccttg gcatcggccc tgaattcctt ctgccgctct gctacccggt   6720

gcttctgtcc gaagcagggg ttgctaggga tcgctccgag tccgcaaacc cttgtcgcgt   6780

ggcggggctt gttcgagctt gaagagc                                       6807


<210> SEQ ID NO 110
<211> LENGTH: 6744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110

gctcttcgcc gccgccactc ctgctcgagc gcgcccgcgc gtgcgccgcc agcgccttgg     60

ccttttcgcc gcgctcgtgc gcgtcgctga tgtccatcac caggtccatg aggtctgcct    120

tgcgccggct gagccactgc ttcgtccggg cggccaagag gagcatgagg gaggactcct    180

ggtccagggt cctgacgtgg tcgcggctct gggagcgggc cagcatcatc tggctctgcc    240

gcaccgaggc cgcctccaac tggtcctcca gcagccgcag tcgccgccga ccctggcaga    300

ggaagacagg tgaggggggt atgaattgta cagaacaacc acgagccttg tctaggcaga    360

atccctacca gtcatggctt tacctggatg acggcctgcg aacagctgtc cagcgaccct    420

cgctgccgcc gcttctcccg cacgcttctt tccagcaccg tgatggcgcg agccagcgcc    480

gcacgctggc gctgcgcttc gccgatctga ggacagtcgg ggaactctga tcagtctaaa    540

ccccccttgcg cgttagtgtt gccatccttt gcagaccggt gagagccgac ttgttgtgcg    600

ccaccccccca caccacctcc tcccagacca attctgtcac ctttttggcg aaggcatcgg    660

cctcggcctg cagagaggac agcagtgccc agccgctggg ggttggcgga tgcacgctca    720

ggtacccttt cttgcgctat gacacttcca gcaaaaggta gggcgggctg cgagacggct    780

tcccggcgct gcatgcaaca ccgatgatgc ttcgaccccc cgaagctcct tcggggctgc    840

atgggcgctc cgatgccgct ccagggcgag cgctgtttaa atagccaggc ccccgattgc    900

aaagacatta tagcgagcta ccaaagccat attcaaacac ctagatcact accacttcta    960

cacaggccac tcgagcttgt gatcgcactc cgctaagggg gcgcctcttc ctcttcgttt   1020

cagtcacaac ccgcaaactc tagaatatca atgctgctgc aggccttcct gttcctgctg   1080

gccggcttcg ccgccaagat cagcgcctcc atgacgaacg agacgtccga ccgcccccctg   1140

gtgcacttca cccccaacaa gggctggatg aacgacccca acggcctgtg gtacgacgag   1200

aaggacgcca agtggcacct gtacttccag tacaacccga acgacaccgt ctgggggacg   1260

cccttgttct ggggccacgc cacgtccgac gacctgacca actgggagga ccagcccatc   1320

gccatcgccc cgaagcgcaa cgactccggc gccttctccg gctccatggt ggtggactac   1380

aacaacacct ccggcttctt caacgacacc atcgacccgc gccagcgctg cgtggccatc   1440

tggacctaca acaccccgga gtccgaggag cagtacatct cctacagcct ggacggcggc   1500

tacaccttca ccgagtacca gaagaacccc gtgctggccg ccaactccac ccagttccgc   1560

gacccgaagg tcttctggta cgagccctcc cagaagtgga tcatgaccgc ggccaagtcc   1620

caggactaca agatcgagat ctactcctcc gacgacctga agtcctggaa gctggagtcc   1680

gcgttcgcca acgagggctt cctcggctac cagtacgagt gccccggcct gatcgaggtc   1740

cccaccgagc aggaccccag caagtcctac tgggtgatgt tcatctccat caaccccggc   1800
```

-continued

```
gccccggccg gcggctcctt caaccagtac ttcgtcggca gcttcaacgg cacccacttc   1860
gaggccttcg acaaccagtc ccgcgtggtg gacttcggca aggactacta cgccctgcag   1920
accttcttca acaccgaccc gacctacggg agcgccctgg gcatcgcgtg ggcctccaac   1980
tgggagtact ccgccttcgt gcccaccaac ccctggcgct cctccatgtc cctcgtgcgc   2040
aagttctccc tcaacaccga gtaccaggcc aacccggaga cggagctgat caacctgaag   2100
gccgagccga tcctgaacat cagcaacgcc ggcccctgga gccggttcgc caccaacacc   2160
acgttgacga aggccaacag ctacaacgtc gacctgtcca acagcaccgg caccctggag   2220
ttcgagctgg tgtacgccgt caacaccacc cagacgatct ccaagtccgt gttcgcggac   2280
ctctccctct ggttcaaggg cctggaggac cccgaggagt acctccgcat gggcttcgag   2340
gtgtccgcgt cctccttctt cctggaccgc gggaacagca aggtgaagtt cgtgaaggag   2400
aacccctact tcaccaaccg catgagcgtg aacaaccagc ccttcaagag cgagaacgac   2460
ctgtcctact acaaggtgta cggcttgctg gaccagaaca tcctggagct gtacttcaac   2520
gacggcgacg tcgtgtccac caacacctac ttcatgacca ccgggaacgc cctgggctcc   2580
gtgaacatga cgacgggggt ggacaacctg ttctacatcg acaagttcca ggtgcgcgag   2640
gtcaagtgac aattggcagc agcagctcgg atagtatcga cacactctgg acgctggtcg   2700
tgtgatggac tgttgccgcc acacttgctg ccttgacctg tgaatatccc tgccgctttt   2760
atcaaacagc ctcagtgtgt ttgatcttgt gtgtacgcgc ttttgcgagt tgctagctgc   2820
ttgtgctatt tgcgaatacc acccccagca tccccttccc tcgtttcata tcgcttgcat   2880
cccaaccgca acttatctac gctgtcctgc tatccctcag cgctgctcct gctcctgctc   2940
actgcccctc gcacagcctt ggtttgggct ccgcctgtat tctcctggta ctgcaacctg   3000
taaaccagca ctgcaatgct gatgcacggg aagtagtggg atgggaacac aaatggagga   3060
tcccgcgtct cgaacagagc gcgcagagga acgctgaagg tctcgcctct gtcgcacctc   3120
agcgcggcat acaccacaat aaccacctga cgaatgcgct tggttcttcg tccattagcg   3180
aagcgtccgg ttcacacacg tgccacgttg gcgaggtggc aggtgacaat gatcggtgga   3240
gctgatggtc gaaacgttca cagcctaggg atatcgaatt cggccgacag gacgcgcgtc   3300
aaaggtgctg gtcgtgtatg ccctggccgg caggtcgttg ctgctgctgg ttagtgattc   3360
cgcaaccctg attttggcgt cttattttgg cgtggcaaac gctggcgccc gcgagccggg   3420
ccggcggcga tgcggtgccc cacggctgcc ggaatccaag ggaggcaaga gcgcccgggt   3480
cagttgaagg gctttacgcg caaggtacag ccgctcctgc aaggctgcgt ggtggaattg   3540
gacgtgcagg tcctgctgaa gttcctccac cgcctcacca gcggacaaag caccggtgta   3600
tcaggtccgt gtcatccact ctaaagaact cgactacgac ctactgatgg ccctagattc   3660
ttcatcaaaa acgcctgaga cacttgccca ggattgaaac tccctgaagg gaccaccagg   3720
ggccctgagt tgttccttcc ccccgtggcg agctgccagc caggctgtac ctgtgatcga   3780
ggctggcggg aaaataggct tcgtgtgctc aggtcatggg aggtgcagga cagctcatga   3840
aacgccaaca atcgcacaat tcatgtcaag ctaatcagct atttcctctt cacgagctgt   3900
aattgtccca aaattctggt ctaccggggg tgatccttcg tgtacgggcc cttccctcaa   3960
ccctaggtat gcgcgcatgc ggtcgccgcg caactcgcgc gagggccgag ggtttgggac   4020
gggccgtccc gaaatgcagt tgcacccgga tgcgtggcac ctttttttgcg ataatttatg   4080
caatggactg ctctgcaaaa ttctggctct gtcgccaacc ctaggatcag cggcgtagga   4140
tttcgtaatc attcgtcctg atggggagct accgactacc ctaatatcag cccgactgcc   4200
```

-continued

```
tgacgccagc gtccactttt gtgcacacat tccattcgtg cccaagacat ttcattgtgg   4260

tgcgaagcgt ccccagttac gctcacctgt ttcccgacct ccttactgtt ctgtcgacag   4320

agcgggccca caggccggtc gcagccacta gtatggccac cgcctccacc ttctccgcct   4380

tcaacgcccg ctgcggcgac ctgcgccgct ccgccggctc cggcccccgc cgcccc gccc   4440

gccccctgcc cgtgcgcgcc gccatcgcct ccgaggtgcc cgtggccacc acctcccccc   4500

gccccggccc caccgtgtac tccaagctgg acaaggccca caccctgacc cccgagcgca   4560

tggagctgat caacggcatg tccgccttcg ccgaggagcg catcctgccc gtgctgcagc   4620

ccgtggagaa gctgtggcag ccccaggacc tgctgcccga ccccgagtcc cccgacttcc   4680

tggaccaggt ggccgagctg cgcgcccgcg ccgccaacgt gcccgacgac tacttcgtgg   4740

tgctggtggg cgacatgatc accgaggagg ccctgcccac ctacatggcc atgctgaaca   4800

ccctggacgg cgtgcgcgac gagaccggcg ccgccgacca cccctggggc cgctggaccc   4860

gccagtgggt ggccgaggag aaccgccacg gcgacctgct gaacaagtac tgctggctga   4920

ccggccgcgt gaacatgaag gccatcgagg tgaccatcca gaacctgatc ggctccggca   4980

tgaaccccaa gaccgagaac aacccctacc tgggcttcgt gtacacctcc ttccaggagc   5040

gcgccaccaa gtactcccac ggcaacaccg cccgcctggc cgcccagtac ggcgacgcca   5100

ccctgtccaa ggtgtgcggc gtgatcgccg ccgacgaggg ccgccacgag atcgcctaca   5160

cccgcatcgt ggaggagttc ttccgcctgg accccgaggg cgccatgtcc gcctacgccg   5220

acatgatgcg caagcagatc accatgcccg cccacctgat ggacgaccag cagcacggca   5280

cccgcaacac cggccgcaac ctgttcgccg acttctccgc cgtgaccgag aagctggacg   5340

tgtacgacgc cgaggactac tgcaagatcc tggagcacct gaactcccgc tggaagatcg   5400

ccgaccgcac cgtgtccggc gacgccggcg ccgaccagga gtacgtgctg cgcctgccct   5460

cccgcttccg caagctggcc gagaagtccg ccgccaagcg cgccaagacc aagcccaagc   5520

ccgtggcctt ctcctggctg tccggccgcg aggtgatggt gtgaatcgat agatctctta   5580

aggcagcagc agctcggata gtatcgacac actctggacg ctggtcgtgt gatggactgt   5640

tgccgccaca cttgctgcct tgacctgtga atatccctgc cgcttttatc aaacagcctc   5700

agtgtgtttg atcttgtgtg tacgcgcttt tgcgagttgc tagctgcttg tgctatttgc   5760

gaataccacc cccagcatcc ccttccctcg tttcatatcg cttgcatccc aaccgcaact   5820

tatctacgct gtcctgctat ccctcagcgc tgctcctgct cctgctcact gcccctcgca   5880

cagccttggt ttgggctccg cctgtattct cctggtactg caacctgtaa accagcactg   5940

caatgctgat gcacgggaag tagtgggatg ggaacacaaa tggaaagctt aattaagagc   6000

tcttgttttc cagaaggagt tgctccttga gcctttcatt ctcagcctcg ataacctcca   6060

aagccgctct aattgtggag ggggttcgaa tttaaaagct tggaatgttg gttcgtgcgt   6120

ctggaacaag cccagacttg ttgctcactg ggaaaaggac catcagctcc aaaaaacttg   6180

ccgctcaaac cgcgtacctc tgctttcgcg caatctgccc tgttgaaatc gccaccacat   6240

tcatattgtg acgcttgagc agtctgtaat tgcctcagaa tgtggaatca tctgcccccct   6300

gtgcgagccc atgccaggca tgtcgcgggc gaggacaccc gccactcgta cagcagacca   6360

ttatgctacc tcacaatagt tcataacagt gaccatattt ctcgaagctc cccaacgagc   6420

acctccatgc tctgagtggc caccccccgg ccctggtgct tgcggagggc aggtcaaccg   6480

gcatggggct accgaaatcc ccgaccggat cccaccaccc ccgcgatggg aagaatctct   6540
```

ccccgggatg tgggcccacc accagcacaa cctgctggcc caggcgagcg tcaaaccata 6600
ccacacaaat atccttggca tcggccctga attccttctg ccgctctgct acccggtgct 6660
tctgtccgaa gcaggggttg ctagggatcg ctccgagtcc gcaaaccctt gtcgcgtggc 6720
ggggcttgtt cgagcttgaa gagc 6744

<210> SEQ ID NO 111
<211> LENGTH: 542
<212> TYPE: PRT
<213> ORGANISM: Artificial Sequence
<220> FEATURE:
<223> OTHER INFORMATION: Description of Artificial Sequence: Synthetic consensus polypeptide
<220> FEATURE:
<221> NAME/KEY: MOD_RES
<222> LOCATION: (22)..(22)
<223> OTHER INFORMATION: Asp, Met or absent
<220> FEATURE:
<221> NAME/KEY: MOD_RES
<222> LOCATION: (24)..(24)
<223> OTHER INFORMATION: Ser, Gly or absent
<220> FEATURE:
<221> NAME/KEY: MOD_RES
<222> LOCATION: (25)..(25)
<223> OTHER INFORMATION: Ser, Thr or absent
<220> FEATURE:
<221> NAME/KEY: MOD_RES
<222> LOCATION: (26)..(26)
<223> OTHER INFORMATION: Ala, Lys or absent
<220> FEATURE:
<221> NAME/KEY: MOD_RES
<222> LOCATION: (27)..(27)
<223> OTHER INFORMATION: Val, Ala or absent
<220> FEATURE:
<221> NAME/KEY: MOD_RES
<222> LOCATION: (28)..(28)
<223> OTHER INFORMATION: Ile, Thr or absent
<220> FEATURE:
<221> NAME/KEY: MOD_RES
<222> LOCATION: (29)..(29)
<223> OTHER INFORMATION: Arg, Ser or absent
<220> FEATURE:
<221> NAME/KEY: MOD_RES
<222> LOCATION: (30)..(30)
<223> OTHER INFORMATION: Ile, Val or absent
<220> FEATURE:
<221> NAME/KEY: MOD_RES
<222> LOCATION: (31)..(31)
<223> OTHER INFORMATION: Arg, Ser or absent
<220> FEATURE:
<221> NAME/KEY: MOD_RES
<222> LOCATION: (32)..(32)
<223> OTHER INFORMATION: Arg, Val or absent
<220> FEATURE:
<221> NAME/KEY: MOD_RES
<222> LOCATION: (33)..(33)
<223> OTHER INFORMATION: Arg, Pro or absent
<220> FEATURE:
<221> NAME/KEY: MOD_RES
<222> LOCATION: (92)..(92)
<223> OTHER INFORMATION: Leu or Ile
<220> FEATURE:
<221> NAME/KEY: MOD_RES
<222> LOCATION: (93)..(93)
<223> OTHER INFORMATION: Ala, Leu, Thr or Ile
<220> FEATURE:
<221> NAME/KEY: MOD_RES
<222> LOCATION: (128)..(128)
<223> OTHER INFORMATION: Cys, Arg, Leu or His
<220> FEATURE:
<221> NAME/KEY: MOD_RES
<222> LOCATION: (129)..(129)
<223> OTHER INFORMATION: Arg, Lys or Ser
<220> FEATURE:
<221> NAME/KEY: MOD_RES
<222> LOCATION: (130)..(130)

<223> OTHER INFORMATION: Ser, Met, Cys or Ala
<220> FEATURE:
<221> NAME/KEY: MOD_RES
<222> LOCATION: (142)..(142)
<223> OTHER INFORMATION: Val, Ile, Met or absent
<220> FEATURE:
<221> NAME/KEY: MOD_RES
<222> LOCATION: (145)..(145)
<223> OTHER INFORMATION: Ala, Ser or absent
<220> FEATURE:
<221> NAME/KEY: MOD_RES
<222> LOCATION: (148)..(148)
<223> OTHER INFORMATION: Ser, Phe, Leu or absent
<220> FEATURE:
<221> NAME/KEY: MOD_RES
<222> LOCATION: (153)..(153)
<223> OTHER INFORMATION: Cys, Phe, Leu or Tyr
<220> FEATURE:
<221> NAME/KEY: MOD_RES
<222> LOCATION: (158)..(158)
<223> OTHER INFORMATION: Trp, Ser or absent
<220> FEATURE:
<221> NAME/KEY: MOD_RES
<222> LOCATION: (182)..(182)
<223> OTHER INFORMATION: Leu, Thr, Val or Phe
<220> FEATURE:
<221> NAME/KEY: MOD_RES
<222> LOCATION: (184)..(184)
<223> OTHER INFORMATION: Val, Thr, Met or Ile
<220> FEATURE:
<221> NAME/KEY: MOD_RES
<222> LOCATION: (192)..(192)
<223> OTHER INFORMATION: Arg, Glu, Ala or Ser
<220> FEATURE:
<221> NAME/KEY: MOD_RES
<222> LOCATION: (202)..(202)
<223> OTHER INFORMATION: Ile, Phe, Val or Asn
<220> FEATURE:
<221> NAME/KEY: MOD_RES
<222> LOCATION: (206)..(206)
<223> OTHER INFORMATION: Glu, Asp or Lys
<220> FEATURE:
<221> NAME/KEY: MOD_RES
<222> LOCATION: (249)..(249)
<223> OTHER INFORMATION: Val or Ile
<220> FEATURE:
<221> NAME/KEY: MOD_RES
<222> LOCATION: (295)..(295)
<223> OTHER INFORMATION: Ala, Phe, Thr or Leu
<220> FEATURE:
<221> NAME/KEY: MOD_RES
<222> LOCATION: (310)..(310)
<223> OTHER INFORMATION: Val or Met
<220> FEATURE:
<221> NAME/KEY: MOD_RES
<222> LOCATION: (322)..(322)
<223> OTHER INFORMATION: Arg, Gln, Gly or Ser
<220> FEATURE:
<221> NAME/KEY: MOD_RES
<222> LOCATION: (350)..(350)
<223> OTHER INFORMATION: Gln, Tyr, Arg or Thr
<220> FEATURE:
<221> NAME/KEY: MOD_RES
<222> LOCATION: (352)..(352)
<223> OTHER INFORMATION: Gly, Lys or Glu
<220> FEATURE:
<221> NAME/KEY: MOD_RES
<222> LOCATION: (353)..(353)
<223> OTHER INFORMATION: Asp or Glu
<220> FEATURE:
<221> NAME/KEY: MOD_RES
<222> LOCATION: (356)..(356)
<223> OTHER INFORMATION: Asn, Arg, Ser or Asp
<220> FEATURE:
<221> NAME/KEY: MOD_RES
<222> LOCATION: (359)..(359)
<223> OTHER INFORMATION: Thr or Ile
<220> FEATURE:
<221> NAME/KEY: MOD_RES
<222> LOCATION: (373)..(373)
<223> OTHER INFORMATION: Arg, Asp, Lys or Ile
<220> FEATURE:
<221> NAME/KEY: MOD_RES
<222> LOCATION: (380)..(380)
<223> OTHER INFORMATION: Ala or Thr
<220> FEATURE:
<221> NAME/KEY: MOD_RES
<222> LOCATION: (399)..(399)
<223> OTHER INFORMATION: Phe or Leu
<220> FEATURE:
<221> NAME/KEY: MOD_RES
<222> LOCATION: (400)..(400)
<223> OTHER INFORMATION: Met or Val
<220> FEATURE:
<221> NAME/KEY: MOD_RES
<222> LOCATION: (490)..(490)
<223> OTHER INFORMATION: Leu, Phe, Ile or Val
<220> FEATURE:
<221> NAME/KEY: MOD_RES
<222> LOCATION: (529)..(529)
<223> OTHER INFORMATION: Asp, Gly, Asn or absent

<400> SEQUENCE: 111

```
Met Glu Arg Thr Asn Ser Ile Glu Met Asp Gln Glu Arg Leu Thr Ala
1               5                   10                  15

Glu Met Ala Phe Lys Xaa Ser Xaa Xaa Xaa Xaa Xaa Xaa Xaa Xaa Xaa
            20                  25                  30

Xaa Leu Pro Asp Phe Met Thr Ser Ile Asn Val Lys Leu Leu Tyr His
        35                  40                  45

Tyr Val Ile Thr Asn Leu Phe Asn Leu Cys Phe Phe Pro Leu Thr Ala
    50                  55                  60

Ile Val Ala Gly Lys Ala Ser Arg Leu Thr Ile Asx Asp Leu His His
65                  70                  75                  80

Leu Tyr Ser Tyr Leu Gln His Asn Leu Ile Thr Xaa Xaa Leu Leu Phe
                85                  90                  95

Ala Phe Thr Val Phe Gly Ser Ile Leu Tyr Ile Val Thr Arg Pro Lys
            100                 105                 110

Pro Val Tyr Leu Val Asp Tyr Ser Cys Tyr Leu Pro Pro Thr His Xaa
        115                 120                 125

Xaa Xaa Ser Ile Ser Lys Val Met Asp Ile Phe Tyr Gln Xaa Arg Lys
    130                 135                 140

Xaa Asp Pro Xaa Arg Asn Gly Thr Xaa Asp Asp Ser Ser Xaa Leu Asp
145                 150                 155                 160

Phe Leu Arg Lys Ile Gln Glu Arg Ser Gly Leu Gly Asp Glu Thr Tyr
                165                 170                 175

Gly Pro Glu Gly Leu Xaa Gln Xaa Pro Pro Arg Lys Asn Phe Ala Xaa
            180                 185                 190

Ala Arg Glu Glu Thr Glu Gln Val Ile Xaa Gly Ala Leu Xaa Asn Leu
        195                 200                 205

Phe Glu Asn Thr Lys Val Asn Pro Lys Glu Ile Gly Ile Leu Val Val
    210                 215                 220

Asn Ser Ser Met Phe Asn Pro Thr Pro Ser Leu Ser Ala Met Val Val
225                 230                 235                 240

Asn Thr Phe Lys Leu Arg Ser Asn Xaa Lys Ser Phe Asn Leu Gly Gly
                245                 250                 255

Met Gly Cys Ser Ala Gly Val Ile Ala Ile Asp Leu Ala Lys Asp Leu
            260                 265                 270

Leu His Val His Lys Asn Thr Tyr Ala Leu Val Val Ser Thr Glu Asn
        275                 280                 285
```

-continued

```
Ile Thr Tyr Asn Ile Tyr Xaa Gly Asp Asn Arg Ser Met Met Val Ser
    290                 295                 300

Asn Cys Leu Phe Arg Xaa Gly Gly Ala Ala Ile Leu Leu Ser Asn Lys
305                 310                 315                 320

Pro Xaa Asp Arg Arg Arg Ser Lys Tyr Glu Leu Val His Thr Val Arg
                325                 330                 335

Thr His Thr Gly Ala Asp Asp Lys Ser Phe Arg Cys Val Xaa Gln Xaa
            340                 345                 350

Xaa Asp Glu Xaa Gly Lys Xaa Gly Val Ser Leu Ser Lys Asp Ile Thr
        355                 360                 365

Ala Val Ala Gly Xaa Thr Val Lys Lys Asn Ile Xaa Thr Leu Gly Pro
    370                 375                 380

Leu Val Leu Pro Leu Ser Glu Lys Leu Leu Phe Phe Val Thr Xaa Xaa
385                 390                 395                 400

Ala Lys Lys Leu Phe Lys Asp Lys Ile Lys His Tyr Tyr Val Pro Asp
                405                 410                 415

Phe Lys Leu Ala Ile Asp His Phe Cys Ile His Ala Gly Gly Arg Ala
            420                 425                 430

Val Ile Asp Val Leu Glu Lys Asn Leu Gly Leu Ser Pro Ile Asp Val
        435                 440                 445

Glu Ala Ser Arg Ser Thr Leu His Arg Phe Gly Asn Thr Ser Ser Ser
    450                 455                 460

Ser Ile Trp Tyr Glu Leu Ala Tyr Ile Glu Ala Lys Gly Arg Met Lys
465                 470                 475                 480

Lys Gly Asn Lys Val Trp Gln Ile Ala Xaa Gly Ser Gly Phe Lys Cys
                485                 490                 495

Asn Ser Ala Val Trp Val Ala Leu Arg Asn Val Lys Ala Ser Thr Asn
            500                 505                 510

Ser Pro Trp Glu His Cys Ile Asp Arg Tyr Pro Val Lys Ile Asp Ser
        515                 520                 525

Xaa Ser Ser Lys Ser Glu Thr Arg Ala Gln Asn Gly Arg Ser
    530                 535                 540


<210> SEQ ID NO 112
<211> LENGTH: 505
<212> TYPE: PRT
<213> ORGANISM: Brassica napus

<400> SEQUENCE: 112

Met Thr Ser Ile Asn Val Lys Leu Leu Tyr His Tyr Val Ile Thr Asn
1               5                   10                  15

Leu Phe Asn Leu Cys Phe Phe Pro Leu Thr Ala Ile Val Ala Gly Lys
            20                  25                  30

Ala Tyr Leu Thr Ile Asp Asp Leu His His Leu Tyr Tyr Ser Tyr Leu
        35                  40                  45

Gln His Asn Leu Ile Thr Ile Ala Pro Leu Leu Ala Phe Thr Val Phe
    50                  55                  60

Gly Ser Val Leu Tyr Ile Ala Thr Arg Pro Lys Pro Val Tyr Leu Val
65                  70                  75                  80

Glu Tyr Ser Cys Tyr Leu Pro Pro Thr His Cys Arg Ser Ser Ile Ser
                85                  90                  95

Lys Val Met Asp Ile Phe Phe Gln Val Arg Lys Ala Asp Pro Ser Arg
            100                 105                 110

Asn Gly Thr Cys Asp Asp Ser Ser Trp Leu Asp Phe Leu Arg Lys Ile
        115                 120                 125
```

```
Gln Glu Arg Ser Gly Leu Gly Asp Glu Thr His Gly Pro Glu Gly Leu
    130                 135                 140

Leu Gln Val Pro Pro Arg Lys Thr Phe Ala Arg Ala Arg Glu Glu Thr
145                 150                 155                 160

Glu Gln Val Ile Ile Gly Ala Leu Glu Asn Leu Phe Lys Asn Thr Asn
                165                 170                 175

Val Asn Pro Lys Asp Ile Gly Ile Leu Val Val Asn Ser Ser Met Phe
            180                 185                 190

Asn Pro Thr Pro Ser Leu Ser Ala Met Val Val Asn Thr Phe Lys Leu
        195                 200                 205

Arg Ser Asn Val Arg Ser Phe Asn Leu Gly Gly Met Gly Cys Ser Ala
    210                 215                 220

Gly Val Ile Ala Ile Asp Leu Ala Lys Asp Leu Leu His Val His Lys
225                 230                 235                 240

Asn Thr Tyr Ala Leu Val Val Ser Thr Glu Asn Ile Thr Tyr Asn Ile
                245                 250                 255

Tyr Ala Gly Asp Asn Arg Ser Met Met Val Ser Asn Cys Leu Phe Arg
            260                 265                 270

Val Gly Gly Ala Ala Ile Leu Leu Ser Asn Lys Pro Arg Asp Arg Arg
        275                 280                 285

Arg Ser Lys Tyr Glu Leu Val His Thr Val Arg Thr His Thr Gly Ala
    290                 295                 300

Asp Asp Lys Ser Phe Arg Cys Val Gln Gln Gly Asp Asp Glu Asn Gly
305                 310                 315                 320

Gln Thr Gly Val Ser Leu Ser Lys Asp Ile Thr Asp Val Ala Gly Arg
                325                 330                 335

Thr Val Lys Lys Asn Ile Ala Thr Leu Gly Pro Leu Ile Leu Pro Leu
            340                 345                 350

Ser Glu Lys Leu Leu Phe Phe Val Thr Phe Met Gly Lys Lys Leu Phe
        355                 360                 365

Lys Asp Glu Ile Lys His Tyr Tyr Val Pro Asp Phe Lys Leu Ala Ile
    370                 375                 380

Asp His Phe Cys Ile His Ala Gly Gly Lys Ala Val Ile Asp Val Leu
385                 390                 395                 400

Glu Lys Asn Leu Gly Leu Ala Pro Ile Asp Val Glu Ala Ser Arg Ser
                405                 410                 415

Thr Leu His Arg Phe Gly Asn Thr Ser Ser Ser Ser Ile Trp Tyr Glu
            420                 425                 430

Leu Ala Tyr Ile Glu Pro Lys Gly Arg Met Lys Lys Gly Asn Lys Val
        435                 440                 445

Trp Gln Ile Ala Leu Gly Ser Gly Phe Lys Cys Asn Ser Ala Val Trp
    450                 455                 460

Val Ala Leu Asn Asn Val Lys Ala Ser Thr Asn Ser Pro Trp Glu His
465                 470                 475                 480

Cys Ile Asp Arg Tyr Pro Val Lys Ile Asp Ser Asp Ser Gly Lys Ser
                485                 490                 495

Glu Thr Arg Val Pro Asn Gly Arg Ser
            500                 505
```

<210> SEQ ID NO 113
<211> LENGTH: 528
<212> TYPE: PRT
<213> ORGANISM: Brassica napus -continued

<400> SEQUENCE: 113

```
Met Glu Arg Thr Asn Ser Ile Glu Met Asp Gln Glu Arg Leu Thr Ala
1               5                   10                  15

Glu Met Ala Phe Lys Asp Ser Ser Ser Ala Val Ile Arg Ile Arg Arg
            20                  25                  30

Arg Leu Pro Asp Phe Leu Thr Ser Val Lys Leu Lys Tyr Val Lys Leu
        35                  40                  45

Gly Leu His Asn Ser Phe Asn Phe Thr Thr Phe Leu Phe Leu Leu Ile
    50                  55                  60

Ile Leu Pro Leu Thr Gly Thr Val Leu Val Gln Leu Thr Gly Leu Thr
65                  70                  75                  80

Phe Glu Thr Phe Ser Glu Leu Trp Tyr Asn His Ala Ala Gln Leu Asp
                85                  90                  95

Gly Val Thr Arg Leu Ala Cys Leu Val Ser Leu Cys Phe Val Leu Ile
            100                 105                 110

Ile Tyr Val Thr Asn Arg Ser Lys Pro Val Tyr Leu Val Asp Phe Ser
        115                 120                 125

Cys Tyr Lys Pro Glu Asp Glu Arg Lys Met Ser Val Asp Ser Phe Leu
    130                 135                 140

Lys Met Thr Glu Gln Asn Gly Ala Phe Thr Asp Asp Thr Val Gln Phe
145                 150                 155                 160

Gln Gln Arg Ile Ser Asn Arg Ala Gly Leu Gly Asp Glu Thr Tyr Leu
                165                 170                 175

Pro Arg Gly Ile Thr Ser Thr Pro Pro Lys Leu Asn Met Ser Glu Ala
            180                 185                 190

Arg Ala Glu Ala Glu Ala Val Met Phe Gly Ala Leu Asp Ser Leu Phe
        195                 200                 205

Glu Lys Thr Gly Ile Lys Pro Ala Glu Val Gly Ile Leu Ile Val Ser
    210                 215                 220

Cys Ser Leu Phe Asn Pro Thr Pro Ser Leu Ser Ala Met Ile Val Asn
225                 230                 235                 240

His Tyr Lys Met Arg Glu Asp Ile Lys Ser Tyr Asn Leu Gly Gly Met
                245                 250                 255

Gly Cys Ser Ala Gly Leu Ile Ser Ile Asp Leu Ala Asn Asn Leu Leu
            260                 265                 270

Lys Ala Asn Pro Asn Ser Tyr Ala Val Val Val Ser Thr Glu Asn Ile
        275                 280                 285

Thr Leu Asn Trp Tyr Phe Gly Asn Asp Arg Ser Met Leu Leu Cys Asn
    290                 295                 300

Cys Ile Phe Arg Met Gly Gly Ala Ala Ile Leu Leu Ser Asn Arg Arg
305                 310                 315                 320

Gln Asp Arg Ser Lys Ser Lys Tyr Glu Leu Val Asn Val Val Arg Thr
                325                 330                 335

His Lys Gly Ser Asp Asp Lys Asn Tyr Asn Cys Val Tyr Gln Lys Glu
            340                 345                 350

Asp Glu Arg Gly Thr Ile Gly Val Ser Leu Ala Arg Glu Leu Met Ser
        355                 360                 365

Val Ala Gly Asp Ala Leu Lys Thr Asn Ile Thr Thr Leu Gly Pro Met
    370                 375                 380

Val Leu Pro Leu Ser Gly Gln Leu Met Phe Ser Val Ser Leu Val Lys
385                 390                 395                 400

Arg Lys Leu Leu Lys Leu Lys Val Lys Pro Tyr Ile Pro Asp Phe Lys
                405                 410                 415
```

```
Leu Ala Phe Glu His Phe Cys Ile His Ala Gly Gly Arg Ala Val Leu
            420                 425                 430

Asp Glu Val Gln Lys Asn Leu Asp Leu Glu Asp Trp His Met Glu Pro
        435                 440                 445

Ser Arg Met Thr Leu His Arg Phe Gly Asn Thr Ser Ser Ser Ser Leu
    450                 455                 460

Trp Tyr Glu Met Ala Tyr Thr Glu Ala Lys Gly Arg Val Lys Ala Gly
465                 470                 475                 480

Asp Arg Leu Trp Gln Ile Ala Phe Gly Ser Gly Phe Lys Cys Asn Ser
                485                 490                 495

Ala Val Trp Lys Ala Leu Arg Val Val Ser Thr Glu Glu Leu Thr Gly
            500                 505                 510

Asn Ala Trp Ala Gly Ser Ile Glu Asn Tyr Pro Val Lys Ile Val Gln
        515                 520                 525


<210> SEQ ID NO 114
<211> LENGTH: 506
<212> TYPE: PRT
<213> ORGANISM: Crambe abyssinica

<400> SEQUENCE: 114

Met Thr Ser Ile Asn Val Lys Leu Leu Tyr His Tyr Val Ile Thr Asn
1               5                   10                  15

Leu Phe Asn Leu Cys Phe Phe Pro Leu Thr Ala Ile Val Ala Gly Lys
            20                  25                  30

Ala Ser Arg Leu Thr Ile Asp Asp Leu His His Leu Tyr Tyr Ser Tyr
        35                  40                  45

Leu Gln His Asn Val Ile Thr Ile Ala Pro Leu Phe Ala Phe Thr Val
    50                  55                  60

Phe Gly Ser Ile Leu Tyr Ile Val Thr Arg Pro Lys Pro Val Tyr Leu
65                  70                  75                  80

Val Glu Tyr Ser Cys Tyr Leu Pro Pro Thr Gln Cys Arg Ser Ser Ile
                85                  90                  95

Ser Lys Val Met Asp Ile Phe Tyr Gln Val Arg Lys Ala Asp Pro Phe
            100                 105                 110

Arg Asn Gly Thr Cys Asp Asp Ser Ser Trp Leu Asp Phe Leu Arg Lys
        115                 120                 125

Ile Gln Glu Arg Ser Gly Leu Gly Asp Glu Thr His Gly Pro Glu Gly
    130                 135                 140

Leu Leu Gln Val Pro Pro Arg Lys Thr Phe Ala Ala Ala Arg Glu Glu
145                 150                 155                 160

Thr Glu Gln Val Ile Val Gly Ala Leu Lys Asn Leu Phe Glu Asn Thr
                165                 170                 175

Lys Val Asn Pro Lys Asp Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Val Arg Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
```

```
            260                 265                 270

Arg Val Gly Gly Ala Ala Ile Leu Leu Ser Asn Lys Pro Arg Asp Arg
        275                 280                 285

Arg Arg Ser Lys Tyr Glu Leu Val His Thr Val Arg Thr His Thr Gly
    290                 295                 300

Ala Asp Asp Lys Ser Phe Arg Cys Val Gln Gln Gly Asp Asp Glu Asn
305                 310                 315                 320

Gly Lys Thr Gly Val Ser Leu Ser Lys Asp Ile Thr Glu Val Ala Gly
                325                 330                 335

Arg Thr Val Lys Lys Asn Ile Ala Thr Leu Gly Pro Leu Ile Leu Pro
            340                 345                 350

Leu Ser Glu Lys Leu Leu Phe Phe Val Thr Phe Met Ala Lys Lys Leu
        355                 360                 365

Phe Lys Asp Lys Val Lys His Tyr Tyr Val Pro Asp Phe Lys Leu Ala
    370                 375                 380

Ile Asp His Phe Cys Ile His Ala Gly Gly Arg Ala Val Ile Asp Val
385                 390                 395                 400

Leu Glu Lys Asn Leu Gly Leu Ala Pro Ile Asp Val Glu Ala Ser Arg
                405                 410                 415

Ser Thr Leu His Arg Phe Gly Asn Thr Ser Ser Ser Ser Ile Trp Tyr
            420                 425                 430

Glu Leu Ala Tyr Ile Glu Ala Lys Gly Arg Met Lys Lys Gly Asn Lys
        435                 440                 445

Val Trp Gln Ile Ala Leu Gly Ser Gly Phe Lys Cys Asn Ser Ala Val
    450                 455                 460

Trp Val Ala Leu Ser Asn Val Lys Ala Ser Thr Asn Ser Pro Trp Glu
465                 470                 475                 480

His Cys Ile Asp Arg Tyr Pro Val Lys Ile Asp Ser Asp Ser Ala Lys
                485                 490                 495

Ser Glu Thr Arg Ala Gln Asn Gly Arg Ser
            500                 505


<210> SEQ ID NO 115
<211> LENGTH: 506
<212> TYPE: PRT
<213> ORGANISM: Cardamine graeca

<400> SEQUENCE: 115

Met Thr Ser Ile Asn Val Lys Leu Leu Tyr His Tyr Val Leu Thr Asn
1               5                   10                  15

Phe Phe Asn Leu Cys Leu Phe Pro Leu Thr Ala Phe Pro Ala Gly Lys
            20                  25                  30

Ala Ser Gln Leu Thr Thr Asn Asp Leu His His Leu Tyr Ser Tyr Leu
        35                  40                  45

His His Asn Leu Ile Thr Val Thr Leu Leu Phe Ala Phe Thr Val Phe
    50                  55                  60

Gly Ser Ile Leu Tyr Ile Val Thr Arg Pro Lys Pro Val Tyr Leu Val
65                  70                  75                  80

Asp Tyr Ser Cys Tyr Leu Pro Pro Arg His Leu Ser Cys Gly Ile Ser
                85                  90                  95

Arg Val Met Glu Ile Phe Tyr Glu Ile Arg Lys Ser Asp Pro Ser Arg
            100                 105                 110

Glu Val Pro Phe Asp Asp Pro Ser Ser Leu Glu Phe Leu Arg Lys Ile
        115                 120                 125
```

-continued

```
Gln Glu Arg Ser Gly Leu Gly Asp Glu Thr Tyr Gly Pro Gln Gly Leu
    130                 135                 140

Val His Asp Met Pro Leu Arg Met Asn Phe Ala Ala Ala Arg Glu Glu
145                 150                 155                 160

Thr Glu Gln Val Ile Asn Gly Ala Leu Glu Lys Leu Phe Glu Asn Thr
                165                 170                 175

Lys Val Asn Pro Arg Glu Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Ile Lys Ser Phe Ser Leu Gly Gly Met Gly Cys Ser
    210                 215                 220

Ala Gly Ile Ile Ala Ile Asp Leu Ala Lys Asp Leu Leu His Val His
225                 230                 235                 240

Lys Asn Thr Tyr Ala Leu Val Val Ser Thr Glu Asn Ile Thr His Ser
                245                 250                 255

Thr Tyr Thr Gly Asp Asn Arg Ser Met Met Val Ser Asn Cys Leu Phe
            260                 265                 270

Arg Met Gly Gly Ala Ala Ile Leu Leu Ser Asn Lys Ala Gly Asp Arg
        275                 280                 285

Arg Arg Ser Lys Tyr Lys Leu Ala His Thr Val Arg Thr His Thr Gly
    290                 295                 300

Ala Asp Asp Gln Ser Phe Arg Cys Val Arg Gln Glu Asp Asp Asp Arg
305                 310                 315                 320

Gly Lys Ile Gly Val Cys Leu Ser Lys Asp Ile Thr Ala Val Ala Gly
                325                 330                 335

Lys Thr Val Thr Lys Asn Ile Ala Thr Leu Gly Pro Leu Val Leu Pro
            340                 345                 350

Leu Ser Glu Lys Phe Leu Tyr Val Val Ser Leu Met Ala Lys Lys Leu
        355                 360                 365

Phe Lys Asn Lys Ile Lys His Thr Tyr Val Pro Asp Phe Lys Leu Ala
    370                 375                 380

Ile Asp His Phe Cys Ile His Ala Gly Gly Arg Ala Val Ile Asp Val
385                 390                 395                 400

Leu Glu Lys Asn Leu Ala Leu Ser Pro Val Asp Val Glu Ala Ser Arg
                405                 410                 415

Ser Thr Leu His Arg Phe Gly Asn Thr Ser Ser Ser Ser Ile Trp Tyr
            420                 425                 430

Glu Leu Ala Tyr Ile Glu Ala Lys Gly Arg Met Lys Lys Gly Asn Lys
        435                 440                 445

Val Trp Gln Ile Ala Ile Gly Ser Gly Phe Lys Cys Asn Ser Ala Val
    450                 455                 460

Trp Val Ala Leu Cys Asn Val Lys Pro Ser Val Asn Ser Pro Trp Glu
465                 470                 475                 480

His Cys Ile Asp Arg Tyr Pro Val Glu Ile Asn Tyr Gly Ser Ser Lys
                485                 490                 495

Ser Glu Thr Arg Ala Gln Asn Gly Arg Ser
            500                 505
```

<210> SEQ ID NO 116
<211> LENGTH: 505
<212> TYPE: PRT
<213> ORGANISM: Lunaria annua

<400> SEQUENCE: 116

-continued

```
Met Thr Ser Ile Asn Val Lys Leu Leu Tyr His Tyr Val Ile Thr Asn
1               5                   10                  15

Phe Phe Asn Leu Cys Phe Phe Pro Leu Thr Ala Ile Leu Ala Gly Lys
            20                  25                  30

Ala Ser Arg Leu Thr Thr Asn Asp Leu His His Phe Tyr Ser Tyr Leu
        35                  40                  45

Gln His Asn Leu Ile Thr Leu Thr Leu Leu Phe Ala Phe Thr Val Phe
    50                  55                  60

Gly Ser Val Leu Tyr Phe Val Thr Arg Pro Lys Pro Val Tyr Leu Val
65                  70                  75                  80

Asp Tyr Ser Cys Tyr Leu Pro Pro Gln His Leu Ser Ala Gly Ile Ser
                85                  90                  95

Lys Thr Met Glu Ile Phe Tyr Gln Ile Arg Lys Ser Asp Pro Leu Arg
            100                 105                 110

Asn Val Ala Leu Asp Asp Ser Ser Ser Leu Asp Phe Leu Arg Lys Ile
        115                 120                 125

Gln Glu Arg Ser Gly Leu Gly Asp Glu Thr Tyr Gly Pro Glu Gly Leu
    130                 135                 140

Phe Glu Ile Pro Pro Arg Lys Asn Leu Ala Ser Ala Arg Glu Glu Thr
145                 150                 155                 160

Glu Gln Val Ile Asn Gly Ala Leu Lys Asn Leu Phe Glu Asn Thr Lys
                165                 170                 175

Val Asn Pro Lys Glu Ile Gly Ile Leu Val Val Asn Ser Ser Met Phe
            180                 185                 190

Asn Pro Thr Pro Ser Leu Ser Ala Met Val Val Asn Thr Phe Lys Leu
        195                 200                 205

Arg Ser Asn Ile Lys Ser Phe Asn Leu Gly Gly Met Gly Cys Ser Ala
    210                 215                 220

Gly Val Ile Ala Ile Asp Leu Ala Lys Asp Leu Leu His Val His Lys
225                 230                 235                 240

Asn Thr Tyr Ala Leu Val Val Ser Thr Glu Asn Ile Thr Gln Asn Ile
                245                 250                 255

Tyr Thr Gly Asp Asn Arg Ser Met Met Val Ser Asn Cys Leu Phe Arg
            260                 265                 270

Val Gly Gly Ala Ala Ile Leu Leu Ser Asn Lys Pro Gly Asp Arg Arg
        275                 280                 285

Arg Ser Lys Tyr Arg Leu Ala His Thr Val Arg Thr His Thr Gly Ala
    290                 295                 300

Asp Asp Lys Ser Phe Gly Cys Val Arg Gln Glu Glu Asp Asp Ser Gly
305                 310                 315                 320

Lys Thr Gly Val Ser Leu Ser Lys Asp Ile Thr Gly Val Ala Gly Ile
                325                 330                 335

Thr Val Gln Lys Asn Ile Thr Thr Leu Gly Pro Leu Val Leu Pro Leu
            340                 345                 350

Ser Glu Lys Ile Leu Phe Val Val Thr Phe Val Ala Lys Lys Leu Leu
        355                 360                 365

Lys Asp Lys Ile Lys His Tyr Tyr Val Pro Asp Phe Lys Leu Ala Val
    370                 375                 380

Asp His Phe Cys Ile His Ala Gly Gly Arg Ala Val Ile Asp Val Leu
385                 390                 395                 400

Glu Lys Asn Leu Gly Leu Ser Pro Ile Asp Val Glu Ala Ser Arg Ser
                405                 410                 415
```

```
Thr Leu His Arg Phe Gly Asn Thr Ser Ser Ser Ser Ile Trp Tyr Glu
            420                 425                 430

Leu Ala Tyr Ile Glu Ala Lys Gly Arg Met Lys Lys Gly Asn Lys Ala
        435                 440                 445

Trp Gln Ile Ala Val Gly Ser Gly Phe Lys Cys Asn Ser Ala Val Trp
    450                 455                 460

Val Ala Leu Arg Asn Val Lys Ala Ser Ala Asn Ser Pro Trp Glu His
465                 470                 475                 480

Cys Ile His Lys Tyr Pro Val Gln Met Tyr Ser Gly Ser Ser Lys Ser
                485                 490                 495

Glu Thr Arg Ala Gln Asn Gly Arg Ser
            500                 505


<210> SEQ ID NO 117
<211> LENGTH: 503
<212> TYPE: PRT
<213> ORGANISM: Tropaeolum majus

<400> SEQUENCE: 117

Met Ser Gly Thr Lys Ala Thr Ser Val Ser Val Pro Leu Pro Asp Phe
1               5                   10                  15

Lys Gln Ser Val Asn Leu Lys Tyr Val Lys Leu Gly Tyr His Tyr Ser
            20                  25                  30

Ile Thr His Ala Met Tyr Leu Phe Leu Thr Pro Leu Leu Leu Ile Met
        35                  40                  45

Ser Ala Gln Ile Ser Thr Phe Ser Ile Gln Asp Phe His His Leu Tyr
    50                  55                  60

Asn His Leu Ile Leu His Asn Leu Ser Ser Leu Ile Leu Cys Ile Ala
65                  70                  75                  80

Leu Leu Leu Phe Val Leu Thr Leu Tyr Phe Leu Thr Arg Pro Thr Pro
                85                  90                  95

Val Tyr Leu Leu Asn Phe Ser Cys Tyr Lys Pro Asp Ala Ile His Lys
            100                 105                 110

Cys Asp Arg Arg Arg Phe Met Asp Thr Ile Arg Gly Met Gly Thr Tyr
        115                 120                 125

Thr Glu Glu Asn Ile Glu Phe Gln Arg Lys Val Leu Glu Arg Ser Gly
    130                 135                 140

Ile Gly Glu Ser Ser Tyr Leu Pro Pro Thr Val Phe Lys Ile Pro Pro
145                 150                 155                 160

Arg Val Tyr Asp Ala Glu Glu Arg Ala Glu Ala Glu Met Leu Met Phe
                165                 170                 175

Gly Ala Val Asp Gly Leu Phe Glu Lys Ile Ser Val Lys Pro Asn Gln
            180                 185                 190

Ile Gly Val Leu Val Val Asn Cys Gly Leu Phe Asn Pro Ile Pro Ser
        195                 200                 205

Leu Ser Ser Met Ile Val Asn Arg Tyr Lys Met Arg Gly Asn Val Phe
    210                 215                 220

Ser Tyr Asn Leu Gly Gly Met Gly Cys Ser Ala Gly Val Ile Ser Ile
225                 230                 235                 240

Asp Leu Ala Lys Asp Leu Leu Gln Val Arg Pro Asn Ser Tyr Ala Leu
                245                 250                 255

Val Val Ser Leu Glu Cys Ile Ser Lys Asn Leu Tyr Leu Gly Glu Gln
            260                 265                 270

Arg Ser Met Leu Val Ser Asn Cys Leu Phe Arg Met Gly Gly Ala Ala
        275                 280                 285
```

-continued

```
Ile Leu Leu Ser Asn Lys Met Ser Asp Arg Trp Arg Ser Lys Tyr Arg
    290                 295                 300

Leu Val His Thr Val Arg Thr His Lys Gly Thr Glu Asp Asn Cys Phe
305                 310                 315                 320

Ser Cys Val Thr Arg Lys Glu Asp Ser Asp Gly Lys Ile Gly Ile Ser
                325                 330                 335

Leu Ser Lys Asn Leu Met Ala Val Ala Gly Asp Ala Leu Lys Thr Asn
            340                 345                 350

Ile Thr Thr Leu Gly Pro Leu Val Leu Pro Met Ser Glu Gln Leu Leu
        355                 360                 365

Phe Phe Ala Thr Leu Val Gly Lys Lys Val Phe Lys Met Lys Leu Gln
    370                 375                 380

Pro Tyr Ile Pro Asp Phe Lys Leu Ala Phe Glu His Phe Cys Ile His
385                 390                 395                 400

Ala Gly Gly Arg Ala Val Leu Asp Glu Leu Glu Lys Asn Leu Lys Leu
                405                 410                 415

Ser Ser Trp His Met Glu Pro Ser Arg Met Ser Leu Tyr Arg Phe Gly
            420                 425                 430

Asn Thr Ser Ser Ser Ser Leu Trp Tyr Glu Leu Ala Tyr Ser Glu Ala
        435                 440                 445

Lys Gly Arg Ile Lys Lys Gly Asp Arg Val Trp Gln Ile Ala Phe Gly
    450                 455                 460

Ser Gly Phe Lys Cys Asn Ser Ala Val Trp Lys Ala Leu Arg Asn Val
465                 470                 475                 480

Asn Pro Ala Glu Glu Lys Asn Pro Trp Met Asp Glu Ile His Leu Phe
                485                 490                 495

Pro Val Glu Val Pro Leu Asn
            500
```